US010220090B2

(12) United States Patent
Armitage et al.

(10) Patent No.: US 10,220,090 B2
(45) Date of Patent: *Mar. 5, 2019

(54) BCMA ANTIGEN BINDING PROTEINS

(71) Applicant: Amgen Inc., Thousand Oaks, CA (US)

(72) Inventors: Richard J. Armitage, Bainbridge Island, WA (US); Michelle Blake, Arlington, MA (US); William C. Fanslow, III, Normandy Park, WA (US); Jason Charles O'Neill, Brier, WA (US); Gunasekaran Kannan, Daly City, CA (US); Jiangchun Xu, San Diego, CA (US); Mark Edward Tometsko, Seattle, WA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/967,167

(22) Filed: Dec. 11, 2015

(65) Prior Publication Data

US 2017/0165373 A1 Jun. 15, 2017
US 2019/0008974 A9 Jan. 10, 2019

Related U.S. Application Data

(62) Division of application No. 14/098,275, filed on Dec. 5, 2013, now Pat. No. 9,243,058.

(60) Provisional application No. 61/759,702, filed on Feb. 1, 2013, provisional application No. 61/775,125, filed on Mar. 8, 2013, provisional application No. 61/734,767, filed on Dec. 7, 2012.

(51) Int. Cl.
| | |
|---|---|
| *C07K 16/18* | (2006.01) |
| *A61K 45/06* | (2006.01) |
| *A61K 39/00* | (2006.01) |
| *C07K 16/28* | (2006.01) |
| *A61K 39/395* | (2006.01) |
| *A61K 31/395* | (2006.01) |
| *A61K 47/68* | (2017.01) |

(52) U.S. Cl.
CPC ........ *A61K 39/3955* (2013.01); *A61K 31/395* (2013.01); *A61K 45/06* (2013.01); *A61K 47/6803* (2017.08); *A61K 47/6849* (2017.08); *A61K 47/6867* (2017.08); *C07K 16/18* (2013.01); *C07K 16/2878* (2013.01); *A61K 2039/505* (2013.01); *A61K 2039/572* (2013.01); *C07K 2317/21* (2013.01); *C07K 2317/24* (2013.01); *C07K 2317/33* (2013.01); *C07K 2317/56* (2013.01); *C07K 2317/565* (2013.01); *C07K 2317/732* (2013.01); *C07K 2317/76* (2013.01); *C07K 2317/77* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 9,243,058 B2 | 1/2016 | Armitage et al. | |
| 2014/0161828 A1* | 6/2014 | Armitage | A61K 45/06 424/181.1 |
| 2015/0344583 A1* | 12/2015 | Armitage | C07K 16/2878 424/133.1 |

FOREIGN PATENT DOCUMENTS

| | | |
|---|---|---|
| WO | WO 2002/066516 A2 | 8/2002 |
| WO | WO2006067210 A1 | 6/2006 |
| WO | WO2012066058 A1 | 5/2012 |
| WO | WO 2012/143498 A1 | 10/2012 |
| WO | WO2012163805 A1 | 12/2012 |
| WO | WO 2013/072406 A1 | 5/2013 |
| WO | WO 2013/072415 A1 | 5/2013 |
| WO | WO 2014/140248 A1 | 9/2014 |

OTHER PUBLICATIONS

Bellucci et al., "Graft-versus-tumor response in patients with multiple myeloma is associated with antibody response to BCMA, a plasma-cell membrane receptor", BLOOD (2005), 105:10:3945-3950.
Asundi et al., An Antibody-Drug Conjugate Targeting the Endothelin B Receptor for the Treatment of Melanoma, Clin Cancer Res (2011), 17(5):965-975.
Ryan et al., Antibody Targeting of B-Cell Maturation Antigen on Malignant Plasma Cells, Molecular Cancer Therapeutics (2007), 6(11):3009-3018.
Brown et al., Tolerance to Single, but not Multiple, Amino Acide Replacements in Antibody V-H CDR2: A Means of Minimizing B Cell Wastage from Somatic Hypermutation?, The Journal of Immunology, 156(9): 3285-3291, Jan. 1, 1996.
Jakobovits et al., From XenoMouse Technology to Panitumumab, the First Fully Humn Antibody Product from Transgenic Mice, Nature Biotechnology, 25(10): 1134-1143, Oct. 1, 2007.
Jespers et al., Guiding the Selection of Humn Antibodies from Phage Display Repertoires to a Single Epitope of an Antigen, Nature Biotechnology, 12: 899-903, Sep. 12, 1994.
McCarthy et al., Altering the Fine Specificity of an Anti-Legionella Single Chain Antibody by a Single Amino Acid Insertion, J. Immunol. Methods, 251(1-2): 137-149, Oct. 22, 2000.

(Continued)

*Primary Examiner* — Julie Wu
(74) *Attorney, Agent, or Firm* — Lawrence B. Kong

(57) ABSTRACT

The present invention relates to BCMA (B-Cell Maturation Antigen) antigen binding proteins, such as antibodies, polynucleotide sequences encoding said antigen binding proteins, and compositions and methods for diagnosing and treating diseases. The present invention also relates to BCMA antibody drug conjugates.

17 Claims, 53 Drawing Sheets
Specification includes a Sequence Listing.

(56) References Cited

OTHER PUBLICATIONS

Rudikoff et al., Single Amino Acid Substitution Altering Antigen-Binding Specificity, Proc. Natl. Sci. USA, 79(6): 1979-1983, Mar. 1982.

Ryan et al., Antibody Targeting of B-Cell Maturation Antigen on Malignant Plasma Cells, Molecular Cancer Therapeutics, 6(11): 3009-3018, Nov. 1, 2007.

Winkler et al., Changing the Antigen Binding Specificity by Single Point Mutations of an Anti-p24 (HIV-1) Antibody, The Journal of Immunology, 165(8): 4505-4514, Oct. 15, 2000.

Xu et al., Two Monoclonal Antibodies to Precisely the Same Epitope of Type II Collagen Select Non-Crossreactive Phage Clones by Phage Display: Implications for Autoimmumity and Molecular Mimicry, 41: 411-419, Apr. 30, 2004.

* cited by examiner

Human BCMA

MLQMAGQCSQ NEYFDSLLHA CIPCQLRCSS NTPPLTCQRY CNASVTNSVK
GTNAILWTCL GLSLIISLAV FVLMFLLRKI SSEPLKDEFK NTGSGLLGMA
NIDLEKSRTG DEIILPRGLE YTVEECTCED CIKSKPKVDS DHCFPLPAME
EGATILVTTK TNDYCKSLPA ALSATEIEKS ISAR (SEQ ID NO:285)

Cynomolgus (Macaca fascicularis) BCMA

MLQMARQCSQ NEYFDSLLHD CKPCQLRCSS TPPLTCQRYC NASMTNSVKG
MNAILWTCLG LSLIISLAVF VLTFLLRKMS SEPLKDEFKN TGSGLLGMAN
IDLEKGRTGD EIVLPRGLEY TVEECTCEDC IKNKPKVDSD HCFPLPAMEE
GATILVTTKT NDYCNSLSAA LSVTEIEKSI SAR (SEQ ID NO:286)

*Fig. 1*

| mAB | Avg % inhibition | H929 FACS | L363 FACS | MoBCMA binding on 293T transients by FMAT | FACS binding BCMA/293 transients (background subtracted) HuBCMA | FACS binding BCMA/293 transients (background subtracted) MoBCMA | FACS binding BCMA/293 transients (background subtracted) CynoBCMA | CynoBCMA binding on 293T transients FMAT | FACS binding BCMA/293 transients (background subtracted) CynoBCMA | Immunogen |
|---|---|---|---|---|---|---|---|---|---|---|
| 19F11 | 16% | 84.9 | - | - | - | - | - | Y | 165.8 | A |
| 20C10 | 20% | 57.4 | - | - | - | - | - | Y | 139.2 | A |
| 1C1 | 24% | - | - | - | - | - | - | Y | 50.8 | A |
| 1E1 | 72% | - | - | - | - | - | - | Y | 91.1 | A |
| 2A1 | 89% | - | 47.8 | Y | 128.2 | 4.4 | 70.7 | Y | 210.2 | B |
| 16B2 | 86% | 48.0 | - | Y | 131.8 | 31.6 | 54.4 | Y | 143.1 | B |
| 7B9 | 78% | 58.5 | - | Y | 144.9 | 29.0 | 57.4 | Y | 138.2 | B |
| 11C9 | 69% | 56.1 | - | Y | 118.1 | 19.4 | 33.7 | Y | 113.8 | B |
| 3H9 | 72% | 60.5 | - | Y | 126.8 | 12.9 | 30.1 | Y | 85.8 | B |
| 9F10 | 81% | 49.9 | - | Y | 114 | 11.2 | 17.9 | Y | 64.3 | B |
| 12H11 | 38% | 75.1 | - | Y | 144.7 | 17.6 | 18.3 | Y | 55.7 | B |
| 18H9 | 71% | 60.0 | - | Y | 115.6 | 11.8 | 14.3 | Y | 48.4 | B |
| 5A7 | 34% | 40.6 | - | Y | 106.3 | 11.4 | 18.9 | Y | 46.4 | B |

Fig. 5A

| mAB | Avg % inhibition | H929 FACS | L363 FACS | MoBCMA binding on 293T transients by FMAT | FACS binding BCMA/293 transients (background subtracted): HuBCMA | FACS binding BCMA/293 transients (background subtracted): MoBCMA | FACS binding BCMA/293 transients (background subtracted): CynoBCMA | CynoBCMA binding on 293T transients FMAT | FACS binding BCMA/293 transients (background subtracted): CynoBCMA | Immunogen |
|---|---|---|---|---|---|---|---|---|---|---|
| 3F8 | 16% | 54.6 | - | Y | 106.5 | 16.1 | 16.3 | Y | 46.4 | B |
| 13B10 | 40% | 38.4 | - | Y | 135.0 | 24.0 | 19.5 | Y | 43.0 | B |
| 3G1 | 65% | 61.3 | - | Y | 101.0 | 7.7 | 8.9 | Y | 35.3 | B |
| 7F9 | 29% | 40.6 | - | Y | 77.7 | 7.7 | 14.3 | Y | 35.1 | B |
| 13B3 | 1% | 56.5 | - | Y | 98.5 | 14.6 | 19.2 | Y | 33.5 | B |
| 3D1 | 28% | 31.0 | - | Y | 63.2 | 7.9 | 12.4 | Y | 31.9 | B |
| 8C3 | 20% | 34.8 | - | Y | 66.0 | 7.2 | 13.0 | Y | 31.2 | B |
| 6B9 | 52% | 49.7 | - | Y | 101.5 | 11.2 | 12.1 | Y | 29.7 | B |
| 4A9 | 73% | 63.5 | - | Y | 146.2 | 31.4 | 7.4 | Y | 28.6 | B |

Fig. 5B

| Antibody ID | hu BCMA | Cyno BCMA | FACS Binding (MFI) | | | | | FACS Binding (MFI) | APRIL Blocking | | | CynoBCMA DN FACS Binding (MFI) |
|---|---|---|---|---|---|---|---|---|---|---|---|---|
| | | | Positive for Cyno Binding | hu BAFFR | hu TACI | BCMA (Mol. detect) | BAFFR/ TACI/ Mol. | | % Inhibition n=1 | % Inhibition n=2 | Avg. % Inhibition | |
| 30D5 | 160451 | 206088 | Y | -1733 | 2455 | -4468 | N | | 78% | 101% | 90% | 166.0 |
| 35D2 | 129445 | 198499 | Y | -119 | 508 | -6991 | N | | 57% | 82% | 70% | 151.6 |
| 38B3 | 146555 | 198505 | Y | -2849 | 371 | -749 | N | | 76% | 105% | 90% | 137.7 |
| 35A4 | 114426 | 101450 | Y | -495 | 592 | 689 | N | | 42% | 34% | 38% | 129.8 |
| 30E1 | 108585 | 78469 | Y | -935 | 555 | -2342 | N | | 31% | 46% | 38% | 129.7 |
| 32H3 | 97721 | 51189 | Y | -942 | 1356 | -4228 | N | | 20% | 47% | 33% | 121.6 |
| 38G2 | 161545 | 235326 | Y | -507 | 562 | 1083 | N | | 70% | 95% | 82% | 115.8 |
| 32H4 | 141081 | 213465 | Y | -324 | 687 | -4532 | N | | 50% | 62% | 56% | 111.1 |
| 35H7 | 89718 | 163681 | Y | -104 | 15 | -422 | N | | 41% | 58% | 49% | 110.6 |
| 29C12 | 82865 | 97267 | Y | -3102 | 256 | -5194 | N | | 30% | 62% | 46% | 109.8 |
| 33C7 | 132175 | 238807 | Y | -251 | 887 | 347 | N | | 68% | 88% | 78% | 109.1 |
| 31D5 | 142124 | 183962 | Y | 436 | 1151 | 1249 | N | | 54% | 81% | 68% | 108.7 |
| 32B5 | 137058 | 256791 | Y | -1093 | 274 | -5762 | N | | 87% | 116% | 101% | 108.5 |
| 32G12 | 162354 | 265751 | Y | -975 | 514 | -2904 | N | | 83% | 107% | 95% | 108.0 |
| 37B2 | 83676 | 135996 | Y | -351 | 1039 | -1083 | N | | 37% | 58% | 48% | 104.1 |
| 35A8 | 77459 | 89438 | Y | -363 | 522 | -1237 | N | | 35% | NA | 35% | 101.6 |
| 32B11 | 44741 | 68112 | Y | 407 | 1853 | -2817 | N | | 20% | 38% | 29% | 99.6 |
| 31D11 | 94187 | 137457 | Y | 278 | 220 | -1013 | N | | 44% | 53% | 49% | 96.3 |

Fig. 5C-1

| Antibody ID | FACS Binding (MFI) | | | | | | | APRIL Blocking | | | |
|---|---|---|---|---|---|---|---|---|---|---|---|
| | hu BCMA | Cyno BCMA | Positive for Cyno Binding | hu BAFFR | hu TACI | BCMA (Mol. detect) | BAFFR/ TACI Mol. | % Inhibition n=1 | % Inhibition n=2 | Avg. % Inhibition | CynoBCMA ON FACS Binding (MFI) |
| 30G7 | 103535 | 42884 | Y | -189 | 469 | -920 | N | 39% | 58% | 49% | 91.2 |
| 30E2 | 37196 | 37828 | Y | -77 | 409 | 322 | N | 19% | 26% | 22% | 90.8 |
| 30B1 | 32881 | 36359 | Y | -282 | 301 | -432 | N | 9% | 27% | 18% | 85.0 |
| 40D7 | 36313 | 39335 | Y | -444 | 1386 | -989 | N | 23% | 25% | 24% | 72.7 |
| 31A11 | 80147 | 26528 | Y | -1907 | 172 | -9413 | N | 28% | 33% | 31% | 71.5 |
| 32G10 | 25705 | 31341 | Y | -358 | 255 | -1126 | N | 13% | 36% | 24% | 61.7 |
| 43H8 | 30840 | 2556 | Y | 641 | 355 | -881 | N | 53% | 60% | 56% | 56.0 |
| 28G5 | 117875 | 119979 | Y | -11685 | 331 | -736 | N | 45% | 71% | 58% | 56.0 |
| 38D5 | 43575 | 59724 | Y | -2394 | 769 | -15667 | N | 26% | 40% | 33% | 55.7 |
| 33D4 | 89926 | 19377 | Y | 723 | 261 | -1080 | N | 19% | 30% | 24% | 55.6 |
| 37E1 | 2329 | 3323 | Y | -308 | 297 | -4698 | N | 11% | 22% | 17% | 31.4 |
| 33E7 | 139459 | 5242 | Y | -269 | 536 | -673 | N | 58% | 90% | 74% | 30.3 |
| 33C12 | 66304 | 2702 | Y | -943 | 296 | -543 | N | 26% | 23% | 24% | 19.84 |
| 29G8 | 48959 | 4249 | Y | -1228 | 1577 | -1753 | N | 25% | 51% | 38% | 16.36 |
| 39H2 | 153869 | 7699 | Y | -42 | -563 | 965 | N | 82% | 110% | 96% | 15.39 |
| 31C6 | 96865 | 3525 | Y | -827 | 325 | 80 | N | 35% | 63% | 49% | 11.51 |
| 32E5 | 79989 | 6279 | Y | -2861 | 1186 | -2252 | N | 26% | 54% | 40% | 10.68 |
| 30H2 | 144412 | 1743 | Y | -570 | 168 | 897 | N | 61% | 86% | 73% | 9.21 |
| 35F8 | 11738 | 1867 | Y | 484 | 2441 | -1416 | N | 19% | 31% | 25% | 7.64 |
| 38C6 | 62160 | 2579 | Y | -2415 | 997 | -556 | N | 59% | 65% | 62% | 7.3 |
| 35D4 | 63542 | 5405 | Y | -91 | 1057 | -4007 | N | 33% | 51% | 42% | 6.37 |
| 39D4 | 22286 | 4349 | Y | -50 | 521 | -2895 | N | 33% | 66% | 49% | 6.23 |
| 32G2 | 10256 | 2508 | Y | -779 | 3213 | -5196 | N | 18% | 33% | 26% | 5.93 |

Fig. 5C-2

| Antibody ID | hu BCMA | Cyno BCMA | Positive for Cyno Binding | hu BAFFR | hu TACI | BCMA (Mol. detect) | BAFFR/ TACI/ Mol. | % Inhibition n=1 | % Inhibition n=2 | Avg. % Inhibition | CynoBCMA O/N FACS Binding (MFI) |
|---|---|---|---|---|---|---|---|---|---|---|---|
| | | | | | | | | | | APRIL Blocking | |
| | FACS Binding (MFI) | | | | | | | | | | |
| 32E6 | 42268 | 1691 | Y | -95 | 1889 | -5121 | N | 28% | 35% | 32% | 5.23 |
| 31G6 | 154678 | 5854 | Y | -617 | 1011 | 1100 | N | 81% | 96% | 88% | 4.15 |
| 33E3 | 27393 | 5085 | Y | -185 | 213 | -913 | N | 18% | 22% | 20% | 3.85 |
| 29B8 | 44354 | 221350 | Y | 877 | 351 | -1430 | Y | 86% | 116% | 101% | 129.39 |
| 29H10 | 45527 | 27640 | Y | 23 | 3099 | 76790 | Y | 23% | 32% | 28% | 45.11 |
| 29D11 | 25215 | 12933 | Y | 6165 | 71 | 1392 | Y | 22% | 30% | 26% | 63.29 |
| 29D12 | 178813 | 153427 | Y | 1704 | 1680 | -2258 | Y | 52% | 84% | 68% | 174.22 |
| 30H1 | 58514 | 1958 | Y | 703 | -1046 | 7860 | Y | 26% | 51% | 39% | 11.25 |
| 30G2 | 104029 | 67738 | Y | 2514 | 538 | -2742 | Y | 29% | 46% | 37% | 107.87 |
| 30H3 | 20195 | 1729 | Y | -1173 | 318 | 34788 | Y | 29% | 37% | 33% | 47.09 |
| 30G5 | 29027 | 16087 | Y | 670 | 250 | 53331 | Y | 22% | 46% | 34% | 73.54 |
| 30D9 | 29633 | 1755 | Y | 1661 | 346 | -4298 | Y | 22% | 28% | 25% | 19.8 |
| 30C11 | 110056 | 15274 | Y | 2168 | 673 | 137874 | Y | 54% | 71% | 63% | 82.49 |
| 31F4 | 136023 | 265326 | Y | 405 | 1804 | 1586 | Y | 73% | 97% | 85% | 134.1 |
| 31C5 | 26190 | 30427 | Y | 2597 | 527 | -7931 | Y | 32% | 50% | 41% | 63.91 |
| 31F6 | 202340 | 186148 | Y | 3861 | -939 | -3147 | Y | 83% | 119% | 101% | 123.82 |
| 31E11 | 118670 | 12507 | Y | -1610 | 154 | 2106 | Y | 46% | 57% | 51% | 12.88 |
| 31H12 | 140883 | 151986 | Y | 1733 | 27 | -1527 | Y | 50% | 68% | 59% | 98.06 |
| 32A2 | 28897 | 12885 | Y | 2625 | 3856 | -1125 | Y | 25% | 38% | 31% | 5.02 |
| 32G5 | 103178 | 2220 | Y | 1370 | 292 | -11836 | Y | 20% | 14% | 17% | 3.08 |
| 32E11 | 46680 | 26201 | Y | 794 | 347 | 87883 | Y | 35% | 59% | 47% | 67.49 |
| 33B3 | 35322 | 29608 | Y | 1177 | 991 | -6849 | Y | 38% | 47% | 42% | 76.81 |
| 33D3 | 183320 | 13901 | Y | -329 | 385 | 1633 | Y | 66% | 85% | 76% | 6.08 |

| Antibody ID | FACS Binding (MFI) | | | | | | BAFFR/ TACI/ Mol | APRIL Blocking | | | CynoBCMA O/N FACS Binding (MFI) |
|---|---|---|---|---|---|---|---|---|---|---|---|
| | hu BCMA | Cyno BCMA | Positive for Cyno Binding | hu BAFFR | hu TACI | BCMA (Mol. detect) | | % Inhibition n=1 | % Inhibition n=2 | Avg. % Inhibition | |
| 33E6 | 12309 | 8142 | Y | -180 | 1760 | 27038 | Y | 22% | 23% | 22% | 40.75 |
| 33D9 | 78697 | 132778 | Y | 1244 | 521 | -1694 | Y | 35% | 50% | 43% | 76.74 |
| 34E2 | 189614 | 245860 | Y | 2584 | 585 | -1544 | Y | 79% | 102% | 90% | 93.41 |
| 34G5 | 115973 | 113760 | Y | -413 | 814 | 176225 | Y | 65% | 76% | 70% | 101.52 |
| 34C11 | 120846 | 139430 | Y | -311 | 338 | 6785 | Y | 46% | 57% | 52% | 110.11 |
| 34E11 | 81112 | 3874 | Y | 9 | -103 | 2942 | Y | 62% | 71% | 66% | 10.58 |
| 35B3 | 33122 | 18880 | Y | -380 | 489 | 52894 | Y | 24% | 39% | 32% | 40.28 |
| 36C4 | 115182 | 53740 | Y | -180 | 675 | 113439 | Y | 53% | 62% | 58% | 72.77 |
| 36E12 | 58750 | 82422 | Y | 31153 | 328 | 925 | Y | 44% | 59% | 51% | 142.83 |
| 37B3 | 93835 | 75554 | Y | -273 | 752 | 117310 | Y | 53% | 64% | 59% | 68.84 |
| 37C3 | 118160 | 65297 | Y | -249 | 428 | 153353 | Y | 61% | 80% | 70% | 114.89 |
| 37D3 | 108195 | 2283 | Y | -236 | 390 | 3085 | Y | 83% | 104% | 93% | 14.11 |
| 37H5 | 20382 | 11408 | Y | 192 | 26 | 33378 | Y | 30% | 45% | 37% | 61.3 |
| 37F7 | 142820 | 233237 | Y | 1042 | 1392 | 1452 | Y | 69% | 99% | 84% | 113.09 |
| 38A2 | 80016 | 68239 | Y | -230 | -1680 | 113711 | Y | 63% | 76% | 70% | 120.85 |
| 38G10 | 94432 | 91159 | Y | 50882 | 372 | -2987 | Y | 45% | 48% | 46% | 91.66 |
| 38A12 | 86795 | 2384 | Y | 3035 | 1045 | 1784 | Y | 49% | 53% | 51% | 8.77 |
| 39E1 | 48465 | 26900 | Y | 32 | 2132 | 67970 | Y | 31% | 48% | 39% | 53.17 |
| 35F8 | 22218 | 4466 | Y | -115 | 103 | 2868 | Y | 19% | 25% | 22% | 18.75 |
| 38C6 | 102974 | 37705 | Y | 20079 | 1543 | -1015 | Y | 54% | 47% | 51% | 34.22 |
| 35D4 | 24920 | 9255 | Y | -71 | 1858 | 17137 | Y | 29% | 33% | 31% | 25.88 |
| 39D4 | 55284 | 6167 | Y | -4599 | 9530 | 397 | Y | 59% | 84% | 71% | 300.6 |
| 32G2 | 31677 | 5170 | Y | -1275 | 7837 | -856 | Y | 28% | 46% | 37% | 205 |

Human Anti-human BCMA-2A1CV5-MCC-DM1 Mediated Receptor Internalization in H929 Cells

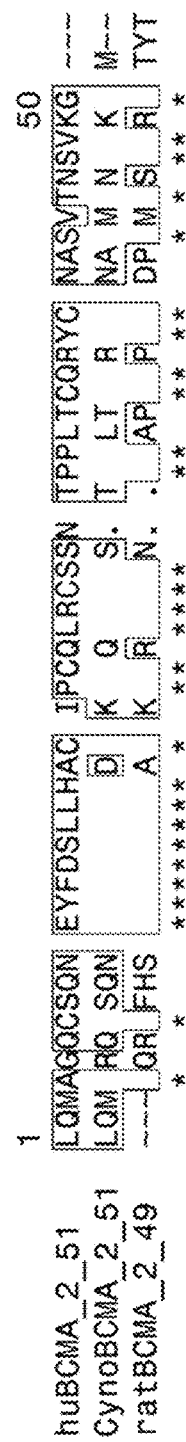
Fig. 43E
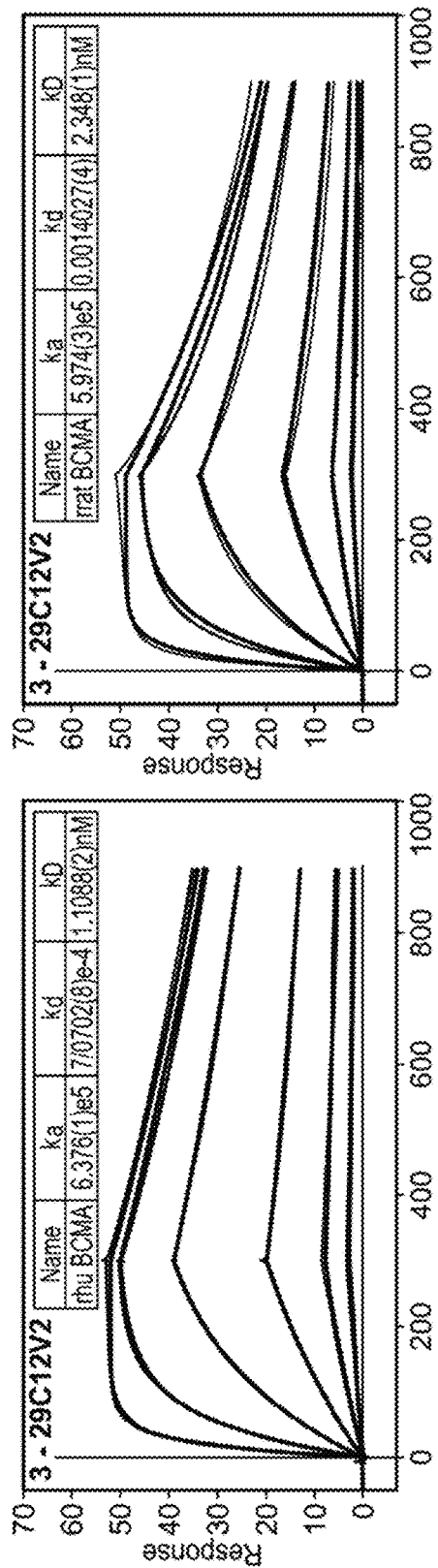
Fig. 43F
Fig. 44 rhuBCMA (6xHis::Sumo::huBCMA(aa 2-51)::GGS::G3::Avi) fusion protein:

MGSSHHHHHHGSGLVPRGSAS MSDSEVNQEAKPEVKP ETHINLKVSDGSSEIFFKIK KTTPLRRLMEAFAKRQGKEM
DSLRFLYDGIRIQADQTPED LDMEDNDIIEAHREQIGG AGQCSQNEYFDSLLHACIPCQL EAQKIEWHE (SEQ ID NO:350)
RCSSNTPPLTCQRYCNASVT NSVKGTNAGGGSGGGLNDIF

GSSHHHHHHGSGLVPRGSAS MSDSEVNQEAKPEVKP ETHINLKVSDGSSEIFFKIK KTTPLRRLMEAFAKRQGKEM
DSLRFLYDGIRIQADQTPED LDMEDNDIIEAHREQIGG AGQCSQNEYFDSLLHACIPCQL
RCSSNTPPLTCQRYC (SEQ ID NO:354)

GSSHHHHHHGSGLVPRGSAS MSDSEVNQEAKPEVKP ETHINLKVSDGSSEIFFKIK KTTPLRRLMEAFAKRQGKEM
DSLRFLYDGIRIQADQTPED LDMEDNDIIEAHREQIGG AGQCSQNEYFDSLLHACIPCQL R (SEQ ID NO:355)

GSSHHHHHHGSGLVPRGSAS MSDSEVNQEAKPEVKP ETHINLKVSDGSSEIFFKIK KTTPLRRLMEAFAKRQGKEM
DSLRFLYDGIRIQADQTPED LDMEDNDIIEAHREQIGG AGQCSQNEYFDSLLHA (SEQ ID NO:356)

Fig. 45

BCMA ANTIGEN BINDING PROTEINS

CROSS REFERENCE TO RELATED APPLICATIONS

This application is a divisional of Ser. No. 14/098,275 filed Dec. 5, 2013, which claims the benefit under 35 U.S.C. § 119 of U.S. Provisional Application Ser. No. 61/734,767, filed Dec. 7, 2012, U.S. Provisional Application Ser. No. 61/759,702, filed Feb. 1, 2013 and U.S. Provisional Application Ser. No. 61/775,125, filed Mar. 8, 2013 which are hereby incorporated by reference.

REFERENCE TO SEQUENCE LISTING

The present application is being filed along with a Sequence Listing in text format. The Sequence Listing is provided as a file entitled A-1782-US-NP_seq_listing.txt, created Nov. 20, 2013, which is 331 KB in size. The information in the electronic format of the Sequence Listing is incorporated herein by reference in its entirety.

FIELD OF THE INVENTION

The present invention relates to B-Cell Maturation Antigen (BCMA) antigen binding proteins, particularly antibodies, polynucleotide sequences encoding said antigen binding proteins, and compositions and methods for treating diseases. Aspects of the invention also include antibody drug conjugates and uses thereof.

BACKGROUND

B-cell maturation antigen (BCMA), B-cell activating factor receptor (BAFF-R), and transmembrane activator and calcium modulator and cyclophilin ligand interactor (TACI) promote B-cell survival at distinct stages of development by engaging a proliferation-inducing ligand (APRIL) and/or BAFF (B-cell activating factor). Dysregulated signaling can promote B-cell survival and proliferation, causing autoimmunity and neoplasia. For a review, see Rickert, et al., *Immunological Reviews* 2011, Vol. 244: 115-133.

BAFF and APRIL exhibit structural similarity and overlapping yet distinct receptor binding specificity. BAFF and APRIL bind BCMA, but the APRIL:BCMA interaction is of higher affinity, whereas BAFF-R only binds BAFF with high affinity. The negative regulator TACI binds to both BAFF and APRIL with similar affinity. BCMA expression in the B cell lineage is restricted to germinal center B cells, memory B cells (in humans), and plasma cells. BCMA is a receptor for BAFF and APRIL engagement on bone marrow plasma cells, although TACI is also expressed on these cells. The survival of long-lived plasma cells does not require BAFF but is dependent upon APRIL.

BCMA expression is highly restricted to plasma cells. Multiple myeloma is caused by a clonal expansion of malignant plasma cells. By 2020, the total number of incident cases of multiple myeloma (MM) in the major markets will increase from 46,400 to 55,300. Newly diagnosed cases of myeloma are similarly distributed between three disease stages with stage 1, 2 and 3 accounting for about 33% of the diagnosed cases each. In the US, approximately 20,500 people are diagnosed with multiple myeloma each year and almost 11,000 MM patients die each year. Despite advances in therapy, multiple myeloma remains an incurable disease, see Jemal A, et al. *CA Cancer J Clin.* 2008; 58:71-96; Kyle R A, et al. *Mayo Clin Proc.* 2003; 778:21-33; Bergsagel D E, et al. *Blood.* 1999, 94:1174-1182.

BRIEF DESCRIPTION OF THE DRAWINGS

FIG. 1 shows the amino acid sequence of human BCMA (SEQ ID NO:285) and cynomolgus (*Macaca fascicularis*) BCMA (SEQ ID NO:286).

FIGS. 5A-F are data tables for the monoclonal antibody generation, screening, and characterization for the two campaigns.

FIGS. 43A-F depicts biosensor data showing Ab-1 specifically bound human BCMA with an equilibrium dissociation rate constant ($K_d$) of approximately 155 pM, and only marginally interacted (i.e., did not specifically bind) with rat BCMA with an equilibrium dissociation rate constant ($K_d$) >10 nM. Ab-2 and Ab-3 bound human BCMA with equilibrium dissociation rate constants ($K_d$) of approximately 1.11 nM and 750 pM, respectively. Ab-2 and Ab-3 specifically bound rat BCMA with equilibrium dissociation rate constants ($K_d$) of approximately 2.35 nM and 2.07 nM, respectively.

FIG. 44 shows a sequence alignment of amino acids 2-51 of the extracellular domain of human BCMA: SEQ ID NO:352, amino acids 2-51 of the extracellular domain of cynomolgus BCMA: SEQ ID NO:353; and amino acids 2-49 of the extracellular domain of rat BCMA: SEQ ID NO:351.

FIG. 45 provides the sequences for the three progressively smaller fragments of the amino terminus of the extracellular domain of human BCMA (SEQ ID NO:354, SEQ ID NO:355, and SEQ ID NO:356) from the rhuBCMA fusion protein (6×His::Sumo::huBCMA(aa 5-51)::GGS::G3::Avi) of SEQ ID NO:350.

FIG. 47A shows the retention time for SEQ ID NO:350. FIG. 47B shows the retention time for Ab-1. FIG. 47C shows that an excess amount of Ab-1 (60 ug) relative to 3 ug of BCMA (SEQ ID NO:350) resulted in no free BCMA including the clipped fragments (i.e., SEQ ID NOS:354-356), and the two peaks represent Ab-1 bound to the various BCMA fragments (retention time of 2.748) and unbound excess Ab-1 (retention time 3.078). FIG. 47D shows that the Ab-1 antibody (30 ug) in an excess amount of BCMA (60 ug of SEQ ID NO:350) bound the BCMA, but there was also a small amount of the fragments of BCMA (SEQ ID NOS:354-356).

DETAILED DESCRIPTION OF THE INVENTION

The section headings used herein are for organizational purposes only and are not to be construed as limiting the subject matter described. The Examples and Claims are part of the detailed description of the invention. Additional claims beyond what are presently presented may be drafted from this description.

Standard techniques may be used for recombinant DNA, oligonucleotide synthesis, tissue culture and transformation, protein purification etc. Enzymatic reactions and purification techniques may be performed according to the manufacturer's specifications or as commonly accomplished in the art or as described herein. The following procedures and techniques may be generally performed according to conventional methods well known in the art and as described in various general and more specific references that are cited and discussed throughout the specification. See, e.g., Sambrook et al., 2001, *Molecular Cloning: A Laboratory Manual*, 3rd ed., Cold Spring Harbor Laboratory Press, Cold Spring Harbor, N.Y., which is incorporated herein by reference for any purpose. Unless specific definitions are provided, the nomenclature used in connection with, and the laboratory procedures and techniques of, analytical chemistry, organic chemistry, and medicinal and pharmaceutical chemistry described herein are those well known and commonly used in the art. Standard techniques may be used for chemical synthesis, chemical analyses, pharmaceutical preparation, formulation, and delivery and treatment of patients.

Aspects of the invention provide antigen binding proteins that specifically bind BCMA and inhibit BCMA activation mediated by BCMA ligands, such as, but not limited to, BAFF and APRIL, as described more fully herein. Aspects of the invention include antibody drug conjugates (ADCs) that specifically bind human BCMA. Upon binding to BCMA expressed on the cell surface, the BCMA antibodies facilitate internalization of the BCMA/ADC complex into the endosomal compartment and ultimate delivery of the ADC to the lysosome. The internalized ADCs specifically kill the cell via the drug conjugated to the antibody. Aspects of the invention include the use of the ADCs in the treatment of B-cell related cancers, including multiple myeloma, as more fully described herein.

BCMA

Figure 40:
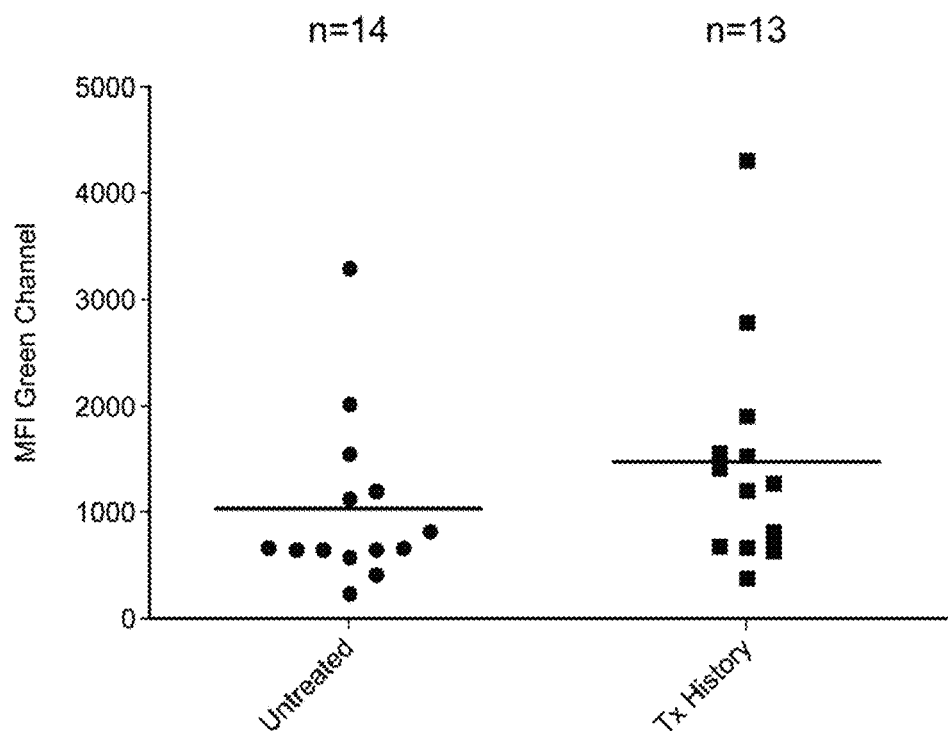
FIG. 40 shows that BCMA expression does not appear to be altered based on treatment history in multiple myeloma patient BMMC samples.

"BCMA" as used herein is meant the cell surface receptor (or receptor complexes comprising BCMA) that binds BAFF and/or APRIL. The amino acid sequence of human BCMA (huBCMA) is provided in NCBI Acession Q02223 (GI:313104029) and is shown in FIG. 1 (SEQ ID NO:285). BCMA proteins may also include variants. BCMA proteins may also include fragments, such as the extracellular domain that don't have all or part of the transmembrane and/or the intracellular domain, as well as fragments of the extracellular domain. Examples of the extracellular domain include amino acids 1-50 to 54 or 8-48 of SEQ ID N0:285. Soluble forms of huBCMA include the extracellular domain or a fragment of the extracellular domain that retains the capacity to bind BAFF and/or APRIL. The term "BCMA" also includes post-translational modifications of the BCMA amino acid sequence. Post-translational modifications include, but are not limited to, N- and O-linked glycosylation. Aspects of the invention relate antibodies that cross-react to cynomolgus BCMA BCMA Antigen Binding Proteins The present invention provides antigen binding proteins that specifically bind BCMA. Embodiments include monoclonal antibodies that bind huBCMA. Embodiments include polypeptides comprising part or all of the polypeptide sequences of one or more of the monoclonal antibodies described herein. Normal tissue expression of BCMA is highly restricted to the B-cell lineage where it is predominately expressed in the secondary follicle/germinal center of tonsils/lymph nodes, on plasmablasts and on differentiated plasma cells. BCMA is expressed at relatively higher levels in malignant plasma cells than the levels observed on normal plasma cells, particularly in multiple myeloma, smoldering myeloma, and monoclonal gammopathy of unknown significance (MGUS) plasma cells. BCMA is an especially desirable target for treating B-cell related malignanacies that express BCMA because its expression is highly restricted to normal and malignant plasma cells, and therefore should have minimal non-target tissue toxicity. In addition, BCMA expression remains persistent on multiple myeloma patient samples in the face of ongoing or previous treatment regimens, as shown in FIG. 40.

Rare, highly specific human anti-huBCMA Xenomouse® antibodies were generated that bound to native huBCMA, did not cross-react to huBAFF-R or huTACI, and internalized rapidly into BCMA-expressing myeloma cell lines and primary isolates from multiple myeloma patients.

Embodiments include antibodies that bind huBCMA and also cross-react to cynomolgus BCMA (SEQ ID NO:286 in FIG. 1). This is a unique and advantageous feature of the antibodies provided herein. Anti-huBCMA antibodies, and ADCs made therefrom, that bind to cynomolgus BCMA (see for example Example 2) may be used in cynomolgus animal models to test for toxicity, pharmacokinetics, and other pharmacological characteristics.

A further unique and advantageous feature of the antibodies described herein is the specificity to huBCMA with regard to other related receptors. Embodiments of the antibodies described herein were specifically selected for high affinity binding to huBCMA and screened for no specific binding to huTACI and huBAFF-R (see for example Example 2). The specificity for huBCMA and the lack of cross-reactivity to huTACI and huBAFF-R provides the antibodies described herein a distinct advantage for targeting plasma B-cells and in the treatment of multiple myeloma and other B-cell related cancers.

A further unique and advantageous feature of embodiments described herein is that the antibodies inhibit the activation of huBCMA by inhibiting the biological activity of its ligand APRIL. Embodiments provided herein were selectively screened for this important biological attribute (see for example Example 2).

A further unique and advantageous feature of embodiments provided herein is that the antibodies were selected for an exceptionally high degree of ADCC activity (see for example Examples 4 and 8).

A further unique and advantageous feature of embodiments provided herein is that the antibodies are not agonistic to huBCMA and therefore will not activate huBCMA upon binding.

A further unique and advantageous feature of embodiments provided herein is the capacity to be internalized upon binding to huBCMA expressed on the surface of cells. This is not trivial and certainly not predictable due to the extracellular domain of huBCMA being very small (approximately 50 amino acids). Especially important is the ability to bind to and be internalized via huBCMA-mediated endocytosis in multiple myeloma primary isolates, as well as multiple myeloma samples that have been processed and frozen, as well as in multiple myeloma cell lines (see for example Examples 3, 5, 7, 8, 10, 11, 13, and 14).

A further unique and advantageous feature of select embodiments provided herein is the empirically engineered enhanced stability and manufacturability of the antibodies through site-directed mutagenesis (see for example Example 8).

A further unique and advantageous feature of embodiments provided herein is the capacity to be successfully conjugated to a linker and drug (aka, toxin) and yet retain the ability to bind huBCMA with high affinity, be internalized, and successfully kill the cell (see for example Examples 6, 7, and 9-11). It is unpredictable and highly desirable that the conjugated version of the Ab-1 antibody (i.e., Ab-1 ADC, also referred to herein as 2A1CV5-MCC-DM1 or 2A1CV5 ADC) binds with such high affinity.

A further unique and advantageous feature of embodiments provided herein is that upon binding huBCMA on the surface of myeloma cells, for example the Ab-1 ADC, is internalized similarly to the unconjugated antibody and has an $IC_{50}$ of approximately 78 pM (antibody concentration) in an H929 tumor cell growth inhibition assay (see for example Example 11).

A further unique and advantageous feature of embodiments provided herein is that multiple myeloma cell lines, with an average BCMA expression density of as low as 3,000 sites per cell, can be killed by the Ab-1 ADC and other anti-huBCMA ADCs (see for example Example 10).

A further unique and advantageous feature of embodiments provided herein is that the Ab-1 ADC is effectively internalized in primary isolates of multiple myeloma patient samples (see for example Examples 13 and 14).

A further unique and advantageous feature of embodiments provided herein is that in three in vivo myeloma tumor xenograft models, anti-huBCMA ADC mediated anti-tumor activity in all three models and tumor regression in 2 out of 3 models. Complete tumor regression with no detectable tumor burden was observed in the bone after administration of a single intravenous dose of Ab-1 ADC in an established bone-tropic multiple myeloma mouse model (see for example Examples 9 and 12).

Thus, the antibodies provided herein have been selectively screened, empirically engineered, and chemically altered to maximize many unique, unpredictable, and surprising attributes that distinguish them over other antibodies.

Embodiments of antigen binding proteins comprise peptides and/or polypeptides (that optionally include post-translational modifications) that specifically bind huBCMA. Embodiments of antigen binding proteins comprise antibodies and fragments thereof, as variously defined herein, that specifically bind huBCMA. Aspects of the invention include antibodies that specifically bind to huBCMA and inhibit BAFF and/or APRIL from binding and/or activating huBCMA, or a multimeric or heteromeric receptor complex comprising huBCMA.

The antigen binding proteins of the invention specifically bind to human BCMA. "Specifically binds" as used herein means that the antigen binding protein preferentially binds human BCMA over other proteins. In some embodiments "specifically binds" means that the BCMA antigen binding proteins have a higher affinity for BCMA than for other proteins. For example, the equilibrium dissociation constant is $<10^{-7}$ to $10^{-11}$ M, or $<10^{-8}$ to $<10^{-10}$ M, or $<10^{-9}$ to $<10^{-10}$ M. Examples of assays for determining whether an antigen binding protein specifically binds to huBCMA may be found in Example 2 and 16.

It is understood that when reference is made to the various embodiments of the BCMA antibodies described herein, that it also encompasses BCMA-binding fragments thereof. A BCMA-binding fragment comprises any of the antibody fragments or domains described herein that retains the ability to specifically bind to human BCMA. Said BCMA-binding fragments may be in any of the scaffolds described herein. Said BCMA-binding fragments also have the capacity to inhibit activation of the BCMA, as described throughout the specification.

Aspects of the invention include antibodies that bind to the same or similar epitope on huBCMA as the Ab-1, Ab-2, and/or the Ab-3 antibodies. An antibody epitope is generally defined as the three-dimensional structure within an antigen that can be bound to the variable region of an antibody. (Greenbaum, et al., *J Molec Recognition*, 2007, 20:75-82). The "same or similar epitope" is defined as that identified by x-ray crystallography. Aspects of the invention include isolated monoclonal antibodies that competitively inhibit the binding of Ab-1, Ab-2, and/or the Ab-3 antibodies to huBCMA. Aspects of the invention include isolated human monoclonal antibodies that competitively inhibit the binding of Ab-1, Ab-2, and/or the Ab-3 antibodies to huBCMA. Aspects of the invention include isolated human monoclonal IgG antibodies that competitively inhibit the binding to of Ab-1, Ab-2, and/or the Ab-3 antibodies huBCMA. Aspects of the invention include isolated monoclonal antibodies that competitively inhibit the binding of Ab-1, as variously defined herein, to huBCMA. Aspects of the invention include isolated human monoclonal antibodies that competitively inhibit the binding of Ab-1, as variously defined herein, to huBCMA. Aspects of the invention include isolated human monoclonal IgG antibodies that competitively inhibit the binding of Ab-1, as variously defined herein, to huBCMA. An antibody competitively inhibits binding of Ab-1 if it reduces Ab-1 binding to huBCMA by 90% when the competing antibody (i.e., not Ab-1) is at equimolar or two-fold molar excess relative to Ab-1 in a cell-based or recombinant protein-based ELISA assay.

Example 16 provides evidence that Ab-1 specifically binds human BCMA of SEQ ID NO:285 and cynomolgus BCMA of SEQ ID NO:286, but does not specifically bind rat BCMA of SEQ ID NO:351. In the context of this differential binding and in describing the embodiments below, the phrase "does not specifically bind" means that the antibody binds the target protein with an equilibrium dissociation rate constant ($K_a$) >10 nM in an assay as described in Example 16, or in a comparable assay known in the art. FIG. 44 shows a sequence alignment of amino acids 2-51 of the extracellular domain of human BCMA: SEQ ID NO:352, amino acids 2-51 of the extracellular domain of cynomolgus BCMA: SEQ ID NO:353; and amino acids 2-49 of the extracellular domain of rat BCMA: SEQ ID NO:351.

The differential binding of Ab-1 in light of the limited sequence diversity between species suggests that Ab-1 binds a neutralizing determinant on human BCMA comprising amino acids 1-20 of SEQ ID NO:285, and more specifically comprising amino acids 1-11 of SEQ ID NO:285. Experimental evidence provided herein demonstrates that Ab-1 specifically binds the extracellular domain of human BCMA of SEQ ID NO:352, but does not specifically bind the extracellular domain of rat BCMA of SEQ ID NO:351. Therefore, aspects of the invention include isolated monoclonal antibodies that specifically binds to SEQ ID NO:285 and SEQ ID NO:286, but does not specifically bind SEQ ID NO:351. Aspects of the invention include isolated monoclonal antibodies that specifically bind SEQ ID NO:352, but does not specifically bind SEQ ID NO:351. Aspects of the invention include isolated human monoclonal antibodies that specifically binds to SEQ ID NO:285 and SEQ ID NO:286, but does not specifically bind SEQ ID NO:351. Aspects of the invention include isolated human monoclonal antibodies that specifically bind SEQ ID NO:352, but does not specifically bind SEQ ID NO:351. Aspects of the invention include isolated human monoclonal IgG antibodies that specifically binds to SEQ ID NO:285 and SEQ ID NO:286, but does not specifically bind SEQ ID NO:351. Aspects of the invention include isolated human monoclonal IgG antibodies that specifically bind SEQ ID NO:352, but does not specifically bind SEQ ID NO:351. Aspects of the invention include isolated human monoclonal IgG1 antibodies that specifically binds to SEQ ID NO:285 and SEQ ID NO:286, but does not specifically bind SEQ ID NO:351. Aspects of the invention include isolated human monoclonal IgG1 antibodies that specifically bind SEQ ID NO:352, but does not specifically bind SEQ ID NO:351.

Aspects of the invention include isolated monoclonal antibodies that specifically bind SEQ ID NO:352 with a Kd of between 1 nM and 0.01 nM, and binds SEQ ID NO:351 with a Kd of greater than 10 nM. Aspects of the invention include isolated human monoclonal antibodies that specifically bind SEQ ID NO:352 with a Kd of between 1 nM and 0.01 nM, and binds SEQ ID NO:351 with a Kd of greater than 10 nM. Aspects of the invention include isolated human monoclonal IgG antibodies that specifically bind SEQ ID NO:352 with a Kd of between 1 nM and 0.01 nM, and binds SEQ ID NO:351 with a Kd of greater than 10 nM. Aspects of the invention include isolated human monoclonal IgG1 antibodies that specifically bind SEQ ID NO:352 with a Kd of between 1 nM and 0.01 nM, and binds SEQ ID NO:351 with a Kd of greater than 10 nM. The Kd values may be determined using the assay described in Example 16, or a comparable assay.

Aspects of the invention include isolated monoclonal antibodies that specifically bind SEQ ID NO:352 with a Kd of about 0.16 nM, and binds SEQ ID NO:351 with a Kd of greater than 10 nM. "About 0.16 nM" means 0.16 nM±0.1 nM. Aspects of the invention include isolated human monoclonal antibodies that specifically bind SEQ ID NO:352 with a Kd of about 0.16 nM, and binds SEQ ID NO:351 with a Kd of greater than 10 nM. Aspects of the invention include isolated human monoclonal IgG antibodies that specifically bind SEQ ID NO:352 with a Kd of about 0.16 nM, and binds SEQ ID NO:351 with a Kd of greater than 10 nM. Aspects of the invention include isolated human monoclonal IgG1 antibodies that specifically bind SEQ ID NO:352 with a Kd of about 0.16 nM, and binds SEQ ID NO:351 with a Kd of greater than 10 nM. The Kd values may be determined using the assay described in Example 16, or a comparable assay.

Example 16 also provides evidence that Ab-1 bound progressively smaller fragments of the amino terminus of the extracellular domain of human BCMA (i.e., SEQ ID NOS:350, 354, 357, 355, and 356, as shown in FIGS. 45-47A-D and FIG. 50A). SEQ ID NO:356 is common to all the BCMA fragments, and therefore shows Ab-1 binds to the amino-terminus of human BCMA. This evidence, together with the differential binding of Ab-1 to different orthologues of BCMA, shows that Ab-1 binds a neutralizing determinant on human BCMA comprising amino acids 1-20 of SEQ ID NO:285, or more specifically a neutralizing determinant comprising 1-11 of SEQ ID NO:285. Embodiments of the invention include isolated monoclonal antibodies that bind a neutralizing determinant comprising amino acids 1 though 20 (inclusive) of SEQ ID NO: 285. Preferred embodiments of the invention include isolated monoclonal antibodies that bind a neutralizing determinant comprising amino acids 1 through 11 (inclusive) of SEQ ID NO: 285. Embodiments of the invention include isolated human monoclonal antibodies that bind a neutralizing determinant comprising amino acids 1 though 20 (inclusive) of SEQ ID NO: 285. Preferred embodiments of the invention include isolated human monoclonal antibodies that bind a neutralizing determinant comprising amino acids 1 through 11 (inclusive) of SEQ ID NO: 285. Embodiments of the invention include isolated human monoclonal IgG antibodies that bind a neutralizing determinant comprising amino acids 1 though 20 (inclusive) of SEQ ID NO: 285. Preferred embodiments of the invention include isolated human monoclonal IgG antibodies that bind a neutralizing determinant comprising amino acids 1 through 11 (inclusive) of SEQ ID NO: 285. Embodiments of the invention include isolated human monoclonal IgG1 antibodies that bind a neutralizing determinant comprising amino acids 1 though 20 (inclusive) of SEQ ID NO: 285. Preferred embodiments of the invention include isolated human monoclonal IgG1 antibodies that bind a neutralizing determinant comprising amino acids 1 through 11 (inclusive) of SEQ ID NO: 285. The aforementioned embodiments need not bind every amino acid in the 1 to 20 amino acid domain or the 1 to 11 amino acid domain.

Embodiments of the invention include isolated monoclonal antibodies that bind a neutralizing determinant comprising amino acids 1 though 20 (inclusive) of SEQ ID NO: 285, wherein said antibody binds SEQ ID NO: 285 with a Kd of less than or equal to 1 nM. Preferred embodiments of the invention include isolated monoclonal antibodies that bind a neutralizing determinant comprising amino acids 1 through 11 (inclusive) of SEQ ID NO: 285, wherein said antibody binds SEQ ID NO: 285 with a Kd of less than or equal to 1 nM. Embodiments of the invention include isolated human monoclonal antibodies that bind a neutralizing determinant comprising amino acids 1 though 20 (inclusive) of SEQ ID NO: 285, wherein said antibody binds SEQ ID NO: 285 with a Kd of less than or equal to 1 nM. Preferred embodiments of the invention include isolated human monoclonal antibodies that bind a neutralizing determinant comprising amino acids 1 through 11 (inclusive) of SEQ ID NO: 285, wherein said antibody binds SEQ ID NO: 285 with a Kd of less than or equal to 1 nM. Embodiments of the invention include isolated human monoclonal IgG antibodies that bind a neutralizing determinant comprising amino acids 1 though 20 (inclusive) of SEQ ID NO: 285, wherein said antibody binds SEQ ID NO: 285 with a Kd of less than or equal to 1 nM. Preferred embodiments of the invention include isolated human monoclonal IgG antibodies that bind a neutralizing determinant comprising amino acids 1 through 11 (inclusive) of SEQ ID NO: 285, wherein said antibody binds SEQ ID NO: 285 with a Kd of less than or equal to 1 nM. Embodiments of the invention include isolated human monoclonal IgG1 antibodies that bind a neutralizing determinant comprising amino acids 1 though 20 (inclusive) of SEQ ID NO: 285, wherein said antibody binds SEQ ID NO: 285 with a Kd of less than or equal to 1 nM. Preferred embodiments of the invention include isolated human monoclonal IgG1 antibodies that bind a neutralizing determinant comprising amino acids 1 through 11 (inclusive) of SEQ ID NO: 285, wherein said antibody binds SEQ ID NO: 285 with a Kd of less than or equal to 1 nM.

Embodiments of the invention include isolated monoclonal antibodies that bind a neutralizing determinant comprising amino acids 1 though 20 (inclusive) of SEQ ID NO: 285, wherein said antibody binds SEQ ID NO: 352 with a Kd of about 0.16 nM as measured in a biosensor assay described in Example 16. Preferred embodiments of the invention include isolated monoclonal antibodies that bind a neutralizing determinant comprising amino acids 1 through 11 (inclusive) of SEQ ID NO: 285, wherein said antibody binds SEQ ID NO: 352 with a Kd of about 0.16 nM as measured in a biosensor assay described in Example 16. Embodiments of the invention include isolated human monoclonal antibodies that bind a neutralizing determinant comprising amino acids 1 though 20 (inclusive) of SEQ ID NO: 285, wherein said antibody binds SEQ ID NO: 352 with a Kd of about 0.16 nM as measured in a biosensor assay described in Example 16. Preferred embodiments of the invention include isolated human monoclonal antibodies that bind a neutralizing determinant comprising amino acids 1 through 11 (inclusive) of SEQ ID NO: 285, wherein said antibody binds SEQ ID NO: 352 with a Kd of about 0.16 nM as measured in a biosensor assay described in Example 16. Embodiments of the invention include isolated human monoclonal IgG antibodies that bind a neutralizing determinant comprising amino acids 1 though 20 (inclusive) of SEQ ID NO: 285, wherein said antibody binds SEQ ID NO: 352 with a Kd of about 0.16 nM as measured in a biosensor assay described in Example 16. Preferred embodiments of the invention include isolated human monoclonal IgG antibodies that bind a neutralizing determinant comprising amino acids 1 through 11 (inclusive) of SEQ ID NO: 285, wherein said antibody binds SEQ ID NO: 352 with a Kd of about 0.16 nM as measured in a biosensor assay described in Example 16. Embodiments of the invention include isolated human monoclonal IgG1 antibodies that bind a neutralizing determinant comprising amino acids 1 though 20 (inclusive) of SEQ ID NO: 285, wherein said antibody binds SEQ ID NO: 352 with a Kd of about 0.16 nM as measured in a biosensor assay described in Example 16. Preferred embodiments of the invention include isolated human monoclonal IgG1 antibodies that bind a neutralizing determinant comprising amino acids 1 through 11 (inclusive) of SEQ ID NO: 285, wherein said antibody binds SEQ ID NO: 352 with a Kd of about 0.16 nM as measured in a biosensor assay described in Example 16.

Embodiments of the invention include isolated monoclonal antibodies that bind a neutralizing determinant comprising amino acids 1 though 20 (inclusive) of SEQ ID NO: 285, wherein said antibody binds SEQ ID NO: 285 expressed on the surface of H929 cells with an EC50 of less than or equal to 10 nM. Preferred embodiments of the invention include isolated monoclonal antibodies that bind a neutralizing determinant comprising amino acids 1 through 11 (inclusive) of SEQ ID NO: 285, wherein said antibody binds SEQ ID NO: 285 expressed on the surface of H929 cells with an EC50 of less than or equal to 10 nM. Embodiments of the invention include isolated human monoclonal antibodies that bind a neutralizing determinant comprising amino acids 1 though 20 (inclusive) of SEQ ID NO: 285, wherein said antibody binds SEQ ID NO: 285 expressed on the surface of H929 cells with an EC50 of less than or equal to 10 nM. Preferred embodiments of the invention include isolated human monoclonal antibodies that bind a neutralizing determinant comprising amino acids 1 through 11 (inclusive) of SEQ ID NO: 285, wherein said antibody binds SEQ ID NO: 285 expressed on the surface of H929 cells with an EC50 of less than or equal to 10 nM. Embodiments of the invention include isolated human monoclonal IgG antibodies that bind a neutralizing determinant comprising amino acids 1 though 20 (inclusive) of SEQ ID NO: 285, wherein said antibody binds SEQ ID NO: 285 expressed on the surface of H929 cells with an EC50 of less than or equal to 10 nM. Preferred embodiments of the invention include isolated human monoclonal IgG antibodies that bind a neutralizing determinant comprising amino acids 1 through 11 (inclusive) of SEQ ID NO: 285, wherein said antibody binds SEQ ID NO: 285 expressed on the surface of H929 cells with an EC50 of less than or equal to 10 nM. Embodiments of the invention include isolated human monoclonal IgG1 antibodies that bind a neutralizing determinant comprising amino acids 1 though 20 (inclusive) of SEQ ID NO: 285, wherein said antibody binds SEQ ID NO: 285 expressed on the surface of H929 cells with an EC50 of less than or equal to 10 nM. Preferred embodiments of the invention include isolated human monoclonal IgG1 antibodies that bind a neutralizing determinant comprising amino acids 1 through 11 (inclusive) of SEQ ID NO: 285, wherein said antibody binds SEQ ID NO: 285 expressed on the surface of H929 cells with an EC50 of less than or equal to 10 nM.

Embodiments of the invention include isolated monoclonal antibodies that bind a neutralizing determinant comprising amino acids 1 though 20 (inclusive) of SEQ ID NO: 285, wherein said antibody binds SEQ ID NO: 285 expressed on the surface of H929 cells with an EC50 of about 1.2 nM in a FACS assay as described in Example 11. Preferred embodiments of the invention include isolated monoclonal antibodies that bind a neutralizing determinant comprising amino acids 1 through 11 (inclusive) of SEQ ID NO: 285, wherein said antibody binds SEQ ID NO: 285 expressed on the surface of H929 cells with an EC50 of about 1.2 nM in a FACS assay as described in Example 11. Embodiments of the invention include isolated human monoclonal antibodies that bind a neutralizing determinant comprising amino acids 1 though 20 (inclusive) of SEQ ID NO: 285, wherein said antibody binds SEQ ID NO: 285 expressed on the surface of H929 cells with an EC50 of about 1.2 nM in a FACS assay as described in Example 11. Preferred embodiments of the invention include isolated human monoclonal antibodies that bind a neutralizing determinant comprising amino acids 1 through 11 (inclusive) of SEQ ID NO: 285, wherein said antibody binds SEQ ID NO: 285 expressed on the surface of H929 cells with an EC50 of about 1.2 nM in a FACS assay as described in Example 11. Embodiments of the invention include isolated human monoclonal IgG antibodies that bind a neutralizing determinant comprising amino acids 1 though 20 (inclusive) of SEQ ID NO: 285, wherein said antibody binds SEQ ID NO: 285 expressed on the surface of H929 cells with an EC50 of about 1.2 nM in a FACS assay as described in Example 11. Preferred embodiments of the invention include isolated human monoclonal IgG antibodies that bind a neutralizing determinant comprising amino acids 1 through 11 (inclusive) of SEQ ID NO: 285, wherein said antibody binds SEQ ID NO: 285 expressed on the surface of H929 cells with an EC50 of about 1.2 nM in a FACS assay as described in Example 11. Embodiments of the invention include isolated human monoclonal IgG1 antibodies that bind a neutralizing determinant comprising amino acids 1 though 20 (inclusive) of SEQ ID NO: 285, wherein said antibody binds SEQ ID NO: 285 expressed on the surface of H929 cells with an EC50 of about 1.2 nM in a FACS assay as described in Example 11. Preferred embodiments of the invention include isolated human monoclonal IgG1 antibodies that bind a neutralizing determinant comprising amino acids 1 through 11 (inclusive) of SEQ ID NO: 285, wherein said antibody binds SEQ ID NO: 285 expressed on the surface of H929 cells with an EC50 of about 1.2 nM in a FACS assay as described in Example 11.

Embodiments of the invention include isolated monoclonal antibodies that bind a neutralizing determinant comprising amino acids 1 though 20 (inclusive) of SEQ ID NO: 285, wherein said antibody binds SEQ ID NO: 285 with a Kd of less than or equal to 1 nM, and wherein said antibody binds SEQ ID NO: 285 expressed on the surface of H929 cells with an EC50 of less than or equal to 10 nM. Preferred embodiments of the invention include isolated monoclonal antibodies that bind a neutralizing determinant comprising amino acids 1 through 11 (inclusive) of SEQ ID NO: 285, wherein said antibody binds SEQ ID NO: 285 with a Kd of less than or equal to 1 nM, and wherein said antibody binds SEQ ID NO: 285 expressed on the surface of H929 cells with an EC50 of less than or equal to 10 nM. Embodiments of the invention include isolated human monoclonal antibodies that bind a neutralizing determinant comprising amino acids 1 though 20 (inclusive) of SEQ ID NO: 285, wherein said antibody binds SEQ ID NO: 285 with a Kd of less than or equal to 1 nM, and wherein said antibody binds SEQ ID NO: 285 expressed on the surface of H929 cells with an EC50 of less than or equal to 10 nM. Preferred embodiments of the invention include isolated human monoclonal antibodies that bind a neutralizing determinant comprising amino acids 1 through 11 (inclusive) of SEQ ID NO: 285, wherein said antibody binds SEQ ID NO: 285 with a Kd of less than or equal to 1 nM, and wherein said antibody binds SEQ ID NO: 285 expressed on the surface of H929 cells with an EC50 of less than or equal to 10 nM. Embodiments of the invention include isolated human monoclonal IgG antibodies that bind a neutralizing determinant comprising amino acids 1 though 20 (inclusive) of SEQ ID NO: 285, wherein said antibody binds SEQ ID NO: 285 with a Kd of less than or equal to 1 nM, and wherein said antibody binds SEQ ID NO: 285 expressed on the surface of H929 cells with an EC50 of less than or equal to 10 nM. Preferred embodiments of the invention include isolated human monoclonal IgG antibodies that bind a neutralizing determinant comprising amino acids 1 through 11 (inclusive) of SEQ ID NO: 285, wherein said antibody binds SEQ ID NO: 285 with a Kd of less than or equal to 1 nM, and wherein said antibody binds SEQ ID NO: 285 expressed on the surface of H929 cells with an EC50 of less than or equal to 10 nM. Embodiments of the invention include isolated human monoclonal IgG1 antibodies that bind a neutralizing determinant comprising amino acids 1 though 20 (inclusive) of SEQ ID NO: 285, wherein said antibody binds SEQ ID NO: 285 with a Kd of less than or equal to 1 nM, and wherein said antibody binds SEQ ID NO: 285 expressed on the surface of H929 cells with an EC50 of less than or equal to 10 nM. Preferred embodiments of the invention include isolated human monoclonal IgG1 antibodies that bind a neutralizing determinant comprising amino acids 1 through 11 (inclusive) of SEQ ID NO: 285, wherein said antibody binds SEQ ID NO: 285 with a Kd of less than or equal to 1 nM, and wherein said antibody binds SEQ ID NO: 285 expressed on the surface of H929 cells with an EC50 of less than or equal to 10 nM.

Embodiments of the invention include isolated monoclonal antibodies that bind a neutralizing determinant comprising amino acids 1 though 20 (inclusive) of SEQ ID NO: 285, wherein said antibody binds SEQ ID NO: 352 with a Kd of about 0.16 nM as measured in a biosensor assay described in Example 16, and wherein said antibody binds SEQ ID NO: 285 expressed on the surface of H929 cells with an EC50 of about 1.2 nM in a FACS assay as described in Example 11. Preferred embodiments of the invention include isolated monoclonal antibodies that bind a neutralizing determinant comprising amino acids 1 through 11 (inclusive) of SEQ ID NO: 285, wherein said antibody binds SEQ ID NO: 352 with a Kd of about 0.16 nM as measured in a biosensor assay described in Example 16, and wherein said antibody binds SEQ ID NO: 285 expressed on the surface of H929 cells with an EC50 of about 1.2 nM in a FACS assay as described in Example 11. Embodiments of the invention include isolated human monoclonal antibodies that bind a neutralizing determinant comprising amino acids 1 though 20 (inclusive) of SEQ ID NO: 285, wherein said antibody binds SEQ ID NO: 352 with a Kd of about 0.16 nM as measured in a biosensor assay described in Example 16, and wherein said antibody binds SEQ ID NO: 285 expressed on the surface of H929 cells with an EC50 of about 1.2 nM in a FACS assay as described in Example 11. Preferred embodiments of the invention include isolated human monoclonal antibodies that bind a neutralizing determinant comprising amino acids 1 through 11 (inclusive) of SEQ ID NO: 285, wherein said antibody binds SEQ ID NO: 352 with a Kd of about 0.16 nM as measured in a biosensor assay described in Example 16, and wherein said antibody binds SEQ ID NO: 285 expressed on the surface of H929 cells with an EC50 of about 1.2 nM in a FACS assay as described in Example 11. Embodiments of the invention include isolated human monoclonal IgG antibodies that bind a neutralizing determinant comprising amino acids 1 though 20 (inclusive) of SEQ ID NO: 285, wherein said antibody binds SEQ ID NO: 352 with a Kd of about 0.16 nM as measured in a biosensor assay described in Example 16, and wherein said antibody binds SEQ ID NO: 285 expressed on the surface of H929 cells with an EC50 of about 1.2 nM in a FACS assay as described in Example 11. Preferred embodiments of the invention include isolated human monoclonal IgG antibodies that bind a neutralizing determinant comprising amino acids 1 through 11 (inclusive) of SEQ ID NO: 285, wherein said antibody binds SEQ ID NO: 352 with a Kd of about 0.16 nM as measured in a biosensor assay described in Example 16, and wherein said antibody binds SEQ ID NO: 285 expressed on the surface of H929 cells with an EC50 of about 1.2 nM in a FACS assay as described in Example 11. Embodiments of the invention include isolated human monoclonal IgG1 antibodies that bind a neutralizing determinant comprising amino acids 1 though 20 (inclusive) of SEQ ID NO: 285, wherein said antibody binds SEQ ID NO: 352 with a Kd of about 0.16 nM as measured in a biosensor assay described in Example 16, and wherein said antibody binds SEQ ID NO: 285 expressed on the surface of H929 cells with an EC50 of about 1.2 nM in a FACS assay as described in Example 11. Preferred embodiments of the invention include isolated human monoclonal IgG1 antibodies that bind a neutralizing determinant comprising amino acids 1 through 11 (inclusive) of SEQ ID NO: 285, wherein said antibody binds SEQ ID NO: 352 with a Kd of about 0.16 nM as measured in a biosensor assay described in Example 16, and wherein said antibody binds SEQ ID NO: 285 expressed on the surface of H929 cells with an EC50 of about 1.2 nM in a FACS assay as described in Example 11.

Aspects of the invention include, but are not limited to, embodiments such as Embodiment 1: An isolated antibody, or BCMA-binding fragment thereof, selected from the group consisting of: an antibody comprising the six CDRs of Ab-1; an antibody comprising the six CDRs of Ab-2; an antibody comprising the six CDRs of Ab-3; an antibody comprising the six CDRs of Ab-4; an antibody comprising the six CDRs of Ab-5; an antibody comprising the six CDRs of Ab-6; an antibody comprising the six CDRs of Ab-7; an antibody comprising the six CDRs of Ab-8; an antibody comprising the six CDRs of Ab-9; an antibody comprising the six CDRs of Ab-10; an antibody comprising the six CDRs of Ab-11; an antibody comprising the six CDRs of Ab-12; an antibody comprising the six CDRs of Ab-13; an antibody comprising the six CDRs of Ab-14; an antibody comprising the six CDRs of Ab-15; an antibody comprising the six CDRs of Ab-16; an antibody comprising the six CDRs of Ab-17; an antibody comprising the six CDRs of Ab-18; an antibody comprising the six CDRs of Ab-19; an antibody comprising the six CDRs of Ab-20; an antibody comprising the six CDRs of Ab-21; an antibody comprising the six CDRs of Ab-22; an antibody comprising the six CDRs of Ab-23; an antibody comprising the six CDRs of Ab-24; an antibody comprising the six CDRs of Ab-25; an antibody comprising the six CDRs of Ab-26; an antibody comprising the six CDRs of Ab-27; an antibody comprising the six CDRs of Ab-28; an antibody comprising the six CDRs of Ab-29; an antibody comprising the six CDRs of Ab-30; an antibody comprising the six CDRs of Ab-31; an antibody comprising the six CDRs of Ab-32; an antibody comprising the six CDRs of Ab-33; an antibody comprising the six CDRs of Ab-34; an antibody comprising the six CDRs of Ab-35; an antibody comprising the six CDRs of Ab-36; an antibody comprising the six CDRs of Ab-37; and an antibody comprising the six CDRs of Ab-38. Embodiment 2: The antibody or fragment of Embodiment 1, wherein said antibody or fragment is selected from the group consisting of: an antibody comprising the six CDRs of Ab-1; an antibody comprising the six CDRs of Ab-2; and an antibody comprising the six CDRs of Ab-3. Embodiment 3: The antibody or fragment of Embodiments 1 or 2, wherein said antibody or fragment is an antibody comprising the six CDRs of Ab-1. Embodiment 4: The antibody or fragment of Embodiments 1-3, wherein said CDRs of Ab-1 comprises a Vh-CDR1 comprising SEQ ID NO:4, a Vh-CDR2 comprising SEQ ID NO:5, a Vh-CDR3 comprising SEQ ID NO:6, a Vl-CDR1 comprising SEQ ID NO:106, a Vl-CDR2 comprising SEQ ID NO:107, and a Vl-CDR3 comprising SEQ ID NO:108; wherein said CDRs of Ab-2 comprise a Vh-CDR1 comprising SEQ ID NO:10, a Vh-CDR2 comprising SEQ ID NO:11, a Vh-CDR3 comprising SEQ ID NO:12, a Vl-CDR1 comprising SEQ ID NO:112, a Vl-CDR2 comprising SEQ ID NO:113, and a Vl-CDR3 comprising SEQ ID NO:114; wherein said CDRs of Ab-3 comprise a Vh-CDR1 comprising SEQ ID NO:16, a Vh-CDR2 comprising SEQ ID NO:17, a Vh-CDR3 comprising SEQ ID NO:18, a Vl-CDR1 comprising SEQ ID NO:118, a Vl-CDR2 comprising SEQ ID NO:119, and a Vl-CDR3 comprising SEQ ID NO:120; wherein said CDRs of Ab-4 comprise a Vh-CDR1 comprising SEQ ID NO:22, a Vh-CDR2 comprising SEQ ID NO:23, a Vh-CDR3 comprising SEQ ID NO:24, a Vl-CDR1 comprising SEQ ID NO:124, a Vl-CDR2 comprising SEQ ID NO:125, and a Vl-CDR3 comprising SEQ ID NO:126; wherein said CDRs of Ab-5 comprises a Vh-CDR1 comprising SEQ ID NO:28, a Vh-CDR2 comprising SEQ ID NO:29, a Vh-CDR3 comprising SEQ ID NO:30, a Vl-CDR1 comprising SEQ ID NO:130, a Vl-CDR2 comprising SEQ ID NO:131, and a Vl-CDR3 comprising SEQ ID NO:132; wherein said CDRs of Ab-6 comprise a Vh-CDR1 comprising SEQ ID NO:34, a Vh-CDR2 comprising SEQ ID NO:35, a Vh-CDR3 comprising SEQ ID NO:36, a Vl-CDR1 comprising SEQ ID NO:136, a Vl-CDR2 comprising SEQ ID NO:137, and a Vl-CDR3 comprising SEQ ID NO:138; wherein said CDRs of Ab-7 comprise a Vh-CDR1 comprising SEQ ID NO:40, a Vh-CDR2 comprising SEQ ID NO:41, a Vh-CDR3 comprising SEQ ID NO:42, a Vl-CDR1 comprising SEQ ID NO:142, a Vl-CDR2 comprising SEQ ID NO:143, and a Vl-CDR3 comprising SEQ ID NO:144; wherein said CDRs of Ab-8 comprise a Vh-CDR1 comprising SEQ ID NO:46, a Vh-CDR2 comprising SEQ ID NO:47, a Vh-CDR3 comprising SEQ ID NO:48, a Vl-CDR1 comprising SEQ ID NO:148, a Vl-CDR2 comprising SEQ ID NO:149, and a Vl-CDR3 comprising SEQ ID NO:150; wherein said CDRs of Ab-9 comprise a Vh-CDR1 comprising SEQ ID NO:52, a Vh-CDR2 comprising SEQ ID NO:53, a Vh-CDR3 comprising SEQ ID NO:54, a Vl-CDR1 comprising SEQ ID NO:154, a Vl-CDR2 comprising SEQ ID NO:155, and a Vl-CDR3 comprising SEQ ID NO:156; wherein said CDRs of Ab-10 comprise a Vh-CDR1 comprising SEQ ID NO:58, a Vh-CDR2 comprising SEQ ID NO:59, a Vh-CDR3 comprising SEQ ID NO:60, a Vl-CDR1 comprising SEQ ID NO:160, a Vl-CDR2 comprising SEQ ID NO:161, and a Vl-CDR3 comprising SEQ ID NO:162; wherein said CDRs of Ab-11 comprise a Vh-CDR1 comprising SEQ ID NO:64, a Vh-CDR2 comprising SEQ ID NO:65, a Vh-CDR3 comprising SEQ ID NO:66, a Vl-CDR1 comprising SEQ ID NO:166, a Vl-CDR2 comprising SEQ ID NO:167, and a Vl-CDR3 comprising SEQ ID NO:168; wherein said CDRs of Ab-12 comprise a Vh-CDR1 comprising SEQ ID NO:70, a Vh-CDR2 comprising SEQ ID NO:71, a Vh-CDR3 comprising SEQ ID NO:72, a Vl-CDR1 comprising SEQ ID NO:172, a Vl-CDR2 comprising SEQ ID NO:173, and a Vl-CDR3 comprising SEQ ID NO:174; wherein said CDRs of Ab-13 comprise a Vh-CDR1 comprising SEQ ID NO:76, a Vh-CDR2 comprising SEQ ID NO:77, a Vh-CDR3 comprising SEQ ID NO:78, a Vl-CDR1 comprising SEQ ID NO:178, a Vl-CDR2 comprising SEQ ID NO:179, and a Vl-CDR3 comprising SEQ ID NO:180; wherein said CDRs of Ab-14 comprise a Vh-CDR1 comprising SEQ ID NO:82, a Vh-CDR2 comprising SEQ ID NO:83, a Vh-CDR3 comprising SEQ ID NO:84, a Vl-CDR1 comprising SEQ ID NO:184, a Vl-CDR2 comprising SEQ ID NO:185, and a Vl-CDR3 comprising SEQ ID NO:186; wherein said CDRs of Ab-15 comprise a Vh-CDR1 comprising SEQ ID NO:88, a Vh-CDR2 comprising SEQ ID NO:89, a Vh-CDR3 comprising SEQ ID NO:90, a Vl-CDR1 comprising SEQ ID NO:190, a Vl-CDR2 comprising SEQ ID NO:191, and a Vl-CDR3 comprising SEQ ID NO:192; wherein said CDRs of Ab-16 comprise a Vh-CDR1 comprising SEQ ID NO:94, a Vh-CDR2 comprising SEQ ID NO:95, a Vh-CDR3 comprising SEQ ID NO:96, a Vl-CDR1 comprising SEQ ID NO:196, a Vl-CDR2 comprising SEQ ID NO:197, and a Vl-CDR3 comprising SEQ ID NO:198; and wherein said CDRs of Ab-17 comprise a Vh-CDR1 comprising SEQ ID NO:100, a Vh-CDR2 comprising SEQ ID NO:101, a Vh-CDR3 comprising SEQ ID NO:102, a Vl-CDR1 comprising SEQ ID NO:202, a Vl-CDR2 comprising SEQ ID NO:203, and a Vl-CDR3 comprising SEQ ID NO:204. Embodiment 5: The antibody or fragment of Embodiments 1-4, wherein said CDRs of Ab-1 comprises a Vh-CDR1 comprising SEQ ID NO:4, a Vh-CDR2 comprising SEQ ID NO:5, a Vh-CDR3 comprising SEQ ID NO:6, a Vl-CDR1 comprising SEQ ID NO:106, a Vl-CDR2 comprising SEQ ID NO:107, and a Vl-CDR3 comprising SEQ ID NO:108; wherein said CDRs of Ab-2 comprise a Vh-CDR1 comprising SEQ ID NO:10, a Vh-CDR2 comprising SEQ ID NO:11, a Vh-CDR3 comprising SEQ ID NO:12, a Vl-CDR1 comprising SEQ ID NO:112, a Vl-CDR2 comprising SEQ ID NO:113, and a Vl-CDR3 comprising SEQ ID NO:114; and wherein said CDRs of Ab-3 comprise a Vh-CDR1 comprising SEQ ID NO:16, a Vh-CDR2 comprising SEQ ID NO:17, a Vh-CDR3 comprising SEQ ID NO:18, a Vl-CDR1 comprising SEQ ID NO:118, a Vl-CDR2 comprising SEQ ID NO:119, and a Vl-CDR3 comprising SEQ ID NO:120. Embodiment 6: The antibody or fragment of Embodiments 1-5, wherein said CDRs of Ab-1 comprises a Vh-CDR1 comprising SEQ ID NO:4, a Vh-CDR2 comprising SEQ ID NO:5, a Vh-CDR3 comprising SEQ ID NO:6, a Vl-CDR1 comprising SEQ ID NO:106, a Vl-CDR2 comprising SEQ ID NO:107, and a Vl-CDR3 comprising SEQ ID NO:108. Embodiment 7: The antibody or fragment of Embodiments 1-6, wherein said antibody or fragment comprises an Ab-1Vl domain comprising SEQ ID NO:240 and an Ab-1Vh domain comprising SEQ ID NO:206; wherein said antibody or fragment comprises an Ab-2Vl domain comprising SEQ ID NO:242 and an Ab-2Vh domain comprising SEQ ID NO:208; wherein said antibody or fragment comprises an Ab-3Vl domain comprising SEQ ID NO:244 and an Ab-3Vh domain comprising SEQ ID NO:210; wherein said antibody or fragment comprises an Ab-4Vl domain comprising SEQ ID NO:246 and an Ab-4Vh domain comprising SEQ ID NO:212; wherein said antibody or fragment comprises an Ab-5Vl domain comprising SEQ ID NO:248 and an Ab-5Vh domain comprising SEQ ID NO:214; wherein said antibody or fragment comprises an Ab-6Vl domain comprising SEQ ID NO:250 and an Ab-6Vh domain comprising SEQ ID NO:216; wherein said antibody or fragment comprises an Ab-7Vl domain comprising SEQ ID NO:252 and an Ab-7Vh domain comprising SEQ ID NO:218; wherein said antibody or fragment comprises an Ab-8Vl domain comprising SEQ ID NO:254 and an Ab-8Vh domain comprising SEQ ID NO:220; wherein said antibody or fragment comprises an Ab-9Vl domain comprising SEQ ID NO:256 and an Ab-9Vh domain comprising SEQ ID NO:222; wherein said antibody or fragment comprises an Ab-10Vl domain comprising SEQ ID NO:258 and an Ab-10Vh domain comprising SEQ ID NO:224; wherein said antibody or fragment comprises an Ab-11Vl domain comprising SEQ ID NO:260 and an Ab-11Vh domain comprising SEQ ID NO:226; wherein said antibody or fragment comprises an Ab-12Vl comprising SEQ ID NO:262 and an Ab-12Vh domain comprising SEQ ID NO:228; wherein said antibody or fragment comprises an Ab-13Vl domain comprising SEQ ID NO:264 and an Ab-13Vh domain comprising SEQ ID NO:230; wherein said antibody or fragment comprises an Ab-14Vl domain comprising SEQ ID NO:266 and an Ab-14Vh domain comprising SEQ ID NO:232; wherein said antibody or fragment comprises an Ab-15Vl domain comprising SEQ ID NO:268 and an Ab-15Vh domain comprising SEQ ID NO:234; wherein said antibody or fragment comprises an Ab-16Vl domain comprising SEQ ID NO:270 and an Ab-16Vh domain comprising SEQ ID NO:236; and wherein said antibody or fragment comprises an Ab-17Vl domain comprising SEQ ID NO:272 and an Ab-17Vh domain comprising SEQ ID NO:238) domain. Embodiment 8: The antibody or fragment of Embodiments 1-7, wherein said antibody or fragment comprises an Ab-1Vl domain comprising SEQ ID NO:240 and an Ab-1Vh domain comprising SEQ ID NO:206; wherein said antibody or fragment comprises an Ab-2Vl domain comprising SEQ ID NO:242 and an Ab-2Vh domain comprising SEQ ID NO:208; and wherein said antibody or fragment comprises an Ab-3Vl domain comprising SEQ ID NO:244 and an Ab-3Vh domain comprising SEQ ID NO:210. Embodiment 9: The antibody or fragment of Embodiments 1-8, wherein said antibody or fragment comprises an Ab-1Vl domain comprising SEQ ID NO:240 and an Ab-1Vh domain comprising SEQ ID NO:206. Embodiment 10: The antibody or fragment of Embodiments 1-9, wherein said antibody or fragment comprises an Ab-1 light chain comprising SEQ ID NO:280 and Ab-1 heavy chain comprising SEQ ID NO:274; wherein said antibody or fragment comprises an Ab-2 light chain comprising SEQ ID NO:282 and an Ab-2 heavy chain comprising SEQ ID NO:276; wherein said antibody or fragment comprises an Ab-3 light chain comprising SEQ ID NO:284 and an Ab-3 heavy chain comprising SEQ ID NO:278; wherein said antibody or fragment comprises two Ab-1 light chains comprising SEQ ID NO:280 and two Ab-1 heavy chains comprising SEQ ID NO:274; wherein said antibody or fragment comprises two Ab-2 light chains comprising SEQ ID NO:282 and two Ab-2 heavy chains comprising SEQ ID NO:276; and wherein said antibody or fragment comprises two Ab-3 light chains comprising SEQ ID NO:284 and two Ab-3 heavy chains comprising SEQ ID NO:278). Embodiment 11: The antibody or fragment of Embodiments 1-10, wherein said antibody or fragment comprises an Ab-1 light chain comprising SEQ ID NO:280 and Ab-1 heavy chain comprising SEQ ID NO:274; and wherein said antibody or fragment comprises two Ab-1 light chains comprising SEQ ID NO:280 and two Ab-1 heavy chains comprising SEQ ID NO:274. Embodiment 12: The antibody or fragment of Embodiments 1-11, wherein said antibody or fragment comprises two Ab-1 light chains comprising SEQ ID NO:280 and two Ab-1 heavy chains comprising SEQ ID NO:274. Embodiment 13: The antibody or fragment of Embodiments 1-12, wherein said antibody or fragment is human. Embodiment 14: The antibody or fragment of Embodiments 1-13, wherein said antibody or fragment is a human monoclonal antibody. Embodiment 15: The antibody or fragment of Embodiments 1-12, wherein said antibody or fragment is a chimeric monoclonal antibody. Embodiment 16: The antibody or fragment of Embodiments 1-15, wherein said antibody or fragment specifically binds human BCMA. Embodiment 17: The antibody or fragment of Embodiments 1-16, wherein said antibody or fragment specifically binds human BCMA and cross-reacts to cynomolgus BCMA. Embodiment 18: The antibody or fragment of Embodiments 1-17, wherein said antibody or fragment does not specifically bind to TACT or BAFF-R. Embodiment 19: The antibody or fragment of Embodiments 1-18, wherein said antibody or fragment binds BCMA on the surface of human myeloma cells. Embodiment 20: The antibody or fragment of Embodiments 1-19, wherein said antibody or fragment binds BCMA on the surface of human multiple myeloma cells. Embodiment 21: The antibody or fragment of Embodiments 1-20, wherein said antibody or fragment binds BCMA on the surface of human cells and is internalized by said cells. Embodiment 22: The antibody or fragment of Embodiments 1-21, wherein said antibody or fragment further comprises a linker. Embodiment 23: The antibody or fragment of Embodiments 1-22, wherein said antibody or fragment further comprises a drug or chemotherapeutic agent. Embodiment 24: The antibody or fragment of Embodiments 1-23, wherein said antibody or fragment further comprises a linker selected from the group consisting of: 6-maleimidocaproyl, maleimidopropanoyl, valine-citrulline, alanine-phenylalanine, p-aminobenzyloxycarbonyl, Mal-dPEG4-NHS, N-succinimidyl 4-(2-pyridylthio) pentanoate ("SPP"), N-succinimidyl 4-(N-maleimidomethyl) cyclohexane-1 carboxylate ("SMCC" or "MCC"), and N-succinimidyl (4-iodo-acetyl) aminobenzoate ("STAB"). Embodiment 25: The antibody or fragment of Embodiments 1-24, wherein said antibody or fragment further comprises a linker wherein said linker is N-succinimidyl 4-(N-maleimidomethyl) cyclohexane-1 carboxylate ("SMCC" or "MCC"). Embodiment 26: The antibody or fragment of Embodiments 1-25, wherein said antibody or fragment further comprises a drug or chemotherapeutic agent selected from the group consisting of: thiotepa and cyclophosphamide (CYTOXAN™); alkyl sulfonates such as busulfan, improsulfan and piposulfan; aziridines, such as benzodopa, carboquone, meturedopa, and uredopa; ethylenimines and methylamelamines including altretamine, triethylenemelamine, trietylenephosphoramide, triethylenethiophosphaoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics, such as the enediyne antibiotics (e.g. calicheamicin, especially calicheamicin .gamma1 and calicheamicin theta I, see, e.g., Angew Chem. Intl. Ed. Engl. 33:183-186 (1994); dynemicin, including dynemicin A; an esperamicin; as well as neocarzinostatin chromophore and related chromoprotein enediyne antiobiotic chromomophores), aclacinomysins, actinomycin, authramycin, azaserine, bleomycins, cactinomycin, carabicin, caminomycin, carzinophilin; chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, nitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites, such as methotrexate and 5-fluorouracil (5-FU); folic acid analogues, such as denopterin, methotrexate, pteropterin, trimetrexate; purine analogs, such as fludarabine, 6-mercaptopurine, thiamiprine, thioguanine; pyrimidine analogs such as, ancitabine, azacitidine, 6-azauridine, carmofur, cytarabine, dideoxyuridine, doxifluridine, enocitabine, floxuridine, 5-FU; androgens, such as calusterone, dromostanolone propionate, epitiostanol, mepitiostane, testolactone; anti-adrenals, such as aminoglutethimide, mitotane, trilostane; folic acid replenisher, such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidamine; maytansinoids, such as maytansine and ansamitocins; mitoguazone; mitoxantrone; mopidamol; nitracrine; pentostatin; phenamet; pirarubicin; podophyllinic acid; 2-ethylhydrazide; procarbazine; PSK®; razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL™, Bristol-Myers Squibb Oncology, Princeton, N.J.) and doxetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid; capecitabine; tamoxifen, raloxifene, aromatase inhibiting 4(5)-imidazoles, 4-hydroxytamoxifen, trioxifene, keoxifene, LY117018, onapristone, and toremifene (Fareston); and anti-androgens, such as flutamide, nilutamide, bicalutamide, leuprolide, goserelin, Colchicine-site Binders (Curacin), Combretastatins (AVE806, Combretastatin A-4 prodrug (CA4P), Oxi-4503), Cryptophycins (LY355703), Discodermolide, Dolastatin and Analogs (Auristatin PHE, Dolastatin 10, ILX-651, Symplostatin 1, TZT-1027), Epothilones (BMS-247550, BMS-310705, EP0906, KOS-862, ZK-EPO), Eleutherobin, FR182877, Halichondrin B (E7389), Halimide (NPI-2352 and NPI-2358), Hemiasterlins (HTI-286), Laulimalide, Maytansinoids ("DM1," "DM3" or "DM4") (Bivatuzumab mertansine, Cantuzumab mertansine, huN901-DM1/BB-10901TAP, MLN591DM1, My9-6-DM1, Trastuzumab-DM1), PC-SPES, Peloruside A, Resveratrol, S-allylmercaptocysteine (SAMC), Spongistatins, Vitilevuamide, Molecular Motor-Kinesins (SB-715992), Designed Colchicine-Site Binders (A-289099, A-293620/A-318315, ABT-751/E7010, D-24851/D-64131, ZD6126), Other Novel Spindle Poisons (2-Methoxyestradiol (2-ME2), Bezimidazole Carbamates (ANG 600 series, Mebendazole), CP248/CP461, HMN-214, R440, SDX-103, T67/T607). Embodiment 27: The antibody or fragment of Embodiments 1-26, wherein said antibody or fragment further comprises a drug or chemotherapeutic agent selected from the group consisting of: Maytansinoids ("DM1," "DM3" or "DM4"). Embodiment 28: The antibody or fragment of Embodiments 1-27, wherein said antibody or fragment further comprises DM1. Embodiment 29: The antibody or fragment of Embodiments 1-28, wherein said antibody or fragment has a drug to antibody ratio of between 1 and 10. Embodiment 30: The antibody or fragment of Embodiments 1-29, wherein said antibody or fragment has a drug to antibody ratio of between 2 and 5. Embodiment 31: An isolated polypeptide, or BCMA-binding fragment thereof, selected from the group consisting of: a polypeptide comprising the six CDRs of Ab-1; a polypeptide comprising the six CDRs of Ab-2; a polypeptide comprising the six CDRs of Ab-3; a polypeptide comprising the six CDRs of Ab-4; a polypeptide comprising the six CDRs of Ab-5; a polypeptide comprising the six CDRs of Ab-6; a polypeptide comprising the six CDRs of Ab-7; a polypeptide comprising the six CDRs of Ab-8; a polypeptide comprising the six CDRs of Ab-9; a polypeptide comprising the six CDRs of Ab-10; a polypeptide comprising the six CDRs of Ab-11; a polypeptide comprising the six CDRs of Ab-12; a polypeptide comprising the six CDRs of Ab-13; a polypeptide comprising the six CDRs of Ab-14; a polypeptide comprising the six CDRs of Ab-15; a polypeptide comprising the six CDRs of Ab-16; a polypeptide comprising the six CDRs of Ab-17; a polypeptide comprising the six CDRs of Ab-18; a polypeptide comprising the six CDRs of Ab-19; a polypeptide comprising the six CDRs of Ab-20; a polypeptide comprising the six CDRs of Ab-21; a polypeptide comprising the six CDRs of Ab-22; a polypeptide comprising the six CDRs of Ab-23; a polypeptide comprising the six CDRs of Ab-24; a polypeptide comprising the six CDRs of Ab-25; a polypeptide comprising the six CDRs of Ab-26; a polypeptide comprising the six CDRs of Ab-27; a polypeptide comprising the six CDRs of Ab-28; a polypeptide comprising the six CDRs of Ab-29; a polypeptide comprising the six CDRs of Ab-30; a polypeptide comprising the six CDRs of Ab-31; a polypeptide comprising the six CDRs of Ab-32; a polypeptide comprising the six CDRs of Ab-33; a polypeptide comprising the six CDRs of Ab-34; a polypeptide comprising the six CDRs of Ab-35; a polypeptide comprising the six CDRs of Ab-36; a polypeptide comprising the six CDRs of Ab-37; and a polypeptide comprising the six CDRs of Ab-38. Embodiment 32: The polypeptide or fragment of Embodiment 31, wherein said polypeptide or fragment is selected from the group consisting of: a polypeptide comprising the six CDRs of Ab-1; a polypeptide comprising the six CDRs of Ab-2; and a polypeptide comprising the six CDRs of Ab-3. Embodiment 33: The polypeptide or fragment of Embodiment 31-32, wherein said polypeptide or fragment is a polypeptide comprising the six CDRs of Ab-1. Embodiment 34: The polypeptide or fragment of Embodiments 31-33, wherein said CDRs comprises a Vh-CDR1 comprising SEQ ID NO:4, a Vh-CDR2 comprising SEQ ID NO:5, a Vh-CDR3 comprising SEQ ID NO:6, a Vl-CDR1 comprising SEQ ID NO:106, a Vl-CDR2 comprising SEQ ID NO:107, and a Vl-CDR3 comprising SEQ ID NO:108; wherein said CDRs comprise a Vh-CDR1 comprising SEQ ID NO:10, a Vh-CDR2 comprising SEQ ID NO:11, a Vh-CDR3 comprising SEQ ID NO:12, a Vl-CDR1 comprising SEQ ID NO:112, a Vl-CDR2 comprising SEQ ID NO:113, and a Vl-CDR3 comprising SEQ ID NO:114; wherein said CDRs comprise a Vh-CDR1 comprising SEQ ID NO:16, a Vh-CDR2 comprising SEQ ID NO:17, a Vh-CDR3 comprising SEQ ID NO:18, a Vl-CDR1 comprising SEQ ID NO:118, a Vl-CDR2 comprising SEQ ID NO:119, and a Vl-CDR3 comprising SEQ ID NO:120; wherein said CDRs comprise a Vh-CDR1 comprising SEQ ID NO:22, a Vh-CDR2 comprising SEQ ID NO:23, a Vh-CDR3 comprising SEQ ID NO:24, a Vl-CDR1 comprising SEQ ID NO:124, a Vl-CDR2 comprising SEQ ID NO:125, and a Vl-CDR3 comprising SEQ ID NO:126; wherein said CDRs comprises a Vh-CDR1 comprising SEQ ID NO:28, a Vh-CDR2 comprising SEQ ID NO:29, a Vh-CDR3 comprising SEQ ID NO:30, a Vl-CDR1 comprising SEQ ID NO:130, a Vl-CDR2 comprising SEQ ID NO:131, and a Vl-CDR3 comprising SEQ ID NO:132; wherein said CDRs comprise a Vh-CDR1 comprising SEQ ID NO:34, a Vh-CDR2 comprising SEQ ID NO:35, a Vh-CDR3 comprising SEQ ID NO:36, a Vl-CDR1 comprising SEQ ID NO:136, a Vl-CDR2 comprising SEQ ID NO:137, and a Vl-CDR3 comprising SEQ ID NO:138; wherein said CDRs comprise a Vh-CDR1 comprising SEQ ID NO:40, a Vh-CDR2 comprising SEQ ID NO:41, a Vh-CDR3 comprising SEQ ID NO:42, a Vl-CDR1 comprising SEQ ID NO:142, a Vl-CDR2 comprising SEQ ID NO:143, and a Vl-CDR3 comprising SEQ ID NO:144; wherein said CDRs comprise a Vh-CDR1 comprising SEQ ID NO:46, a Vh-CDR2 comprising SEQ ID NO:47, a Vh-CDR3 comprising SEQ ID NO:48, a Vl-CDR1 comprising SEQ ID NO:148, a Vl-CDR2 comprising SEQ ID NO:149, and a Vl-CDR3 comprising SEQ ID NO:150; wherein said CDRs comprise a Vh-CDR1 comprising SEQ ID NO:52, a Vh-CDR2 comprising SEQ ID NO:53, a Vh-CDR3 comprising SEQ ID NO:54, a Vl-CDR1 comprising SEQ ID NO:154, a Vl-CDR2 comprising SEQ ID NO:155, and a Vl-CDR3 comprising SEQ ID NO:156; wherein said CDRs comprise a Vh-CDR1 comprising SEQ ID NO:58, a Vh-CDR2 comprising SEQ ID NO:59, a Vh-CDR3 comprising SEQ ID NO:60, a Vl-CDR1 comprising SEQ ID NO:160, a Vl-CDR2 comprising SEQ ID NO:161, and a Vl-CDR3 comprising SEQ ID NO:162; wherein said CDRs comprise a Vh-CDR1 comprising SEQ ID NO:64, a Vh-CDR2 comprising SEQ ID NO:65, a Vh-CDR3 comprising SEQ ID NO:66, a Vl-CDR1 comprising SEQ ID NO:166, a Vl-CDR2 comprising SEQ ID NO:167, and a Vl-CDR3 comprising SEQ ID NO:168; wherein said CDRs comprise a Vh-CDR1 comprising SEQ ID NO:70, a Vh-CDR2 comprising SEQ ID NO:71, a Vh-CDR3 comprising SEQ ID NO:72, a Vl-CDR1 comprising SEQ ID NO:172, a Vl-CDR2 comprising SEQ ID NO:173, and a Vl-CDR3 comprising SEQ ID NO:174; wherein said CDRs comprise a Vh-CDR1 comprising SEQ ID NO:76, a Vh-CDR2 comprising SEQ ID NO:77, a Vh-CDR3 comprising SEQ ID NO:78, a Vl-CDR1 comprising SEQ ID NO:178, a Vl-CDR2 comprising SEQ ID NO:179, and a Vl-CDR3 comprising SEQ ID NO:180; wherein said CDRs comprise a Vh-CDR1 comprising SEQ ID NO:82, a Vh-CDR2 comprising SEQ ID NO:83, a Vh-CDR3 comprising SEQ ID NO:84, a Vl-CDR1 comprising SEQ ID NO:184, a Vl-CDR2 comprising SEQ ID NO:185, and a Vl-CDR3 comprising SEQ ID NO:186; wherein said CDRs comprise a Vh-CDR1 comprising SEQ ID NO:88, a Vh-CDR2 comprising SEQ ID NO:89, a Vh-CDR3 comprising SEQ ID NO:90, a Vl-CDR1 comprising SEQ ID NO:190, a Vl-CDR2 comprising SEQ ID NO:191, and a Vl-CDR3 comprising SEQ ID NO:192; wherein said CDRs comprise a Vh-CDR1 comprising SEQ ID NO:94, a Vh-CDR2 comprising SEQ ID NO:95, a Vh-CDR3 comprising SEQ ID NO:96, a Vl-CDR1 comprising SEQ ID NO:196, a Vl-CDR2 comprising SEQ ID NO:197, and a Vl-CDR3 comprising SEQ ID NO:198; and wherein said CDRs comprise a Vh-CDR1 comprising SEQ ID NO:100, a Vh-CDR2 comprising SEQ ID NO:101, a Vh-CDR3 comprising SEQ ID NO:102, a Vl-CDR1 comprising SEQ ID NO:202, a Vl-CDR2 comprising SEQ ID NO:203, and a Vl-CDR3 comprising SEQ ID NO:204.

Embodiment 35: The polypeptide or fragment of Embodiments 31-34, wherein said CDRs comprises a Vh-CDR1 comprising SEQ ID NO:4, a Vh-CDR2 comprising SEQ ID NO:5, a Vh-CDR3 comprising SEQ ID NO:6, a Vl-CDR1 comprising SEQ ID NO:106, a Vl-CDR2 comprising SEQ ID NO:107, and a Vl-CDR3 comprising SEQ ID NO:108; wherein said CDRs comprise a Vh-CDR1 comprising SEQ ID NO:10, a Vh-CDR2 comprising SEQ ID NO:11, a Vh-CDR3 comprising SEQ ID NO:12, a Vl-CDR1 comprising SEQ ID NO:112, a Vl-CDR2 comprising SEQ ID NO:113, and a Vl-CDR3 comprising SEQ ID NO:114; and wherein said CDRs comprise a Vh-CDR1 comprising SEQ ID NO:16, a Vh-CDR2 comprising SEQ ID NO:17, a Vh-CDR3 comprising SEQ ID NO:18, a Vl-CDR1 comprising SEQ ID NO:118, a Vl-CDR2 comprising SEQ ID NO:119, and a Vl-CDR3 comprising SEQ ID NO:120.

Embodiment 36: The polypeptide or fragment of Embodiments 31-35, wherein said CDRs comprises a Vh-CDR1 comprising SEQ ID NO:4, a Vh-CDR2 comprising SEQ ID NO:5, a Vh-CDR3 comprising SEQ ID NO:6, a Vl-CDR1 comprising SEQ ID NO:106, a Vl-CDR2 comprising SEQ ID NO:107, and a Vl-CDR3 comprising SEQ ID NO:108.

Embodiment 37: The polypeptide or fragment of Embodiments 31-36, wherein said polypeptide or fragment comprises a Vl domain comprising SEQ ID NO:240 and an Vh domain comprising SEQ ID NO:206; wherein said polypeptide or fragment comprises a Vl domain comprising SEQ ID NO:242 and a Vh domain comprising SEQ ID NO:208; wherein said polypeptide or fragment comprises a Vl domain comprising SEQ ID NO:244 and a Vh domain comprising SEQ ID NO:210; wherein said polypeptide or fragment comprises a Vl domain comprising SEQ ID NO:246 and a Vh domain comprising SEQ ID NO:212; wherein said polypeptide or fragment comprises a Vl domain comprising SEQ ID NO:248 and a Vh domain comprising SEQ ID NO:214; wherein said polypeptide or fragment comprises a Vl domain comprising SEQ ID NO:250 and a Vh domain comprising SEQ ID NO:216; wherein said polypeptide or fragment comprises a Vl domain comprising SEQ ID NO:252 and a Vh domain comprising SEQ ID NO:218; wherein said polypeptide or fragment comprises a Vl domain comprising SEQ ID NO:254 and a Vh domain comprising SEQ ID NO:220; wherein said polypeptide or fragment comprises a Vl domain comprising SEQ ID NO:256 and a Vh domain comprising SEQ ID NO:222; wherein said polypeptide or fragment comprises a Vl domain comprising SEQ ID NO:258 and a Vh domain comprising SEQ ID NO:224; wherein said polypeptide or fragment comprises a Vl domain comprising SEQ ID NO:260 and a Vh domain comprising SEQ ID NO:226; wherein said polypeptide or fragment comprises a Vl comprising SEQ ID NO:262 and a Vh domain comprising SEQ ID NO:228; wherein said polypeptide or fragment comprises a Vl domain comprising SEQ ID NO:264 and a Vh domain comprising SEQ ID NO:230; wherein said polypeptide or fragment comprises a Vl domain comprising SEQ ID NO:266 and a Vh domain comprising SEQ ID NO:232; wherein said polypeptide or fragment comprises a Vl domain comprising SEQ ID NO:268 and a Vh domain comprising SEQ ID NO:234; wherein said polypeptide or fragment comprises a Vl domain comprising SEQ ID NO:270 and a Vh domain comprising SEQ ID NO:236; and wherein said polypeptide or fragment comprises a Vl domain comprising SEQ ID NO:272 and a Vh domain comprising SEQ ID NO:238) domain. Embodiment 38: The polypeptide or fragment of Embodiments 31-37, wherein said polypeptide or fragment comprises a Vl domain comprising SEQ ID NO:240 and a Vh domain comprising SEQ ID NO:206; wherein said polypeptide or fragment comprises a Vl domain comprising SEQ ID NO:242 and a Vh domain comprising SEQ ID NO:208; and wherein said polypeptide or fragment comprises a Vl domain comprising SEQ ID NO:244 and a Vh domain comprising SEQ ID NO:210. Embodiment 39: The polypeptide or fragment of Embodiments 31-38, wherein said polypeptide or fragment comprises a Vl domain comprising SEQ ID NO:240 and a Vh domain comprising SEQ ID NO:206. Embodiment 40: The polypeptide or fragment of Embodiments 31-39, wherein said polypeptide or fragment comprises an Ab-1 light chain comprising SEQ ID NO:280 and Ab-1 heavy chain comprising SEQ ID NO:274; wherein said polypeptide or fragment comprises an Ab-2 light chain comprising SEQ ID NO:282 and an Ab-2 heavy chain comprising SEQ ID NO:276; wherein said polypeptide or fragment comprises an Ab-3 light chain comprising SEQ ID NO:284 and an Ab-3 heavy chain comprising SEQ ID NO:278; wherein said polypeptide or fragment comprises two Ab-1 light chains comprising SEQ ID NO:280 and two Ab-1 heavy chains comprising SEQ ID NO:274; wherein said polypeptide or fragment comprises two Ab-2 light chains comprising SEQ ID NO:282 and two Ab-2 heavy chains comprising SEQ ID NO:276; and wherein said polypeptide or fragment comprises two Ab-3 light chains comprising SEQ ID NO:284 and two Ab-3 heavy chains comprising SEQ ID NO:278). Embodiment 41: The polypeptide or fragment of Embodiments 31-40, wherein said polypeptide or fragment comprises an Ab-1 light chain comprising SEQ ID NO:280 and Ab-1 heavy chain comprising SEQ ID NO:274; and wherein said polypeptide or fragment comprises two Ab-1 light chains comprising SEQ ID NO:280 and two Ab-1 heavy chains comprising SEQ ID NO:274. Embodiment 42: The polypeptide or fragment of Embodiments 31-41, wherein said polypeptide or fragment comprises two Ab-1 light chains comprising SEQ ID NO:280 and two Ab-1 heavy chains comprising SEQ ID NO:274. Embodiment 43: The polypeptide or fragment of Embodiments 31-42, wherein said polypeptide or fragment specifically binds human BCMA. Embodiment 44: The polypeptide or fragment of Embodiments 31-43, wherein said polypeptide or fragment specifically binds human BCMA and cross-reacts to cynomolgus BCMA. Embodiment 45: The polypeptide or fragment of Embodiments 31-44, wherein said polypeptide or fragment does not specifically bind to TACI or BAFF-R. Embodiment 46: The polypeptide or fragment of Embodiments 31-45, wherein said polypeptide or fragment binds BCMA on the surface of human myeloma cells. Embodiment 47: The polypeptide or fragment of Embodiments 31-46, wherein said polypeptide or fragment binds BCMA on the surface of human multiple myeloma cells. Embodiment 48: The polypeptide or fragment of Embodiments 31-47, wherein said polypeptide or fragment binds BCMA on the surface of human cells and is internalized by said cells. Embodiment 49: The polypeptide or fragment of Embodiments 31-48, wherein said polypeptide or fragment further comprises a linker. Embodiment 50: The polypeptide or fragment of Embodiments 31-49, wherein said polypeptide or fragment further comprises a drug or chemotherapeutic agent. Embodiment 51: The polypeptide or fragment of Embodiments 31-50, wherein said polypeptide or fragment further comprises a linker selected from the group consisting of: 6-maleimidocaproyl, maleimidopropanoyl, valine-citrulline, alanine-phenylalanine, p-aminobenzyloxycarbonyl, Mal-dPEG4-NHS, N-succinimidyl 4-(2-pyridylthio) pentanoate ("SPP"), N-succinimidyl 4-(N-maleimidomethyl) cyclohexane-1 carboxylate ("SMCC" or "MCC"), and N-succinimidyl (4-iodo-acetyl) aminobenzoate ("STAB"). Embodiment 52: The polypeptide or fragment of Embodiments 31-51, wherein said polypeptide or fragment further comprises a linker wherein said linker is N-succinimidyl 4-(N-maleimidomethyl) cyclohexane-1 carboxylate ("SMCC" or "MCC"). Embodiment 53: The polypeptide or fragment of Embodiments 31-52, wherein said polypeptide or fragment further comprises a drug or chemotherapeutic agent selected from the group consisting of: thiotepa and cyclophosphamide (CYTOXAN™); alkyl sulfonates such as busulfan, improsulfan and piposulfan; aziridines, such as benzodopa, carboquone, meturedopa, and uredopa; ethylenimines and methylamelamines including altretamine, triethylenemelamine, trietylenephosphoramide, triethylenethiophosphaoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics, such as the enediyne antibiotics (e.g. calicheamicin, especially calicheamicin .gamma1 and calicheamicin theta I, see, e.g., Angew Chem. Intl. Ed. Engl. 33:183-186 (1994); dynemicin, including dynemicin A; an esperamicin; as well as neocarzinostatin chromophore and related chromoprotein enediyne antiobiotic chromomophores), aclacinomysins, actinomycin, authramycin, azaserine, bleomycins, cactinomycin, carabicin, caminomycin, carzinophilin; chromomycins, dactinomycin, daunorubicin, detorubicin, 6-diazo-5-oxo-L-norleucine, doxorubicin (including morpholinodoxorubicin, cyanomorpholino-doxorubicin, 2-pyrrolinodoxorubicin and deoxydoxorubicin), epirubicin, esorubicin, idarubicin, marcellomycin, nitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites, such as methotrexate and 5-fluorouracil (5-FU); folic acid analogues, such as denopterin, methotrexate, pteropterin, trimetrexate; purine analogs, such as fludarabine, 6-mercaptopurine, thiamiprine, thioguanine; pyrimidine analogs such as, ancitabine, azacitidine, 6-azauridine, carmofur, cytarabine, dideoxyuridine, doxifluridine, enocitabine, floxuridine, 5-FU; androgens, such as calusterone, dromostanolone propionate, epitiostanol, mepitiostane, testolactone; anti-adrenals, such as aminoglutethimide, mitotane, trilostane; folic acid replenisher, such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidamine; maytansinoids, such as maytansine and ansamitocins; mitoguazone; mitoxantrone; mopidamol; nitracrine; pentostatin; phenamet; pirarubicin; podophyllinic acid; 2-ethylhydrazide; procarbazine; PSK®; razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL™, Bristol-Myers Squibb Oncology, Princeton, N.J.) and doxetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid; capecitabine; tamoxifen, raloxifene, aromatase inhibiting 4(5)-imidazoles, 4-hydroxytamoxifen, trioxifene, keoxifene, LY117018, onapristone, and toremifene (Fareston); and anti-androgens, such as flutamide, nilutamide, bicalutamide, leuprolide, goserelin, Colchicinesite Binders (Curacin), Combretastatins (AVE806, Combretastatin A-4 prodrug (CA4P), Oxi-4503), Cryptophycins (LY355703), Discodermolide, Dolastatin and Analogs (Auristatin PHE, Dolastatin 10, ILX-651, Symplostatin 1, TZT-1027), Epothilones (BMS-247550, BMS-310705, EP0906, KOS-862, ZK-EPO), Eleutherobin, FR182877, Halichondrin B (E7389), Halimide (NPI-2352 and NPI-2358), Hemiasterlins (HTI-286), Laulimalide, Maytansinoids ("DM1," "DM3" or "DM4") (Bivatuzumab mertansine, Cantuzumab mertansine, huN901-DM1/BB-10901TAP, MLN591DM1, My9-6-DM1, Trastuzumab-DM1), PC-SPES, Peloruside A, Resveratrol, S-allylmercaptocysteine (SAMC), Spongistatins, Vitilevuamide, Molecular Motor-Kinesins (SB-715992), Designed Colchicine-Site Binders (A-289099, A-293620/A-318315, ABT-751/E7010, D-24851/D-64131, ZD6126), Other Novel Spindle Poisons (2-Methoxyestradiol (2-ME2), Bezimidazole Carbamates (ANG 600 series, Mebendazole), CP248/CP461, HMN-214, R440, SDX-103, T67/T607). Embodiment 54: The polypeptide or fragment of Embodiments 31-53, wherein said polypeptide or fragment further comprises a drug or chemotherapeutic agent selected from the group consisting of: Maytansinoids ("DM1," "DM3" or "DM4"). Embodiment 55: The polypeptide or fragment of Embodiments 31-54, wherein said polypeptide or fragment further comprises DM1. Embodiment 56: The polypeptide or fragment of Embodiments 31-55, wherein said polypeptide or fragment has a drug to polypeptide ratio of between 1 and 10. Embodiment 57: The polypeptide or fragment of Embodiments 31-57, wherein said polypeptide or fragment has a drug to polypeptide ratio of between 2 and 5. Embodiment 58: A composition comprising the antibody, polypeptide, or fragments thereof of any of Embodiments 1-57. Embodiment 59: A pharmaceutical composition comprising the antibody, polypeptide, or fragments thereof of any of Embodiments 1-58. Embodiment 60: The pharmaceutical composition of Embodiment 59 further comprising a pharmaceutically acceptable diluent, carrier, solubilizer, emulsifier, and/or a preservative. Embodiment 61: A method of treating a disease, comprising administering an effective amount of the compositions of any of Embodiments 58-60, wherein the disease is selected from the group consisting of: B-cell cancers, multiple myeloma, malignant plasma cell neoplasms, Kahler's disease and Myelomatosis; Plasma cell leukemia; Plasmacytoma; B-cell prolymphocytic leukemia; Hairy cell leukemia; B-cell non-Hodgkin's lymphoma (NHL); Acute myeloid leukemia (AML); Chronic myeloid leukemia (CML); Acute lymphocytic leukemia (ALL); Chronic lymphocytic leukemia (CLL); Follicular lymphoma (including follicular non-Hodgkin's lymphoma types); Burkitt's lymphoma (Endemic Burkitt's lymphoma; Sporadic Burkitt's lymphoma); Marginal zone lymphoma (Mucosa-Associated Lymphoid Tissue; MALT/MALToma; Monocytoid B cell lymphoma; Splenic lymphoma with villous lymphocytes); Mantle cell lymphoma; Large cell lymphoma (Diffuse large cell; Diffuse Mixed Cell; Immunoblastic Lymphoma; Primary Mediastinal B Cell Lymphoma; Angiocentric Lymphoma—pulmonary B cell); Small lymphocytic lymphoma (SLL); Precursor B-lymphoblastic lymphoma; Myeloid leukemia (granulocytic; myelogenous; Acute myeloid leukemia; Chronic myeloid leukemia; Subacute myeloid leukemia; Myeloid sarcoma; Chloroma; Granulocytic sarcoma; Acute promyelocytic leukemia; Acute myelomonocytic leukemia); Waldenstrom's macroglobulinemia, or other B-cell lymphoma. Embodiment 62: The method of Embodiment 61, wherein the disease is selected from the group consisting of: B-cell cancers, multiple myeloma, malignant plasma cell neoplasms, or other B-cell lymphoma. Embodiment 63: The method of Embodiment 62, wherein the disease is multiple myeloma. Embodiment 64: The method of Embodiments 61-63, further comprising administering one of more additional treatments selected from the group consisting of: chemotherapy, radiation therapy, surgery, proteasome inhibitors, corticosteroids, and stem cell transplants. Embodiment 65: The method of Embodiment 64, wherein the administering of said additional treatment is prior to, concurrent with, or subsequent to, or a combination of each, the administration of the compositions of any of Embodiments 58-60. Embodiment 66: The method of Embodiments 62-65, wherein the compositions of any of Embodiments 58-60 is administered parenterally. Embodiment 67: An isolated polynucleotide, wherein said polynucleotide encodes the antibody or polypeptide of any of Embodiments 1-21 and 31-48. Embodiment 68: The polynucleotide of Embodiment 67, wherein said polynucleotide sequence comprises a Vh-CDR1 comprising SEQ ID NO:1, a Vh-CDR2 comprising SEQ ID NO:2, a Vh-CDR3 comprising SEQ ID NO:3, a Vl-CDR1 comprising SEQ ID NO:103, a Vl-CDR2 comprising SEQ ID NO:104, and a Vl-CDR3 comprising SEQ ID NO:105; wherein the polynucleotide sequence comprises a Vh-CDR1 comprising SEQ ID NO:7, a Vh-CDR2 comprising SEQ ID NO:8, a Vh-CDR3 comprising SEQ ID NO:9, a Vl-CDR1 comprising SEQ ID NO:109, a Vl-CDR2 comprising SEQ ID NO:110, and a Vl-CDR3 comprising SEQ ID NO:111; wherein the polynucleotide sequence comprises a Vh-CDR1 comprising SEQ ID NO:13, a Vh-CDR2 comprising SEQ ID NO:14, a Vh-CDR3 comprising SEQ ID NO:15, a Vl-CDR1 comprising SEQ ID NO:115, a Vl-CDR2 comprising SEQ ID NO:116, and a Vl-CDR3 comprising SEQ ID NO:117; wherein the polynucleotide sequence comprises a Vh-CDR1 comprising SEQ ID NO:19 comprising, a Vh-CDR2 comprising SEQ ID NO:20, a Vh-CDR3 comprising SEQ ID NO:21, a Vl-CDR1 comprising SEQ ID NO:121, a Vl-CDR2 comprising SEQ ID NO:122, and a Vl-CDR3 comprising SEQ ID NO:123; wherein the polynucleotide sequence comprises a Vh-CDR1 comprising SEQ ID NO:25, a Vh-CDR2 comprising SEQ ID NO:26, a Vh-CDR3 comprising SEQ ID NO:27, a Vl-CDR1 comprising SEQ ID NO:127, a Vl-CDR2 comprising SEQ ID NO:128, and a Vl-CDR3 comprising SEQ ID NO:129; wherein the polynucleotide sequence comprises a Vh-CDR1 comprising SEQ ID NO:31, a Vh-CDR2 comprising SEQ ID NO:32, a Vh-CDR3 comprising SEQ ID NO:33, a Vl-CDR1 comprising SEQ ID NO:133, a Vl-CDR2 comprising SEQ ID NO:134, and a Vl-CDR3 comprising SEQ ID NO:135; wherein the polynucleotide sequence comprises a Vh-CDR1 comprising SEQ ID NO:37, a Vh-CDR2 comprising SEQ ID NO:38, a Vh-CDR3 comprising SEQ ID NO:39, a Vl-CDR1 comprising SEQ ID NO:139, a Vl-CDR2 comprising SEQ ID NO:140, and a Vl-CDR3 comprising SEQ ID NO:141; wherein the polynucleotide sequence comprises a Vh-CDR1 comprising SEQ ID NO:43, a Vh-CDR2 comprising SEQ ID NO:44, a Vh-CDR3 comprising SEQ ID NO:45, a Vl-CDR1 comprising SEQ ID NO:145, a Vl-CDR2 comprising SEQ ID NO:146, and a Vl-CDR3 comprising SEQ ID NO:147; wherein the polynucleotide sequence comprises a Vh-CDR1 comprising SEQ ID NO:49, a Vh-CDR2 comprising SEQ ID NO:50, a Vh-CDR3 comprising SEQ ID NO:51, a Vl-CDR1 comprising SEQ ID NO:151, a Vl-CDR2 comprising SEQ ID NO:152, and a Vl-CDR3 comprising SEQ ID NO:153; wherein the polynucleotide sequence comprises a Vh-CDR1 comprising SEQ ID NO:55, a Vh-CDR2 comprising SEQ ID NO:56, a Vh-CDR3 comprising SEQ ID NO:57, a Vl-CDR1 comprising SEQ ID NO:157, a Vl-CDR2 comprising SEQ ID NO:158, and a Vl-CDR3 comprising SEQ ID NO:159; wherein the polynucleotide sequence comprises a Vh-CDR1 comprising SEQ ID NO:61, a Vh-CDR2 comprising SEQ ID NO:62, a Vh-CDR3 comprising SEQ ID NO:63, a Vl-CDR1 comprising SEQ ID NO:163, a Vl-CDR2 comprising SEQ ID NO:164, and a Vl-CDR3 comprising SEQ ID NO:165; wherein the polynucleotide sequence comprises a Vh-CDR1 comprising SEQ ID NO:67, a Vh-CDR2 comprising SEQ ID NO:68, a Vh-CDR3 comprising SEQ ID NO:69, a Vl-CDR1 comprising SEQ ID NO:169, a Vl-CDR2 comprising SEQ ID NO:170, and a Vl-CDR3 comprising SEQ ID NO:171; wherein the polynucleotide sequence comprises a Vh-CDR1 comprising SEQ ID NO:73, a Vh-CDR2 comprising SEQ ID NO:74, a Vh-CDR3 comprising SEQ ID NO:75, a Vl-CDR1 comprising SEQ ID NO:175, a Vl-CDR2 comprising SEQ ID NO:176, and a Vl-CDR3 comprising SEQ ID NO:177; wherein the polynucleotide sequence comprises a Vh-CDR1 comprising SEQ ID NO:79, a Vh-CDR2 comprising SEQ ID NO:80, a Vh-CDR3 comprising SEQ ID NO:81, a Vl-CDR1 comprising SEQ ID NO:181, a Vl-CDR2 comprising SEQ ID NO:182, and a Vl-CDR3 comprising SEQ ID NO:183; wherein the polynucleotide sequence comprises a Vh-CDR1 comprising SEQ ID NO:85, a Vh-CDR2 comprising SEQ ID NO:86, a Vh-CDR3 comprising SEQ ID NO:87, a Vl-CDR1 comprising SEQ ID NO:187, a Vl-CDR2 comprising SEQ ID NO:188, and a Vl-CDR3 comprising SEQ ID NO:189; wherein the polynucleotide sequence comprises a Vh-CDR1 comprising SEQ ID NO:91, a Vh-CDR2 comprising SEQ ID NO:92, a Vh-CDR3 comprising SEQ ID NO:93, a Vl-CDR1 comprising SEQ ID NO:193, a Vl-CDR2 comprising SEQ ID NO:194, and a Vl-CDR3 comprising SEQ ID NO:195; and wherein the polynucleotide sequence comprises a Vh-CDR1 comprising SEQ ID NO:97, a Vh-CDR2 comprising SEQ ID NO:98, a Vh-CDR3 comprising SEQ ID NO:99, a Vl-CDR1 comprising SEQ ID NO:199, a Vl-CDR2 comprising SEQ ID NO:200, and a Vl-CDR3 comprising SEQ ID NO:201. Embodiment 69: The polynucleotide of Embodiments 67-68, wherein said polynucleotide sequence comprises a Vh-CDR1 comprising SEQ ID NO:1, a Vh-CDR2 comprising SEQ ID NO:2, a Vh-CDR3 comprising SEQ ID NO:3, a Vl-CDR1 comprising SEQ ID NO:103, a Vl-CDR2 comprising SEQ ID NO:104, and a Vl-CDR3 comprising SEQ ID NO:105; wherein the polynucleotide sequence comprises a Vh-CDR1 comprising SEQ ID NO:7, a Vh-CDR2 comprising SEQ ID NO:8, a Vh-CDR3 comprising SEQ ID NO:9, a Vl-CDR1 comprising SEQ ID NO:109, a Vl-CDR2 comprising SEQ ID NO:110, and a Vl-CDR3 comprising SEQ ID NO:111; and wherein the polynucleotide sequence comprises a Vh-CDR1 comprising SEQ ID NO:13, a Vh-CDR2 comprising SEQ ID NO:14, a Vh-CDR3 comprising SEQ ID NO:15, a Vl-CDR1 comprising SEQ ID NO:115, a Vl-CDR2 comprising SEQ ID NO:116, and a Vl-CDR3 comprising SEQ ID NO:117. Embodiment 70: The polynucleotide of Embodiments 67-69, wherein said polynucleotide sequence comprises a Vh-CDR1 comprising SEQ ID NO:1, a Vh-CDR2 comprising SEQ ID NO:2, a Vh-CDR3 comprising SEQ ID NO:3, a Vl-CDR1 comprising SEQ ID NO:103, a Vl-CDR2 comprising SEQ ID NO:104, and a Vl-CDR3 comprising SEQ ID NO:105. Embodiment 71: The polynucleotide of Embodiments 67-70, wherein said polynucleotide sequence comprises an Ab-1Vl comprising SEQ ID NO:239 and an Ab-1Vh comprising SEQ ID NO:205; wherein the polynucleotide sequence comprises an Ab-2Vl comprising SEQ ID NO:241 and an Ab-2Vh comprising SEQ ID NO:207; wherein the polynucleotide sequence comprises an Ab-3Vl comprising SEQ ID NO:243 and an Ab-3Vh comprising SEQ ID NO:209; wherein the polynucleotide sequence comprises an Ab-4Vl comprising SEQ ID NO:245 and an Ab-4Vh comprising SEQ ID NO:211; wherein the polynucleotide sequence comprises an Ab-5Vl comprising SEQ ID NO:247 and an Ab-5Vh comprising SEQ ID NO:213; wherein the polynucleotide sequence comprises an Ab-6Vl comprising SEQ ID NO:249 and an Ab-6Vh comprising SEQ ID NO:215; wherein the polynucleotide sequence comprises an Ab-7Vl comprising SEQ ID NO:251 and an Ab-7Vh comprising SEQ ID NO:217; wherein the polynucleotide sequence comprises an Ab-8Vl comprising SEQ ID NO:253 and an Ab-8Vh comprising SEQ ID NO:219; wherein the polynucleotide sequence comprises an Ab-9Vl comprising SEQ ID NO:255 and an Ab-9Vh comprising SEQ ID NO:221; wherein the polynucleotide sequence comprises an Ab-10Vl comprising SEQ ID NO:257 and an Ab-10Vh comprising SEQ ID NO:223; wherein the polynucleotide sequence comprises an Ab-11Vl comprising SEQ ID NO:259 and an Ab-11Vh comprising SEQ ID NO:225; wherein the polynucleotide sequence comprises an Ab-12Vl comprising SEQ ID NO:261 and an Ab-12Vh comprising SEQ ID NO:227; wherein the polynucleotide sequence comprises an Ab-13Vl comprising SEQ ID NO:263 and an Ab-13Vh comprising SEQ ID NO:229; wherein the polynucleotide sequence comprises an Ab-14Vl comprising SEQ ID NO:265 and an Ab-14Vh comprising SEQ ID NO:231; wherein the polynucleotide sequence comprises an Ab-15Vl comprising SEQ ID NO:267 and an Ab-15Vh comprising SEQ ID NO:233; wherein the polynucleotide sequence comprises an Ab-16Vl comprising SEQ ID NO:269 and an Ab-16Vh comprising SEQ ID NO:235; and wherein the polynucleotide sequence comprises an Ab-17Vl comprising SEQ ID NO:271 and an Ab-17Vh comprising SEQ ID NO:237. Embodiment 72: The polynucleotide of Embodiments 67-71, wherein said polynucleotide sequence comprises an Ab-1Vl comprising SEQ ID NO:239 and an Ab-1Vh comprising SEQ ID NO:205; wherein the polynucleotide sequence comprises an Ab-2Vl comprising SEQ ID NO:241 and an Ab-2Vh comprising SEQ ID NO:207; and wherein the polynucleotide sequence comprises an Ab-3Vl comprising SEQ ID NO:243 and an Ab-3Vh comprising SEQ ID NO:209. Embodiment 73: The polynucleotide of Embodiments 67-72, wherein said polynucleotide sequence comprises an Ab-1Vl comprising SEQ ID NO:239 and an Ab-1Vh comprising SEQ ID NO:205. Embodiment 74: The polynucleotide of Embodiments 67-72, wherein said polynucleotide sequence comprises a light chain comprising SEQ ID NO:279 and a heavy chain comprising SEQ ID NO:273; wherein the polynucleotide sequence comprises a light chain comprising SEQ ID NO:281 and a heavy chain comprising SEQ ID NO:275; and wherein the polynucleotide sequence comprises a light chain comprising SEQ ID NO:283 and a heavy chain comprising SEQ ID NO:277. Embodiment 75: A plasmid, comprising the polynucleotide of any of Embodiments 67-72. Embodiment 76: The plasmid of Embodiment 75, wherein said plasmid comprises an expression vector. Embodiment 77: An isolated cell, comprising said plasmid of Embodiment 76, wherein said cell is selected from the group consisting of: a. a prokaryotic cell; b. a eukaryotic cell; c. a mammalian cell; d. an insect cell; and e. a CHO cell. Embodiment 78: A method of making the antibody or polypeptide of any of Embodiments 1-21 and 31-48, comprising incubating said isolated cell of Embodiment 77 under conditions that allow it to express said antibody or polypeptide. Embodiment 79: An isolated antibody, comprising an antibody produced by the CHO cell of Embodiment 77, wherein the antibody comprises a heavy chain encoded by a sequence comprising SEQ ID NO:273 and a light chain encoded by a sequence comprising SEQ ID NO:279. Embodiment 80: A pharmaceutical composition, comprising the antibody of Embodiment 79. Embodiment 81: An isolated monoclonal antibody, comprising a monoclonal antibody that specifically binds to SEQ ID NO:285 and SEQ ID NO:286, but does not specifically bind SEQ ID NO:351. Embodiment 82: The antibody of Embodiment 81, wherein said antibody is a human monoclonal antibody. Embodiment 83: The antibody of Embodiment 82, wherein said antibody is an IgG. Embodiment 84: An isolated monoclonal antibody, comprising a monoclonal antibody that specifically binds to SEQ ID NO:352, but does not specifically bind SEQ ID NO:351. Embodiment 85: The antibody of Embodiment 84, wherein said antibody is a human monoclonal antibody. Embodiment 86: The antibody of Embodiment 85, wherein said antibody is an IgG. Embodiment 87: The antibody of Embodiment 85, wherein said antibody is an IgG1. Embodiment 88: The antibody of any of Embodiments 81 to 87, wherein said antibody specifically binds SEQ ID NO:352 with a Kd of between 1 nM and 0.01 nM, and binds SEQ ID NO:351 with a Kd of greater than 10 nM. Embodiment 89: The antibody of any of Embodiments 81 to 88, wherein said antibody specifically binds SEQ ID NO:352 with a Kd of about 0.16 nM, and binds SEQ ID NO:351 with a Kd of greater than 10 nM. Embodiment 90: An isolated monoclonal antibody, comprising a monoclonal antibody that binds a neutralizing determinant comprising amino acids 1 though 20 (inclusive) of SEQ ID NO: 285. Embodiment 91: The antibody of Embodiment 90, wherein said antibody is a human monoclonal antibody. Embodiment 92: The antibody of Embodiment 91, wherein said antibody is an IgG. Embodiment 93: The antibody of Embodiment 92, wherein said antibody is an IgG1. Embodiment 94: An isolated monoclonal antibody, comprising a monoclonal antibody that binds a neutralizing determinant comprising amino acids 1 through 11 (inclusive) of SEQ ID NO: 285. Embodiment 95: The antibody of Embodiment 94, wherein said antibody is a human monoclonal antibody. Embodiment 96: The antibody of Embodiment 95, wherein said antibody is an IgG. Embodiment 97: The antibody of Embodiment 96, wherein said antibody is an IgG1. Embodiment 98: The antibody of any of Embodiments 90 to 97, wherein said antibody binds SEQ ID NO: 285 with a Kd of less than or equal to 1 nM. Embodiment 99: The antibody of any of Embodiments 90 to 98, wherein said antibody binds SEQ ID NO: 352 with a Kd of about 0.16 nM±0.1 nM as measured in a biosensor assay. Embodiment 100: The antibody of any of Embodiments 90 to 97, wherein said antibody binds SEQ ID NO: 285 expressed on the surface of H929 cells with an EC50 of less than or equal to 10 nM. Embodiment 101: The antibody of any of Embodiments 90 to 97, wherein said antibody binds SEQ ID NO: 285 expressed on the surface of H929 cells with an EC50 of less than or equal to 10 nM. Embodiment 102: The antibody of any of Embodiments 90 to 97 and 101, wherein said antibody binds SEQ ID NO: 285 expressed on the surface of H929 cells with an EC50 of about 1.2 nM by FACS analysis. Embodiment 103: The antibody of any of Embodiments 90 to 97, wherein said antibody binds SEQ ID NO: 285 with a Kd of less than or equal to 1 nM, and wherein said antibody binds SEQ ID NO: 285 expressed on the surface of H929 cells with an EC50 of less than or equal to 10 nM. Embodiment 104: The antibody of any of Embodiments 90 to 97 and 103, wherein said antibody binds SEQ ID NO: 352 with a Kd of about 0.16 nM as measured in a biosensor assay described in Example 16, and wherein said antibody binds SEQ ID NO: 285 expressed on the surface of H929 cells with an EC50 of about 1.2 nM by FACS analysis. Embodiment 105: The antibody of any of Embodiments 1-3 and 31-33, wherein the six CDRs are determined by any one of the AHo, Kabat, or Clothia numbering systems. Embodiment 106: The antibody of any of Embodiments 1-14, wherein the antibody is a human monoclonal IgG antibody. Embodiment 107: The antibody of any of Embodiments 1-14 and 106, wherein the antibody is a human monoclonal IgG1 antibody.

In embodiments where the BCMA antigen binding protein is used for therapeutic applications, one characteristic of a BCMA antigen binding protein is that it can inhibit BAFF and/or APRIL from activating BCMA. Such antibodies are considered neutralizing antibodies because of their capacity to inhibit BAFF and/or APRIL from activating BCMA. In this case, an antigen binding protein specifically binds BCMA and inhibits the biological activity of BAFF and/or APRIL to BCMA from anywhere between 10 to 100%, such as by at least about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% or more (for example by measuring binding in an in vitro competitive binding assay as described herein, such as in Example 2. Aspects of the invention include human monoclonal antibodies that specifically bind human BCMA and inhibit the binding of human APRIL to human BCMA by about 89% (±5%), such as Ab-1, under the assay conditions described in Example 2, or a comparable assay.

Embodiments of antigen binding proteins comprise a scaffold structure, as variously define herein, with one or more complementarity determining regions (CDRs). Embodiments of antigen binding proteins comprise a scaffold structure with one or more variable domains. Embodiments include antibodies listed in TABLE 1, as well as fragments, derivatives, muteins, and variants thereof. Embodiments include ADCs of the antibodies listed in TABLE 1. The sequences for the antibodies listed in TABLE 1 are provided in the sequence listing.

TABLE 1

| Antibody | Amino Acid SEQ ID NO: | Nucleic Acid SEQ ID NO: |
| --- | --- | --- |
| Ab-1 (2A1CV5) | | |
| Full length heavy chain | 274 | 273 |
| Full length light chain | 280 | 279 |
| Vh | 206 | 205 |
| Vl | 240 | 239 |
| Vh CDR1 | 4 | 1 |
| Vh CDR2 | 5 | 2 |
| Vh CDR3 | 6 | 3 |
| Vl CDR1 | 106 | 103 |
| Vl CDR2 | 107 | 104 |
| Vl CDR3 | 108 | 105 |
| Ab-2 (29C12_mut) | | |
| Full length heavy chain | 276 | 275 |
| Full length light chain | 282 | 281 |
| Vh | 208 | 207 |
| Vl | 242 | 241 |
| Vh CDR1 | 10 | 7 |
| Vh CDR2 | 11 | 8 |
| Vh CDR3 | 12 | 9 |
| Vl CDR1 | 112 | 109 |
| Vl CDR2 | 113 | 110 |
| Vl CDR3 | 114 | 111 |
| Ab-3 (32B5_mut) | | |
| Full length heavy chain | 278 | 277 |
| Full length light chain | 284 | 283 |
| Vh | 210 | 209 |
| Vl | 244 | 243 |
| Vh CDR1 | 16 | 13 |
| Vh CDR2 | 17 | 14 |
| Vh CDR3 | 18 | 15 |
| Vl CDR1 | 118 | 115 |
| Vl CDR2 | 119 | 116 |
| Vl CDR3 | 120 | 117 |
| Ab-4 (1E1) | | |
| Vh | 212 | 211 |
| Vl | 246 | 245 |
| Vh CDR1 | 22 | 19 |
| Vh CDR2 | 23 | 20 |
| Vh CDR3 | 24 | 21 |
| Vl CDR1 | 124 | 121 |
| Vl CDR2 | 125 | 122 |
| Vl CDR3 | 126 | 123 |
| Ab-5 (2A1) | | |
| Vh | 214 | 213 |
| Vl | 248 | 247 |
| Vh CDR1 | 28 | 25 |
| Vh CDR2 | 29 | 26 |
| Vh CDR3 | 30 | 27 |
| Vl CDR1 | 130 | 127 |
| Vl CDR2 | 131 | 128 |
| Vl CDR3 | 132 | 129 |
| Ab-6 (11F12_LC#1) | | |
| Vh | 216 | 215 |
| Vl | 250 | 249 |
| Vh CDR1 | 34 | 31 |
| Vh CDR2 | 35 | 32 |
| Vh CDR3 | 36 | 33 |
| Vl CDR1 | 136 | 133 |
| Vl CDR2 | 137 | 134 |
| Vl CDR3 | 138 | 135 |
| Ab-7 (11F12_LC#2) | | |
| Vh | 218 | 217 |
| Vl | 252 | 251 |
| Vh CDR1 | 40 | 37 |
| Vh CDR2 | 41 | 38 |
| Vh CDR3 | 42 | 39 |
| Vl CDR1 | 142 | 139 |
| Vl CDR2 | 143 | 140 |
| Vl CDR3 | 144 | 141 |
| Ab-8 (29C12) | | |
| Vh | 220 | 219 |
| Vl | 254 | 253 |
| Vh CDR1 | 46 | 43 |
| Vh CDR2 | 47 | 44 |
| Vh CDR3 | 48 | 45 |
| Vl CDR1 | 148 | 145 |
| Vl CDR2 | 149 | 146 |
| Vl CDR3 | 150 | 147 |
| Ab-9 (30E1) | | |
| Vh | 222 | 221 |
| Vl | 256 | 255 |
| Vh CDR1 | 52 | 49 |
| Vh CDR2 | 53 | 50 |
| Vh CDR3 | 54 | 51 |
| Vl CDR1 | 154 | 151 |
| Vl CDR2 | 155 | 152 |
| Vl CDR3 | 156 | 153 |
| Ab-10 (32B5) | | |
| Vh | 224 | 223 |
| Vl | 258 | 257 |
| Vh CDR1 | 58 | 55 |
| Vh CDR2 | 59 | 56 |
| Vh CDR3 | 60 | 57 |
| Vl CDR1 | 160 | 157 |
| Vl CDR2 | 161 | 158 |
| Vl CDR3 | 162 | 159 |
| Ab-11 (33C7_HC#1) | | |
| Vh | 226 | 225 |
| Vl | 260 | 259 |
| Vh CDR1 | 64 | 61 |
| Vh CDR2 | 65 | 62 |
| Vh CDR3 | 66 | 63 |
| Vl CDR1 | 166 | 163 |
| Vl CDR2 | 167 | 164 |
| Vl CDR3 | 168 | 165 |
| Ab-12 (32H3) | | |
| Vh | 228 | 227 |
| Vl | 262 | 261 |
| Vh CDR1 | 70 | 67 |
| Vh CDR2 | 71 | 68 |
| Vh CDR3 | 72 | 69 |
| Vl CDR1 | 172 | 169 |
| Vl CDR2 | 173 | 170 |
| Vl CDR3 | 174 | 171 |
| Ab-13 (33C7_HC#2) | | |
| Vh | 230 | 229 |
| Vl | 264 | 263 |
| Vh CDR1 | 76 | 73 |
| Vh CDR2 | 77 | 74 |
| Vh CDR3 | 78 | 75 |
| Vl CDR1 | 178 | 175 |
| Vl CDR2 | 178 | 176 |
| Vl CDR3 | 180 | 177 |
| Ab-14 (33D4) | | |
| Vh | 232 | 231 |
| Vl | 266 | 265 |

TABLE 1-continued

| Antibody | Amino Acid SEQ ID NO: | Nucleic Acid SEQ ID NO: |
|---|---|---|
| Vh CDR1 | 82 | 79 |
| Vh CDR2 | 83 | 80 |
| Vh CDR3 | 84 | 81 |
| Vl CDR1 | 184 | 181 |
| Vl CDR2 | 185 | 182 |
| Vl CDR3 | 186 | 183 |
| Ab-15 (35D2) | | |
| Vh | 234 | 233 |
| Vl | 268 | 267 |
| Vh CDR1 | 88 | 85 |
| Vh CDR2 | 89 | 86 |
| Vh CDR3 | 90 | 87 |
| Vl CDR1 | 190 | 187 |
| Vl CDR2 | 191 | 188 |
| Vl CDR3 | 192 | 189 |
| Ab-16 (37B2) | | |
| Vh | 236 | 235 |
| Vl | 270 | 269 |
| Vh CDR1 | 94 | 91 |
| Vh CDR2 | 95 | 92 |
| Vh CDR3 | 96 | 93 |
| Vl CDR1 | 196 | 193 |
| Vl CDR2 | 197 | 194 |
| Vl CDR3 | 198 | 195 |
| Ab-17 (40D7) | | |
| Vh | 238 | 237 |
| Vl | 272 | 271 |
| Vh CDR1 | 100 | 97 |
| Vh CDR2 | 101 | 98 |
| Vh CDR3 | 103 | 99 |
| Vl CDR1 | 202 | 199 |
| Vl CDR2 | 203 | 200 |
| Vl CDR3 | 204 | 201 |

The CDR domains for the various antibodies described herein were characterized using the AHo system of numbering. The AHo system of numbering is well known in the art, see Honegger, A., and Plückthun, A. (2001), *J. Mol. Biol.* 309, 657-670. Embodiments of the invention include antibodies comprising the CDRs found in the Vh and Vl domains in TABLE 2 that are identified using other conventional numbering systems, such as the Kabat and Clothia numbering systems. Such numbering systems are well-known in the art (see, http://www.bioc.uzh.ch/antibody). For a comparison of these CDR numbering systems see: http://www.bioc.uzh.ch/antibody/Numbering/NumFrame.html.

Aspects of the invention include isolated monoclonal antibodies comprising the six CDRs of Ab-1. Aspects of the invention include isolated monoclonal antibodies comprising the six CDRs of Ab-2. Aspects of the invention include isolated monoclonal antibodies comprising the six CDRs of Ab-3. Aspects of the invention include isolated monoclonal antibodies comprising the six CDRs of Ab-4. Aspects of the invention include isolated monoclonal antibodies comprising the six CDRs of Ab-5. Aspects of the invention include isolated monoclonal antibodies comprising the six CDRs of Ab-6. Aspects of the invention include isolated monoclonal antibodies comprising the six CDRs of Ab-7. Aspects of the invention include isolated monoclonal antibodies comprising the six CDRs of Ab-8. Aspects of the invention include isolated monoclonal antibodies comprising the six CDRs of Ab-9. Aspects of the invention include isolated monoclonal antibodies comprising the six CDRs of Ab-10. Aspects of the invention include isolated monoclonal antibodies comprising the six CDRs of Ab-11. Aspects of the invention include isolated monoclonal antibodies comprising the six CDRs of Ab-12. Aspects of the invention include isolated monoclonal antibodies comprising the six CDRs of Ab-13. Aspects of the invention include isolated monoclonal antibodies comprising the six CDRs of Ab-14. Aspects of the invention include isolated monoclonal antibodies comprising the six CDRs of Ab-15. Aspects of the invention include isolated monoclonal antibodies comprising the six CDRs of Ab-16. Aspects of the invention include isolated monoclonal antibodies comprising the six CDRs of Ab-17. Aspects of the aforementioned embodiments include human monoclonal antibodies, human monoclonal IgG antibodies, and human monoclonal IgG1 antibodies.

Aspects of the invention include isolated monoclonal antibodies comprising the six CDRs of Ab-1 as determined by any one of the AHo, Kabat, or Clothia numbering systems. Aspects of the invention include isolated monoclonal antibodies comprising the six CDRs of Ab-2 as determined by any one of the AHo, Kabat, or Clothia numbering systems. Aspects of the invention include isolated monoclonal antibodies comprising the six CDRs of Ab-3 as determined by any one of the AHo, Kabat, or Clothia numbering systems. Aspects of the invention include isolated monoclonal antibodies comprising the six CDRs of Ab-4 as determined by any one of the AHo, Kabat, or Clothia numbering systems. Aspects of the invention include isolated monoclonal antibodies comprising the six CDRs of Ab-5 as determined by any one of the AHo, Kabat, or Clothia numbering systems. Aspects of the invention include isolated monoclonal antibodies comprising the six CDRs of Ab-6 as determined by any one of the AHo, Kabat, or Clothia numbering systems. Aspects of the invention include isolated monoclonal antibodies comprising the six CDRs of Ab-7 as determined by any one of the AHo, Kabat, or Clothia numbering systems. Aspects of the invention include isolated monoclonal antibodies comprising the six CDRs of Ab-8 as determined by any one of the AHo, Kabat, or Clothia numbering systems. Aspects of the invention include isolated monoclonal antibodies comprising the six CDRs of Ab-9 as determined by any one of the AHo, Kabat, or Clothia numbering systems. Aspects of the invention include isolated monoclonal antibodies comprising the six CDRs of Ab-10 as determined by any one of the AHo, Kabat, or Clothia numbering systems. Aspects of the invention include isolated monoclonal antibodies comprising the six CDRs of Ab-11 as determined by any one of the AHo, Kabat, or Clothia numbering systems. Aspects of the invention include isolated monoclonal antibodies comprising the six CDRs of Ab-12 as determined by any one of the AHo, Kabat, or Clothia numbering systems. Aspects of the invention include isolated monoclonal antibodies comprising the six CDRs of Ab-13 as determined by any one of the AHo, Kabat, or Clothia numbering systems. Aspects of the invention include isolated monoclonal antibodies comprising the six CDRs of Ab-14 as determined by any one of the AHo, Kabat, or Clothia numbering systems. Aspects of the invention include isolated monoclonal antibodies comprising the six CDRs of Ab-15 as determined by any one of the AHo, Kabat, or Clothia numbering systems. Aspects of the invention include isolated monoclonal antibodies comprising the six CDRs of Ab-16 as determined by any one of the AHo, Kabat, or Clothia numbering systems. Aspects of the invention include isolated monoclonal antibodies comprising the six CDRs of Ab-17 as determined by any one of the AHo, Kabat, or Clothia numbering systems. Aspects of the aforementioned embodiments include human monoclonal antibodies, human monoclonal IgG antibodies, and human monoclonal IgG1 antibodies.

Aspects of the invention include isolated monoclonal antibodies comprising the six CDRs of Ab-1, specifically Vh-CDR1 (SEQ ID NO:4), Vh-CDR2 (SEQ ID NO:5), Vh-CDR3 (SEQ ID NO:6), Vl-CDR1 (SEQ ID NO:106), Vl-CDR2 (SEQ ID NO:107), and Vl-CDR3 (SEQ ID NO:108). Aspects of the invention include isolated monoclonal antibodies comprising the six CDRs of Ab-2, specifically Vh-CDR1 (SEQ ID NO:10), Vh-CDR2 (SEQ ID NO:11), Vh-CDR3 (SEQ ID NO:12), Vl-CDR1 (SEQ ID NO:112), Vl-CDR2 (SEQ ID NO:113), and Vl-CDR3 (SEQ ID NO:114). Aspects of the invention include isolated monoclonal antibodies comprising the six CDRs of Ab-3, specifically Vh-CDR1 (SEQ ID NO:16), Vh-CDR2 (SEQ ID NO:17), Vh-CDR3 (SEQ ID NO:18), Vl-CDR1 (SEQ ID NO:118), Vl-CDR2 (SEQ ID NO:119), and Vl-CDR3 (SEQ ID NO:120). Aspects of the invention include isolated monoclonal antibodies comprising the six CDRs of Ab-4, specifically Vh-CDR1 (SEQ ID NO:22), Vh-CDR2 (SEQ ID NO:23), Vh-CDR3 (SEQ ID NO:24), Vl-CDR1 (SEQ ID NO:124), Vl-CDR2 (SEQ ID NO:125), and Vl-CDR3 (SEQ ID NO:126). Aspects of the invention include isolated monoclonal antibodies comprising the six CDRs of Ab-5, specifically Vh-CDR1 (SEQ ID NO:28), Vh-CDR2 (SEQ ID NO:29), Vh-CDR3 (SEQ ID NO:30), Vl-CDR1 (SEQ ID NO:130), Vl-CDR2 (SEQ ID NO:131), and Vl-CDR3 (SEQ ID NO:132). Aspects of the invention include isolated monoclonal antibodies comprising the six CDRs of Ab-6, specifically Vh-CDR1 (SEQ ID NO:34), Vh-CDR2 (SEQ ID NO:35), Vh-CDR3 (SEQ ID NO:36), Vl-CDR1 (SEQ ID NO:136), Vl-CDR2 (SEQ ID NO:137), and Vl-CDR3 (SEQ ID NO:138). Aspects of the invention include isolated monoclonal antibodies comprising the six CDRs of Ab-7, specifically Vh-CDR1 (SEQ ID NO:40), Vh-CDR2 (SEQ ID NO:41), Vh-CDR3 (SEQ ID NO:42), Vl-CDR1 (SEQ ID NO:142), Vl-CDR2 (SEQ ID NO:143), and Vl-CDR3 (SEQ ID NO:144). Aspects of the invention include isolated monoclonal antibodies comprising the six CDRs of Ab-8, specifically Vh-CDR1 (SEQ ID NO:46), Vh-CDR2 (SEQ ID NO:47), Vh-CDR3 (SEQ ID NO:48), Vl-CDR1 (SEQ ID NO:148), Vl-CDR2 (SEQ ID NO:149), and Vl-CDR3 (SEQ ID NO:150). Aspects of the invention include isolated monoclonal antibodies comprising the six CDRs of Ab-9, specifically Vh-CDR1 (SEQ ID NO:52), Vh-CDR2 (SEQ ID NO:53), Vh-CDR3 (SEQ ID NO:54), Vl-CDR1 (SEQ ID NO:154), Vl-CDR2 (SEQ ID NO:155), and Vl-CDR3 (SEQ ID NO:156). Aspects of the invention include isolated monoclonal antibodies comprising the six CDRs of Ab-10, specifically Vh-CDR1 (SEQ ID NO:58), Vh-CDR2 (SEQ ID NO:59), Vh-CDR3 (SEQ ID NO:60), Vl-CDR1 (SEQ ID NO:160), Vl-CDR2 (SEQ ID NO:161), and Vl-CDR3 (SEQ ID NO:162). Aspects of the invention include isolated monoclonal antibodies comprising the six CDRs of Ab-11, specifically Vh-CDR1 (SEQ ID NO:64), Vh-CDR2 (SEQ ID NO:65), Vh-CDR3 (SEQ ID NO:66), Vl-CDR1 (SEQ ID NO:166), Vl-CDR2 (SEQ ID NO:167), and Vl-CDR3 (SEQ ID NO:168). Aspects of the invention include isolated monoclonal antibodies comprising the six CDRs of Ab-12, specifically Vh-CDR1 (SEQ ID NO:70), Vh-CDR2 (SEQ ID NO:71), Vh-CDR3 (SEQ ID NO:72), Vl-CDR1 (SEQ ID NO:172), Vl-CDR2 (SEQ ID NO:173), and Vl-CDR3 (SEQ ID NO:174). Aspects of the invention include isolated monoclonal antibodies comprising the six CDRs of Ab-13, specifically Vh-CDR1 (SEQ ID NO:76), Vh-CDR2 (SEQ ID NO:77), Vh-CDR3 (SEQ ID NO:78), Vl-CDR1 (SEQ ID NO:178), Vl-CDR2 (SEQ ID NO:179), and Vl-CDR3 (SEQ ID NO:180). Aspects of the invention include isolated monoclonal antibodies comprising the six CDRs of Ab-14, specifically Vh-CDR1 (SEQ ID NO:82), Vh-CDR2 (SEQ ID NO:83), Vh-CDR3 (SEQ ID NO:84), Vl-CDR1 (SEQ ID NO:184), Vl-CDR2 (SEQ ID NO:185), and Vl-CDR3 (SEQ ID NO:186). Aspects of the invention include isolated monoclonal antibodies comprising the six CDRs of Ab-15, specifically Vh-CDR1 (SEQ ID NO:88), Vh-CDR2 (SEQ ID NO:89), Vh-CDR3 (SEQ ID NO:90), Vl-CDR1 (SEQ ID NO:190), Vl-CDR2 (SEQ ID NO:191), and Vl-CDR3 (SEQ ID NO:192). Aspects of the invention include isolated monoclonal antibodies comprising the six CDRs of Ab-16, specifically Vh-CDR1 (SEQ ID NO:94), Vh-CDR2 (SEQ ID NO:95), Vh-CDR3 (SEQ ID NO:96), Vl-CDR1 (SEQ ID NO:196), Vl-CDR2 (SEQ ID NO:197), and Vl-CDR3 (SEQ ID NO:198). Aspects of the invention include isolated monoclonal antibodies comprising the six CDRs of Ab-17, specifically Vh-CDR1 (SEQ ID NO:100), Vh-CDR2 (SEQ ID NO:101), Vh-CDR3 (SEQ ID NO:102), Vl-CDR1 (SEQ ID NO:202), Vl-CDR2 (SEQ ID NO:203), and Vl-CDR3 (SEQ ID NO:204). Aspects of the aforementioned embodiments include human monoclonal antibodies, human monoclonal IgG antibodies, and human monoclonal IgG1 antibodies. Aspects of the invention include fragments, derivatives, muteins, and variants of the aforementioned.

Aspects of the invention include isolated monoclonal antibodies comprising an Ab-1Vl (SEQ ID NO:240) and an Ab-1Vh (SEQ ID NO:206) domain. Aspects of the invention include isolated monoclonal antibodies comprising an Ab-2Vl (SEQ ID NO:242) and an Ab-2Vh (SEQ ID NO:208) domain. Aspects of the invention include isolated monoclonal antibodies comprising an Ab-3Vl (SEQ ID NO:244) and an Ab-3Vh (SEQ ID NO:210) domain. Aspects of the invention include isolated monoclonal antibodies comprising an Ab-4Vl (SEQ ID NO:246) and an Ab-4Vh (SEQ ID NO:212) domain. Aspects of the invention include isolated monoclonal antibodies comprising an Ab-5Vl (SEQ ID NO:248) and an Ab-5Vh (SEQ ID NO:214) domain. Aspects of the invention include isolated monoclonal antibodies comprising an Ab-6Vl (SEQ ID NO:250) and an Ab-6Vh (SEQ ID NO:216) domain. Aspects of the invention include monoclonal antibodies comprising an Ab-7Vl (SEQ ID NO:252) and an Ab-7Vh (SEQ ID NO:218) domain. Aspects of the invention include isolated monoclonal antibodies comprising an Ab-8Vl (SEQ ID NO:254) and an Ab-8Vh (SEQ ID NO:220) domain. Aspects of the invention include isolated monoclonal antibodies comprising an Ab-9Vl (SEQ ID NO:256) and an Ab-9Vh (SEQ ID NO:222) domain. Aspects of the invention include isolated monoclonal antibodies comprising an Ab-10Vl (SEQ ID NO:258) and an Ab-10Vh (SEQ ID NO:224) domain. Aspects of the invention include isolated monoclonal antibodies comprising an Ab-11Vl (SEQ ID NO:260) and an Ab-11Vh (SEQ ID NO:226) domain. Aspects of the invention include isolated monoclonal antibodies comprising an Ab-12Vl (SEQ ID NO:262) and an Ab-12Vh (SEQ ID NO:228) domain. Aspects of the invention include isolated monoclonal antibodies comprising an Ab-13Vl (SEQ ID NO:264) and an Ab-13Vh (SEQ ID NO:230) domain. Aspects of the invention include isolated monoclonal antibodies comprising an Ab-14Vl (SEQ ID NO:266) and an Ab-14Vh (SEQ ID NO:232) domain. Aspects of the invention include isolated monoclonal antibodies comprising an Ab-15Vl (SEQ ID NO:268) and an Ab-15Vh (SEQ ID NO:234) domain. Aspects of the invention include isolated monoclonal antibodies comprising an Ab-16Vl (SEQ ID NO:270) and an Ab-16Vh (SEQ ID NO:236) domain. Aspects of the invention include isolated antibodies comprising an Ab-17Vl (SEQ ID NO:272) and an Ab-17Vh (SEQ ID NO:238) domain. Aspects of the aforementioned embodiments include human monoclonal antibodies, human monoclonal IgG antibodies, and human monoclonal IgG1 antibodies. Aspects of the invention include fragments, derivatives, muteins, and variants of the aforementioned.

Aspects of the invention include isolated monoclonal antibodies comprising an Ab-1 light chain (SEQ ID NO:280) and Ab-1 heavy chain (SEQ ID NO:274). Aspects of the invention include isolated monoclonal antibodies comprising an Ab-2 light chain (SEQ ID NO:282) and an Ab-2 heavy chain (SEQ ID NO:276). Aspects of the invention include isolated monoclonal antibodies comprising an Ab-3 light chain (SEQ ID NO:284) and an Ab-3 heavy chain (SEQ ID NO:278). Aspects of the invention include isolated monoclonal antibodies comprising two Ab-1 light chains (SEQ ID NO:280) and two Ab-1 heavy chains (SEQ ID NO:274). Aspects of the invention include isolated monoclonal antibodies comprising two Ab-2 light chains (SEQ ID NO:282) and two Ab-2 heavy chains (SEQ ID NO:276). Aspects of the invention include isolated monoclonal antibodies comprising two Ab-3 light chains (SEQ ID NO:284) and two Ab-3 heavy chains (SEQ ID NO:278). Aspects of the aforementioned embodiments include human monoclonal antibodies, human monoclonal IgG antibodies, and human monoclonal IgG1 antibodies. Aspects of the invention include fragments, derivatives, muteins, and variants of the aforementioned.

Aspects of the invention include isolated monoclonal antibodies comprising the six CDRs of Ab-1, wherein the CDRs include no more than one, two, three, four, five, or six amino acid additions, deletions, or substitutions of Vh-CDR1 (SEQ ID NO:4), Vh-CDR2 (SEQ ID NO:5), Vh-CDR3 (SEQ ID NO:6), Vl-CDR1 (SEQ ID NO:106), Vl-CDR2 (SEQ ID NO:107), and Vl-CDR3 (SEQ ID NO:108). Aspects of the invention include isolated monoclonal antibodies comprising the six CDRs of Ab-2, wherein the CDRs include no more than one, two, three, four, five, or six amino acid additions, deletions, or substitutions of Vh-CDR1 (SEQ ID NO:10), Vh-CDR2 (SEQ ID NO:11), Vh-CDR3 (SEQ ID NO:12), Vl-CDR1 (SEQ ID NO:112), Vl-CDR2 (SEQ ID NO:113), and Vl-CDR3 (SEQ ID NO:114). Aspects of the invention include isolated monoclonal antibodies comprising the six CDRs of Ab-3, wherein the CDRs include no more than one, two, three, four, five, or six amino acid additions, deletions, or substitutions of Vh-CDR1 (SEQ ID NO:16), Vh-CDR2 (SEQ ID NO:17), Vh-CDR3 (SEQ ID NO:18), Vl-CDR1 (SEQ ID NO:118), Vl-CDR2 (SEQ ID NO:119), and Vl-CDR3 (SEQ ID NO:120). Aspects of the invention include isolated monoclonal antibodies comprising the six CDRs of Ab-4, wherein the CDRs include no more than one, two, three, four, five, or six amino acid additions, deletions, or substitutions of Vh-CDR1 (SEQ ID NO:22), Vh-CDR2 (SEQ ID NO:23), Vh-CDR3 (SEQ ID NO:24), Vl-CDR1 (SEQ ID NO:124), Vl-CDR2 (SEQ ID NO:125), and Vl-CDR3 (SEQ ID NO:126). Aspects of the invention include isolated monoclonal antibodies comprising the six CDRs of Ab-5, wherein the CDRs include no more than one, two, three, four, five, or six amino acid additions, deletions, or substitutions of Vh-CDR1 (SEQ ID NO:28), Vh-CDR2 (SEQ ID NO:29), Vh-CDR3 (SEQ ID NO:30), Vl-CDR1 (SEQ ID NO:130), Vl-CDR2 (SEQ ID NO:131), and Vl-CDR3 (SEQ ID NO:132). Aspects of the invention include isolated monoclonal antibodies comprising the six CDRs of Ab-6, wherein the CDRs include no more than one, two, three, four, five, or six amino acid additions, deletions, or substitutions of Vh-CDR1 (SEQ ID NO:34), Vh-CDR2 (SEQ ID NO:35), Vh-CDR3 (SEQ ID NO:36), Vl-CDR1 (SEQ ID NO:136), Vl-CDR2 (SEQ ID NO:137), and Vl-CDR3 (SEQ ID NO:138). Aspects of the invention include isolated monoclonal antibodies comprising the six CDRs of Ab-7, wherein the CDRs include no more than one, two, three, four, five, or six amino acid additions, deletions, or substitutions of Vh-CDR1 (SEQ ID NO:40), Vh-CDR2 (SEQ ID NO:41), Vh-CDR3 (SEQ ID NO:42), Vl-CDR1 (SEQ ID NO:142), Vl-CDR2 (SEQ ID NO:143), and Vl-CDR3 (SEQ ID NO:144). Aspects of the invention include isolated monoclonal antibodies comprising the six CDRs of Ab-8, wherein the CDRs include no more than one, two, three, four, five, or six amino acid additions, deletions, or substitutions of Vh-CDR1 (SEQ ID NO:46), Vh-CDR2 (SEQ ID NO:47), Vh-CDR3 (SEQ ID NO:48), Vl-CDR1 (SEQ ID NO:148), Vl-CDR2 (SEQ ID NO:149), and Vl-CDR3 (SEQ ID NO:150). Aspects of the invention include isolated monoclonal antibodies comprising the six CDRs of Ab-9, wherein the CDRs include no more than one, two, three, four, five, or six amino acid additions, deletions, or substitutions of Vh-CDR1 (SEQ ID NO:52), Vh-CDR2 (SEQ ID NO:53), Vh-CDR3 (SEQ ID NO:54), Vl-CDR1 (SEQ ID NO:154), Vl-CDR2 (SEQ ID NO:155), and Vl-CDR3 (SEQ ID NO:156). Aspects of the invention include isolated monoclonal antibodies comprising the six CDRs of Ab-10, wherein the CDRs include no more than one, two, three, four, five, or six amino acid additions, deletions, or substitutions of Vh-CDR1 (SEQ ID NO:58), Vh-CDR2 (SEQ ID NO:59), Vh-CDR3 (SEQ ID NO:60), Vl-CDR1 (SEQ ID NO:160), Vl-CDR2 (SEQ ID NO:161), and Vl-CDR3 (SEQ ID NO:162). Aspects of the invention include isolated monoclonal antibodies comprising the six CDRs of Ab-11, wherein the CDRs include no more than one, two, three, four, five, or six amino acid additions, deletions, or substitutions of Vh-CDR1 (SEQ ID NO:64), Vh-CDR2 (SEQ ID NO:65), Vh-CDR3 (SEQ ID NO:66), Vl-CDR1 (SEQ ID NO:166), Vl-CDR2 (SEQ ID NO:167), and Vl-CDR3 (SEQ ID NO:168). Aspects of the invention include isolated monoclonal antibodies comprising the six CDRs of Ab-12, wherein the CDRs include no more than one, two, three, four, five, or six amino acid additions, deletions, or substitutions of Vh-CDR1 (SEQ ID NO:70), Vh-CDR2 (SEQ ID NO:71), Vh-CDR3 (SEQ ID NO:72), Vl-CDR1 (SEQ ID NO:172), Vl-CDR2 (SEQ ID NO:173), and Vl-CDR3 (SEQ ID NO:174). Aspects of the invention include isolated monoclonal antibodies comprising the six CDRs of Ab-13, wherein the CDRs include no more than one, two, three, four, five, or six amino acid additions, deletions, or substitutions of Vh-CDR1 (SEQ ID NO:76), Vh-CDR2 (SEQ ID NO:77), Vh-CDR3 (SEQ ID NO:78), Vl-CDR1 (SEQ ID NO:178), Vl-CDR2 (SEQ ID NO:179), and Vl-CDR3 (SEQ ID NO:180). Aspects of the invention include isolated monoclonal antibodies comprising the six CDRs of Ab-14, wherein the CDRs include no more than one, two, three, four, five, or six amino acid additions, deletions, or substitutions of Vh-CDR1 (SEQ ID NO:82), Vh-CDR2 (SEQ ID NO:83), Vh-CDR3 (SEQ ID NO:84), Vl-CDR1 (SEQ ID NO:184), Vl-CDR2 (SEQ ID NO:185), and Vl-CDR3 (SEQ ID NO:186). Aspects of the invention include isolated monoclonal antibodies comprising the six CDRs of Ab-15, wherein the CDRs include no more than one, two, three, four, five, or six amino acid additions, deletions, or substitutions of Vh-CDR1 (SEQ ID NO:88), Vh-CDR2 (SEQ ID NO:89), Vh-CDR3 (SEQ ID NO:90), Vl-CDR1 (SEQ ID NO:190), Vl-CDR2 (SEQ ID NO:191), and Vl-CDR3 (SEQ ID NO:192). Aspects of the invention include isolated monoclonal antibodies comprising the six CDRs of Ab-16, wherein the CDRs include no more than one, two, three, four, five, or six amino acid additions, deletions, or substitutions of Vh-CDR1 (SEQ ID NO:94), Vh-CDR2 (SEQ ID NO:95), Vh-CDR3 (SEQ ID NO:96), Vl-CDR1 (SEQ ID NO:196), Vl-CDR2 (SEQ ID NO:197), and Vl-CDR3 (SEQ ID NO:198). Aspects of the invention include isolated monoclonal antibodies comprising the six CDRs of Ab-17, wherein the CDRs include no more than one, two, three, four, five, or six amino acid additions, deletions, or substitutions of Vh-CDR1 (SEQ ID NO:100), Vh-CDR2 (SEQ ID NO:101), Vh-CDR3 (SEQ ID NO:102), Vl-CDR1 (SEQ ID NO:202), Vl-CDR2 (SEQ ID NO:203), and Vl-CDR3 (SEQ ID NO:204). Aspects of the aforementioned embodiments include human monoclonal antibodies, human monoclonal IgG antibodies, and human monoclonal IgG1 antibodies.

Aspects of the invention include isolated monoclonal antibodies comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-1Vl (SEQ ID NO:240) and Ab-1Vh (SEQ ID NO:206), respectively. Aspects of the invention include isolated monoclonal antibodies comprising a Vl and a Vh amino acid sequences that are at least 95% identical to Ab-1Vl (SEQ ID NO:240) and Ab-1Vh (SEQ ID NO:206), respectively. Aspects of the invention include isolated monoclonal antibodies comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-2Vl (SEQ ID NO:242) and Ab-2Vh (SEQ ID NO:208), respectively. Aspects of the invention include isolated monoclonal antibodies comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-3Vl (SEQ ID NO:244) and Ab-3Vh (SEQ ID NO:210), respectively. Aspects of the invention include isolated monoclonal antibodies comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-4Vl (SEQ ID NO:246) and Ab-4Vh (SEQ ID NO:212), respectively. Aspects of the invention include isolated monoclonal antibodies comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-5Vl (SEQ ID NO:248) and Ab-5Vh (SEQ ID NO:214), respectively. Aspects of the invention include isolated monoclonal antibodies comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-6Vl (SEQ ID NO:250) and Ab-6Vh (SEQ ID NO:216), respectively. Aspects of the invention include isolated monoclonal antibodies comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-7Vl (SEQ ID NO:252) and Ab-7Vh (SEQ ID NO:218), respectively. Aspects of the invention include isolated monoclonal antibodies comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-8Vl (SEQ ID NO:254) and Ab-8Vh (SEQ ID NO:220), respectively. Aspects of the invention include isolated monoclonal antibodies comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-9Vl (SEQ ID NO:256) and Ab-9Vh (SEQ ID NO:222), respectively. Aspects of the invention include isolated monoclonal antibodies comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-10Vl (SEQ ID NO:258) and Ab-10Vh (SEQ ID NO:224), respectively. Aspects of the invention include isolated monoclonal antibodies comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-11Vl (SEQ ID NO:260) and Ab-11Vh (SEQ ID NO:226), respectively. Aspects of the invention include isolated monoclonal antibodies comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-12Vl (SEQ ID NO:262) and Ab-12Vh (SEQ ID NO:228), respectively. Aspects of the invention include isolated monoclonal antibodies comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-13Vl (SEQ ID NO:264) and Ab-13Vh (SEQ ID NO:230), respectively. Aspects of the invention include isolated monoclonal antibodies comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-14Vl (SEQ ID NO:266) and Ab-14Vh (SEQ ID NO:232), respectively. Aspects of the invention include isolated monoclonal antibodies comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-15Vl (SEQ ID NO:268) and Ab-15Vh (SEQ ID NO:234), respectively. Aspects of the invention include isolated monoclonal antibodies comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-16Vl (SEQ ID NO:270) and Ab-16Vh (SEQ ID NO:236), respectively. Aspects of the invention include isolated monoclonal antibodies comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-17Vl (SEQ ID NO:272) and Ab-17Vh (SEQ ID NO:238), respectively. Aspects of the aforementioned embodiments include human monoclonal antibodies, human monoclonal IgG antibodies, and human monoclonal IgG1 antibodies.

Aspects of the invention include isolated monoclonal antibodies that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-1 light chain (SEQ ID NO:280) and Ab-1 heavy chain (SEQ ID NO:274). Aspects of the invention include isolated monoclonal antibodies that are at least 95% identical to Ab-1 light chain (SEQ ID NO:280) and Ab-1 heavy chain (SEQ ID NO:274). Aspects of the invention include isolated monoclonal antibodies that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-2 light chain (SEQ ID NO:282) and an Ab-2 heavy chain (SEQ ID NO:276). Aspects of the invention include isolated monoclonal antibodies that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-3 light chain (SEQ ID NO:284) and an Ab-3 heavy chain (SEQ ID NO:278). Aspects of the aforementioned embodiments include human monoclonal antibodies, human monoclonal IgG antibodies, and human monoclonal IgG1 antibodies.

As used herein, the term "antibody" refers to the various forms of monomeric or multimeric proteins comprising one or more polypeptide chains that specifically binds to an antigen, as variously described herein. In certain embodiments, antibodies are produced by recombinant DNA techniques. In additional embodiments, antibodies are produced by enzymatic or chemical cleavage of naturally occurring antibodies. In another aspect, the antibody is selected from the group consisting of: a human antibody; a humanized antibody; a chimeric antibody; a monoclonal antibody; an antigen-binding antibody fragment; a single chain antibody; a diabody; a triabody; a tetrabody; a Fab fragment; a F(ab')$_2$ fragment; an IgD antibody; an IgE antibody; an IgM antibody; an IgA antibody; an IgG1 antibody; an IgG2 antibody; an IgG3 antibody; and an IgG4 antibody.

As a general structure, the antigen binding proteins of the invention comprise (a) a scaffold, and (b) a plurality of CDRs. A "complementary determining region" or "CDR," as used herein, refers to a binding protein region that constitutes the major surface contact points for antigen binding. Embodiments of the invention include one or more CDRs embedded in a scaffold structure of the antigen binding protein. The scaffold structure of the antigen binding proteins may be the framework of an antibody, or fragment or variant thereof, or may be completely synthetic in nature. Examples of various scaffold structures of the antigen binding proteins of the invention are further described hereinbelow.

The term "naturally occurring" as used throughout the specification in connection with biological materials such as peptides, polypeptides, nucleic acids, host cells, and the like, refers to materials which are found in nature. In naturally occurring antibodies, a H-CDR1 typically comprises about five (5) to about seven (7) amino acids, H-CDR2 typically comprises about sixteen (16) to about nineteen (19) amino acids, and H-CDR3 typically comprises about three (3) to about twenty five (25) amino acids. L-CDR1 typically comprises about ten (10) to about seventeen (17) amino acids, L-CDR2 typically comprises about seven (7) amino acids, and L-CDR3 typically comprises about seven (7) to about ten (10) amino acids. The sequence identifiers for the specific CDRs of the various antibodies of the invention are provided in TABLE 1.

Naturally occurring antibodies typically include a signal sequence, which directs the antibody into the cellular pathway for protein secretion and which is not present in the mature antibody. A polynucleotide encoding an antibody of the invention may encode a naturally occurring signal sequence or a heterologous signal sequence as described below.

The general structure and properties of CDRs within naturally occurring antibodies have been described in the art. Briefly, in a traditional antibody scaffold, the CDRs are embedded within a framework in the heavy and light chain variable region where they constitute the regions largely responsible for antigen binding and recognition. A variable region comprises at least three heavy or light chain CDRs, see, supra (Kabat et al., 1991, *Sequences of Proteins of Immunological Interest*, Public Health Service N.I.H., Bethesda, Md.; see also Chothia and Lesk, 1987, *J. Mol. Biol.* 196:901-917; Chothia et al., 1989, *Nature* 342: 877-883), within a framework region (designated framework regions 1-4, FR1, FR2, FR3, and FR4, by Kabat et al., 1991, supra; see also Chothia and Lesk, 1987, supra). See, infra. The CDRs provided by the present invention, however, may not only be used to define the antigen binding domain of a traditional antibody structure, but may be embedded in a variety of other scaffold structures, as described herein.

Antibodies of the invention can comprise any constant region known in the art. The light chain constant region can be, for example, a kappa- or lambda-type light chain constant region, e.g., a human kappa- or lambda-type light chain constant region. The heavy chain constant region can be, for example, an alpha-, delta-, epsilon-, gamma-, or mu-type heavy chain constant regions, e.g., a human alpha-, delta-, epsilon-, gamma-, or mu-type heavy chain constant region. In one embodiment, the light or heavy chain constant region is a fragment, derivative, variant, or mutein of a naturally occurring constant region.

Embodiments include the use of human antibody scaffold components (e.g., constant domains). A preferred embodiment of a human IgG1 constant domain for the heavy chain is depicted in SEQ ID NO:274 (together with the Vh domain) and a preferred human IgG1 constant domain for the heavy chain is depicted in SEQ ID NO:280 (together with the Vl domain) Embodiments include the use of human antibody scaffold components. Of course it is understood that any suitable antibody scaffold known in the art may be employed.

Traditional antibody structural units typically comprise a tetramer. Each tetramer is typically composed of two identical pairs of polypeptide chains, each pair having one "light" (typically having a molecular weight of about 25 kDa) and one "heavy" chain (typically having a molecular weight of about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains Heavy chains are classified as mu, delta, gamma, alpha, or epsilon, and define the antibody's isotype as IgM, IgD, IgG, IgA, and IgE, respectively. IgG has several subclasses, including, but not limited to IgG1, IgG2, IgG3, and IgG4. IgM has subclasses, including, but not limited to, IgM1 and IgM2. Embodiments of the invention include all such classes of antibodies that incorporate the variable domains or the CDRs of the antigen binding proteins, as described herein.

Within light and heavy chains, the variable and constant regions are joined by a "J" region of about twelve (12) or more amino acids, with the heavy chain also including a "D" region of about ten (10) more amino acids. See, generally, Paul, W., ed., 1989, Fundamental Immunology Ch. 7, 2nd ed. Raven Press, N.Y. The variable regions of each light/heavy chain pair form the antibody binding site. Scaffolds of the invention include such regions.

In some embodiments, however, the scaffold components can be a mixture from different species. As such, if the antigen binding protein is an antibody, such antibody may be a chimeric antibody and/or a humanized antibody. In general, both "chimeric antibodies" and "humanized antibodies" refer to antibodies that combine regions from more than one species. For example, "chimeric antibodies" traditionally comprise variable region(s) from a mouse (or rat, in some cases) and the constant region(s) from a human.

"Humanized antibodies" generally refer to non-human antibodies that have had the variable-domain framework regions swapped for sequences found in human antibodies.

Generally, in a humanized antibody, the entire antibody, except the CDRs, is encoded by a polynucleotide of human origin or is identical to such an antibody except within its CDRs. The CDRs, some or all of which are encoded by nucleic acids originating in a non-human organism, are grafted into the beta-sheet framework of a human antibody variable region to create an antibody, the specificity of which is determined by the engrafted CDRs. The creation of such antibodies is described in, e.g., WO 92/11018, Jones, 1986, *Nature* 321:522-525, Verhoeyen et al., 1988, *Science* 239: 1534-1536. Humanized antibodies can also be generated using mice with a genetically engineered immune system. Roque et al., 2004, *Biotechnol. Prog.* 20:639-654. In the present invention, the identified CDRs are human, and thus both humanized and chimeric antibodies in this context include some non-human CDRs; for example, humanized antibodies may be generated that comprise the CDRH3 and CDRL3 regions, with one or more of the other CDR regions being of a different special origin.

In one embodiment, the BCMA antigen binding protein is a multispecific antibody, and notably a bispecific antibody, also sometimes referred to as "diabodies". These are antibodies that bind to two (or more) different antigens. Diabodies can be manufactured in a variety of ways known in the art (Holliger and Winter, 1993, *Current Opinion Biotechnol.* 4:446-449), e.g., prepared chemically or from hybrid hybridomas.

In one embodiment, the BCMA antigen binding protein is a minibody. Minibodies are minimized antibody-like proteins comprising a scFv joined to a CH3 domain. Hu et al., 1996, *Cancer Res.* 56:3055-3061.

In one embodiment, the BCMA antigen binding protein is a domain antibody; see, for example U.S. Pat. No. 6,248, 516. Domain antibodies (dAbs) are functional binding domains of antibodies, corresponding to the variable regions of either the heavy (VH) or light (VL) chains of human antibodies dABs have a molecular weight of approximately 13 kDa, or less than one-tenth the size of a full antibody. dABs are well expressed in a variety of hosts including bacterial, yeast, and mammalian cell systems. In addition, dAbs are highly stable and retain activity even after being subjected to harsh conditions, such as freeze-drying or heat denaturation. See, for example, U.S. Pat. Nos. 6,291,158; 6,582,915; 6,593,081; 6,172,197; US Serial No. 2004/0110941; European Patent 0368684; U.S. Pat. No. 6,696, 245, WO04/058821, WO04/003019 and WO03/002609.

In one embodiment, the BCMA antigen binding protein is an antibody fragment that is a fragment of any of the antibodies outlined herein that retain binding specificity to BCMA. In various embodiments, the antibody binding proteins comprise, but are not limited to, a F(ab), F(ab'), F(ab')2, Fv, or a single chain Fv fragments (ScFv). At a minimum, an antibody, as meant herein, comprises a polypeptide that can bind specifically to BCMA comprising all or part of a light or heavy chain variable region, such as one or more CDRs.

Further examples of BCMA-binding antibody fragments include, but are not limited to, (i) the Fab fragment consisting of VL, VH, CL and CH1 domains, (ii) the Fd fragment consisting of the VH and CH1 domains, (iii) the Fv fragment consisting of the VL and VH domains of a single antibody; (iv) the dAb fragment (Ward et al., 1989, *Nature* 341:544-546) which consists of a single variable, (v) isolated CDR regions, (vi) F(ab')$_2$ fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., 1988, *Science* 242:423-426, Huston et al., 1988, *Proc. Natl. Acad. Sci. U.S.A.* 85:5879-5883), (viii) bispecific single chain Fv dimers (PCT/US92/09965) and (ix) "diabodies" or "triabodies", multivalent or multispecific fragments constructed by gene fusion (Tomlinson et. al., 2000, *Methods Enzymol.* 326:461-479; WO94/13804; Holliger et al., 1993, *Proc. Natl. Acad. Sci. U.S.A.* 90:6444-6448). The antibody fragments may be modified. For example, the molecules may be stabilized by the incorporation of disulphide bridges linking the VH and VL domains (Reiter et al., 1996, *Nature Biotech.* 14:1239-1245). Aspects of the invention include embodiments wherein the non-CDR components of these fragments are human sequences.

Particular embodiments include BCMA antibodies that are fully human. In this embodiment, as outlined above, specific structures comprise complete heavy and light chains depicted comprising the CDR regions. Additional embodiments utilize one or more of the CDRs of the invention, with the other CDRs, framework regions, J and D regions, constant regions, etc., coming from other human antibodies. For example, the CDRs of the invention can replace the CDRs of any number of human antibodies, particularly commercially relevant antibodies.

XenoMouse® technology was used to make the human antibodies provided herein (see Example 2). This technology is capable of producing human immunoglobulin molecules and antibodies that are deficient in the production of murine immunoglobulin molecules and antibodies. Through use of such technology, fully human monoclonal antibodies to BCMA can be produced. In one embodiment, XenoMouse® lines of mice are immunized with huBCMA, lymphatic cells are recovered (such as B-cells) from the mice that expressed antibodies, and such cells are fused with a myeloid-type cell line to prepare immortal hybridoma cell lines, and such hybridoma cell lines are screened and selected to identify hybridoma cell lines that produce antibodies specific to the antigen of interest. Provided herein are methods for the production of multiple hybridoma cell lines that produce antibodies specific to BCMA. Further, provided herein are characterization of the antibodies produced by such cell lines, including nucleotide and amino acid sequences of the heavy and light chains of such antibodies.

Alternatively, instead of being fused to myeloma cells to generate hybridomas, the antibody produced by recovered cells, isolated from immunized XenoMouse® lines of mice, are screened further for reactivity against the initial antigen, preferably BCMA protein. Such screening includes ELISA with BCMA protein, in vitro binding to 293T cells (for example) stably expressing full length BCMA. Single B cells secreting antibodies of interest are then isolated using standard BCMA-specific binding assays (such as by FACS). The single antigen-specific plasma cells are isolated and the genetic information that encodes the specificity of the antibody is isolated from the single plasma cell. Using reverse-transcriptase PCR, the DNA encoding the variable region of the antibody secreted can be cloned. Such cloned DNA can then be further inserted into a suitable expression vector, preferably a vector cassette such as a pcDNA, more preferably such a pcDNA vector containing the constant domains of immunoglobulin heavy and light chain. The generated vector can then be transfected into host cells, preferably CHO cells, and cultured in conventional nutrient media modified as appropriate for inducing promoters, selecting transformants, or amplifying the genes encoding the desired sequences.

B cells from XenoMouse® mice may be also be used as a source of genetic material from which antibody display libraries may be generated. Such libraries may be made in bacteriophage, yeast or in vitro via ribosome display using ordinary skills in the art. Hyperimmunized XenoMouse® mice may be a rich source from which high-affinity, antigen-reactive antibodies may be isolated. Accordingly, XenoMouse® mice hyperimmunized against BCMA may be used to generate antibody display libraries from which high-affinity antibodies against BCMA may be isolated. Such libraries could be screened against cells expressing BCMA to confirm specificity for the natively display antigen. Full IgG antibody may then be expressed using recombinant DNA technology. See e.g., WO 99/53049.

In general, antibodies produced by the above-mentioned cell lines possessed fully human IgG1 or IgG2 heavy chains with human kappa light chains. In one embodiment, the antibodies possessed high affinities, typically possessing affinity constants of from about $10^{-9}$ through about $10^{-13}$ M, when measured by either solid phase or solution phase. As appreciated by one of skill in the art, antibodies in accordance with the present embodiments can be expressed in cell lines other than hybridoma cell lines. Sequences encoding particular antibodies can be used for transformation of a suitable mammalian host cell. Transformation can be by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216, 4,912,040, 4,740,461, and 4,959,455 (which patents are hereby incorporated herein by reference). The transformation procedure used depends upon the host to be transformed. Methods for introduction of heterologous polynucleotides into mammalian cells are well known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei. Mammalian cell lines available as hosts for expression are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. Cell lines of particular preference are selected through determining which cell lines have high expression levels and produce antibodies with constitutive BCMA-binding properties.

Single chain antibodies may be formed by linking heavy and light chain variable domain (Fv region) fragments via an amino acid bridge (short peptide linker), resulting in a single polypeptide chain Such single-chain Fvs (scFvs) have been prepared by fusing DNA encoding a peptide linker between DNAs encoding the two variable domain polypeptides ($V_L$ and $V_H$). The resulting polypeptides can fold back on themselves to form antigen-binding monomers, or they can form multimers (e.g., dimers, trimers, or tetramers), depending on the length of a flexible linker between the two variable domains (Kortt et al., 1997, Prot. Eng. 10:423; Kora et al., 2001, Biomol. Eng. 18:95-108). By combining different $V_L$ and $V_H$-comprising polypeptides, one can form multimeric scFvs that bind to different epitopes (Kriangkum et al., 2001, Biomol. Eng. 18:31-40). Techniques developed for the production of single chain antibodies include those described in U.S. Pat. No. 4,946,778; Bird, 1988, Science 242:423; Huston et al., 1988, Proc. Natl. Acad. Sci. USA 85:5879; Ward et al., 1989, Nature 334:544, de Graaf et al., 2002, Methods Mol Biol. 178:379-87.

In one embodiment, the BCMA antigen binding protein is an antibody fusion protein (sometimes referred to herein as an "antibody conjugate" or "antibody-drug-conjugate" or "ADC"). The conjugate partner can be proteinaceous or non-proteinaceous; the latter generally being generated using functional groups on the antigen binding protein (see the discussion on covalent modifications of the antigen binding proteins) and on the conjugate partner. For example linkers are known in the art; for example, homo- or heterobifunctional linkers as are well known (see, 1994 Pierce Chemical Company catalog, technical section on cross-linkers, pages 155-200, incorporated herein by reference). The ADCs of the invention are described in more detail below and in the Examples.

In one embodiment, the BCMA antigen binding protein is an antibody analog, sometimes referred to as "synthetic antibodies." For example, a variety of recent work utilizes either alternative protein scaffolds or artificial scaffolds with grafted CDRs. Such scaffolds include, but are not limited to, mutations introduced to stabilize the three-dimensional structure of the binding protein as well as wholly synthetic scaffolds consisting for example of biocompatible polymers. See, for example, Korndorfer et al., 2003, *Proteins: Structure, Function, and Bioinformatics*, Volume 53, Issue 1:121-129. Roque et al., 2004, *Biotechnol. Prog.* 20:639-654. In addition, peptide antibody mimetics ("PAMs") can be used, as well as work based on antibody mimetics utilizing fibronectin components as a scaffold.

Additional examples of scaffolds that are envisioned, beyond the human IgG1 scaffolds exemplified in Ab-1, 2, and 3, include: fibronectin, neocarzinostatin CBM4-2, lipocalins, T-cell receptor, protein-A domain (protein Z), Im9, TPR proteins, zinc finger domains, pVIII, avian pancreatic polypeptide, GCN4, WW domain, Src homology domain 3, PDZ domains, TEM-1 Beta-lactamase, thioredoxin, staphylococcal nuclease, PHD-finger domains, CL-2, BPTI, APPI, HPSTI, ecotin, LACI-D1, LDTI, MTI-II, scorpion toxins, insect defensin-A peptide, EETI-II, Min-23, CBD, PBP, cytochrome b-562, Ldl receptor domains, gamma-crystallin, ubiquitin, transferring, and/or C-type lectin-like domains.

Aspects of the invention include isolated polypeptides comprising the six CDRs of Ab-1, specifically Vh-CDR1 (SEQ ID NO:4), Vh-CDR2 (SEQ ID NO:5), Vh-CDR3 (SEQ ID NO:6), Vl-CDR1 (SEQ ID NO:106), Vl-CDR2 (SEQ ID NO:107), and Vl-CDR3 (SEQ ID NO:108). Aspects of the invention include isolated polypeptides comprising the six CDRs of Ab-2, specifically Vh-CDR1 (SEQ ID NO:10), Vh-CDR2 (SEQ ID NO:11), Vh-CDR3 (SEQ ID NO:12), Vl-CDR1 (SEQ ID NO:112), Vl-CDR2 (SEQ ID NO:113), and Vl-CDR3 (SEQ ID NO:114). Aspects of the invention include isolated polypeptides comprising the six CDRs of Ab-3, specifically Vh-CDR1 (SEQ ID NO:16), Vh-CDR2 (SEQ ID NO:17), Vh-CDR3 (SEQ ID NO:18), Vl-CDR1 (SEQ ID NO:118), Vl-CDR2 (SEQ ID NO:119), and Vl-CDR3 (SEQ ID NO:120). Aspects of the invention include isolated polypeptides comprising the six CDRs of Ab-4, specifically Vh-CDR1 (SEQ ID NO:22), Vh-CDR2 (SEQ ID NO:23), Vh-CDR3 (SEQ ID NO:24), Vl-CDR1 (SEQ ID NO:124), Vl-CDR2 (SEQ ID NO:125), and Vl-CDR3 (SEQ ID NO:126). Aspects of the invention include isolated polypeptides comprising the six CDRs of Ab-5, specifically Vh-CDR1 (SEQ ID NO:28), Vh-CDR2 (SEQ ID NO:29), Vh-CDR3 (SEQ ID NO:30), Vl-CDR1 (SEQ ID NO:130), Vl-CDR2 (SEQ ID NO:131), and Vl-CDR3 (SEQ ID NO:132). Aspects of the invention include isolated polypeptides comprising the six CDRs of Ab-6, specifically Vh-CDR1 (SEQ ID NO:34), Vh-CDR2 (SEQ ID NO:35), Vh-CDR3 (SEQ ID NO:36), Vl-CDR1 (SEQ ID NO:136), Vl-CDR2 (SEQ ID NO:137), and Vl-CDR3 (SEQ ID NO:138). Aspects of the invention include isolated polypeptides comprising the six CDRs of Ab-7, specifically Vh-CDR1 (SEQ ID NO:40), Vh-CDR2 (SEQ ID NO:41), Vh-CDR3 (SEQ ID NO:42), Vl-CDR1 (SEQ ID NO:142), Vl-CDR2 (SEQ ID NO:143), and Vl-CDR3 (SEQ ID NO:144). Aspects of the invention include isolated polypeptides comprising the six CDRs of Ab-8, specifically Vh-CDR1 (SEQ ID NO:46), Vh-CDR2 (SEQ ID NO:47), Vh-CDR3 (SEQ ID NO:48), Vl-CDR1 (SEQ ID NO:148), Vl-CDR2 (SEQ ID NO:149), and Vl-CDR3 (SEQ ID NO:150). Aspects of the invention include isolated polypeptides comprising the six CDRs of Ab-9, specifically Vh-CDR1 (SEQ ID NO:52), Vh-CDR2 (SEQ ID NO:53), Vh-CDR3 (SEQ ID NO:54), Vl-CDR1 (SEQ ID NO:154), Vl-CDR2 (SEQ ID NO:155), and Vl-CDR3 (SEQ ID NO:156). Aspects of the invention include isolated polypeptides comprising the six CDRs of Ab-10, specifically Vh-CDR1 (SEQ ID NO:58), Vh-CDR2 (SEQ ID NO:59), Vh-CDR3 (SEQ ID NO:60), Vl-CDR1 (SEQ ID NO:160), Vl-CDR2 (SEQ ID NO:161), and Vl-CDR3 (SEQ ID NO:162). Aspects of the invention include isolated polypeptides comprising the six CDRs of Ab-11, specifically Vh-CDR1 (SEQ ID NO:64), Vh-CDR2 (SEQ ID NO:65), Vh-CDR3 (SEQ ID NO:66), Vl-CDR1 (SEQ ID NO:166), Vl-CDR2 (SEQ ID NO:167), and Vl-CDR3 (SEQ ID NO:168). Aspects of the invention include isolated polypeptides comprising the six CDRs of Ab-12, specifically Vh-CDR1 (SEQ ID NO:70), Vh-CDR2 (SEQ ID NO:71), Vh-CDR3 (SEQ ID NO:72), Vl-CDR1 (SEQ ID NO:172), Vl-CDR2 (SEQ ID NO:173), and Vl-CDR3 (SEQ ID NO:174). Aspects of the invention include isolated polypeptides comprising the six CDRs of Ab-13, specifically Vh-CDR1 (SEQ ID NO:76), Vh-CDR2 (SEQ ID NO:77), Vh-CDR3 (SEQ ID NO:78), Vl-CDR1 (SEQ ID NO:178), Vl-CDR2 (SEQ ID NO:179), and Vl-CDR3 (SEQ ID NO:180). Aspects of the invention include isolated polypeptides comprising the six CDRs of Ab-14, specifically Vh-CDR1 (SEQ ID NO:82), Vh-CDR2 (SEQ ID NO:83), Vh-CDR3 (SEQ ID NO:84), Vl-CDR1 (SEQ ID NO:184), Vl-CDR2 (SEQ ID NO:185), and Vl-CDR3 (SEQ ID NO:186). Aspects of the invention include isolated polypeptides comprising the six CDRs of Ab-15, specifically Vh-CDR1 (SEQ ID NO:88), Vh-CDR2 (SEQ ID NO:89), Vh-CDR3 (SEQ ID NO:90), Vl-CDR1 (SEQ ID NO:190), Vl-CDR2 (SEQ ID NO:191), and Vl-CDR3 (SEQ ID NO:192). Aspects of the invention include isolated polypeptides comprising the six CDRs of Ab-16, specifically Vh-CDR1 (SEQ ID NO:94), Vh-CDR2 (SEQ ID NO:95), Vh-CDR3 (SEQ ID NO:96), Vl-CDR1 (SEQ ID NO:196), Vl-CDR2 (SEQ ID NO:197), and Vl-CDR3 (SEQ ID NO:198). Aspects of the invention include isolated polypeptides comprising the six CDRs of Ab-17, specifically Vh-CDR1 (SEQ ID NO:100), Vh-CDR2 (SEQ ID NO:101), Vh-CDR3 (SEQ ID NO:102), Vl-CDR1 (SEQ ID NO:202), Vl-CDR2 (SEQ ID NO:203), and Vl-CDR3 (SEQ ID NO:204). Aspects of the invention include fragments, derivatives, muteins, and variants of the aforementioned.

Aspects of the invention include isolated polypeptides comprising an Ab-1Vl (SEQ ID NO:240) and an Ab-1Vh (SEQ ID NO:206) domain. Aspects of the invention include isolated polypeptides comprising an Ab-2Vl (SEQ ID NO:242) and an Ab-2Vh (SEQ ID NO:208) domain. Aspects of the invention include isolated polypeptides comprising an Ab-3Vl (SEQ ID NO:244) and an Ab-3Vh (SEQ ID NO:210) domain. Aspects of the invention include isolated polypeptides comprising an Ab-4Vl (SEQ ID NO:246) and an Ab-4Vh (SEQ ID NO:212) domain. Aspects of the invention include isolated polypeptides comprising an Ab-5Vl (SEQ ID NO:248) and an Ab-5Vh (SEQ ID NO:214) domain. Aspects of the invention include isolated polypeptides comprising an Ab-6Vl (SEQ ID NO:250) and an Ab-6Vh (SEQ ID NO:216) domain. Aspects of the invention include polypeptides comprising an Ab-7Vl (SEQ ID NO:252) and an Ab-7Vh (SEQ ID NO:218) domain. Aspects of the invention include isolated polypeptides comprising an Ab-8Vl (SEQ ID NO:254) and an Ab-8Vh (SEQ ID NO:220) domain. Aspects of the invention include isolated polypeptides comprising an Ab-9Vl (SEQ ID NO:256) and an Ab-9Vh (SEQ ID NO:222) domain. Aspects of the invention include isolated polypeptides comprising an Ab-10Vl (SEQ ID NO:258) and an Ab-10Vh (SEQ ID NO:224) domain. Aspects of the invention include isolated polypeptides comprising an Ab-11Vl (SEQ ID NO:260) and an Ab-11Vh (SEQ ID NO:226) domain. Aspects of the invention include isolated polypeptides comprising an Ab-12Vl (SEQ ID NO:262) and an Ab-12Vh (SEQ ID NO:228) domain. Aspects of the invention include isolated polypeptides comprising an Ab-13Vl (SEQ ID NO:264) and an Ab-13Vh (SEQ ID NO:230) domain. Aspects of the invention include isolated polypeptides comprising an Ab-14Vl (SEQ ID NO:266) and an Ab-14Vh (SEQ ID NO:232) domain. Aspects of the invention include isolated polypeptides comprising an Ab-15Vl (SEQ ID NO:268) and an Ab-15Vh (SEQ ID NO:234) domain. Aspects of the invention include isolated polypeptides comprising an Ab-16Vl (SEQ ID NO:270) and an Ab-16Vh (SEQ ID NO:236) domain. Aspects of the invention include isolated polypeptides comprising an Ab-17Vl (SEQ ID NO:272) and an Ab-17Vh (SEQ ID NO:238) domain. Aspects of the invention include fragments, derivatives, muteins, and variants of the aforementioned.

Aspects of the invention include isolated polypeptides comprising an Ab-1 light chain (SEQ ID NO:280) and Ab-1 heavy chain (SEQ ID NO:274). Aspects of the invention include isolated polypeptides comprising an Ab-2 light chain (SEQ ID NO:282) and an Ab-2 heavy chain (SEQ ID NO:276). Aspects of the invention include isolated polypeptides comprising an Ab-3 light chain (SEQ ID NO:284) and an Ab-3 heavy chain (SEQ ID NO:278). Aspects of the invention include isolated polypeptides comprising two or more Ab-1 light chains (SEQ ID NO:280) and two or more Ab-1 heavy chains (SEQ ID NO:274). Aspects of the invention include isolated polypeptides comprising two or more Ab-2 light chains (SEQ ID NO:282) and two or more Ab-2 heavy chains (SEQ ID NO:276). Aspects of the invention include isolated polypeptides comprising two or more Ab-3 light chains (SEQ ID NO:284) and two or more Ab-3 heavy chains (SEQ ID NO:278). Aspects of the invention include fragments, derivatives, muteins, and variants of the aforementioned.

Aspects of the invention include isolated polypeptides comprising the six CDRs of Ab-1, wherein the CDRs include no more than one, two, three, four, five, or six amino acid additions, deletions, or substitutions of Vh-CDR1 (SEQ ID NO:4), Vh-CDR2 (SEQ ID NO:5), Vh-CDR3 (SEQ ID NO:6), Vl-CDR1 (SEQ ID NO:106), Vl-CDR2 (SEQ ID NO:107), and Vl-CDR3 (SEQ ID NO:108). Aspects of the invention include isolated polypeptides comprising the six CDRs of Ab-2, wherein the CDRs include no more than one, two, three, four, five, or six amino acid additions, deletions, or substitutions of Vh-CDR1 (SEQ ID NO:10), Vh-CDR2 (SEQ ID NO:11), Vh-CDR3 (SEQ ID NO:12), Vl-CDR1 (SEQ ID NO:112), Vl-CDR2 (SEQ ID NO:113), and Vl-CDR3 (SEQ ID NO:114). Aspects of the invention include isolated polypeptides comprising the six CDRs of Ab-3, wherein the CDRs include no more than one, two, three, four, five, or six amino acid additions, deletions, or substitutions of Vh-CDR1 (SEQ ID NO:16), Vh-CDR2 (SEQ ID NO:17), Vh-CDR3 (SEQ ID NO:18), Vl-CDR1 (SEQ ID NO:118), Vl-CDR2 (SEQ ID NO:119), and Vl-CDR3 (SEQ ID NO:120). Aspects of the invention include isolated polypeptides comprising the six CDRs of Ab-4, wherein the CDRs include no more than one, two, three, four, five, or six amino acid additions, deletions, or substitutions of Vh-CDR1 (SEQ ID NO:22), Vh-CDR2 (SEQ ID NO:23), Vh-CDR3 (SEQ ID NO:24), Vl-CDR1 (SEQ ID NO:124), Vl-CDR2 (SEQ ID NO:125), and Vl-CDR3 (SEQ ID NO:126). Aspects of the invention include isolated polypeptides comprising the six CDRs of Ab-5, wherein the CDRs include no more than one, two, three, four, five, or six amino acid additions, deletions, or substitutions of Vh-CDR1 (SEQ ID NO:28), Vh-CDR2 (SEQ ID NO:29), Vh-CDR3 (SEQ ID NO:30), Vl-CDR1 (SEQ ID NO:130), Vl-CDR2 (SEQ ID NO:131), and Vl-CDR3 (SEQ ID NO:132). Aspects of the invention include isolated polypeptides comprising the six CDRs of Ab-6, wherein the CDRs include no more than one, two, three, four, five, or six amino acid additions, deletions, or substitutions of Vh-CDR1 (SEQ ID NO:34), Vh-CDR2 (SEQ ID NO:35), Vh-CDR3 (SEQ ID NO:36), Vl-CDR1 (SEQ ID NO:136), Vl-CDR2 (SEQ ID NO:137), and Vl-CDR3 (SEQ ID NO:138). Aspects of the invention include isolated polypeptides comprising the six CDRs of Ab-7, wherein the CDRs include no more than one, two, three, four, five, or six amino acid additions, deletions, or substitutions of Vh-CDR1 (SEQ ID NO:40), Vh-CDR2 (SEQ ID NO:41), Vh-CDR3 (SEQ ID NO:42), Vl-CDR1 (SEQ ID NO:142), Vl-CDR2 (SEQ ID NO:143), and Vl-CDR3 (SEQ ID NO:144). Aspects of the invention include isolated polypeptides comprising the six CDRs of Ab-8, wherein the CDRs include no more than one, two, three, four, five, or six amino acid additions, deletions, or substitutions of Vh-CDR1 (SEQ ID NO:46), Vh-CDR2 (SEQ ID NO:47), Vh-CDR3 (SEQ ID NO:48), Vl-CDR1 (SEQ ID NO:148), Vl-CDR2 (SEQ ID NO:149), and Vl-CDR3 (SEQ ID NO:150). Aspects of the invention include isolated polypeptides comprising the six CDRs of Ab-9, wherein the CDRs include no more than one, two, three, four, five, or six amino acid additions, deletions, or substitutions of Vh-CDR1 (SEQ ID NO:52), Vh-CDR2 (SEQ ID NO:53), Vh-CDR3 (SEQ ID NO:54), Vl-CDR1 (SEQ ID NO:154), Vl-CDR2 (SEQ ID NO:155), and Vl-CDR3 (SEQ ID NO:156). Aspects of the invention include isolated polypeptides comprising the six CDRs of Ab-10, wherein the CDRs include no more than one, two, three, four, five, or six amino acid additions, deletions, or substitutions of Vh-CDR1 (SEQ ID NO:58), Vh-CDR2 (SEQ ID NO:59), Vh-CDR3 (SEQ ID NO:60), Vl-CDR1 (SEQ ID NO:160), Vl-CDR2 (SEQ ID NO:161), and Vl-CDR3 (SEQ ID NO:162). Aspects of the invention include isolated polypeptides comprising the six CDRs of Ab-11, wherein the CDRs include no more than one, two, three, four, five, or six amino acid additions, deletions, or substitutions of Vh-CDR1 (SEQ ID NO:64), Vh-CDR2 (SEQ ID NO:65), Vh-CDR3 (SEQ ID NO:66), Vl-CDR1 (SEQ ID NO:166), Vl-CDR2 (SEQ ID NO:167), and Vl-CDR3 (SEQ ID NO:168). Aspects of the invention include isolated polypeptides comprising the six CDRs of Ab-12, wherein the CDRs include no more than one, two, three, four, five, or six amino acid additions, deletions, or substitutions of Vh-CDR1 (SEQ ID NO:70), Vh-CDR2 (SEQ ID NO:71), Vh-CDR3 (SEQ ID NO:72), Vl-CDR1 (SEQ ID NO:172), Vl-CDR2 (SEQ ID NO:173), and Vl-CDR3 (SEQ ID NO:174). Aspects of the invention include isolated polypeptides comprising the six CDRs of Ab-13, wherein the CDRs include no more than one, two, three, four, five, or six amino acid additions, deletions, or substitutions of Vh-CDR1 (SEQ ID NO:76), Vh-CDR2 (SEQ ID NO:77), Vh-CDR3 (SEQ ID NO:78), Vl-CDR1 (SEQ ID NO:178), Vl-CDR2 (SEQ ID NO:179), and Vl-CDR3 (SEQ ID NO:180). Aspects of the invention include isolated polypeptides comprising the six CDRs of Ab-14, wherein the CDRs include no more than one, two, three, four, five, or six amino acid additions, deletions, or substitutions of Vh-CDR1 (SEQ ID NO:82), Vh-CDR2 (SEQ ID NO:83), Vh-CDR3 (SEQ ID NO:84), Vl-CDR1 (SEQ ID NO:184), Vl-CDR2 (SEQ ID NO:185), and Vl-CDR3 (SEQ ID NO:186). Aspects of the invention include isolated polypeptides comprising the six CDRs of Ab-15, wherein the CDRs include no more than one, two, three, four, five, or six amino acid additions, deletions, or substitutions of Vh-CDR1 (SEQ ID NO:88), Vh-CDR2 (SEQ ID NO:89), Vh-CDR3 (SEQ ID NO:90), Vl-CDR1 (SEQ ID NO:190), Vl-CDR2 (SEQ ID NO:191), and Vl-CDR3 (SEQ ID NO:192). Aspects of the invention include isolated polypeptides comprising the six CDRs of Ab-16, wherein the CDRs include no more than one, two, three, four, five, or six amino acid additions, deletions, or substitutions of Vh-CDR1 (SEQ ID NO:94), Vh-CDR2 (SEQ ID NO:95), Vh-CDR3 (SEQ ID NO:96), Vl-CDR1 (SEQ ID NO:196), Vl-CDR2 (SEQ ID NO:197), and Vl-CDR3 (SEQ ID NO:198). Aspects of the invention include isolated polypeptides comprising the six CDRs of Ab-17, wherein the CDRs include no more than one, two, three, four, five, or six amino acid additions, deletions, or substitutions of Vh-CDR1 (SEQ ID NO:100), Vh-CDR2 (SEQ ID NO:101), Vh-CDR3 (SEQ ID NO:102), Vl-CDR1 (SEQ ID NO:202), Vl-CDR2 (SEQ ID NO:203), and Vl-CDR3 (SEQ ID NO:204).

Aspects of the invention include isolated polypeptides comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-1Vl (SEQ ID NO:240) and Ab-1Vh (SEQ ID NO:206), respectively. Aspects of the invention include isolated polypeptides comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-2Vl (SEQ ID NO:242) and Ab-2Vh (SEQ ID NO:208), respectively. Aspects of the invention include isolated polypeptides comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-3Vl (SEQ ID NO:244) and Ab-3Vh (SEQ ID NO:210), respectively. Aspects of the invention include isolated polypeptides comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-4Vl (SEQ ID NO:246) and Ab-4Vh (SEQ ID NO:212), respectively. Aspects of the invention include isolated polypeptides comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-5Vl (SEQ ID NO:248) and Ab-5Vh (SEQ ID NO:214), respectively. Aspects of the invention include polypeptides comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-6Vl (SEQ ID NO:250) and Ab-6Vh (SEQ ID NO:216), respectively. Aspects of the invention include isolated polypeptides comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-7Vl (SEQ ID NO:252) and Ab-7Vh (SEQ ID NO:218), respectively. Aspects of the invention include isolated polypeptides comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-8Vl (SEQ ID NO:254) and Ab-8Vh (SEQ ID NO:220), respectively. Aspects of the invention include isolated polypeptides comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-9Vl (SEQ ID NO:256) and Ab-9Vh (SEQ ID NO:222), respectively. Aspects of the invention include isolated polypeptides comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-10Vl (SEQ ID NO:258) and Ab-10Vh (SEQ ID NO:224), respectively. Aspects of the invention include isolated polypeptides comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-11Vl (SEQ ID NO:260) and Ab-11Vh (SEQ ID NO:226), respectively. Aspects of the invention include isolated polypeptides comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-12Vl (SEQ ID NO:262) and Ab-12Vh (SEQ ID NO:228), respectively. Aspects of the invention include isolated polypeptides comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-13Vl (SEQ ID NO:264) and Ab-13Vh (SEQ ID NO:230), respectively. Aspects of the invention include isolated polypeptides comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-14Vl (SEQ ID NO:266) and Ab-14Vh (SEQ ID NO:232), respectively. Aspects of the invention include isolated polypeptides comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-15Vl (SEQ ID NO:268) and Ab-15Vh (SEQ ID NO:234), respectively. Aspects of the invention include isolated polypeptides comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-16Vl (SEQ ID NO:270) and Ab-16Vh (SEQ ID NO:236), respectively. Aspects of the invention include isolated polypeptides comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-17Vl (SEQ ID NO:272) and Ab-17Vh (SEQ ID NO:238), respectively.

Aspects of the invention include isolated polypeptides that are at least 80%, 81%, 82%, 83%, 84%, 85%, 86%, 87%, 88%, 89%, 90%, 91%, 92%, 93%, 94%, 95%, 96%, 97%, 98%, or 99% identical to a polypeptide comprising an Ab-1 light chain (SEQ ID NO:280) and/or an Ab-1 heavy chain (SEQ ID NO:274). Aspects of the invention include isolated polypeptides that are at least 80%, 81%, 82%, 83%, 84%, 85%, 86%, 87%, 88%, 89%, 90%, 91%, 92%, 93%, 94%, 95%, 96%, 97%, 98%, or 99% identical to a polypeptide comprising an Ab-2 light chain (SEQ ID NO:282) and/or an Ab-2 heavy chain (SEQ ID NO:276). Aspects of the invention include isolated polypeptides that are at least 80%, 81%, 82%, 83%, 84%, 85%, 86%, 87%, 88%, 89%, 90%, 91%, 92%, 93%, 94%, 95%, 96%, 97%, 98%, or 99% identical to a polypeptide comprising an Ab-3 light chain (SEQ ID NO:284) and/or an Ab-3 heavy chain (SEQ ID NO:278). Aspects of the invention include fragments, derivatives, muteins, and variants of the aforementioned.

By "protein," as used herein, is meant at least two covalently attached amino acids, which includes proteins, polypeptides, oligopeptides and peptides. In some embodiments, the two or more covalently attached amino acids are attached by a peptide bond. The protein may be made up of naturally occurring amino acids and peptide bonds, for example when the protein is made recombinantly using expression systems and host cells, as outlined below. Alternatively, the protein may include synthetic amino acids (e.g., homophenylalanine, citrulline, ornithine, and norleucine), or peptidomimetic structures, i.e., "peptide or protein analogs", such as peptoids (see, Simon et al., 1992, *Proc. Natl. Acad. Sci. U.S.A.* 89:9367, incorporated by reference herein), which can be resistant to proteases or other physiological and/or storage conditions. Such synthetic amino acids may be incorporated in particular when the antigen binding protein is synthesized in vitro by conventional methods well known in the art. In addition, any combination of peptidomimetic, synthetic and naturally occurring residues/structures can be used. "Amino acid" also includes imino acid residues such as proline and hydroxyproline. The amino acid "R group" or "side chain" may be in either the (L)- or the (S)-configuration. In a specific embodiment, the amino acids are in the (L)- or (S)-configuration.

A "recombinant protein" is a protein made using recombinant techniques using any techniques and methods known in the art, i.e., through the expression of a recombinant nucleic acid as described herein. Methods and techniques for the production of recombinant proteins are well known in the art.

In some embodiments, the antigen binding proteins of the invention are isolated proteins or substantially pure proteins. An "isolated" protein is unaccompanied by at least some of the material with which it is normally associated in its natural state, for example constituting at least about 5%, or at least about 50% by weight of the total protein in a given sample. It is understood that the isolated protein may constitute from 5 to 99.9% by weight of the total protein content depending on the circumstances. For example, the protein may be made at a significantly higher concentration through the use of an inducible promoter or high expression promoter, such that the protein is made at increased concentration levels. The definition includes the production of an antigen binding protein in a wide variety of organisms and/or host cells that are known in the art.

For amino acid sequences, sequence identity and/or similarity is determined by using standard techniques known in the art, including, but not limited to, the local sequence identity algorithm of Smith and Waterman, 1981, *Adv. Appl.*

*Math.* 2:482, the sequence identity alignment algorithm of Needleman and Wunsch, 1970, *J. Mol. Biol.* 48:443, the search for similarity method of Pearson and Lipman, 1988, *Proc. Nat. Acad. Sci. U.S.A.* 85:2444, computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., 1984, *Nucl. Acid Res.* 12:387-395, preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127-149 (1988), Alan R. Liss, Inc.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, 1987, *J. Mol. Evol.* 35:351-360; the method is similar to that described by Higgins and Sharp, 1989, *CABIOS* 5:151-153. Useful PILEUP parameters including a default gap weight of 3.00, a default gap length weight of 0.10, and weighted end gaps.

Another example of a useful algorithm is the BLAST algorithm, described in: Altschul et al., 1990, *J. Mol. Biol.* 215:403-410; Altschul et al., 1997, *Nucleic Acids Res.* 25:3389-3402; and Karin et al., 1993, *Proc. Natl. Acad. Sci. U.S.A.* 90:5873-5787. A particularly useful BLAST program is the WU-BLAST-2 program which was obtained from Altschul et al., 1996, *Methods in Enzymology* 266:460-480. WU-BLAST-2 uses several search parameters, most of which are set to the default values. The adjustable parameters are set with the following values: overlap span=1, overlap fraction=0.125, word threshold (T)=II. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., 1993, *Nucl. Acids Res.* 25:3389-3402. Gapped BLAST uses BLOSUM-62 substitution scores; threshold T parameter set to 9; the two-hit method to trigger ungapped extensions, charges gap lengths of k a cost of 10+k; $X_u$ set to 16, and $X_g$ set to 40 for database search stage and to 67 for the output stage of the algorithms. Gapped alignments are triggered by a score corresponding to about 22 bits.

Generally, the amino acid homology, similarity, or identity between individual variant CDRs are at least 80% to the sequences depicted herein, and more typically with preferably increasing homologies or identities of at least 85%, 90%, 91%, 92%, 93%, 94%, 95%, 96%, 97%, 98%, 99%, and almost 100%. In a similar manner, "percent (%) nucleic acid sequence identity" with respect to the nucleic acid sequence of the binding proteins identified herein is defined as the percentage of nucleotide residues in a candidate sequence that are identical with the nucleotide residues in the coding sequence of the antigen binding protein. A specific method utilizes the BLASTN module of WU-BLAST-2 set to the default parameters, with overlap span and overlap fraction set to 1 and 0.125, respectively.

While the site or region for introducing an amino acid sequence variation is predetermined, the mutation per se need not be predetermined. For example, in order to optimize the performance of a mutation at a given site, random mutagenesis may be conducted at the target codon or region and the expressed antigen binding protein CDR variants screened for the optimal combination of desired activity. Techniques for making substitution mutations at predetermined sites in DNA having a known sequence are well known, for example, M13 primer mutagenesis and PCR mutagenesis. Screening of the mutants is done using assays described in the Examples, for example Amino acid substitutions are typically of single residues; insertions usually will be on the order of from about one (1) to about twenty (20) amino acid residues, although considerably larger insertions may be tolerated. Deletions range from about one (1) to about twenty (20) amino acid residues, although in some cases deletions may be much larger. Substitutions, deletions, insertions or any combination thereof may be used to arrive at a final derivative or variant. Generally these changes are done on a few amino acids to minimize the alteration of the molecule, particularly the immunogenicity and specificity of the antigen binding protein. However, larger changes may be tolerated in certain circumstances. Conservative substitutions are generally made in accordance with the following chart depicted as TABLE 2.

TABLE 2

| Original Residue | Exemplary Substitutions |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in TABLE 2. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e g., glycine.

The variants typically exhibit the same qualitative biological activity and will elicit the same immune response as the naturally-occurring analogue, although variants also are selected to modify the characteristics of the antigen binding protein proteins as needed. Alternatively, the variant may be designed such that the biological activity of the antigen binding protein is altered. For example, glycosylation sites may be altered or removed as discussed herein. Such a modification of the BCMA antigen binding proteins, including antibodies, is an example of a derivative. A "derivative" of a polypeptide is a polypeptide (e.g., an antibody) that has been chemically modified, e.g., via conjugation to another chemical moiety such as, for example, polyethylene glycol, albumin (e.g., human serum albumin), phosphorylation, and glycosylation.

Other derivatives of BCMA antibodies within the scope of this invention include covalent or aggregative conjugates of BCMA antibodies, or fragments thereof, with other proteins or polypeptides, such as by expression of recombinant fusion proteins comprising heterologous polypeptides fused to the N-terminus or C-terminus of a BCMA antibody polypeptide. For example, the conjugated peptide may be a heterologous signal (or leader) polypeptide, e.g., the yeast alpha-factor leader, or a peptide such as an epitope tag. BCMA antibody-containing fusion proteins can comprise peptides added to facilitate purification or identification of the BCMA antibody (e.g., poly-His). An BCMA antibody polypeptide also can be linked to the FLAG peptide DYKDDDDK (SEQ ID NO:447) as described in Hopp et al., Bio/Technology 6:1204, 1988, and U.S. Pat. No. 5,011,912. The FLAG peptide is highly antigenic and provides an epitope reversibly bound by a specific monoclonal antibody (mAb), enabling rapid assay and facile purification of expressed recombinant protein. Reagents useful for preparing fusion proteins in which the FLAG peptide is fused to a given polypeptide are commercially available (Sigma, St. Louis, Mo.).

Oligomers that contain one or more BCMA antibody polypeptides may be employed as BCMA antagonists. Oligomers may be in the form of covalently-linked or non-covalently-linked dimers, trimers, or higher oligomers. Oligomers comprising two or more BCMA antibody polypeptides are contemplated for use, with one example being a homodimer. Other oligomers include heterodimers, homotrimers, heterotrimers, homotetramers, heterotetramers, etc. One embodiment is directed to oligomers comprising multiple BCMA antibody polypeptides joined via covalent or non-covalent interactions between peptide moieties fused to the BCMA antibody polypeptides. Such peptides may be peptide linkers (spacers), or peptides that have the property of promoting oligomerization. Leucine zippers and certain polypeptides derived from antibodies are among the peptides that can promote oligomerization of BCMA antibody polypeptides attached thereto, as described in more detail below. In particular embodiments, the oligomers comprise from two to four BCMA antibody polypeptides. The BCMA antibody moieties of the oligomer may be in any of the forms described above, e.g., variants or fragments.

One embodiment of the present invention is directed to a dimer comprising two fusion proteins created by fusing an BCMA binding fragment of an BCMA antibody to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain disulfide bonds form between the Fc moieties to yield the dimer. Alternatively, the oligomer is a fusion protein comprising multiple BCMA antibody polypeptides, with or without peptide linkers (spacer peptides). Among the suitable peptide linkers are those described in U.S. Pat. Nos. 4,751,180 and 4,935,233.

Another method for preparing oligomeric BCMA antibody derivatives involves use of a leucine zipper. Leucine zipper domains are peptides that promote oligomerization of the proteins in which they are found. Leucine zippers were originally identified in several DNA-binding proteins (Landschulz et al., 1988, Science 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in PCT application WO 94/10308, and the leucine zipper derived from lung surfactant protein D (SPD) described in Hoppe et al., 1994, FEBS Letters 344:191, hereby incorporated by reference. The use of a modified leucine zipper that allows for stable trimerization of a heterologous protein fused thereto is described in Fanslow et al., 1994, Semin. Immunol. 6:267-78. In one approach, recombinant fusion proteins comprising an BCMA antibody fragment or derivative fused to a leucine zipper peptide are expressed in suitable host cells, and the soluble oligomeric BCMA antibody fragments or derivatives that form are recovered from the culture supernatant.

Covalent modifications are also considered derivatives of the BCMA antigen binding proteins and are included within the scope of this invention, and are generally, but not always, done post-translationally. For example, several types of covalent modifications of the antigen binding protein are introduced into the molecule by reacting specific amino acid residues of the antigen binding protein with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}$I or $^{131}$I to prepare labeled proteins for use in radioimmunoassay, the chloramine T method described above being suitable.

Carboxyl side groups (aspartyl or glutamyl) are selectively modified by reaction with carbodiimides (R'—N=C=N—R'), where R and R' are optionally different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for cross-linking antigen binding proteins to a water-insoluble support matrix or surface for use in a variety of methods. Commonly used crosslinking agents include, e.g., 1,1-bis(diazoacetyl)-2-phenylethane, glutaraldehyde, N-hydroxysuccinimide esters, for example, esters with 4-azidosalicylic acid, homo-bifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues, respectively. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W.H. Freeman & Co., San Francisco, 1983, pp. 79-86), acetylation of the N-terminal amine, and amidation of any C-terminal carboxyl group.

Another type of covalent modification of the antigen binding protein included within the scope of this invention comprises altering the glycosylation pattern of the protein. As is known in the art, glycosylation patterns can depend on both the sequence of the protein (e.g., the presence or absence of particular glycosylation amino acid residues, discussed below), or the host cell or organism in which the protein is produced. Particular expression systems are discussed below.

Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used.

Addition of glycosylation sites to the antigen binding protein is conveniently accomplished by altering the amino acid sequence such that it contains one or more of the above-described tri-peptide sequences (for N-linked glycosylation sites). The alteration may also be made by the addition of, or substitution by, one or more serine or threonine residues to the starting sequence (for O-linked glycosylation sites). For ease, the antigen binding protein amino acid sequence is preferably altered through changes at the DNA level, particularly by mutating the DNA encoding the target polypeptide at preselected bases such that codons are generated that will translate into the desired amino acids.

Another means of increasing the number of carbohydrate moieties on the antigen binding protein is by chemical or enzymatic coupling of glycosides to the protein. These procedures are advantageous in that they do not require production of the protein in a host cell that has glycosylation capabilities for N- and O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published Sep. 11, 1987, and in Aplin and Wriston, 1981, *CRC Crit. Rev. Biochem., pp.* 259-306.

Removal of carbohydrate moieties present on the starting antigen binding protein may be accomplished chemically or enzymatically. Chemical deglycosylation requires exposure of the protein to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin et al., 1987, *Arch. Biochem. Biophys.* 259:52 and by Edge et al., 1981, *Anal. Biochem.* 118:131. Enzymatic cleavage of carbohydrate moieties on polypeptides can be achieved by the use of a variety of endo- and exo-glycosidases as described by Thotakura et al., 1987, *Meth. Enzymol.* 138:350. Glycosylation at potential glycosylation sites may be prevented by the use of the compound tunicamycin as described by Duskin et al., 1982, *J. Biol. Chem.* 257:3105. Tunicamycin blocks the formation of protein-N-glycoside linkages.

Another type of covalent modification of the antigen binding protein comprises linking the antigen binding protein to various nonproteinaceous polymers, including, but not limited to, various polyols such as polyethylene glycol, polypropylene glycol or polyoxyalkylenes, in the manner set forth in U.S. Pat. Nos. 4,640,835; 4,496,689; 4,301,144; 4,670,417; 4,791,192 or 4,179,337. In addition, as is known in the art, amino acid substitutions may be made in various positions within the antigen binding protein to facilitate the addition of polymers such as PEG.

In some embodiments, the covalent modification of the antigen binding proteins of the invention comprises the addition of one or more labels. The term "labelling group" means any detectable label. Examples of suitable labelling groups include, but are not limited to, the following: radioisotopes or radionuclides (e.g., $^{3}$H, $^{14}$C, $^{15}$N, $^{35}$S, $^{90}$Y, $^{99}$Tc, $^{111}$In, $^{125}$I, $^{131}$I), fluorescent groups (e.g., FITC, rhodamine, lanthanide phosphors), enzymatic groups (e.g., horseradish peroxidase, β-galactosidase, luciferase, alkaline phosphatase), chemiluminescent groups, biotinyl groups, or predetermined polypeptide epitopes recognized by a secondary reporter (e.g., leucine zipper pair sequences, binding sites for secondary antibodies, metal binding domains, epitope tags). In some embodiments, the labelling group is coupled to the antigen binding protein via spacer arms of various lengths to reduce potential steric hindrance. Various methods for labelling proteins are known in the art and may be used in performing the present invention.

In general, labels fall into a variety of classes, depending on the assay in which they are to be detected: a) isotopic labels, which may be radioactive or heavy isotopes; b) magnetic labels (e.g., magnetic particles); c) redox active moieties; d) optical dyes; enzymatic groups (e.g. horseradish peroxidase, β-galactosidase, luciferase, alkaline phosphatase); e) biotinylated groups; and f) predetermined polypeptide epitopes recognized by a secondary reporter (e.g., leucine zipper pair sequences, binding sites for secondary antibodies, metal binding domains, epitope tags, etc.). In some embodiments, the labeling group is coupled to the antigen binding protein via spacer arms of various lengths to reduce potential steric hindrance. Various methods for labeling proteins are known in the art and may be used in performing the present invention.

Specific labels include optical dyes, including, but not limited to, chromophores, phosphors and fluorophores, with the latter being specific in many instances. Fluorophores can be either "small molecule" fluores, or proteinaceous fluores.

By "fluorescent label" is meant any molecule that may be detected via its inherent fluorescent properties. Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade BlueJ, Texas Red, IAEDANS, EDANS, BODIPY FL, LC Red 640, Cy 5, Cy 5.5, LC Red 705, Oregon green, the Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 660, Alexa Fluor 680), Cascade Blue, Cascade Yellow and R-phycoerythrin (PE) (Molecular Probes, Eugene, Oreg.), FITC, Rhodamine, and Texas Red (Pierce, Rockford, Ill., Cy5, Cy5.5, Cy7 (Amersham Life Science, Pittsburgh, Pa.). Suitable optical dyes, including fluorophores, are described in Molecular Probes Handbook by Richard P. Haugland, hereby expressly incorporated by reference.

Suitable proteinaceous fluorescent labels also include, but are not limited to, green fluorescent protein, including a Renilla, Ptilosarcus, or Aequorea species of GFP (Chalfie et al., 1994, *Science* 263:802-805), EGFP (Clontech Laboratories, Inc., Genbank Accession Number U55762), blue fluorescent protein (BFP, Quantum Biotechnologies, Inc. 1801 de Maisonneuve Blvd. West, 8th Floor, Montreal, Quebec, Canada H3H 1J9; Stauber, 1998, *Biotechniques* 24:462-471; Heim et al., 1996, *Curr. Biol.* 6:178-182), enhanced yellow fluorescent protein (EYFP, Clontech Laboratories, Inc.), luciferase (Ichiki et al., 1993, *J. Immunol.* 150:5408-5417), β galactosidase (Nolan et al., 1988, *Proc. Natl. Acad. Sci. U.S.A.* 85:2603-2607) and Renilla (WO92/15673, WO95/07463, WO98/14605, WO98/26277, WO99/49019, U.S. Pat. Nos. 5,292,658, 5,418,155, 5,683,888, 5,741,668, 5,777,079, 5,804,387, 5,874,304, 5,876,995, 5,925,558). All of the above-cited references are expressly incorporated herein by reference.

Polynucleotides Encoding BCMA Antigen Binding Proteins

Encompassed within the invention are polynucleotides encoding BCMA antigen binding proteins, in particular the antibodies as defined herein. The polynucleotide sequences for the heavy chain variable and light chain variable regions, the CDRs, and the full length heavy and light chains for select antibodies are provided in herein.

Aspects of the invention include isolated polynucleotides that encode a monoclonal antibody comprising the six CDRs of Ab-1. Aspects of the invention include isolated polynucleotides that encode a monoclonal antibody comprising the six CDRs of Ab-2. Aspects of the invention include isolated polynucleotides that encode a monoclonal antibody comprising the six CDRs of Ab-3. Aspects of the invention include isolated polynucleotides that encode a monoclonal antibody comprising the six CDRs of Ab-4. Aspects of the invention include isolated polynucleotides that encode a monoclonal antibody comprising the six CDRs of Ab-5. Aspects of the invention include isolated polynucleotides that encode a monoclonal antibody comprising the six CDRs of Ab-6. Aspects of the invention include isolated polynucleotides that encode a monoclonal antibody comprising the six CDRs of Ab-7. Aspects of the invention include isolated polynucleotides that encode a monoclonal antibody comprising the six CDRs of Ab-8. Aspects of the invention include isolated polynucleotides that encode a monoclonal antibody comprising the six CDRs of Ab-9. Aspects of the invention include isolated polynucleotides that encode a monoclonal antibody comprising the six CDRs of Ab-10. Aspects of the invention include isolated polynucleotides that encode a monoclonal antibody comprising the six CDRs of Ab-11. Aspects of the invention include isolated polynucleotides that encode a monoclonal antibody comprising the six CDRs of Ab-12. Aspects of the invention include isolated polynucleotides that encode a monoclonal antibody comprising the six CDRs of Ab-13. Aspects of the invention include isolated polynucleotides that encode a monoclonal antibody comprising the six CDRs of Ab-14. Aspects of the invention include isolated polynucleotides that encode a monoclonal antibody comprising the six CDRs of Ab-15. Aspects of the invention include isolated polynucleotides that encode a monoclonal antibody comprising the six CDRs of Ab-16. Aspects of the invention include isolated polynucleotides that encode a monoclonal antibody comprising the six CDRs of Ab-17. Aspects of the aforementioned embodiments include human monoclonal antibodies, human monoclonal IgG antibodies, and human monoclonal IgG1 antibodies.

Aspects of the invention include isolated polynucleotides that encode a monoclonal antibody comprising the six CDRs of Ab-1 as determined by any one of the AHo, Kabat, or Clothia numbering systems. Aspects of the invention include isolated polynucleotides that encode a monoclonal antibody comprising the six CDRs of Ab-2 as determined by any one of the AHo, Kabat, or Clothia numbering systems. Aspects of the invention include isolated polynucleotides that encode a monoclonal antibody comprising the six CDRs of Ab-3 as determined by any one of the AHo, Kabat, or Clothia numbering systems. Aspects of the invention include isolated polynucleotides that encode a monoclonal antibody comprising the six CDRs of Ab-4 as determined by any one of the AHo, Kabat, or Clothia numbering systems. Aspects of the invention include isolated polynucleotides that encode a monoclonal antibody comprising the six CDRs of Ab-5 as determined by any one of the AHo, Kabat, or Clothia numbering systems. Aspects of the invention include isolated polynucleotides that encode a monoclonal antibody comprising the six CDRs of Ab-6 as determined by any one of the AHo, Kabat, or Clothia numbering systems. Aspects of the invention include isolated polynucleotides that encode a monoclonal antibody comprising the six CDRs of Ab-7 as determined by any one of the AHo, Kabat, or Clothia numbering systems. Aspects of the invention include isolated polynucleotides that encode a monoclonal antibody comprising the six CDRs of Ab-8 as determined by any one of the AHo, Kabat, or Clothia numbering systems. Aspects of the invention include isolated polynucleotides that encode a monoclonal antibody comprising the six CDRs of Ab-9 as determined by any one of the AHo, Kabat, or Clothia numbering systems. Aspects of the invention include isolated polynucleotides that encode a monoclonal antibody comprising the six CDRs of Ab-10 as determined by any one of the AHo, Kabat, or Clothia numbering systems. Aspects of the invention include isolated polynucleotides that encode a monoclonal antibody comprising the six CDRs of Ab-11 as determined by any one of the AHo, Kabat, or Clothia numbering systems. Aspects of the invention include isolated polynucleotides that encode a monoclonal antibody comprising the six CDRs of Ab-12 as determined by any one of the AHo, Kabat, or Clothia numbering systems. Aspects of the invention include isolated polynucleotides that encode a monoclonal antibody comprising the six CDRs of Ab-13 as determined by any one of the AHo, Kabat, or Clothia numbering systems. Aspects of the invention include isolated polynucleotides that encode a monoclonal antibody comprising the six CDRs of Ab-14 as determined by any one of the AHo, Kabat, or Clothia numbering systems. Aspects of the invention include isolated polynucleotides that encode a monoclonal antibody comprising the six CDRs of Ab-15 as determined by any one of the AHo, Kabat, or Clothia numbering systems. Aspects of the invention include isolated polynucleotides that encode a monoclonal antibody comprising the six CDRs of Ab-16 as determined by any one of the AHo, Kabat, or Clothia numbering systems. Aspects of the invention include isolated polynucleotides that encode a monoclonal antibody comprising the six CDRs of Ab-17 as determined by any one of the AHo, Kabat, or Clothia numbering systems. Aspects of the aforementioned embodiments include human monoclonal antibodies, human monoclonal IgG antibodies, and human monoclonal IgG1 antibodies.

Aspects of the invention include isolated polynucleotides that encode a monoclonal antibody comprising the six CDRs of Ab-1, specifically Vh-CDR1 (SEQ ID NO:4), Vh-CDR2 (SEQ ID NO:5), Vh-CDR3 (SEQ ID NO:6), Vl-CDR1 (SEQ ID NO:106), Vl-CDR2 (SEQ ID NO:107), and Vl-CDR3 (SEQ ID NO:108). Aspects of the invention include isolated polynucleotides that encode a monoclonal antibody comprising the six CDRs of Ab-2, specifically Vh-CDR1 (SEQ ID NO:10), Vh-CDR2 (SEQ ID NO:11), Vh-CDR3 (SEQ ID NO:12), Vl-CDR1 (SEQ ID NO:112), Vl-CDR2 (SEQ ID NO:113), and Vl-CDR3 (SEQ ID NO:114). Aspects of the invention include isolated polynucleotides that encode a monoclonal antibody comprising the six CDRs of Ab-3, specifically Vh-CDR1 (SEQ ID NO:16), Vh-CDR2 (SEQ ID NO:17), Vh-CDR3 (SEQ ID NO:18), Vl-CDR1 (SEQ ID NO:118), Vl-CDR2 (SEQ ID NO:119), and Vl-CDR3 (SEQ ID NO:120). Aspects of the invention include isolated polynucleotides that encode a monoclonal antibody comprising the six CDRs of Ab-4, specifically Vh-CDR1 (SEQ ID NO:22), Vh-CDR2 (SEQ ID NO:23), Vh-CDR3 (SEQ ID NO:24), Vl-CDR1 (SEQ ID NO:124), Vl-CDR2 (SEQ ID NO:125), and Vl-CDR3 (SEQ ID NO:126). Aspects of the invention include isolated polynucleotides that encode a monoclonal antibody comprising the six CDRs of Ab-5, specifically Vh-CDR1 (SEQ ID NO:28), Vh-CDR2 (SEQ ID NO:29), Vh-CDR3 (SEQ ID NO:30), Vl-CDR1 (SEQ ID NO:130), Vl-CDR2 (SEQ ID NO:131), and Vl-CDR3 (SEQ ID NO:132). Aspects of the invention include isolated polynucleotides that encode a monoclonal antibody comprising the six CDRs of Ab-6, specifically Vh-CDR1 (SEQ ID NO:34), Vh-CDR2 (SEQ ID NO:35), Vh-CDR3 (SEQ ID NO:36), Vl-CDR1 (SEQ ID NO:136), Vl-CDR2 (SEQ ID NO:137), and Vl-CDR3 (SEQ ID NO:138). Aspects of the invention include isolated polynucleotides that encode a monoclonal antibody comprising the six CDRs of Ab-7, specifically Vh-CDR1 (SEQ ID NO:40), Vh-CDR2 (SEQ ID NO:41), Vh-CDR3 (SEQ ID NO:42), Vl-CDR1 (SEQ ID NO:142), Vl-CDR2 (SEQ ID NO:143), and Vl-CDR3 (SEQ ID NO:144). Aspects of the invention include isolated polynucleotides that encode a monoclonal antibody comprising the six CDRs of Ab-8, specifically Vh-CDR1 (SEQ ID NO:46), Vh-CDR2 (SEQ ID NO:47), Vh-CDR3 (SEQ ID NO:48), Vl-CDR1 (SEQ ID NO:148), Vl-CDR2 (SEQ ID NO:149), and Vl-CDR3 (SEQ ID NO:150). Aspects of the invention include isolated polynucleotides that encode a monoclonal antibody comprising the six CDRs of Ab-9, specifically Vh-CDR1 (SEQ ID NO:52), Vh-CDR2 (SEQ ID NO:53), Vh-CDR3 (SEQ ID NO:54), Vl-CDR1 (SEQ ID NO:154), Vl-CDR2 (SEQ ID NO:155), and Vl-CDR3 (SEQ ID NO:156). Aspects of the invention include isolated polynucleotides that encode a monoclonal antibody comprising the six CDRs of Ab-10, specifically Vh-CDR1 (SEQ ID NO:58), Vh-CDR2 (SEQ ID NO:59), Vh-CDR3 (SEQ ID NO:60), Vl-CDR1 (SEQ ID NO:160), Vl-CDR2 (SEQ ID NO:161), and Vl-CDR3 (SEQ ID NO:162). Aspects of the invention include isolated polynucleotides that encode a monoclonal antibody comprising the six CDRs of Ab-11, specifically Vh-CDR1 (SEQ ID NO:64), Vh-CDR2 (SEQ ID NO:65), Vh-CDR3 (SEQ ID NO:66), Vl-CDR1 (SEQ ID NO:166), Vl-CDR2 (SEQ ID NO:167), and Vl-CDR3 (SEQ ID NO:168). Aspects of the invention include isolated polynucleotides that encode a monoclonal antibody comprising the six CDRs of Ab-12, specifically Vh-CDR1 (SEQ ID NO:70), Vh-CDR2 (SEQ ID NO:71), Vh-CDR3 (SEQ ID NO:72), Vl-CDR1 (SEQ ID NO:172), Vl-CDR2 (SEQ ID NO:173), and Vl-CDR3 (SEQ ID NO:174). Aspects of the invention include isolated polynucleotides that encode a monoclonal antibody comprising the six CDRs of Ab-13, specifically Vh-CDR1 (SEQ ID NO:76), Vh-CDR2 (SEQ ID NO:77), Vh-CDR3 (SEQ ID NO:78), Vl-CDR1 (SEQ ID NO:178), Vl-CDR2 (SEQ ID NO:179), and Vl-CDR3 (SEQ ID NO:180). Aspects of the invention include isolated polynucleotides that encode a monoclonal antibody comprising the six CDRs of Ab-14, specifically Vh-CDR1 (SEQ ID NO:82), Vh-CDR2 (SEQ ID NO:83), Vh-CDR3 (SEQ ID NO:84), Vl-CDR1 (SEQ ID NO:184), Vl-CDR2 (SEQ ID NO:185), and Vl-CDR3 (SEQ ID NO:186). Aspects of the invention include isolated polynucleotides that encode a monoclonal antibody comprising the six CDRs of Ab-15, specifically Vh-CDR1 (SEQ ID NO:88), Vh-CDR2 (SEQ ID NO:89), Vh-CDR3 (SEQ ID NO:90), Vl-CDR1 (SEQ ID NO:190), Vl-CDR2 (SEQ ID NO:191), and Vl-CDR3 (SEQ ID NO:192). Aspects of the invention include isolated polynucleotides that encode a monoclonal antibody comprising the six CDRs of Ab-16, specifically Vh-CDR1 (SEQ ID NO:94), Vh-CDR2 (SEQ ID NO:95), Vh-CDR3 (SEQ ID NO:96), Vl-CDR1 (SEQ ID NO:196), Vl-CDR2 (SEQ ID NO:197), and Vl-CDR3 (SEQ ID NO:198). Aspects of the invention include isolated polynucleotides that encode a monoclonal antibody comprising the six CDRs of Ab-17, specifically Vh-CDR1 (SEQ ID NO:100), Vh-CDR2 (SEQ ID NO:101), Vh-CDR3 (SEQ ID NO:102), Vl-CDR1 (SEQ ID NO:202), Vl-CDR2 (SEQ ID NO:203), and Vl-CDR3 (SEQ ID NO:204). Aspects of the aforementioned embodiments include human monoclonal antibodies, human monoclonal IgG antibodies, and human monoclonal IgG1 antibodies. Aspects of the invention include fragments, derivatives, muteins, and variants of the aforementioned.

Aspects of the invention include isolated polynucleotides that encode a monoclonal antibody comprising an Ab-1Vl (SEQ ID NO:240) and an Ab-1Vh (SEQ ID NO:206) domain. Aspects of the invention include isolated polynucleotides that encode a monoclonal antibody comprising an Ab-2Vl (SEQ ID NO:242) and an Ab-2Vh (SEQ ID NO:208) domain. Aspects of the invention include isolated polynucleotides that encode a monoclonal antibody comprising an Ab-3Vl (SEQ ID NO:244) and an Ab-3Vh (SEQ ID NO:210) domain. Aspects of the invention include isolated polynucleotides that encode a monoclonal antibody comprising an Ab-4Vl (SEQ ID NO:246) and an Ab-4Vh (SEQ ID NO:212) domain. Aspects of the invention include isolated polynucleotides that encode a monoclonal antibody comprising an Ab-5Vl (SEQ ID NO:248) and an Ab-5Vh (SEQ ID NO:214) domain. Aspects of the invention include isolated polynucleotides that encode a monoclonal antibody comprising an Ab-6Vl (SEQ ID NO:250) and an Ab-6Vh (SEQ ID NO:216) domain. Aspects of the invention include isolated polynucleotides that encode a monoclonal antibody comprising an Ab-7Vl (SEQ ID NO:252) and an Ab-7Vh (SEQ ID NO:218) domain. Aspects of the invention include isolated polynucleotides that encode a monoclonal antibody comprising an Ab-8Vl (SEQ ID NO:254) and an Ab-8Vh (SEQ ID NO:220) domain. Aspects of the invention include isolated polynucleotides that encode a monoclonal antibody comprising an Ab-9Vl (SEQ ID NO:256) and an Ab-9Vh (SEQ ID NO:222) domain. Aspects of the invention include isolated polynucleotides that encode a monoclonal antibody comprising an Ab-10Vl (SEQ ID NO:258) and an Ab-10Vh (SEQ ID NO:224) domain. Aspects of the invention include isolated polynucleotides that encode a monoclonal antibody comprising an Ab-11Vl (SEQ ID NO:260) and an Ab-11Vh (SEQ ID NO:226) domain. Aspects of the invention include isolated polynucleotides that encode a monoclonal antibody comprising an Ab-12Vl (SEQ ID NO:262) and an Ab-12Vh (SEQ ID NO:228) domain. Aspects of the invention include isolated polynucleotides that encode a monoclonal antibody comprising an Ab-13Vl (SEQ ID NO:264) and an Ab-13Vh (SEQ ID NO:230) domain. Aspects of the invention include isolated polynucleotides that encode a monoclonal antibody comprising an Ab-14Vl (SEQ ID NO:266) and an Ab-14Vh (SEQ ID NO:232) domain. Aspects of the invention include isolated polynucleotides that encode a monoclonal antibody comprising an Ab-15Vl (SEQ ID NO:268) and an Ab-15Vh (SEQ ID NO:234) domain. Aspects of the invention include isolated polynucleotides that encode a monoclonal antibody comprising an Ab-16Vl (SEQ ID NO:270) and an Ab-16Vh (SEQ ID NO:236) domain. Aspects of the invention include isolated polynucleotides that encode a monoclonal antibody comprising an Ab-17Vl (SEQ ID NO:272) and an Ab-17Vh (SEQ ID NO:238) domain. Aspects of the aforementioned embodiments include human monoclonal antibodies, human monoclonal IgG antibodies, and human monoclonal IgG1 antibodies. Aspects of the invention include fragments, derivatives, muteins, and variants of the aforementioned.

Aspects of the invention include isolated polynucleotides that encode a monoclonal antibody comprising an Ab-1 light chain (SEQ ID NO:280) and Ab-1 heavy chain (SEQ ID NO:274). Aspects of the invention include isolated polynucleotides that encode a monoclonal antibody comprising an Ab-2 light chain (SEQ ID NO:282) and an Ab-2 heavy chain (SEQ ID NO:276). Aspects of the invention include isolated polynucleotides that encode a monoclonal antibody comprising an Ab-3 light chain (SEQ ID NO:284) and an Ab-3 heavy chain (SEQ ID NO:278). Aspects of the invention include isolated polynucleotides that encode a monoclonal antibody comprising two Ab-1 light chains (SEQ ID NO:280) and two Ab-1 heavy chains (SEQ ID NO:274). Aspects of the invention include isolated polynucleotides that encode a monoclonal antibody comprising two Ab-2 light chains (SEQ ID NO:282) and two Ab-2 heavy chains (SEQ ID NO:276). Aspects of the invention include isolated polynucleotides that encode a monoclonal antibody comprising two Ab-3 light chains (SEQ ID NO:284) and two Ab-3 heavy chains (SEQ ID NO:278). Aspects of the aforementioned embodiments include human monoclonal antibodies, human monoclonal IgG antibodies, and human monoclonal IgG1 antibodies. Aspects of the invention include fragments, derivatives, muteins, and variants of the aforementioned.

Aspects of the invention include isolated polynucleotides that encode a monoclonal antibody comprising the six CDRs of Ab-1, wherein the CDRs include no more than one, two, three, four, five, or six amino acid additions, deletions, or substitutions of Vh-CDR1 (SEQ ID NO:4), Vh-CDR2 (SEQ ID NO:5), Vh-CDR3 (SEQ ID NO:6), Vl-CDR1 (SEQ ID NO:106), Vl-CDR2 (SEQ ID NO:107), and Vl-CDR3 (SEQ ID NO:108). Aspects of the invention include isolated polynucleotides that encode a monoclonal antibody comprising the six CDRs of Ab-2, wherein the CDRs include no more than one, two, three, four, five, or six amino acid additions, deletions, or substitutions of Vh-CDR1 (SEQ ID NO:10), Vh-CDR2 (SEQ ID NO:11), Vh-CDR3 (SEQ ID NO:12), Vl-CDR1 (SEQ ID NO:112), Vl-CDR2 (SEQ ID NO:113), and Vl-CDR3 (SEQ ID NO:114). Aspects of the invention include isolated polynucleotides that encode a monoclonal antibody comprising the six CDRs of Ab-3, wherein the CDRs include no more than one, two, three, four, five, or six amino acid additions, deletions, or substitutions of Vh-CDR1 (SEQ ID NO:16), Vh-CDR2 (SEQ ID NO:17), Vh-CDR3 (SEQ ID NO:18), Vl-CDR1 (SEQ ID NO:118), Vl-CDR2 (SEQ ID NO:119), and Vl-CDR3 (SEQ ID NO:120). Aspects of the invention include isolated polynucleotides that encode a monoclonal antibody comprising the six CDRs of Ab-4, wherein the CDRs include no more than one, two, three, four, five, or six amino acid additions, deletions, or substitutions of Vh-CDR1 (SEQ ID NO:22), Vh-CDR2 (SEQ ID NO:23), Vh-CDR3 (SEQ ID NO:24), Vl-CDR1 (SEQ ID NO:124), Vl-CDR2 (SEQ ID NO:125), and Vl-CDR3 (SEQ ID NO:126). Aspects of the invention include isolated polynucleotides that encode a monoclonal antibody comprising the six CDRs of Ab-5, wherein the CDRs include no more than one, two, three, four, five, or six amino acid additions, deletions, or substitutions of Vh-CDR1 (SEQ ID NO:28), Vh-CDR2 (SEQ ID NO:29), Vh-CDR3 (SEQ ID NO:30), Vl-CDR1 (SEQ ID NO:130), Vl-CDR2 (SEQ ID NO:131), and Vl-CDR3 (SEQ ID NO:132). Aspects of the invention include isolated polynucleotides that encode a monoclonal antibody comprising the six CDRs of Ab-6, wherein the CDRs include no more than one, two, three, four, five, or six amino acid additions, deletions, or substitutions of Vh-CDR1 (SEQ ID NO:34), Vh-CDR2 (SEQ ID NO:35), Vh-CDR3 (SEQ ID NO:36), Vl-CDR1 (SEQ ID NO:136), Vl-CDR2 (SEQ ID NO:137), and Vl-CDR3 (SEQ ID NO:138). Aspects of the invention include isolated polynucleotides that encode a monoclonal antibody comprising the six CDRs of Ab-7, wherein the CDRs include no more than one, two, three, four, five, or six amino acid additions, deletions, or substitutions of Vh-CDR1 (SEQ ID NO:40), Vh-CDR2 (SEQ ID NO:41), Vh-CDR3 (SEQ ID NO:42), Vl-CDR1 (SEQ ID NO:142), Vl-CDR2 (SEQ ID NO:143), and Vl-CDR3 (SEQ ID NO:144). Aspects of the invention include isolated polynucleotides that encode a monoclonal antibody comprising the six CDRs of Ab-8, wherein the CDRs include no more than one, two, three, four, five, or six amino acid additions, deletions, or substitutions of Vh-CDR1 (SEQ ID NO:46), Vh-CDR2 (SEQ ID NO:47), Vh-CDR3 (SEQ ID NO:48), Vl-CDR1 (SEQ ID NO:148), Vl-CDR2 (SEQ ID NO:149), and Vl-CDR3 (SEQ ID NO:150). Aspects of the invention include isolated polynucleotides that encode a monoclonal antibody comprising the six CDRs of Ab-9, wherein the CDRs include no more than one, two, three, four, five, or six amino acid additions, deletions, or substitutions of Vh-CDR1 (SEQ ID NO:52), Vh-CDR2 (SEQ ID NO:53), Vh-CDR3 (SEQ ID NO:54), Vl-CDR1 (SEQ ID NO:154), Vl-CDR2 (SEQ ID NO:155), and Vl-CDR3 (SEQ ID NO:156). Aspects of the invention include isolated polynucleotides that encode a monoclonal antibody comprising the six CDRs of Ab-10, wherein the CDRs include no more than one, two, three, four, five, or six amino acid additions, deletions, or substitutions of Vh-CDR1 (SEQ ID NO:58), Vh-CDR2 (SEQ ID NO:59), Vh-CDR3 (SEQ ID NO:60), Vl-CDR1 (SEQ ID NO:160), Vl-CDR2 (SEQ ID NO:161), and Vl-CDR3 (SEQ ID NO:162). Aspects of the invention include isolated polynucleotides that encode a monoclonal antibody comprising the six CDRs of Ab-11, wherein the CDRs include no more than one, two, three, four, five, or six amino acid additions, deletions, or substitutions of Vh-CDR1 (SEQ ID NO:64), Vh-CDR2 (SEQ ID NO:65), Vh-CDR3 (SEQ ID NO:66), Vl-CDR1 (SEQ ID NO:166), Vl-CDR2 (SEQ ID NO:167), and Vl-CDR3 (SEQ ID NO:168). Aspects of the invention include isolated polynucleotides that encode a monoclonal antibody comprising the six CDRs of Ab-12, wherein the CDRs include no more than one, two, three, four, five, or six amino acid additions, deletions, or substitutions of Vh-CDR1 (SEQ ID NO:70), Vh-CDR2 (SEQ ID NO:71), Vh-CDR3 (SEQ ID NO:72), Vl-CDR1 (SEQ ID NO:172), Vl-CDR2 (SEQ ID NO:173), and Vl-CDR3 (SEQ ID NO:174). Aspects of the invention include isolated polynucleotides that encode a monoclonal antibody comprising the six CDRs of Ab-13, wherein the CDRs include no more than one, two, three, four, five, or six amino acid additions, deletions, or substitutions of Vh-CDR1 (SEQ ID NO:76), Vh-CDR2 (SEQ ID NO:77), Vh-CDR3 (SEQ ID NO:78), Vl-CDR1 (SEQ ID NO:178), Vl-CDR2 (SEQ ID NO:179), and Vl-CDR3 (SEQ ID NO:180). Aspects of the invention include isolated polynucleotides that encode a monoclonal antibody comprising the six CDRs of Ab-14, wherein the CDRs include no more than one, two, three, four, five, or six amino acid additions, deletions, or substitutions of Vh-CDR1 (SEQ ID NO:82), Vh-CDR2 (SEQ ID NO:83), Vh-CDR3 (SEQ ID NO:84), Vl-CDR1 (SEQ ID NO:184), Vl-CDR2 (SEQ ID NO:185), and Vl-CDR3 (SEQ ID NO:186). Aspects of the invention include isolated polynucleotides that encode a monoclonal antibody comprising the six CDRs of Ab-15, wherein the CDRs include no more than one, two, three, four, five, or six amino acid additions, deletions, or substitutions of Vh-CDR1 (SEQ ID NO:88), Vh-CDR2 (SEQ ID NO:89), Vh-CDR3 (SEQ ID NO:90), Vl-CDR1 (SEQ ID NO:190), Vl-CDR2 (SEQ ID NO:191), and Vl-CDR3 (SEQ ID NO:192). Aspects of the invention include isolated polynucleotides that encode a monoclonal antibody comprising the six CDRs of Ab-16, wherein the CDRs include no more than one, two, three, four, five, or six amino acid additions, deletions, or substitutions of Vh-CDR1 (SEQ ID NO:94), Vh-CDR2 (SEQ ID NO:95), Vh-CDR3 (SEQ ID NO:96), Vl-CDR1 (SEQ ID NO:196), Vl-CDR2 (SEQ ID NO:197), and Vl-CDR3 (SEQ ID NO:198). Aspects of the invention include isolated polynucleotides that encode a monoclonal antibody comprising the six CDRs of Ab-17, wherein the CDRs include no more than one, two, three, four, five, or six amino acid additions, deletions, or substitutions of Vh-CDR1 (SEQ ID NO:100), Vh-CDR2 (SEQ ID NO:101), Vh-CDR3 (SEQ ID NO:102), Vl-CDR1 (SEQ ID NO:202), Vl-CDR2 (SEQ ID NO:203), and Vl-CDR3 (SEQ ID NO:204). Aspects of the aforementioned embodiments include human monoclonal antibodies, human monoclonal IgG antibodies, and human monoclonal IgG1 antibodies.

Aspects of the invention include isolated polynucleotides that encode a monoclonal antibody comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-1Vl (SEQ ID NO:240) and Ab-1Vh (SEQ ID NO:206), respectively. Aspects of the invention include isolated polynucleotides that encode a monoclonal antibody comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-2Vl (SEQ ID NO:242) and Ab-2Vh (SEQ ID NO:208), respectively. Aspects of the invention include isolated polynucleotides that encode a monoclonal antibody comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-3Vl (SEQ ID NO:244) and Ab-3Vh (SEQ ID NO:210), respectively. Aspects of the invention include isolated polynucleotides that encode a monoclonal antibody comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-4Vl (SEQ ID NO:246) and Ab-4Vh (SEQ ID NO:212), respectively. Aspects of the invention include isolated polynucleotides that encode a monoclonal antibody comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-5Vl (SEQ ID NO:248) and Ab-5Vh (SEQ ID NO:214), respectively. Aspects of the invention include isolated polynucleotides that encode a monoclonal antibody comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-6Vl (SEQ ID NO:250) and Ab-6Vh (SEQ ID NO:216), respectively. Aspects of the invention include isolated polynucleotides that encode a monoclonal antibody comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-7Vl (SEQ ID NO:252) and Ab-7Vh (SEQ ID NO:218), respectively. Aspects of the invention include isolated polynucleotides that encode a monoclonal antibody comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-8Vl (SEQ ID NO:254) and Ab-8Vh (SEQ ID NO:220), respectively. Aspects of the invention include isolated polynucleotides that encode a monoclonal antibody comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-9Vl (SEQ ID NO:256) and Ab-9Vh (SEQ ID NO:222), respectively. Aspects of the invention include isolated polynucleotides that encode a monoclonal antibody comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-10Vl (SEQ ID NO:258) and Ab-10Vh (SEQ ID NO:224), respectively. Aspects of the invention include isolated polynucleotides that encode a monoclonal antibody comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-11Vl (SEQ ID NO:260) and Ab-11Vh (SEQ ID NO:226), respectively. Aspects of the invention include isolated polynucleotides that encode a monoclonal antibody comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-12Vl (SEQ ID NO:262) and Ab-12Vh (SEQ ID NO:228), respectively. Aspects of the invention include isolated polynucleotides that encode a monoclonal antibody comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-13Vl (SEQ ID NO:264) and Ab-13Vh (SEQ ID NO:230), respectively. Aspects of the invention include isolated polynucleotides that encode a monoclonal antibody comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-14Vl (SEQ ID NO:266) and Ab-14Vh (SEQ ID NO:232), respectively. Aspects of the invention include isolated polynucleotides that encode a monoclonal antibody comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-15Vl (SEQ ID NO:268) and Ab-15Vh (SEQ ID NO:234), respectively. Aspects of the invention include isolated polynucleotides that encode a monoclonal antibody comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-16Vl (SEQ ID NO:270) and Ab-16Vh (SEQ ID NO:236), respectively. Aspects of the invention include isolated polynucleotides that encode a monoclonal antibody comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-17Vl (SEQ ID NO:272) and Ab-17Vh (SEQ ID NO:238), respectively. Aspects of the aforementioned embodiments include human monoclonal antibodies, human monoclonal IgG antibodies, and human monoclonal IgG1 antibodies.

Aspects of the invention include isolated polynucleotides that encode a monoclonal antibody comprising the six CDRs of Ab-1, wherein the polynucleotide sequence comprises Vh-CDR1 (SEQ ID NO:1), Vh-CDR2 (SEQ ID NO:2), Vh-CDR3 (SEQ ID NO:3), Vl-CDR1 (SEQ ID NO:103), Vl-CDR2 (SEQ ID NO:104), and Vl-CDR3 (SEQ ID NO:105). Aspects of the invention include isolated polynucleotides that encode a monoclonal antibody comprising the six CDRs of Ab-2, wherein the polynucleotide sequence comprises Vh-CDR1 (SEQ ID NO:7), Vh-CDR2 (SEQ ID NO:8), Vh-CDR3 (SEQ ID NO:9), Vl-CDR1 (SEQ ID NO:109), Vl-CDR2 (SEQ ID NO:110), and Vl-CDR3 (SEQ ID NO:111). Aspects of the invention include isolated polynucleotides that encode a monoclonal antibody comprising the six CDRs of Ab-3, wherein the polynucleotide sequence comprises Vh-CDR1 (SEQ ID NO:13), Vh-CDR2 (SEQ ID NO:14), Vh-CDR3 (SEQ ID NO:15), Vl-CDR1 (SEQ ID NO:115), Vl-CDR2 (SEQ ID NO:116), and Vl-CDR3 (SEQ ID NO:117). Aspects of the invention include isolated polynucleotides that encode a monoclonal antibody comprising the six CDRs of Ab-4, wherein the polynucleotide sequence comprises Vh-CDR1 (SEQ ID NO:19), Vh-CDR2 (SEQ ID NO:20), Vh-CDR3 (SEQ ID NO:21), Vl-CDR1 (SEQ ID NO:121), Vl-CDR2 (SEQ ID NO:122), and Vl-CDR3 (SEQ ID NO:123). Aspects of the invention include isolated polynucleotides that encode a monoclonal antibody comprising the six CDRs of Ab-5, wherein the polynucleotide sequence comprises Vh-CDR1 (SEQ ID NO:25), Vh-CDR2 (SEQ ID NO:26), Vh-CDR3 (SEQ ID NO:27), Vl-CDR1 (SEQ ID NO:127), Vl-CDR2 (SEQ ID NO:128), and Vl-CDR3 (SEQ ID NO:129). Aspects of the invention include isolated polynucleotides that encode a monoclonal antibody comprising the six CDRs of Ab-6, wherein the polynucleotide sequence comprises Vh-CDR1 (SEQ ID NO:31), Vh-CDR2 (SEQ ID NO:32), Vh-CDR3 (SEQ ID NO:33), Vl-CDR1 (SEQ ID NO:133), Vl-CDR2 (SEQ ID NO:134), and Vl-CDR3 (SEQ ID NO:135). Aspects of the invention include isolated polynucleotides that encode a monoclonal antibody comprising the six CDRs of Ab-7, wherein the polynucleotide sequence comprises Vh-CDR1 (SEQ ID NO:37), Vh-CDR2 (SEQ ID NO:38), Vh-CDR3 (SEQ ID NO:39), Vl-CDR1 (SEQ ID NO:139), Vl-CDR2 (SEQ ID NO:140), and Vl-CDR3 (SEQ ID NO:141). Aspects of the invention include isolated polynucleotides that encode a monoclonal antibody comprising the six CDRs of Ab-8, wherein the polynucleotide sequence comprises Vh-CDR1 (SEQ ID NO:43), Vh-CDR2 (SEQ ID NO:44), Vh-CDR3 (SEQ ID NO:45), Vl-CDR1 (SEQ ID NO:145), Vl-CDR2 (SEQ ID NO:146), and Vl-CDR3 (SEQ ID NO:147). Aspects of the invention include isolated polynucleotides that encode a monoclonal antibody comprising the six CDRs of Ab-9, wherein the polynucleotide sequence comprises Vh-CDR1 (SEQ ID NO:49), Vh-CDR2 (SEQ ID NO:50), Vh-CDR3 (SEQ ID NO:51), Vl-CDR1 (SEQ ID NO:151), Vl-CDR2 (SEQ ID NO:152), and Vl-CDR3 (SEQ ID NO:153). Aspects of the invention include isolated polynucleotides that encode a monoclonal antibody comprising the six CDRs of Ab-10, wherein the polynucleotide sequence comprises Vh-CDR1 (SEQ ID NO:55), Vh-CDR2 (SEQ ID NO:56), Vh-CDR3 (SEQ ID NO:57), Vl-CDR1 (SEQ ID NO:157), Vl-CDR2 (SEQ ID NO:158), and Vl-CDR3 (SEQ ID NO:159). Aspects of the invention include isolated polynucleotides that encode a monoclonal antibody comprising the six CDRs of Ab-11, wherein the polynucleotide sequence comprises Vh-CDR1 (SEQ ID NO:61), Vh-CDR2 (SEQ ID NO:62), Vh-CDR3 (SEQ ID NO:63), Vl-CDR1 (SEQ ID NO:163), Vl-CDR2 (SEQ ID NO:164), and Vl-CDR3 (SEQ ID NO:165). Aspects of the invention include isolated polynucleotides that encode a monoclonal antibody comprising the six CDRs of Ab-12, wherein the polynucleotide sequence comprises Vh-CDR1 (SEQ ID NO:67), Vh-CDR2 (SEQ ID NO:68), Vh-CDR3 (SEQ ID NO:69), Vl-CDR1 (SEQ ID NO:169), Vl-CDR2 (SEQ ID NO:170), and Vl-CDR3 (SEQ ID NO:171). Aspects of the invention include isolated polynucleotides that encode a monoclonal antibody comprising the six CDRs of Ab-13, wherein the polynucleotide sequence comprises Vh-CDR1 (SEQ ID NO:73), Vh-CDR2 (SEQ ID NO:74), Vh-CDR3 (SEQ ID NO:75), Vl-CDR1 (SEQ ID NO:175), Vl-CDR2 (SEQ ID NO:176), and Vl-CDR3 (SEQ ID NO:177). Aspects of the invention include isolated polynucleotides that encode a monoclonal antibody comprising the six CDRs of Ab-14, wherein the polynucleotide sequence comprises Vh-CDR1 (SEQ ID NO:79), Vh-CDR2 (SEQ ID NO:80), Vh-CDR3 (SEQ ID NO:81), Vl-CDR1 (SEQ ID NO:181), Vl-CDR2 (SEQ ID NO:182), and Vl-CDR3 (SEQ ID NO:183). Aspects of the invention include isolated polynucleotides that encode a monoclonal antibody comprising the six CDRs of Ab-15, wherein the polynucleotide sequence comprises Vh-CDR1 (SEQ ID NO:85), Vh-CDR2 (SEQ ID NO:86), Vh-CDR3 (SEQ ID NO:87), Vl-CDR1 (SEQ ID NO:187), Vl-CDR2 (SEQ ID NO:188), and Vl-CDR3 (SEQ ID NO:189). Aspects of the invention include isolated polynucleotides that encode a monoclonal antibody comprising the six CDRs of Ab-16, wherein the polynucleotide sequence comprises Vh-CDR1 (SEQ ID NO:91), Vh-CDR2 (SEQ ID NO:92), Vh-CDR3 (SEQ ID NO:93), Vl-CDR1 (SEQ ID NO:193), Vl-CDR2 (SEQ ID NO:194), and Vl-CDR3 (SEQ ID NO:195). Aspects of the invention include isolated polynucleotides that encode a monoclonal antibody comprising the six CDRs of Ab-17, wherein the polynucleotide sequence comprises Vh-CDR1 (SEQ ID NO:97), Vh-CDR2 (SEQ ID NO:98), Vh-CDR3 (SEQ ID NO:99), Vl-CDR1 (SEQ ID NO:199), Vl-CDR2 (SEQ ID NO:200), and Vl-CDR3 (SEQ ID NO:201). Aspects of the aforementioned embodiments include human monoclonal antibodies, human monoclonal IgG antibodies, and human monoclonal IgG1 antibodies.

Aspects of the invention include isolated polynucleotides that encode a monoclonal antibody comprising the Vl and Vh domains of Ab-1, wherein the polynucleotide sequence comprises Ab-1Vl (SEQ ID NO:239) and Ab-1Vh (SEQ ID NO:205). Aspects of the invention include isolated polynucleotides that encode a monoclonal antibody comprising the Vl and Vh domains of Ab-2, wherein the polynucleotide sequence comprises Ab-2Vl (SEQ ID NO:241) and Ab-2Vh (SEQ ID NO:207). Aspects of the invention include isolated polynucleotides that encode a monoclonal antibody comprising the Vl and Vh domains of Ab-3, wherein the polynucleotide sequence comprises Ab-3Vl (SEQ ID NO:243) and Ab-3Vh (SEQ ID NO:209). Aspects of the invention include isolated polynucleotides that encode a monoclonal antibody comprising the Vl and Vh domains of Ab-4, wherein the polynucleotide sequence comprises Ab-4Vl (SEQ ID NO:245) and an Ab-4Vh (SEQ ID NO:211). Aspects of the invention include isolated polynucleotides that encode a monoclonal antibody comprising the Vl and Vh domains of Ab-5, wherein the polynucleotide sequence comprises Ab-5Vl (SEQ ID NO:247) and Ab-5Vh (SEQ ID NO:213). Aspects of the invention include isolated polynucleotides that encode a monoclonal antibody comprising the Vl and Vh domains of Ab-6, wherein the polynucleotide sequence comprises Ab-6Vl (SEQ ID NO:249) and Ab-6Vh (SEQ ID NO:215). Aspects of the invention include isolated polynucleotides that encode a monoclonal antibody comprising the Vl and Vh domains of Ab-7, wherein the polynucleotide sequence comprises Ab-7Vl (SEQ ID NO:251) and Ab-7Vh (SEQ ID NO:217). Aspects of the invention include isolated polynucleotides that encode a monoclonal antibody comprising the Vl and Vh domains of Ab-8, wherein the polynucleotide sequence comprises Ab-8Vl (SEQ ID NO:253) and Ab-8Vh (SEQ ID NO:219). Aspects of the invention include isolated polynucleotides that encode a monoclonal antibody comprising the Vl and Vh domains of Ab-9, wherein the polynucleotide sequence comprises Ab-9Vl (SEQ ID NO:255) and Ab-9Vh (SEQ ID NO:221). Aspects of the invention include isolated polynucleotides that encode a monoclonal antibody comprising the Vl and Vh domains of Ab-10, wherein the polynucleotide sequence comprises Ab-10Vl (SEQ ID NO:257) and Ab-10Vh (SEQ ID NO:223) domain. Aspects of the invention include isolated polynucleotides that encode a monoclonal antibody comprising the Vl and Vh domains of Ab-11, wherein the polynucleotide sequence comprises Ab-11Vl (SEQ ID NO:259) and Ab-11Vh (SEQ ID NO:225). Aspects of the invention include isolated polynucleotides that encode a monoclonal antibody comprising the Vl and Vh domains of Ab-12, wherein the polynucleotide sequence comprises Ab-12Vl (SEQ ID NO:261) and Ab-12Vh (SEQ ID NO:227). Aspects of the invention include isolated polynucleotides that encode a monoclonal antibody comprising the Vl and Vh domains of Ab-13, wherein the polynucleotide sequence comprises Ab-13Vl (SEQ ID NO:263) and Ab-13Vh (SEQ ID NO:229). Aspects of the invention include isolated polynucleotides that encode a monoclonal antibody comprising the Vl and Vh domains of Ab-14, wherein the polynucleotide sequence comprises Ab-14Vl (SEQ ID NO:265) and Ab-14Vh (SEQ ID NO:231). Aspects of the invention include isolated polynucleotides that encode a monoclonal antibody comprising the Vl and Vh domains of Ab-15, wherein the polynucleotide sequence comprises Ab-15Vl (SEQ ID NO:267) and Ab-15Vh (SEQ ID NO:233). Aspects of the invention include isolated polynucleotides that encode a monoclonal antibody comprising the Vl and Vh domains of Ab-16, wherein the polynucleotide sequence comprises Ab-16Vl (SEQ ID NO:269) and Ab-16Vh (SEQ ID NO:235). Aspects of the invention include isolated polynucleotides that encode a monoclonal antibody comprising the Vl and Vh domains of Ab-17, wherein the polynucleotide sequence comprises Ab-17Vl (SEQ ID NO:271) and Ab-17Vh (SEQ ID NO:237). Aspects of the aforementioned embodiments include human monoclonal antibodies, human monoclonal IgG antibodies, and human monoclonal IgG1 antibodies.

Aspects of the invention include isolated polynucleotides that encode a monoclonal antibody comprising antibody Ab-1, wherein the polynucleotide sequence comprises a light chain (SEQ ID NO:279) and a heavy chain (SEQ ID NO:273). Aspects of the invention include isolated polynucleotides that encode a monoclonal antibody comprising antibody Ab-2, wherein the polynucleotide sequence comprises a light chain (SEQ ID NO:281) and a heavy chain (SEQ ID NO:275). Aspects of the invention include isolated polynucleotides that encode a monoclonal antibody comprising antibody Ab-3, wherein the polynucleotide sequence comprises a light chain (SEQ ID NO:283) and a heavy chain (SEQ ID NO:277). Aspects of the aforementioned embodiments include human monoclonal antibodies, human monoclonal IgG antibodies, and human monoclonal IgG1 antibodies.

Aspects of the invention include isolated polynucleotides that encode a polypeptide comprising the six CDRs of Ab-1, specifically Vh-CDR1 (SEQ ID NO:4), Vh-CDR2 (SEQ ID NO:5), Vh-CDR3 (SEQ ID NO:6), Vl-CDR1 (SEQ ID NO:106), Vl-CDR2 (SEQ ID NO:107), and Vl-CDR3 (SEQ ID NO:108). Aspects of the invention include isolated polynucleotides that encode a polypeptide comprising the six CDRs of Ab-2, specifically Vh-CDR1 (SEQ ID NO:10), Vh-CDR2 (SEQ ID NO:11), Vh-CDR3 (SEQ ID NO:12), Vl-CDR1 (SEQ ID NO:112), Vl-CDR2 (SEQ ID NO:113), and Vl-CDR3 (SEQ ID NO:114). Aspects of the invention include isolated polynucleotides that encode a polypeptide comprising the six CDRs of Ab-3, specifically Vh-CDR1 (SEQ ID NO:16), Vh-CDR2 (SEQ ID NO:17), Vh-CDR3 (SEQ ID NO:18), Vl-CDR1 (SEQ ID NO:118), Vl-CDR2 (SEQ ID NO:119), and Vl-CDR3 (SEQ ID NO:120). Aspects of the invention include isolated polynucleotides that encode a polypeptide comprising the six CDRs of Ab-4, specifically Vh-CDR1 (SEQ ID NO:22), Vh-CDR2 (SEQ ID NO:23), Vh-CDR3 (SEQ ID NO:24), Vl-CDR1 (SEQ ID NO:124), Vl-CDR2 (SEQ ID NO:125), and Vl-CDR3 (SEQ ID NO:126). Aspects of the invention include isolated polynucleotides that encode a polypeptide comprising the six CDRs of Ab-5, specifically Vh-CDR1 (SEQ ID NO:28), Vh-CDR2 (SEQ ID NO:29), Vh-CDR3 (SEQ ID NO:30), Vl-CDR1 (SEQ ID NO:130), Vl-CDR2 (SEQ ID NO:131), and Vl-CDR3 (SEQ ID NO:132). Aspects of the invention include isolated polynucleotides that encode a polypeptide comprising the six CDRs of Ab-6, specifically Vh-CDR1 (SEQ ID NO:34), Vh-CDR2 (SEQ ID NO:35), Vh-CDR3 (SEQ ID NO:36), Vl-CDR1 (SEQ ID NO:136), Vl-CDR2 (SEQ ID NO:137), and Vl-CDR3 (SEQ ID NO:138). Aspects of the invention include isolated polynucleotides that encode a polypeptide comprising the six CDRs of Ab-7, specifically Vh-CDR1 (SEQ ID NO:40), Vh-CDR2 (SEQ ID NO:41), Vh-CDR3 (SEQ ID NO:42), Vl-CDR1 (SEQ ID NO:142), Vl-CDR2 (SEQ ID NO:143), and Vl-CDR3 (SEQ ID NO:144). Aspects of the invention include isolated polynucleotides that encode a polypeptide comprising the six CDRs of Ab-8, specifically Vh-CDR1 (SEQ ID NO:46), Vh-CDR2 (SEQ ID NO:47), Vh-CDR3 (SEQ ID NO:48), Vl-CDR1 (SEQ ID NO:148), Vl-CDR2 (SEQ ID NO:149), and Vl-CDR3 (SEQ ID NO:150). Aspects of the invention include isolated polynucleotides that encode a polypeptide comprising the six CDRs of Ab-9, specifically Vh-CDR1 (SEQ ID NO:52), Vh-CDR2 (SEQ ID NO:53), Vh-CDR3 (SEQ ID NO:54), Vl-CDR1 (SEQ ID NO:154), Vl-CDR2 (SEQ ID NO:155), and Vl-CDR3 (SEQ ID NO:156). Aspects of the invention include isolated polynucleotides that encode a polypeptide comprising the six CDRs of Ab-10, specifically Vh-CDR1 (SEQ ID NO:58), Vh-CDR2 (SEQ ID NO:59), Vh-CDR3 (SEQ ID NO:60), Vl-CDR1 (SEQ ID NO:160), Vl-CDR2 (SEQ ID NO:161), and Vl-CDR3 (SEQ ID NO:162). Aspects of the invention include isolated polynucleotides that encode a polypeptide comprising the six CDRs of Ab-11, specifically Vh-CDR1 (SEQ ID NO:64), Vh-CDR2 (SEQ ID NO:65), Vh-CDR3 (SEQ ID NO:66), Vl-CDR1 (SEQ ID NO:166), Vl-CDR2 (SEQ ID NO:167), and Vl-CDR3 (SEQ ID NO:168). Aspects of the invention include isolated polynucleotides that encode a polypeptide comprising the six CDRs of Ab-12, specifically Vh-CDR1 (SEQ ID NO:70), Vh-CDR2 (SEQ ID NO:71), Vh-CDR3 (SEQ ID NO:72), Vl-CDR1 (SEQ ID NO:172), Vl-CDR2 (SEQ ID NO:173), and Vl-CDR3 (SEQ ID NO:174). Aspects of the invention include isolated polynucleotides that encode a polypeptide comprising the six CDRs of Ab-13, specifically Vh-CDR1 (SEQ ID NO:76), Vh-CDR2 (SEQ ID NO:77), Vh-CDR3 (SEQ ID NO:78), Vl-CDR1 (SEQ ID NO:178), Vl-CDR2 (SEQ ID NO:179), and Vl-CDR3 (SEQ ID NO:180). Aspects of the invention include isolated polynucleotides that encode a polypeptide comprising the six CDRs of Ab-14, specifically Vh-CDR1 (SEQ ID NO:82), Vh-CDR2 (SEQ ID NO:83), Vh-CDR3 (SEQ ID NO:84), Vl-CDR1 (SEQ ID NO:184), Vl-CDR2 (SEQ ID NO:185), and Vl-CDR3 (SEQ ID NO:186).

Aspects of the invention include isolated polynucleotides that encode a polypeptide comprising the six CDRs of Ab-15, specifically Vh-CDR1 (SEQ ID NO:88), Vh-CDR2 (SEQ ID NO:89), Vh-CDR3 (SEQ ID NO:90), Vl-CDR1 (SEQ ID NO:190), Vl-CDR2 (SEQ ID NO:191), and Vl-CDR3 (SEQ ID NO:192). Aspects of the invention include isolated polynucleotides that encode a polypeptide comprising the six CDRs of Ab-16, specifically Vh-CDR1 (SEQ ID NO:94), Vh-CDR2 (SEQ ID NO:95), Vh-CDR3 (SEQ ID NO:96), Vl-CDR1 (SEQ ID NO:196), Vl-CDR2 (SEQ ID NO:197), and Vl-CDR3 (SEQ ID NO:198). Aspects of the invention include isolated polynucleotides that encode a polypeptide comprising the six CDRs of Ab-17, specifically Vh-CDR1 (SEQ ID NO:100), Vh-CDR2 (SEQ ID NO:101), Vh-CDR3 (SEQ ID NO:102), Vl-CDR1 (SEQ ID NO:202), Vl-CDR2 (SEQ ID NO:203), and Vl-CDR3 (SEQ ID NO:204). Aspects of the invention include fragments, derivatives, muteins, and variants of the aforementioned.

Aspects of the invention include isolated polynucleotides that encode a polypeptide comprising an Ab-1Vl (SEQ ID NO:240) and an Ab-1Vh (SEQ ID NO:206) domain. Aspects of the invention include isolated polynucleotides that encode a polypeptide comprising an Ab-2Vl (SEQ ID NO:242) and an Ab-2Vh (SEQ ID NO:208) domain. Aspects of the invention include isolated polynucleotides that encode a polypeptide comprising an Ab-3Vl (SEQ ID NO:244) and an Ab-3Vh (SEQ ID NO:210) domain. Aspects of the invention include isolated polynucleotides that encode a polypeptide comprising an Ab-4Vl (SEQ ID NO:246) and an Ab-4Vh (SEQ ID NO:212) domain. Aspects of the invention include isolated polynucleotides that encode a polypeptide comprising an Ab-5Vl (SEQ ID NO:248) and an Ab-5Vh (SEQ ID NO:214) domain. Aspects of the invention include isolated polynucleotides that encode a polypeptide comprising an Ab-6Vl (SEQ ID NO:250) and an Ab-6Vh (SEQ ID NO:216) domain. Aspects of the invention include isolated polynucleotides that encode a polypeptide comprising an Ab-7Vl (SEQ ID NO:252) and an Ab-7Vh (SEQ ID NO:218) domain. Aspects of the invention include isolated polynucleotides that encode a polypeptide comprising an Ab-8Vl (SEQ ID NO:254) and an Ab-8Vh (SEQ ID NO:220) domain. Aspects of the invention include isolated polynucleotides that encode a polypeptide comprising an Ab-9Vl (SEQ ID NO:256) and an Ab-9Vh (SEQ ID NO:222) domain. Aspects of the invention include isolated polynucleotides that encode a polypeptide comprising an Ab-10Vl (SEQ ID NO:258) and an Ab-10Vh (SEQ ID NO:224) domain. Aspects of the invention include isolated polynucleotides that encode a polypeptide comprising an Ab-11Vl (SEQ ID NO:260) and an Ab-11Vh (SEQ ID NO:226) domain. Aspects of the invention include isolated polynucleotides that encode a polypeptide comprising an Ab-12Vl (SEQ ID NO:262) and an Ab-12Vh (SEQ ID NO:228) domain. Aspects of the invention include isolated polynucleotides that encode a polypeptide comprising an Ab-13Vl (SEQ ID NO:264) and an Ab-13Vh (SEQ ID NO:230) domain. Aspects of the invention include isolated polynucleotides that encode a polypeptide comprising an Ab-14Vl (SEQ ID NO:266) and an Ab-14Vh (SEQ ID NO:232) domain. Aspects of the invention include isolated polynucleotides that encode a polypeptide comprising an Ab-15Vl (SEQ ID NO:268) and an Ab-15Vh (SEQ ID NO:234) domain. Aspects of the invention include isolated polynucleotides that encode a polypeptide comprising an Ab-16Vl (SEQ ID NO:270) and an Ab-16Vh (SEQ ID NO:236) domain. Aspects of the invention include isolated polynucleotides that encode a polypeptide comprising an Ab-17Vl (SEQ ID NO:272) and an Ab-17Vh (SEQ ID NO:238) domain. Aspects of the invention include fragments, derivatives, muteins, and variants of the aforementioned.

Aspects of the invention include isolated polynucleotides that encode a polypeptide comprising an Ab-1 light chain (SEQ ID NO:280) and Ab-1 heavy chain (SEQ ID NO:274). Aspects of the invention include isolated polynucleotides that encode a polypeptide comprising an Ab-2 light chain (SEQ ID NO:282) and an Ab-2 heavy chain (SEQ ID NO:276). Aspects of the invention include isolated polynucleotides that encode a polypeptide comprising an Ab-3 light chain (SEQ ID NO:284) and an Ab-3 heavy chain (SEQ ID NO:278). Aspects of the invention include isolated polynucleotides that encode a polypeptide comprising two Ab-1 light chains (SEQ ID NO:280) and two Ab-1 heavy chains (SEQ ID NO:274). Aspects of the invention include isolated polynucleotides that encode a polypeptide comprising two or more Ab-2 light chains (SEQ ID NO:282) and two or more Ab-2 heavy chains (SEQ ID NO:276). Aspects of the invention include isolated polynucleotides that encode a polypeptide comprising two or more Ab-3 light chains (SEQ ID NO:284) and two or more Ab-3 heavy chains (SEQ ID NO:278). Aspects of the invention include fragments, derivatives, muteins, and variants of the aforementioned.

Aspects of the invention include isolated polynucleotides that encode a polypeptide comprising the six CDRs of Ab-1, wherein the CDRs include no more than one, two, three, four, five, or six amino acid additions, deletions, or substitutions of Vh-CDR1 (SEQ ID NO:4), Vh-CDR2 (SEQ ID NO:5), Vh-CDR3 (SEQ ID NO:6), Vl-CDR1 (SEQ ID NO:106), Vl-CDR2 (SEQ ID NO:107), and Vl-CDR3 (SEQ ID NO:108). Aspects of the invention include isolated polynucleotides that encode a polypeptide comprising the six CDRs of Ab-2, wherein the CDRs include no more than one, two, three, four, five, or six amino acid additions, deletions, or substitutions of Vh-CDR1 (SEQ ID NO:10), Vh-CDR2 (SEQ ID NO:11), Vh-CDR3 (SEQ ID NO:12), Vl-CDR1 (SEQ ID NO:112), Vl-CDR2 (SEQ ID NO:113), and Vl-CDR3 (SEQ ID NO:114). Aspects of the invention include isolated polynucleotides that encode a polypeptide comprising the six CDRs of Ab-3, wherein the CDRs include no more than one, two, three, four, five, or six amino acid additions, deletions, or substitutions of Vh-CDR1 (SEQ ID NO:16), Vh-CDR2 (SEQ ID NO:17), Vh-CDR3 (SEQ ID NO:18), Vl-CDR1 (SEQ ID NO:118), Vl-CDR2 (SEQ ID NO:119), and Vl-CDR3 (SEQ ID NO:120). Aspects of the invention include isolated polynucleotides that encode a polypeptide comprising the six CDRs of Ab-4, wherein the CDRs include no more than one, two, three, four, five, or six amino acid additions, deletions, or substitutions of Vh-CDR1 (SEQ ID NO:22), Vh-CDR2 (SEQ ID NO:23), Vh-CDR3 (SEQ ID NO:24), Vl-CDR1 (SEQ ID NO:124), Vl-CDR2 (SEQ ID NO:125), and Vl-CDR3 (SEQ ID NO:126). Aspects of the invention include isolated polynucleotides that encode a polypeptide comprising the six CDRs of Ab-5, wherein the CDRs include no more than one, two, three, four, five, or six amino acid additions, deletions, or substitutions of Vh-CDR1 (SEQ ID NO:28), Vh-CDR2 (SEQ ID NO:29), Vh-CDR3 (SEQ ID NO:30), Vl-CDR1 (SEQ ID NO:130), Vl-CDR2 (SEQ ID NO:131), and Vl-CDR3 (SEQ ID NO:132). Aspects of the invention include isolated polynucleotides that encode a polypeptide comprising the six CDRs of Ab-6, wherein the CDRs include no more than one, two, three, four, five, or six amino acid additions, deletions, or substitutions of Vh-CDR1 (SEQ ID NO:34), Vh-CDR2 (SEQ ID NO:35), Vh-CDR3 (SEQ ID NO:36), Vl-CDR1 (SEQ ID NO:136), Vl-CDR2 (SEQ ID NO:137), and Vl-CDR3 (SEQ ID NO:138). Aspects of the invention include isolated polynucleotides that encode a polypeptide comprising the six CDRs of Ab-7, wherein the CDRs include no more than one, two, three, four, five, or six amino acid additions, deletions, or substitutions of Vh-CDR1 (SEQ ID NO:40), Vh-CDR2 (SEQ ID NO:41), Vh-CDR3 (SEQ ID NO:42), Vl-CDR1 (SEQ ID NO:142), Vl-CDR2 (SEQ ID NO:143), and Vl-CDR3 (SEQ ID NO:144). Aspects of the invention include isolated polynucleotides that encode a polypeptide comprising the six CDRs of Ab-8, wherein the CDRs include no more than one, two, three, four, five, or six amino acid additions, deletions, or substitutions of Vh-CDR1 (SEQ ID NO:46), Vh-CDR2 (SEQ ID NO:47), Vh-CDR3 (SEQ ID NO:48), Vl-CDR1 (SEQ ID NO:148), Vl-CDR2 (SEQ ID NO:149), and Vl-CDR3 (SEQ ID NO:150). Aspects of the invention include isolated polynucleotides that encode a polypeptide comprising the six CDRs of Ab-9, wherein the CDRs include no more than one, two, three, four, five, or six amino acid additions, deletions, or substitutions of Vh-CDR1 (SEQ ID NO:52), Vh-CDR2 (SEQ ID NO:53), Vh-CDR3 (SEQ ID NO:54), Vl-CDR1 (SEQ ID NO:154), Vl-CDR2 (SEQ ID NO:155), and Vl-CDR3 (SEQ ID NO:156). Aspects of the invention include isolated polynucleotides that encode a polypeptide comprising the six CDRs of Ab-10, wherein the CDRs include no more than one, two, three, four, five, or six amino acid additions, deletions, or substitutions of Vh-CDR1 (SEQ ID NO:58), Vh-CDR2 (SEQ ID NO:59), Vh-CDR3 (SEQ ID NO:60), Vl-CDR1 (SEQ ID NO:160), Vl-CDR2 (SEQ ID NO:161), and Vl-CDR3 (SEQ ID NO:162). Aspects of the invention include isolated polynucleotides that encode a polypeptide comprising the six CDRs of Ab-11, wherein the CDRs include no more than one, two, three, four, five, or six amino acid additions, deletions, or substitutions of Vh-CDR1 (SEQ ID NO:64), Vh-CDR2 (SEQ ID NO:65), Vh-CDR3 (SEQ ID NO:66), Vl-CDR1 (SEQ ID NO:166), Vl-CDR2 (SEQ ID NO:167), and Vl-CDR3 (SEQ ID NO:168). Aspects of the invention include isolated polynucleotides that encode a polypeptide comprising the six CDRs of Ab-12, wherein the CDRs include no more than one, two, three, four, five, or six amino acid additions, deletions, or substitutions of Vh-CDR1 (SEQ ID NO:70), Vh-CDR2 (SEQ ID NO:71), Vh-CDR3 (SEQ ID NO:72), Vl-CDR1 (SEQ ID NO:172), Vl-CDR2 (SEQ ID NO:173), and Vl-CDR3 (SEQ ID NO:174). Aspects of the invention include isolated polynucleotides that encode a polypeptide comprising the six CDRs of Ab-13, wherein the CDRs include no more than one, two, three, four, five, or six amino acid additions, deletions, or substitutions of Vh-CDR1 (SEQ ID NO:76), Vh-CDR2 (SEQ ID NO:77), Vh-CDR3 (SEQ ID NO:78), Vl-CDR1 (SEQ ID NO:178), Vl-CDR2 (SEQ ID NO:179), and Vl-CDR3 (SEQ ID NO:180). Aspects of the invention include isolated polynucleotides that encode a polypeptide comprising the six CDRs of Ab-14, wherein the CDRs include no more than one, two, three, four, five, or six amino acid additions, deletions, or substitutions of Vh-CDR1 (SEQ ID NO:82), Vh-CDR2 (SEQ ID NO:83), Vh-CDR3 (SEQ ID NO:84), Vl-CDR1 (SEQ ID NO:184), Vl-CDR2 (SEQ ID NO:185), and Vl-CDR3 (SEQ ID NO:186). Aspects of the invention include isolated polynucleotides that encode a polypeptide comprising the six CDRs of Ab-15, wherein the CDRs include no more than one, two, three, four, five, or six amino acid additions, deletions, or substitutions of Vh-CDR1 (SEQ ID NO:88), Vh-CDR2 (SEQ ID NO:89), Vh-CDR3 (SEQ ID NO:90), Vl-CDR1 (SEQ ID NO:190), Vl-CDR2 (SEQ ID NO:191), and Vl-CDR3 (SEQ ID NO:192). Aspects of the invention include isolated polynucleotides that encode a polypeptide comprising the six CDRs of Ab-16, wherein the CDRs include no more than one, two, three, four, five, or six amino acid additions, deletions, or substitutions of Vh-CDR1 (SEQ ID NO:94), Vh-CDR2 (SEQ ID NO:95), Vh-CDR3 (SEQ ID NO:96), Vl-CDR1 (SEQ ID NO:196), Vl-CDR2 (SEQ ID NO:197), and Vl-CDR3 (SEQ ID NO:198). Aspects of the invention include isolated polynucleotides that encode a polypeptide comprising the six CDRs of Ab-17, wherein the CDRs include no more than one, two, three, four, five, or six amino acid additions, deletions, or substitutions of Vh-CDR1 (SEQ ID NO:100), Vh-CDR2 (SEQ ID NO:101), Vh-CDR3 (SEQ ID NO:102), Vl-CDR1 (SEQ ID NO:202), Vl-CDR2 (SEQ ID NO:203), and Vl-CDR3 (SEQ ID NO:204).

Aspects of the invention include isolated polynucleotides that encode a polypeptide comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-1Vl (SEQ ID NO:240) and Ab-1Vh (SEQ ID NO:206), respectively. Aspects of the invention include isolated polynucleotides that encode a polypeptide comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-2Vl (SEQ ID NO:242) and Ab-2Vh (SEQ ID NO:208), respectively. Aspects of the invention include isolated polynucleotides that encode a polypeptide comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-3Vl (SEQ ID NO:244) and Ab-3Vh (SEQ ID NO:210), respectively. Aspects of the invention include isolated polynucleotides that encode a polypeptide comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-4Vl (SEQ ID NO:246) and Ab-4Vh (SEQ ID NO:212), respectively. Aspects of the invention include isolated polynucleotides that encode a polypeptide comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-5Vl (SEQ ID NO:248) and Ab-5Vh (SEQ ID NO:214), respectively. Aspects of the invention include isolated polynucleotides that encode a polypeptide comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-6Vl (SEQ ID NO:250) and Ab-6Vh (SEQ ID NO:216), respectively. Aspects of the invention include isolated polynucleotides that encode a polypeptide comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-7Vl (SEQ ID NO:252) and Ab-7Vh (SEQ ID NO:218), respectively. Aspects of the invention include isolated polynucleotides that encode a polypeptide comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-8Vl (SEQ ID NO:254) and Ab-8Vh (SEQ ID NO:220), respectively. Aspects of the invention include isolated polynucleotides that encode a polypeptide comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-9Vl (SEQ ID NO:256) and Ab-9Vh (SEQ ID NO:222), respectively. Aspects of the invention include isolated polynucleotides that encode a polypeptide comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-10Vl (SEQ ID NO:258) and Ab-10Vh (SEQ ID NO:224), respectively. Aspects of the invention include isolated polynucleotides that encode a polypeptide comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-11Vl (SEQ ID NO:260) and Ab-11Vh (SEQ ID NO:226), respectively. Aspects of the invention include isolated polynucleotides that encode a polypeptide comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-12Vl (SEQ ID NO:262) and Ab-12Vh (SEQ ID NO:228), respectively. Aspects of the invention include isolated polynucleotides that encode a polypeptide comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-13Vl (SEQ ID NO:264) and Ab-13Vh (SEQ ID NO:230), respectively. Aspects of the invention include isolated polynucleotides that encode a polypeptide comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-14Vl (SEQ ID NO:266) and Ab-14Vh (SEQ ID NO:232), respectively. Aspects of the invention include isolated polynucleotides that encode a polypeptide comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-15Vl (SEQ ID NO:268) and Ab-15Vh (SEQ ID NO:234), respectively. Aspects of the invention include isolated polynucleotides that encode a polypeptide comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-16Vl (SEQ ID NO:270) and Ab-16Vh (SEQ ID NO:236), respectively. Aspects of the invention include isolated polynucleotides that encode a polypeptide comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-17Vl (SEQ ID NO:272) and Ab-17Vh (SEQ ID NO:238), respectively.

Aspects of the invention include isolated polynucleotides that encode a polypeptide comprising the six CDRs of Ab-1, wherein the polynucleotide sequence comprises Vh-CDR1 (SEQ ID NO:1), Vh-CDR2 (SEQ ID NO:2), Vh-CDR3 (SEQ ID NO:3), Vl-CDR1 (SEQ ID NO:103), Vl-CDR2 (SEQ ID NO:104), and Vl-CDR3 (SEQ ID NO:105). Aspects of the invention include isolated polynucleotides that encode a polypeptide comprising the six CDRs of Ab-2, wherein the polynucleotide sequence comprises Vh-CDR1 (SEQ ID NO:7), Vh-CDR2 (SEQ ID NO:8), Vh-CDR3 (SEQ ID NO:9), Vl-CDR1 (SEQ ID NO:109), Vl-CDR2 (SEQ ID NO:110), and Vl-CDR3 (SEQ ID NO:111). Aspects of the invention include isolated polynucleotides that encode a polypeptide comprising the six CDRs of Ab-3, wherein the polynucleotide sequence comprises Vh-CDR1 (SEQ ID NO:13), Vh-CDR2 (SEQ ID NO:14), Vh-CDR3

(SEQ ID NO:15), Vl-CDR1 (SEQ ID NO:115), Vl-CDR2 (SEQ ID NO:116), and Vl-CDR3 (SEQ ID NO:117). Aspects of the invention include isolated polynucleotides that encode a polypeptide comprising the six CDRs of Ab-4, wherein the polynucleotide sequence comprises Vh-CDR1 (SEQ ID NO:19), Vh-CDR2 (SEQ ID NO:20), Vh-CDR3 (SEQ ID NO:21), Vl-CDR1 (SEQ ID NO:121), Vl-CDR2 (SEQ ID NO:122), and Vl-CDR3 (SEQ ID NO:123). Aspects of the invention include isolated polynucleotides that encode a polypeptide comprising the six CDRs of Ab-5, wherein the polynucleotide sequence comprises Vh-CDR1 (SEQ ID NO:25), Vh-CDR2 (SEQ ID NO:26), Vh-CDR3 (SEQ ID NO:27), Vl-CDR1 (SEQ ID NO:127), Vl-CDR2 (SEQ ID NO:128), and Vl-CDR3 (SEQ ID NO:129). Aspects of the invention include isolated polynucleotides that encode a polypeptide comprising the six CDRs of Ab-6, wherein the polynucleotide sequence comprises Vh-CDR1 (SEQ ID NO:31), Vh-CDR2 (SEQ ID NO:32), Vh-CDR3 (SEQ ID NO:33), Vl-CDR1 (SEQ ID NO:133), Vl-CDR2 (SEQ ID NO:134), and Vl-CDR3 (SEQ ID NO:135). Aspects of the invention include isolated polynucleotides that encode a polypeptide comprising the six CDRs of Ab-7, wherein the polynucleotide sequence comprises Vh-CDR1 (SEQ ID NO:37), Vh-CDR2 (SEQ ID NO:38), Vh-CDR3 (SEQ ID NO:39), Vl-CDR1 (SEQ ID NO:139), Vl-CDR2 (SEQ ID NO:140), and Vl-CDR3 (SEQ ID NO:141). Aspects of the invention include isolated polynucleotides that encode a polypeptide comprising the six CDRs of Ab-8, wherein the polynucleotide sequence comprises Vh-CDR1 (SEQ ID NO:43), Vh-CDR2 (SEQ ID NO:44), Vh-CDR3 (SEQ ID NO:45), Vl-CDR1 (SEQ ID NO:145), Vl-CDR2 (SEQ ID NO:146), and Vl-CDR3 (SEQ ID NO:147). Aspects of the invention include isolated polynucleotides that encode a polypeptide comprising the six CDRs of Ab-9, wherein the polynucleotide sequence comprises Vh-CDR1 (SEQ ID NO:49), Vh-CDR2 (SEQ ID NO:50), Vh-CDR3 (SEQ ID NO:51), Vl-CDR1 (SEQ ID NO:151), Vl-CDR2 (SEQ ID NO:152), and Vl-CDR3 (SEQ ID NO:153). Aspects of the invention include isolated polynucleotides that encode a polypeptide comprising the six CDRs of Ab-10, wherein the polynucleotide sequence comprises Vh-CDR1 (SEQ ID NO:55), Vh-CDR2 (SEQ ID NO:56), Vh-CDR3 (SEQ ID NO:57), Vl-CDR1 (SEQ ID NO:157), Vl-CDR2 (SEQ ID NO:158), and Vl-CDR3 (SEQ ID NO:159). Aspects of the invention include isolated polynucleotides that encode a polypeptide comprising the six CDRs of Ab-11, wherein the polynucleotide sequence comprises Vh-CDR1 (SEQ ID NO:61), Vh-CDR2 (SEQ ID NO:62), Vh-CDR3 (SEQ ID NO:63), Vl-CDR1 (SEQ ID NO:163), Vl-CDR2 (SEQ ID NO:164), and Vl-CDR3 (SEQ ID NO:165). Aspects of the invention include isolated polynucleotides that encode a polypeptide comprising the six CDRs of Ab-12, wherein the polynucleotide sequence comprises Vh-CDR1 (SEQ ID NO:67), Vh-CDR2 (SEQ ID NO:68), Vh-CDR3 (SEQ ID NO:69), Vl-CDR1 (SEQ ID NO:169), Vl-CDR2 (SEQ ID NO:170), and Vl-CDR3 (SEQ ID NO:171). Aspects of the invention include isolated polynucleotides that encode a polypeptide comprising the six CDRs of Ab-13, wherein the polynucleotide sequence comprises Vh-CDR1 (SEQ ID NO:73), Vh-CDR2 (SEQ ID NO:74), Vh-CDR3 (SEQ ID NO:75), Vl-CDR1 (SEQ ID NO:175), Vl-CDR2 (SEQ ID NO:176), and Vl-CDR3 (SEQ ID NO:177). Aspects of the invention include isolated polynucleotides that encode a polypeptide comprising the six CDRs of Ab-14, wherein the polynucleotide sequence comprises Vh-CDR1 (SEQ ID NO:79), Vh-CDR2 (SEQ ID NO:80), Vh-CDR3 (SEQ ID NO:81), Vl-CDR1 (SEQ ID NO:181), Vl-CDR2 (SEQ ID NO:182), and Vl-CDR3 (SEQ ID NO:183). Aspects of the invention include isolated polynucleotides that encode a polypeptide comprising the six CDRs of Ab-15, wherein the polynucleotide sequence comprises Vh-CDR1 (SEQ ID NO:85), Vh-CDR2 (SEQ ID NO:86), Vh-CDR3 (SEQ ID NO:87), Vl-CDR1 (SEQ ID NO:187), Vl-CDR2 (SEQ ID NO:188), and Vl-CDR3 (SEQ ID NO:189). Aspects of the invention include isolated polynucleotides that encode a polypeptide comprising the six CDRs of Ab-16, wherein the polynucleotide sequence comprises Vh-CDR1 (SEQ ID NO:91), Vh-CDR2 (SEQ ID NO:92), Vh-CDR3 (SEQ ID NO:93), Vl-CDR1 (SEQ ID NO:193), Vl-CDR2 (SEQ ID NO:194), and Vl-CDR3 (SEQ ID NO:195). Aspects of the invention include isolated polynucleotides that encode a polypeptide comprising the six CDRs of Ab-17, wherein the polynucleotide sequence comprises Vh-CDR1 (SEQ ID NO:97), Vh-CDR2 (SEQ ID NO:98), Vh-CDR3 (SEQ ID NO:99), Vl-CDR1 (SEQ ID NO:199), Vl-CDR2 (SEQ ID NO:200), and Vl-CDR3 (SEQ ID NO:201).

Aspects of the invention include isolated polynucleotides that encode a polypeptide comprising the Vl and Vh domains of Ab-1, wherein the polynucleotide sequence comprises Ab-1Vl (SEQ ID NO:239) and Ab-1Vh (SEQ ID NO:205). Aspects of the invention include isolated polynucleotides that encode a polypeptide comprising the Vl and Vh domains of Ab-2, wherein the polynucleotide sequence comprises Ab-2Vl (SEQ ID NO:241) and Ab-2Vh (SEQ ID NO:207). Aspects of the invention include isolated polynucleotides that encode a polypeptide comprising the Vl and Vh domains of Ab-3, wherein the polynucleotide sequence comprises Ab-3Vl (SEQ ID NO:243) and Ab-3Vh (SEQ ID NO:209). Aspects of the invention include isolated polynucleotides that encode a polypeptide comprising the Vl and Vh domains of Ab-4, wherein the polynucleotide sequence comprises Ab-4Vl (SEQ ID NO:245) and an Ab-4Vh (SEQ ID NO:211). Aspects of the invention include isolated polynucleotides that encode a polypeptide comprising the Vl and Vh domains of Ab-5, wherein the polynucleotide sequence comprises Ab-5Vl (SEQ ID NO:247) and Ab-5Vh (SEQ ID NO:213). Aspects of the invention include isolated polynucleotides that encode a polypeptide comprising the Vl and Vh domains of Ab-6, wherein the polynucleotide sequence comprises Ab-6Vl (SEQ ID NO:249) and Ab-6Vh (SEQ ID NO:215). Aspects of the invention include isolated polynucleotides that encode a polypeptide comprising the Vl and Vh domains of Ab-7, wherein the polynucleotide sequence comprises Ab-7Vl (SEQ ID NO:251) and Ab-7Vh (SEQ ID NO:217). Aspects of the invention include isolated polynucleotides that encode a polypeptide comprising the Vl and Vh domains of Ab-8, wherein the polynucleotide sequence comprises Ab-8Vl (SEQ ID NO:253) and Ab-8Vh (SEQ ID NO:219). Aspects of the invention include isolated polynucleotides that encode a polypeptide comprising the Vl and Vh domains of Ab-9, wherein the polynucleotide sequence comprises Ab-9Vl (SEQ ID NO:255) and Ab-9Vh (SEQ ID NO:221). Aspects of the invention include isolated polynucleotides that encode a polypeptide comprising the Vl and Vh domains of Ab-10, wherein the polynucleotide sequence comprises Ab-10Vl (SEQ ID NO:257) and Ab-10Vh (SEQ ID NO:223) domain. Aspects of the invention include isolated polynucleotides that encode a polypeptide comprising the Vl and Vh domains of Ab-11, wherein the polynucleotide sequence comprises Ab-11Vl (SEQ ID NO:259) and Ab-11Vh (SEQ ID NO:225). Aspects of the invention include isolated polynucleotides that encode a polypeptide comprising the Vl and Vh domains of Ab-12, wherein the polynucleotide sequence comprises Ab-12Vl (SEQ ID NO:261) and Ab-12Vh (SEQ ID NO:227). Aspects of the invention include isolated polynucleotides that encode a polypeptide comprising the Vl and Vh domains of Ab-13, wherein the polynucleotide sequence comprises Ab-13Vl (SEQ ID NO:263) and Ab-13Vh (SEQ ID NO:229). Aspects of the invention include isolated polynucleotides that encode a polypeptide comprising the Vl and Vh domains of Ab-14, wherein the polynucleotide sequence comprises Ab-14Vl (SEQ ID NO:265) and Ab-14Vh (SEQ ID NO:231). Aspects of the invention include isolated polynucleotides that encode a polypeptide comprising the Vl and Vh domains of Ab-15, wherein the polynucleotide sequence comprises Ab-15Vl (SEQ ID NO:267) and Ab-15Vh (SEQ ID NO:233). Aspects of the invention include isolated polynucleotides that encode a polypeptide comprising the Vl and Vh domains of Ab-16, wherein the polynucleotide sequence comprises Ab-16Vl (SEQ ID NO:269) and Ab-16Vh (SEQ ID NO:235). Aspects of the invention include isolated polynucleotides that encode a polypeptide comprising the Vl and Vh domains of Ab-17, wherein the polynucleotide sequence comprises Ab-17Vl (SEQ ID NO:271) and Ab-17Vh (SEQ ID NO:237).

Aspects of the invention include isolated polynucleotides that encode a polypeptide comprising the heavy and light chains of antibody Ab-1, wherein the polynucleotide sequence comprises a light chain (SEQ ID NO:279) and a heavy chain (SEQ ID NO:273). Aspects of the invention include isolated polynucleotides that encode polypeptide comprising the heavy and light chains of antibody Ab-2, wherein the polynucleotide sequence comprises a light chain (SEQ ID NO:281) and a heavy chain (SEQ ID NO:275). Aspects of the invention include isolated polynucleotides that encode polypeptide comprising the heavy and light chains of antibody Ab-3, wherein the polynucleotide sequence comprises a light chain (SEQ ID NO:283) and a heavy chain (SEQ ID NO:277).

Nucleotide sequences corresponding to the amino acid sequences described herein, to be used as probes or primers for the isolation of nucleic acids or as query sequences for database searches, can be obtained by "back-translation" from the amino acid sequences, or by identification of regions of amino acid identity with polypeptides for which the coding DNA sequence has been identified. The well-known polymerase chain reaction (PCR) procedure can be employed to isolate and amplify a DNA sequence encoding a BCMA antigen binding proteins or a desired combination of BCMA antigen binding protein polypeptide fragments. Oligonucleotides that define the desired termini of the combination of DNA fragments are employed as 5' and 3' primers. The oligonucleotides can additionally contain recognition sites for restriction endonucleases, to facilitate insertion of the amplified combination of DNA fragments into an expression vector. PCR techniques are described in Saiki et al., *Science* 239:487 (1988); *Recombinant DNA Methodology*, Wu et al., eds., Academic Press, Inc., San Diego (1989), pp. 189-196; and *PCR Protocols: A Guide to Methods and Applications*, Innis et. al., eds., Academic Press, Inc. (1990).

Nucleic acid molecules of the invention include DNA and RNA in both single-stranded and double-stranded form, as well as the corresponding complementary sequences. DNA includes, for example, cDNA, genomic DNA, chemically synthesized DNA, DNA amplified by PCR, and combinations thereof. The nucleic acid molecules of the invention include full-length genes or cDNA molecules as well as a combination of fragments thereof. The nucleic acids of the invention are preferentially derived from human sources, but the invention includes those derived from non-human species, as well.

An "isolated nucleic acid" is a nucleic acid that has been separated from adjacent genetic sequences present in the genome of the organism from which the nucleic acid was isolated, in the case of nucleic acids isolated from naturally-occurring sources. In the case of nucleic acids synthesized enzymatically from a template or chemically, such as PCR products, cDNA molecules, or oligonucleotides for example, it is understood that the nucleic acids resulting from such processes are isolated nucleic acids. An isolated nucleic acid molecule refers to a nucleic acid molecule in the form of a separate fragment or as a component of a larger nucleic acid construct. In one preferred embodiment, the nucleic acids are substantially free from contaminating endogenous material. The nucleic acid molecule has preferably been derived from DNA or RNA isolated at least once in substantially pure form and in a quantity or concentration enabling identification, manipulation, and recovery of its component nucleotide sequences by standard biochemical methods (such as those outlined in Sambrook et al., *Molecular Cloning: A Laboratory Manual,* 2nd ed., Cold Spring Harbor Laboratory, Cold Spring Harbor, N.Y. (1989)). Such sequences are preferably provided and/or constructed in the form of an open reading frame uninterrupted by internal non-translated sequences, or introns, that are typically present in eukaryotic genes. Sequences of non-translated DNA can be present 5' or 3' from an open reading frame, where the same do not interfere with manipulation or expression of the coding region.

The present invention also includes nucleic acids that hybridize under moderately stringent conditions, and more preferably highly stringent conditions, to nucleic acids encoding BCMA antigen binding proteins as described herein. The basic parameters affecting the choice of hybridization conditions and guidance for devising suitable conditions are set forth by Sambrook, Fritsch, and Maniatis (1989, Molecular Cloning: A Laboratory Manual, Cold Spring Harbor Laboratory Press, Cold Spring Harbor, N.Y., chapters 9 and 11; and Current Protocols in Molecular Biology, 1995, Ausubel et al., eds., John Wiley & Sons, Inc., sections 2.10 and 6.3-6.4), and can be readily determined by those having ordinary skill in the art based on, for example, the length and/or base composition of the DNA. One way of achieving moderately stringent conditions involves the use of a prewashing solution containing 5×SSC, 0.5% SDS, 1.0 mM EDTA (pH 8.0), hybridization buffer of about 50% formamide, 6×SSC, and a hybridization temperature of about 55 degrees C. (or other similar hybridization solutions, such as one containing about 50% formamide, with a hybridization temperature of about 42 degrees C.), and washing conditions of about 60 degrees C., in 0.5×SSC, 0.1% SDS. Generally, highly stringent conditions are defined as hybridization conditions as above, but with washing at approximately 68 degrees C., 0.2×SSC, 0.1% SDS. SSPE (1×SSPE is 0.15M NaCl, 10 mM NaH.sub.2 PO.sub.4, and 1.25 mM EDTA, pH 7.4) can be substituted for SSC (1×SSC is 0.15M NaCl and 15 mM sodium citrate) in the hybridization and wash buffers; washes are performed for 15 minutes after hybridization is complete. It should be understood that the wash temperature and wash salt concentration can be adjusted as necessary to achieve a desired degree of stringency by applying the basic principles that govern hybridization reactions and duplex stability, as known to those skilled in the art and described further below (see, e.g., Sambrook et al., 1989). When hybridizing a nucleic acid to a target nucleic acid of unknown sequence, the hybrid length is assumed to be that of the hybridizing nucleic acid. When nucleic acids of known sequence are hybridized, the hybrid length can be determined by aligning the sequences of the nucleic acids and identifying the region or regions of optimal sequence complementarity. The hybridization temperature for hybrids anticipated to be less than 50 base pairs in length should be 5 to 10.degrees C. less than the melting temperature (Tm) of the hybrid, where Tm is determined according to the following equations. For hybrids less than 18 base pairs in length, Tm (degrees C.)=2(# of A+T bases)+4(# of #G+C bases). For hybrids above 18 base pairs in length, Tm (degrees C.)=81.5+16.6 ($\log_{10}$ [Na$^+$])+0.41(% G+C)−(600/N), where N is the number of bases in the hybrid, and [Na$^+$] is the concentration of sodium ions in the hybridization buffer ([Na$^+$] for 1×SSC=0.165M). Preferably, each such hybridizing nucleic acid has a length that is at least 15 nucleotides (or more preferably at least 18 nucleotides, or at least 20 nucleotides, or at least 25 nucleotides, or at least 30 nucleotides, or at least 40 nucleotides, or most preferably at least 50 nucleotides), or at least 25% (more preferably at least 50%, or at least 60%, or at least 70%, and most preferably at least 80%) of the length of the nucleic acid of the present invention to which it hybridizes, and has at least 60% sequence identity (more preferably at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, and most preferably at least 99.5%) with the nucleic acid of the present invention to which it hybridizes, where sequence identity is determined by comparing the sequences of the hybridizing nucleic acids when aligned so as to maximize overlap and identity while minimizing sequence gaps as described in more detail above.

The variants according to the invention are ordinarily prepared by site specific mutagenesis of nucleotides in the DNA encoding the antigen binding protein, using cassette or PCR mutagenesis or other techniques well known in the art, to produce DNA encoding the variant, and thereafter expressing the recombinant DNA in cell culture as outlined herein. However, antigen binding protein fragments comprising variant CDRs having up to about 100-150 residues may be prepared by in vitro synthesis using established techniques. The variants typically exhibit the same qualitative biological activity as the naturally occurring analogue, e.g., binding to BCMA and inhibiting signaling, although variants can also be selected which have modified characteristics as will be more fully outlined below.

As will be appreciated by those in the art, due to the degeneracy of the genetic code, an extremely large number of nucleic acids may be made, all of which encode the CDRs (and heavy and light chains or other components of the antigen binding protein) of the present invention. Thus, having identified a particular amino acid sequence, those skilled in the art could make any number of different nucleic acids, by simply modifying the sequence of one or more codons in a way which does not change the amino acid sequence of the encoded protein.

The present invention also provides expression systems and constructs in the form of plasmids, expression vectors, transcription or expression cassettes which comprise at least one polynucleotide as above. In addition, the invention provides host cells comprising such expression systems or constructs.

Typically, expression vectors used in any of the host cells will contain sequences for plasmid maintenance and for cloning and expression of exogenous nucleotide sequences. Such sequences, collectively referred to as "flanking sequences" in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Each of these sequences is discussed below.

Optionally, the vector may contain a "tag"-encoding sequence, i.e., an oligonucleotide molecule located at the 5' or 3' end of the BCMA antigen binding protein coding sequence; the oligonucleotide sequence encodes polyHis (such as hexaHis), or another "tag" such as FLAG, HA (hemaglutinin influenza virus), or myc, for which commercially available antibodies exist. This tag is typically fused to the polypeptide upon expression of the polypeptide, and can serve as a means for affinity purification or detection of the BCMA antigen binding protein from the host cell. Affinity purification can be accomplished, for example, by column chromatography using antibodies against the tag as an affinity matrix. Optionally, the tag can subsequently be removed from the purified BCMA antigen binding protein by various means such as using certain peptidases for cleavage.

Flanking sequences may be homologous (i.e., from the same species and/or strain as the host cell), heterologous (i.e., from a species other than the host cell species or strain), hybrid (i.e., a combination of flanking sequences from more than one source), synthetic or native. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences useful in the vectors of this invention may be obtained by any of several methods well known in the art. Typically, flanking sequences useful herein will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Whether all or only a portion of the flanking sequence is known, it may be obtained using polymerase chain reaction (PCR) and/or by screening a genomic library with a suitable probe such as an oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, Calif.), or other methods known to the skilled artisan. The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. If the vector of choice does not contain an origin of replication site, one may be chemically synthesized based on a known sequence, and ligated into the vector. For example, the origin of replication from the plasmid pBR322 (New England Biolabs, Beverly, Mass.) is suitable for most gram-negative bacteria, and various viral origins (e g., SV40, polyoma, adenovirus, vesicular stomatitus virus (VSV), or papillomaviruses such as HPV or BPV) are useful for cloning vectors in mammalian cells. Generally, the origin of replication component is not needed for mammalian expression vectors (for example, the SV40 origin is often used only because it also contains the virus early promoter).

A transcription termination sequence is typically located 3' to the end of a polypeptide coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using methods for nucleic acid synthesis such as those described herein.

A selectable marker gene encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex or defined media. Specific selectable markers are the kanamycin resistance gene, the ampicillin resistance gene, and the tetracycline resistance gene. Advantageously, a neomycin resistance gene may also be used for selection in both prokaryotic and eukaryotic host cells.

Other selectable genes may be used to amplify the gene that will be expressed. Amplification is the process wherein genes that are required for production of a protein critical for growth or cell survival are reiterated in tandem within the chromosomes of successive generations of recombinant cells. Examples of suitable selectable markers for mammalian cells include dihydrofolate reductase (DHFR) and promoterless thymidine kinase genes Mammalian cell transformants are placed under selection pressure wherein only the transformants are uniquely adapted to survive by virtue of the selectable gene present in the vector. Selection pressure is imposed by culturing the transformed cells under conditions in which the concentration of selection agent in the medium is successively increased, thereby leading to the amplification of both the selectable gene and the DNA that encodes another gene, such as an antigen binding protein antibody that binds to BCMA polypeptide. As a result, increased quantities of a polypeptide such as a BCMA antigen binding protein are synthesized from the amplified DNA.

A ribosome-binding site is usually necessary for translation initiation of rnRNA and is characterized by a Shine-Dalgarno sequence (prokaryotes) or a Kozak sequence (eukaryotes). The element is typically located 3' to the promoter and 5' to the coding sequence of the polypeptide to be expressed.

In some cases, such as where glycosylation is desired in a eukaryotic host cell expression system, one may manipulate the various pre- or prosequences to improve glycosylation or yield. For example, one may alter the peptidase cleavage site of a particular signal peptide, or add prosequences, which also may affect glycosylation. The final protein product may have, in the −1 position (relative to the first amino acid of the mature protein) one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated form of the desired polypeptide, if the enzyme cuts at such area within the mature polypeptide.

Expression and cloning vectors of the invention will typically contain a promoter that is recognized by the host organism and operably linked to the molecule encoding the BCMA antigen binding protein. Promoters are untranscribed sequences located upstream (i.e., 5') to the start codon of a structural gene (generally within about 100 to 1000 bp) that control transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, uniformly transcribe gene to which they are operably linked, that is, with little or no control over gene expression. A large number of promoters, recognized by a variety of potential host cells, are well known. A suitable promoter is operably linked to the DNA encoding heavy chain or light chain comprising a BCMA antigen binding protein of the invention by removing the promoter from the source DNA by restriction enzyme digestion and inserting the desired promoter sequence into the vector.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and most preferably Simian Virus 40 (SV40). Other suitable mammalian promoters include heterologous mammalian promoters, for example, heat-shock promoters and the actin promoter.

Additional promoters which may be of interest include, but are not limited to: SV40 early promoter (Benoist and Chambon, 1981, Nature 290:304-310); CMV promoter (Thornsen et al., 1984, *Proc. Natl. Acad. U.S.A.* 81:659-663); the promoter contained in the 3' long terminal repeat of Rous sarcoma virus (Yamamoto et al., 1980, *Cell* 22:787-797); herpes thymidine kinase promoter (Wagner et al., 1981, *Proc. Natl. Acad. Sci. U.S.A.* 78:1444-1445); promoter and regulatory sequences from the metallothionine gene Prinster et al., 1982, *Nature* 296:39-42); and prokaryotic promoters such as the beta-lactamase promoter (Villa-Kamaroff et al., 1978, *Proc. Natl. Acad. Sci. U.S.A.* 75:3727-3731); or the tac promoter (DeBoer et al., 1983, *Proc. Natl. Acad. Sci. U.S.A.* 80:21-25). Also of interest are the following animal transcriptional control regions, which exhibit tissue specificity and have been utilized in transgenic animals: the elastase I gene control region that is active in pancreatic acinar cells (Swift et al., 1984, *Cell* 38:639-646; Ornitz et al., 1986, *Cold Spring Harbor Symp. Quant. Biol.* 50:399-409; MacDonald, 1987, *Hepatology* 7:425-515); the insulin gene control region that is active in pancreatic beta cells (Hanahan, 1985, *Nature* 315:115-122); the immunoglobulin gene control region that is active in lymphoid cells (Grosschedl et al., 1984, *Cell* 38:647-658; Adames et al., 1985, *Nature* 318:533-538; Alexander et al., 1987, *Mol. Cell. Biol.* 7:1436-1444); the mouse mammary tumor virus control region that is active in testicular, breast, lymphoid and mast cells (Leder et al., 1986, *Cell* 45:485-495); the albumin gene control region that is active in liver (Pinkert et al., 1987, *Genes and Devel.* 1:268-276); the alpha-fetoprotein gene control region that is active in liver (Krumlauf et al., 1985, *Mol. Cell. Biol.* 5:1639-1648; Hammer et al., 1987, *Science* 253:53-58); the alpha 1-antitrypsin gene control region that is active in liver (Kelsey et al., 1987, *Genes and Devel.* 1:161-171); the beta-globin gene control region that is active in myeloid cells (Mogram et al., 1985, *Nature* 315:338-340; Kollias et al., 1986, *Cell* 46:89-94); the myelin basic protein gene control region that is active in oligodendrocyte cells in the brain (Readhead et al., 1987, *Cell* 48:703-712); the myosin light chain-2 gene control region that is active in skeletal muscle (Sani, 1985, *Nature* 314:283-286); and the gonadotropic releasing hormone gene control region that is active in the hypothalamus (Mason et al., 1986, *Science* 234:1372-1378).

An enhancer sequence may be inserted into the vector to increase transcription of DNA encoding light chain or heavy chain comprising an BCMA antigen binding protein of the invention by higher eukaryotes. Enhancers are cis-acting elements of DNA, usually about 10-300 bp in length, that act on the promoter to increase transcription. Enhancers are relatively orientation and position independent, having been found at positions both 5' and 3' to the transcription unit. Several enhancer sequences available from mammalian genes are known (e.g., globin, elastase, albumin, alpha-fetoprotein and insulin). Typically, however, an enhancer from a virus is used. The SV40 enhancer, the cytomegalovirus early promoter enhancer, the polyoma enhancer, and adenovirus enhancers known in the art are exemplary enhancing elements for the activation of eukaryotic promoters. While an enhancer may be positioned in the vector either 5' or 3' to a coding sequence, it is typically located at a site 5' from the promoter. A sequence encoding an appropriate native or heterologous signal sequence (leader sequence or signal peptide) can be incorporated into an expression vector, to promote extracellular secretion of the antibody. The choice of signal peptide or leader depends on the type of host cells in which the antibody is to be produced, and a heterologous signal sequence can replace the native signal sequence. Examples of signal peptides that are functional in mammalian host cells include the following: the signal sequence for interleukin-7 (IL-7) described in U.S. Pat. No. 4,965,195; the signal sequence for interleukin-2 receptor described in Cosman et al., 1984, *Nature* 312:768; the interleukin-4 receptor signal peptide described in EP Patent No. 0367 566; the type I interleukin-1 receptor signal peptide described in U.S. Pat. No. 4,968,607; the type II interleukin-1 receptor signal peptide described in EP Patent No. 0 460 846.

Expression vectors of the invention may be constructed from a starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

After the vector has been constructed and a nucleic acid molecule encoding light chain, a heavy chain, or a light chain and a heavy chain comprising an BCMA antigen binding sequence has been inserted into the proper site of the vector, the completed vector may be inserted into a suitable host cell for amplification and/or polypeptide expression. The transformation of an expression vector for an BCMA antigen binding protein into a selected host cell may be accomplished by well known methods including transfection, infection, calcium phosphate co-precipitation, electroporation, microinjection, lipofection, DEAE-dextran mediated transfection, or other known techniques. The method selected will in part be a function of the type of host cell to be used. These methods and other suitable methods are well known to the skilled artisan, and are set forth, for example, in Sambrook et al., 2001, supra.

A host cell, when cultured under appropriate conditions, synthesizes an BCMA antigen binding protein that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule. A host cell may be eukaryotic or prokaryotic.

Mammalian cell lines available as hosts for expression are well known in the art and include, but are not limited to, immortalized cell lines available from the American Type Culture Collection (ATCC) and any cell lines used in an expression system known in the art can be used to make the recombinant polypeptides of the invention. In general, host cells are transformed with a recombinant expression vector that comprises DNA encoding a desired anti-BCMA antibody polypeptide. Among the host cells that may be employed are prokaryotes, yeast or higher eukaryotic cells. Prokaryotes include gram negative or gram positive organisms, for example *E. coli* or bacilli. Higher eukaryotic cells include insect cells and established cell lines of mammalian origin. Examples of suitable mammalian host cell lines include the COS-7 line of monkey kidney cells (ATCC CRL 1651) (Gluzman et al., 1981, *Cell* 23:175), L cells, 293 cells, C127 cells, 3T3 cells (ATCC CCL 163), Chinese hamster ovary (CHO) cells, or their derivatives such as Veggie CHO and related cell lines which grow in serum-free media (Rasmussen et al., 1998, *Cytotechnology* 28: 31), HeLa cells, BHK (ATCC CRL 10) cell lines, and the CVI/EBNA cell line derived from the African green monkey kidney cell line CVI (ATCC CCL 70) as described by McMahan et al., 1991, *EMBO J.* 10: 2821, human embryonic kidney cells such as 293, 293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Optionally, mammalian cell lines such as HepG2/3B, KB, NIH 3T3 or S49, for example, can be used for expression of the polypeptide when it is desirable to use the polypeptide in various signal transduction or reporter assays. Alternatively, it is possible to produce the polypeptide in lower eukaryotes such as yeast or in prokaryotes such as bacteria. Suitable yeasts include *Saccharomyces cerevisiae, Schizosaccharomyces pombe, Kluyveromyces* strains, *Candida*, or any yeast strain capable of expressing heterologous polypeptides. Suitable bacterial strains include *Escherichia coli, Bacillus subtilis, Salmonella typhimurium*, or any bacterial strain capable of expressing heterologous polypeptides. If the polypeptide is made in yeast or bacteria, it may be desirable to modify the polypeptide produced therein, for example by phosphorylation or glycosylation of the appropriate sites, in order to obtain the functional polypeptide. Such covalent attachments can be accomplished using known chemical or enzymatic methods. The polypeptide can also be produced by operably linking the isolated nucleic acid of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBac® kit), and such methods are well known in the art, as described in Summers and Smith, Texas Agricultural Experiment Station Bulletin No. 1555 (1987), and Luckow and Summers, *Bio/Technology* 6:47 (1988). Cell-free translation systems could also be employed to produce polypeptides using RNAs derived from nucleic acid constructs disclosed herein. Appropriate cloning and expression vectors for use with bacterial, fungal, yeast, and mammalian cellular hosts are described by Pouwels et al. (*Cloning Vectors: A Laboratory Manual*, Elsevier, New York, 1985). A host cell that comprises an isolated nucleic acid of the invention, preferably operably linked to at least one expression control sequence, is a "recombinant host cell".

In certain embodiments, cell lines may be selected through determining which cell lines have high expression levels and constitutively produce antigen binding proteins with BCMA binding properties. In another embodiment, a cell line from the B cell lineage that does not make its own antibody but has a capacity to make and secrete a heterologous antibody can be selected.

Antibody Drug Conjugates (ADCs)

Embodiments of the invention include antibody drug conjugates (ADCs). As will be appreciated, antibodies conjugated to drugs, such as toxins or other molecules, are highly useful in the targeted killing of cells that express a molecule that can be specifically bound by a specific binding molecule, such as an antibody. BCMA is expressed at relatively higher levels in malignant plasma cells (multiple myeloma and smoldering myeloma) and in monoclonal gammopathy of unknown significance (MGUS) plasma cells than the levels observed on normal plasma cell, as shown in Example 1.

Generally, the ADC comprises a BCMA antigen binding protein described herein, preferably an antibody (more preferably a human monoclonal anti-huBCMA antibody, such as Ab-1, Ab-2 or Ab-3), that is conjugated to a chemotherapeutic agent, e.g., a cytotoxic agent, a cytostatic agent, a toxin, or a radioactive agent. A linker molecule can be used to conjugate the drug to the antibody. A variety of linkers and drugs useful in ADC technology are known in the art and may be used in embodiments of the present invention. (See US20090028856; US2009/0274713; US2007/0031402; WO2005/084390; WO2009/099728; U.S. Pat. No. 5,208, 020; U.S. Pat. No. 5,416,064; U.S. Pat. Nos. 5,475,092; 5,585,499; 6,436,931; 6,372,738; and 6,340,701, all incorporated herein by reference).

Figure 2:
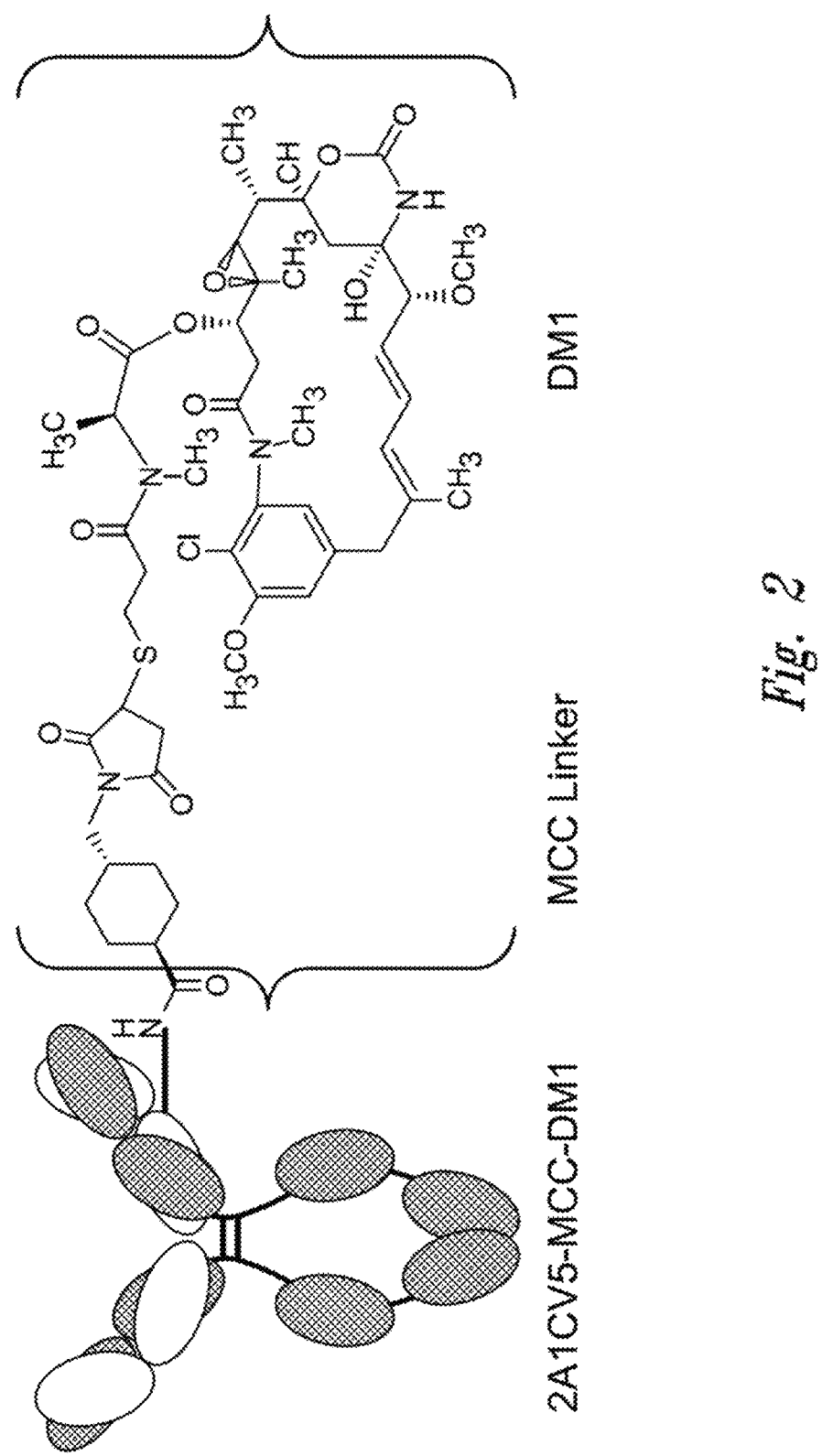
FIG. 2 is a schematic of one embodiment of an antibody drug conjugate showing the structures of an exemplary linker and toxin.

Embodiments include the BCMA antigen binding proteins comprising the sequences provided throughout the application conjugated to a drug, as defined herein. Preferred embodiments comprise a drug conjugated to an anti-huBCMA antibody as described herein. Preferred embodiments comprise a drug conjugated to an anti-huBCMA antibody as described herein using a linker. Preferred embodiments comprise a drug conjugated to an anti-huBCMA antibody as described herein using a linker, wherein the linkers are non-cleavable, such as MCC or Mal-dPEG4-NHS. Preferred embodiments comprise a drug conjugated to an anti-huBCMA antibody as described herein using a non-cleavable linker, wherein the linker is MCC (also referred to herein as SMCC, see FIG. 2). A preferred drug comprises maytansinoids, and in particular DM1 or DM4, as described below. Thus, in preferred embodiments, the anti-huBCMA antibody as described herein is conjugated to DM1 by a MCC linker. In particularly preferred embodiments, the anti-huBCMA antibody is Ab-1, Ab-2, or Ab-3 as variously described herein conjugated to DM1 by a MCC linker.

Linkers

In certain embodiments, the ADC comprises a linker made up of one or more linker components. Exemplary linker components include 6-maleimidocaproyl, maleimidopropanoyl, valine-citrulline, alanine-phenylalanine, p-aminobenzyloxycarbonyl, Mal-dPEG4-NHS (QuantaBiodesign), and those resulting from conjugation with linker reagents, including, but not limited to, N-succinimidyl 4-(2-pyridylthio) pentanoate ("SPP"), N-succinimidyl 4-(N-maleimidomethyl) cyclohexane-1 carboxylate ("SMCC," also referred to herein also as "MCC"), and N-succinimidyl (4-iodo-acetyl) aminobenzoate ("SIAB"). Linkers may be a "cleavable" linker or a "non-cleavable" linker (Ducry and Stump, Bioconjugate Chem. 2010, 21, 5-13; incorporated herein by reference in its entirety). Cleavable linkers are designed to release the drug when subjected to certain environment factors, e.g., when internalized into the target cell. Cleavable linkers include acid labile linkers, protease sensitive linkers, photolabile linkers, dimethyl linker or disulfide-containing linkers. Non-cleavable linkers tend to remain covalently associated with at least one amino acid of the antibody and the drug upon internalization by and degradation within the target cell. An exemplary non-cleavable linker is MCC (also referred to herein as SMCC). The most preferred non-cleavable linkers for the BCMA ADCs are N-succinimidyl 4-(N-maleimidomethyl) cyclohexane-1 carboxylate ("SMCC," also referred to herein also as "MCC") or Mal-dPEG4-NHS, as shown below.

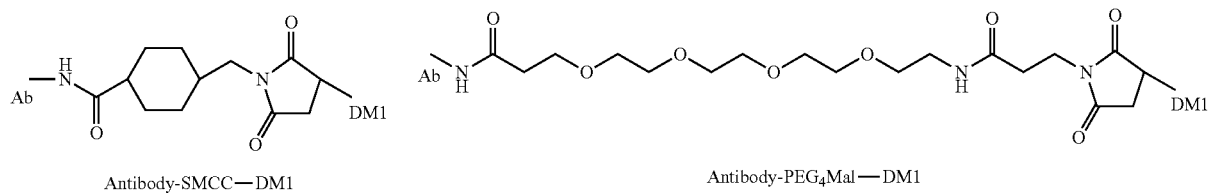

Antibody-SMCC—DM1                    Antibody-PEG$_4$Mal—DM1

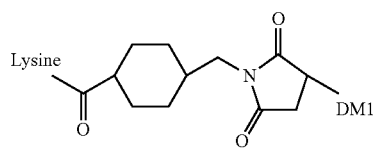

Lysine-SMCC—DM1

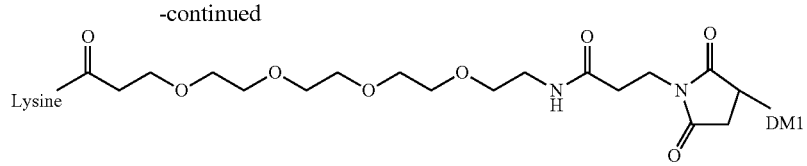

Lysine-PEG4Mal—DM1

Drugs

In certain embodiments, the antibody is conjugated to a chemotherapeutic agent. Examples of chemotherapeutic agents include alkylating agents, such as thiotepa and cyclophosphamide (CYTOXAN™); alkyl sulfonates such as busulfan, improsulfan and piposulfan; aziridines, such as benzodopa, carboquone, meturedopa, and uredopa; ethylenimines and methylamelamines including altretamine, triethylenemelamine, trietylenephosphoramide, triethylenethiophosphaoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics, such as the enediyne antibiotics (e.g. calicheamicin, especially calicheamicin .gamma1 and calicheamicin theta I, see, e.g., Angew Chem. Intl. Ed. Engl. 33:183-186 (1994); dynemicin, including dynemicin A; an esperamicin; as well as neocarzinostatin chromophore and related chromoprotein enediyne antiobiotic chromomophores), aclacinomysins, actinomycin, authramycin, azaserine, bleomycins, cactinomycin, carabicin, caminomycin, carzinophilin; chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, nitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites, such as methotrexate and 5-fluorouracil (5-FU); folic acid analogues, such as denopterin, methotrexate, pteropterin, trimetrexate; purine analogs, such as fludarabine, 6-mercaptopurine, thiamiprine, thioguanine; pyrimidine analogs such as, ancitabine, azacitidine, 6-azauridine, carmofur, cytarabine, dideoxyuridine, doxifluridine, enocitabine, floxuridine, 5-FU; androgens, such as calusterone, dromostanolone propionate, epitiostanol, mepitiostane, testolactone; anti-adrenals, such as aminoglutethimide, mitotane, trilostane; folic acid replenisher, such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidamine; maytansinoids, such as maytansine and ansamitocins; mitoguazone; mitoxantrone; mopidamol; nitracrine; pentostatin; phenamet; pirarubicin; podophyllinic acid; 2-ethylhydrazide; procarbazine; PSK®; razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL™, Bristol-Myers Squibb Oncology, Princeton, N.J.) and doxetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid; capecitabine; and pharmaceutically acceptable salts, acids or derivatives of any of the above. Also included in this definition are anti-hormonal agents that act to regulate or inhibit hormone action on tumors, such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens, such as flutamide, nilutamide, bicalutamide, leuprolide, and goserelin; siRNA and pharmaceutically acceptable salts, acids or derivatives of any of the above. Other chemotherapeutic agents that can be used with the present invention are disclosed in US Publication No. 20080171040 or US Publication No. 20080305044 and are incorporated in their entirety by reference.

There are a number of compounds that affect cellular microtubules that were obtained from natural sources-extracts, and semisynthetic and synthetic analogs that appear to possess potential as toxins for the generation of immunoconjugates. Such molecules and examples of drug products utilizing them, include the following: Colchicine-site Binders (Curacin), Combretastatins (AVE806, Combretastatin A-4 prodrug (CA4P), Oxi-4503), Cryptophycins (LY355703), Discodermolide, Dolastatin and Analogs (Auristatin PHE, Dolastatin 10, ILX-651, Symplostatin 1, TZT-1027), Epothilones (BMS-247550, BMS-310705, EP0906, KOS-862, ZK-EPO), Eleutherobin, FR182877, Halichondrin B (E7389), Halimide (NPI-2352 and NPI-2358), Hemiasterlins (HTI-286), Laulimalide, Maytansinoids ("DM1," "DM3" or "DM4") (Bivatuzumab mertansine, Cantuzumab mertansine, huN901-DM1/BB-10901TAP, MLN591DM1, My9-6-DM1, Trastuzumab-DM1), PC-SPES, Peloruside A, Resveratrol, S-allylmercaptocysteine (SAMC), Spongistatins, Vitilevuamide, Molecular Motor-Kinesins (SB-715992), Designed Colchicine-Site Binders (A-289099, A-293620/A-318315, ABT-751/E7010, D-24851/D-64131, ZD6126), Other Novel Spindle Poisons (2-Methoxyestradiol (2-ME2), Bezimidazole Carbamates (ANG 600 series, Mebendazole), CP248/CP461, HMN-214, R440, SDX-103, T67/T607). Further, additional marine derived toxins are reviewed in Mayer, A. M. S. Marine Pharmacology in 1998: Antitumor and Cytotoxic Compounds. The Pharmacologist. 41(4):159-164 (1999).

In preferred embodiments, the BCMA ADC comprises an antibody as described herein conjugated to one or more maytansinoid molecules, which are mitotic inhibitors that act by inhibiting tubulin polymerization. Maytansinoids, including various modifications, are described in U.S. Pat. Nos. 3,896,111; 4,151,042; 4,137,230; 4,248,870; 4,256,746; 4,260,608; 4,265,814; 4,294,757; 4,307,016; 4,308,268; 4,309,428; 4,313,946; 4,315,929; 4,317,821; 4,322,348; 4,331,598; 4,361,650; 4,364,866; 4,424,219; 4,450,254; 4,362,663; 4,371,533; and WO 2009/099728. Maytansinoid drug moieties may be isolated from natural sources, produced using recombinant technology, or prepared synthetically. Exemplary maytansinoids include C-19-dechloro (U.S. Pat. No. 4,256,746), C-20-hydroxy (or C-20-demethyl)+/−C-19-dechloro (U.S. Pat. Nos. 4,307,016 and 4,361,650), C-20-demethoxy (or C-20-acyloxy (—OCOR), +/−dechrolo (U.S. Pat. No. 4,294,757), C-9-SH (U.S. Pat. No. 4,424,219), C-14-alkoxymethyl (demethoxy/CH2OR) (U.S. Pat. No. 4,331,598), C-14-hydroxymethyl or acyloxymethyl (CH2OH or CH2OAc) (U.S. Pat. No. 4,450,254), C-15-hydroxy/acyloxy (U.S. Pat. No. 4,364,866), C-15-methoxy (U.S. Pat. Nos. 4,313,946 and 4,315,929), C-18-N-demethyl (U.S. Pat. Nos. 4,362,663 and 4,322,348), and 4,5-deoxy (U.S. Pat. No. 4,371,533). Various positions on maytansinoid compounds may be used as the linkage position, depending upon the type of link desired. For example, for forming an ester linkage, the C-3 position having a hydroxyl group, the C-14 position modified with hydrozymethyl, the C-15 position modified with a hydroxyl a group, and the C-20 position having a hydroxyl group are all suitable (U.S. Pat. No. 5,208,020, RE39151, and U.S. Pat. No. 6,913,748; US Patent Appl. Pub. Nos. 20060167245 and 20070037972, and WO 2009099728).

Preferred maytansinoids include those known in the art as DM1, DM3, and DM4 (US Pat. Appl. Pub. Nos. 2009030924 and 20050276812, incorporated herein by reference). Ansamitocin P-3 is synthetically altered to produce the warhead DM1. DM1 is reported to bind to tubulin in the vinca alkaloid binding site and to inhibit tubulin polymerization.

ADCs containing maytansinoids, methods of making such ADCs, and their therapeutic use are disclosed in U.S. Pat. Nos. 5,208,020 and 5,416,064, US Pat. Appl. Pub. No. 20050276812, and WO 2009099728 (all incorporated by reference herein). Linkers that are useful for making maytansinoid ADCs are know in the art (U.S. Pat. No. 5,208,020 and US Pat. Appl. Pub. Nos. 2005016993 and 20090274713; all incorporated herein by reference). Maytansinoid ADCs comprising an SMCC linker may be prepared as disclosed in US Pat. Publ. No. 2005/0276812.

Embodiments of the present invention include Ab-1-MCC-DM1, Ab-2-MCC-DM1, Ab-3-MCC-DM1, Ab-4-MCC-DM1, Ab-5-MCC-DM1, Ab-6-MCC-DM1, Ab-7-MCC-DM1, Ab-8-MCC-DM1, Ab-9-MCC-DM1, Ab-10-MCC-DM1, Ab-11-MCC-DM1, Ab-12-MCC-DM1, Ab-13-MCC-DM1, Ab-14-MCC-DM1, Ab-15-MCC-DM1, Ab-16-MCC-DM1, and Ab-17-MCC-DM1.

Drug Loading

A major drawback with existing antibody-drug conjugates is their inability to deliver a sufficient concentration of drug to the target site because of the limited number of targeted antigens and the relatively moderate cytotoxicity of cancerostatic drugs like methotrexate, daunorubicin and vincristine. In order to achieve significant cytotoxicity, linkage of a large number of drug molecules either directly to the antibody or through a polymeric carrier molecule becomes necessary. However such heavily modified antibodies often display impaired binding to the target antigen and fast in vivo clearance from the blood stream.

Current methods of conjugation of maytansinoids with cell binding agents (such as antibodies) are well-known in the art and may be used to create the BCMA ADCs. Conjugation methods may involve two reaction steps, as described in U.S. Pat. No. 5,208,020. A one-step process for conjugation of maytansinoids may be used to create the BCMA ADCs and is described in U.S. Pat. No. 6,441,163. Maytansinoid-based immunotoxin technology is available from ImmunoGen Corporation (Cambridge, Mass.).

The process of conjugating maytansinoids (e.g., DM1) to a BCMA antibody as described herein will produce a composition comprising a population of maytansinoids (e.g., DM1)-conjugated antibodies having a range of maytansinoids (e.g., DM1) molecules per antibody (a drug-antibody ratio, or DAR). A BCMA ADC may have 1 to 20 chemotherapeutic agents per antibody. Compositions of BCMA ADCs may be characterized by the average number of drug moieties per antibody molecule in the composition. The average number of drug moieties may be determined by conventional means such as mass spectrometry, immunoassay, and HPLC (e.g., see EXAMPLE 7). In some instances, a homogeneous BCMA ADC population may be separated and purified by means of reverse phase HPLC or electrophoresis. Thus, pharmaceutical BCMA ADC compositions may contain a heterogeneous or homogeneous population of antibodies linked to 1, 2, 3, 4, 5, 6, 7 or more drug moieties. Embodiments of the invention include compositions comprising an average number of maytansinoids (e.g., DM1) molecules per BCMA ADC is between 1 and 10, between 2 and 7, or preferably between 3 and 5. In preferred embodiments, the composition of a BCMA ADC has an average number of maytansinoids (e.g., DM1) molecules per BCMA ADC of about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, or about 5.0. Such a composition may contain a therapeutically effective amount of the BCMA ADC and may be lyophilized. In particularly preferred embodiments, the BCMA ADC comprises antibody Ab-1, Ab-2, or Ab-3, as variously described herein, conjugated to DM1 by a MCC linker at the ratios described above.

Aspects of the invention include isolated monoclonal antibodies comprising the six CDRs of Ab-1, wherein said antibody further comprises a linker and a drug. Aspects of the invention include isolated monoclonal antibodies comprising the six CDRs of Ab-2, wherein said antibody further comprises a linker and a drug. Aspects of the invention include isolated monoclonal antibodies comprising the six CDRs of Ab-3, wherein said antibody further comprises a linker and a drug. Aspects of the invention include isolated monoclonal antibodies comprising the six CDRs of Ab-4, wherein said antibody further comprises a linker and a drug. Aspects of the invention include isolated monoclonal antibodies comprising the six CDRs of Ab-5, wherein said antibody further comprises a linker and a drug. Aspects of the invention include isolated monoclonal antibodies comprising the six CDRs of Ab-6, wherein said antibody further comprises a linker and a drug. Aspects of the invention include isolated monoclonal antibodies comprising the six CDRs of Ab-7, wherein said antibody further comprises a linker and a drug. Aspects of the invention include isolated monoclonal antibodies comprising the six CDRs of Ab-8, wherein said antibody further comprises a linker and a drug. Aspects of the invention include isolated monoclonal antibodies comprising the six CDRs of Ab-9, wherein said antibody further comprises a linker and a drug. Aspects of the invention include isolated monoclonal antibodies comprising the six CDRs of Ab-10, wherein said antibody further comprises a linker and a drug. Aspects of the invention include isolated monoclonal antibodies comprising the six CDRs of Ab-11, wherein said antibody further comprises a linker and a drug. Aspects of the invention include isolated monoclonal antibodies comprising the six CDRs of Ab-12, wherein said antibody further comprises a linker and a drug. Aspects of the invention include isolated monoclonal antibodies comprising the six CDRs of Ab-13, wherein said antibody further comprises a linker and a drug. Aspects of the invention include isolated monoclonal antibodies comprising the six CDRs of Ab-14, wherein said antibody further comprises a linker and a drug. Aspects of the invention include isolated monoclonal antibodies comprising the six CDRs of Ab-15, wherein said antibody further comprises a linker and a drug. Aspects of the invention include isolated monoclonal antibodies comprising the six CDRs of Ab-16, wherein said antibody further comprises a linker and a drug. Aspects of the invention include isolated monoclonal antibodies comprising the six CDRs of Ab-17, wherein said antibody further comprises a linker and a drug. Aspects of the aforementioned embodiments include human monoclonal antibodies, human monoclonal IgG antibodies, and human monoclonal IgG1 antibodies.

Aspects of the invention include isolated monoclonal antibodies comprising the six CDRs of Ab-1 as determined by any one of the AHo, Kabat, or Clothia numbering systems, wherein said antibody further comprises a linker and a drug. Aspects of the invention include isolated monoclonal antibodies comprising the six CDRs of Ab-2 as determined by any one of the AHo, Kabat, or Clothia numbering systems, wherein said antibody further comprises a linker and a drug. Aspects of the invention include isolated monoclonal antibodies comprising the six CDRs of Ab-3 as determined by any one of the AHo, Kabat, or Clothia numbering systems, wherein said antibody further comprises a linker and a drug. Aspects of the invention include isolated monoclonal antibodies comprising the six CDRs of Ab-4 as determined by any one of the AHo, Kabat, or Clothia numbering systems, wherein said antibody further comprises a linker and a drug. Aspects of the invention include isolated monoclonal antibodies comprising the six CDRs of Ab-5 as determined by any one of the AHo, Kabat, or Clothia numbering systems, wherein said antibody further comprises a linker and a drug. Aspects of the invention include isolated monoclonal antibodies comprising the six CDRs of Ab-6 as determined by any one of the AHo, Kabat, or Clothia numbering systems, wherein said antibody further comprises a linker and a drug. Aspects of the invention include isolated monoclonal antibodies comprising the six CDRs of Ab-7 as determined by any one of the AHo, Kabat, or Clothia numbering systems, wherein said antibody further comprises a linker and a drug. Aspects of the invention include isolated monoclonal antibodies comprising the six CDRs of Ab-8 as determined by any one of the AHo, Kabat, or Clothia numbering systems, wherein said antibody further comprises a linker and a drug. Aspects of the invention include isolated monoclonal antibodies comprising the six CDRs of Ab-9 as determined by any one of the AHo, Kabat, or Clothia numbering systems, wherein said antibody further comprises a linker and a drug. Aspects of the invention include isolated monoclonal antibodies comprising the six CDRs of Ab-10 as determined by any one of the AHo, Kabat, or Clothia numbering systems, wherein said antibody further comprises a linker and a drug. Aspects of the invention include isolated monoclonal antibodies comprising the six CDRs of Ab-11 as determined by any one of the AHo, Kabat, or Clothia numbering systems, wherein said antibody further comprises a linker and a drug. Aspects of the invention include isolated monoclonal antibodies comprising the six CDRs of Ab-12 as determined by any one of the AHo, Kabat, or Clothia numbering systems, wherein said antibody further comprises a linker and a drug. Aspects of the invention include isolated monoclonal antibodies comprising the six CDRs of Ab-13 as determined by any one of the AHo, Kabat, or Clothia numbering systems, wherein said antibody further comprises a linker and a drug. Aspects of the invention include isolated monoclonal antibodies comprising the six CDRs of Ab-14 as determined by any one of the AHo, Kabat, or Clothia numbering systems, wherein said antibody further comprises a linker and a drug. Aspects of the invention include isolated monoclonal antibodies comprising the six CDRs of Ab-15 as determined by any one of the AHo, Kabat, or Clothia numbering systems, wherein said antibody further comprises a linker and a drug. Aspects of the invention include isolated monoclonal antibodies comprising the six CDRs of Ab-16 as determined by any one of the AHo, Kabat, or Clothia numbering systems, wherein said antibody further comprises a linker and a drug. Aspects of the invention include isolated monoclonal antibodies comprising the six CDRs of Ab-17 as determined by any one of the AHo, Kabat, or Clothia numbering systems, wherein said antibody further comprises a linker and a drug. Aspects of the aforementioned embodiments include human monoclonal antibodies, human monoclonal IgG antibodies, and human monoclonal IgG1 antibodies.

Aspects of the invention include isolated monoclonal antibodies comprising the six CDRs of Ab-1, specifically Vh-CDR1 (SEQ ID NO:4), Vh-CDR2 (SEQ ID NO:5), Vh-CDR3 (SEQ ID NO:6), Vl-CDR1 (SEQ ID NO:106), Vl-CDR2 (SEQ ID NO:107), and Vl-CDR3 (SEQ ID NO:108), wherein said antibody further comprises a linker and a drug. Aspects of the invention include isolated monoclonal antibodies comprising the six CDRs of Ab-2, specifically Vh-CDR1 (SEQ ID NO:10), Vh-CDR2 (SEQ ID NO:11), Vh-CDR3 (SEQ ID NO:12), Vl-CDR1 (SEQ ID NO:112), Vl-CDR2 (SEQ ID NO:113), and Vl-CDR3 (SEQ ID NO:114), wherein said antibody further comprises a linker and a drug. Aspects of the invention include isolated monoclonal antibodies comprising the six CDRs of Ab-3, specifically Vh-CDR1 (SEQ ID NO:16), Vh-CDR2 (SEQ ID NO:17), Vh-CDR3 (SEQ ID NO:18), Vl-CDR1 (SEQ ID NO:118), Vl-CDR2 (SEQ ID NO:119), and Vl-CDR3 (SEQ ID NO:120), wherein said antibody further comprises a linker and a drug. Aspects of the invention include isolated monoclonal antibodies comprising the six CDRs of Ab-4, specifically Vh-CDR1 (SEQ ID NO:22), Vh-CDR2 (SEQ ID NO:23), Vh-CDR3 (SEQ ID NO:24), Vl-CDR1 (SEQ ID NO:124), Vl-CDR2 (SEQ ID NO:125), and Vl-CDR3 (SEQ ID NO:126), wherein said antibody further comprises a linker and a drug. Aspects of the invention include isolated monoclonal antibodies comprising the six CDRs of Ab-5, specifically Vh-CDR1 (SEQ ID NO:28), Vh-CDR2 (SEQ ID NO:29), Vh-CDR3 (SEQ ID NO:30), Vl-CDR1 (SEQ ID NO:130), Vl-CDR2 (SEQ ID NO:131), and Vl-CDR3 (SEQ ID NO:132), wherein said antibody further comprises a linker and a drug. Aspects of the invention include isolated monoclonal antibodies comprising the six CDRs of Ab-6, specifically Vh-CDR1 (SEQ ID NO:34), Vh-CDR2 (SEQ ID NO:35), Vh-CDR3 (SEQ ID NO:36), Vl-CDR1 (SEQ ID NO:136), Vl-CDR2 (SEQ ID NO:137), and Vl-CDR3 (SEQ ID NO:138), wherein said antibody further comprises a linker and a drug. Aspects of the invention include isolated monoclonal antibodies comprising the six CDRs of Ab-7, specifically Vh-CDR1 (SEQ ID NO:40), Vh-CDR2 (SEQ ID NO:41), Vh-CDR3 (SEQ ID NO:42), Vl-CDR1 (SEQ ID NO:142), Vl-CDR2 (SEQ ID NO:143), and Vl-CDR3 (SEQ ID NO:144), wherein said antibody further comprises a linker and a drug. Aspects of the invention include isolated monoclonal antibodies comprising the six CDRs of Ab-8, specifically Vh-CDR1 (SEQ ID NO:46), Vh-CDR2 (SEQ ID NO:47), Vh-CDR3 (SEQ ID NO:48), Vl-CDR1 (SEQ ID NO:148), Vl-CDR2 (SEQ ID NO:149), and Vl-CDR3 (SEQ ID NO:150), wherein said antibody further comprises a linker and a drug. Aspects of the invention include isolated monoclonal antibodies comprising the six CDRs of Ab-9, specifically Vh-CDR1 (SEQ ID NO:52), Vh-CDR2 (SEQ ID NO:53), Vh-CDR3 (SEQ ID NO:54), Vl-CDR1 (SEQ ID NO:154), Vl-CDR2 (SEQ ID NO:155), and Vl-CDR3 (SEQ ID NO:156), wherein said antibody further comprises a linker and a drug. Aspects of the invention include isolated monoclonal antibodies comprising the six CDRs of Ab-10, specifically Vh-CDR1 (SEQ ID NO:58), Vh-CDR2 (SEQ ID NO:59), Vh-CDR3 (SEQ ID NO:60), Vl-CDR1 (SEQ ID NO:160), Vl-CDR2 (SEQ ID NO:161), and Vl-CDR3 (SEQ ID NO:162), wherein said antibody further comprises a linker and a drug. Aspects of the invention include isolated monoclonal antibodies comprising the six CDRs of Ab-11, specifically Vh-CDR1 (SEQ ID NO:64), Vh-CDR2 (SEQ ID NO:65), Vh-CDR3 (SEQ ID NO:66), Vl-CDR1 (SEQ ID NO:166), Vl-CDR2 (SEQ ID NO:167), and Vl-CDR3 (SEQ ID NO:168), wherein said antibody further comprises a linker and a drug. Aspects of the invention include isolated monoclonal antibodies comprising the six CDRs of Ab-12, specifically Vh-CDR1 (SEQ ID NO:70), Vh-CDR2 (SEQ ID NO:71), Vh-CDR3 (SEQ ID NO:72), Vl-CDR1 (SEQ ID NO:172), Vl-CDR2 (SEQ ID NO:173), and Vl-CDR3 (SEQ ID NO:174), wherein said antibody further comprises a linker and a drug. Aspects of the invention include isolated monoclonal antibodies comprising the six CDRs of Ab-13, specifically Vh-CDR1 (SEQ ID NO:76), Vh-CDR2 (SEQ ID NO:77), Vh-CDR3 (SEQ ID NO:78), Vl-CDR1 (SEQ ID NO:178), Vl-CDR2 (SEQ ID NO:179), and Vl-CDR3 (SEQ ID NO:180), wherein said antibody further comprises a linker and a drug. Aspects of the invention include isolated monoclonal antibodies comprising the six CDRs of Ab-14, specifically Vh-CDR1 (SEQ ID NO:82), Vh-CDR2 (SEQ ID NO:83), Vh-CDR3 (SEQ ID NO:84), Vl-CDR1 (SEQ ID NO:184), Vl-CDR2 (SEQ ID NO:185), and Vl-CDR3 (SEQ ID NO:186), wherein said antibody further comprises a linker and a drug. Aspects of the invention include isolated monoclonal antibodies comprising the six CDRs of Ab-15, specifically Vh-CDR1 (SEQ ID NO:88), Vh-CDR2 (SEQ ID NO:89), Vh-CDR3 (SEQ ID NO:90), Vl-CDR1 (SEQ ID NO:190), Vl-CDR2 (SEQ ID NO:191), and Vl-CDR3 (SEQ ID NO:192), wherein said antibody further comprises a linker and a drug. Aspects of the invention include isolated monoclonal antibodies comprising the six CDRs of Ab-16, specifically Vh-CDR1 (SEQ ID NO:94), Vh-CDR2 (SEQ ID NO:95), Vh-CDR3 (SEQ ID NO:96), Vl-CDR1 (SEQ ID NO:196), Vl-CDR2 (SEQ ID NO:197), and Vl-CDR3 (SEQ ID NO:198), wherein said antibody further comprises a linker and a drug. Aspects of the invention include isolated monoclonal antibodies comprising the six CDRs of Ab-17, specifically Vh-CDR1 (SEQ ID NO:100), Vh-CDR2 (SEQ ID NO:101), Vh-CDR3 (SEQ ID NO:102), Vl-CDR1 (SEQ ID NO:202), Vl-CDR2 (SEQ ID NO:203), and Vl-CDR3 (SEQ ID NO:204), wherein said antibody further comprises a linker and a drug. Aspects of the aforementioned embodiments include human monoclonal antibodies, human monoclonal IgG antibodies, and human monoclonal IgG1 antibodies. Aspects of the invention include fragments, derivatives, muteins, and variants of the aforementioned.

Aspects of the invention include isolated monoclonal antibodies comprising an Ab-1Vl (SEQ ID NO:240) and an Ab-1Vh (SEQ ID NO:206) domain, wherein said antibody further comprises a linker and a drug. Aspects of the invention include isolated monoclonal antibodies comprising an Ab-2Vl (SEQ ID NO:242) and an Ab-2Vh (SEQ ID NO:208) domain, wherein said antibody further comprises a linker and a drug. Aspects of the invention include isolated monoclonal antibodies comprising an Ab-3Vl (SEQ ID NO:244) and an Ab-3Vh (SEQ ID NO:210) domain, wherein said antibody further comprises a linker and a drug. Aspects of the invention include isolated monoclonal antibodies comprising an Ab-4Vl (SEQ ID NO:246) and an Ab-4Vh (SEQ ID NO:212) domain, wherein said antibody further comprises a linker and a drug. Aspects of the invention include isolated monoclonal antibodies comprising an Ab-5Vl (SEQ ID NO:248) and an Ab-5Vh (SEQ ID NO:214) domain, wherein said antibody further comprises a linker and a drug. Aspects of the invention include isolated monoclonal antibodies comprising an Ab-6Vl (SEQ ID NO:250) and an Ab-6Vh (SEQ ID NO:216) domain, wherein said antibody further comprises a linker and a drug. Aspects of the invention include isolated monoclonal antibodies comprising an Ab-7Vl (SEQ ID NO:252) and an Ab-7Vh (SEQ ID NO:218) domain, wherein said antibody further comprises a linker and a drug. Aspects of the invention include isolated monoclonal antibodies comprising an Ab-8Vl (SEQ ID NO:254) and an Ab-8Vh (SEQ ID NO:220) domain, wherein said antibody further comprises a linker and a drug. Aspects of the invention include isolated monoclonal antibodies comprising an Ab-9Vl (SEQ ID NO:256) and an Ab-9Vh (SEQ ID NO:222) domain, wherein said antibody further comprises a linker and a drug. Aspects of the invention include isolated monoclonal antibodies comprising an Ab-10Vl (SEQ ID NO:258) and an Ab-10Vh (SEQ ID NO:224) domain, wherein said antibody further comprises a linker and a drug. Aspects of the invention include isolated monoclonal antibodies comprising an Ab-11Vl (SEQ ID NO:260) and an Ab-11Vh (SEQ ID NO:226) domain, wherein said antibody further comprises a linker and a drug. Aspects of the invention include isolated monoclonal antibodies comprising an Ab-12Vl (SEQ ID NO:262) and an Ab-12Vh (SEQ ID NO:228) domain, wherein said antibody further comprises a linker and a drug. Aspects of the invention include isolated monoclonal antibodies comprising an Ab-13Vl (SEQ ID NO:264) and an Ab-13Vh (SEQ ID NO:230) domain, wherein said antibody further comprises a linker and a drug. Aspects of the invention include isolated monoclonal antibodies comprising an Ab-14Vl (SEQ ID NO:266) and an Ab-14Vh (SEQ ID NO:232) domain, wherein said antibody further comprises a linker and a drug. Aspects of the invention include isolated monoclonal antibodies comprising an Ab-15Vl (SEQ ID NO:268) and an Ab-15Vh (SEQ ID NO:234) domain, wherein said antibody further comprises a linker and a drug. Aspects of the invention include isolated monoclonal antibodies comprising an Ab-16Vl (SEQ ID NO:270) and an Ab-16Vh (SEQ ID NO:236) domain, wherein said antibody further comprises a linker and a drug. Aspects of the invention include isolated monoclonal antibodies comprising an Ab-17Vl (SEQ ID NO:272) and an Ab-17Vh (SEQ ID NO:238) domain, wherein said antibody further comprises a linker and a drug. Aspects of the aforementioned embodiments include human monoclonal antibodies, human monoclonal IgG antibodies, and human monoclonal IgG1 antibodies. Aspects of the invention include fragments, derivatives, muteins, and variants of the aforementioned.

Aspects of the invention include isolated monoclonal antibodies comprising an Ab-1 light chain (SEQ ID NO:280) and Ab-1 heavy chain (SEQ ID NO:274), wherein said antibody further comprises a linker and a drug. Aspects of the invention include isolated monoclonal antibodies comprising an Ab-2 light chain (SEQ ID NO:282) and an Ab-2 heavy chain (SEQ ID NO:276), wherein said antibody further comprises a linker and a drug. Aspects of the invention include isolated monoclonal antibodies comprising an Ab-3 light chain (SEQ ID NO:284) and an Ab-3 heavy chain (SEQ ID NO:278), wherein said antibody further comprises a linker and a drug. Aspects of the invention include isolated monoclonal antibodies comprising two Ab-1 light chains (SEQ ID NO:280) and two Ab-1 heavy chains (SEQ ID NO:274), wherein said antibody further comprises a linker and a drug. Aspects of the invention include isolated monoclonal antibodies comprising two Ab-2 light chains (SEQ ID NO:282) and two Ab-2 heavy chains (SEQ ID NO:276), wherein said antibody further comprises a linker and a drug. Aspects of the invention include isolated monoclonal antibodies comprising two Ab-3 light chains (SEQ ID NO:284) and two Ab-3 heavy chains (SEQ ID NO:278), wherein said antibody further comprises a linker and a drug. Aspects of the aforementioned embodiments include human monoclonal antibodies, human monoclonal IgG antibodies, and human monoclonal IgG1 antibodies. Aspects of the invention include fragments, derivatives, muteins, and variants of the aforementioned.

Aspects of the invention include isolated monoclonal antibodies comprising the six CDRs of Ab-1, wherein the CDRs include no more than one, two, three, four, five, or six amino acid additions, deletions, or substitutions of Vh-CDR1 (SEQ ID NO:4), Vh-CDR2 (SEQ ID NO:5), Vh-CDR3 (SEQ ID NO:6), Vl-CDR1 (SEQ ID NO:106), Vl-CDR2 (SEQ ID NO:107), and Vl-CDR3 (SEQ ID NO:108), wherein said antibody further comprises a linker and a drug. Aspects of the invention include isolated monoclonal antibodies comprising the six CDRs of Ab-2, wherein the CDRs include no more than one, two, three, four, five, or six amino acid additions, deletions, or substitutions of Vh-CDR1 (SEQ ID NO:10), Vh-CDR2 (SEQ ID NO:11), Vh-CDR3 (SEQ ID NO:12), Vl-CDR1 (SEQ ID NO:112), Vl-CDR2 (SEQ ID NO:113), and Vl-CDR3 (SEQ ID NO:114), wherein said antibody further comprises a linker and a drug. Aspects of the invention include isolated monoclonal antibodies comprising the six CDRs of Ab-3, wherein the CDRs include no more than one, two, three, four, five, or six amino acid additions, deletions, or substitutions of Vh-CDR1 (SEQ ID NO:16), Vh-CDR2 (SEQ ID NO:17), Vh-CDR3 (SEQ ID NO:18), Vl-CDR1 (SEQ ID NO:118), Vl-CDR2 (SEQ ID NO:119), and Vl-CDR3 (SEQ ID NO:120), wherein said antibody further comprises a linker and a drug. Aspects of the invention include isolated monoclonal antibodies comprising the six CDRs of Ab-4, wherein the CDRs include no more than one, two, three, four, five, or six amino acid additions, deletions, or substitutions of Vh-CDR1 (SEQ ID NO:22), Vh-CDR2 (SEQ ID NO:23), Vh-CDR3 (SEQ ID NO:24), Vl-CDR1 (SEQ ID NO:124), Vl-CDR2 (SEQ ID NO:125), and Vl-CDR3 (SEQ ID NO:126), wherein said antibody further comprises a linker and a drug. Aspects of the invention include isolated monoclonal antibodies comprising the six CDRs of Ab-5, wherein the CDRs include no more than one, two, three, four, five, or six amino acid additions, deletions, or substitutions of Vh-CDR1 (SEQ ID NO:28), Vh-CDR2 (SEQ ID NO:29), Vh-CDR3 (SEQ ID NO:30), Vl-CDR1 (SEQ ID NO:130), Vl-CDR2 (SEQ ID NO:131), and Vl-CDR3 (SEQ ID NO:132), wherein said antibody further comprises a linker and a drug. Aspects of the invention include isolated monoclonal antibodies comprising the six CDRs of Ab-6, wherein the CDRs include no more than one, two, three, four, five, or six amino acid additions, deletions, or substitutions of Vh-CDR1 (SEQ ID NO:34), Vh-CDR2 (SEQ ID NO:35), Vh-CDR3 (SEQ ID NO:36), Vl-CDR1 (SEQ ID NO:136), Vl-CDR2 (SEQ ID NO:137), and Vl-CDR3 (SEQ ID NO:138), wherein said antibody further comprises a linker and a drug. Aspects of the invention include isolated monoclonal antibodies comprising the six CDRs of Ab-7, wherein the CDRs include no more than one, two, three, four, five, or six amino acid additions, deletions, or substitutions of Vh-CDR1 (SEQ ID NO:40), Vh-CDR2 (SEQ ID NO:41), Vh-CDR3 (SEQ ID NO:42), Vl-CDR1 (SEQ ID NO:142), Vl-CDR2 (SEQ ID NO:143), and Vl-CDR3 (SEQ ID NO:144), wherein said antibody further comprises a linker and a drug. Aspects of the invention include isolated monoclonal antibodies comprising the six CDRs of Ab-8, wherein the CDRs include no more than one, two, three, four, five, or six amino acid additions, deletions, or substitutions of Vh-CDR1 (SEQ ID NO:46), Vh-CDR2 (SEQ ID NO:47), Vh-CDR3 (SEQ ID NO:48), Vl-CDR1 (SEQ ID NO:148), Vl-CDR2 (SEQ ID NO:149), and Vl-CDR3 (SEQ ID NO:150), wherein said antibody further comprises a linker and a drug. Aspects of the invention include isolated monoclonal antibodies comprising the six CDRs of Ab-9, wherein the CDRs include no more than one, two, three, four, five, or six amino acid additions, deletions, or substitutions of Vh-CDR1 (SEQ ID NO:52), Vh-CDR2 (SEQ ID NO:53), Vh-CDR3 (SEQ ID NO:54), Vl-CDR1 (SEQ ID NO:154), Vl-CDR2 (SEQ ID NO:155), and Vl-CDR3 (SEQ ID NO:156), wherein said antibody further comprises a linker and a drug. Aspects of the invention include isolated monoclonal antibodies comprising the six CDRs of Ab-10, wherein the CDRs include no more than one, two, three, four, five, or six amino acid additions, deletions, or substitutions of Vh-CDR1 (SEQ ID NO:58), Vh-CDR2 (SEQ ID NO:59), Vh-CDR3 (SEQ ID NO:60), Vl-CDR1 (SEQ ID NO:160), Vl-CDR2 (SEQ ID NO:161), and Vl-CDR3 (SEQ ID NO:162), wherein said antibody further comprises a linker and a drug. Aspects of the invention include isolated monoclonal antibodies comprising the six CDRs of Ab-11, wherein the CDRs include no more than one, two, three, four, five, or six amino acid additions, deletions, or substitutions of Vh-CDR1 (SEQ ID NO:64), Vh-CDR2 (SEQ ID NO:65), Vh-CDR3 (SEQ ID NO:66), Vl-CDR1 (SEQ ID NO:166), Vl-CDR2 (SEQ ID NO:167), and Vl-CDR3 (SEQ ID NO:168), wherein said antibody further comprises a linker and a drug. Aspects of the invention include isolated monoclonal antibodies comprising the six CDRs of Ab-12, wherein the CDRs include no more than one, two, three, four, five, or six amino acid additions, deletions, or substitutions of Vh-CDR1 (SEQ ID NO:70), Vh-CDR2 (SEQ ID NO:71), Vh-CDR3 (SEQ ID NO:72), Vl-CDR1 (SEQ ID NO:172), Vl-CDR2 (SEQ ID NO:173), and Vl-CDR3 (SEQ ID NO:174), wherein said antibody further comprises a linker and a drug. Aspects of the invention include isolated monoclonal antibodies comprising the six CDRs of Ab-13, wherein the CDRs include no more than one, two, three, four, five, or six amino acid additions, deletions, or substitutions of Vh-CDR1 (SEQ ID NO:76), Vh-CDR2 (SEQ ID NO:77), Vh-CDR3 (SEQ ID NO:78), Vl-CDR1 (SEQ ID NO:178), Vl-CDR2 (SEQ ID NO:179), and Vl-CDR3 (SEQ ID NO:180), wherein said antibody further comprises a linker and a drug. Aspects of the invention include isolated monoclonal antibodies comprising the six CDRs of Ab-14, wherein the CDRs include no more than one, two, three, four, five, or six amino acid additions, deletions, or substitutions of Vh-CDR1 (SEQ ID NO:82), Vh-CDR2 (SEQ ID NO:83), Vh-CDR3 (SEQ ID NO:84), Vl-CDR1 (SEQ ID NO:184), Vl-CDR2 (SEQ ID NO:185), and Vl-CDR3 (SEQ ID NO:186), wherein said antibody further comprises a linker and a drug. Aspects of the invention include isolated monoclonal antibodies comprising the six CDRs of Ab-15, wherein the CDRs include no more than one, two, three, four, five, or six amino acid additions, deletions, or substitutions of Vh-CDR1 (SEQ ID NO:88), Vh-CDR2 (SEQ ID NO:89), Vh-CDR3 (SEQ ID NO:90), Vl-CDR1 (SEQ ID NO:190), Vl-CDR2 (SEQ ID NO:191), and Vl-CDR3 (SEQ ID NO:192), wherein said antibody further comprises a linker and a drug. Aspects of the invention include isolated monoclonal antibodies comprising the six CDRs of Ab-16, wherein the CDRs include no more than one, two, three, four, five, or six amino acid additions, deletions, or substitutions of Vh-CDR1 (SEQ ID NO:94), Vh-CDR2 (SEQ ID NO:95), Vh-CDR3 (SEQ ID NO:96), Vl-CDR1 (SEQ ID NO:196), Vl-CDR2 (SEQ ID NO:197), and Vl-CDR3 (SEQ ID NO:198), wherein said antibody further comprises a linker and a drug. Aspects of the invention include isolated monoclonal antibodies comprising the six CDRs of Ab-17, wherein the CDRs include no more than one, two, three, four, five, or six amino acid additions, deletions, or substitutions of Vh-CDR1 (SEQ ID NO:100), Vh-CDR2 (SEQ ID NO:101), Vh-CDR3 (SEQ ID NO:102), Vl-CDR1 (SEQ ID NO:202), Vl-CDR2 (SEQ ID NO:203), and Vl-CDR3 (SEQ ID NO:204), wherein said antibody further comprises a linker and a drug. Aspects of the aforementioned embodiments include human monoclonal antibodies, human monoclonal IgG antibodies, and human monoclonal IgG1 antibodies.

Aspects of the invention include isolated monoclonal antibodies comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-1Vl (SEQ ID NO:240) and Ab-1Vh (SEQ ID NO:206), respectively, wherein said antibody further comprises a linker and a drug. Aspects of the invention include isolated monoclonal antibodies comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-2Vl (SEQ ID NO:242) and Ab-2Vh (SEQ ID NO:208), respectively, wherein said antibody further comprises a linker and a drug. Aspects of the invention include isolated monoclonal antibodies comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-3Vl (SEQ ID NO:244) and Ab-3Vh (SEQ ID NO:210), respectively, wherein said antibody further comprises a linker and a drug. Aspects of the invention include isolated monoclonal antibodies comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-4Vl (SEQ ID NO:246) and Ab-4Vh (SEQ ID NO:212), respectively, wherein said antibody further comprises a linker and a drug. Aspects of the invention include isolated monoclonal antibodies comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-5Vl (SEQ ID NO:248) and Ab-5Vh (SEQ ID NO:214), respectively, wherein said antibody further comprises a linker and a drug. Aspects of the invention include isolated monoclonal antibodies comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-6Vl (SEQ ID NO:250) and Ab-6Vh (SEQ ID NO:216), respectively, wherein said antibody further comprises a linker and a drug. Aspects of the invention include isolated monoclonal antibodies comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-7Vl (SEQ ID NO:252) and Ab-7Vh (SEQ ID NO:218), respectively, wherein said antibody further comprises a linker and a drug. Aspects of the invention include isolated monoclonal antibodies comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-8Vl (SEQ ID NO:254) and Ab-8Vh (SEQ ID NO:220), respectively, wherein said antibody further comprises a linker and a drug. Aspects of the invention include isolated monoclonal antibodies comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-9Vl (SEQ ID NO:256) and Ab-9Vh (SEQ ID NO:222), respectively, wherein said antibody further comprises a linker and a drug. Aspects of the invention include isolated monoclonal antibodies comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-10Vl (SEQ ID NO:258) and Ab-10Vh (SEQ ID NO:224), respectively, wherein said antibody further comprises a linker and a drug. Aspects of the invention include isolated monoclonal antibodies comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-11Vl (SEQ ID NO:260) and Ab-11Vh (SEQ ID NO:226), respectively, wherein said antibody further comprises a linker and a drug. Aspects of the invention include isolated monoclonal antibodies comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-12Vl (SEQ ID NO:262) and Ab-12Vh (SEQ ID NO:228), respectively, wherein said antibody further comprises a linker and a drug. Aspects of the invention include isolated monoclonal antibodies comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-13Vl (SEQ ID NO:264) and Ab-13Vh (SEQ ID NO:230), respectively, wherein said antibody further comprises a linker and a drug. Aspects of the invention include isolated monoclonal antibodies comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-14Vl (SEQ ID NO:266) and Ab-14Vh (SEQ ID NO:232), respectively, wherein said antibody further comprises a linker and a drug. Aspects of the invention include isolated monoclonal antibodies comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-15Vl (SEQ ID NO:268) and Ab-15Vh (SEQ ID NO:234), respectively, wherein said antibody further comprises a linker and a drug. Aspects of the invention include isolated monoclonal antibodies comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-16Vl (SEQ ID NO:270) and Ab-16Vh (SEQ ID NO:236), respectively, wherein said antibody further comprises a linker and a drug. Aspects of the invention include isolated monoclonal antibodies comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-17Vl (SEQ ID NO:272) and Ab-17Vh (SEQ ID NO:238), respectively, wherein said antibody further comprises a linker and a drug. Aspects of the aforementioned embodiments include human monoclonal antibodies, human monoclonal IgG antibodies, and human monoclonal IgG1 antibodies.

Aspects of the invention include isolated monoclonal antibodies that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-1 light chain (SEQ ID NO:280) and Ab-1 heavy chain (SEQ ID NO:274), wherein said antibody further comprises a linker and a drug. Aspects of the invention include isolated monoclonal antibodies that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-2 light chain (SEQ ID NO:282) and an Ab-2 heavy chain (SEQ ID NO:276), wherein said antibody further comprises a linker and a drug. Aspects of the invention include isolated monoclonal antibodies that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-3 light chain (SEQ ID NO:284) and an Ab-3 heavy chain (SEQ ID NO:278), wherein said antibody further comprises a linker and a drug. Aspects of the aforementioned embodiments include human monoclonal antibodies, human monoclonal IgG antibodies, and human monoclonal IgG1 antibodies.

Aspects of the invention include isolated monoclonal antibodies comprising the six CDRs of Ab-1, wherein said antibody further comprises a linker and a drug, and wherein said linker is MCC and said drug is a maytansinoid, such as DM1. Aspects of the invention include isolated monoclonal antibodies comprising the six CDRs of Ab-2, wherein said antibody further comprises a linker and a drug, and wherein said linker is MCC and said drug is a maytansinoid, such as DM1. Aspects of the invention include isolated monoclonal antibodies comprising the six CDRs of Ab-3, wherein said antibody further comprises a linker and a drug, and wherein said linker is MCC and said drug is a maytansinoid, such as DM1. Aspects of the invention include isolated monoclonal antibodies comprising the six CDRs of Ab-4, wherein said antibody further comprises a linker and a drug, and wherein said linker is MCC and said drug is a maytansinoid, such as DM1. Aspects of the invention include isolated monoclonal antibodies comprising the six CDRs of Ab-5, wherein said antibody further comprises a linker and a drug, and wherein said linker is MCC and said drug is a maytansinoid, such as DM1. Aspects of the invention include isolated monoclonal antibodies comprising the six CDRs of Ab-6, wherein said antibody further comprises a linker and a drug, and wherein said linker is MCC and said drug is a maytansinoid, such as DM1. Aspects of the invention include isolated monoclonal antibodies comprising the six CDRs of Ab-7, wherein said antibody further comprises a linker and a drug, and wherein said linker is MCC and said drug is a maytansinoid, such as DM1. Aspects of the invention include isolated monoclonal antibodies comprising the six CDRs of Ab-8, wherein said antibody further comprises a linker and a drug, and wherein said linker is MCC and said drug is a maytansinoid, such as DM1. Aspects of the invention include isolated monoclonal antibodies comprising the six CDRs of Ab-9, wherein said antibody further comprises a linker and a drug, and wherein said linker is MCC and said drug is a maytansinoid, such as DM1. Aspects of the invention include isolated monoclonal antibodies comprising the six CDRs of Ab-10, wherein said antibody further comprises a linker and a drug, and wherein said linker is MCC and said drug is a maytansinoid, such as DM1. Aspects of the invention include isolated monoclonal antibodies comprising the six CDRs of Ab-11, wherein said antibody further comprises a linker and a drug, and wherein said linker is MCC and said drug is a maytansinoid, such as DM1. Aspects of the invention include isolated monoclonal antibodies comprising the six CDRs of Ab-12, wherein said antibody further comprises a linker and a drug, and wherein said linker is MCC and said drug is a maytansinoid, such as DM1. Aspects of the invention include isolated monoclonal antibodies comprising the six CDRs of Ab-13, wherein said antibody further comprises a linker and a drug, and wherein said linker is MCC and said drug is a maytansinoid, such as DM1. Aspects of the invention include isolated monoclonal antibodies comprising the six CDRs of Ab-14, wherein said antibody further comprises a linker and a drug, and wherein said linker is MCC and said drug is a maytansinoid, such as DM1. Aspects of the invention include isolated monoclonal antibodies comprising the six CDRs of Ab-15, wherein said antibody further comprises a linker and a drug, and wherein said linker is MCC and said drug is a maytansinoid, such as DM1. Aspects of the invention include isolated monoclonal antibodies comprising the six CDRs of Ab-16, wherein said antibody further comprises a linker and a drug, and wherein said linker is MCC and said drug is a maytansinoid, such as DM1. Aspects of the invention include isolated monoclonal antibodies comprising the six CDRs of Ab-17, wherein said antibody further comprises a linker and a drug, and wherein said linker is MCC and said drug is a maytansinoid, such as DM1. Aspects of the aforementioned embodiments include human monoclonal antibodies, human monoclonal IgG antibodies, and human monoclonal IgG1 antibodies.

Aspects of the invention include isolated monoclonal antibodies comprising the six CDRs of Ab-1 as determined by any one of the AHo, Kabat, or Clothia numbering systems, wherein said antibody further comprises a linker and a drug, and wherein said linker is MCC and said drug is a maytansinoid, such as DM1. Aspects of the invention include isolated monoclonal antibodies comprising the six CDRs of Ab-2 as determined by any one of the AHo, Kabat, or Clothia numbering systems, wherein said antibody further comprises a linker and a drug, and wherein said linker is MCC and said drug is a maytansinoid, such as DM1. Aspects of the invention include isolated monoclonal antibodies comprising the six CDRs of Ab-3 as determined by any one of the AHo, Kabat, or Clothia numbering systems, wherein said antibody further comprises a linker and a drug, and wherein said linker is MCC and said drug is a maytansinoid, such as DM1. Aspects of the invention include isolated monoclonal antibodies comprising the six CDRs of Ab-4 as determined by any one of the AHo, Kabat, or Clothia numbering systems, wherein said antibody further comprises a linker and a drug, and wherein said linker is MCC and said drug is a maytansinoid, such as DM1. Aspects of the invention include isolated monoclonal antibodies comprising the six CDRs of Ab-5 as determined by any one of the AHo, Kabat, or Clothia numbering systems, wherein said antibody further comprises a linker and a drug, and wherein said linker is MCC and said drug is a maytansinoid, such as DM1. Aspects of the invention include isolated monoclonal antibodies comprising the six CDRs of Ab-6 as determined by any one of the AHo, Kabat, or Clothia numbering systems, wherein said antibody further comprises a linker and a drug, and wherein said linker is MCC and said drug is a maytansinoid, such as DM1. Aspects of the invention include isolated monoclonal antibodies comprising the six CDRs of Ab-7 as determined by any one of the AHo, Kabat, or Clothia numbering systems, wherein said antibody further comprises a linker and a drug, and wherein said linker is MCC and said drug is a maytansinoid, such as DM1. Aspects of the invention include isolated monoclonal antibodies comprising the six CDRs of Ab-8 as determined by any one of the AHo, Kabat, or Clothia numbering systems, wherein said antibody further comprises a linker and a drug, and wherein said linker is MCC and said drug is a maytansinoid, such as DM1. Aspects of the invention include isolated monoclonal antibodies comprising the six CDRs of Ab-9 as determined by any one of the AHo, Kabat, or Clothia numbering systems, wherein said antibody further comprises a linker and a drug, and wherein said linker is MCC and said drug is a maytansinoid, such as DM1. Aspects of the invention include isolated monoclonal antibodies comprising the six CDRs of Ab-10 as determined by any one of the AHo, Kabat, or Clothia numbering systems, wherein said antibody further comprises a linker and a drug, and wherein said linker is MCC and said drug is a maytansinoid, such as DM1. Aspects of the invention include isolated monoclonal antibodies comprising the six CDRs of Ab-11 as determined by any one of the AHo, Kabat, or Clothia numbering systems, wherein said antibody further comprises a linker and a drug, and wherein said linker is MCC and said drug is a maytansinoid, such as DM1. Aspects of the invention include isolated monoclonal antibodies comprising the six CDRs of Ab-12 as determined by any one of the AHo, Kabat, or Clothia numbering systems, wherein said antibody further comprises a linker and a drug, and wherein said linker is MCC and said drug is a maytansinoid, such as DM1. Aspects of the invention include isolated monoclonal antibodies comprising the six CDRs of Ab-13 as determined by any one of the AHo, Kabat, or Clothia numbering systems, wherein said antibody further comprises a linker and a drug, and wherein said linker is MCC and said drug is a maytansinoid, such as DM1. Aspects of the invention include isolated monoclonal antibodies comprising the six CDRs of Ab-14 as determined by any one of the AHo, Kabat, or Clothia numbering systems, wherein said antibody further comprises a linker and a drug, and wherein said linker is MCC and said drug is a maytansinoid, such as DM1. Aspects of the invention include isolated monoclonal antibodies comprising the six CDRs of Ab-15 as determined by any one of the AHo, Kabat, or Clothia numbering systems, wherein said antibody further comprises a linker and a drug, and wherein said linker is MCC and said drug is a maytansinoid, such as DM1. Aspects of the invention include isolated monoclonal antibodies comprising the six CDRs of Ab-16 as determined by any one of the AHo, Kabat, or Clothia numbering systems, wherein said antibody further comprises a linker and a drug, and wherein said linker is MCC and said drug is a maytansinoid, such as DM1. Aspects of the invention include isolated monoclonal antibodies comprising the six CDRs of Ab-17 as determined by any one of the AHo, Kabat, or Clothia numbering systems, wherein said antibody further comprises a linker and a drug, and wherein said linker is MCC and said drug is a maytansinoid, such as DM1. Aspects of the aforementioned embodiments include human monoclonal antibodies, human monoclonal IgG antibodies, and human monoclonal IgG1 antibodies.

Aspects of the invention include isolated monoclonal antibodies comprising the six CDRs of Ab-1, specifically Vh-CDR1 (SEQ ID NO:4), Vh-CDR2 (SEQ ID NO:5), Vh-CDR3 (SEQ ID NO:6), Vl-CDR1 (SEQ ID NO:106), Vl-CDR2 (SEQ ID NO:107), and Vl-CDR3 (SEQ ID NO:108), wherein said antibody further comprises a linker and a drug, and wherein said linker is MCC and said drug is a maytansinoid, such as DM1. Aspects of the invention include isolated monoclonal antibodies comprising the six CDRs of Ab-2, specifically Vh-CDR1 (SEQ ID NO:10), Vh-CDR2 (SEQ ID NO:11), Vh-CDR3 (SEQ ID NO:12), Vl-CDR1 (SEQ ID NO:112), Vl-CDR2 (SEQ ID NO:113), and Vl-CDR3 (SEQ ID NO:114), wherein said antibody further comprises a linker and a drug, and wherein said linker is MCC and said drug is a maytansinoid, such as DM1. Aspects of the invention include isolated monoclonal antibodies comprising the six CDRs of Ab-3, specifically Vh-CDR1 (SEQ ID NO:16), Vh-CDR2 (SEQ ID NO:17), Vh-CDR3 (SEQ ID NO:18), Vl-CDR1 (SEQ ID NO:118), Vl-CDR2 (SEQ ID NO:119), and Vl-CDR3 (SEQ ID NO:120), wherein said antibody further comprises a linker and a drug, and wherein said linker is MCC and said drug is a maytansinoid, such as DM1. Aspects of the invention include isolated monoclonal antibodies comprising the six CDRs of Ab-4, specifically Vh-CDR1 (SEQ ID NO:22), Vh-CDR2 (SEQ ID NO:23), Vh-CDR3 (SEQ ID NO:24), Vl-CDR1 (SEQ ID NO:124), Vl-CDR2 (SEQ ID NO:125), and Vl-CDR3 (SEQ ID NO:126), wherein said antibody further comprises a linker and a drug, and wherein said linker is MCC and said drug is a maytansinoid, such as DM1. Aspects of the invention include isolated monoclonal antibodies comprising the six CDRs of Ab-5, specifically Vh-CDR1 (SEQ ID NO:28), Vh-CDR2 (SEQ ID NO:29), Vh-CDR3 (SEQ ID NO:30), Vl-CDR1 (SEQ ID NO:130), Vl-CDR2 (SEQ ID NO:131), and Vl-CDR3 (SEQ ID NO:132), wherein said antibody further comprises a linker and a drug, and wherein said linker is MCC and said drug is a maytansinoid, such as DM1. Aspects of the invention include isolated monoclonal antibodies comprising the six CDRs of Ab-6, specifically Vh-CDR1 (SEQ ID NO:34), Vh-CDR2 (SEQ ID NO:35), Vh-CDR3 (SEQ ID NO:36), Vl-CDR1 (SEQ ID NO:136), Vl-CDR2 (SEQ ID NO:137), and Vl-CDR3 (SEQ ID NO:138), wherein said antibody further comprises a linker and a drug, and wherein said linker is MCC and said drug is a maytansinoid, such as DM1. Aspects of the invention include isolated monoclonal antibodies comprising the six CDRs of Ab-7, specifically Vh-CDR1 (SEQ ID NO:40), Vh-CDR2 (SEQ ID NO:41), Vh-CDR3 (SEQ ID NO:42), Vl-CDR1 (SEQ ID NO:142), Vl-CDR2 (SEQ ID NO:143), and Vl-CDR3 (SEQ ID NO:144), wherein said antibody further comprises a linker and a drug, and wherein said linker is MCC and said drug is a maytansinoid, such as DM1. Aspects of the invention include isolated monoclonal antibodies comprising the six CDRs of Ab-8, specifically Vh-CDR1 (SEQ ID NO:46), Vh-CDR2 (SEQ ID NO:47), Vh-CDR3 (SEQ ID NO:48), Vl-CDR1 (SEQ ID NO:148), Vl-CDR2 (SEQ ID NO:149), and Vl-CDR3 (SEQ ID NO:150), wherein said antibody further comprises a linker and a drug, and wherein said linker is MCC and said drug is a maytansinoid, such as DM1. Aspects of the invention include isolated monoclonal antibodies comprising the six CDRs of Ab-9, specifically Vh-CDR1 (SEQ ID NO:52), Vh-CDR2 (SEQ ID NO:53), Vh-CDR3 (SEQ ID NO:54), Vl-CDR1 (SEQ ID NO:154), Vl-CDR2 (SEQ ID NO:155), and Vl-CDR3 (SEQ ID NO:156), wherein said antibody further comprises a linker and a drug, and wherein said linker is MCC and said drug is a maytansinoid, such as DM1. Aspects of the invention include isolated monoclonal antibodies comprising the six CDRs of Ab-10, specifically Vh-CDR1 (SEQ ID NO:58), Vh-CDR2 (SEQ ID NO:59), Vh-CDR3 (SEQ ID NO:60), Vl-CDR1 (SEQ ID NO:160), Vl-CDR2 (SEQ ID NO:161), and Vl-CDR3 (SEQ ID NO:162), wherein said antibody further comprises a linker and a drug, and wherein said linker is MCC and said drug is a maytansinoid, such as DM1. Aspects of the invention include isolated monoclonal antibodies comprising the six CDRs of Ab-11, specifically Vh-CDR1 (SEQ ID NO:64), Vh-CDR2 (SEQ ID NO:65), Vh-CDR3 (SEQ ID NO:66), Vl-CDR1 (SEQ ID NO:166), Vl-CDR2 (SEQ ID NO:167), and Vl-CDR3 (SEQ ID NO:168), wherein said antibody further comprises a linker and a drug, and wherein said linker is MCC and said drug is a maytansinoid, such as DM1. Aspects of the invention include isolated monoclonal antibodies comprising the six CDRs of Ab-12, specifically Vh-CDR1 (SEQ ID NO:70), Vh-CDR2 (SEQ ID NO:71), Vh-CDR3 (SEQ ID NO:72), Vl-CDR1 (SEQ ID NO:172), Vl-CDR2 (SEQ ID NO:173), and Vl-CDR3 (SEQ ID NO:174), wherein said antibody further comprises a linker and a drug, and wherein said linker is MCC and said drug is a maytansinoid, such as DM1. Aspects of the invention include isolated monoclonal antibodies comprising the six CDRs of Ab-13, specifically Vh-CDR1 (SEQ ID NO:76), Vh-CDR2 (SEQ ID NO:77), Vh-CDR3 (SEQ ID NO:78), Vl-CDR1 (SEQ ID NO:178), Vl-CDR2 (SEQ ID NO:179), and Vl-CDR3 (SEQ ID NO:180), wherein said antibody further comprises a linker and a drug, and wherein said linker is MCC and said drug is a maytansinoid, such as DM1. Aspects of the invention include isolated monoclonal antibodies comprising the six CDRs of Ab-14, specifically Vh-CDR1 (SEQ ID NO:82), Vh-CDR2 (SEQ ID NO:83), Vh-CDR3 (SEQ ID NO:84), Vl-CDR1 (SEQ ID NO:184), Vl-CDR2 (SEQ ID NO:185), and Vl-CDR3 (SEQ ID NO:186), wherein said antibody further comprises a linker and a drug, and wherein said linker is MCC and said drug is a maytansinoid, such as DM1. Aspects of the invention include isolated monoclonal antibodies comprising the six CDRs of Ab-15, specifically Vh-CDR1 (SEQ ID NO:88), Vh-CDR2 (SEQ ID NO:89), Vh-CDR3 (SEQ ID NO:90), Vl-CDR1 (SEQ ID NO:190), Vl-CDR2 (SEQ ID NO:191), and Vl-CDR3 (SEQ ID NO:192), wherein said antibody further comprises a linker and a drug, and wherein said linker is MCC and said drug is a maytansinoid, such as DM1. Aspects of the invention include isolated monoclonal antibodies comprising the six CDRs of Ab-16, specifically Vh-CDR1 (SEQ ID NO:94), Vh-CDR2 (SEQ ID NO:95), Vh-CDR3 (SEQ ID NO:96), Vl-CDR1 (SEQ ID NO:196), Vl-CDR2 (SEQ ID NO:197), and Vl-CDR3 (SEQ ID NO:198), wherein said antibody further comprises a linker and a drug, and wherein said linker is MCC and said drug is a maytansinoid, such as DM1. Aspects of the invention include isolated monoclonal antibodies comprising the six CDRs of Ab-17, specifically Vh-CDR1 (SEQ ID NO:100), Vh-CDR2 (SEQ ID NO:101), Vh-CDR3 (SEQ ID NO:102), Vl-CDR1 (SEQ ID NO:202), Vl-CDR2 (SEQ ID NO:203), and Vl-CDR3 (SEQ ID NO:204), wherein said antibody further comprises a linker and a drug, and wherein said linker is MCC and said drug is a maytansinoid, such as DM1. Aspects of the aforementioned embodiments include human monoclonal antibodies, human monoclonal IgG antibodies, and human monoclonal IgG1 antibodies. Aspects of the invention include fragments, derivatives, muteins, and variants of the aforementioned.

Aspects of the invention include isolated monoclonal antibodies comprising an Ab-1Vl (SEQ ID NO:240) and an Ab-1Vh (SEQ ID NO:206) domain, wherein said antibody further comprises a linker and a drug, and wherein said linker is MCC and said drug is a maytansinoid, such as DM1. Aspects of the invention include isolated monoclonal antibodies comprising an Ab-2Vl (SEQ ID NO:242) and an Ab-2Vh (SEQ ID NO:208) domain, wherein said antibody further comprises a linker and a drug, and wherein said linker is MCC and said drug is a maytansinoid, such as DM1. Aspects of the invention include isolated monoclonal antibodies comprising an Ab-3Vl (SEQ ID NO:244) and an Ab-3Vh (SEQ ID NO:210) domain, wherein said antibody further comprises a linker and a drug, and wherein said linker is MCC and said drug is a maytansinoid, such as DM1. Aspects of the invention include isolated monoclonal antibodies comprising an Ab-4Vl (SEQ ID NO:246) and an Ab-4Vh (SEQ ID NO:212) domain, wherein said antibody further comprises a linker and a drug, and wherein said linker is MCC and said drug is a maytansinoid, such as DM1. Aspects of the invention include isolated monoclonal antibodies comprising an Ab-5Vl (SEQ ID NO:248) and an Ab-5Vh (SEQ ID NO:214) domain, wherein said antibody further comprises a linker and a drug. Aspects of the invention include isolated monoclonal antibodies comprising an Ab-6Vl (SEQ ID NO:250) and an Ab-6Vh (SEQ ID NO:216) domain, wherein said antibody further comprises a linker and a drug, and wherein said linker is MCC and said drug is a maytansinoid, such as DM1. Aspects of the invention include monoclonal antibodies comprising an Ab-7Vl (SEQ ID NO:252) and an Ab-7Vh (SEQ ID NO:218) domain, wherein said antibody further comprises a linker and a drug, and wherein said linker is MCC and said drug is a maytansinoid, such as DM1. Aspects of the invention include isolated monoclonal antibodies comprising an Ab-8Vl (SEQ ID NO:254) and an Ab-8Vh (SEQ ID NO:220) domain, wherein said antibody further comprises a linker and a drug, and wherein said linker is MCC and said drug is a maytansinoid, such as DM1. Aspects of the invention include isolated monoclonal antibodies comprising an Ab-9Vl (SEQ ID NO:256) and an Ab-9Vh (SEQ ID NO:222) domain, wherein said antibody further comprises a linker and a drug, and wherein said linker is MCC and said drug is a maytansinoid, such as DM1. Aspects of the invention include isolated monoclonal antibodies comprising an Ab-10Vl (SEQ ID NO:258) and an Ab-10Vh (SEQ ID NO:224) domain, wherein said antibody further comprises a linker and a drug, and wherein said linker is MCC and said drug is a maytansinoid, such as DM1. Aspects of the invention include isolated monoclonal antibodies comprising an Ab-11Vl (SEQ ID NO:260) and an Ab-11Vh (SEQ ID NO:226) domain, wherein said antibody further comprises a linker and a drug, and wherein said linker is MCC and said drug is a maytansinoid, such as DM1. Aspects of the invention include isolated monoclonal antibodies comprising an Ab-12Vl (SEQ ID NO:262) and an Ab-12Vh (SEQ ID NO:228) domain, wherein said antibody further comprises a linker and a drug, and wherein said linker is MCC and said drug is a maytansinoid, such as DM1. Aspects of the invention include isolated monoclonal antibodies comprising an Ab-13Vl (SEQ ID NO:264) and an Ab-13Vh (SEQ ID NO:230) domain, wherein said antibody further comprises a linker and a drug, and wherein said linker is MCC and said drug is a maytansinoid, such as DM1. Aspects of the invention include isolated monoclonal antibodies comprising an Ab-14Vl (SEQ ID NO:266) and an Ab-14Vh (SEQ ID NO:232) domain, wherein said antibody further comprises a linker and a drug, and wherein said linker is MCC and said drug is a maytansinoid, such as DM1. Aspects of the invention include isolated monoclonal antibodies comprising an Ab-15Vl (SEQ ID NO:268) and an Ab-15Vh (SEQ ID NO:234) domain, wherein said antibody further comprises a linker and a drug, and wherein said linker is MCC and said drug is a maytansinoid, such as DM1. Aspects of the invention include isolated monoclonal antibodies comprising an Ab-16Vl (SEQ ID NO:270) and an Ab-16Vh (SEQ ID NO:236) domain, wherein said antibody further comprises a linker and a drug, and wherein said linker is MCC and said drug is a maytansinoid, such as DM1. Aspects of the invention include isolated monoclonal antibodies comprising an Ab-17Vl (SEQ ID NO:272) and an Ab-17Vh (SEQ ID NO:238) domain, wherein said antibody further comprises a linker and a drug, and wherein said linker is MCC and said drug is a maytansinoid, such as DM1. Aspects of the aforementioned embodiments include human monoclonal antibodies, human monoclonal IgG antibodies, and human monoclonal IgG1 antibodies. Aspects of the invention include fragments, derivatives, muteins, and variants of the aforementioned.

Aspects of the invention include isolated monoclonal antibodies comprising an Ab-1 light chain (SEQ ID NO:280) and Ab-1 heavy chain (SEQ ID NO:274), wherein said antibody further comprises a linker and a drug, and wherein said linker is MCC and said drug is a maytansinoid, such as DM1. Aspects of the invention include isolated monoclonal antibodies comprising an Ab-2 light chain (SEQ ID NO:282) and an Ab-2 heavy chain (SEQ ID NO:276), wherein said antibody further comprises a linker and a drug, and wherein said linker is MCC and said drug is a maytansinoid, such as DM1. Aspects of the invention include isolated monoclonal antibodies comprising an Ab-3 light chain (SEQ ID NO:284) and an Ab-3 heavy chain (SEQ ID NO:278), wherein said antibody further comprises a linker and a drug, and wherein said linker is MCC and said drug is a maytansinoid, such as DM1. Aspects of the invention include isolated monoclonal antibodies comprising two Ab-1 light chains (SEQ ID NO:280) and two Ab-1 heavy chains (SEQ ID NO:274), wherein said antibody further comprises a linker and a drug, and wherein said linker is MCC and said drug is a maytansinoid, such as DM1. Aspects of the invention include isolated monoclonal antibodies comprising two Ab-2 light chains (SEQ ID NO:282) and two Ab-2 heavy chains (SEQ ID NO:276), wherein said antibody further comprises a linker and a drug, and wherein said linker is MCC and said drug is a maytansinoid, such as DM1. Aspects of the invention include isolated monoclonal antibodies comprising two Ab-3 light chains (SEQ ID NO:284) and two Ab-3 heavy chains (SEQ ID NO:278), wherein said antibody further comprises a linker and a drug, and wherein said linker is MCC and said drug is a maytansinoid, such as DM1. Aspects of the aforementioned embodiments include human monoclonal antibodies, human monoclonal IgG antibodies, and human monoclonal IgG1 antibodies. Aspects of the invention include fragments, derivatives, muteins, and variants of the aforementioned.

Aspects of the invention include isolated monoclonal antibodies comprising the six CDRs of Ab-1, wherein the CDRs include no more than one, two, three, four, five, or six amino acid additions, deletions, or substitutions of Vh-CDR1 (SEQ ID NO:4), Vh-CDR2 (SEQ ID NO:5), Vh-CDR3 (SEQ ID NO:6), Vl-CDR1 (SEQ ID NO:106), Vl-CDR2 (SEQ ID NO:107), and Vl-CDR3 (SEQ ID NO:108), wherein said antibody further comprises a linker and a drug, and wherein said linker is MCC and said drug is a maytansinoid, such as DM1. Aspects of the invention include isolated monoclonal antibodies comprising the six CDRs of Ab-2, wherein the CDRs include no more than one, two, three, four, five, or six amino acid additions, deletions, or substitutions of Vh-CDR1 (SEQ ID NO:10), Vh-CDR2 (SEQ ID NO:11), Vh-CDR3 (SEQ ID NO:12), Vl-CDR1 (SEQ ID NO:112), Vl-CDR2 (SEQ ID NO:113), and Vl-CDR3 (SEQ ID NO:114), wherein said antibody further comprises a linker and a drug, and wherein said linker is MCC and said drug is a maytansinoid, such as DM1. Aspects of the invention include isolated monoclonal antibodies comprising the six CDRs of Ab-3, wherein the CDRs include no more than one, two, three, four, five, or six amino acid additions, deletions, or substitutions of Vh-CDR1 (SEQ ID NO:16), Vh-CDR2 (SEQ ID NO:17), Vh-CDR3 (SEQ ID NO:18), Vl-CDR1 (SEQ ID NO:118), Vl-CDR2 (SEQ ID NO:119), and Vl-CDR3 (SEQ ID NO:120), wherein said antibody further comprises a linker and a drug, and wherein said linker is MCC and said drug is a maytansinoid, such as DM1. Aspects of the invention include isolated monoclonal antibodies comprising the six CDRs of Ab-4, wherein the CDRs include no more than one, two, three, four, five, or six amino acid additions, deletions, or substitutions of Vh-CDR1 (SEQ ID NO:22), Vh-CDR2 (SEQ ID NO:23), Vh-CDR3 (SEQ ID NO:24), Vl-CDR1 (SEQ ID NO:124), Vl-CDR2 (SEQ ID NO:125), and Vl-CDR3 (SEQ ID NO:126), wherein said antibody further comprises a linker and a drug, and wherein said linker is MCC and said drug is a maytansinoid, such as DM1. Aspects of the invention include isolated monoclonal antibodies comprising the six CDRs of Ab-5, wherein the CDRs include no more than one, two, three, four, five, or six amino acid additions, deletions, or substitutions of Vh-CDR1 (SEQ ID NO:28), Vh-CDR2 (SEQ ID NO:29), Vh-CDR3 (SEQ ID NO:30), Vl-CDR1 (SEQ ID NO:130), Vl-CDR2 (SEQ ID NO:131), and Vl-CDR3 (SEQ ID NO:132), wherein said antibody further comprises a linker and a drug, and wherein said linker is MCC and said drug is a maytansinoid, such as DM1. Aspects of the invention include isolated monoclonal antibodies comprising the six CDRs of Ab-6, wherein the CDRs include no more than one, two, three, four, five, or six amino acid additions, deletions, or substitutions of Vh-CDR1 (SEQ ID NO:34), Vh-CDR2 (SEQ ID NO:35), Vh-CDR3 (SEQ ID NO:36), Vl-CDR1 (SEQ ID NO:136), Vl-CDR2 (SEQ ID NO:137), and Vl-CDR3 (SEQ ID NO:138), wherein said antibody further comprises a linker and a drug, and wherein said linker is MCC and said drug is a maytansinoid, such as DM1. Aspects of the invention include isolated monoclonal antibodies comprising the six CDRs of Ab-7, wherein the CDRs include no more than one, two, three, four, five, or six amino acid additions, deletions, or substitutions of Vh-CDR1 (SEQ ID NO:40), Vh-CDR2 (SEQ ID NO:41), Vh-CDR3 (SEQ ID NO:42), Vl-CDR1 (SEQ ID NO:142), Vl-CDR2 (SEQ ID NO:143), and Vl-CDR3 (SEQ ID NO:144), wherein said antibody further comprises a linker and a drug, and wherein said linker is MCC and said drug is a maytansinoid, such as DM1. Aspects of the invention include isolated monoclonal antibodies comprising the six CDRs of Ab-8, wherein the CDRs include no more than one, two, three, four, five, or six amino acid additions, deletions, or substitutions of Vh-CDR1 (SEQ ID NO:46), Vh-CDR2 (SEQ ID NO:47), Vh-CDR3 (SEQ ID NO:48), Vl-CDR1 (SEQ ID NO:148), Vl-CDR2 (SEQ ID NO:149), and Vl-CDR3 (SEQ ID NO:150), wherein said antibody further comprises a linker and a drug, and wherein said linker is MCC and said drug is a maytansinoid, such as DM1. Aspects of the invention include isolated monoclonal antibodies comprising the six CDRs of Ab-9, wherein the CDRs include no more than one, two, three, four, five, or six amino acid additions, deletions, or substitutions of Vh-CDR1 (SEQ ID NO:52), Vh-CDR2 (SEQ ID NO:53), Vh-CDR3 (SEQ ID NO:54), Vl-CDR1 (SEQ ID NO:154), Vl-CDR2 (SEQ ID NO:155), and Vl-CDR3 (SEQ ID NO:156), wherein said antibody further comprises a linker and a drug, and wherein said linker is MCC and said drug is a maytansinoid, such as DM1. Aspects of the invention include isolated monoclonal antibodies comprising the six CDRs of Ab-10, wherein the CDRs include no more than one, two, three, four, five, or six amino acid additions, deletions, or substitutions of Vh-CDR1 (SEQ ID NO:58), Vh-CDR2 (SEQ ID NO:59), Vh-CDR3 (SEQ ID NO:60), Vl-CDR1 (SEQ ID NO:160), Vl-CDR2 (SEQ ID NO:161), and Vl-CDR3 (SEQ ID NO:162), wherein said antibody further comprises a linker and a drug, and wherein said linker is MCC and said drug is a maytansinoid, such as DM1. Aspects of the invention include isolated monoclonal antibodies comprising the six CDRs of Ab-11, wherein the CDRs include no more than one, two, three, four, five, or six amino acid additions, deletions, or substitutions of Vh-CDR1 (SEQ ID NO:64), Vh-CDR2 (SEQ ID NO:65), Vh-CDR3 (SEQ ID NO:66), Vl-CDR1 (SEQ ID NO:166), Vl-CDR2 (SEQ ID NO:167), and Vl-CDR3 (SEQ ID NO:168), wherein said antibody further comprises a linker and a drug, and wherein said linker is MCC and said drug is a maytansinoid, such as DM1. Aspects of the invention include isolated monoclonal antibodies comprising the six CDRs of Ab-12, wherein the CDRs include no more than one, two, three, four, five, or six amino acid additions, deletions, or substitutions of Vh-CDR1 (SEQ ID NO:70), Vh-CDR2 (SEQ ID NO:71), Vh-CDR3 (SEQ ID NO:72), Vl-CDR1 (SEQ ID NO:172), Vl-CDR2 (SEQ ID NO:173), and Vl-CDR3 (SEQ ID NO:174), wherein said antibody further comprises a linker and a drug, and wherein said linker is MCC and said drug is a maytansinoid, such as DM1. Aspects of the invention include isolated monoclonal antibodies comprising the six CDRs of Ab-13, wherein the CDRs include no more than one, two, three, four, five, or six amino acid additions, deletions, or substitutions of Vh-CDR1 (SEQ ID NO:76), Vh-CDR2 (SEQ ID NO:77), Vh-CDR3 (SEQ ID NO:78), Vl-CDR1 (SEQ ID NO:178), Vl-CDR2 (SEQ ID NO:179), and Vl-CDR3 (SEQ ID NO:180), wherein said antibody further comprises a linker and a drug, and wherein said linker is MCC and said drug is a maytansinoid, such as DM1. Aspects of the invention include isolated monoclonal antibodies comprising the six CDRs of Ab-14, wherein the CDRs include no more than one, two, three, four, five, or six amino acid additions, deletions, or substitutions of Vh-CDR1 (SEQ ID NO:82), Vh-CDR2 (SEQ ID NO:83), Vh-CDR3 (SEQ ID NO:84), Vl-CDR1 (SEQ ID NO:184), Vl-CDR2 (SEQ ID NO:185), and Vl-CDR3 (SEQ ID NO:186), wherein said antibody further comprises a linker and a drug, and wherein said linker is MCC and said drug is a maytansinoid, such as DM1. Aspects of the invention include isolated monoclonal antibodies comprising the six CDRs of Ab-15, wherein the CDRs include no more than one, two, three, four, five, or six amino acid additions, deletions, or substitutions of Vh-CDR1 (SEQ ID NO:88), Vh-CDR2 (SEQ ID NO:89), Vh-CDR3 (SEQ ID NO:90), Vl-CDR1 (SEQ ID NO:190), Vl-CDR2 (SEQ ID NO:191), and Vl-CDR3 (SEQ ID NO:192), wherein said antibody further comprises a linker and a drug, and wherein said linker is MCC and said drug is a maytansinoid, such as DM1. Aspects of the invention include isolated monoclonal antibodies comprising the six CDRs of Ab-16, wherein the CDRs include no more than one, two, three, four, five, or six amino acid additions, deletions, or substitutions of Vh-CDR1 (SEQ ID NO:94), Vh-CDR2 (SEQ ID NO:95), Vh-CDR3 (SEQ ID NO:96), Vl-CDR1 (SEQ ID NO:196), Vl-CDR2 (SEQ ID NO:197), and Vl-CDR3 (SEQ ID NO:198), wherein said antibody further comprises a linker and a drug, and wherein said linker is MCC and said drug is a maytansinoid, such as DM1. Aspects of the invention include isolated monoclonal antibodies comprising the six CDRs of Ab-17, wherein the CDRs include no more than one, two, three, four, five, or six amino acid additions, deletions, or substitutions of Vh-CDR1 (SEQ ID NO:100), Vh-CDR2 (SEQ ID NO:101), Vh-CDR3 (SEQ ID NO:102), Vl-CDR1 (SEQ ID NO:202), Vl-CDR2 (SEQ ID NO:203), and Vl-CDR3 (SEQ ID NO:204), wherein said antibody further comprises a linker and a drug, and wherein said linker is MCC and said drug is a maytansinoid, such as DM1. Aspects of the aforementioned embodiments include human monoclonal antibodies, human monoclonal IgG antibodies, and human monoclonal IgG1 antibodies.

Aspects of the invention include isolated monoclonal antibodies comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-1Vl (SEQ ID NO:240) and Ab-1Vh (SEQ ID NO:206), respectively, wherein said antibody further comprises a linker and a drug, and wherein said linker is MCC and said drug is a maytansinoid, such as DM1. Aspects of the invention include isolated monoclonal antibodies comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-2Vl (SEQ ID NO:242) and Ab-2Vh (SEQ ID NO:208), respectively, wherein said antibody further comprises a linker and a drug, and wherein said linker is MCC and said drug is a maytansinoid, such as DM1. Aspects of the invention include isolated monoclonal antibodies comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-3Vl (SEQ ID NO:244) and Ab-3Vh (SEQ ID NO:210), respectively, wherein said antibody further comprises a linker and a drug, and wherein said linker is MCC and said drug is a maytansinoid, such as DM1. Aspects of the invention include isolated monoclonal antibodies comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-4Vl (SEQ ID NO:246) and Ab-4Vh (SEQ ID NO:212), respectively, wherein said antibody further comprises a linker and a drug, and wherein said linker is MCC and said drug is a maytansinoid, such as DM1. Aspects of the invention include isolated monoclonal antibodies comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-5Vl (SEQ ID NO:248) and Ab-5Vh (SEQ ID NO:214), respectively, wherein said antibody further comprises a linker and a drug, and wherein said linker is MCC and said drug is a maytansinoid, such as DM1. Aspects of the invention include isolated monoclonal antibodies comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-6Vl (SEQ ID NO:250) and Ab-6Vh (SEQ ID NO:216), respectively, wherein said antibody further comprises a linker and a drug, and wherein said linker is MCC and said drug is a maytansinoid, such as DM1. Aspects of the invention include isolated monoclonal antibodies comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-7Vl (SEQ ID NO:252) and Ab-7Vh (SEQ ID NO:218), respectively, wherein said antibody further comprises a linker and a drug, and wherein said linker is MCC and said drug is a maytansinoid, such as DM1. Aspects of the invention include isolated monoclonal antibodies comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-8Vl (SEQ ID NO:254) and Ab-8Vh (SEQ ID NO:220), respectively, wherein said antibody further comprises a linker and a drug, and wherein said linker is MCC and said drug is a maytansinoid, such as DM1. Aspects of the invention include isolated monoclonal antibodies comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-9Vl (SEQ ID NO:256) and Ab-9Vh (SEQ ID NO:222), respectively, wherein said antibody further comprises a linker and a drug, and wherein said linker is MCC and said drug is a maytansinoid, such as DM1. Aspects of the invention include isolated monoclonal antibodies comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-10Vl (SEQ ID NO:258) and Ab-10Vh (SEQ ID NO:224), respectively, wherein said antibody further comprises a linker and a drug, and wherein said linker is MCC and said drug is a maytansinoid, such as DM1. Aspects of the invention include isolated monoclonal antibodies comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-11Vl (SEQ ID NO:260) and Ab-11Vh (SEQ ID NO:226), respectively, wherein said antibody further comprises a linker and a drug, and wherein said linker is MCC and said drug is a maytansinoid, such as DM1. Aspects of the invention include isolated monoclonal antibodies comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-12Vl (SEQ ID NO:262) and Ab-12Vh (SEQ ID NO:228), respectively, wherein said antibody further comprises a linker and a drug, and wherein said linker is MCC and said drug is a maytansinoid, such as DM1. Aspects of the invention include isolated monoclonal antibodies comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-13Vl (SEQ ID NO:264) and Ab-13Vh (SEQ ID NO:230), respectively, wherein said antibody further comprises a linker and a drug, and wherein said linker is MCC and said drug is a maytansinoid, such as DM1. Aspects of the invention include isolated monoclonal antibodies comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-14Vl (SEQ ID NO:266) and Ab-14Vh (SEQ ID NO:232), respectively, wherein said antibody further comprises a linker and a drug, and wherein said linker is MCC and said drug is a maytansinoid, such as DM1. Aspects of the invention include isolated monoclonal antibodies comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-15Vl (SEQ ID NO:268) and Ab-15Vh (SEQ ID NO:234), respectively, wherein said antibody further comprises a linker and a drug, and wherein said linker is MCC and said drug is a maytansinoid, such as DM1. Aspects of the invention include isolated monoclonal antibodies comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-16Vl (SEQ ID NO:270) and Ab-16Vh (SEQ ID NO:236), respectively, wherein said antibody further comprises a linker and a drug, and wherein said linker is MCC and said drug is a maytansinoid, such as DM1. Aspects of the invention include isolated monoclonal antibodies comprising a Vl and a Vh amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-17Vl (SEQ ID NO:272) and Ab-17Vh (SEQ ID NO:238), respectively, wherein said antibody further comprises a linker and a drug, and wherein said linker is MCC and said drug is a maytansinoid, such as DM1. Aspects of the aforementioned embodiments include human monoclonal antibodies, human monoclonal IgG antibodies, and human monoclonal IgG1 antibodies.

Aspects of the invention include isolated monoclonal antibodies that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-1 light chain (SEQ ID NO:280) and Ab-1 heavy chain (SEQ ID NO:274), wherein said antibody further comprises a linker and a drug, and wherein said linker is MCC and said drug is a maytansinoid, such as DM1. Aspects of the invention include isolated antibodies that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-2 light chain (SEQ ID NO:282) and an Ab-2 heavy chain (SEQ ID NO:276), wherein said antibody further comprises a linker and a drug, and wherein said linker is MCC and said drug is a maytansinoid, such as DM1. Aspects of the invention include isolated monoclonal antibodies that are at least 80%, 81%, 82%, 83%, 84%, 85%, 86%, 87%, 88%, 89%, 90%, 91%, 92%, 93%, 94%, 95%, 96%, 97%, 98%, or 99% identical to Ab-3 light chain (SEQ ID NO:284) and an Ab-3 heavy chain (SEQ ID NO:278), wherein said antibody further comprises a linker and a drug, and wherein said linker is MCC and said drug is a maytansinoid, such as DM1. Aspects of the aforementioned embodiments include human monoclonal antibodies, human monoclonal IgG antibodies, and human monoclonal IgG1 antibodies.

Use of BCMA Antigen Binding Proteins for Therapeutic Purposes

All aspects of the BCMA antigen binding proteins described throughout this specification may be used in the preparation of a medicament for the treatment of the various conditions and diseases described herein. All aspects of the BCMA antigen binding proteins described throughout this specification may be used for the treatment of diseases or conditions associated with B-cells expressing BCMA, and in particular, memory B-cells and plasma B-cells. BCMA is expressed at relatively higher levels in malignant plasma cells (multiple myeloma and smoldering myeloma) and in monoclonal gammopathy of unknown significance (MGUS) plasma cells than the levels observed on normal plasma cells, as shown in Example 1.

The BCMA ADCs, particularly Ab-1, Ab-2, or Ab-3 ADC, and more particularly Ab-1 ADC, as variously described herein, may be used to treat B-cell related cancers wherein the malignant B-cells express BCMA on their surface. The BCMA ADC binds BCMA on the surface of malignant B-cells, is internalized by receptor-mediated endocytosis, releases the chemotherapeutic drug within the cell (typically via the acidic environment of the lysosome-endosome pathway) and thereby kills the malignant cell. Releasing the drug within the cell reduces bystander killing of non-malignant cells by free drug. Thus, the BCMA ADCs, particularly Ab-1, Ab-2, or Ab-3 ADC, and more particularly Ab-1 ADC, as variously described herein, may be used to treat diseases including, but are not limited to, B-cell cancers, and in particular multiple myeloma and malignant plasma cell neoplasms, as well as BCMA+ high-grade lymphoma. The BCMA ADCs, particularly Ab-1, Ab-2, or Ab-3 ADC, and more particularly Ab-1 ADC, as variously described herein, may also be used to treat Kahler's disease and Myelomatosis; Plasma cell leukemia; Plasmacytoma; B-cell prolymphocytic leukemia; Hairy cell leukemia; B-cell non-Hodgkin's lymphoma (NHL); Acute myeloid leukemia (AML); Chronic myeloid leukemia (CML); Acute lymphocytic leukemia (ALL); Chronic lymphocytic leukemia (CLL); Follicular lymphoma (including follicular non-Hodgkin's lymphoma types); Burkitt's lymphoma (Endemic Burkitt's lymphoma; Sporadic Burkitt's lymphoma); Marginal zone lymphoma (Mucosa-Associated Lymphoid Tissue; MALT/MALToma; Monocytoid B cell lymphoma; Splenic lymphoma with villous lymphocytes); Mantle cell lymphoma; Large cell lymphoma (Diffuse large cell; Diffuse Mixed Cell; Immunoblastic Lymphoma; Primary Mediastinal B Cell Lymphoma; Angiocentric Lymphoma—pulmonary B cell); Small lymphocytic lymphoma (SLL); Precursor B-lymphoblastic lymphoma; Myeloid leukemia (granulocytic; myelogenous; Acute myeloid leukemia; Chronic myeloid leukemia; Subacute myeloid leukemia; Myeloid sarcoma; Chloroma; Granulocytic sarcoma; Acute promyelocytic leukemia; Acute myelomonocytic leukemia); Waldenstrom's macroglobulinemia, or other B-cell lymphoma.

The BCMA ADCs, particularly Ab-1, Ab-2, or Ab-3 ADC, and more particularly Ab-1 ADC, as variously described herein, may be used in combination with standard cancer therapies, such as, but not limited to surgery, radiation therapy, and chemotherapy, as well as proteasome inhibitors, corticosteroids, and stem cell transplants. The BCMA ADCs, particularly Ab-1, Ab-2, or Ab-3 ADC, and more particularly Ab-1 ADC, as variously described herein, may be used in combination with administration of a chemotherapeutic agent. The chemotherapeutic agent may be administered prior to, concurrent with, or subsequent to administration of one or more BCMA ADCs, particularly Ab-1, Ab-2, or Ab-3 ADC, and more particularly Ab-1 ADC, as variously described herein. A chemotherapeutic agent is a compound used in the treatment of cancer. Examples of chemotherapeutic agents include, but is not limited to: 13-cis-Retinoic Acid, 2-CdA 2-Chlorodeoxyadenosine, 5-Azacitidine 5-Fluorouracil 5-FU, 6-Mercaptopurine, 6-MP 6-TG 6-Thioguanine, Abraxane, Accutane®, Actinomycin-D, Adriamycin®, Adrucil®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide Anagrelide, Anandron®, Anastrozole, Arabinosylcytosine, Ara-C, Aranesp®, Aredia®, Arimidex®, Aromasin®, Arranon®, Arsenic Trioxide, Asparaginase, ATRA, Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, C225, Calcium Leucovorin, Campath®, Camptosar®, Camptothecin-11, Capecitabine Carac™, Carboplatin, Carmustine, Carmustine Wafer, Casodex®, CC-5013, CCI-779, CCNU, CDDP, CeeNU, Cerubidine®, Cetuximab, Chlorambucil, Cisplatin, Citrovorum Factor, Cladribine, Cortisone, Cosmegen®, CPT-11, Cyclophosphamide, Cytadren®, Cytarabine, Cytarabine Liposomal, Cytosar-U®, Cytoxan®, Dacarbazine, Dacogen, Dactinomycin, Darbepoetin Alfa, Dasatinib, Daunomycin, Daunorubicin, Daunorubicin Hydrochloride, Daunorubicin Liposomal, DaunoXome®, Decadron, Decitabine, Delta-Cortef®, Deltasone®, Denileukin, Diftitox, DepoCyt™, Dexamethasone, Dexamethasone Acetate, Dexamethasone Sodium Phosphate, Dexasone, Dexrazoxane, DHAD, DIC, Diodex, Docetaxel, Doxil®, Doxorubicin, Doxorubicin Liposomal, Droxia™, DTIC, DTIC-Dome®, Duralone®, Efudex®, Eligard™, Ellence™, Eloxatin™, Elspar®, Emcyt®, Epirubicin, Epoetin Alfa, Erbitux, Erlotinib, Erwinia L-asparaginase, Estramustine, Ethyol, Etopophos®, Etoposide, Etoposide Phosphate, Eulexin®, Evista®, Exemestane, Fareston®, Faslodex®, Femara®, Filgrastim, Floxuridine, Fludara®, Fludarabine, Fluoroplex®, Fluorouracil, Fluoxymesterone, Flutamide, Folinic Acid, FUDR®, Fulvestrant, G-CSF, Gefitinib, Gemcitabine, Gemtuzumab, ozogamicin, Gemzar, Gleevec™, Gliadel® Wafer, GM-CSF, Goserelin, Halotestin®, Herceptin,®, Hexadrol, Hexalen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab Tiuxetan, Idamycin®, Idarubicin, Ifex®, IFN-alpha, Ifosfamide, Imatinib, mesylate, Imidazole, Carboxamide, Interferon alfa, Interferon Alfa-2b (PEG Conjugate), Interleukin-2, Interleukin-11, Intron A® (interferon alfa-2b), Iressa®, Irinotecan, Isotretinoin, Ixabepilone, Ixempra™, Kidrolase, Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcoly sin, Lupron®, Lupron Depot®, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, Mustine, Mutamycin®, Myleran®, Mylocel™, Mylotarg®, Navelbine®, Nelarabine, Neosar®, Neulasta™, Neumega®, Neupogen®, Nexavar®, Nilandron®, Nilutamide, Nipent®, Nitrogen Mustard, Novaldex®, Novantrone®, Octreotide, Octreotide acetate, Oncospar®, Oncovin®, Ontak®, Onxal™, Oprevelkin, Orapred®, Orasone®, Oxaliplatin, Paclitaxel, Paclitaxel Protein-bound, Pamidronate, Panitumumab, Panretin®, Paraplatin®, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant, Purinethol®, Raloxifene, Revlimid®, Rheumatrex®, Rituxan®, Rituximab, Roferon-A® (Interferon Alfa-2a), Rubex®, Rubidomycin hydrochloride, Sandostatin®, Sandostatin LAR®, Sargramostim, Solu-Cortef®, Solu-Medrol®, Sorafenib, SPRYCEL™, STI-571, Streptozocin, SU11248, Sunitinib, Sutent®, Tamoxifen, Tarceva®, Targretin®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, VCR, Vectibix™, Velban®, Velcade®, VePesid®, Vesanoid®, Viadur™, Vidaza®, Vinblastine, Vinblastine Sulfate, Vincasar, Pfs®, Vincristine, Vinorelbine, Vinorelbine tartrate, VLB, VM-26, Vorinostat, VP-16, Vumon*, Xeloda®, Zanosar®, Zevalin™, Zinecard®, Zoladex®, Zoledronic acid, Zolinza, Zometa®, and the like.

In addition, the BCMA ADCs, particularly Ab-1, Ab-2, or Ab-3 ADC, and more particularly Ab-1 ADC, as variously described herein, may be used in treat autoimmune disorders wherein the antibodies produced by plasma cells contribute to the immunopathogenesis of the disease, such as but not limited to, systemic lupus erythematosus (SLE), rheumatoid arthritis (RA), multiple sclerosis (MS), Sjogrens, immune-mediated thrombocytopenia, haemolytic anaemia, bullous pemphigoid, myasthenia gravis, Type I diabetes mellitus, Graves' disease, Addison's disease, pemphigus foliaceus, psoriasis, psoriatic arthritis, and ankylosing spondylitis. In other embodiments, the anti-huBCMA antibodies without being conjugated to a drug may be used to treat the auto-immune diseases listed in this paragraph, particularly Ab-1, Ab-2, or Ab-3, and more particularly Ab-1, as variously described herein. More particularly, Ab-1 may be used to treat SLE. More particularly, Ab-1 may be used to treat MS. It is understood that the above-described methods also encompasses comparable methods for first and second medical uses and claims thereto, as described elsewhere in this specification.

Diagnostic Use, Assays, and Kits

The BCMA antigen binding proteins of the invention can be used in diagnostic assays, e.g., binding assays to detect and/or quantify BCMA expressed in a tissue (such as bone marrow) or cell (such as a plasma cell). The BCMA antigen binding proteins may be used in research to further investigate the role of BCMA in disease. The BCMA antigen binding proteins may be used to further investigate the role of BCMA in forming homomeric and/or heteromeric receptor complexes and the role of said BCMA receptor complexes in disease.

In certain embodiments, patient stratification assays that may be used to determine whether or not a patient will be eligible for treatment with a BCMA ADC. In particular, multiple myeloma patients may be prescreened for treatment. By way of example, if a threshold level of BCMA expression on the patients B-cells is detected, the patient is eligible for treatment. Conversely, if the threshold level of BCMA expression on the patients B-cells is insufficient, the patient may not be eligible for treatment. BCMA expression may be determined by testing for the presence of BCMA-encoding RNA in the patient's cells, or for the presence of BCMA protein expressed on the surface of the cells. The sample may be a blood sample or biopsy. The BCMA antibodies described herein may be used in such assays to quantitate the amount of BCMA expressed on the surface of the patient's cells.

Aspects of the invention include assays to measure the pharmacodynamics of the BCMA ADCs. As described herein, the BCMA ADCs bind to cell surface BCMA and are internalized, whereby the antibody is catabolized, releasing lys-MCC-DM1 into the cytoplasm where it inhibits tubulin polymerization and induces mitotic arrest and cell death. Multiple myeloma is a disease driven by plasma cell expansion in the bone marrow, but the number of peripheral plasma cells is typically too small to use as surrogate to tumor cells in the bone marrow compartment (Dingli D, Nowakowski G S, Dispenzieri A, et al., *Blood* 107, 3384-8 (2006)). One embodiment of pharmacodynamics surrogate markers to assess the effect of the BCMA ADCs on plasma cells, is to measure a reduction in tumor burden by serum analytes. The level of tumor burden is a common assessment in multiple myeloma and one that is used in determining disease status and in separating MGUS from multiple myeloma (Waxman A J, et al., *Clin Lymphoma Myeloma Leuk.* 10, 248-57 (2010)). A level of 3 g/dL of serum monoclonal (M) protein is a criterion used in the diagnosis of MM and reduction of serum M-protein is one criterion used for defining clinical response (Schaefer E W, et al., *Cancer* 116, 640-6 (2010)). The serum M-protein assay measures the amount of monoclonal protein circulating in the blood. This assay is a clinically validated assay that is commonly utilized in multiple myeloma diagnosis. A small subset of MM patients (2-5%) is non-secreting for monoclonal protein in serum.

Serum levels of BCMA may be prognostic and a new tool for measuring tumor load (Sanchez E, et al., Serum B-cell maturation antigen is elevated in multiple myeloma and correlates with disease status and survival. Br *J Haematology* 158, 727-38 (2012)). Embodiments of the invention include diagnostic assays and kits to measure soluble BCMA is a potential surrogate to membrane bound BCMA on tumor cells. For example, measuring soluble BCMA before treatment with one or more of the BCMA ADCs alone or in combination with conventional therapies to establish baseline level of serum BCMA and periodically testing to monitor responses to said therapy. BCMA ligands BAFF and APRIL are secreted by the bone marrow stromal cells into the tumor microenvironment and BAFF has been detected in MM serum samples Moreaux J, et al., *Blood* 106, 1021-30 (2005); Tai Y T, et al., *Cancer Res.* 66, 6675-82 (2006); and Fragioudaki M, et al., *Leuk Res.* 36, 1004-8 (2012)). Just as describe above, soluble BMCA, APRIL and BAFF diagnostic assays, such as ELISA, flow cytometry, etc., for use in monitoring the clinical status of patients are envisioned. If appropriate assays are identified, MM serum will be tested for the levels of soluble BCMA, APRIL and BAFF.

Figure 38:
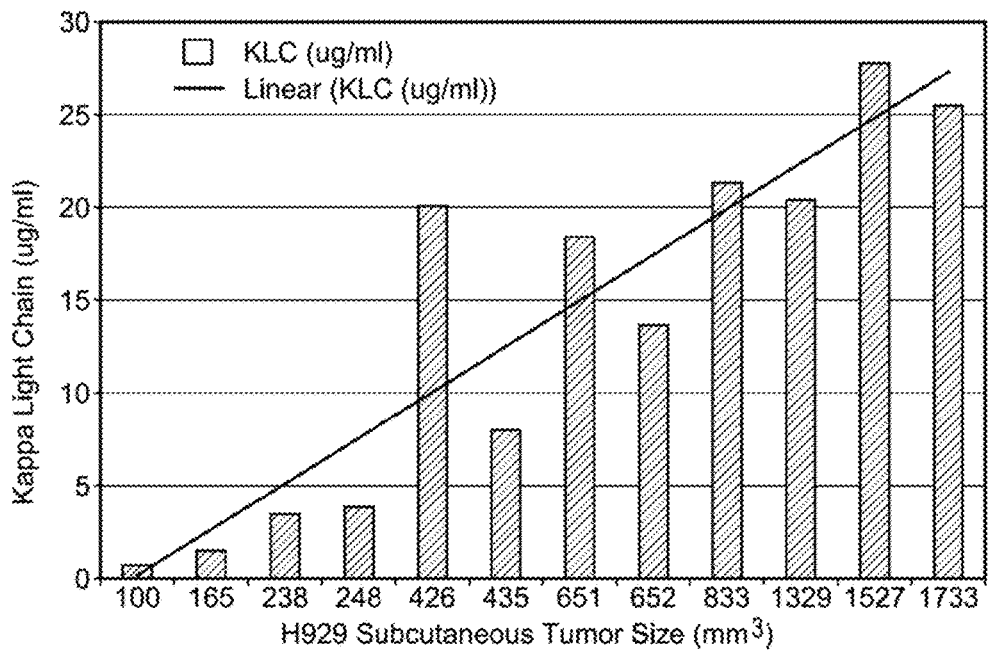
Figure 39:
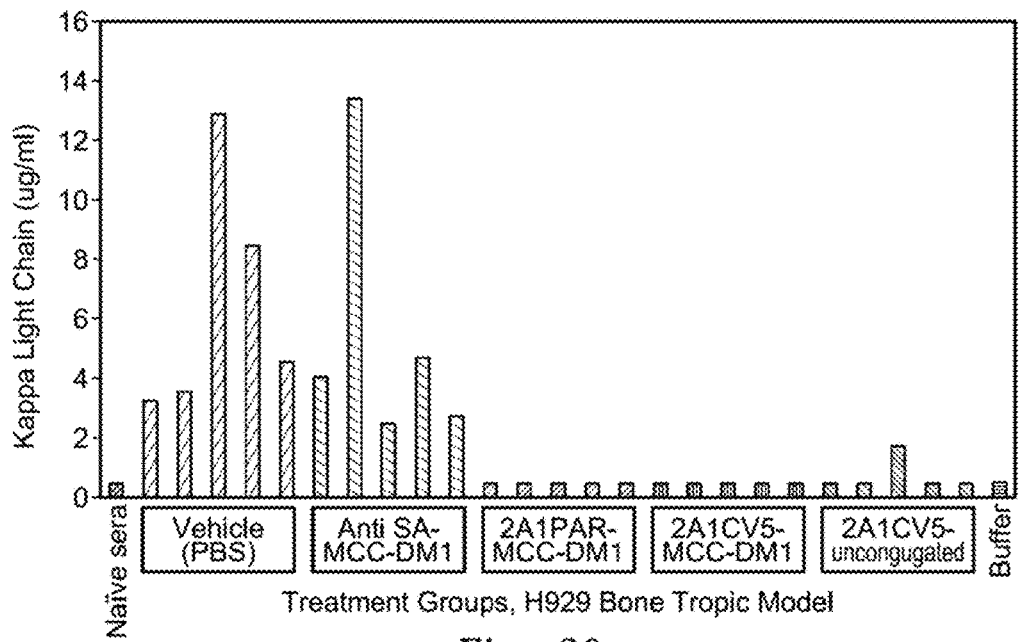
FIG. 39 show that kappa light chain is detected in sera from H929 xenografts, but not in sera from mice treated with 2A1CV5-MCC-DM1.

Human IgG free light chain (kappa) was investigated as a potential iomarker as part of the in vivo pharmacology of the Ab-1 (2A1CV5) ADC experiments showing that the Ab-1 (2A1CV5) ADC mediates tumor regression in an H929 bone-tropic xenograft model (see Example 12). Human immunoglobulin molecules consist of two heavy chains which define class (IgG, IgA, IgM, IgD, IgE) and identical light chains (kappa or lambda). In healthy individuals the majority of light chains in serum exist bound to heavy chains. Free Light Chains (FLC) are a natural product of B lymphocytes and represent a unique biomarker of neoplastic and reactive B cell related disorders. Increased FLC are associated with various malignant plasma disorders. Detection of FLC is an important diagnostic aid for a variety of diseases including multiple myeloma, smoldering myeloma and monoclonal gammopathy of undetermined significance. Human IgG FLC kappa ELISA (Biovendor, RD 194088100R-K) was used to analyze presence of FLC in sera from H929 xenografts. Kappa light chain antibodies were not detected in sera of mice 18 days after being treated with 2A1CV5-MCC-DM1, but were detected in sera of mice receiving vehicle (PBS) or isotype control conjugate (anti-Streptavidin-MCC-DM1) (see FIGS. 38 and 39). Therefore, measurement of antibody free gamma and kappa light chain in the serum (sFLC) may be used as a multiple myeloma biomarker in a diagnostic panel. One especially useful property of sFLC is their short half-life, which can allow clinicians to determine response to treatment within a few days (Davids M S, et al., Serum free light chain analysis. *Am J. Hematology* 85, 787-790 (2010)).

The antigen binding proteins of the invention can be used for diagnostic purposes to detect, diagnose, or monitor diseases and/or conditions associated with BCMA. The invention provides for the detection of the presence of BCMA in a sample using classical immunohistological methods known to those of skill in the art (e.g., Tijssen, 1993, *Practice and Theory of Enzyme Immunoassays*, vol 15 (Eds R. H. Burdon and P. H. van Knippenberg, Elsevier, Amsterdam); Zola, 1987, *Monoclonal Antibodies: A Manual of Techniques*, pp. 147-158 (CRC Press, Inc.); Jalkanen et al., 1985, *J. Cell. Biol.* 101:976-985; Jalkanen et al., 1987, *J. Cell Biol.* 105:3087-3096). The detection of BCMA can be performed in vivo or in vitro. Examples of methods useful in the detection of the presence of BCMA include ELISA, FACS, RIA, etc.

For diagnostic applications, the BCMA antigen binding protein is typically labeled with a detectable labeling group. Suitable labeling groups include, but are not limited to, the following: radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$), fluorescent groups (e.g., FITC, rhodamine, lanthanide phosphors), enzymatic groups (e.g., horseradish peroxidase, β-galactosidase, luciferase, alkaline phosphatase), chemiluminescent groups, biotinyl groups, or predetermined polypeptide epitopes recognized by a secondary reporter (e.g., leucine zipper pair sequences, binding sites for secondary antibodies, metal binding domains, epitope tags). In some embodiments, the labelling group is coupled to the antigen binding protein via spacer arms of various lengths to reduce potential steric hindrance. Various methods for labelling proteins are known in the art and may be used in performing the present invention.

One aspect of the invention provides for identifying a cell or cells that express BCMA. In a specific embodiment, the antigen binding protein is labeled with a labeling group and the binding of the labeled antigen binding protein to BCMA is detected. In a further specific embodiment, the binding of the antigen binding protein to BCMA detected in vivo. In a further specific embodiment, the antigen binding protein-BCMA is isolated and measured using techniques known in the art. See, for example, *Harlow and Lane*, 1988, *Antibodies: A Laboratory Manual*, New York: Cold Spring Harbor (ed. 1991 and periodic supplements); John E. Coligan, ed., 1993, *Current Protocols In Immunology* New York: John Wiley & Sons.

Another aspect of the invention provides for detecting the presence of a test molecule that competes for binding to BCMA with the antigen binding proteins of the invention. An example of one such assay would involve detecting the amount of free antigen binding protein in a solution containing an amount of BCMA in the presence or absence of the test molecule. An increase in the amount of free antigen binding protein (i.e., the antigen binding protein not bound to BCMA) would indicate that the test molecule is capable of competing for BCMA binding with the antigen binding protein. In one embodiment, the antigen binding protein is labeled with a labeling group. Alternatively, the test molecule is labeled and the amount of free test molecule is monitored in the presence and absence of an antigen binding protein.

Pharmaceutical Formulations, Routes of Administration

In some embodiments, the invention provides pharmaceutical compositions comprising a therapeutically effective amount of one or more of the antigen binding proteins of the invention together with a pharmaceutically acceptable diluent, carrier, solubilizer, emulsifier, preservative, and/or adjuvant. In addition, the invention provides methods of treating a patient by administering such pharmaceutical composition.

In some embodiments, the BCMA ADCs, particularly Ab-1 ADC, are pharmaceutical compositions comprising a therapeutically effective amount of at least one of the BCMA ADCs, particularly Ab-1 ADC, of described herein together with a pharmaceutically acceptable diluent, carrier, solubilizer, emulsifier, preservative, and/or adjuvant. In addition, the invention provides methods of treating a patient by administering such pharmaceutical composition.

Pharmaceutical compositions comprising the BCMA ADCs, particularly Ab-1 ADC, are as variously described herein may be used to treat B-cell related cancers wherein the malignant B-cells express BCMA on their surface. The BCMA ADC binds BCMA on the surface of malignant B-cells, is internalized by receptor-mediated endocytosis, releases the chemotherapeutic drug within the cell (typically via the acidic environment of the lysosome-endosome pathway) and thereby kills the malignant cell. Releasing the chemotherapeutic drug within the cell reduces bystander killing of non-malignant cells by free drug. Thus, pharmaceutical compositions comprising the BCMA ADCs, particularly Ab-1 ADC, as variously described herein may be used to treat diseases including, but are not limited to, B-cell cancers, and in particular multiple myeloma and malignant plasma cell neoplasms. The BCMA ADCs, particularly Ab-1 ADC, as variously described herein may also be used to treat Kahler's disease and Myelomatosis; Plasma cell leukemia; Plasmacytoma; B-cell prolymphocytic leukemia; Hairy cell leukemia; B-cell non-Hodgkin's lymphoma (NHL); Acute myeloid leukemia (AML); Chronic myeloid leukemia (CML); Acute lymphocytic leukemia (ALL); Chronic lymphocytic leukemia (CLL); Follicular lymphoma (including follicular non-Hodgkin's lymphoma types); Burkitt's lymphoma (Endemic Burkitt's lymphoma; Sporadic Burkitt's lymphoma); Marginal zone lymphoma (Mucosa-Associated Lymphoid Tissue; MALT/MALToma; Monocytoid B cell lymphoma; Splenic lymphoma with villous lymphocytes); Mantle cell lymphoma, Large cell lymphoma (Diffuse large cell Diffuse Mixed Cell; Immunoblastic Lymphoma, Primary Mediastinal B Cell Lymphoma; Angiocentric Lymphoma—pulmonary B cell); Small lymphocytic lymphoma (SLL); Precursor B-lymphoblastic lymphoma; Myeloid leukemia (granulocytic; myelogenous; Acute myeloid leukemia; Chronic myeloid leukemia; Subacute myeloid leukemia; Myeloid sarcoma; Chloroma; Granulocytic sarcoma; Acute promyelocytic leukemia; Acute myelomonocytic leukemia); Waldenstrom's macroglobulinemia, or other B-cell lymphoma.

In addition, pharmaceutical compositions comprising the BCMA ADCs, particularly Ab-1, Ab-2, or Ab-3 ADC, and more particularly Ab-1 ADC, as variously described herein, may be used in treat autoimmune disorders wherein the antibodies produced by plasma cells contribute to the immunopathogenesis of the disease, such as but not limited to, systemic lupus erythematosus (SLE), rheumatoid arthritis (RA), multiple sclerosis (MS), Sjogrens, immune-mediated thrombocytopenia, haemolytic anaemia, bullous pemphigoid, myasthenia gravis, Type I diabetes mellitus, Graves' disease, Addison's disease, pemphigus foliaceus, psoriasis, psoriatic arthritis, and ankylosing spondylitis. In other embodiments, pharmaceutical compositions comprising the anti-huBCMA antibodies without being conjugated to a drug may be used to treat the autoimmune diseases listed in this paragraph, particularly Ab-1, Ab-2, or Ab-3, and more particularly Ab-1, as variously described herein. More particularly, pharmaceutical compositions comprising Ab-1 may be used to treat SLE. More particularly, pharmaceutical compositions comprising Ab-1 may be used to treat MS.

In certain embodiments, acceptable formulation materials preferably are nontoxic to recipients at the dosages and concentrations employed. In certain embodiments, the pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, poly sorbates such as polysorbate 20, polysorbate, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. See, REMINGTON'S PHARMACEUTICAL SCIENCES, 18" Edition, (A. R. Genrmo, ed.), 1990, Mack Publishing Company.

In certain embodiments, the optimal pharmaceutical composition will be determined by one skilled in the art depending upon, for example, the intended route of administration, delivery format and desired dosage. See, for example, REMINGTON'S PHARMACEUTICAL SCIENCES, supra. In certain embodiments, such compositions may influence the physical state, stability, rate of in vivo release and rate of in vivo clearance of the antigen binding proteins of the invention. In certain embodiments, the primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. In specific embodiments, pharmaceutical compositions comprise Tris buffer of about pH 7.0-8.5, or acetate buffer of about pH 4.0-5.5, and may further include sorbitol or a suitable substitute therefor. In certain embodiments of the invention, BCMA antigen binding protein compositions may be prepared for storage by mixing the selected composition having the desired degree of purity with optional formulation agents (REMINGTON'S PHARMACEUTICAL SCIENCES, supra) in the form of a lyophilized cake or an aqueous solution. Further, in certain embodiments, the BCMA antigen binding protein product may be formulated as a lyophilizate using appropriate excipients such as sucrose.

The pharmaceutical compositions of the invention can be selected for parenteral delivery. Alternatively, the compositions may be selected for inhalation or for delivery through the digestive tract, such as orally. Preparation of such pharmaceutically acceptable compositions is within the skill of the art.

The formulation components are present preferably in concentrations that are acceptable to the site of administration. In certain embodiments, buffers are used to maintain the composition at physiological pH or at a slightly lower pH, typically within a pH range of from about 5 to about 8.

When parenteral administration is contemplated, the therapeutic compositions for use in this invention may be provided in the form of a pyrogen-free, parenterally acceptable aqueous solution comprising the desired BCMA antigen binding protein in a pharmaceutically acceptable vehicle. A particularly suitable vehicle for parenteral injection is sterile distilled water in which the BCMA antigen binding protein is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that may provide controlled or sustained release of the product which can be delivered via depot injection. In certain embodiments, hyaluronic acid may also be used, having the effect of promoting sustained duration in the circulation. In certain embodiments, implantable drug delivery devices may be used to introduce the desired antigen binding protein.

Pharmaceutical compositions of the invention can be formulated for inhalation. In these embodiments, BCMA antigen binding proteins are advantageously formulated as a dry, inhalable powder. In specific embodiments, BCMA antigen binding protein inhalation solutions may also be formulated with a propellant for aerosol delivery. In certain embodiments, solutions may be nebulized. Pulmonary administration and formulation methods therefore are further described in International Patent Application No. PCT/US94/001875, which is incorporated by reference and describes pulmonary delivery of chemically modified proteins. It is also contemplated that formulations can be administered orally. BCMA antigen binding proteins that are administered in this fashion can be formulated with or without carriers customarily used in the compounding of solid dosage forms such as tablets and capsules. In certain embodiments, a capsule may be designed to release the active portion of the formulation at the point in the gastrointestinal tract when bioavailability is maximized and presystemic degradation is minimized Additional agents can be included to facilitate absorption of the BCMA antigen binding protein. Diluents, flavorings, low melting point waxes, vegetable oils, lubricants, suspending agents, tablet disintegrating agents, and binders may also be employed.

A pharmaceutical composition of the invention is preferably provided to comprise an effective quantity of one or a plurality of BCMA antigen binding proteins in a mixture with non-toxic excipients that are suitable for the manufacture of tablets. By dissolving the tablets in sterile water, or another appropriate vehicle, solutions may be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving BCMA antigen binding proteins in sustained- or controlled-delivery formulations. Techniques for formulating a variety of other sustained- or controlled-delivery means, such as liposome carriers, bio-erodible microparticles or porous beads and depot injections, are also known to those skilled in the art. See, for example, International Patent Application No. PCT/US93/00829, which is incorporated by reference and describes controlled release of porous polymeric microparticles for delivery of pharmaceutical compositions. Sustained-release preparations may include semipermeable polymer matrices in the form of shaped articles, e.g., films, or microcapsules. Sustained release matrices may include polyesters, hydrogels, polylactides (as disclosed in U.S. Pat. No. 3,773,919 and European Patent Application Publication No. EP 058481, each of which is incorporated by reference), copolymers of L-glutamic acid and gamma ethyl-L-glutamate (Sidman et al., 1983, *Biopolymers* 2:547-556), poly (2-hydroxyethyl-inethacrylate) (Langer et al., 1981, *J. Biomed. Mater. Res.* 15:167-277 and Langer, 1982, *Chem.*

*Tech.* 12:98-105), ethylene vinyl acetate (Langer et al., 1981, supra) or poly-D(-)-3-hydroxybutyric acid (European Patent Application Publication No. EP 133,988). Sustained release compositions may also include liposomes that can be prepared by any of several methods known in the art. See, e.g., Eppstein et al., 1985, *Proc. Natl. Acad. Sci. U.S.A.* 82:3688-3692; European Patent Application Publication Nos. EP 036,676; EP 088,046 and EP 143,949, incorporated by reference.

Pharmaceutical compositions used for in vivo administration are typically provided as sterile preparations. Sterilization can be accomplished by filtration through sterile filtration membranes. When the composition is lyophilized, sterilization using this method may be conducted either prior to or following lyophilization and reconstitution. Compositions for parenteral administration can be stored in lyophilized form or in a solution. Parenteral compositions generally are placed into a container having a sterile access port, for example, an intravenous solution bag or vial having a stopper pierceable by a hypodermic injection needle.

A variety of expositions are available on protein stabilization and formulation materials and methods useful in this regard, such as Arakawa et al., "Solvent interactions in pharmaceutical formulations," *Pharm Res.* 8(3): 285-91 (1991); Kendrick et al., "Physical stabilization of proteins in aqueous solution," in: RATIONAL DESIGN OF STABLE PROTEIN FORMULATIONS: THEORY AND PRACTICE, Carpenter and Manning, eds. *Pharmaceutical Biotechnology.* 13: 61-84 (2002), and Randolph et al., "Surfactant-protein interactions," *Pharm Biotechnol.* 13: 159-75 (2002), each of which is herein incorporated by reference in its entirety, particularly in parts pertinent to excipients and processes of the same for self-buffering protein formulations in accordance with the current invention, especially as to protein pharmaceutical products and processes for veterinary and/or human medical uses.

Various excipients useful in the invention are listed in TABLE 3 and further described below.

TABLE 3

Types of Excipients and Their Functions

| Type | Function | |
| --- | --- | --- |
| | Liquids | Lyophilates |
| Tonicity Agents/ Stabilizers | Provides isotonicity to the formulation such that it is suitable for injection<br>Examples include polyols, salts, and amino acids<br>Help maintain the protein in a more compact state (polyols)<br>Minimize electrostatic, solution protein-protein interactions (salts) | Stabilizers include cryo and lyoprotectants<br>Examples include polyols, sugars and polymers<br>Cryoprotectants protect proteins from freezing stresses<br>Lyoprotectants stabilize proteins in the freeze-dried state |
| Bulking Agents | Not applicable | Used to enhance product elegance and to prevent blowout<br>Provides structural strength to the lyo cake<br>Examples include mannitol and glycine |
| Surfactants | Prevent/control aggregation, particle formation and surface adsorption of drug<br>Examples include polysorbate 20 and 80 | Employed if aggregation during the lyophilization process is an issue<br>May serve to reduce reconstitution times<br>Examples include polysorbate 20 and 80 |
| Anti-oxidants | Control protein oxidation | Usually not employed, molecular reactions in the lyophilized cake are greatly retarded |
| Metal Ions/ Chelating Agents | A specific metal ion is included in a liquid formulation only as a co-factor<br>Divalent cations such as zinc and magnesium are utilized in suspension formulations<br>Chelating agents are used to inhibit heavy metal ion catalyzed reactions | May be included if a specific metal ion is included only as a co-factor<br>Chelating agents are generally not needed in lyophilized formulations |

TABLE 3-continued

Types of Excipients and Their Functions

| | Function | |
|---|---|---|
| Type | Liquids | Lyophilates |
| Preservatives | Important particularly for multi-dose formulations<br>Protects against microbial growth,<br>Example: benzyl alcohol | For multi-dose formulations only<br>Provides protection against microbial growth in formulation<br>Is usually included in the reconstitution diluent (e.g. bWFI) |

Salts may be used in accordance with certain embodiments of the invention to, for example, adjust the ionic strength and/or the isotonicity of a formulation and/or to improve the solubility and/or physical stability of a protein. Salts may also be effective for reducing the viscosity of protein formulations and can be used in the invention for that purpose. As is well known, ions can stabilize the native state of proteins by binding to charged residues on the protein's surface and by shielding charged and polar groups in the protein and reducing the strength of their electrostatic interactions, attractive, and repulsive interactions. Ions also can stabilize the denatured state of a protein by binding to, in particular, the denatured peptide linkages (—CONH) of the protein. Furthermore, ionic interaction with charged and polar groups in a protein also can reduce intermolecular electrostatic interactions and, thereby, prevent or reduce protein aggregation and insolubility.

Ionic species differ significantly in their effects on proteins. A number of categorical rankings of ions and their effects on proteins have been developed that can be used in formulating self-buffering protein compositions in accordance with the invention. One example is the Hofmeister series, which ranks ionic and polar non-ionic solutes by their effect on the conformational stability of proteins in solution. Stabilizing solutes are referred to as "kosmotropic." Destabilizing solutes are referred to as chaotropic. Kosmotropes commonly are used at high concentrations (e.g., >1 molar ammonium sulfate) to precipitate proteins from solution ("salting-out"). Chaotropes commonly are used to denture and/or to solubilize proteins ("salting-in"). The relative effectiveness of ions to "salt-in" and "salt-out" defines their position in the Hofmeister series.

In order to maintain isotonicity in a parenteral formulation in accordance with preferred embodiments of the invention, improve protein solubility and/or stability, improve viscosity characteristics, avoid deleterious salt effects on protein stability and aggregation, and prevent salt-mediated protein degradation, the salt concentration in formulations may be less than 150 mM (as to monovalent ions) and 150 mEq/liter for multivalent ions. In this regard, in certain particularly preferred embodiments of the invention, the total salt concentration is from about 75 mEq/L to about 140 mEq/L.

Free amino acids, such as but not limited to, lysine, proline, serine, and alanine can be used for stabilizing proteins in a formulation can be used in BCMA ADC formulations as bulking agents, stabilizers, and antioxidants, as well as other standard uses. Glycine is useful in lyophilization to ensure correct cake structure and properties. Arginine may be useful to inhibit protein aggregation, in both liquid and lyophilized formulations. Methionine is useful as an antioxidant.

Polyols include sugars, e.g., mannitol, sucrose, and sorbitol and polyhydric alcohols such as, for instance, glycerol and propylene glycol, and, for purposes of discussion herein, polyethylene glycol (PEG) and related substances. Polyols are kosmotropic. They are useful stabilizing agents in both liquid and lyophilized formulations to protect proteins from physical and chemical degradation processes. Polyols also are useful for adjusting the tonicity of formulations.

Among polyols useful in select embodiments of the invention is mannitol, commonly used to ensure structural stability of the cake in lyophilized formulations. It ensures structural stability to the cake. It is generally used with a lyoprotectant, e.g., sucrose. Sorbitol and sucrose are among preferred agents for adjusting tonicity and as stabilizers to protect against freeze-thaw stresses during transport or the preparation of bulks during the manufacturing process.

Embodiments of BCMA ADC formulations may optionally further comprise surfactants. Protein molecules may be susceptible to adsorption on surfaces and to denaturation and consequent aggregation at air-liquid, solid-liquid, and liquid-liquid interfaces. These effects generally scale inversely with protein concentration. These deleterious interactions generally scale inversely with protein concentration and typically are exacerbated by physical agitation, such as that generated during the shipping and handling of a product. Surfactants routinely are used to prevent, minimize, or reduce surface adsorption. Useful surfactants in the invention in this regard include polysorbate 20, polysorbate 80, other fatty acid esters of sorbitan polyethoxylates, and poloxamer 188. Surfactants also are commonly used to control protein conformational stability. The use of surfactants in this regard is protein-specific since, any given surfactant typically will stabilize some proteins and destabilize others. Polysorbates are susceptible to oxidative degradation and often, as supplied, contain sufficient quantities of peroxides to cause oxidation of protein residue side-chains, especially methionine. Consequently, polysorbates should be used carefully, and when used, should be employed at their lowest effective concentration. In this regard, polysorbates exemplify the general rule that excipients should be used in their lowest effective concentrations.

Embodiments of BCMA ADC formulations may optionally further comprise one or more antioxidants. To some extent deleterious oxidation of proteins can be prevented in pharmaceutical formulations by maintaining proper levels of ambient oxygen and temperature and by avoiding exposure to light. Antioxidant excipients can be used as well to prevent oxidative degradation of proteins. Among useful antioxidants in this regard are reducing agents, oxygen/free-radical scavengers, and chelating agents. Antioxidants for use in therapeutic protein formulations in accordance with the invention preferably are water-soluble and maintain their activity throughout the shelf life of a product. Antioxidants can damage proteins. For instance, reducing agents, such as glutathione in particular, can disrupt intramolecular disulfide linkages. Thus, antioxidants for use in the invention are selected to, among other things, eliminate or sufficiently reduce the possibility of themselves damaging proteins in the formulation.

Formulations in accordance with the invention may include metal ions that are protein co-factors and that are necessary to form protein coordination complexes. Metal ions also can inhibit some processes that degrade proteins.

Embodiments of BCMA ADC formulations may optionally further comprise one or more preservatives. Preservatives are necessary when developing multi-dose parenteral formulations that involve more than one extraction from the same container. Their primary function is to inhibit microbial growth and ensure product sterility throughout the shelf-life or term of use of the drug product. Commonly used preservatives include benzyl alcohol, phenol and m-cresol. Several aspects need to be considered during the formulation and development of preserved dosage forms. The effective preservative concentration in the drug product must be optimized. This requires testing a given preservative in the dosage form with concentration ranges that confer antimicrobial effectiveness without compromising protein stability.

Development of liquid formulations containing preservatives may be more challenging than lyophilized formulations. Freeze-dried products can be lyophilized without the preservative and reconstituted with a preservative containing diluent at the time of use. This shortens the time for which a preservative is in contact with the protein, significantly minimizing the associated stability risks. With liquid formulations, preservative effectiveness and stability have to be maintained over the entire product shelf-life (~18 to 24 months). An important point to note is that preservative effectiveness has to be demonstrated in the final formulation containing the active drug and all excipient components.

Once the pharmaceutical composition has been formulated, it may be stored in sterile vials as a solution, suspension, gel, emulsion, solid, crystal, or as a dehydrated or lyophilized powder. Such formulations may be stored either in a ready-to-use form or in a form (e.g., lyophilized) that is reconstituted prior to administration. The invention also provides kits for producing a single-dose administration unit. The kits of the invention may each contain both a first container having a dried protein and a second container having an aqueous formulation. In certain embodiments of this invention, kits containing single and multi-chambered pre-filled syringes (e.g., liquid syringes and lyosyringes) are provided.

The therapeutically effective amount of a BCMA ADC-containing pharmaceutical composition to be employed will depend, for example, upon the therapeutic context and objectives. One skilled in the art will appreciate that the appropriate dosage levels for treatment will vary depending, in part, upon the molecule delivered, the indication for which the BCMA ADC is being used, the route of administration, and the size (body weight, body surface or organ size) and/or condition (the age and general health) of the patient. In certain embodiments, the clinician may titer the dosage and modify the route of administration to obtain the optimal therapeutic effect. A typical dosage may range from about 0.1 µg/kg to up to about 30 mg/kg or more, depending on the factors mentioned above.

Dosing frequency will depend upon the pharmacokinetic parameters of the particular BCMA ADC in the formulation used. Typically, a clinician administers the composition until a dosage is reached that achieves the desired effect. The composition may therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages may be ascertained through use of appropriate dose-response data. In certain embodiments, the antigen binding proteins of the invention can be administered to patients throughout an extended time period.

The route of administration of the pharmaceutical composition is in accord with known methods, e.g., orally, through injection by intravenous, intraperitoneal, intracerebral (intra-parenchymal), intracerebroventricular, intramuscular, intra-ocular, intraarterial, intraportal, or intralesional routes; by sustained release systems or by implantation devices. In certain embodiments, the compositions may be administered by bolus injection or continuously by infusion, or by implantation device. The composition also may be administered locally via implantation of a membrane, sponge or another appropriate material onto which the desired molecule has been absorbed or encapsulated. In certain embodiments, where an implantation device is used, the device may be implanted into any suitable tissue or organ, and delivery of the desired molecule may be via diffusion, timed-release bolus, or continuous administration.

All references cited within the body of the instant specification are hereby expressly incorporated by reference in their entirety.

EXAMPLES

The following examples, including the experiments conducted and the results achieved, are provided for illustrative purposes only and are not to be construed as limiting the invention.

Example 1

A comprehensive analysis was performed of BCMA mRNA expression in multiple myeloma, smoldering myeloma and MGUS patient samples in addition to normal tissues that contain resident plasma cells including bone marrow and gut samples from normal individuals. BCMA mRNA expression results were obtained via in silico analysis by interrogating in tumor DNA microarray databases available to Amgen including Oncomine/Oncomine Power Tools and Ascenta™. In the Oncomine™ data set there were 994 primary multiple myeloma samples that were examined for BCMA expression and of those only 5 samples did not express detectable BCMA mRNA signal levels (the signal was at the limit of detection and the same as the signal observed in non-B lineage tissues including melanoma and skin that were consistent with the background levels and are tissues that are known not to express BCMA).

Figure 3:
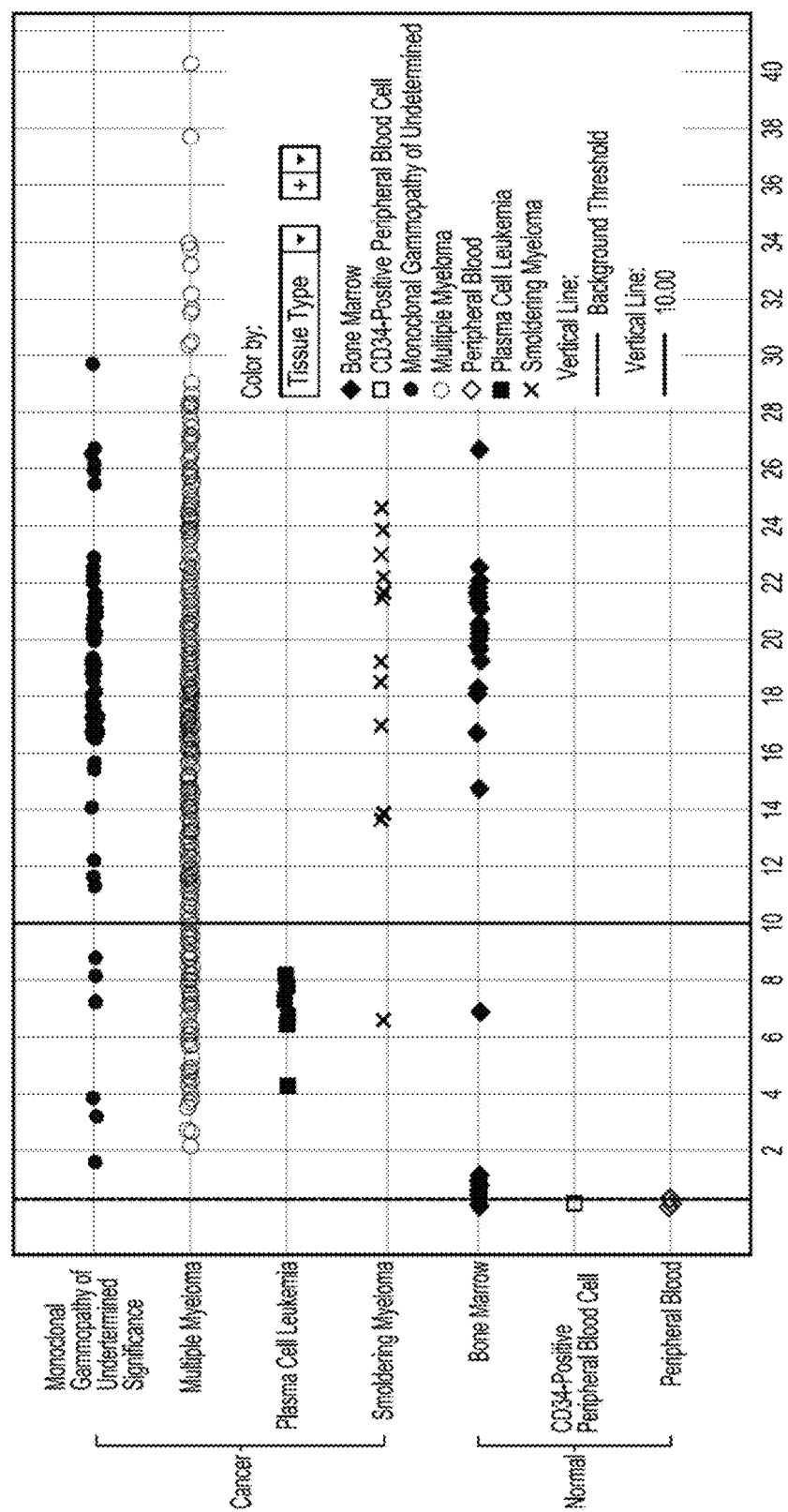
FIG. 3 shows that BCMA mRNA is expressed on >99% of multiple myeloma patient samples.

The results show that BCMA mRNA is highly expressed in multiple myeloma. FIG. 3 shows a scatter plot generated using commercially available Oncomine Power Tools from Compendia Bioscience, (acquired by Life Technologies). The expression plot was constructed using 12 datasets (GSE4452, GSE9782, GSE2912, GSE17498, GSE5788, GSE2361, GSE2113, GSE3526, GSE1133, GSE1159, GSE2658, GSE5900,) and two Affymetrix-based platforms (Human Genome U133 Plus 2.0 Array & Human Genome U133A Array.) BCMA (HUGO Symbol: TNFRSF17) linear expression was determined using the Affymetrix Probeset 206641 and measured across seven Tissue Types (Bone Marrow, CD34+ Peripheral Blood Cell, Monoclonal Gammopathy of Undetermined Significance, Multiple Myeloma, Peripheral Blood, Plasma Cell Leukemia and Smoldering Myeloma) and four sample types (Bone Marrow Aspirate, Bone Marrow Specimen, Peripheral Blood Specimen and Tissue Specimen).

Data Processing and Normalization:

Samples were measured on arrays yielding single intensity values. A common reference was not used. Author-provided data files often have been MAS4, MAS5, or RMA processed. When MAS5 data was incorporated, all expression values are included and absent/present calls were ignored. The median value per microarray experiment was scaled to zero by subtracting the median from each value. This step was performed to remove bias in signal intensity between samples. This assumes that the median expression level was nearly the same between samples and that every sample had an equal number of genes expressed above and below the median. This standardized the median across samples.

Linear Scale Interpretation:

Median=1. Fold change was interpreted "x-axis units"— fold above the median gene expression. For example, a linear scale value of 30 is 30-fold greater than median gene expression of 1.

This data shows that BCMA mRNA is highly expressed in multiple myeloma, soldering myeloma, as well as monoclonal gammopathy of undetermined significance. This data shows that BCMA mRNA is expressed on >99% of multiple myeloma patient samples (85% (796/934) of multiple myeloma samples had a linear expression value of greater than 10). This data shows that BCMA is a highly desirable receptor protein for targeting for the treatment of the aforementioned and other cancers described herein using the BCMA antibodies and ADCs as variously described herein.

Example 2

The development of fully human monoclonal antibodies directed against human BCMA was carried out using Abgenix (now Amgen Fremont Inc.) XenoMouse® technology (U.S. Pat. Nos. 6,114,598; 6,162,963; 6,833,268; 7,049,426; 7,064,244, which are incorporated herein by reference in their entirety; Green et al, 1994, *Nature Genetics* 7:13-21; Mendez et al., 1997, *Nature Genetics* 15:146-156; Green and Jakobovitis, 1998, *J. Ex. Med.* 188:483-495)).

Figure 4A:
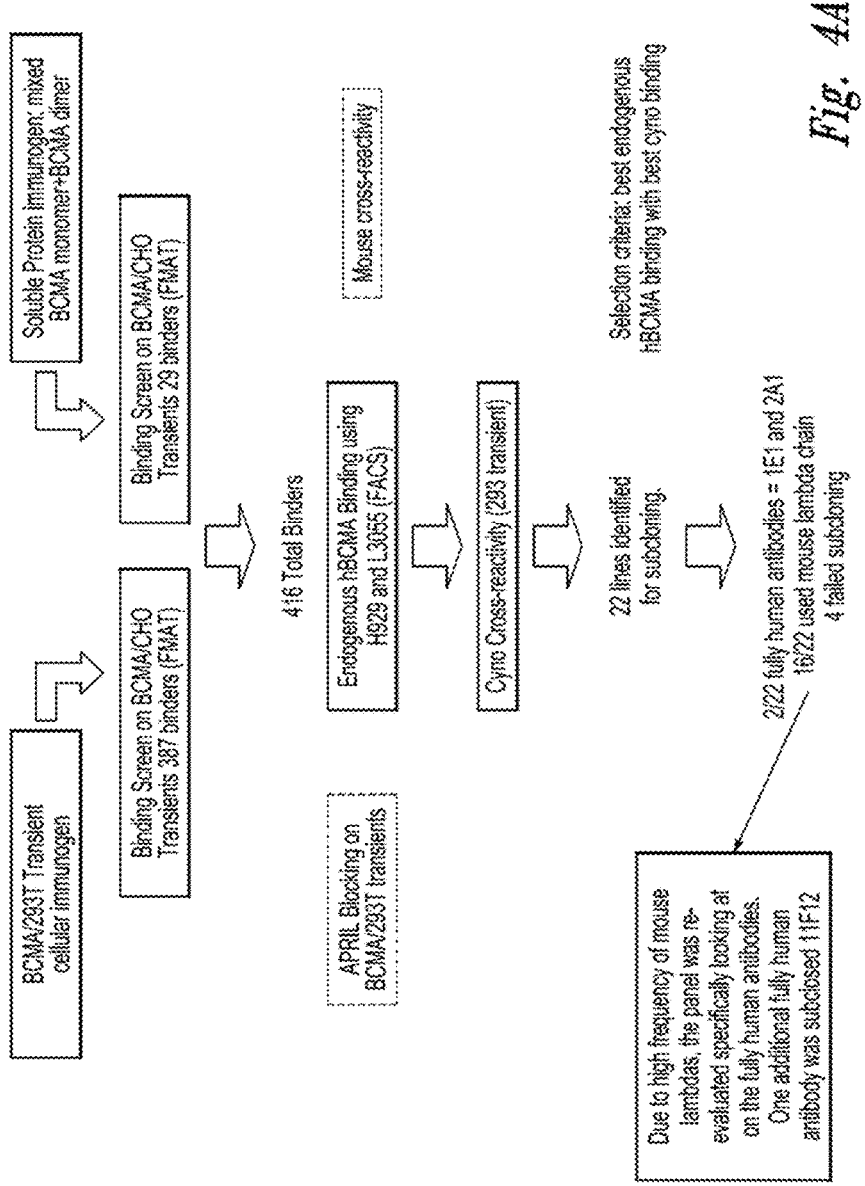
FIGS. 4A and B are schematics of the monoclonal antibody generation, screening, and characterization for the two campaigns.

First Campaign Overview:

An overview is provided in FIG. 4A. XenoMouse® animals were immunized with either 293T/BCMA transiently-expressing cells or a mix of soluble huBCMA proteins containing both a monomeric and dimeric form of huBCMA. Hybridomas were generated and antigen specific binders were identified by FMAT on CHO/BCMA transient cells. The panel of 416 binders was screened for binding to endogenous huBCMA using human H929 and L3055 cell lines. Additional cynomolgus cross-reactivity data was generated using FACs analysis on 293/cyno BCMA transient cells. A lead panel of 22 hybridoma lines were identified by ranking the antibodies by best binding to endogenous human BCMA, and then secondly, by the best cross-reactivity to cynomolgus receptor. This lead panel advanced to subcloning, scale-up, sequencing, and purification. In parallel, the panel of 416 binders was evaluated for APRIL blocking and also cross-reactivity to murine BCMA. Of the 22 hybridoma lines, only three antibodies were fully human, (parental Ab-1 (i.e., 2A1), parental Ab-4 (i.e., 1E1), and parental Ab-6 (i.e., 11F12), the remaining were a combination of human heavy chain and mouse light chain chimerics, three of which failed subcloning. Three antibodies parental Ab-1 (2A1), parental Ab-4 (1E1), and parental Ab-6 (11F12) were recombinantly cloned as IgG1 antibodies. This data demonstrates that creating fully human antibodies with the desirable attributes was not routine and predictable.

Figure 4B:
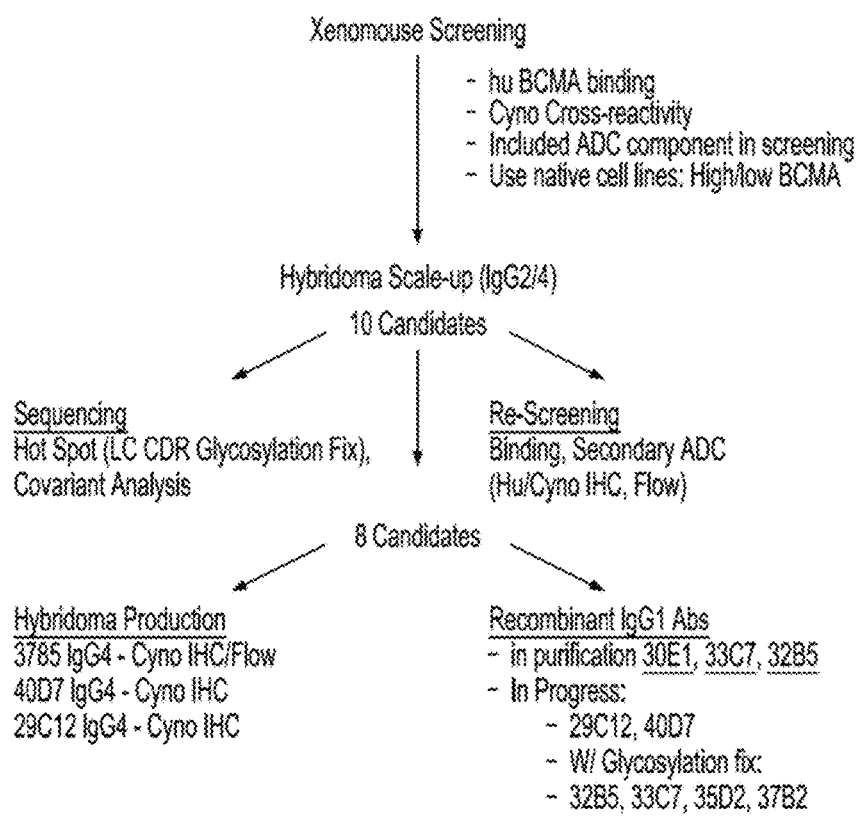
Figure 6:
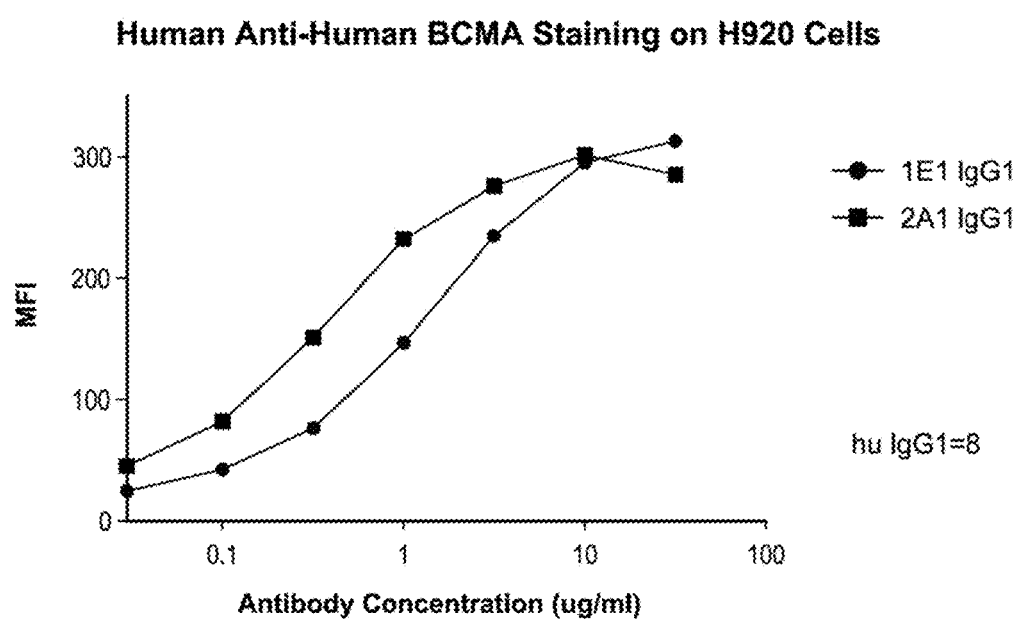
FIG. 6 shows binding of the 2A1 and 1E1 mAbs to the myeloma cell line H929.

Second Campaign Overview:

An overview is provided in FIG. 4B Immunogens and primary screening were the same as for the first campaign. The second campaign yielded a panel of 581 antibodies with specific binding to human BCMA. This panel was tested for cross-reactivity to cynomolgus BCMA by FACs. The cynomolgus cross-reactivity data was used to select 90 antibodies with detectable cynomolgus cross-reactivity. This subset of 90 was tested for binding to TACI and BAFF-R by FACs using transient expression system. Antibodies with any detectable level of binding were eliminated. The 90 antibodies were screened for light chain usage and those with murine lambda light chain were eliminated. These secondary screens resulted in the identification of 45 out of 90 antibodies that were fully human IgGs and selective for human BCMA over TACI and BAFFR. This panel of 45 antibodies was then further refined by using the cynomolgus BCMA FACs data to rank order the panel by degree of cyno binding. The 30 best cyno cross-reactive binders were then advanced to subcloning, scale-up, sequencing, and purification. Included was an additional cell viability screen to identify ADC competent Abs. Here, an anti-huFc secondary antibody conjugated with SMCC-DM1 was utilized in place of direct DM1 conjugation. An initial set of seven antibodies with similar cladding properties met the screening criteria and were recombinantly cloned out in an IgG1 format. A panel of binders (to human and cynomolgus BCMA) were advanced for recombinant cloning (32B5, 37B2, 35D2, 29C12, 40D7, 33C7). Hotspot repair was initiated, fixing an N-linked glycosylation site and covariance violations. Selection of hotspot repaired antibodies included, expression and purification characteristics, FACS evaluation of cell surface binding, ADC conjugation and cell viability assays. The apparent affinity to cell surface expressed BCMA is lower than 2A1 and the ADC potency of 2A1CV5-MCC-DM1 is 2 to 3 fold improved over that observed for 32B5 or 29C12-MCC-DM1. Two sequence-related engineered antibodies (29C12.V1 and 32B5.V1) were identified as having the unique and desirable attributes for generating ADCs and pharmaceutical compositions.

Immunization:

Fully human antibodies to BCMA were generated using XenoMouse® technology, transgenic mice engineered to express diverse repertoires of fully human IgGK and IgG antibodies of the corresponding isotype (Mendez, M. J., et al., (1997) *Nature genetics* 15, 146-156; Kellermann, S A., et al., (2002) *Current opinion in biotechnology* 13, 593-597). XMG1-KL, XMG2-K, XMG2-KL, XMG4-KL strains of mice were immunized with two forms of BCMA immunogen; 293T transfectants expressing full length human BCMA and purified BCMA soluble protein. The BCMA soluble protein immunogen consisted of a mix of two forms; BCMA expressed as a monomeric ectodomain with an avi-His tag and BCMA expressed as a human Fc linked homo-dimer. Soluble protein was immunized at doses of 10 μg/mouse for the first boost and subsequent boosts were administered at doses of five μg/mouse of soluble BCMA (at a monomer:dimer ratio of 1:1). Cellular immunogen was dosed at $4.0\times10^6$ BCMA transfected cells/mouse and subsequent boosts were of $2.0\times10^6$ BCMA transfected cells/mouse. Injection sites used were combinations of subcutaneous base-of-tail and intraperitoneal. Adjuvants used were TiterMax Gold (Sigma; cat. #T2684), Alum (E. M. Sergent Pulp and Chemical Co., Clifton, N.J., cat. #1452-250) were prepared according to manufacturers' instructions and mixed in a 1:1 ratio of adjuvant emulsion to antigen solution. Mice were immunized over a period of 4 to 12 weeks with a range of 11-17 boosts.

Sera were collected at approximately 5 and 9 weeks after the first injection and specific titers were determined by FACs staining of recombinant BCMA receptor transiently expressed on CHO—S cells. A total of 38 animals were identified with specific immune responses, these animals were pooled into 6 groups and advanced to antibody generation.

Preparation of Monoclonal Antibodies:

Draining lymph nodes and spleens were harvested from immune animals and pooled for each cohort. Lymphocytes and splenocytes were dissociated from tissue in a suitable medium (for example, Dulbecco's Modified Eagle Medium; DMEM; obtainable from Invitrogen, Carlsbad, Calif.) to release the cells from the tissues, and suspended in DMEM. B cells were selected and/or expanded using a suitable method, and fused with suitable fusion partner, for example, nonsecretory myeloma P3X63Ag8.653 cells (American Type Culture Collection CRL 1580; Kearney et al, *J. Immunol.* 123, 1979, 1548-1550).

B cells were mixed with fusion partner cells at a ratio of 1:4. The cell mixture was gently pelleted by centrifugation at 400×g for 4 minutes, the supernatant decanted, and the cell mixture gently mixed by using a 1 ml pipette. Fusion was induced with PEG/DMSO (polyethylene glycol/dimethyl sulfoxide; obtained from Sigma-Aldrich, St. Louis Mo.; 1 ml per million of lymphocytes). PEG/DMSO was slowly added with gentle agitation over one minute followed, by one minute of mixing. IDMEM (DMEM without glutamine; 2 ml per million of B cells), was then added over 2 minutes with gentle agitation, followed by additional IDMEM (8 ml per million B-cells) which was added over 3 minutes.

The fused cells were gently pelleted (400×g 6 minutes) and resuspended in 20 ml Selection media (for example, DMEM containing Azaserine and Hypoxanthine [HA] and other supplemental materials as necessary) per million B-cells. Cells were incubated for 20-30 minutes at 37° C. and then resuspended in 200 ml Selection media and cultured for three to four days in T175 flasks prior to 96-well plating.

Cells were distributed into 96-well plates using standard techniques to maximize clonality of the resulting colonies. After several days of culture, the hybridoma supernatants were collected and subjected to screening assays as detailed in the examples below, including confirmation of binding to human BCMA receptor, identification of APRIL blocking antibodies by a ligand binding competition assay and evaluation of cross-reactivity with other receptors related to BCMA receptor (for example, TACI and BAFF receptors). Hybridoma lines that were identified to have the binding properties for interest were then further selected and subjected to standard cloning and subcloning techniques. Clonal lines were expanded in vitro, and the secreted human antibodies obtained for analysis and V gene sequencing was performed.

Selection of BCMA Receptor Specific Binding Antibodies by FMAT:

After 14 days of culture, hybridoma supernatants were screened for BCMA-specific monoclonal antibodies by Fluorometric Microvolume Assay Technology (FMAT) (Applied Biosystems, Foster City, Calif.). The supernatants were screened against CHO—S cells transiently transfected with human BCMA and counter screened against CHO—S cells transiently transfected with the same expression plasmid that did not contain the BCMA gene.

Briefly, the cells in Freestyle media (Invitrogen, Carlsbad, Calif.) were seeded into 384-well FMAT plates in a volume of 50 μL/well at a density of approximately 4000 cells/well for the stable transfectants, and at a density of approximately 16,000 cells/well for the parental cells, and cells were incubated overnight at 37° C. Then, 10 μL/well of supernatant was added and plates were incubated for approximately one hour at 4° C., after which 10 μL/well of anti-human IgG-Cy5 secondary antibody (Jackson Immunoresearch, West Grove, Pa.) was added at a concentration of 2.8 μg/ml (400 ng/ml final concentration). Plates were then incubated for one hour at 4° C., and fluorescence was read using an FMAT macroconfocal scanner (Applied Biosystems, Foster City, Calif.).

After multiple screening campaigns a panel of 897 anti-BCMA binding hybridoma lines were identified and advanced to further characterization assays.

Additional Binding Characterization by Flow Cytometry (FACs):

FACS binding assays were performed to evaluate the binding of the anti-BCMA receptor specific antibodies to endogenous BCMA receptor expressed on H929 and L3055 tumor cell lines. In addition, cross-reactive binding to murine and cynomolgus monkey BCMA orthologues and also binding to related B cell receptors; TACI and BAFF-R was also evaluated by FACs using recombinant forms of the various receptors transiently expressed on 293T cells.

FACs assays were performed by incubating hybridoma supernatants with 10,000 to 25,000 cells at 4° C. for one hour followed by two washes with PBS/2% FBS. Cells were then treated with florochrome-labeled secondary antibodies at 4° C. followed by two washes. The cells were resuspended in 50 ul of PBS/2% FBS and antibody binding was analyzed using a FACSCalibur™ instrument.

Identification of Blocking Antibodies by Ligand Binding Competition Assay By FACS:

A ligand binding competition method was developed to identify antibodies (in the hybridoma supernatants) that bind BCMA receptor and block APRIL ligand binding. In 96-well V-bottom plates (Sarstedt #82.1583.001), 50,000 transiently transfected 293T cells were incubated with 15 μl of anti-BCMA hybridoma supernatant for 1 hr at 4° C. followed by two washes with PBS/2% FBS. 50 μl of 2.5 μg/ml Alexa647-labelled APRIL-Fc was then added to each well and the plates incubated for 1 hour at 4° C. Cells were then washed and the amount of cell associated Alexa647-labelled APRIL-Fc was quantitated by flow cytometry.

The experiments included negative control hybridoma supernatants. The average signal observed in these negative control experiments was adopted as the maximum possible signal for the assay. Experimental supernatants were compared to this maximum signal and a percent inhibition was calculated for each well (% Inhibition=(1-(FL4 Geomean of the anti-BCMA hybridoma supernatant/Maximum FL4 Geomean signal)).

Further Characterization of 2A1 and 1E1:

An important criterion is exquisite selectivity for wild-type human BCMA expressed on the surface of cells. FACS binding on cells transiently transfected to express full length BCMA, TACI, or BAFF-R was performed using standard techniques. Approximately $40 \times 10^6$ of the transiently-transfected target cells were resuspended in a staining solution (2% goat serum, 1% rabbit serum, 0.02% azide in PBS) and aliquoted into round-bottom, 96-well plate (Corning Incorp., Acton, Mass.) as per the experiment design. The cells were incubated at 4 degrees celsius for 30 minutes to block non-specific sites. The antibodies were titrated into the staining solution. The cells were rinsed in a rinse solution (PBS+0.02% azide) by resuspending the cells in 200 ul/well. The cells were centrifuged at 1500 rpm at 4 degrees celsius for 7 minutes. The rinse solution was removed and the rinse step was repeated. The cells were resuspended in the appropriate antibody solution (see the matrix in TABLE 4) at 30 ul/well and incubated at 4 degrees celsius for 30 minutes. The huIgG1 negative control's secondary reagent was a biotinylated anti-huIgG (Jackson Cat. 109-065-098), followed by a streptavidin-phycoerythrin (SA-PE) conjugate (BD Pharmingen Cat. 554061); the 1E1, 2A1 and 11F12 secondary reagents were the same biotinylated anti-huIgG, followed with the SA-PE. For the mouse IgG1 negative control and the two mouse antibodies (1.183 and 1.288), the secondary reagent was an anti-mouse IgG-PE conjugate (BD Pharmingen Cat. 550589). The cells/antibodies were rinsed as described above to remove excess/unbound antibody. After the last rinse, the cells were resuspended in 200 ul of rinse solution with a drop of staining solution added to keep the cells from aggregating. Samples were read at 532 nM wavelength on FACS. A sample was considered positive for binding if the MFI was two times the negative control value.

As shown in TABLE 4, the 2A1 and 1E1 antibodies were specific for BCMA, while 11F12 cross-reacted with structurally homologous receptors TACI and BAFF-R. 1.183 and 1.288 are mouse anti-huBCMA monoclonal antibodies that cross-react to TACI and/or BAFF-R and therefore serve as positive controls for cross-reactivity.

TABLE 4

|       | BCMA | TACI | BAFF-R |
|-------|------|------|--------|
| 1E1   | +    | −    | −      |
| 2A1   | +    | −    | −      |
| 11F12 | +    | +    | −      |
| 1.183 | +    | +    | −      |
| 1.288 | +    | −    | +      |

The binding affinity for the 2A1 and 1E1 antibodies to human and cynomolgus (cyno) BCMA expressed on the surface of cells was evaluated by FACS analysis. In short:
Day 1—Prepared 293T cells transiently transfected with either cyno or human BCMA
Day 2—Added 5 mM Sodium Butyrate to the cells to improve BCMA expression
Day 3—Equilibrium assay was set up at 37° C. in media (Freestyle™ 293 expression media (Gibco/Invitrogen, San Diego, Calif.)+2% FBS+50 ug/mL G418+0.05% Sodium Azide for approximately ~16 hrs
Equilibrium Conditions:
800 nM of each Mab was titrated 1:2 and then 1:4, 10 data points at 4° C. and 37° C.;
$2 \times 10^4$ cells and $3 \times 10^5$ of 293T cells transiently-expressing cells human BCMA were prepared, and
$2 \times 10^4$ cells and $2.6 \times 10^5$ of 293T cells transiently-expressing cells cyno BCMA were prepared
Day 4—FACS analysis: two curves were generated for each mAb, one Kd controlled, one Ab controlled The equilibrium dissociation constant ($K_d$) for the 2A1 and 1E1 antibodies to human and cynomolgus (cyno) BCMA was evaluated by BIAcore™ surface plasmon resonance analysis.

Assay conditions: Biosensor analysis was conducted at 25° C. in a HBS-EP buffer system (10 mM HEPES pH 7.4, 150 mM NaCl, 3.4 mM EDTA, and 0.005% Surfactant P20) using a BIAcore™ 3000 optical biosensor equipped with a CM5 sensor chip (GE Healthcare, Piscataway, N.J.). The autosampler was maintained at 4° C.

Surface Preparation: Goat anti-human IgG capture antibody (Jackson ImmunoResearch Laboratories, Inc., West Grove, Pa.; 109-005-098) was immobilized to all flow cells of the sensor chip using standard amine coupling chemistry (10,000-11,000 RU). This surface type provided a format for reproducibly capturing fresh analysis antibodies (ligand) after each regeneration step.

Ligand Preparation: Flow cells 2, 3, and 4 were used to analyze captured anti-BCMA antibodies (~350-480 RU) while flow cell 1 was used as the reference flow cell.

Analyte Preparation: Seven anti-huBCMA concentrations ranging from 75.0 to 0.103 nM (3-fold dilutions) were prepared in running buffer.

Interaction Parameters: Each of the seven analyte sample concentrations were run in triplicate and in a mixed order, as a means of assessing the reproducibility of binding and managing potential systematic bias to the order of injection. Multiple blank (buffer) injections also were run and used to assess and subtract system artifacts. The association and dissociation phases for all analyte concentrations were monitored for 180 s and 900 s, respectively at a flow rate of 50 uL/min. Additionally, a long dissociation phase experiment of 5400 s was performed, using the 75.0 nM rhu BCMA concentration, at a flow rate of 50 uL/min.

Surface Regeneration: The surface was regenerated with 10 mM glycine, pH 1.5 for 35 s, at a flow rate of 50 uL/min.

Model/Fit: The data was aligned, double referenced, and fit using Scrubber v2.0© software (BioLogic Software Pty Ltd, Campbell, Australia), which is an SPR data processing and non-linear least squares regression fitting program. First, for the 1A2 and 1E1 anti-BCMA antibodies, a dissociation rate coefficient (kd) was determined from the 5400 s dissociation phase data. Second, this value was applied as a fixed parameter in the global fit of the 180 s association phase data to a 1:1 binding model, to determine the association rate coefficient (ka) and the Rmax value. For the 11F12-1 anti-BCMA antibody, the equilibrium dissociation constant ($K_d$) was estimated from the steady state signal and fit to a simple1:1 binding isotherm.

As shown in TABLE 5, 2A1 and 1E1 showed low nM affinity to human BCMA. Importantly, 2A1 bound cyno BCMA with similar affinity as human BCMA. In contrast, 1E1 bound cyno BCMA with comparatively low affinity (i.e., >100 nM). This data further demonstrates the unique and rare characteristics of the 2A1 antibody. The 2A1 antibody was selected for further characterization and development due to its exceptional specificity for BCMA, its high affinity for huBCMA, and its cross-reactivity with cyno BCMA. 1E1 and 11F12 did not share these unique characteristics.

TABLE 5

Biacore-derived equilibrium dissociation constant ($K_d$) and relative FACS affinity for anti-BCMA antibodies

| Anti-huBCMA mAbs | huBCMA Biacore derived (Kd) | huBCMA Transfected 293T FACS: affinity | Cyno BCMA Transfected 293T FACS: affinity |
|---|---|---|---|
| 1E1   | 113 pM   | 2.8 nM | >100 nM |
| 2A1   | 27 pM    | 1.1 nM | 905 pM  |
| 11F12 | 36100 pM | ND     | ND      |

Example 3

Having established that the 2A1 and 1E1 antibodies bound huBCMA expressed on transiently-expressing cells (Example 2), it was important to determine if these antibodies were capable of binding to native BCMA expressed B-lymphocytes isolated from a myeloma patient (e.g., the H929 cell line, which was originally derived from a myeloma patient). In addition, a number of different myeloma and B-cell lines were tested to determine if and to what degree the 2A1 and 1E1 antibodies bound BCMA on the surface of these cells.

Approximately 10 to $40 \times 10^6$ of H929 myeloma cells were resuspended in a staining solution (2% goat serum, 1% rabbit serum, 0.02% azide in PBS) and aliquoted into round-bottom, 96-well plate (Corning Incorp., Acton, Mass.) as per the experiment design. The cells were incubated at 4 degrees celsius for 30 minutes to block non-specific sites. The antibodies were titrated into the staining solution. The cells were rinsed in a rinse solution (PBS+0.02% azide) by resuspending the cells in 200 ul/well. The cells were centrifuged at 1500 rpm at 4 degrees celsius for 7 minutes. The rinse solution was removed and the rinse step was repeated. The cells were resuspended with 2A1 or 1E1 at 30 ul/well and incubated at 4 degrees celsius for 30 minutes. The huIgG1 negative control's secondary reagent was a biotinylated anti-huIgG (Jackson Labs, Bar Harbor, Me., Cat. 109-065-098), followed by a streptavidin-phycoerythrin (SA-PE) conjugate (BD Pharmingen, San Diego, Calif., Cat. 554061). The 2A1 and 1E1 secondary reagents were the same biotinylated anti-huIgG, followed with the SA-PE. The cells/antibodies were rinsed as described above to remove excess/unbound antibody. After the last rinse, the cells were resuspended in 200 ul of rinse solution with a drop of staining solution added to keep the cells from aggregating. Samples were read at 532 nM wavelength on FACS.

As shown in FIG. 5, both 2A1 and 1E1 antibodies bound to human BCMA expressed on the surface of a myeloma cell line (H929). While both antibodies bound well, the 2A1 antibody had considerably better binding characteristics than the 1E1 antibody. This data is further evidence that the 2A1 antibody is unique in that it has superior binding to human BCMA expressed in a myeloma cell.

A number of different myeloma and B-cell lines were tested to determine if and to what degree the 2A1 and 1E1 antibodies bound BCMA on the surface of these cells. The following myeloma cell lines were tested for 2A1 binding: H929, RPMI 8226, OPM2, MM1S, U266, and MM1R, as well as the B-cell lines RAMOS and EW36. Approximately 10 to $40 \times 10^6$ of cells were resuspended in a staining solution (2% goat serum, 1% rabbit serum, 0.02% azide in PBS) and aliquoted into round-bottom, 96-well plate (Corning Incorp., Acton, Mass.) as per the experiment design. The cells were incubated at 4 degrees celsius for 30 minutes to block non-specific sites. The antibodies were titrated into the staining solution. The cells were rinsed in a rinse solution (PBS+0.02% azide) by resuspending the cells in 200 ul/well. The cells were centrifuged at 1500 rpm at 4 degrees celsius for 7 minutes. The rinse solution was removed and the rinse step was repeated. The 2A1 antibody and a human IgG1 isotype control antibody were conjugated to Dy649 using a reactive succinimidyl-ester of DY-649 using standard methods, such as those provided by EMP Biotech (Fluoro-Spin 649 Protein Labeling & Purification Kit for labeling and purification of proteins to form protein-dye conjugates having fluorescence-excitation and fluorescence-emission maxima at around 652 nm and 671 nm, respectively). The cells were resuspended with 2A1 or control antibody at 30 ul/well and incubated at 4 degrees celsius for 30 minutes. The cells/antibodies were rinsed as described above to remove excess/unbound antibody. After the last rinse, the cells were resuspended in 200 ul of rinse solution with a drop of staining solution added to keep the cells from aggregating.

Figure 7:
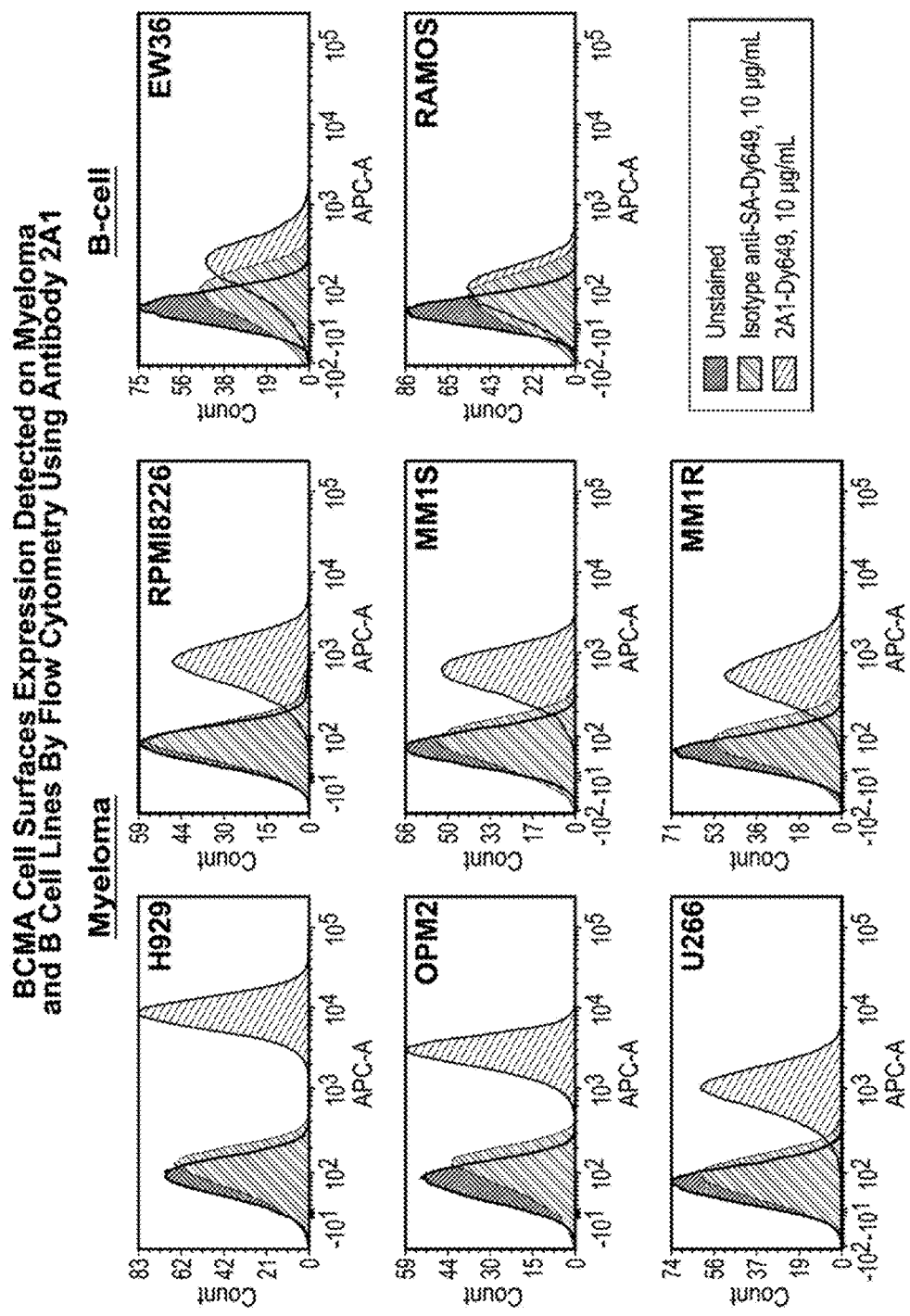
FIG. 7 shows the 2A1 mAb bound BCMA on various myeloma and B-cell lines.

As shown in FIG. 7, the 2A1 antibody bound to all myeloma cell lines and B-cell lines, although the binding to the RAMOS B-cell line was comparatively low. This data shows that the 2A1 antibody has the capacity to bind to BCMA on a variety of human myeloma cells. This data therefore shows the utility of the 2A1 antibody for targeting BCMA on various human myeloma cells that express BCMA.

Example 4

A highly desirable attribute of the preferred embodiments is the ability to kill target cells by a variety of means, including ADCC (Antibody-Dependent Cell-mediated Cytotoxicity). Typically, ADCC involves activation of Natural Killer (NK cells) by antibodies. NK cells express FcγR (an Fc receptor protein). The FcγR binds to the Fc portion of an antibody, such as IgG1, which has bound to the surface of a target cell. Upon binding, the NK cells release cytokines and cytotoxic granules containing perforin and granzymes that enter the target cell and promote cell death by triggering apoptosis. Embodiments of the antibodies and ADCs provided herein are of the IgG1 isotype (as described above) and therefore hold the promise if ADCC activity.

In Vitro ADCC Assay:

Target cell H929, a human B-lymphocyte cell line originally isolated from a myeloma patient that expresses BCMA at a relatively level high, was labeled calcein-AM as follows. H929 cells were harvested and resuspended at $2 \times 10^6$ cells/ml in cRPMI-10 media (RPMI (Life Technologies, Carlsberg, Calif.) +10% fetal bovine serum). Calcein-AM, 4 mM in anhydrous DMSO (Sigma-Aldrich, St. Louis, Mo.) was added to a final concentration of 10 μM (1:400 dilution). The cells were incubated for 30 minutes at 37° C. followed by two washes in PBS (1500 rpm, 5 minutes at 4° C. each). The pellets were resuspended in cRPMI-10 and adjusted to a concentration of $0.2 \times 10^6$ cells/ml and placed on ice for use in the next step. The test antibodies were added to U-bottom 96-well plates (BD, Franklin Lakes, N.J.) at a 10-fold serial titration starting from 10 ug/ml. Rituximab (Genentech, South San Francisco, Calif.) was used as a positive antibody control. In addition, an IgG2 isotype of the 1E1 antibody was used as a control. Calcein-AM-labeled H929 cells were added to each well ($1 \times 10^4$ cells/well) and incubated with the antibodies for 20 minutes at 37° C. Following incubation, 50 μl of NK cells was added to each well at a concentration of $4 \times 10^6$ cells/ml, or PBMC at a concentration of $20 \times 10^6$ cells/ml and incubated for 4 hours at 37° C. NK cells or PBMC, as effector cells, were pelleted at 1500 rpm for 5 minutes at 4° C. and resuspended in cRPMI-10, adjusting the cell concentration to $4 \times 10^6$ cells/ml (NK) or $20 \times 10^6$ cells/ml (PBMC). Following incubation, positive controls were prepared by adding 20 μl/well 9% NP-40 (IGEPAL CA 630, Sigma-Aldrich) to stimulate 100% lysis. All other wells received 20 μl/well of cRPMI-10 media alone. The plates were spun at 800 RPM for 4 minutes at 4° C. Approximately 150 μl of supernatant was removed and transferred to a clear bottom, black 96 well plate (Corning, Lowell, Mass.) and fluorescence read on a standard plate reader (Molecular Devices, Spectra max GEMINI), excitation 485, emission 535. Percent maximum lysis was calculated as (sample value-spontaneous lysis)/(100% lysis-spontaneous lysis)× 100.

Figure 8:
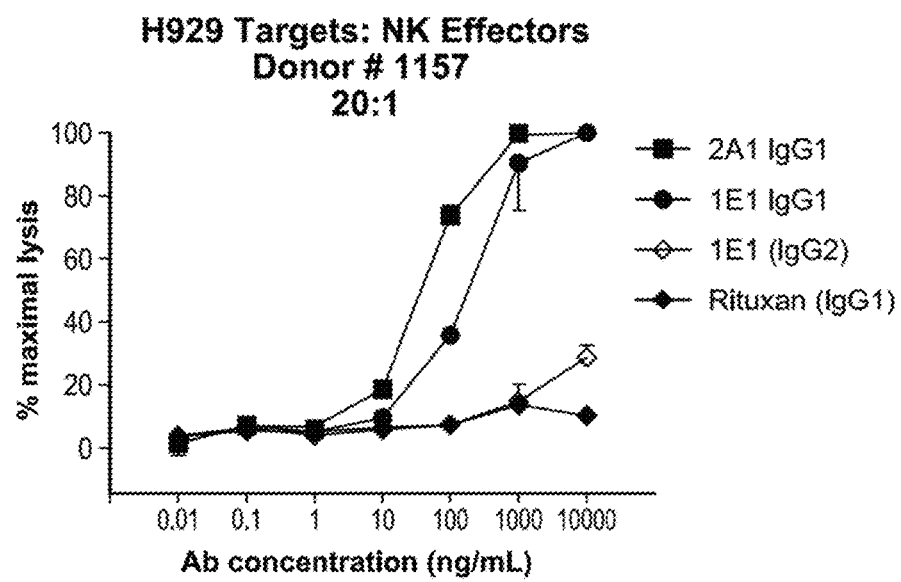
FIG. 8 is a graph of the ADCC activity for the 2A1 and 1E1 antibodies ($EC_{50}$ of 11 ng/ml for 2A1 and 76 ng/ml for 1E1).

As shown in FIG. 8, the 2A1 and 1E1 antibodies showed excellent ADCC activity, with an EC50 of 11 ng/ml for 2A1 and 76 ng/ml for 1E1. The ADCC activity of these antibodies far exceeded that of the Rituxan benchmark antibody. Therefore, the 2A1 and 1E1 antibodies are unique in their exceptional ADCC activity and therefore ADC versions of these antibodies offer multiple avenues for killing BCMA-expressing cells in cancer patients, such as multiple myeloma.

Example 5

These experiments demonstrate that the 2A1 antibody is internalized upon binding to huBCMA on human myeloma cells. This is an important attribute of a candidate antibody for developing into an ADC, in that the antibody is preferably internalized by BCMA-mediated endocytosis in order for the ADC to be internalized into the endosome/lysosome pathway to selectively kill that cell with minimal bystander killing.

H929 myeloma tumor cells were cultured in growth medium (RPMI 1640, 10% FBS, MEM non-essential Amino Acids, HEPES, beta-mercaptoethanol, Pen/Strep, L-glutamine, sodium pyruvate, gentamicin). The H929 cells were collected into two 3-ml FACS tubes at approximately 500,000 cells per tube and washed once with assay medium (PBS containing 2% FBS). The cells were suspended with either the 2A1 or CD138 antibodies at 10 μg/mL per tube (200 μL per tube) in assay medium. After incubation at 4° C. for 30 minutes, the cells were washed once with assay medium. A cocktail of anti-human IgG, Alexa 488 (Molecular Probes Inc., Eugene, Oreg. Catalog#A11013 at a 1:1,000 dilution in assay medium) and Hoechst 33342 (Molecular Probes Inc., Eugene, Oreg. Catalog#H21492 at a 1:2000 dilution in assay medium) was added to the cells. After incubating cells at 4° C. for 15 minutes, the cells were washed once and then resuspended with 0.5 ml of assay medium to reach a concentration of $1 \times 10^6$ cells per ml. Fifty μl at of cells were transferred to a 96-well plate at 8 wells for each antibody. The cells were either fixed and permeabilized, starting with time zero by adding 50 μl of BD cytofix/cytoperm kit (BD Biosicences. catalog#554714) or incubated at 37° C., 5% $CO_2$ for the time points at 0.5, 1 and 2 hours. At each incubation time, cells were fixed and permeabilized using the same steps as indicated for 0 timepoint. The internalization rate was quantified on an ArrayScan $V^{TI}$ HCS reader (version 6, Cellomics, Thermo Fisher Scientific, Pittsburgh, Pa.) with BioApplication "Spot Detector" algorithm employing a 40× objective. The filter setting for internalization was indicated in table below. At least 200 cells were counted in each well.

TABLE 6

| Filter setting for internalization: | | | |
| --- | --- | --- | --- |
| Channel | Target | Label | Filter |
| 1 | Nucleic acid for all cells | Hoechst 33342 | DAPI (blue) |
| 2 | Internalized spots | Alexa 488 | FITC (green) |

The output parameter algorithm of Array Scan was "Spot-CountPerObjectCh2." The results were reported as total spot count per 200 cells. The statistical analysis was performed using Prism 4.01 (GraphPad, San Diego, Calif.). The spot counts were expressed as the mean±standard error of the mean (SEM) for duplicate measurements (n=2). Using the analysis tool, spot count per unit time (internalization rate=$T_{1/2}$) was fit to a one phase exponential association equation. The half-life for internalization was calculated using one-phase exponential association from GraphPad™ Prism.

Figure 9:
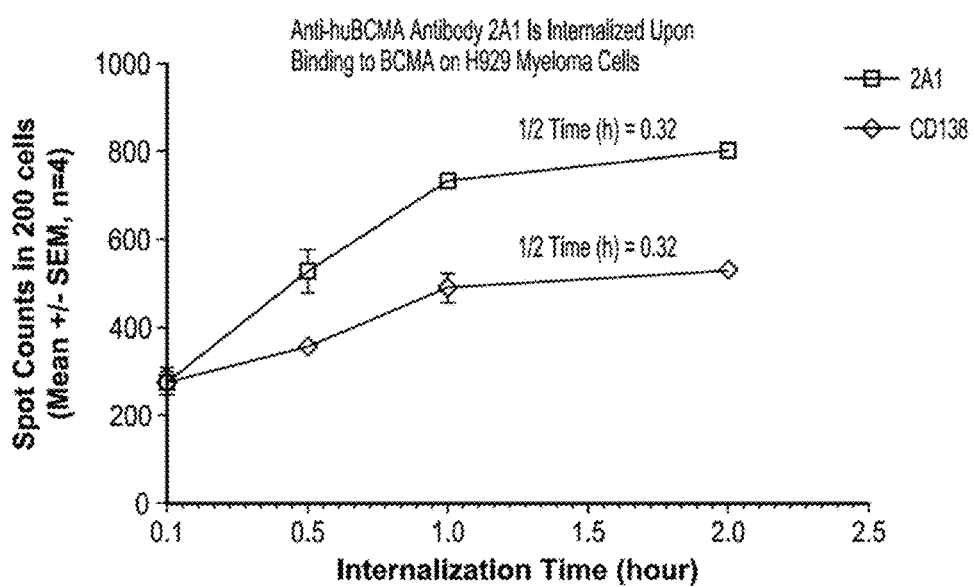
FIG. 9 shows that the 2A1 antibody was readily internalized following binding to BCMA on H929 cells.

FIG. 9 shows that the antibody 2A1 was readily internalized following binding to BCMA on H929 cells. This further demonstrates the unique attributes of this antibody and its usefulness as an ADC for targeting BCMA for the treatment of cancers by eliminating B-cells expressing BCMA.

Example 6

The parental 2A1 antibody (heavy chain amino acid sequence of SEQ ID NO:287 and the light chain amino acid sequence of SEQ ID NO: 288) was conjugated to maytansine (DM1) using a non-cleavable linker (SMCC) resulting in an ADC referred to as 2A1-MCC-DM1.

A single-step conjugation with DM1-SMCC (Succinimidyl 4-[N-maleimidomethyl]cyclohexane-1-carboxylate, which contains an NHS-ester and a maleimide) was developed. The DM1-SMCC reagent was independently synthesized and used as the single conjugation reagent in the ADC process, as shown below. By charging the drug maytansine, for example, and DM1 in this instance) already conjugated to the linker, the generation of a large number of potential process impurities was avoided.

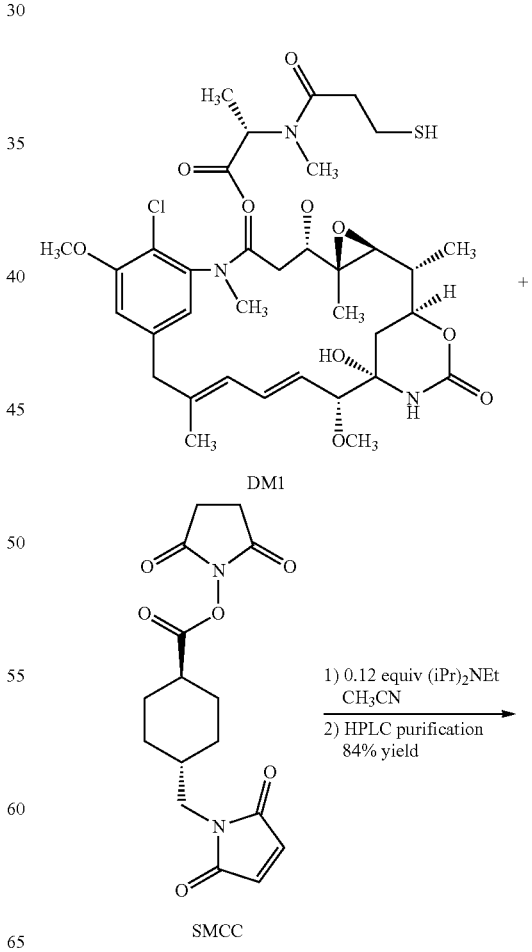

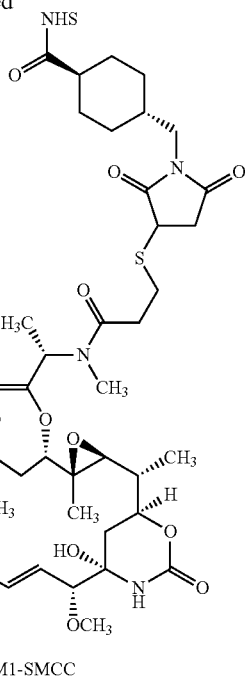

DM1-SMCC

Conjugation Summary:

A one-step preparation of anti-huBCMA 2A1 conjugated to SMCC-DM1 as graphically depicted below. 2.5 mg/mL 2A1 in 50 mM potassium phosphate, 50 mM NaCl, 2 mM EDTA, pH 7.5 was modified with an 8, 10, and 12 fold molar excess of linker-drug in DMA (10%). The reaction was carried out at room temperature for 90 mins on a rocker and then placed on a rocker at 4° C. for overnight incubation. Unreacted linker-drug was removed by HiLoad 16/60 Superdex™ 200. The non-aggregated fractions were pooled and concentrated on Amicon® Ultra-15 30 kD MWCO centrifugal filters, and subsequently filtered using a 0.22 micron filter.

gradient in percentage of B was 5-5, 5-25, 25-80, 80-80, 80-5, 5-, in 3, 5, 30, 32, 33 and 35 min, respectively. The TOF mass spectrometer was tuned and calibrated in the range of 100 to 10000 m/z. TOF MS conditions included capillary voltage of 4500 V, drying gas flow at 12 L/min, dry gas temperature at 300° C., nebulizer gas flow at 40 L/min, and fragmentor voltage of 350 V. MS data was analyzed in Agilent MassHunter Qualitative Analysis program.

As shown in TABLE 7, the resultant 2A1-MCC-DM1 had an average drug:antibody ratio (DAR) of approximately 2.8 to 3.4.

TABLE 7

Preliminary conjugation of parental 2A1

| Molar linker-drug to Ab ratio | Conc (mg/mL) | Vol (mL) | Mass (mg) | DAR | SEC (% Main) | SEC (% HMW) | % Free Drug |
|---|---|---|---|---|---|---|---|
| 8 | 0.84 | 1.90 | 1.60 | 2.75 | 99.7 | 0.3 | 1.27 |
| 10 | 0.73 | 1.65 | 1.20 | 3.06 | 99.8 | 0.2 | 1.60 |
| 12 | 0.56 | 1.60 | 0.89 | 3.36 | 99.7 | 0.3 | 2.17 |

ADCs were generated from the 2A1 and 1E1 antibodies using various linkers and drugs. In addition to the MCC-DM1 conjugation, the 2A1 and 1E1 antibodies were successfully conjugated to PEG4-Mal-DM4. This is evidence that the ADCs described herein were made using linker and drug technology beyond the DM1-SMCC method, in particular for the 2A1 antibody.

Conjugation of 2A1CV5 (Ab-1):

The conjugation of the 2A1CV5 (Ab-1) and 2A1CV4 antibodies with DM1-SMCC was performed essentially as described above. In general, the conjugation was performed in buffered solution at pH 8.5. On completion of the initial conjugation, glycine was introduced to scavenge/quench unreacted DM1-SMCC and hydrolytically unstable DM1-MCC conjugates. The ADC was separated away from the small molecule components by tangential flow filtration (TFF). The conditions for this particular conjugation were:

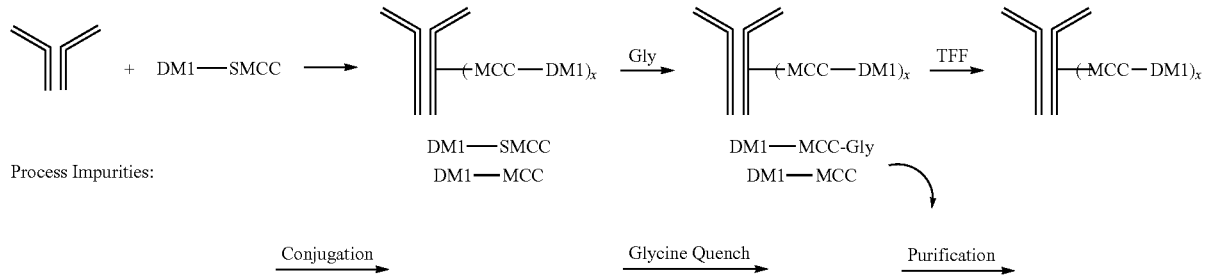

Figure 10:
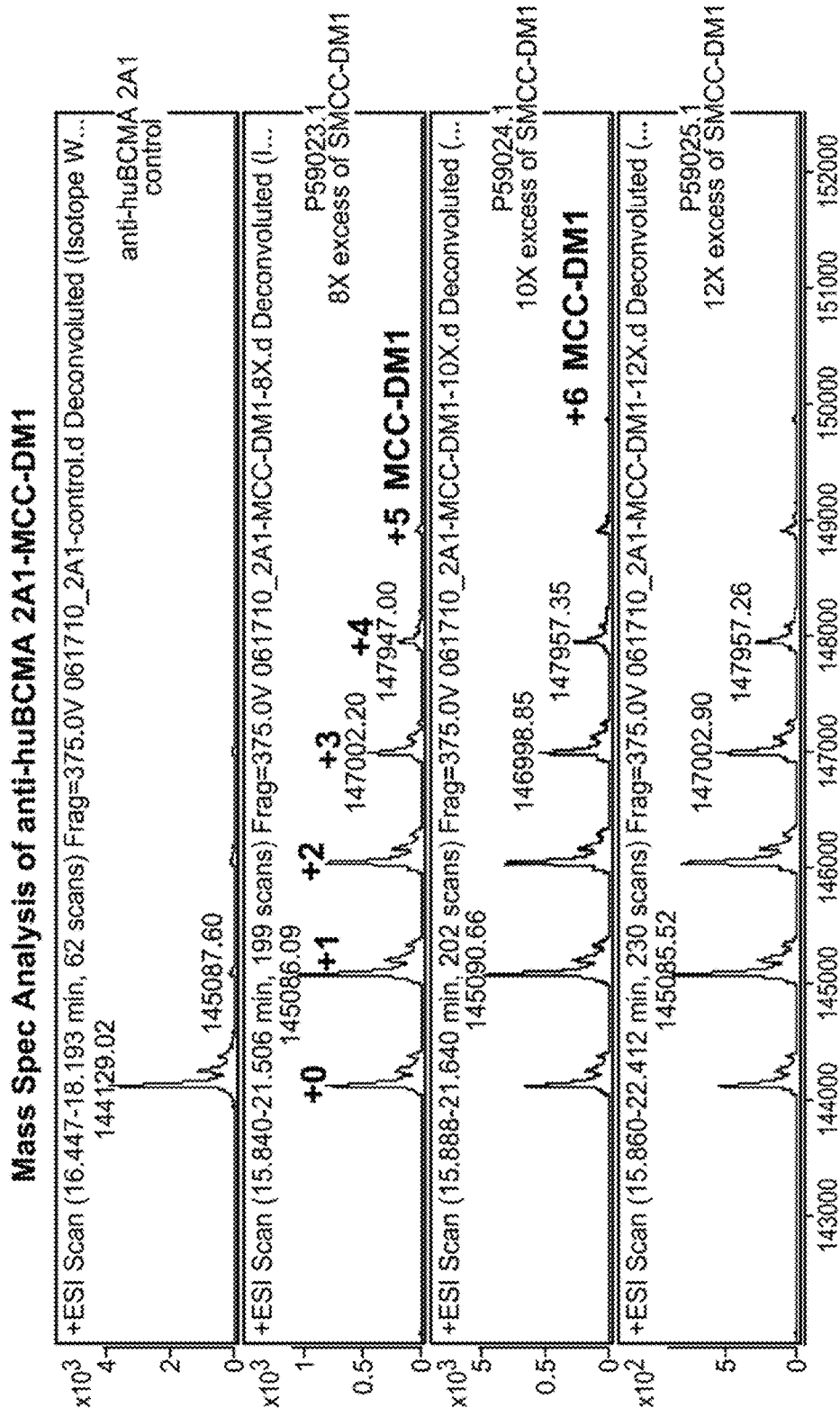
FIG. 10 is various 2A1-MCC-DM1 ADCs analyzed by mass spectrometry.

The various 2A1-MCC-DM1 ADCs were analyzed using mass spectrometry (see FIG. 10). To simplify the intact mass profile, the ADC samples were deglycosylated in PBS buffer using PNGase F (New England Biolabs), an enzyme/substrate ratio of 1/20 by weight, at 37° C. overnight (16 hours). 20 µg of deglycosylated ADC samples were analyzed in an Agilent 6210 TOF LC/MS system with a dual-nebulizer electrospray ion source. A 2.1×150 mm Pursuit Diphenyl column, 5 µM particle size (Agilent Technologies) was connected to the LC system and operated at 0.4 ml/min. The column temperature was 75° C., solvent A was 0.1% TFA in water, and solvent B was 0.1% TFA in acetonitrile. The 5 g/L of the antibodies were diluted in 50 mM boric acid, 50 mM NaCl, 2 mM EDTA, pH 8.5. A 10-fold molar excess of DM1-SMCC (in 7.5% DMAC) was added and incubated at 20° C. for 90 minutes. The reaction was quenched using 200 mM at pH 8.0 for 30 min. The pH was adjusted to pH 5.2 and the solution was subjected to tangential flow filtration to buffer exchange into a formulation buffer (10 mM glutamate, 4% mannitol, 2% sucrose, pH 5.0) and concentrated to approximately 11-14 g/L. The material was then diluted to a final concentration of 10 g/L in 10 mM glutamate, 4% mannitol, 2% sucrose, 0.01% PS-20, pH 5.0. Both the 2A1CV5 (Ab-1) and 2A1CV4 antibodies behaved acceptably and identically through the conjugation process. TABLE 8 summarizes the final conjugation results for 2A1CV5 (Ab-1) and 2A1CV4 ADCs.

TABLE 8

Summary of conjugated 2A1CV5 (Ab-1) and 2A1CV4 ADCs

|  | 2A1CV4 ADC | 2A1CV5 (Ab-1) ADC |
| --- | --- | --- |
| Protein | 1.92 g | 2.36 g |
| DAR | 5.1 | 4.8 |
| Unconjugated Ab | 3% | 3% |
| Purity (aggregate) | 98.2% (1.8%) | 99.4% (0.6%) |
| free DM1 species | 0.2% | 0.5% |
| residual DMAC (solvent) | <10 ppm | 17 ppm |

Upon further analysis, the ADCs having high DAR values had a tendency to precipitate out of solution in an IV pH jump test. Follow-up studies determined an ADC with a DAR of less than 4 showed no observed precipitation or clouding in the IV pH jump test. Further conjugation studies using 2A1CV5 (Ab-1) having a DAR of 3-4 was found to be stable to pH changes. By reducing the molar equivalents of DM1-SMCC used in the conjugation process, the desired average DAR of 3 to 4 was achieved (see above). Methods of conjugating the antibodies described herein, in particular 2A1CV5 (Ab-1), include using the "one-step" method described above using a X-fold molar excess of the pre-coupled maytansine-linker, in particular DM1-MCC, relative to the amount of antibody, wherein X can be 3, 4, 5, 6, 7, 8, 9 or 10, and any value in between.

Example 7

The ADCs were tested for the ability to target and kill BCMA-expressing myeloma cells. The CellTiter-Glo® Luminescent Cell Viability Assay is a homogeneous method to determine the number of viable cells in culture based on quantitation of the ATP present, which signals the presence of metabolically active cells. The CellTiter-Glo® Assay is applicable to cytotoxicity assays (see http://www.promega-.com/products/cell-health-assays/cell-viability-assays/cellti-ter_glo-luminescent-cell-viability-assay/for more information). The cell viability assay was used to assess the relative killing capacity of various ADCs on various multiple myeloma cell lines and B-cell lines. The protocol provided in the Cell Titer-Glo kit (Promega G7572) was followed. In short, $5 \times 10^3$ target cells in 90 ul RPMI 1640, 10% FBS were aliquoted into clear, flat bottom, white walled 96 well plates (Costar #3903). The ADCs were diluted into a 10× stock to create 500 nM maytansine drug equivalents. Each ADC was serially diluted in 2-fold dilutions in RPMI 1640, 10% FBS starting with 500 nM stock. 10 ul of the 10×ADC dilution series was added to the 90 ul of cells in media (triplicate wells). The highest concentration of ADC was approximately 50 nM maytansine drug equivalents, and the lowest concentration of ADC was approximately 50 pM maytansine drug equivalents. An isotype control ADC (an anti-strepta-vidin huIgG1 conjugated to MCC-DM1) was included, as well as a media-only control. The plates were incubated at 37° C., 5% $CO_2$ for 96 hours. After incubation, 100 ul of the Substrate Solution (Promega G7572) was added to each well. Luminescence was read on an EnVision™ Multilabel reader (PerkinElmer) or Analyst HT plate reader (LJL Biosciences). The data was analyzed and graphed using Graph-Pad Prism™ to determine the relative efficacy of the ADCs on various cancer cell lines.

Figure 11:
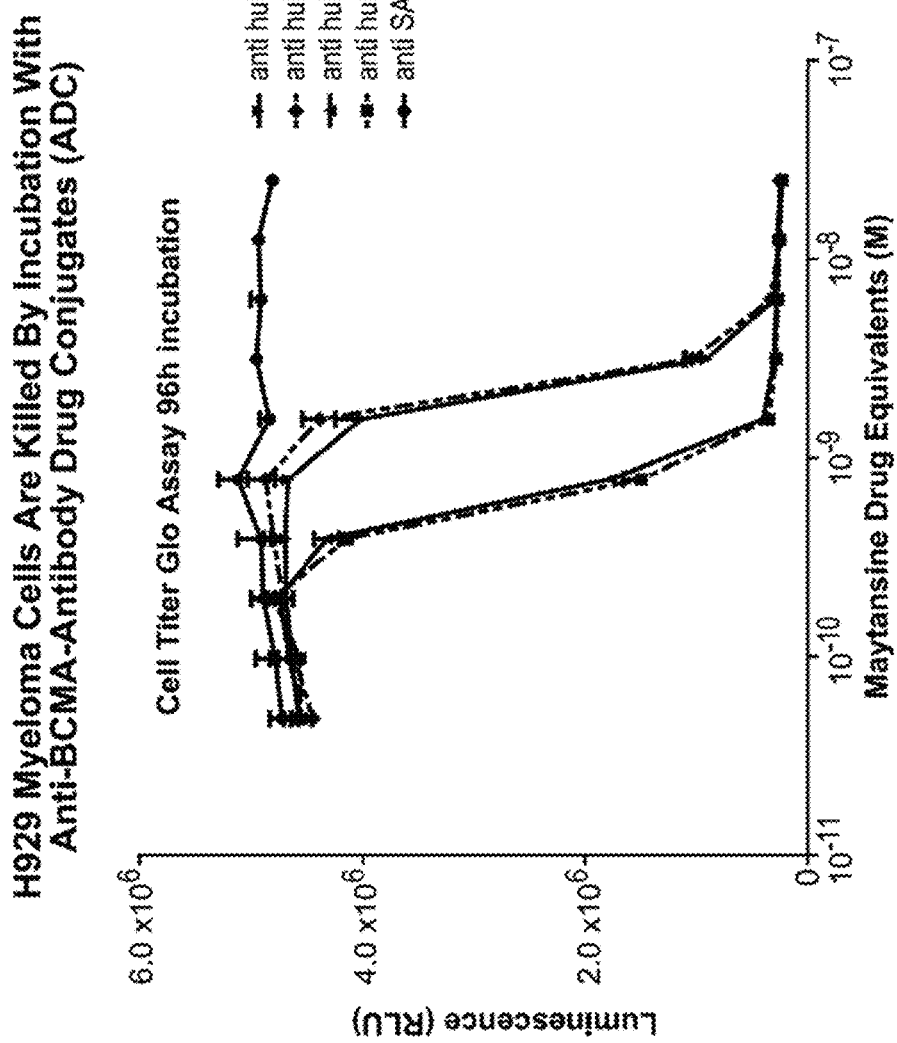
FIG. 11 depicts two different antibodies (2A1 and 1E) that were conjugated with different linkers and maytansine molecules and analyzed for their capacity to kill myeloma cells.
Figure 12A:
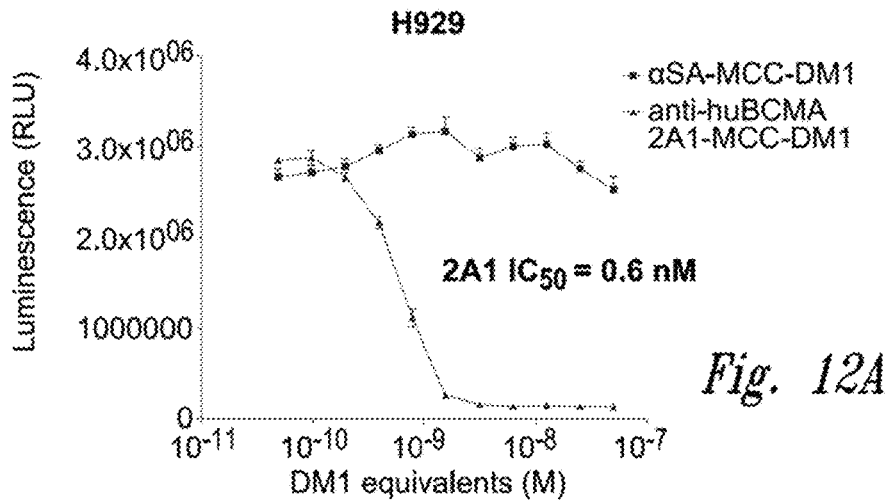
FIGS. 12A-F shows 2A1-MCC-DM1 ADC was tested against various multiple myeloma cell lines, including H929, U266, MMIR, MMIS, the EW36 B-cell lymphoma cell line, and the RAMOS Burkitt's lymphoma cell line.
Figure 12B:
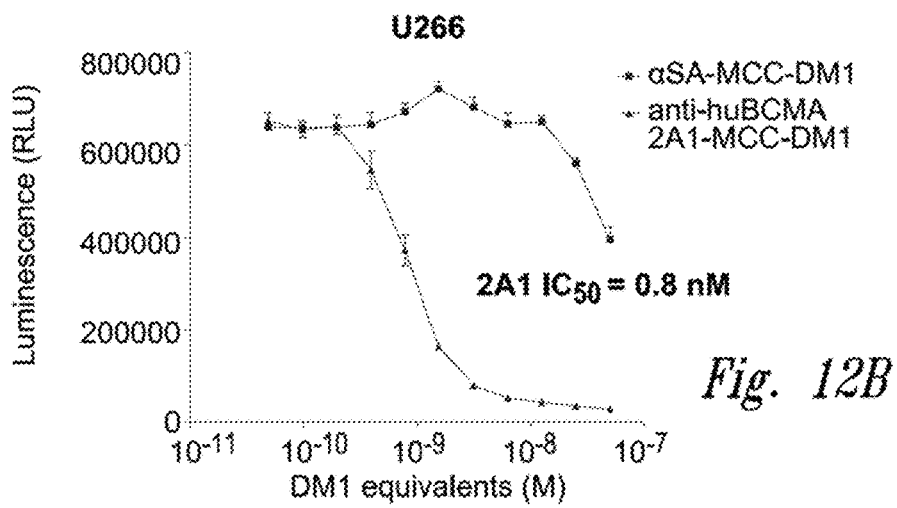
Figure 12C:
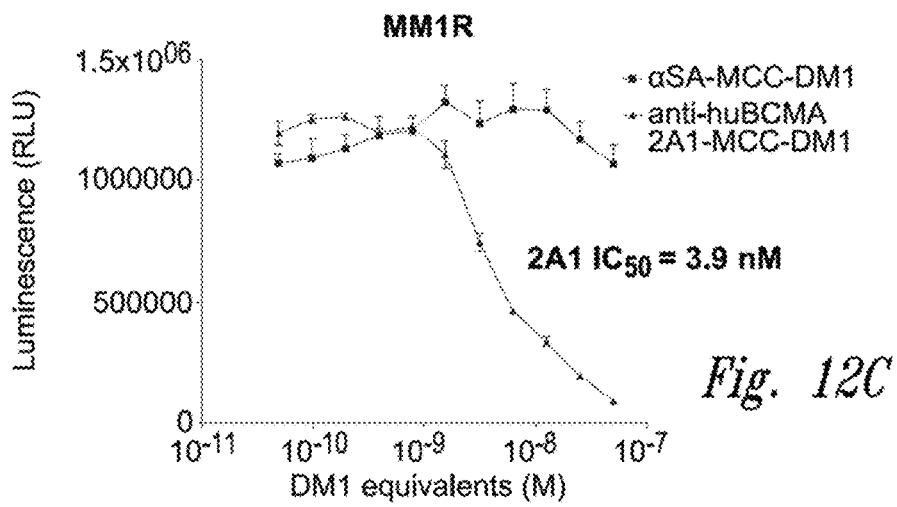
Figure 12D:
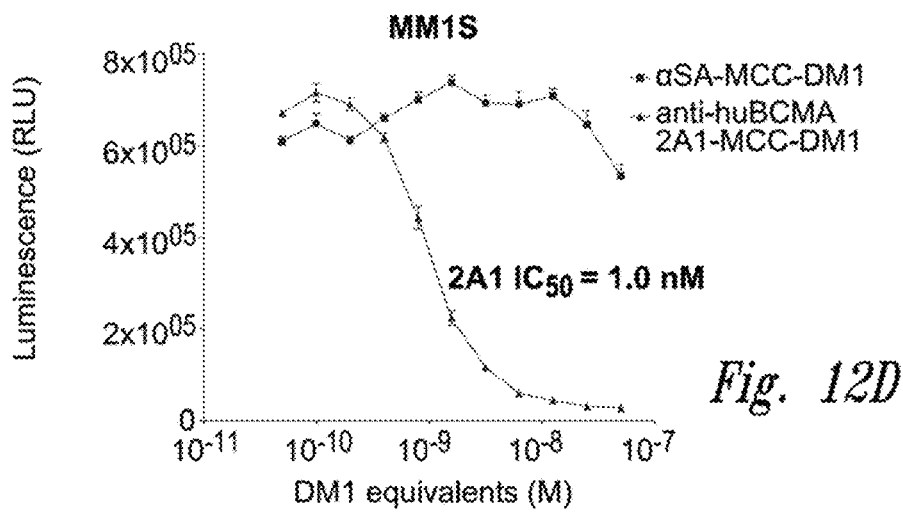
Figure 12E:
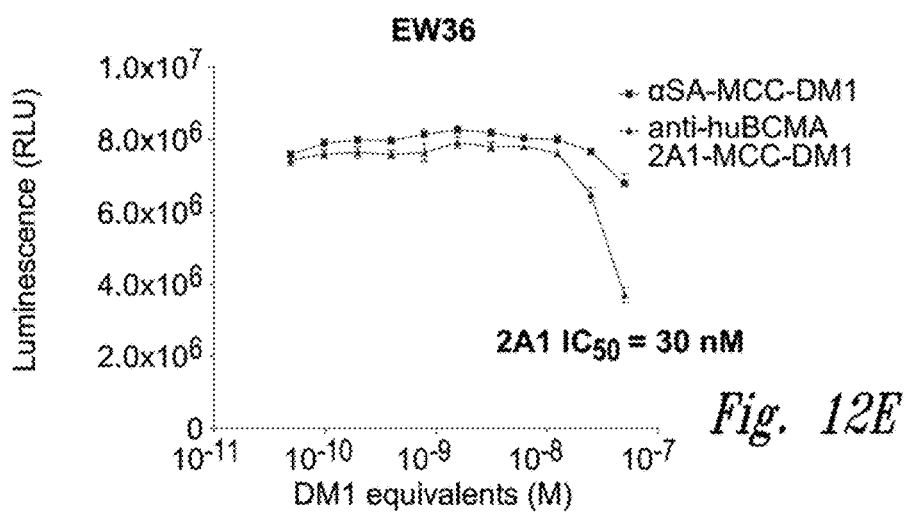
Figure 12F:
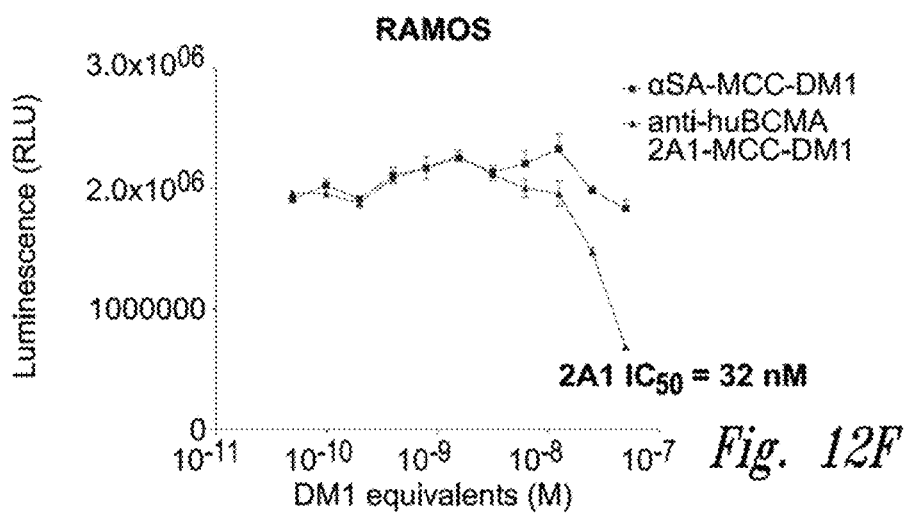

In a first experiment, two different antibodies (2A1 and 1E) were conjugated with different linkers and maytansine molecules and analyzed for their capacity to kill myeloma cells. Specifically, 1E1-PEG4-Mal-DM4, 1E1-MCC-DM1, 2A1-PEG4-Mal-DM4, and 2A1-MCC-DM1 were tested on H929 myeloma cells. As shown in FIG. 11, both the PEG4-Mal-DM4 and the MCC-DM1 ADCs worked extremely well in selectively killing the myeloma cells. The 2A1-PEG4-Mal-DM4 ADC had an $IC_{50}$ of 2.2 nM and the 2A1-MCC-DM1 ADC had an $IC_{50}$ of 2.4 nM, whereas the 1E1-PEG4-Mal-DM4 ADC had an $IC_{50}$ of 680 pM and the 1E1-MCC-DM1 ADC had an $IC_{50}$ of 630 pM. This data shows that both the 2A1 and the 1E1 can be successfully conjugated to create biologically active and potent ADCs. This data also shows the superiority of the 2A1 ADC.

Figure 13:
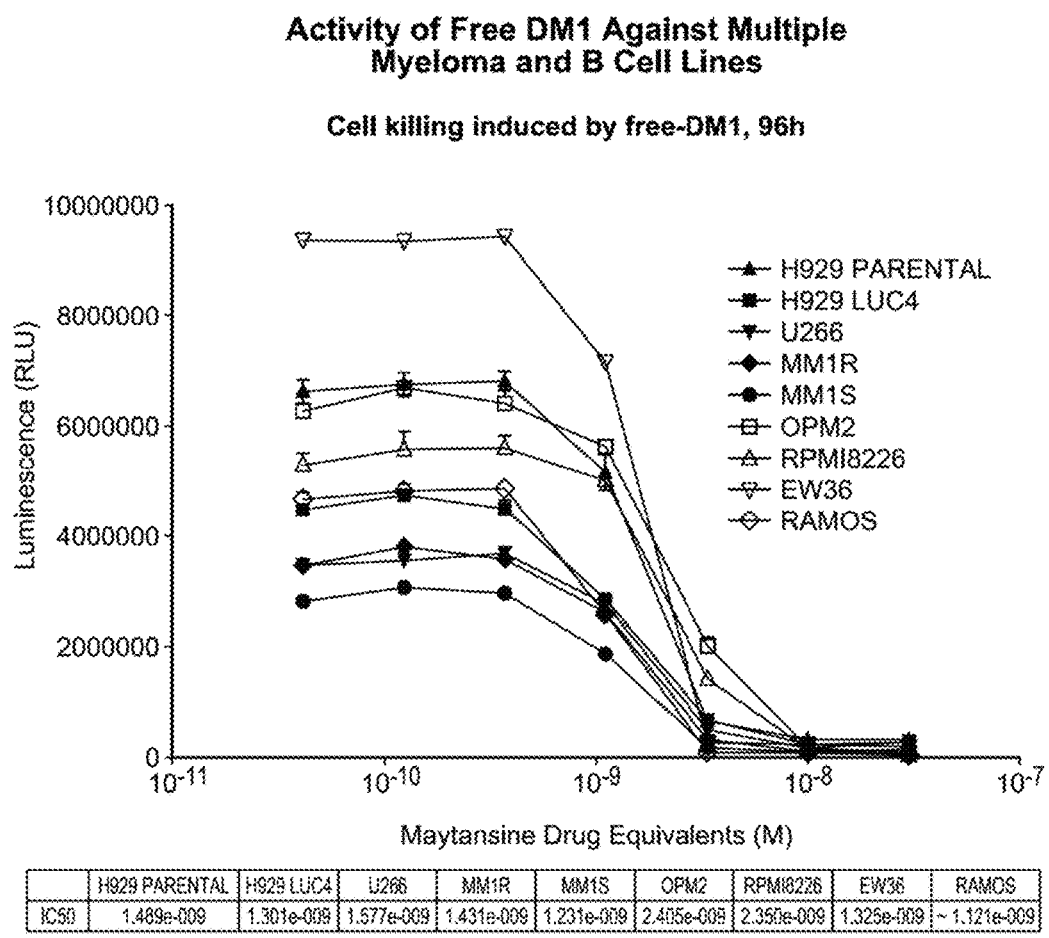
FIG. 13 graphically illustrates that various cell lines exposed to free DM1 are in fact killed by free DM1.

Next, the 2A1-MCC-DM1 ADC was tested against various multiple myeloma cell lines, including H929, U266, MMIR, MMIS, the EW36 B-cell lymphoma cell line, and the RAMOS Burkitt's lymphoma cell line. As a control, various cell lines were exposed to free DM1 to establish that the cells were in fact killed by free DM1 (see FIG. 13). As illustrated in FIGS. 12A-F, the 2A1-MCC-DM1 ADC was very effective in killing a variety of myeloma cell lines and to a much lesser extent the EW36 and RAMOS cells. The $IC_{50}$ (nM DM1) values were:
H929: $IC_{50}$ of 0.6 nM DM1
U266: $IC_{50}$ of 0.8 nM DM1
MM1R: $IC_{50}$ of 3.9 nM DM1
MMIS: $IC_{50}$ of 1.0 nM DM1
EW36: $IC_{50}$ of 30 nM DM1
RAMOS: $IC_{50}$ of 32 nM DM1

Example 8

The 2A1 antibody was analyzed for potential problematic amino acid residues that could result in poor stability, potential aggregation, misfolding, and the like. The light and heavy chain variable regions were PCR amplified from independent sub-clones derived from the parental 2A1 hybridoma. Antibody 2A1 was determined to be composed of a VL1/1c/JL3b lambda light chain variable region and a VH3-15-22/JH4 gamma variable region. The light chain variable region was cloned onto a lambda light constant region with a VK1|O2O12 signal peptide, and the gamma chain variable region was cloned onto an IgG1 (z), non-x, non-a, constant region with a VK1|O2O12 signal peptide. Site-directed mutagenesis was performed essentially as described in WO 2011/005621 using standard techniques and reagents. In short, IgG1 variants were created by mutating the codon for select amino acids using QuikChange™ site-directed mutagenesis (Strategene). Expected mutations were confirmed by DNA sequencing. The wild type and mutant proteins were expressed in 293E cell using a pTT5 transient mammalian expression vector (Durocher Y., et al., *Nucleic Acid Research* 30(2):E9). The mutein proteins were purified using standard protein-A chromatography (5 ml column, Pierce).

Aggregation of the 2A1 parental antibody conjugated to MCC-DM1 was observed. Sequence analysis of the 2A1 antibody identified a Cys residue present at position 107 in the VH, which was changed to Ala (represented in the germline). In addition, three putative Asn deamidation sites in CDRL1 and CDRL3 and Asp isomerization sites in CDRH2 and CDRL3 were identified. CDRL3 and CDRH3 also contained Trp residues that may be prone to oxidation. Several rounds of covariance analysis was applied to increase the stability and biophysical properties of the parent 2A1 Fab region (Tm Fab=66° C.). Covariance violations were identified in the variable heavy domain of the 2A1 antibody (SEQ ID NO:287) and the following covariance mutations were designed to correct the offending amino acid: K14Q, R17G, T24A, G325, F44V, G56S, D84N, F88T, T98A, T107A, and S108K; as well as in the variable light domain (SEQ ID NO:287): E144K. Aspects of the invention include the 2A1 antibody with any combination of the aforementioned mutations.

Covariance violations, which included a non-disulfide bonded Cys, were evaluated (10 VH, 1 LC) for production, binding to cells, and in vitro ADCC potency. The panel of 2A1 muteins is provided in TABLE 9.

TABLE 9

2A1 mutein sequences

| Parental Ab-18 | 2A1<br>Heavy chain: SEQ ID NO: 287<br>Light Chain: SEQ ID NO: 288 | 2A1_VL |
|---|---|---|
| Covariance 1 Ab-19 | 2A1_C107T<br>Heavy chain: SEQ ID NO: 289<br>Light Chain: SEQ ID NO: 288 | 2A1_VL |
| Covariance 2 Ab-20 | 2A1_R17G + C107T<br>Heavy Chain: SEQ ID NO: 290<br>Light Chain: SEQ ID NO: 288 | 2A1_VL |
| Covariance 3 Ab-21 | 2A1_F44V + C107T<br>Heavy Chain: SEQ ID NO: 291<br>Light Chain: SEQ ID NO: 288 | 2A1_VL |
| Covariance 4 Ab-22 | 2A1_D84N + C107T<br>Heavy Chain: SEQ ID NO: 292<br>Light Chain: SEQ ID NO: 288 | 2A1_VL |
| Covariance 5 Ab-23 | 2A1_F88T + C107T<br>Heavy Chain: SEQ ID NO: 293<br>Light Chain: SEQ ID NO: 288 | 2A1_VL |
| Covariance 6 Ab-24 | 2A1_C107A<br>Heavy Chain: SEQ ID NO: 294<br>Light Chain: SEQ ID NO: 288 | 2A1_VL |
| Covariance 7 Ab-25 | 2A1_S108K + C107T<br>Heavy Chain: SEQ ID NO: 295<br>Light Chain: SEQ ID NO: 288 | 2A1_VL |
| Covariance 8 Ab-26 | 2A1_F44V + F88T + C107T<br>Heavy Chain: SEQ ID NO: 296<br>Light Chain: SEQ ID NO: 288 | 2A1_VL |
| Covariance 9 Ab-27 | 2A1_F44V + C107A<br>Heavy Chain: SEQ ID NO: 297<br>Light Chain: SEQ ID NO: 288 | 2A1_VL |
| Covariance 10 Ab-28 | 2A1_T24A + F88T + C107T<br>Heavy Chain: SEQ ID NO: 298<br>Light Chain: SEQ ID NO: 288 | 2A1_VL |
| Covariance 11 Ab-29 | 2A1_F44V + C107A + S108K<br>Heavy Chain: SEQ ID NO: 299<br>Light Chain: SEQ ID NO: 288 | 2A1_VL |
| Covariance 12 Ab-30 | 2A1_T24A + F44V + F88T + C107T<br>Heavy Chain: SEQ ID NO: 300<br>Light Chain: SEQ ID NO: 288 | 2A1_VL |
| Covariance 13 Ab-31 | 2A1_F44V + F88T + C107A<br>Heavy Chain: SEQ ID NO: 301<br>Light Chain: SEQ ID NO: 288 | 2A1_VL |
| Covariance 14 Ab-32 | 2A1_T24A + F44V + F88T + C107A<br>Heavy Chain: SEQ ID NO: 302<br>Light Chain: SEQ ID NO: 288 | 2A1_VL |
| Covariance 15 Ab-33 | 2A1_K14Q + T24A + G32S + F44V + F88T + T98A + C107A<br>Heavy Chain: SEQ ID NO: 303<br>Light Chain: SEQ ID NO: 288 | 2A1_VL |
| Covariance 16 Ab-34 | 2A1_K14Q + T24A + G32S + F44V + F88T + T98A + C107A<br>Heavy Chain: SEQ ID NO: 304<br>Light Chain: SEQ ID NO: 305 | 2A1_E144K VL |
| Covariance 17 Ab-35 | 2A1_K14Q + R17G + T24A + G32S + F44V + G56S + D84N + F88T + T98A + C107A<br>Heavy Chain: SEQ ID NO: 306<br>Light Chain: SEQ ID NO: 288 | 2A1_VL |

TABLE 9-continued

2A1 mutein sequences

| Covariance 18 Ab-36 | 2A1_K14Q + R17G + T24A + G32S + F44V + G56S + D84N + F88T + T98A + C107A<br>Heavy Chain: SEQ ID NO: 307<br>Light Chain: SEQ ID NO: 305 | 2A1_E144K VL |
|---|---|---|
| Covariance 19 Ab-37 | 2A1_K14Q + R17G + T24A + G32S + F44V + G56S + D84N + F88T + T98A + C107A + S108K<br>Heavy Chain: SEQ ID NO: 308<br>Light Chain: SEQ ID NO: 305 | 2A1_E144K VL |

Differential Scanning calorimetry (DSC) was used to compare the thermostability of parent and engineered antibodies. DSC is a thermodynamical tool for direct assessment of the heat energy uptake, which occurs in a sample within a regulated increase or decrease in temperature. DSC is commonly employed to assess the thermal and conformational stability of a protein. The melting temperature of a protein, or of individual domains, can be obtained from the DSC profile, and if the reaction is reversible the thermodynamic parameters of the unfolding can be determined. A protein is considered more thermostable when the Tm (transition temperature) is higher. When thermostability data are compared to other bioanalytical methods, like size exclusion chromatography (SEC), it has been observed that a correlation between greater thermostability (higher Tm) and decreased aggregation. Antibodies with a higher Tm and decreased aggregation formation have the potential for improved long-term stability thus potentially making better biotherapeutics.

DSC was carried out using a MicroCal™ VP-Capillary DSC system (GE Healthcare, Piscataway, N.J.) equipped with an auto-sampler. The temperature differences between the reference and sample cells are continuously measured, and calibrated to power units. For example, the full-length antibodies shown in TABLE 10 were diluted to 0.5 mg/mL in a buffered solution. The solution reference and protein samples were measured in a 135 μL cell from 20 to 110° C. at a heating rate of 60° C./hour. The pre-scan was set at 15 minutes while the filtering period was 10 seconds. Signal from the blank buffer solution was used for baseline subtraction. The data analysis was performed using MicroCal™ Origin 7 software. Heat capacity during protein melting was calculated by normalizing over protein concentration.

TABLE 10

| Identifier(s) | 2A1 mutein |
|---|---|
| P61050.3<br>Covariance 2<br>Ab-20 | 2A1-HC: R17G, C107A |
| P61051.3<br>Covariance 5<br>Ab-23 | 2A1-HC: F88T, C107A |
| P61052.3 | 2A1-HC: T24A, C107A |
| P61053.3<br>Covariance 10<br>Ab-28 | 2A1-HC: T24A, F88T, C107A |
| P61054.3 | 2A1-HC: R17G, F88T, C107A |
| P61055.3<br>2A1CV4<br>Ab-38 | 2A1-HC: R17G, T24A, C107A |
| P61056.3<br>2A1CV5<br>Ab-1 | 2A1-HC: R17G, T24A, F88T, C107A |

Figure 14A:
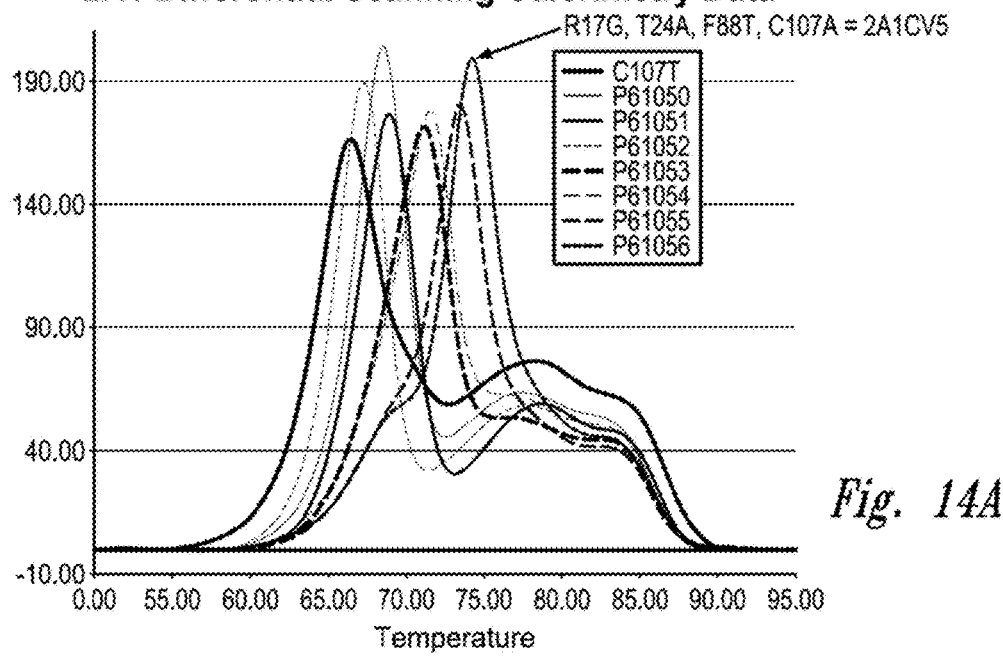
FIGS. 14A and B show the Tm for various 2A1 mAb covariance muteins.
Figure 14B:
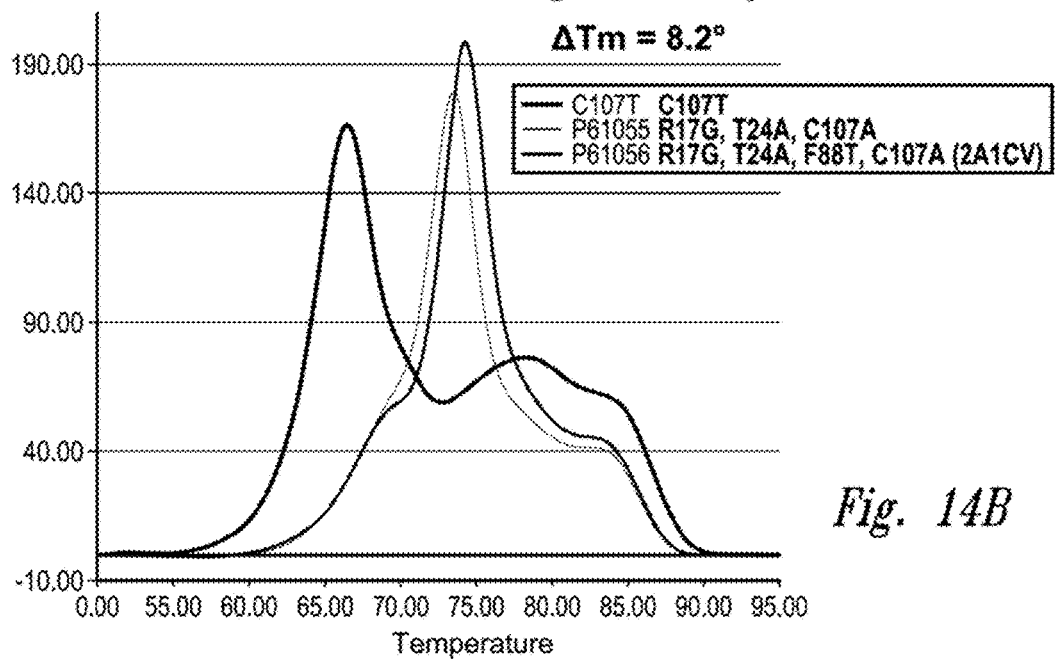

As shown in FIGS. 14A and B, the antibodies that were selectively engineered through site-directed mutagenesis were more thermally stable, as measure by Tm. FIG. 14B shows that three covariant changes resulted in an 8.2° C. increase in Tm. Further studies on additional engineered muteins was conducted and the results are shown in TABLE 11 below. Together this data shows that several of the engineered antibodies, in particular those shown in TABLE 11 (namely Ab-1 (2A1CV5)) had increased stability over other antibodies. Increased thermal stability is a highly desirable attribute in a pharmaceutical preparation.

TABLE 11

Differential Scanning Calorimetry (DSC) results for select antibodies

| Ab | Chain Sub-Type | pI (Whole) | Tm ° C. | Sequences |
|---|---|---|---|---|
| 2A1 CV5 (Ab-1) | VH3/VL1 | 8.39 | 76 | Heavy chain amino acid SEQ ID NO: 274<br>Vh chain amino acid SEQ ID NO: 206<br>Light chain amino acid SEQ ID NO: 280<br>Vl chain amino acid SEQ ID NO: 240 |
| 2A1 CV4 | VH3/VL1 | 8.39 | 75 | Heavy chain amino acid SEQ ID NO: 309<br>Heavy chain DNA SEQ ID NO: 310<br>Vh domain amino acid SEQ ID NO: 311<br>Light chain amino acid SEQ ID NO: 312<br>Light chain DNA SEQ ID NO: 313<br>Vl domain amino acid SEQ ID NO: 314 |
| 32B5 CV1 | VH3/VK2 | 8.55 | 79 | Heavy chain amino acid SEQ ID NO: 315<br>Heavy chain DNA SEQ ID NO: 316<br>Vh domain amino acid SEQ ID NO: 317<br>Light chain amino acid SEQ ID NO: 318<br>Light chain DNA SEQ ID NO: 319<br>Vl domain amino acid SEQ ID NO: 320 |
| 32B5 CV2 Ab-3 (32B5_mut) | VH3/VK2 | 8.55 | 79 | Heavy chain amino acid SEQ ID NO: 278<br>Vh chain amino acid SEQ ID NO: 210<br>Light chain amino acid SEQ ID NO: 284<br>Vl chain amino acid SEQ ID NO: 244 |
| 29C12 CV1 | VH3/VK2 | 8.55 | 82.5 | Heavy chain amino acid SEQ ID NO: 321<br>Heavy chain DNA SEQ ID NO: 322<br>Vh domain amino acid SEQ ID NO: 323<br>Light chain amino acid SEQ ID NO: 324<br>Light chain DNA SEQ ID NO: 325<br>Vl domain amino acid SEQ ID NO: 326 |
| 29C12 CV2 Ab-2 (29C12_mut) | VH3/VK2 | 8.55 | 82.5 | Heavy chain amino acid SEQ ID NO: 276<br>Vh chain amino acid SEQ ID NO: 208<br>Light chain amino acid SEQ ID NO: 282<br>Vl chain amino acid SEQ ID NO: 242 |

Figure 15:
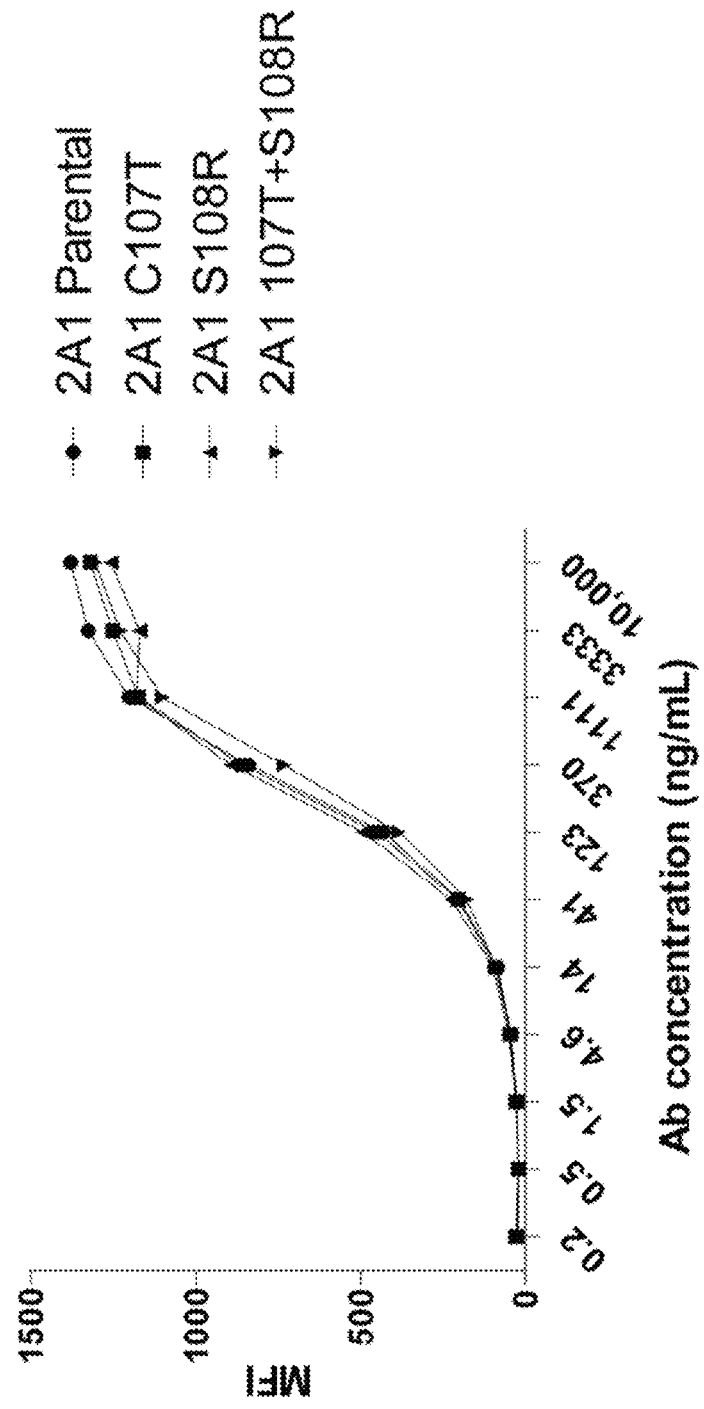
FIG. 15 is a graph showing the binding of various 2A1 mAb covariance muteins to H919 cells.
Figure 16A:
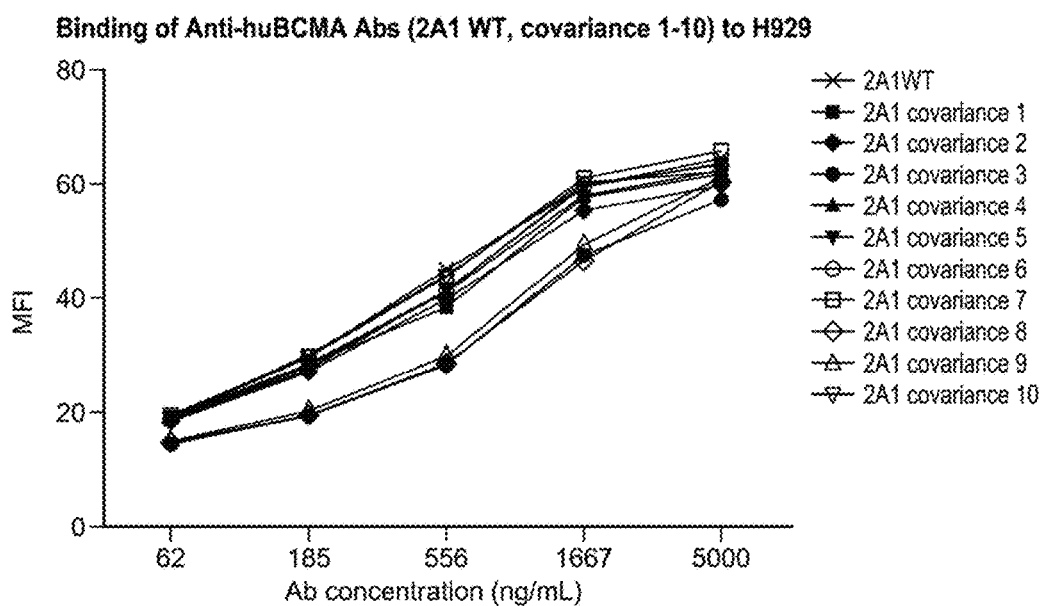
FIGS. 16A and B show that some 2A1 mutein antibodies retained comparable binding to BCMA relative to parental 2A1 (2A1WT), whereas the 2A1 covariance 3, 8, 9 and 11-19 antibodies had reduced binding to BCMA.
Figure 16B:
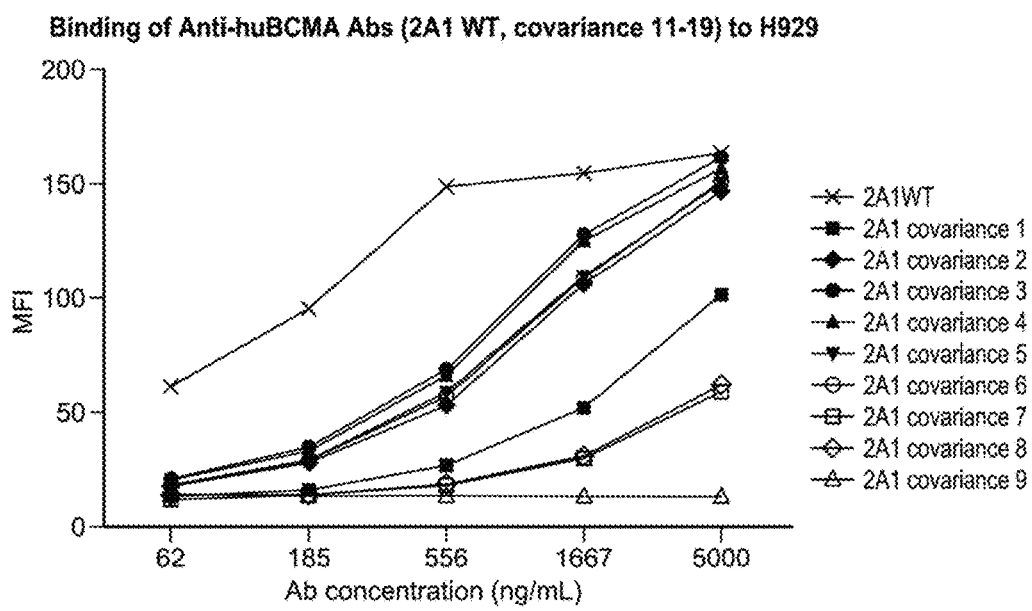

To further characterize the engineered mutein antibodies, they were tested for the ability to bind BCMA by FACS analysis. The antibodies were tested for binding to BCMA endogenously-expressed on a variety of cells, including the H929 cell line, which were developed from B-lymphocytes from a myeloma/plasmacytoma patient (ATCC, Manassa, Va.) using standard FACs techniques. Reagents were prepared using standard methods: 500 mL FACs buffer (PBS, 1% BSA, 5 mM EDTA, 0.02% $NaN_3$), and FACs Block Buffer (30 mL FACs buffer, 5% Normal Rabbit Serum, 5% Normal Human Serum). Approximately 10 to $50 \times 10^6$ H929 cells were aliquoted in a standard 96 well plate (preferably deep-well, such as those provide by Corning). The cell volumes were adjusted to bring all volumes up to 1 mL/tube w/ FACs buffer. The cells were centrifuged at 4° C. for 10 minutes at 1200 rpm. The supernatants were removed and the cell pellets were resuspended in 100 uL of FACs Block Buffer per tube. The cells were incubated for 30 to 60 minutes on ice. The BCMA antibodies were prepared by making premixes of 1:3 serial dilutions of antibodies in FACS Block Buffer starting at 10 ug/ml antibody (for example) in a final volume of 100 ul. The blocked cells were centrifuged at 4° C. for 10 minutes at 1200 rpm. The supernatants were removed and the cell pellets were resuspended in 100 uL of FACs Block Buffer containing the BCMA antibodies. The cells were incubated for 60 minutes on ice. After incubation, 1 mL of cold FACs Block Buffer was added to each tube. The cells were centrifuged at 4° C. for 10 minutes at 1200 rpm. The supernatants were removed and the cell pellets were resuspended in 100 uL of FACs Block Buffer containing biotinylated anti-huIgG (Jackson Labs, Bar Harbor, Me., Cat. 109-065-098) at a 1:100 dilution in FACs Block Buffer. The cells were incubated for 45 minutes on ice. After incubation, 1 mL of cold FACs Block Buffer was added to each tube. The cells were centrifuged at 4° C. for 10 minutes at 1200 rpm. The supernatants were removed and the cell pellets were resuspended in 100 uL of FACs Block Buffer containing streptavidin-phycoerythrin (SA-PE) conjugate (BD Pharmingen, San Diego, Calif., Cat. 554061) at a 1:100 dilution in FACs Block Buffer. The cells were incubated for 45 minutes on ice. After incubation, 1 mL of cold FACs Block Buffer was added to each tube. The cells were centrifuged at 4° C. for 10 minutes at 1200 rpm. The supernatants were removed and the cell pellets were resuspended in 0.2 mL/tube 4% paraformaldehyde in PBS and analyzed by flow cytometry In a preliminary study, the 2A1-C107T, 2A1-S108R, and 2A1-C107T+S108R muteins were tested for binding to BCMA on human myeloma cells (H929 cells) by flow cytometry as described above. FIG. 15 shows comparable binding to BCMA on H929 cells between the 2A1 parental antibody and the three muteins. Next, a larger panel 2A1 mutein (i.e., those listed in TABLE 9) were tested by flow cytometry for binding to BCMA on H929 cells. FIGS. 16A and B show that some 2A1 mutein antibodies retained comparable binding to BCMA relative to parental 2A1 (2A1WT), whereas the 2A1 covariance 3, 8, 9 and 11-19 antibodies had reduced binding to BCMA.

Another important consideration is the impact of mutagenesis on the antibodies ADCC activity and so various mutein antibodies were tested for relative ADCC activity using standard methods. Target cells H929 (having a relatively high level of BCMA expression) and JD38 (having a relatively low level of BCMA expression). JD 38 is an Epstein-Barr virus (EBV)-negative cell line derived from tumor cells circulating in the peripheral blood in a male child with recurrent undifferentiated non-Burkitt lymphoma. H929 and JD38 were labeled with Calcein-AM. H929 and JD38 were harvested and resuspended at $2 \times 10^6$ cells/ml in cRPMI-10 media (RPMI (Life Technologies, Carlsberg, Calif.) +10% fetal bovine serum). Calcein-AM at 4 mM in anhydrous DMSO (Sigma-Aldrich, St. Louis, Mo.) was added to final concentration of 1004 (1:400 dilution). The cells were incubated for 30 minutes at 37° C. followed by two washes in PBS (1500 rpm, 5 minutes at 4° C. each). The pellets were resuspended in cRPMI-10 and adjusted to a concentration of $0.2 \times 10^6$ cells/ml and placed on ice for use in the next step. The various 2A1 mutein antibodies were first added to U-bottom 96-well plates (BD, Franklin Lakes, N.J.) at 10-fold serial titration starting from 10 ug/ml. Rituximab (Genentech, South San Francisco, Calif.), when used, served as a benchmark antibody control. Calcein-AM-labeled target cells from previous were then added to each well (10,000 cells/well) and incubated with antibodies for 20 minutes at 37° C. The effector cells were prepared: NK cells or PBMC were pelleted at 1500 rpm, 5 minutes at 4° C. and resuspended in cRPMI-10 to a final cell concentration of $4 \times 10^6$ cells/ml for NK cells or $20 \times 10^6$ cells/ml for PBMC. Following incubation, 50 µl of NK cells was added to each well at a concentration of $4 \times 10^6$ cells/ml or PBMC at a concentration of $20 \times 10^6$ cells/ml and incubated for 4 hours at 37° C. Following incubation, controls wells were prepared by adding 20 µl/well 9% NP-40 (IGEPAL CA 630, Sigma-Aldrich) to stimulate 100% lysis. All other wells received 20 µl/well of cRPMI-10 media alone. The plates were spun at 800 RPM for 4 minutes at 4° C. The supernatants (150 µl) were removed and transferred to a clear bottom, black 96 well plate (Corning, Lowell, Mass.) and fluorescence read on plate reader (Molecular Devices, Spectra max GEMINI), excitation 485, emission 535. Percent maximum lysis was calculated as (sample value-spontaneous lysis)/(100% lysis–spontaneous lysis)×100.

Figure 17:
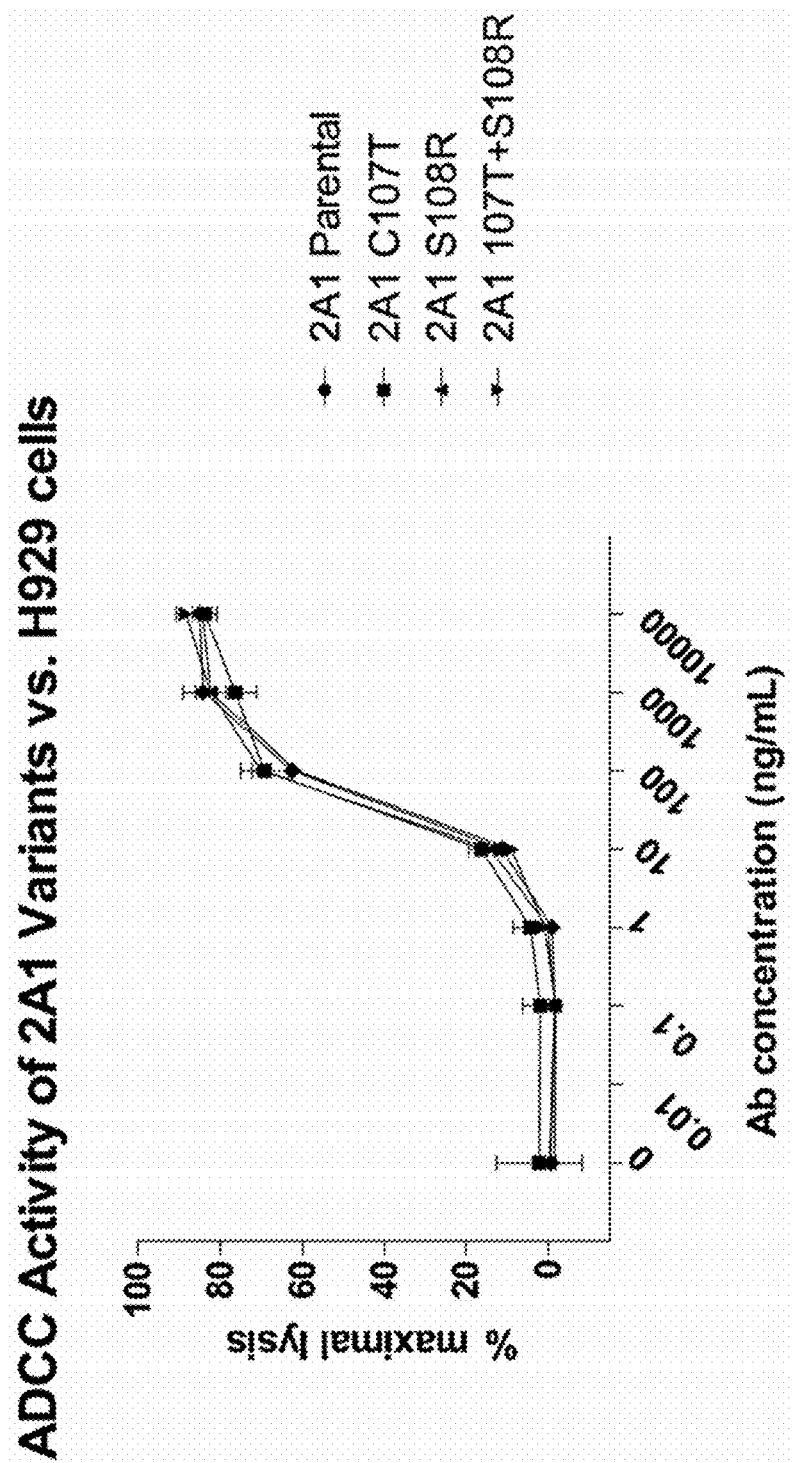
FIG. 17 shows the comparative ADCC activity of various 2A1 mAb covariance muteins.
Figure 18A:
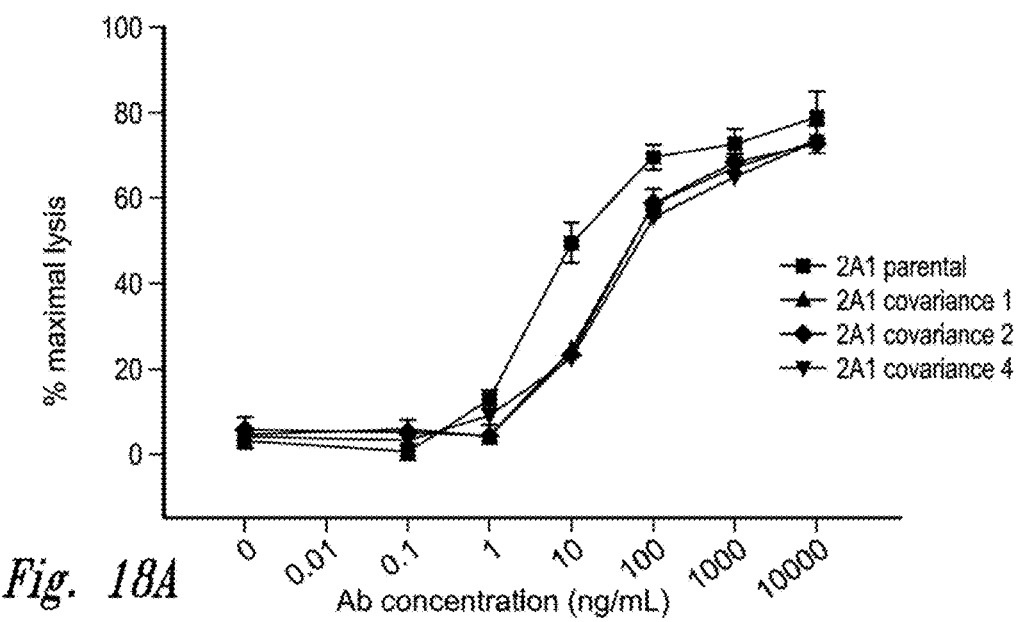
FIGS. 18A and B show the comparative ADCC activity of various 2A1 mAb covariance muteins.
Figure 18B:
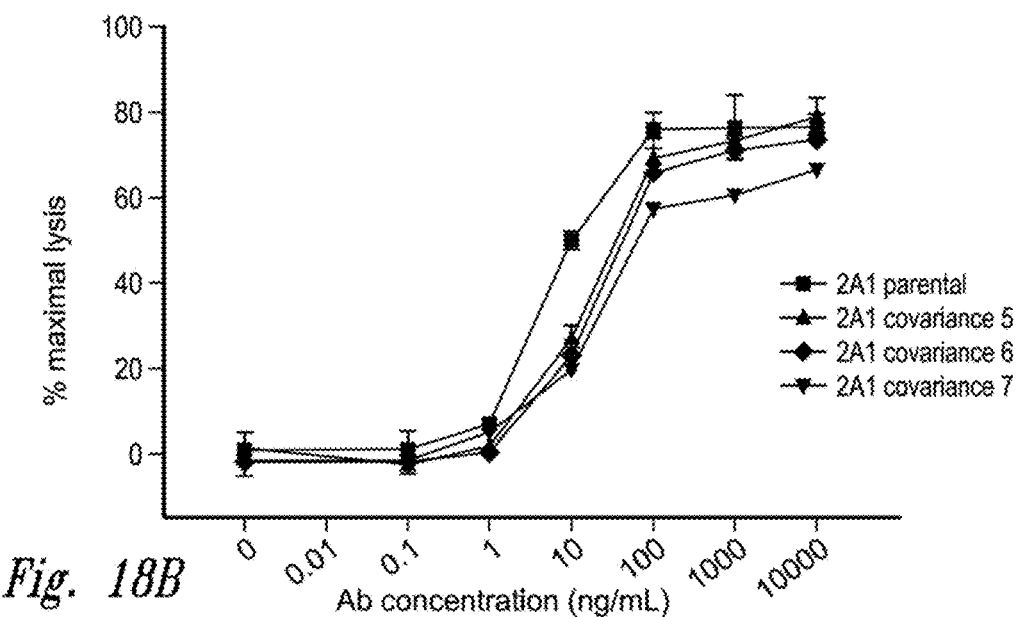
Figure 19A:
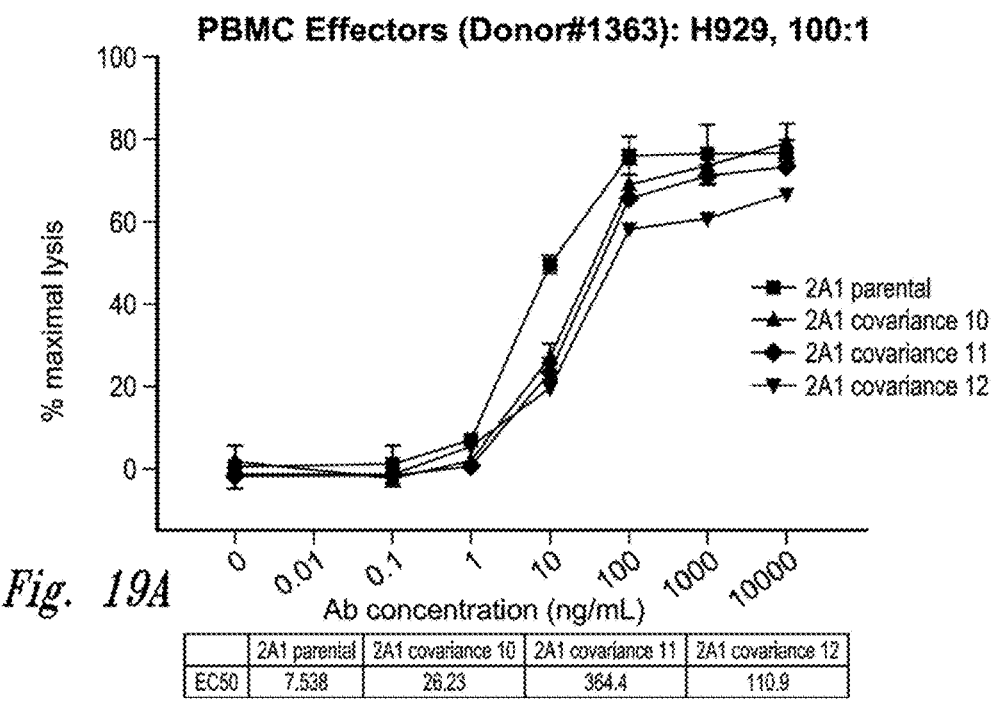
FIGS. 19A and B shows the comparative ADCC activity of various 2A1 mAb covariance muteins.
Figure 19B:
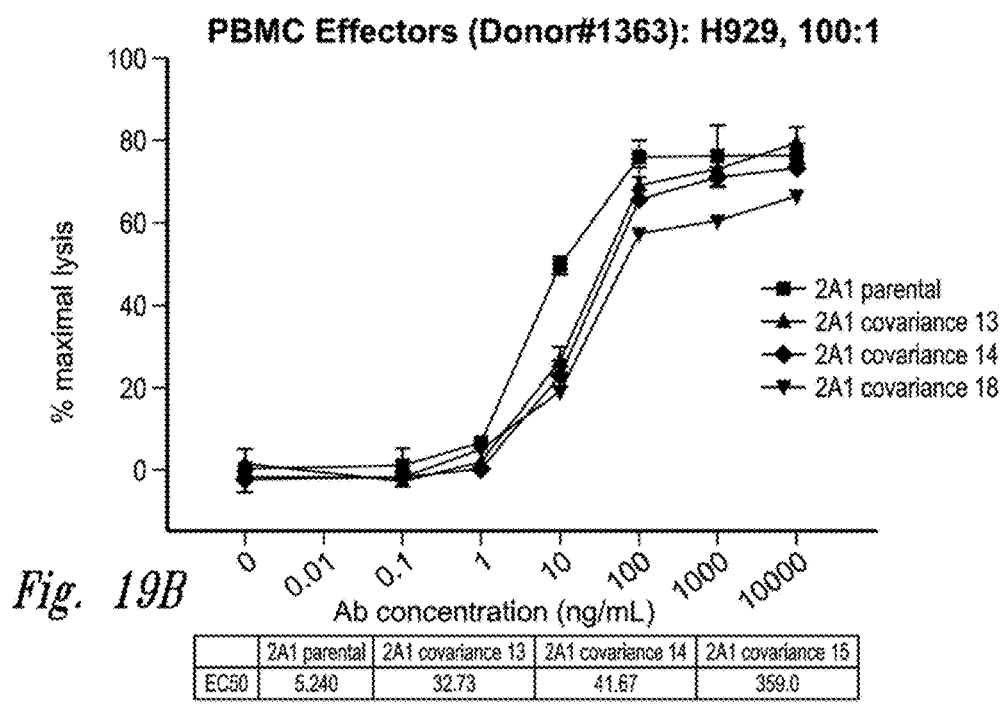

In a preliminary study, the 2A1-C107T, 2A1-S108R, and 2A1-C107T+S108R muteins were tested for ADCC activity as described above. FIG. 17 and TABLE 12, which summarizes the $EC_{50}$ (ng/ml) for 2A1 muteins, shows comparable ADCC activity between the 2A1 parental antibody and the three muteins. Next, a larger panel 2A1 mutein (i.e., some of those listed in TABLE 9) were tested for ADCC activity. FIGS. 18A, 18B, 19A, and 19B and TABLE 13 show that some 2A1 mutein antibodies retained comparable ADCC activity relative to parental 2A1 (2A1WT), whereas some of the 2A1 covariance had reduced ADCC activity relative to parental 2A1.

TABLE 12

ADCC $EC_{50}$ (ng/ml) for 2A1 muteins

| mAb | ADCC $EC_{50}$ (ng/ml) |
|---|---|
| 2A1 Parental | 29 |
| 2A1 C107T | 31 |
| 2A1 S108R | 43 |
| 2A1 C107T + S108R | 49 |

TABLE 13

ADCC $EC_{50}$ (ng/ml) for 2A1 muteins

| mAb (see TABLE 9) | ADCC $EC_{50}$ (ng/ml) |
|---|---|
| 2A1 parental | 5.5, 6.3, 7.5, 5.2 |
| 2A1 covariance 1 | 23.8 |
| 2A1 covariance 2 | 24.1 |
| 2A1 covariance 4 | 28.0 |
| 2A1 covariance 5 | 16.0 |
| 2A1 covariance 6 | 16.9 |
| 2A1 covariance 7 | 19.1 |
| 2A1 covariance 10 | 26.2 |
| 2A1 covariance 11 | 364.4 |
| 2A1 covariance 12 | 111.0 |
| 2A1 covariance 13 | 32.7 |
| 2A1 covariance 14 | 41.7 |
| 2A1 covariance 18 | 359.0 |

Another consideration is the impact of mutagenesis on the expression levels of the engineered antibodies. The antibodies listed in TABLE 9 were transiently expressed in 293-6E mammalian cells using an automated 24-well transfection protocol. The following protocol was used:
Reagents:
  DNA normalized to 20 ng/uL
  25 kDa linear PEI Max™ (Poly sciences, catalog no. 24765) transfection reagent (3 mg/mL stock)
  2936E cells at 1e6 cells/mL and viability >98%
Growth and Transfection Media:
  Growth Media: 1 L 293 Freestyle™ medium (Life Technologies, catalog no. 12338-018) supplemented with 10 mL Pluronic F68 (Life Technologies, catalog no. 24040) and 0.5 mL Geneticin (50 mg/mL, Life Technologies, catalog no. 10131)

Peptone Re-feed: Difco TC Yeastolate UF stock 20% w/v (BD Biosciences, catalog no. 292805)

Supplies:
Autoclaved 24 deep well blocks: Seahorse Bioscience 201272-100 (Fisher 50 995 855)
Autoclaved uflask lids
96-well costar 3799 plate (Fisher 07 200 95)

Automated Transfection Process:

The viable cell density (VCD) was measured on a Vi-Cell (Beckman Coulter) targeting a VCD of approximately $1\times10^6$ cells/mL and a viability of greater than 98%. 0.25 ug of DNA per mL of culture was added. 50 uL of normalized pooled HC/LC DNA was transferred to the 24-well plate (1 ug Total DNA). 200 uL of media (unsupplemented 293 Freestyle)+7 ug PEI to the 24-well plates (1:7 DNA:PEI ratio) was added. The DNA was added to the plate followed by the media plus PEI. The DNA/Media/PEI was allowed to complex for 10 minutes. The cells were dispensed into the plates by aliquoting 4 mL of the 2936E cell suspension at approximately $1\times10^6$ cells/mL to a final volume of 4.25 mL. The cells were placed in a Kuhner™ incubator with sterile uflask lids. A re-feed with the peptone-based media was done 1-4 hours post transfection by adding 20% w/v Yeastolate to a final concentration of 0.5% w/v. The cells were returned to the incubator for the production phase by placing them on an orbital shaker at 240 rpm at 37° C. and 5% $CO_2$. The cells were passaged in growth medium and the VCD measured to keep the cells in log phase (approximately $1.5\times10^5$ to $2\times10^6$ cells/mL). The cells were passaged approximately every other day. The supernatants were harvested on day 6 by spinning the plates at 3000 rpm for 10 minutes and transferring the supernatants to new plate.

The IgG levels were analyzed on the ForteBio Octet QKe™ using the aligned Protein A Basic quantitation with regeneration protocol.

Materials:
Black, flat-bottomed assay plates (BLK NS 96 well half area flat bottom PP microtiter plates from Greiner Bio-One, manufacturer part number 675076, Fisher-Scientific part number_NC9624456)
Neutralization Buffer (ForteBio diluent—PBS, pH 7.4 with 0.1% BSA, 0.02% Tween 20®, 0.05% sodium azide) at 4° C.
Regeneration Buffer (Transient Elution Buffer—10 mM Glycine, 150 mM NaCl, pH 2.0)

The Protein A sensor was used to quantitate human IgGs. The standard curves (STD CRV) were run in the range of 1-500 ug/mL. The sensors were presoaked in ForteBio diluent. One sensor per sample was prepped by adding 100 uL of Fortebio diluent to wells of a black assay plate and resting the rack of sensors on top of the black assay plate. The sensors were soaked for at least 10 min prior to assay. An isotype-matched standard control (huIgG1) was prepared. The control antibody was titrated in the assay plate by adding 100 uL of the ForteBio diluent to columns 2-10 and adding 200 uL of the control antibody diluted to 500 ug/mL in ForteBio diluent to column 1 in duplicate. A serial dilution was performed (100 uL from column 1 through column 10) resulting in a standard curve having the following concentrations: 500, 250, 125, 62.5, 31.25, 15.63, 7.81, 3.91, 1.95, 0.98 ug/mL. In a separate black assay plate, the antibody samples were prepared by diluting the culture media into Fortebio diluent to a total volume of 100 uL. The software used was the "Data Acquisition 7.0" and the "Basic Quantitation with Regeneration." The "Assay Settings" were set such that the 'Time (s)' field was set at 120 seconds and the 'Shake speed' field was at 400. The 'Time (s)' field for the 'Regeneration' and 'Neutralization' steps were set at 5 seconds with a 'Shake speed' of 400. Assay results were analyzed on the "Data Analysis 7.0" software.

Figure 20:
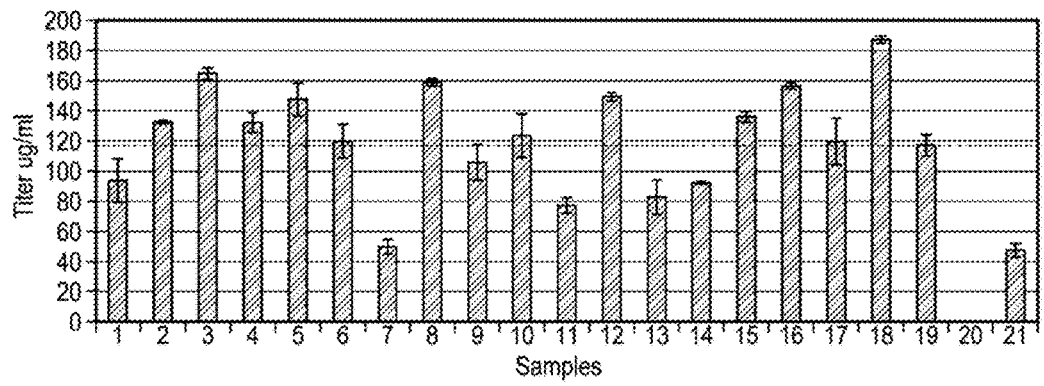
FIG. 20 is a histogram showing the comparative expression titers of various 2A1 mAb covariance muteins.

FIG. 20 shows expression titers in ug/ml for the covariance mutein antibodies listed in TABLE 9. Several of the covariant muteins showed heightened expression levels. Many of the covariant muteins demonstrated acceptable expression levels.

Further analysis on additional 2A1 covariance muteins was performed. The 2A1 muteins (listed as "variant") in TABLE 14 were tested for Tm using the method described above, as well as for assessing the yield (mg/L). This data shows that the Tm for C107A was somewhat preferable over the C107S and C107T variants, but all were acceptable.

TABLE 14

Yield/L and Tm for 2A1 covariance mutein antibodies

| Name | Ref. | Variant | Yield/L | Tm1 | Tm2 | Tm3 |
|---|---|---|---|---|---|---|
| mAb 1 | P52090.13 | HC: C107T LC: WT | 44 (~90 norm) | 64.8 | 76.1 | 83.3 |
| mAb 2 | P58669.8 | HC: D84N + C107T LC: WT | 129 | 71.1 | — | 84.0 |
| mAb 3 | P58671.8 | HC: D84N + C107T LC: WT | 141 | 68.6 | — | 83.6 |
| mAb 4 | P58672.8 | HC: F88T + C107T LC: WT | 156 | 68.4 | 76.2 | 83.7 |
| mAb 5 | P58673.8 | HC: C107A LC: WT | 130 | 69.4 | — | 84.3 |
| mAb 6 | P59720.5 | HC: C107A LC: E144K | 145 | 67.9 | — | 84.0 |
| mAb 7 | P58674.8 | HC: S108K + C107T LC: WT | 67 | 65.7 | 76.2 | 83.2 |
| mAb 8 | P58677.8 | HC: T24A + F88T + C107T LC: WT | 129 | 70.8 | — | 83.7 |
| mAb 9 | P58680.8 | HC: F44V + F88T + C107A LC: WT | 125 | 73.2 | — | 83.7 |
| mAb 10 | P58681.8 | HC: T24A + F44V + F88T + C107A LC: WT | 140 | 67.9 | 76.2 | 83.8 |
| mAb 11 | P58685.6 | HC: K17Q + R17G + T24A + G32S + F44V + G56S + D84N + F88T + T98A + T107A LC: E144K | 72* (>140) | 68.9 | 74.6 | 84.0 |
| mAb 12 | P59721.3 | HC: C107S LC: WT | 35* | 67.3 | 74.0 | 84.3 |

Figure 21A:
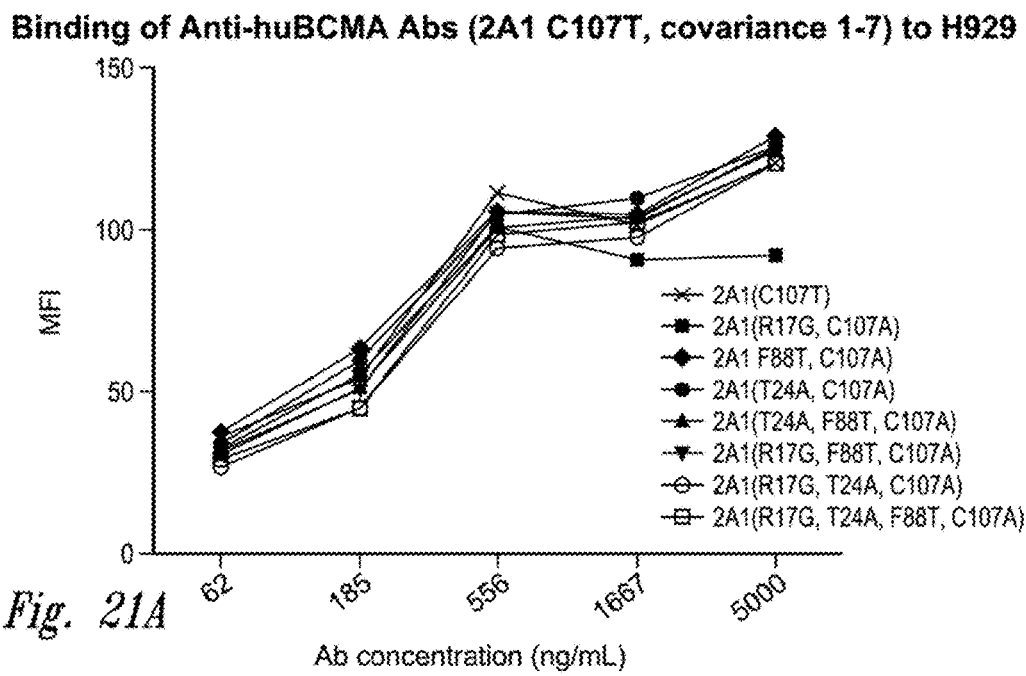
FIGS. 21A and B shows the comparative binding activity of various 2A1 mAb covariance muteins.
Figure 21B:
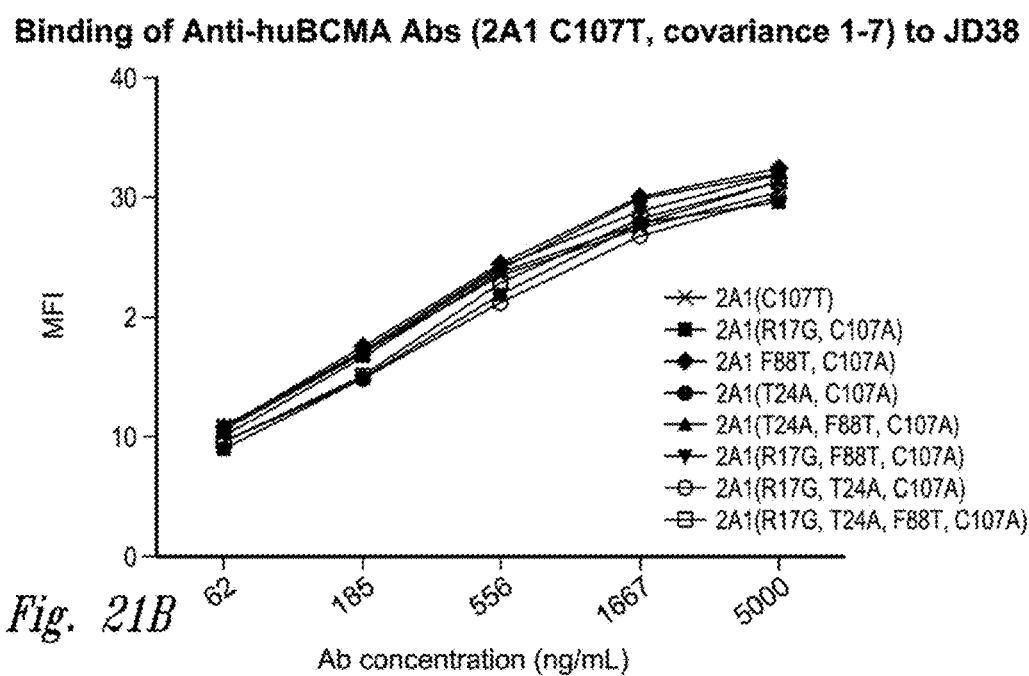
Figure 22A:
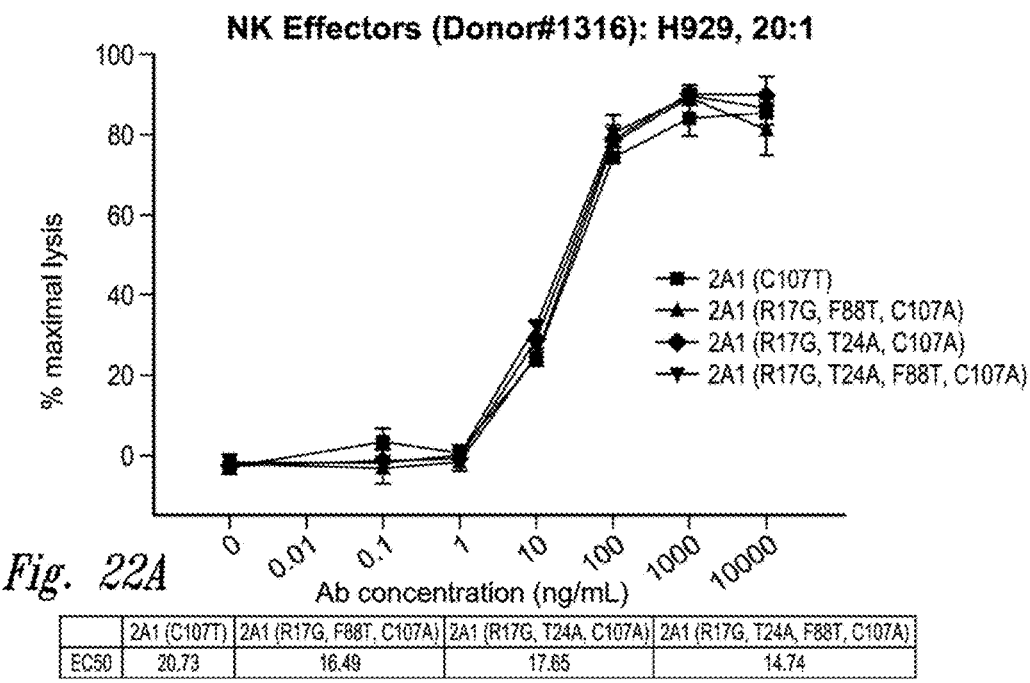
FIGS. 22A and B shows the comparative ADCC activity of various 2A1 mAb covariance muteins.
Figure 22B:
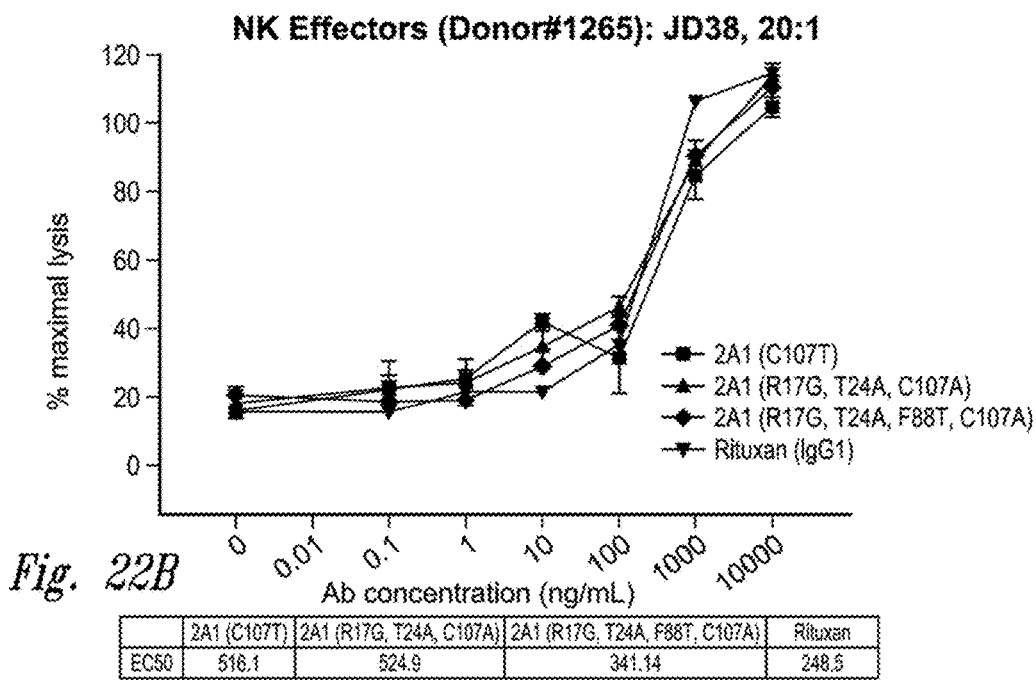

To ensure that the latest round of covariance mutein antibodies retained the desired biological activity, BCMA-binding and ADCC activity for additional 2A1 muteins was performed using two different cell lines. Using the assays described above, the following 2A1 muteins were tested for binding to BCMA on H929 myeloma cell line (having a relatively high surface expression of BCMA) and the JD38 cell line (having a relatively low surface expression of BCMA). The following covariance mutein 2A1 antibodies were tested: 2A1(C107T), 2A1(R17G, C107A), 2A1(F88T, C107A), 2A1(T24A, C107A), 2A1(T24A, F88T, C107A), 2A1(R17G, F88T, C107A), 2A1(R17G, T24A, C107A), and 2A1(R17G, T24A, F88T, C107A). FIGS. 21A and B show that the covariance muteins retained binding to BCMA expressed on myeloma cells and that there were some minor differences in binding amongst the antibodies tested. FIGS. 22A and B show the covariance muteins retained ADCC activity to BCMA expressed on two cancer cell lines.

Figure 23:
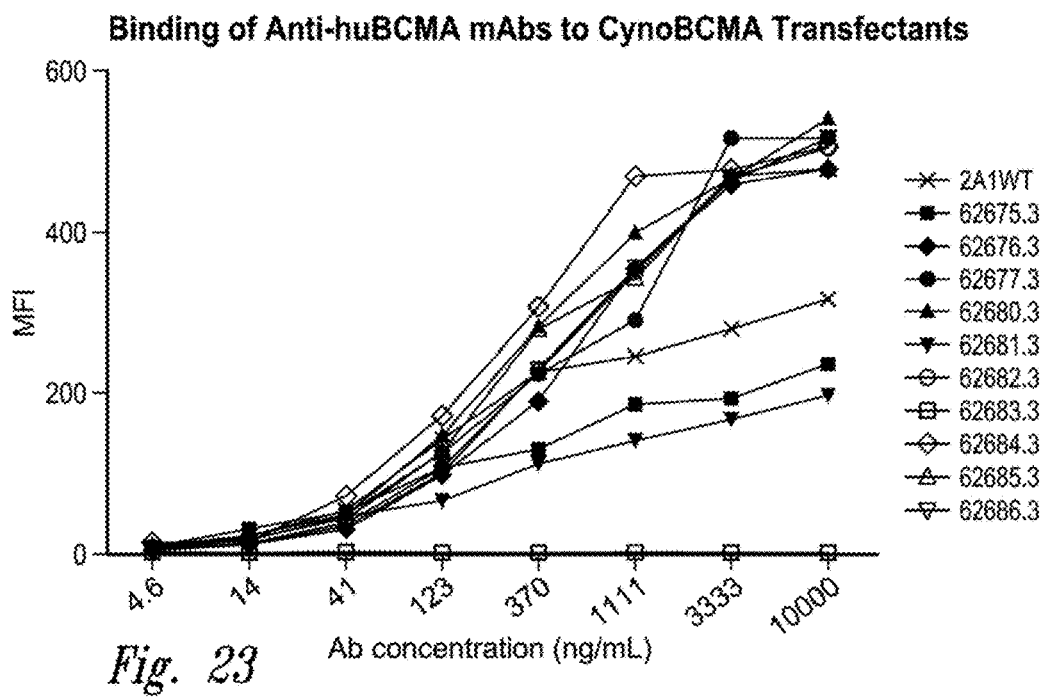
FIG. 23 shows that anti-huBCMA antibodies from the second campaign had the capacity to bind cynomolgus BCMA.
Figure 24:
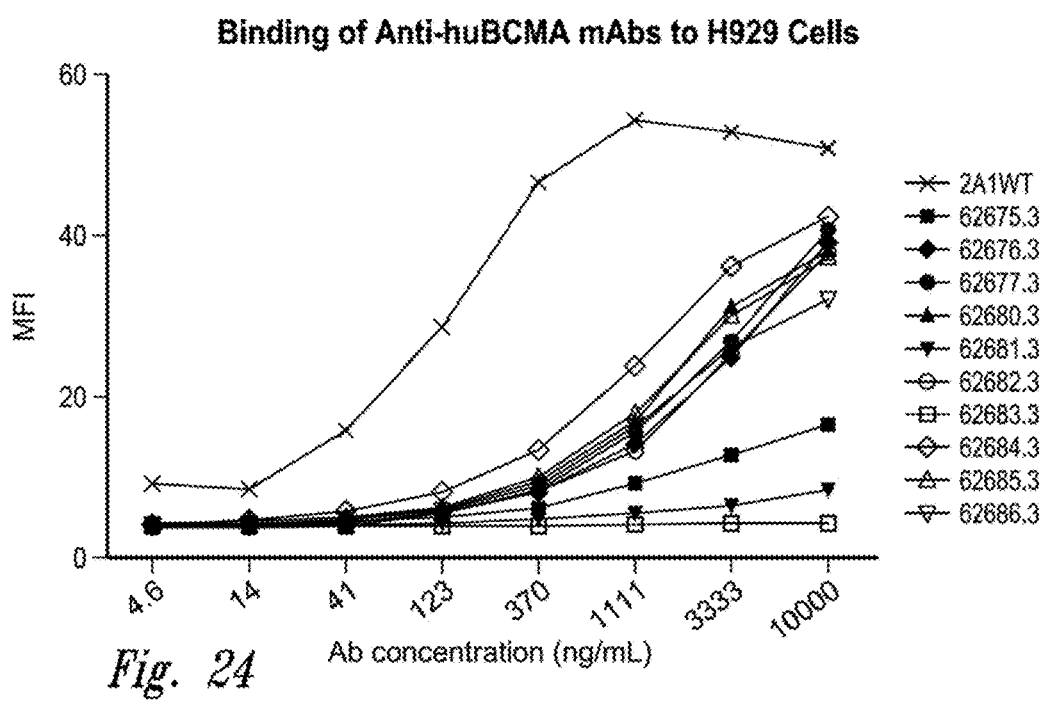
FIG. 24 shows that some of the anti-huBCMA antibodies from the second campaign had the capacity to bind huBCMA on the H929 multiple myeloma cell line.

Characterization and sequence engineering of antibodies from the second campaign was performed using the assays described above. Additional Xenomouse human monoclonal antibodies from purified hybridoma supernatants were prepared as described above (IgG2 or IgG4 anti-huBCMA mAbs 30E1.1, 29C12.1, 29G5.1, 32B5.1, 32H3.1, 33C7.1, 33D4.1, 35D2.1, 37B2.1, and 40D7.1). These antibodies were further analyzed for binding to cynomolgus BCMA on 293T cells transiently transfected to express cynomolgus BCMA, as described herein. FIG. 23 shows that this select group of antibodies showed cross-reactivity to cynomolgus BCMA and that seven out of ten of the antibodies had higher binding to cynomolgus BCMA than did the 2A1 antibody. The panel of antibodies was further characterized for binding to huBCMA on the multiple myeloma cell line H929. FIG. 24 shows that there was a wide spectrum of binding, further demonstrating that acquiring human monoclonal antibodies with sufficient binding capacity to huBCMA was not predictable or routine.

Figure 25A:
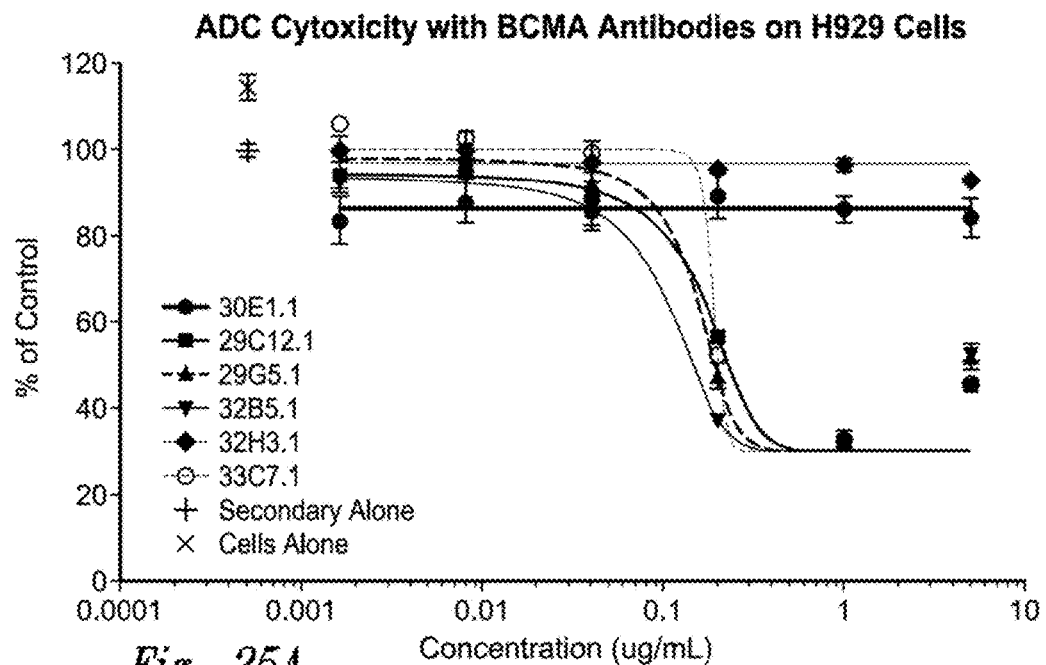
FIGS. 25A and 25B show that ADCs made from the 29C12.1, 29G5.1, 32B5.1, 33C7.1, 35D2.1, 37B2.1, and 40D7.1 antibodies selectively killed huBCMA-expressing target cells.
Figure 25B:
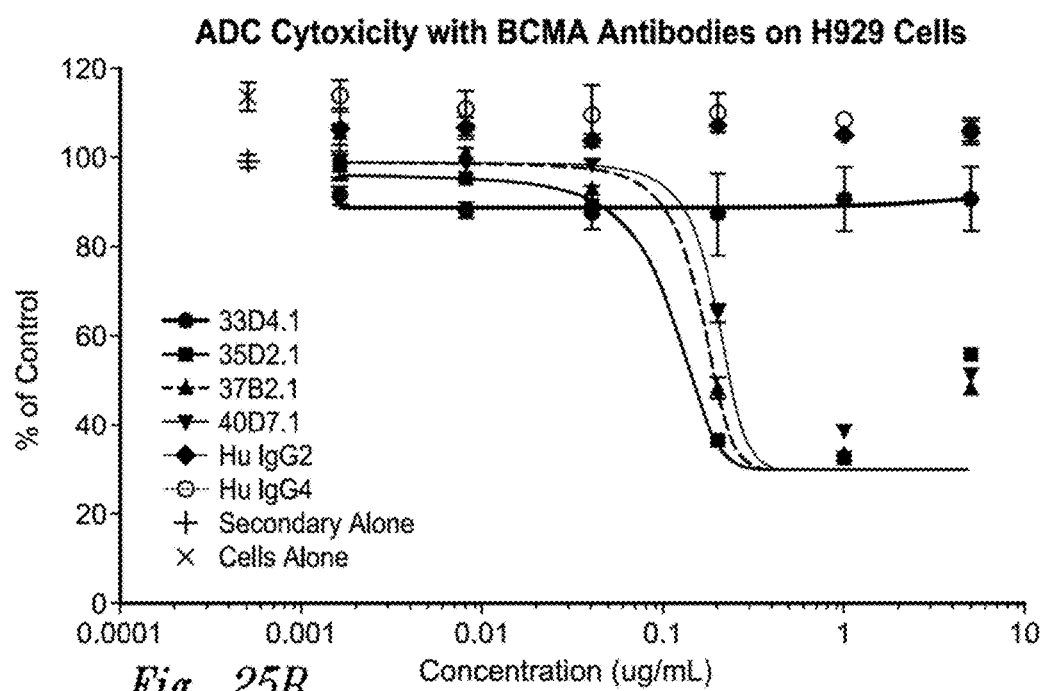

Antibody-drug-conjugates of additional Xenomouse human monoclonal antibodies from purified hybridoma supernatants (anti huBCMA mAbs 30E1.1, 29C12.1, 29G5.1, 32B5.1, 32H3.1, 33C7.1, 33D4.1, 35D2.1, 37B2.1, and 40D7.1) were prepared as essentially described in Example 6. These ADCs were tested for the ability to target and kill huBCMA-expressing myeloma cells (H929 cell line) using the CellTiter-Glo® Luminescent Cell Viability Assay described in Example 10. FIGS. 25A and 25B show that the 29C12.1, 29G5.1, 32B5.1, 33C7.1, 35D2.1, 37B2.1, and 40D7.1 ADCs showed cytotoxicity to the huBCMA-expressing myeloma target cells.

The panel of antibodies from the second campaign were converted to human IgG1 isotype. The sequences were analyzed for covariance violations as described above. TABLE 15 summarizes the list of substitutions for the listed antibodies.

TABLE 15

Covariance analysis of second campaign antibodies

| Name | Number of Violations/ Clade | Violation with proposed substitution |
| --- | --- | --- |
| 32B5_VL | 4/1 | I5T, V1D, F103V, S57Y (43, 35, 33, 24), S51G VH/VL |
| 32B2_VH | 3/1 | A11G, S97R, H92Q (38, 32, 29) |
| 37B2_VL | 4/1 | I5T, V1D, F103V, S57Y (43, 35, 33, 24) |
| 37B2_VH | 3/1 | A11G, S97R, H92Q (38, 32, 29) |
| 35D2_VL | 4/1 | I5T, V1D, F103V, S57Y (43, 35, 33, 24) |
| 35D2_VH | 2/1 | A11G, H92Q (38, 29) |
| 29C12_VL | 2/1 | I5T, S57Y (43, 24) |
| 29C12_VH | 1/1 | A11G (38) |
| 40D7-VL | 3/1 | I5T, L78F, S57Y (43, 37, 23) |
| 40D7-VH | 1/1 | A11G (38) |

A number of covariants were developed through site-directed mutagenesis and analyzed by various means (as described above). TABLE 16 summarizes the sequence changes, titers, yield, purity and Tm. It is noteworthy that the 29C12 (LC: N69Q) and 32B5 (HC: A11G, H92Q, S97R; LC: N69Q, F103V) covariants had notable increases in titer, yield, and Tm. TABLE 17 provides the amino acid sequences for the full length light and heavy chains.

TABLE 16

Characterization of covariance muteins of second campaign antibodies

| ID | Name | Titer (mg/L) | Yield (mg) | SEC Purity | Tm (DSC) |
| --- | --- | --- | --- | --- | --- |
| P70170.3 | 32B5 (LC: T71A) | 9.3 | 9.3 | 99.4 | — |
| P70169.3 | 32B5 (LC: N69Q) | 12 | 12 | 99.6 | — |
| P71567.3 | 35D2/32B5 (LC: N69Q) | 12.3 | 5.4 | 99.9 | 72.8 |
| P71568.3 | 37B2/32B5 (LC: N69Q) | 19.8 | 18.1 | 99.4 | 76.6 |
| P71569.3 | 29C12 (N69Q) | 36.4 | 27.9 | 99.7 | 82.1 |
| P71570.3 | 29C12/40D7 (LC: N69Q) | 24.1 | 13.9 | 99.7 | 77.6 |
| P71562.3 | 32B5 (HC: V1D) | 8.9 | 4.7 | 99.9 | — |
| P71563.3 | 32B5 (LC: I5T) | 10.6 | 5.6 | 99.8 | 75.8 |
| P71564.3 | 32B5 (LC: S57Y) | 2 | 0.3 | 99.9 | — |
| P71565.3 | 32B5 (HC: A11G, S97R) (LC: F103V) | 20.1 | 14.2 | 99.6 | 80 |
| P71566.3 | 32B5 (HC: A11G, H92Q, S97R) (LC: N69Q, F103V) | 31.2 | 22.3 | 98.8 | 79.9 |

TABLE 17

Amino acid sequences for covariance mutein antibodies

| Name | Sequence Identifiers |
| --- | --- |
| 32B5 (LC: T71A) | Light Chain Amino Acid Sequence: SEQ ID NO: 327<br>Heavy Chain Amino Acid Sequence: SEQ ID NO: 328 |
| 32B5 (LC: N69Q) | Light Chain Amino Acid Sequence: SEQ ID NO: 329<br>Heavy Chain Amino Acid Sequence: SEQ ID NO: 330 |
| 35D2/32B5 (LC: N69Q) | Light Chain Amino Acid Sequence: SEQ ID NO: 331<br>Heavy Chain Amino Acid Sequence: SEQ ID NO: 332 |
| 37B2/32B5 (LC: N69Q) | Light Chain Amino Acid Sequence: SEQ ID NO: 333<br>Heavy Chain Amino Acid Sequence: SEQ ID NO: 334 |
| 29C12 (N69Q) | Light Chain Amino Acid Sequence: SEQ ID NO: 335<br>Heavy Chain Amino Acid Sequence: SEQ ID NO: 336 |
| 29C12/40D7 (LC: N69Q) | Light Chain Amino Acid Sequence: SEQ ID NO: 337<br>Heavy Chain Amino Acid Sequence: SEQ ID NO: 338 |
| 32B5 (HC: V1D) | Light Chain Amino Acid Sequence: SEQ ID NO: 339<br>Heavy Chain Amino Acid Sequence: SEQ ID NO: 340 |
| 32B5 (LC: I5T) | Light Chain Amino Acid Sequence: SEQ ID NO: 341<br>Heavy Chain Amino Acid Sequence: SEQ ID NO: 342 |
| 32B5 (LC: S57Y) | Light Chain Amino Acid Sequence: SEQ ID NO: 343<br>Heavy Chain Amino Acid Sequence: SEQ ID NO: 344 |
| 32B5 (HC: A11G, S97R) (LC: F103V) | Light Chain Amino Acid Sequence: SEQ ID NO: 345<br>Heavy Chain Amino Acid Sequence: SEQ ID NO: 346 |
| 32B5 (HC: A11G, H92Q, S97R) (LC: N69Q, F103V) | Light Chain Amino Acid Sequence: SEQ ID NO: 347<br>Heavy Chain Amino Acid Sequence: SEQ ID NO: 348 |

Figure 26:
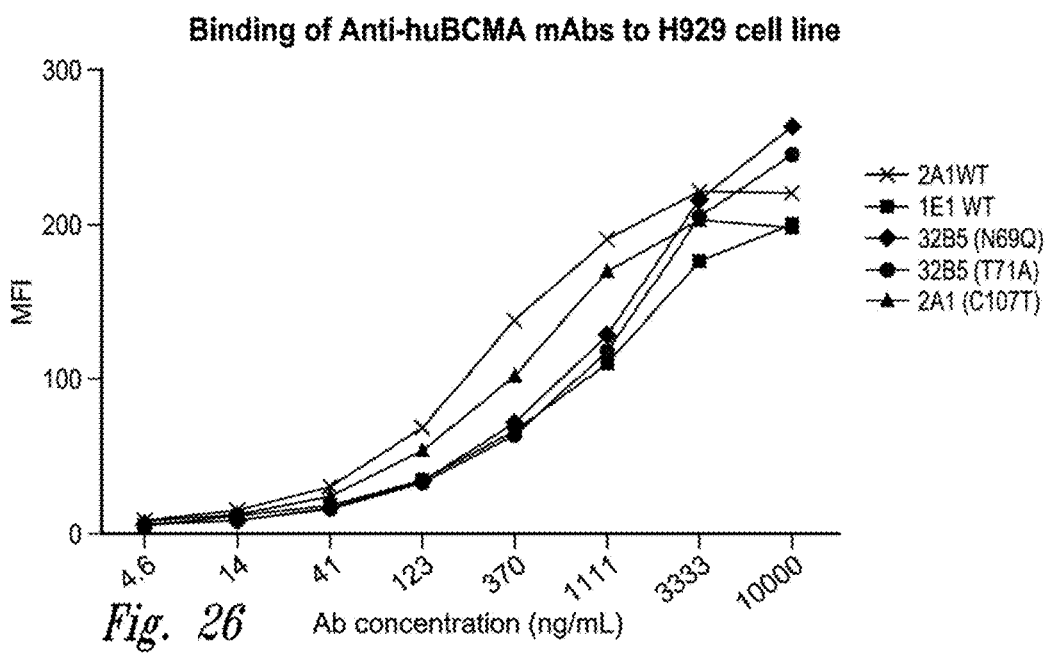
FIG. 26 shows comparative binding to huBCMA on H929 cells among various candidate antibodies (including covariance mutein antibodies from the second campaign).
Figure 27:
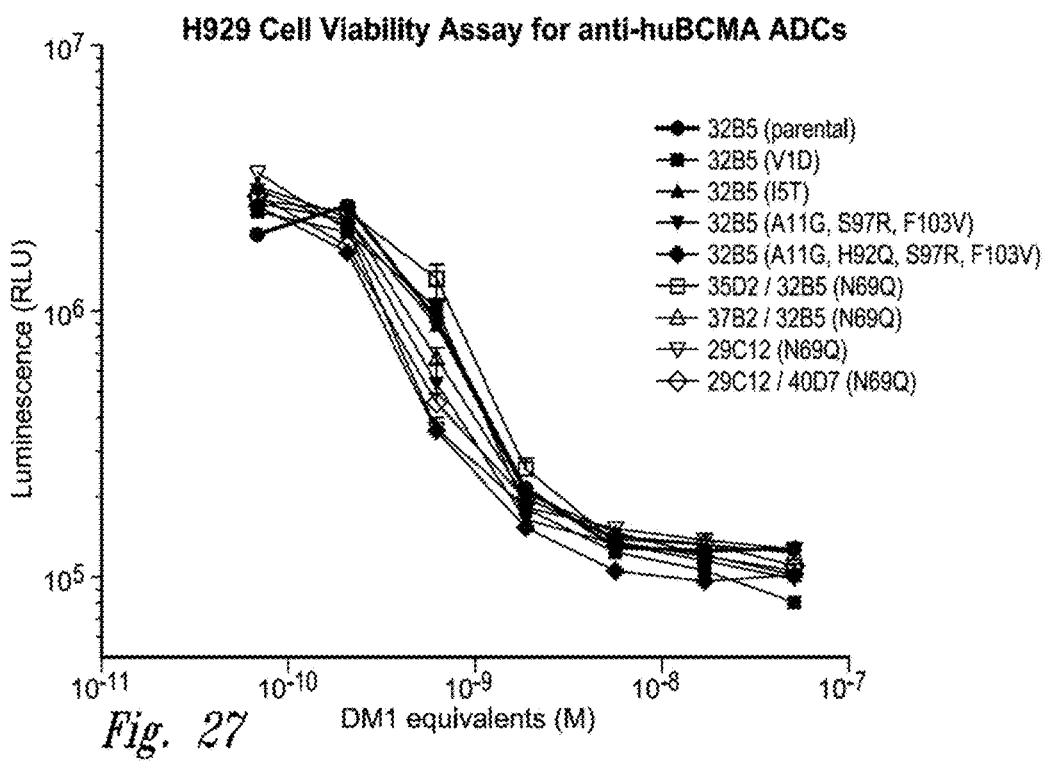
FIG. 27 illustrates the relative killing of H929 cells by various ADCs.
Figure 28:
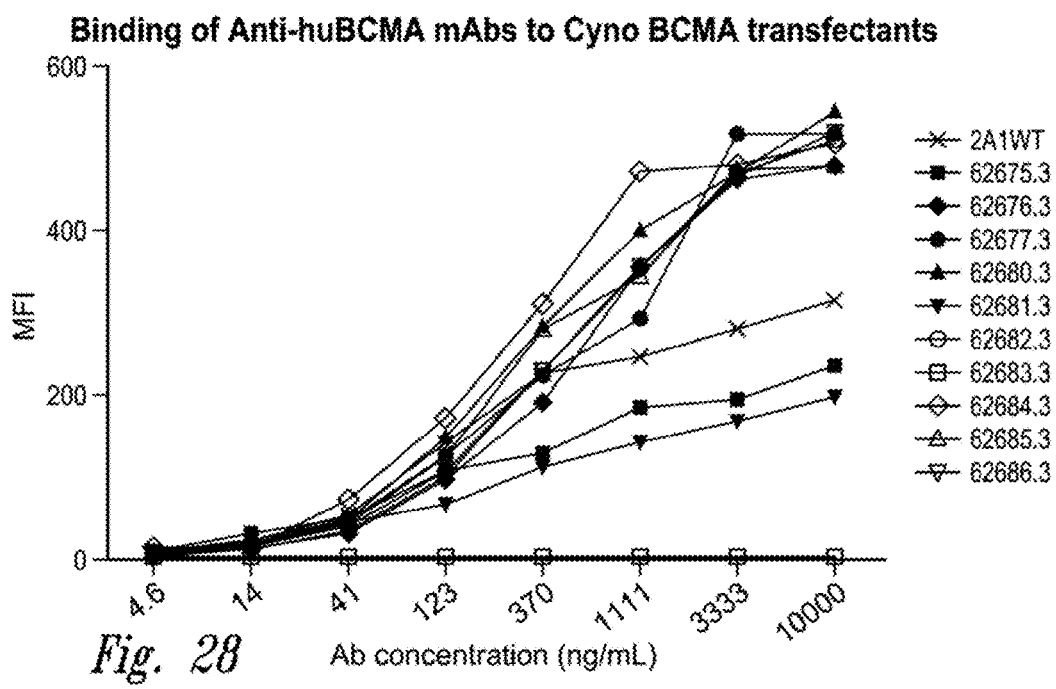
FIG. 28 shows that most of the covariance mutein antibodies from the second campaign retained the capacity to bind cynomolgus BCMA.

Several of the covariant antibodies from the second campaign described above were tested for functional activity to evaluate the effect of mutagenesis on biological activity. FIG. 26 shows comparative binding among various candidate antibodies (including some of the covariant antibodies from the second campaign) for binding to huBCMA on H929 cells. ADCs of the following antibodies were generated as essentially described in Example 6: 32B5 parental, 32B5 (V1D), 32B5 (I5T), 32B5 (A11G, S97R, F103V), 32B5 (A11G, H92Q, S97R, F103V), 35D2/32B5 (N69Q), 37B2/35B5 (N69Q), 29C12 (N69Q), and 29C12/40D7 (N69Q). These ADCs were tested for the ability to target and kill BCMA-expressing myeloma cells (H929 cell line) using the CellTiter-Glo® Luminescent Cell Viability Assay described in Example 10. FIG. 27 shows the relative killing of H929 cells by the various ADCs. FIG. 28 shows that most of the covariant antibodies from the second campaign retained the capacity to bind cynomolgus BCMA (transiently transfected 293T cells).

Figure 41A:
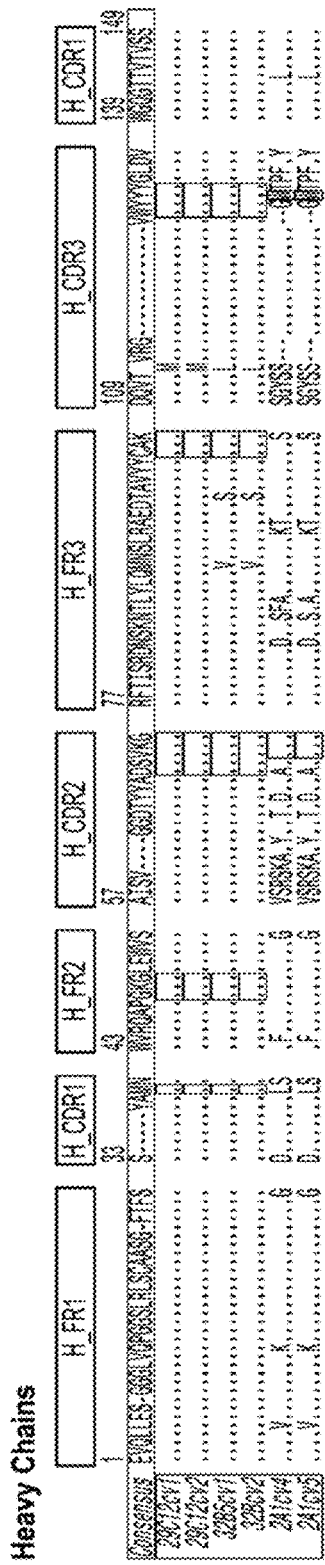
FIGS. 41A and 41B are sequence alignments of the heavy and light variable domains of the covariance muteins having optimal properties.
Figure 41B:
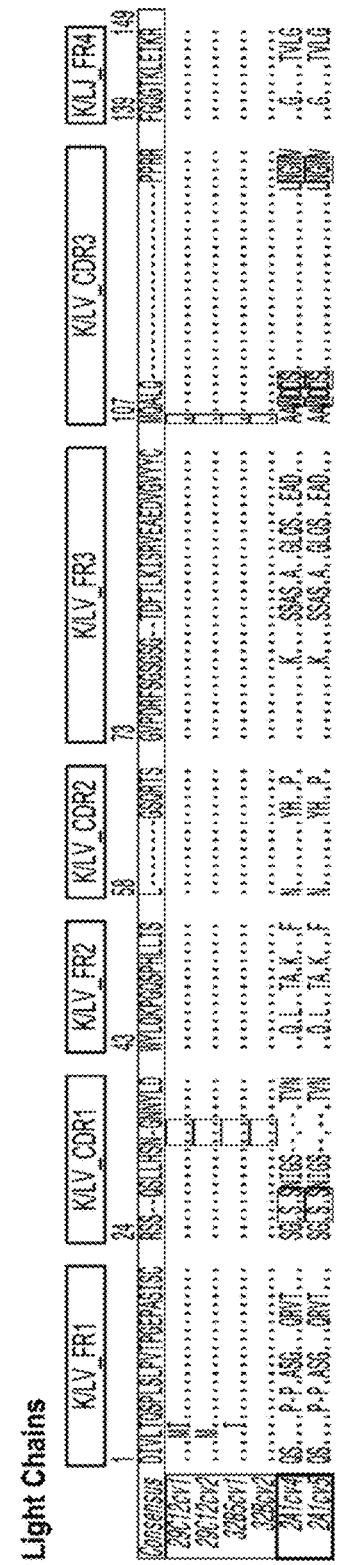
Figure 42A:
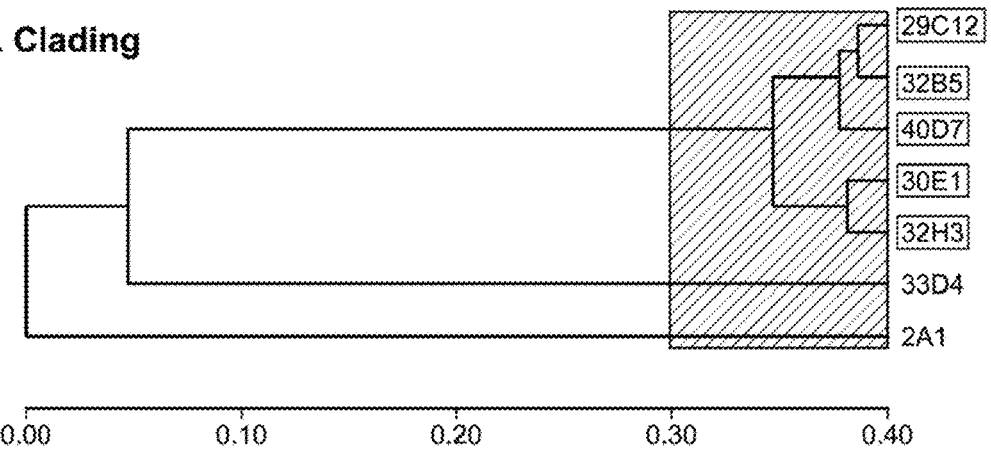
FIGS. 42A and 42B depicts the clading of the parental antibody variable light and heavy domain sequences illustrating the divergence between the 2A1 antibody versus the 29C12, 32B5 and other antibodies from the second campaign.
Figure 42B:
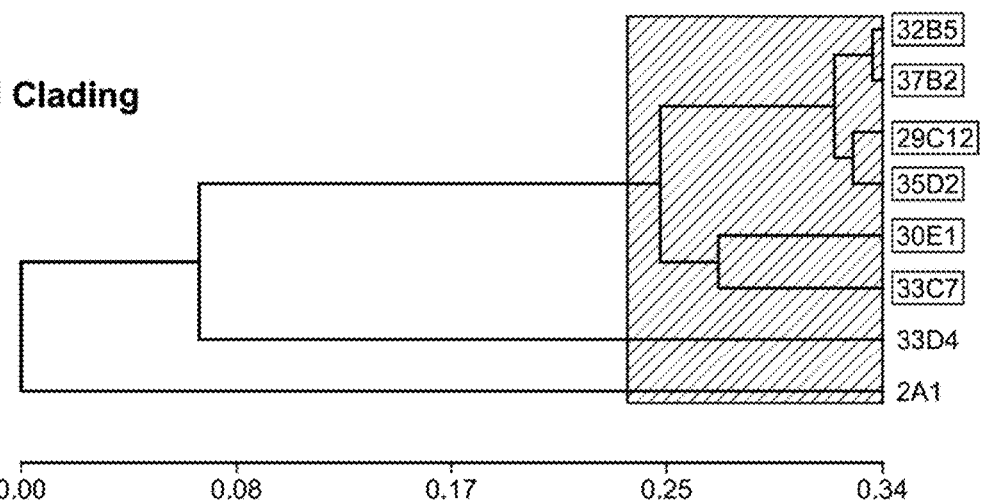
Figure 43A:
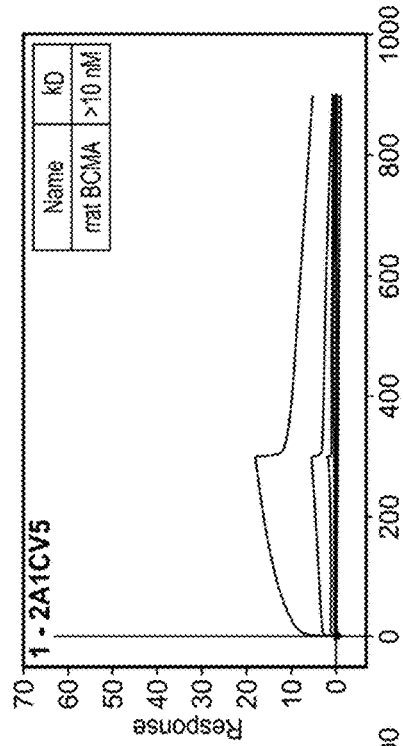
Figure 43B:
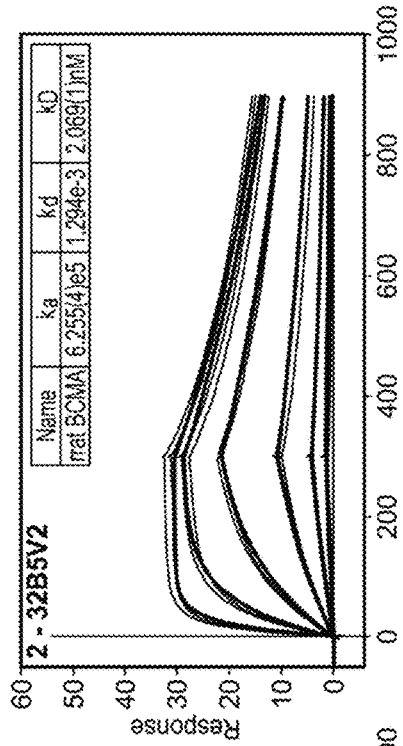
Figure 43C:
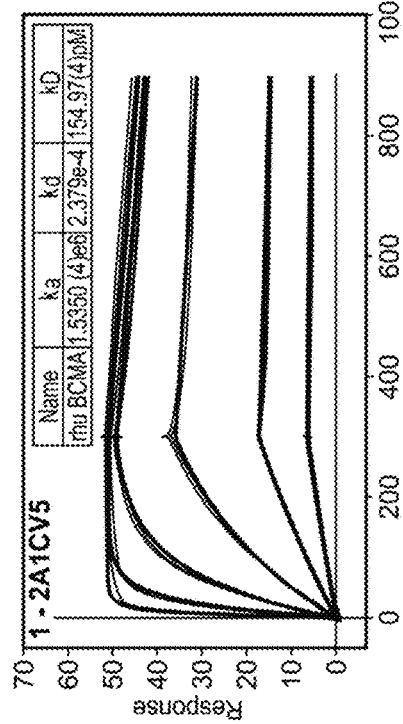
Figure 43D:
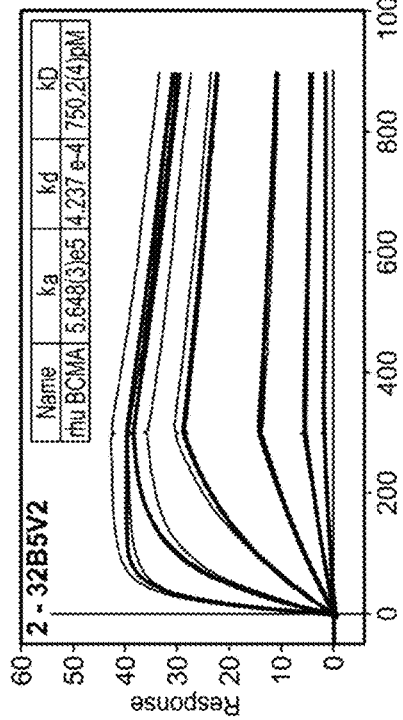

A sequence alignment of the heavy and light variable domains of the covariance muteins having optimal properties, as described herein, is provided in FIGS. 41A and B (29C12cv1 is Ab-8, 29C12cv2 is Ab-2, 32B5cv1 is provided in TABLE 11 as SEQ ID NOs: 315-320, 32B5cv2 is Ab-3, 2A1cv4 is provided in TABLE 11 as SEQ ID NOs:309-314, and 2A1cv5 is Ab-1). This shows that there is significant sequence divergence between the 2A1 versus the 29C12 and 32B5 covariance muteins. Clading of the parental antibody variable light and heavy domain sequences further illustrates the divergence between the 2A1 antibody versus the 29C12, 32B5 and other antibodies from the second campaign (FIGS. 42A and 42B). This sequence divergence in the CDRs, or paratopes of the antibodies, is evidence that the two clades of antibodies likely bind to different epitopes on huBCMA.

Example 9

The following experiment shows that the anti-BCMA ADCs inhibit growth of H929 myeloma cells in a xenograft subcutaneous tumor model. The majority of multiple myeloma tumor cells reside in the bone marrow and tumor burden has been associated with osteolytic bone disease. In addition, bone marrow stromal cells and osteoclasts may protect multiple myeloma tumor cells from chemotherapy. See Dougall, W C, et al., RANKL is a therapeutic target in multiple myeloma, Roodman-G D ed. *Myeloma Bone Disease*. Humana Press. 2010: 169-182. A NSG/NOG mouse model has been reported to be an improved host for growth of multiple myeloma cells in bone (Miyakawa-Y, et al., *BBRC* 313 (2004) 258-262). The NSG mouse model has also been optimized for the use of luciferase labeling for bioluminescent imaging and ex vivo selection for increased tumor take and growth rate (see EXAMPLE 10). $5 \times 10^6$ H929 human myeloma cells were implanted subcutaneously into female NSG (NOD/SCID IL2Rg−/−) mice using growth-factor reduced Matrigel™ (BD Biosciences) to generate tumor xenografts for efficacy studies. H929 cells express an average of approximately 24,000 BCMA sites/cell. Treatment with 2A1-MCC-DM1 or control conjugate (anti-streptavidin-MCC-DM1) was initiated when the tumor size reached an average of approximately 150 mm$^3$. Tumor-bearing animals were randomized by tumor size into groups of ten animals each and dosed intravenously once. A blinded dose response study of 2A1-MCC-DM1 at doses ranging from 20-200 ug DM1/kg (1-10 mg Ab/kg) was performed. No body weight loss was observed in any of the dosing groups over the course of the study. No nutritional supplementation was provided.

Figure 29:
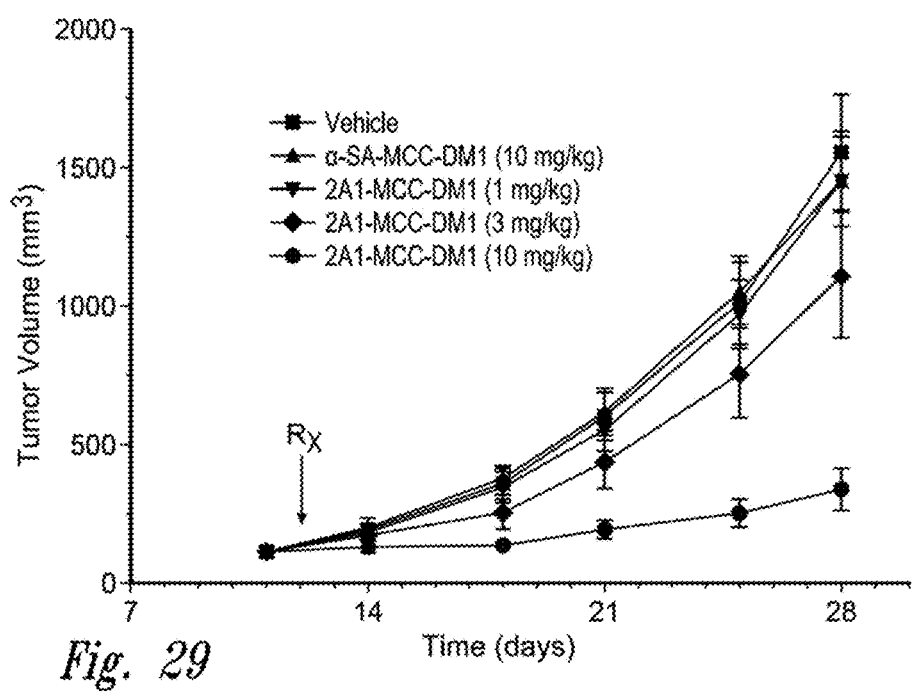
FIG. 29 graphically depicts the BCMA ADCs could inhibit growth of H929 myeloma cells in a xenograft subcutaneous tumor model. Treatment with the 2A1-MCC-DM1 showed robust tumor growth inhibition at the high 200 ug DM1/kg dose (10 mg Ab/kg), and a moderate tumor growth inhibition at the mid 67 ug DM1/kg dose (3 mg Ab/kg).

As shown in FIG. 29, treatment with the 2A1-MCC-DM1 showed robust tumor growth inhibition at the high 200 ug DM1/kg dose (10 mg Ab/kg), and a moderate tumor growth inhibition at the mid 67 ug DM1/kg dose (3 mg Ab/kg). This data is evidence of in vivo efficacy for the 2A1-ADC in an art-recognized multiple myeloma animal model.

Example 10

The 2A1CV5-MCC-DM1, 32B5-MCC-DM1 and 29C12-MCC-DM1 ADCs were tested for the ability to target and kill BCMA-expressing myeloma cells (H929). The CellTiter-Glo® Luminescent Cell Viability Assay is a homogeneous method to determine the number of viable cells in culture based on quantitation of the ATP present, which signals the presence of metabolically active cells. The Cell-Titer-Glo® Assay is applicable to cytotoxicity assays (see http://www.promega.com/products/cell-health-assays/cell-viability-assays/celltiter_glo-luminescent-cell-viability-assay/for more information). The cell viability assay was used to assess the relative killing capacity of various ADCs on various multiple myeloma cell lines and B-cell lines. The protocol provided in the Cell Titer-Glo kit (Promega G7572) was followed. In short, $5 \times 10^3$ target cells in 90 ul RPMI 1640, 10% FBS were aliquoted into clear, flat bottom, white walled 96 well plates (Costar #3903). The ADCs were diluted into a 10× stock to create 500 nM maytansine drug equivalents. Each ADC was serially diluted in 2-fold dilutions in RPMI 1640, 10% FBS starting with 500 nM stock. 10 ul of the 10×ADC dilution series was added to the 90 ul of cells in media (triplicate wells). The highest concentration of ADC was approximately 50 nM maytansine drug equivalents, and the lowest concentration of ADC was approximately 50 pM maytansine drug equivalents. An isotype control ADC (an anti-streptavidin huIgG1 conjugated to MCC-DM1) was included, as well as a media-only control. The plates were incubated at 37° C., 5% $CO_2$ for 96 hours. After incubation, 100 ul of the Substrate Solution (Promega G7572) was added to each well. Luminescence was read on an EnVision™ Multilabel reader (PerkinElmer) or Analyst HT plate reader (LJL Biosciences). The data was analyzed and graphed using GraphPad Prism™ to determine the relative efficacy of the ADCs on various cancer cell lines.

Figure 30:
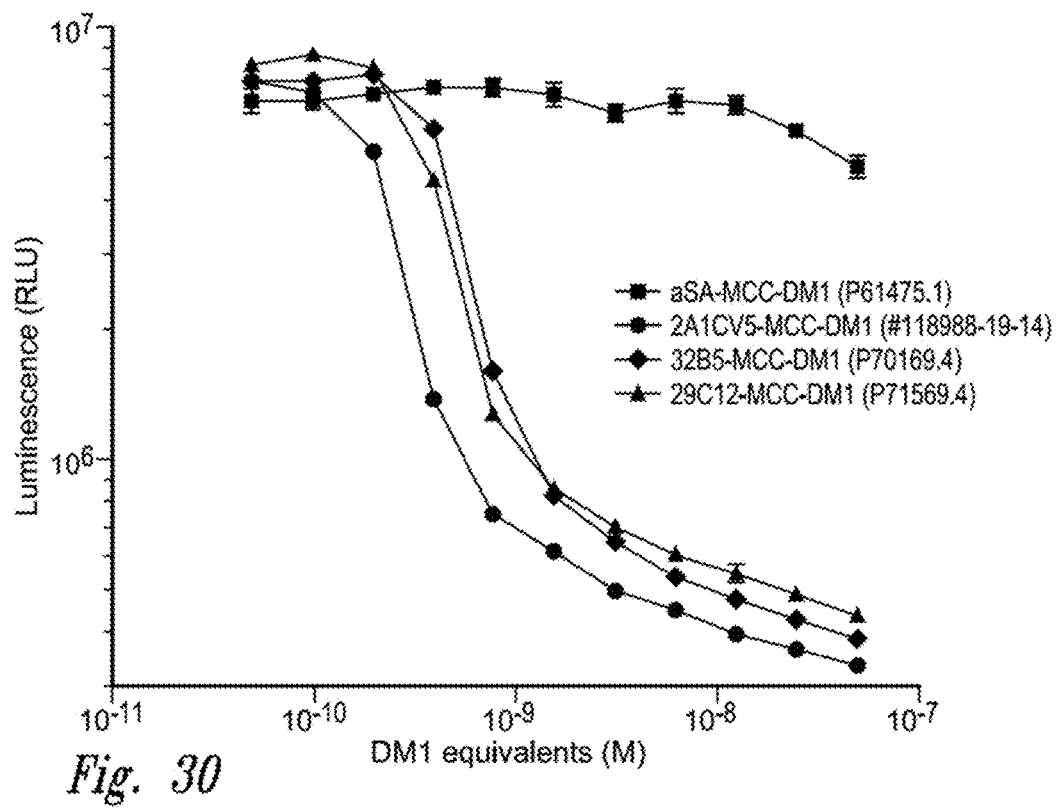
FIG. 30 shows that the 2A1CV5-MCC-DM1, 32B5-MCC-DM1 and 29C12-MCC-DM1 ADCs were able to target and kill BCMA-expressing myeloma cells (H929).

FIG. 30 shows that all three ADCs were potent inhibitors of H929 cell growth compared to control conjugate. 2A1CV5-MCC-DM1 (having an $IC_{50}$ of 234 pM) exhibited a 2-3 fold increase in potency over that observed for 32B5-MCC-DM1 and 29C12-MCC-DM1 (having an $IC_{50}$ of 506 pM and 390 pM, respectively).

Example 11

The following experiments further characterize the Ab-1 (2A1CV5) ADC, also referred to herein as 2A1CV5-MCC-DM1 and provide evidence of BCMA-mediated internalization in a multiple myeloma cell (H929). Using the assay methods described herein, it was found that the fully human anti-huBCMA antibody 2A1CV5 bound to native human BCMA expressed on the human multiple myeloma cell line H929 with an avidity that was 3-fold better than what was observed for the fully human anti-BCMA antibodies 32B5 and 29C12. The 2A1CV5-MCC-DM1 antibody drug conjugate (ADC) demonstrated a magnitude of binding to native human BCMA, as assessed by flow cytometry, that was similar to the binding observed with un-conjugated 2A1CV5. The observed binding $EC_{50}$ for 2A1CV5 was over two-fold better than that observed with 2A1CV5-MCC-DM1 while the binding $EC_{50}$ to native BCMA for 32B5-MCC-DM1 was about 2-fold lower than that observed for 32B5 (TABLE 18). A precise measure of equilibrium binding was determined for 2A1 (2A1CV5 binds identically) and 32B5 by measuring their ability to bind recombinant soluble human BCMA using Biacore™ interaction technology (as described herein). The results showed that 2A1CV5 binds with double-digit pM affinity to recombinant human BCMA.

TABLE 18

Binding comparison of 2A1CV5 and 32B5 to their MCC-DM1 conjugate counterparts

| Measurement | 2A1CV5 | 2A1CV5-MCC- | 32B5 | 32B5-MCC- |
|---|---|---|---|---|
| Biacore-rsol.hu BCMA | 0.027 nM | Not tested | Not tested | Not tested |
| FACS ($EC_{50}$)-H929 cells (Native BCMA, relative binding, indirect | 1.2 nM | 2.9 nM | 4.2 nM | 7.0 nM |

The ability of 2A1CV5-MCC-DM1 to internalize into H929 cells was compared to the internalization of the unconjugated 2A1CV5.

Materials

Anti-Streptavidin-MCC-DM1 (αSA-MCC-DM1 having a DAR of 4.5)

2A1CV5-MCC-DM1 (DAR 4.8)

Tumor cells, H929 were cultured in growth medium: RPMI 1640+10% FBS+MEM non-essential Amino Acids+HEPES+beta-mercaptoethanol+Pen/Strep+L-glutamine+sodium pyruvate+gentamicin.

Goat anti human IgG (H+L), Alexa 488 (Molecular Probes Inc., Eugene, Oreg. Catalog#A11013).

Hoechst 33342, (Molecular Probes Inc., Eugene, Oreg. Catalog#H21492).

H929 myeloma tumor cells were cultured in growth medium (RPMI 1640, 10% FBS, MEM non-essential Amino Acids, HEPES, beta-mercaptoethanol, Pen/Strep, L-glutamine, sodium pyruvate, gentamicin). The H929 cells were collected into two 3-ml FACS tubes at approximately 500,000 cells per tube and washed once with assay medium (PBS containing 2% FBS). The cells were suspended with either the 2A1 or CD138 antibodies at 10 µg/mL per tube (200 µL per tube) in assay medium. After incubation at 4° C. for 30 minutes, the cells were washed once with assay medium. A cocktail of anti-human IgG, Alexa 488 (Molecular Probes Inc., Eugene, Oreg. Catalog#A11013 at a 1:1,000 dilution in assay medium) and Hoechst 33342 (Molecular Probes Inc., Eugene, Oreg. Catalog#H21492 at a 1:2000 dilution in assay medium) was added to the cells. After incubating cells at 4° C. for 15 minutes, the cells were washed once and then resuspended with 0.5 ml of assay medium to reach a concentration of $1\times10^6$ cells per ml. Fifty µL of cells were transferred to a 96-well plate at 8 wells for each antibody (see TABLE 19 below). The cells were either fixed and permeabilized, starting with time zero by adding 50 µl of BD cytofix/cytoperm kit (BD Biosicences. catalog#554714) or incubated at 37° C., 5% $CO_2$ for the time points at 0.5, 1 and 2 hours. At each incubation time, cells were fixed and permeabilized using the same steps as indicated for 0 timepoint. The internalization rate was quantified on an Array Scan $V^{TI}$ HCS reader (version 6, Cellomics, Thermo Fisher Scientific, Pittsburgh, Pa.) with BioApplication "Spot Detector" algorithm employing a 40× objective. The filter setting for internalization was indicated in table below. At least 200 cells were counted in each well.

TABLE 19

| Cell ADC at 5 µg/mL | H929 1, 2 | H929 3, 4 | 5, 6 | 7, 8 | 9, 10 | 11, 12 |
|---|---|---|---|---|---|---|
| A | | | | | | |
| B | αSA-MCC-DM1 @ 5 hs | 2A1CV5-MCC-DM1 @ 5 hs | | | | |
| C | | | | | | |
| D | αSA-MCC-DM1 @ 3 hs | 2A1CV5-MCC-DM1 @ 3 hs | | | | |
| E | | | | | | |
| F | αSA-MCC-DM1 @ 1 h | 2A1CV5-MCC-DM1 @ 1 h | | | | |
| G | | | | | | |
| H | αSA-MCC-DM1 @ 0 h | 2A1CV5-MCC-DM1 @ 0 h | | | | |

TABLE 20

| Filter setting for internalization: | | | |
|---|---|---|---|
| Channel | Target | Label | Filter |
| 1 | Nucleic acid for all cells | Hoechst 33342 | DAPI (blue) |
| 2 | Internalized spots | Alexa 488 | FITC (green) |

The output parameter algorithm of Array Scan was "SpotCountPerObjectCh2." The results were reported as total spot count per 200 cells. The statistical analysis was performed using Prism 4.01 (GraphPad, San Diego, Calif.). The spot counts were expressed as the mean±standard error of the mean (SEM) for duplicate measurements (n=2). Using the analysis tool, spot count per unit time (internalization rate=$T_{1/2}$) was fit to a one phase exponential association equation. The half-life for internalization was calculated using one-phase exponential association from GraphPad™ Prism.

Figure 31:
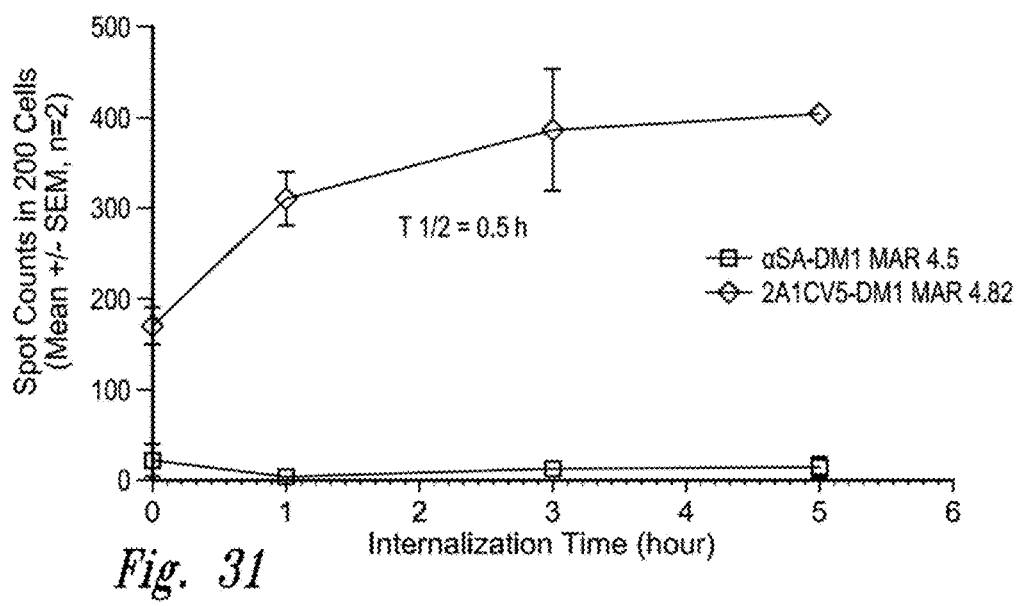
FIG. 31 depicts the level and rate of internalization of 2A1CV5 and 2A1CV5-MCC-DM1 into H929 cells.

The level and rate of internalization into H929 cells was similar for 2A1CV5 and 2A1CV5-MCC-DM1 reaching half-maximal levels of internalization approximately 30 minutes post incubation initiation (FIG. 31). In addition, the rate of internalization of 2A1CV5-MCC-DM1 into the MM1R multiple myeloma cell line was close to that of H929 reaching half maximal levels of internalization at about 50 minutes post incubation initiation. These results demonstrate that after binding to BCMA, that 2A1CV5-MCC-DM1 can be rapidly internalized into BCMA-expressing cells.

The 2A1CV5 ADC was tested for its ability to kill various multiple myeloma cell lines using the assay described herein. As shown in TABLE 21, the 2A1CV5 ADC was able to effectively kill numerous multiple myeloma cell lines having a wide range of cell surface expression of BCMA.

TABLE 21

2A1-CV5-MCC-DM1 kills several multiple myeloma cell lines

| MM cell line name | BCMA Expression determined by Dako Qifikit and anti-huBCMA 1.165 (muIgG) | Cell line killed by BCMA ADC: 2A1-CV5-MCC-DM1 | Cell Viability determined by Promega Cell Titer Glo Assay, 96 h exposure to BCMA ADC: 2A1-CV5-MCC-DM1 (IC50: nM DM1) |
|---|---|---|---|
| H929 | 24,259 | Yes | 1.9 |
| KMS34 | 10,158 | Yes | 5 |
| KMS28BM | 9,795 | Yes | 3.5 |
| U266 | 9,025 | Yes | 2.4 |
| MM1S | 8,179 | Yes | 1.8 |
| KMS11 | 7,676 | Yes | 6.1 |
| KMS28PE | 6,065 | Yes | 4.7 |
| KMS26 | 3,192 | Yes | 3.1 |
| MM1R | 3,155 | Yes | 3.6 |

Example 12

The in vivo pharmacology of the Ab-1 (2A1CV5) ADC was evaluated. These experiment show that the Ab-1 (2A1CV5) ADC mediates tumor regression in an H929 bone-tropic xenograft model. In short, H929 luciferase-labeled myeloma cells that express an average of approximately 24,000 BCMA sites per cell were administered intravenously ($1\times10^6$ cells) into NSG mice. Fourteen days after tumor inoculation, tumor-bearing animals were randomized based on hind limb bioluminescence (tumor burden) into groups of ten animals each and dosed intravenously once. A blinded dosing study of 2A1CV5-MCC-DM1, unconjugated 2A1CV5 and control conjugate employing a single dose of 250 ug DM1/kg (10 mg Ab/kg) was performed in this established bone-tropic tumor model. No nutritional supplementation was provided.

Study Design:
- 1×10$^6$ cells H929-luc cells, IV
- Mice distributed into equal groups determined by hind limb BLI, Day 14
- Single treatment of antibody at 10 mg/kg, I.V., Day 14
- BLI measured 2×/week (blinded)
- Study endpoint day 35
- 80 NSG (NOD/SCID IL2Rg−/−) mice were injected intravenously on 1/13/11, 1×10$^6$ H929luc cells
- BLI was measured twice per week
- Day 14 mice were distributed into five equivalent groups (n=10) based on hind limb tumor burden, as measured by BLI
- Treatment plan: one I.V. injection
- Treatment groups blinded and include:
  - Vehicle (PBS)
  - Anti-huBCMA-huIgG1-2A1-CV5 (unconjugated)
  - Anti-huBCMA-huIgG1-2A1-CV5-MCC-DM1
  - Anti-huBCMA-huIgG1-2A1-WT-MCC-DM1
  - Anti Streptavadin-MCC-DM1
- Anti-huBCMA-2A1-CV5-MCC-DM1 used at 10 mpk
- Anti-huBCMA-2A1-WT-MCC-DM1 and anti Streptavadin-MCC-DM1 were normalized based on maytansinoid drug equivalents of 2A1-CV5-MCC-DM1 at 10 mpk
- Timing: injected H929luc cells, ADC treatment began on day 14, analysis on day 35

Figure 32:
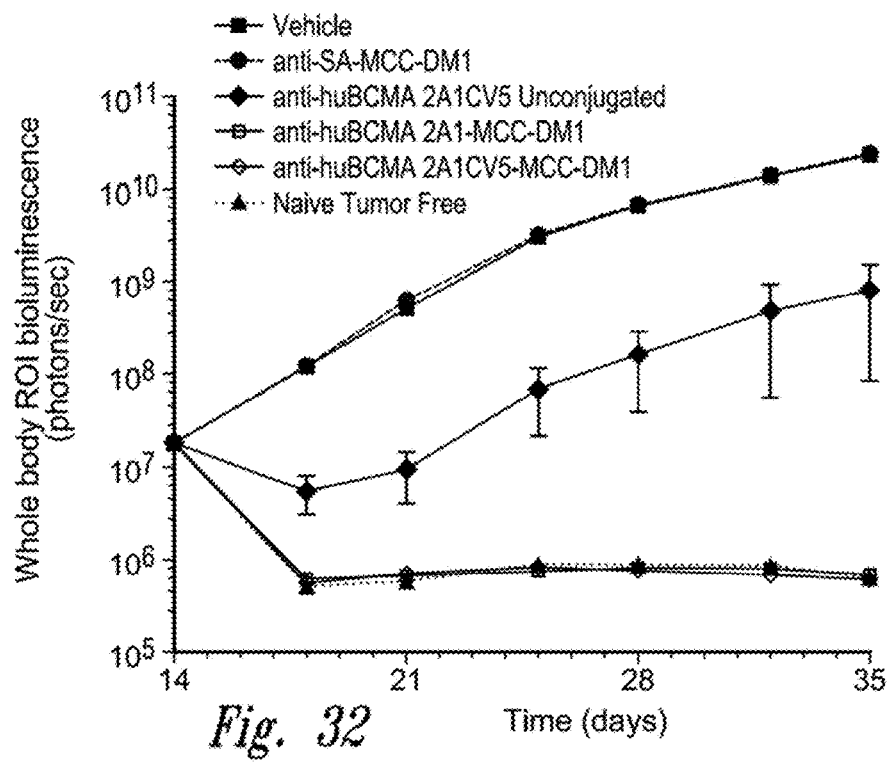
FIG. 32 shows that complete tumor regression was observed after a single treatment with 2A1-MCC-DM1 or 2A1CV5-MCC-DM1 in an H929 bone-tropic xenograft model.

FIG. 32 shows that complete tumor regression was observed after a single treatment with 2A1-MCC-DM1 or 2A1CV5-MCC-DM1 at 250 ug DM1/kg. An intermediate tumor growth inhibitory effect was seen after a single treatment with unconjugated 2A1CV5 at the same antibody dose as the conjugate. In addition, lytic bone lesions were not observed in mice treated with 2A1CV5-MCC-DM1, but were observed in mice receiving vehicle (PBS) or isotype control conjugate (anti-Streptavidin-MCC-DM1). No anti-tumor effect was detected in animals treated with the control conjugate or vehicle. No body weight loss was observed in any of the dosing groups over the course of the study.

In an additional myeloma bone-tropic xenograft model similar to that above, U266 luciferase-labeled myeloma cells that express an average of 9,000 BCMA sites per cell were administered intravenously (1×10$^6$ cells) into NSG mice. Twenty eight days after tumor inoculation, tumor-bearing animals were randomized based on hind limb bioluminescence (tumor burden) into groups of ten animals each and dosed intravenously or intraperitoneally as denoted by the red Rx symbol. A blinded dosing study of 2A1CV5-MCC-DM1, unconjugated 2A1CV5 and PBS employing a single dose of 250 ug DM1/kg (10 mg Ab/kg) administered at day 28 was performed in this established bone-tropic tumor model. Following euthanasia, the animals were radiographed. The hind limbs were disarticulated, fixed in 10% neutral buffered formalin and decalcified. Bones were subsequently processed, embedded, sectioned and a single representative bone from each animal was stained by H&E, TRAP stain and for huCD138 expression (IHC). Bone sections were examined microscopically to determine if residual disease (huCD138+ cells) were present and to estimate the extent of the surface of the medullary cavity and bone spicules that was covered by TRAP+ osteoclasts.

Figure 33:
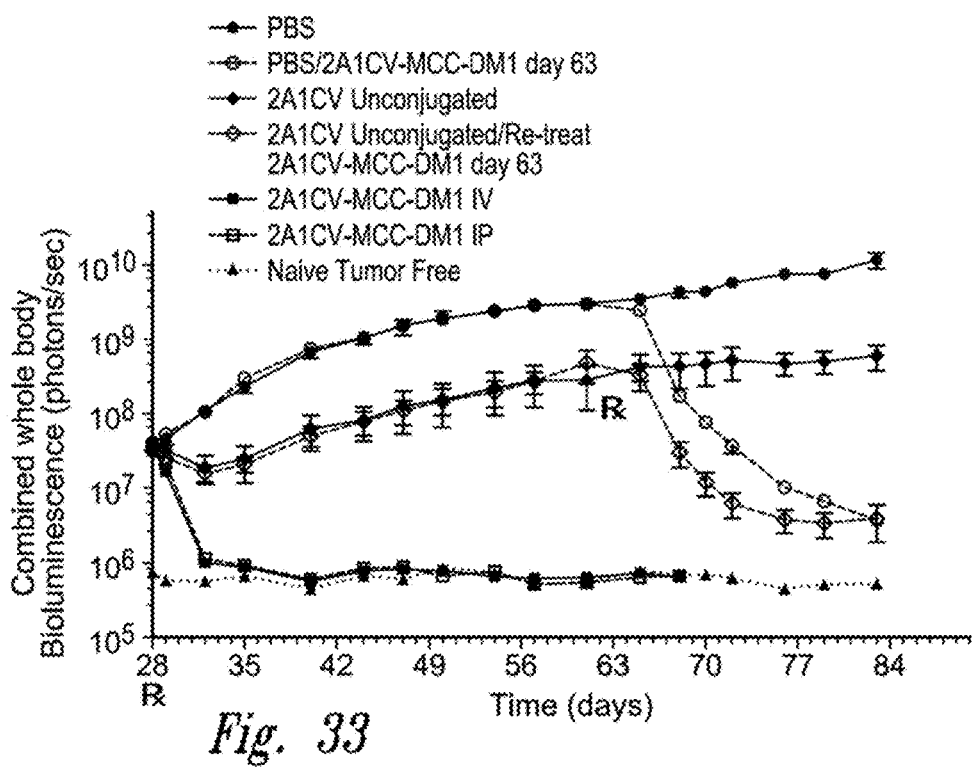
FIG. 33 graphically illustrates that 2A1CV5-MCC-DM1 is capable of mediating significant tumor regression in a U266 human myeloma bone-tropic xenograft model.

The xenograft cells effaced the normal mouse bone marrow cell population Animals with large tumor burden appeared to have an increased number of TRAP+ osteoclasts lining the marrow cavity and covering bone spicules. In animals with viable xenografts, the neoplastic cells occasionally traversed the width of the bone cortex and reached the periosteum. Successful treatment was characterized by a reduction in intramedullary TRAP+ osteoclasts and presence of normal mouse bone marrow. Antibody 2A1CV-MCC-DM1 delivered via the IV or IP route completely cured mice of their disease when delivered as a single injection. The unconjugated antibody 2A1CV slowed tumor growth but did not cure animals of their disease. Animals previously treated with either 2A1CV or vehicle (on Day 28) that were subsequently treated with antibody 2A1CV-MCC-DM1 (on Days 63 and 84) were completely cured of their disease. TRAP+ osteoclasts appeared to be more abundant in animals with significant tumor burden than animals that were successfully treated. Complete tumor regression was observed after a single treatment with 2A1CV5-MCC-DM1 at 250 ug DM1/kg administered by either route (FIG. 33). A modest decrease in tumor growth was observed in animals treated with unconjugated 2A1CV5. At day 63 post tumor inoculation, animals treated with PBS or unconjugated 2A1CV5 were then randomized into two groups of 5 animals each and then administered one additional treatment of 2A1CV5-MCC-DM1 at 10 mg Ab/kg intravenously. 2A1CV5-MCC-DM1 treatment induced robust tumor regression in both of these groups of animals that carried a tumor burden more than 2 orders of magnitude greater than when treatment was initiated at day 28 post tumor inoculation (FIG. 33). These results show that 2A1CV5-MCC-DM1 is capable of mediating significant tumor regression in the U266 human myeloma bone-tropic model where the tumor expresses almost 3-fold lower average receptor density than in the H929 bone-tropic myeloma xenograft model.

Example 13

Figure 34A:
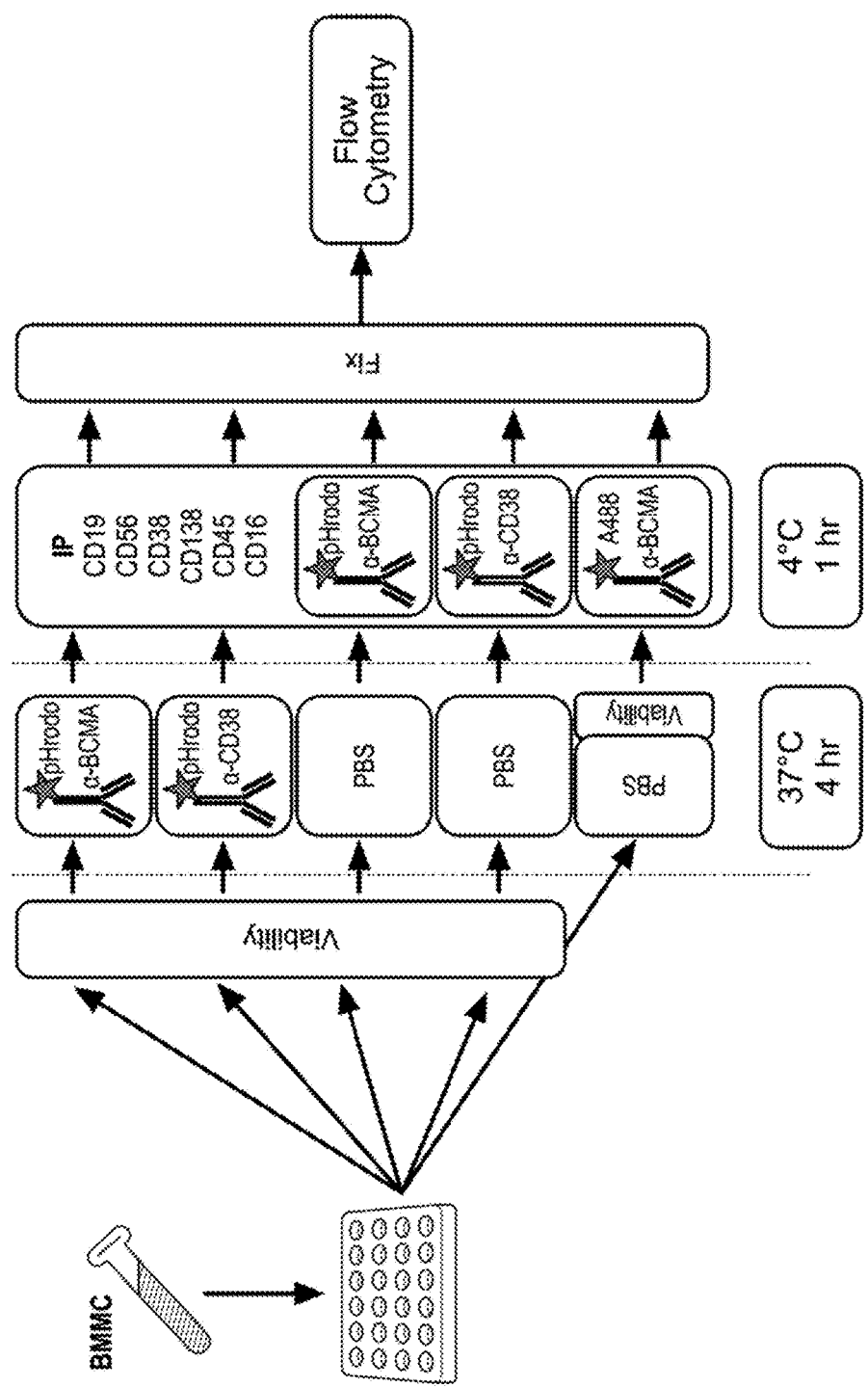
FIGS. 34A and B show the assay protocol and gating methods for Example 13.
Figure 34B:
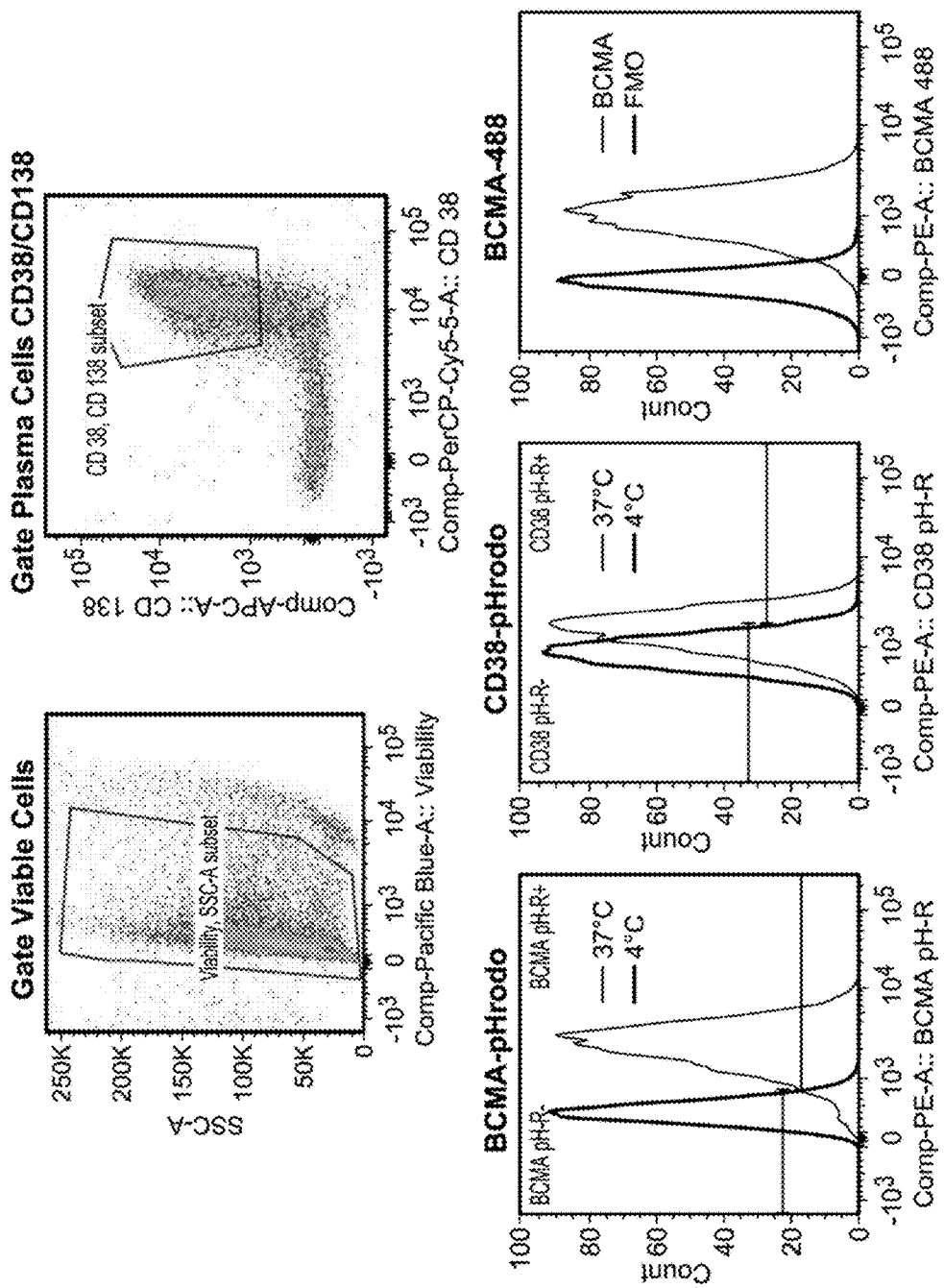

BCMA protein expression was assessed on 42 primary myeloma patient samples by flow cytometry employing BCMA-selective monoclonal antibodies (2A1CV4) that does not cross-react with BAFF-R or TACI. Samples were acquired from commercial sources (AllCells, Conversant, Proteogenex) to acquire approximately 1×10$^6$ plasma cells per sample. Individual multiple myeloma (MM) samples were thawed gently at room temp (RT). The thawed cells were added dropwise into 4 ml of 50% FBS (fetal bovine serum) RPMI buffer at RT. 3 ml of 10% FBS RPMI was added to the cell suspension. The cell suspension was gently inverted to mix and centrifuged at low speed to pellet cells. The media was aspirated and the cell pellet was resuspended in 1% FBS PBS (Phosphate Buffered Saline). The cells were manually counted on a hemocytometer. The cells were added to 10 FBS RPMI and allowed to recover in an incubator for 1 hr at 37° C. with 5% CO$_2$. Cell viability was assessed as follows. Cells from primary MM and H929 cell lines were plated at 200,000 cells per well in a 96 well plate with fresh 10% FBS RPMI buffer with 5 wells per sample. The plate was centrifuged to pellet cells and media aspirated and resuspended in PBS three times. Cells were stained with Violet Live/Dead cell stain (Molecular Probes—L34955) per manufacturer protocol and incubated at RT in the dark for 30 minutes. The plate was then centrifuged to pellet the cells and media aspirated and resuspended in 10% FBS RPMI three times. Internalization/Immunophenotype (IP) was assessed as follows. Anti-BCMA-pHrodo or Anti- CD38-pHrodo reagent was added to 1 well of each sample and all samples were incubated at 37° C. with 5% $CO_2$. After 4 hours, the plate was centrifuged to pellet cells and media aspirated and resuspended in PBS three times. Of the three untreated wells, anti-BCMA-pHrodo, anti-BCMA-DyLight488 or Anti-CD38-pHrodo reagent was added to 1 well of each sample and all samples. All wells were staining with the IP panel (CD19 PE-Cy5, CD56 PE-Cy7, CD38 A594, CD138 APC, CD45 APC-H7, see TABLE 22). The plate was incubated at 4° C. for 1 hr. The fixation and analysis was performed as follows. All wells were fixed in 1% paraformaldehyde. Cells from each well were assessed using a LSRII (BD Bioscience) and FCS files generated. Plasma Cell identification was made using the following gating: samples were gated for viability; the subgates were selected for CD138/CD38 expression; histograms were generated for BCMA expression and internalization as well as CD38 internalization and finally for FMO controls; and cell counts or MFI was exported for summary analysis and graphic representation in Excel™ and GraphPad™ (see FIGS. 34A and 34B).

TABLE 22

| Antibody | Clone | Vendor | Cat # |
| --- | --- | --- | --- |
| CD-19 PE-Cy5 | J3-119 | Beckman Coulter | IM2643U |
| CD-56 PE-CY7 | N901 | Beckman Coulter | A51078 |
| CD-38 PerCP-CY5.5 | HIT2 | BD | 551400 |
| CD-138 APC | MI15 | BD | 347207 |
| CD-45 APC-H7 | 2D1 | BD | 641408 |
| CD-3 Pac Orange | UCHT1 | Invitrogen | CD0330 |
| CD16 Alexa 700 | 3G8 | Invitrogen | MHCD1629 |
| BCMA-488 2A1CV4 | | Amgen | |
| Violet Live/Dead cell stain | | Molecular Probes | L34955 |

Figure 35:
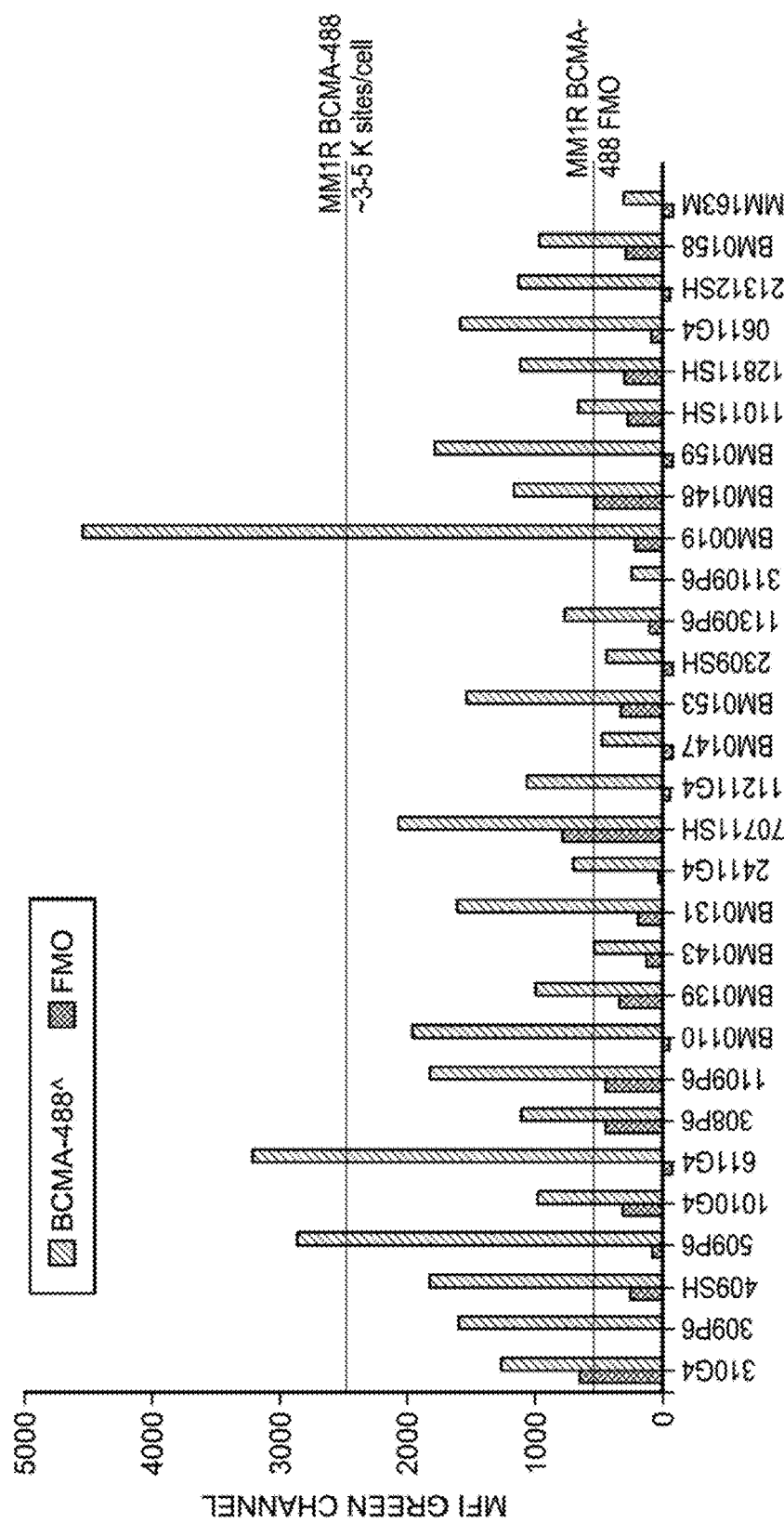
FIG. 35 demonstrates the 2A1 antibody and muteins thereof are able to bind BCMA on nearly all multiple myeloma patient samples tested.

The flow cytometry results demonstrated that 98% (41 of 42) of the multiple myeloma patient samples evaluated express detectable BMCA protein. As shown in FIG. 35, all 29 myeloma patient samples tested (a subset of the total of 42 samples) express detectable BCMA expression (green bars) as compared to the FMO control (black bars). This data further demonstrates that BCMA is expressed on isolated cells from multiple myeloma patients and serves as an excellent target for therapeutic intervention using the BCMA ADCs described herein. This data also demonstrates the 2A1 antibody and muteins thereof are able to bind BCMA on nearly all multiple myeloma patient samples.

Figure 36:
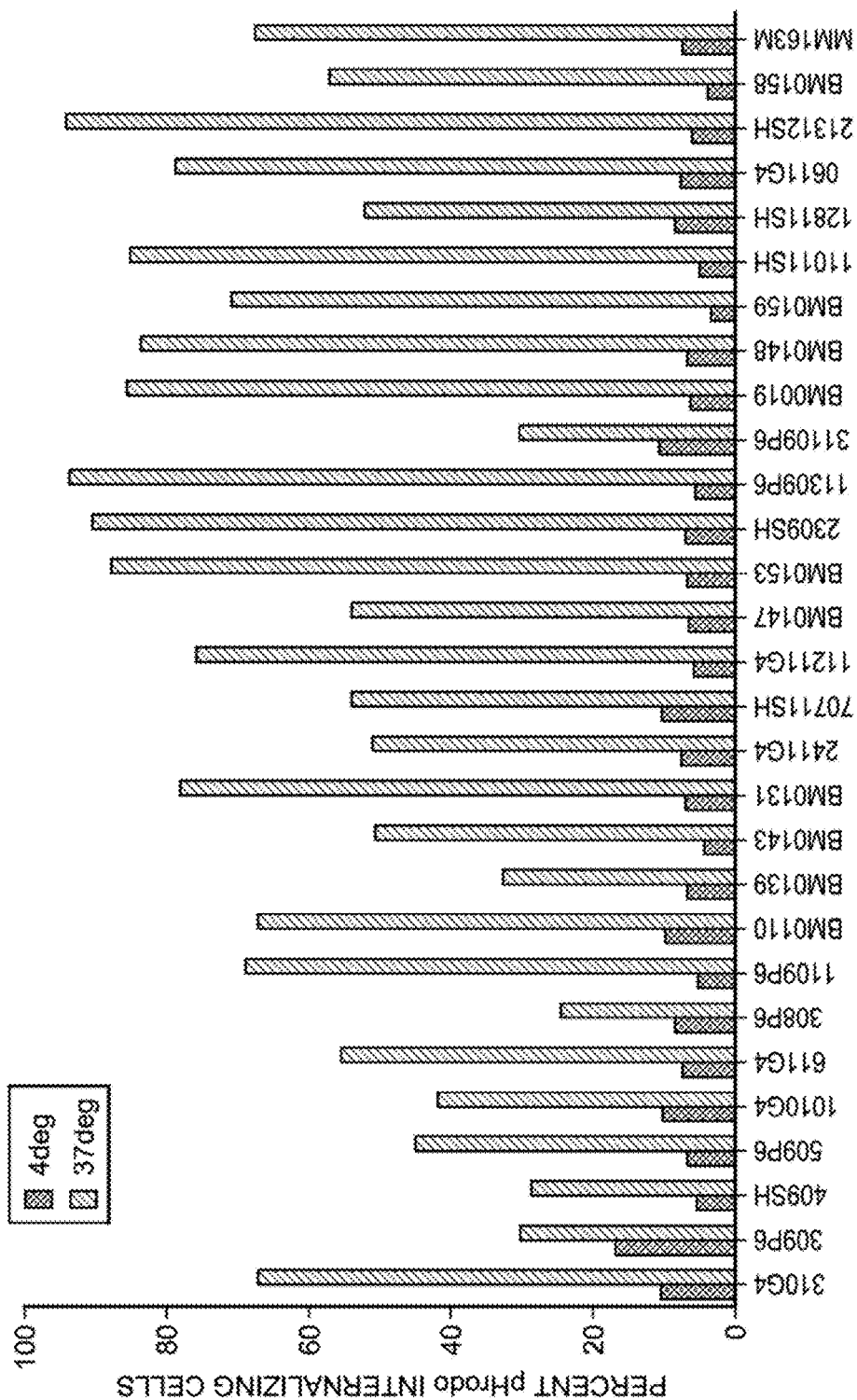
FIG. 36 shows that the BCMA antibody (2A1CV4-pH-rodo labeled) was effectively internalized in all 29 multiple myeloma patient samples, demonstrating the 2A1 antibody and muteins thereof are able to bind BCMA and be effectively internalized on all multiple myeloma patient samples tested.

Internalization of the 2A1 antibody (2A1CV4) on multiple myeloma patient samples was evaluated by flow cytometry of the CD138+ plasma cell fraction from bone marrow mononuclear cell preparations as described above. FIG. 36 shows that the BCMA antibody (2A1CV4-pHrodo labeled) was effectively internalized in all 29 multiple myeloma patient samples. This data also demonstrates the 2A1 antibody and muteins thereof are able to bind BCMA and be effectively internalized on all multiple myeloma patient samples tested.

Example 14

Figure 37:
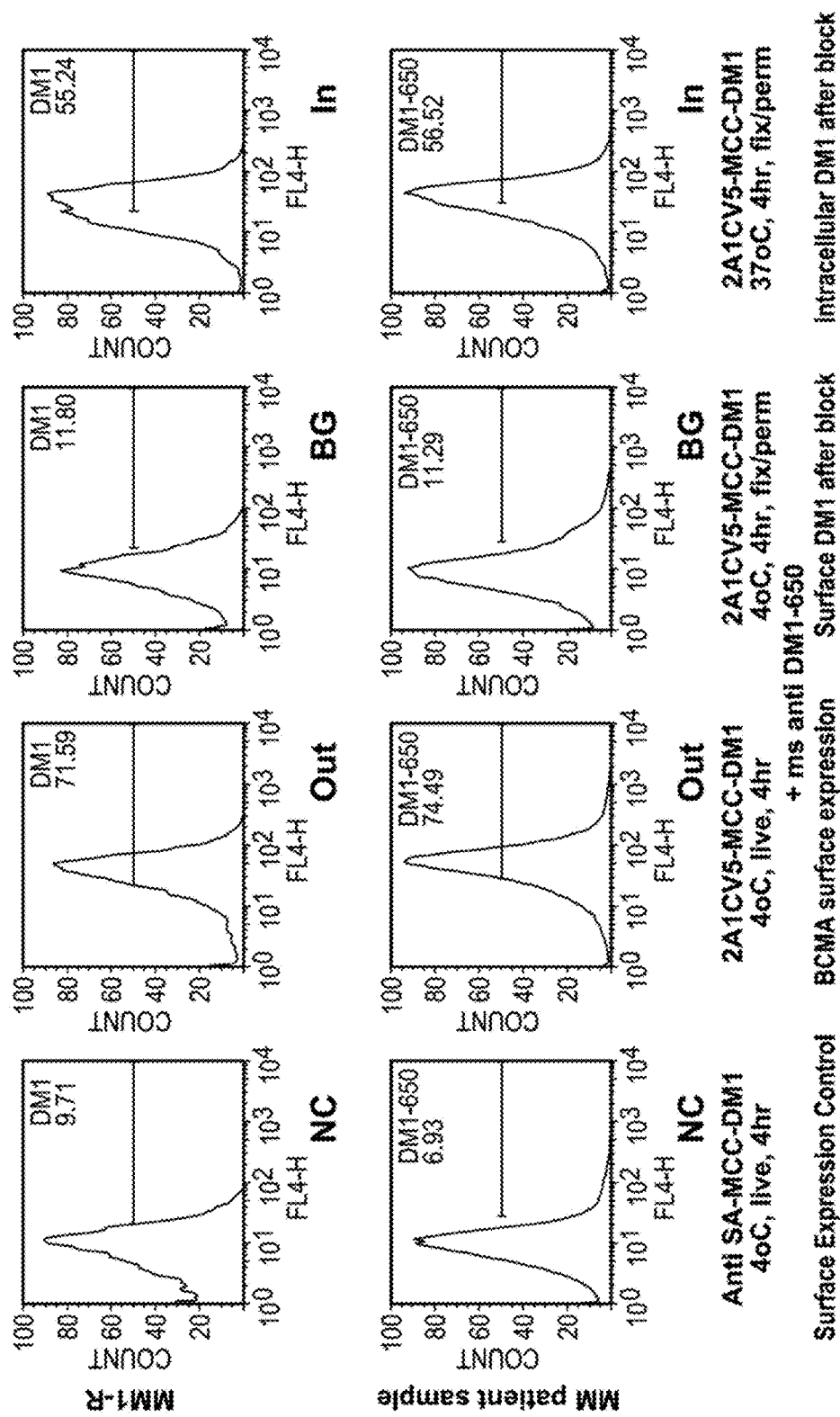
FIG. 37 are histograms showing that the 2A1CV5-MCC-DM1 delivered DM1 into primary myeloma bone marrow mononuclear tumor cell (BMMC) sample and the MM1R myeloma cell line FIG. 38 show that the production of kappa light chain correlates with H929 tumor size.

A flow cytometry-based internalization assay that used an anti-DM1 specific monoclonal antibody as a detection reagent was developed to assess whether 2A1CV5-MCC-DM1 (Ab-1 ADC) was able to deliver DM1 into primary myeloma tumor cells obtained from the bone marrow of multiple myeloma patients. The human myeloma tumor cell line MM1R, which expresses a relatively low level of BCMA, was used as a relative positive control to assess whether sufficient DM1 was delivered into the cell by 2A1CV5-MCC-DM1 to induce cell death. FIG. 37 shows that the 2A1CV5-MCC-DM1 delivered DM1 into the primary myeloma bone marrow mononuclear tumor cell (BMMC) sample and the MM1R myeloma cell line (the peak in the far right histogram for both MM1R and BMMC#12 has shifted to the right compared to the control histogram to its immediate left, demonstrating that DM1 has been internalized into the cell). Of 13 evaluable primary multiple myeloma patient BMMC samples examined, the 2A1CV5-MCC-DM1 delivered varying levels of DM1 into all 13 patient samples. This data provides clear evidence that the 2A1CV5 ADC binds BCMA, is internalized, and selectively kills primary multiple myeloma patient samples.

Example 15

Human IgG free light chain (kappa) was investigated as a potential biomarker as part of the in vivo pharmacology of the Ab-1 (2A1CV5) ADC experiments showing that the Ab-1 (2A1CV5) ADC mediates tumor regression in an H929 bone-tropic xenograft model (see Example 12). Human immunoglobulin molecules consist of two heavy chains which define class (IgG, IgA, IgM, IgD, IgE) and identical light chains (kappa or lambda). In healthy individuals the majority of light chains in serum exist bound to heavy chains. Free Light Chains (FLC) are a natural product of B lymphocytes and represent a unique biomarker of neoplastic and reactive B cell related disorders. Increased FLC are associated with various malignant plasma disorders. Detection of FLC is an important diagnostic aid for a variety of diseases including multiple myeloma, smoldering myeloma and monoclonal gammopathy of undetermined significance. Human IgG FLC kappa ELISA (Biovendor, RD 194088100R-K) was used to analyze presence of FLC in sera from H929 xenografts. Kappa light chain antibodies were not detected in sera of mice 18 days after being treated with 2A1CV5-MCC-DM1, but were detected in sera of mice receiving vehicle (PBS) or isotype control conjugate (anti-Streptavidin-MCC-DM1) (see FIGS. 38 and 39).

Example 16

The association and dissociation rate constants (ka, kd) and the dissociation equilibrium binding constant (Kd) for Ab-1 (i.e., 2A1CV5), Ab-2 (i.e., 29C12_mut) and Ab-3 (i.e., 32B5_mut) binding to recombinant human (rhu) BCMA and recombinant rat (rrat) BCMA was determined.

Assay conditions: Biosensor analysis was conducted at 25° C. in a HBS-P buffer system (10 mM HEPES pH 7.4, 150 mM NaCl, and 0.5% Surfactant P20) using a Biacore T200 optical biosensor equipped with a CM5 sensor chip according to the manufacturer's general protocol. The autosampler was maintained at 8° C.

Surface Preparation: Goat anti-human IgG capture antibody (Jackson Laboratories; 109-005-098) was immobilized to all flow cells of the sensor chip using standard amine coupling chemistry (9,000 RU). This surface type provided a format for reproducibly capturing fresh analysis antibodies (ligand) after each regeneration step.

Ligand Preparation: Flow cells 1, 2, and 3 were used to analyze captured anti-BCMA antibodies (~400-500 RU) while flow cell 4 was used as the reference flow cell.

Analyte Preparation: Six rBCMA concentrations ranging from 75.0 to 0.309 nM (3-fold dilutions) were prepared in running buffer. The rrat BCMA fusion protein (GS::6×His::Sumo::ratBCMA(aa 2-49)::GGS::G3::Avi) sequence:

(SEQ ID NO: 349)
MGSSHHHHHHGSGLVPRGSASMSDSEVNQEAKPEVKPEVKPETHINLKVS

DGSSEIFFKIKKTTPLRRLMEAFAKRQGKEMDSLRFLYDGIRIQADQTPE

DLDMEDNDITEAHREQIGGAQRCFHSEYFDSLLHACKPCRLRCSNPPAPC

QPYCDPSMTSSVRGTYTGGSGGGLNDIFEAQKIEWHE

The rhuBCMA fusion protein (6×His::Sumo::huBCMA(aa 5-51)::GGS::G3::Avi) sequence:

(SEQ ID NO: 350)
MGSSHHHHHHGSGLVPRGSASMSDSEVNQEAKPEVKPEVKPETHINLKVS

DGSSEIFFKIKKTTPLRRLMEAFAKRQGKEMDSLRFLYDGIRIQADQTPE

DLDMEDNDITEAHREQIGGAGQCSQNEYFDSLLHACIPCQLRCSSNTPPL

TCQRYCNASVTNSVKGTNAGGGSGGGLNDIFEAQKIEWHE

Interaction Parameters: Each of the six analyte sample concentrations were run in duplicate and in a mixed order, as a means of assessing the reproducibility of binding and managing potential systematic bias to the order of injection. Multiple blank (buffer) injections also were run and used to assess and subtract system artifacts. The association and dissociation phases for all analyte concentrations were monitored for 300 s and 3600 s, respectively, at a flow rate of 50 uL/min.

Surface Regeneration: The surface was regenerated with 10 mM glycine, pH 1.5 for 30 s, at a flow rate of 50 uL/min.

Model/Fit: The data was aligned, double referenced, and fit using Scrubber 2™ software, which is an SPR data processing and non-linear least squares regression fitting program. First, a dissociation rate coefficient ($k_d$) was determined from the first 600 s of the dissociation phase data. Second, the dissociation rate coefficient was applied as a fixed parameter in the global fit of the 300 s association phase data using a 1:1 binding model to determine the association rate coefficient ($k_a$) and the $R_{max}$ value.

Results:

Ab-1 specifically bound human BCMA in the context of SEQ ID NO: 350 with an equilibrium dissociation rate constant ($K_d$) of approximately 155 pM, and only marginally interacted with rat BCMA with an equilibrium dissociation rate constant ($K_d$) >10 nM. Ab-2 and Ab-3 bound human BCMA in the context of SEQ ID NO: 350 with equilibrium dissociation rate constants ($K_d$) of approximately 1.11 nM and 750 pM, respectively. Ab-2 and Ab-3 bound rat BCMA in the context of SEQ ID NO: 349 with equilibrium dissociation rate constants ($K_d$) of approximately 2.35 nM and 2.07 nM, respectively. Refer to FIGS. 43A-F and TABLE 23.

TABLE 23

| Antibody | Analyte | $R_{max}$ (RU) | $k_a$ (1/Ms) | $k_d$ (1/s) | $K_d$ (nM) |
|---|---|---|---|---|---|
| Ab-1 | rhu BCMA | 51.1 | 1.54E+06 | 2.38E−04 | 0.155 |
| Ab-1 | rrat BCMA | ND | ND | ND | >10 |
| Ab-2 | rhu BCMA | 52.5 | 6.38E+05 | 7.07E−04 | 1.11 |
| Ab-2 | rrat BCMA | 50.2 | 5.97E+05 | 1.40E−03 | 2.35 |
| Ab-3 | rhu BCMA | 40.2 | 5.65E+05 | 4.24E−04 | 0.750 |
| Ab-3 | rrat BCMA | 31.3 | 6.26E+05 | 1.29E−03 | 2.07 |

This data provides evidence of the domains and amino acids on human BCMA that are important for Ab-1 binding. Ab-1 specifically binds human and cynomolgus BCMA, but not rat BCMA. FIG. 44 shows a sequence alignment of amino acids 2-51 of the extracellular domain of human BCMA:

(SEQ ID NO: 352)
LQMAGQCSQNEYFD SLLHACIPCQLRCSSNTPPLTCQRYCNASVTN SVKG;

amino acids 2-51 of the extracellular domain of cynomolgus BCMA:
(SEQ ID NO: 353)
LQMARQCSQNEYFDSLLHDCKPCQLRCSSTPPLT CQRYCNASMTNS VKGM;
and amino acids 2-49 of the extracellular domain of rat BCMA:
(SEQ ID NO: 351)
AQRCFHSEYFDSLLHACKPCRLRCSNPPAPCQPYCDPSMTSSVRGTYT.

The differential binding of Ab-1 in light of the limited sequence diversity between species suggests that Ab-1 binds a neutralizing determinant on human BCMA comprising amino acids 1-20 of SEQ ID NO:285, and more specifically comprising amino acids 1-11 of SEQ ID NO:285.

Size Exclusion Chromatography (SEC) was utilized to detect interactions between anti-huBCMA antibodies (2A1 or 29C12) and monomeric [6×Histidine-SUMO]-huBCMA (SEQ ID NO:350) and its carboxy terminal clipped forms. In practice, antibody isolates of 2A1 and 29C12 (150 kDa) or monomeric [6×Histidine-SUMO]-huBCMA (~15-18 kDa) isolates migrated more slowly on SEC than the complex formed by the incubation of the anti-huBCMA 2A1 or 29C12 with [6×Histidine-SUMO]-huBCMA. To determine which forms of 6×His-SUMO-huBCMA were bound to the anti-huBCMA antibodies, the SEC fractions were isolated and analyzed. Carboxy-terminus fragments of the extracellular domain of human BCMA were generated as clipped forms from the rhuBCMA fusion protein (6×His::Sumo::huBCMA(aa 5-51)::GGS::G3::Avi) of SEQ ID NO:350, as shown in FIG. 45.

Figure 46:
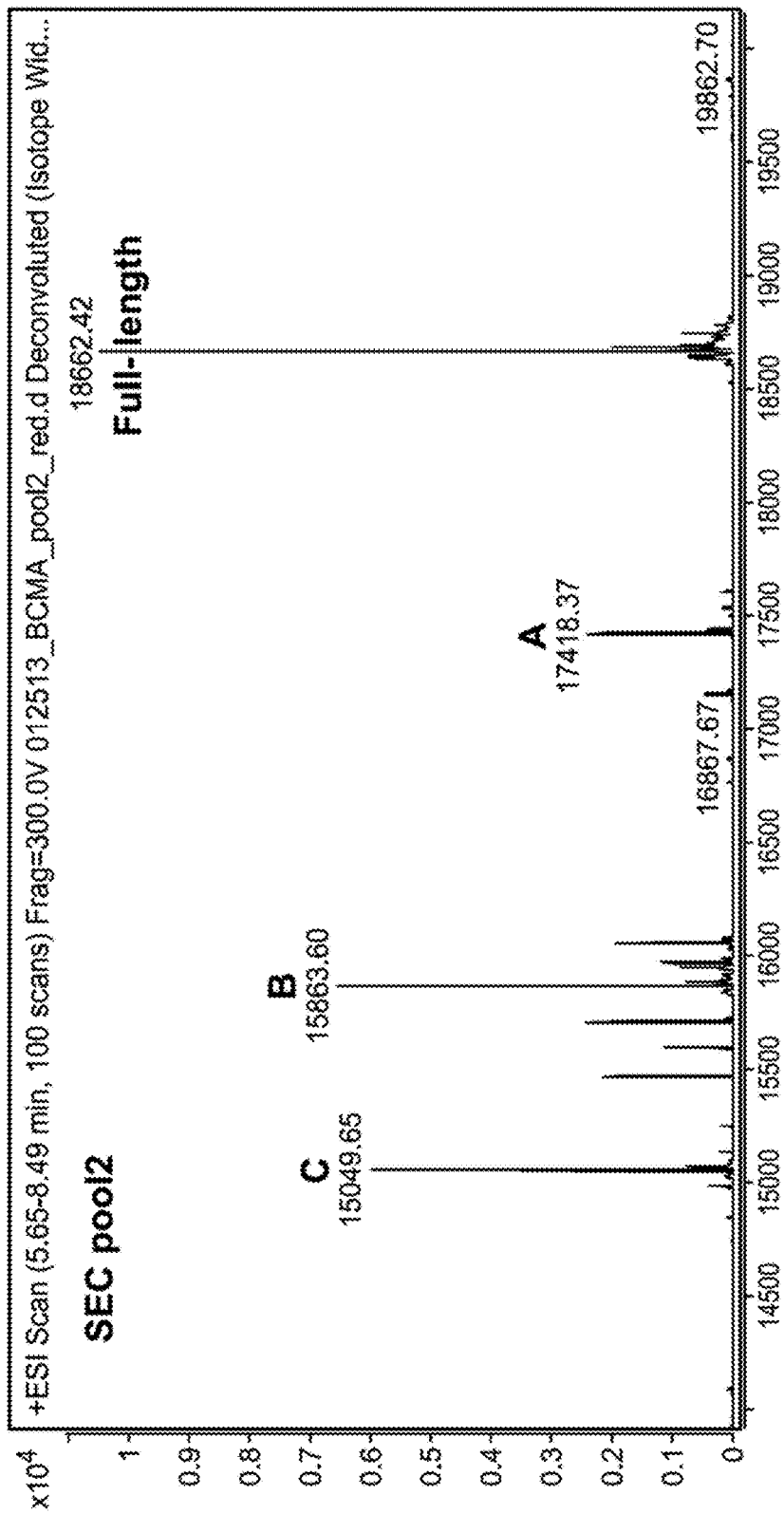
FIG. 46 shows the size exclusion chromatography results (size estimates in Daltons) for SEQ ID NO:350 and the three progressively smaller fragments of the amino terminus of the extracellular domain of human BCMA (Peak A: SEQ ID NO:354, Peak B: SEQ ID NO:355, and Peak C: SEQ ID NO:356).

A Superdex 200™ 10/30 cm SEC column (GE Healthcare Life Sciences) was used according to the manufacturer's recommendations and run in phosphate buffered saline (PBS). Incubations of antibody with excess levels of sumoBCMA were performed at room temperature for at least 30 minutes. FIG. 46 shows the size exclusion chromatography results (size estimates in Daltons) for SEQ ID NO:350 and the three progressively smaller fragments of the amino terminus of the extracellular domain of human BCMA (Peak A: SEQ ID NO:354, Peak B: SEQ ID NO:355, and Peak C: SEQ ID NO:356).

Figure 47A:
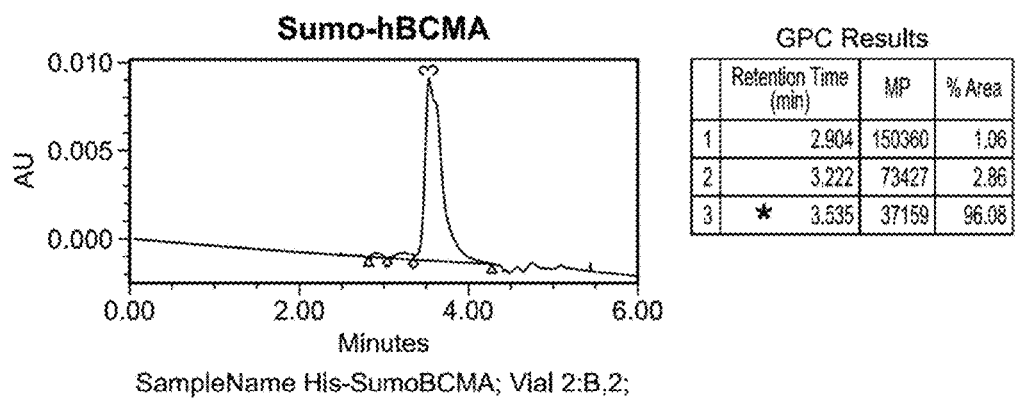
FIGS. 47A-D are chromatograms showing that Ab-1 bound various fragments of human BCMA (i.e., SEQ ID NOS:350, 354, 355, and 356).
Figure 47B:
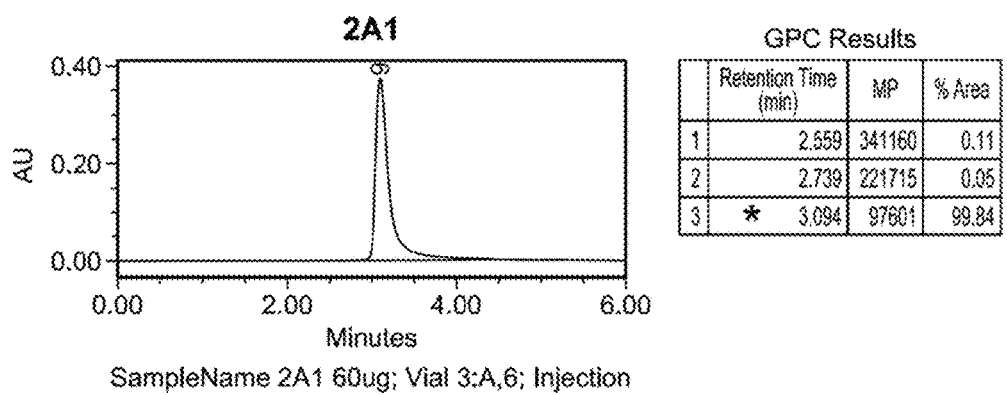
Figure 47C:
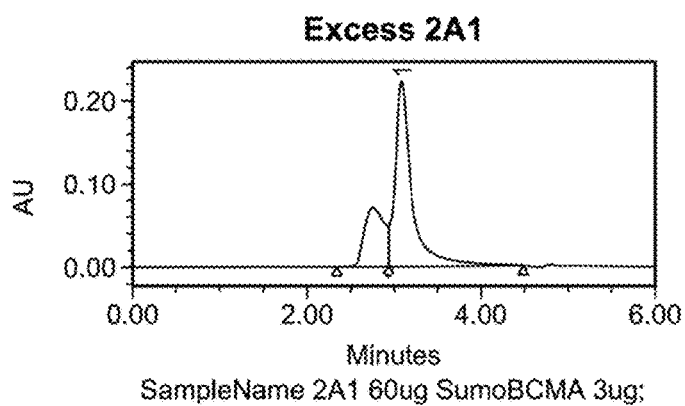
Figure 47D:
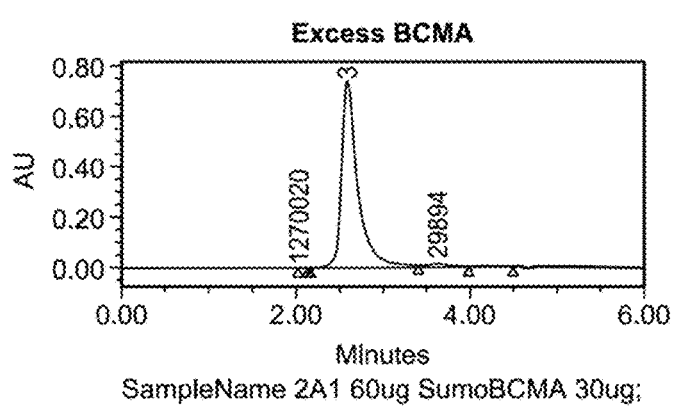
Figure 48A:
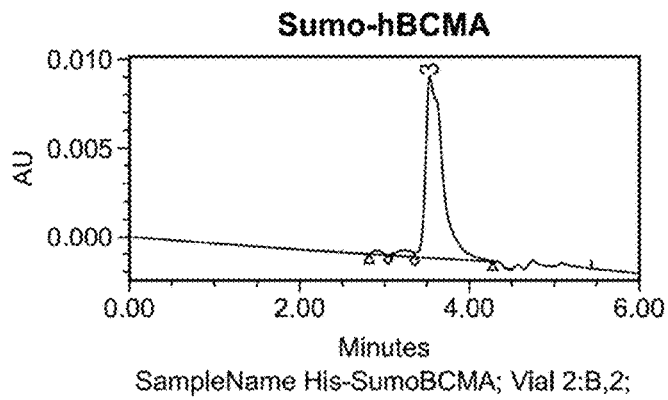
FIGS. 48A-C are chromatograms showing that the 29C12 mAb bound all forms of human BCMA, similar to that seen in FIGS. 47A-D for the 2A1 mAb.
Figure 48B:
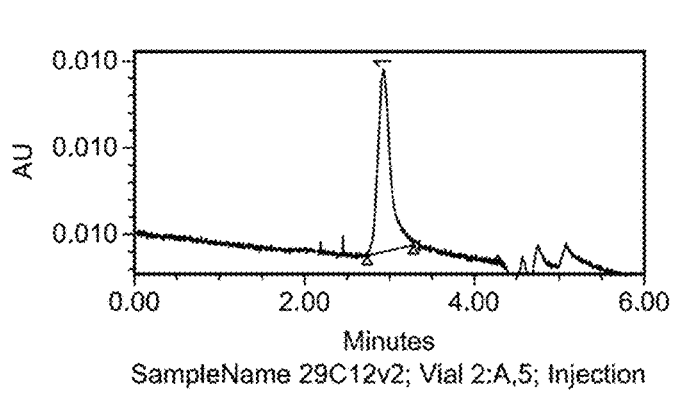
Figure 48C:
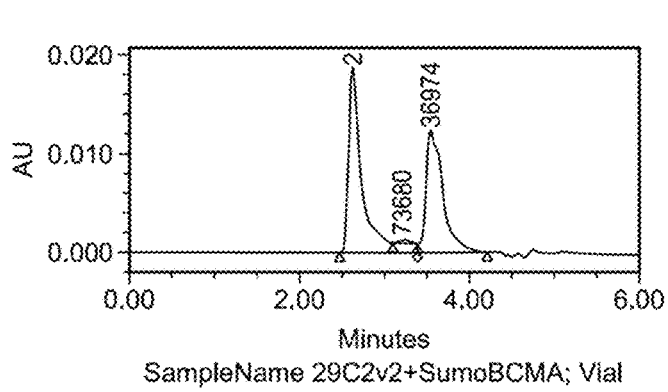

The Ab-1 was shown to bind all fragments of human BCMA (i.e., SEQ ID NOS:350, 354, 355, and 356) as illustrated in the SEC chromatograms shown in FIGS. 47A-D. FIG. 47A shows the retention time for SEQ ID NO:350. FIG. 47B shows the retention time for Ab-1. FIG. 47C shows that an excess amount of Ab-1 (60 ug) relative to 3 ug of BCMA (SEQ ID NO:350) resulted in no free BCMA, including the clipped fragments (i.e., SEQ ID NOS:354-356), and that the two peaks represent Ab-1 bound to the various BCMA fragments (retention time of 2.748) and unbound excess Ab-1 (retention time 3.078). FIG. 47D shows that the Ab-1 antibody (30 ug) in an excess amount of BCMA (60 ug of SEQ ID NO:350) bound BCMA, but there was also a small amount of the fragments of BCMA (SEQ ID NOS:354-356). Similar results were shown for the 29C12 antibody, as shown in FIGS. 48A-C. This data also suggests a 2:1 stoichiometry of BCMA molecules per antibody.

Figure 49A:
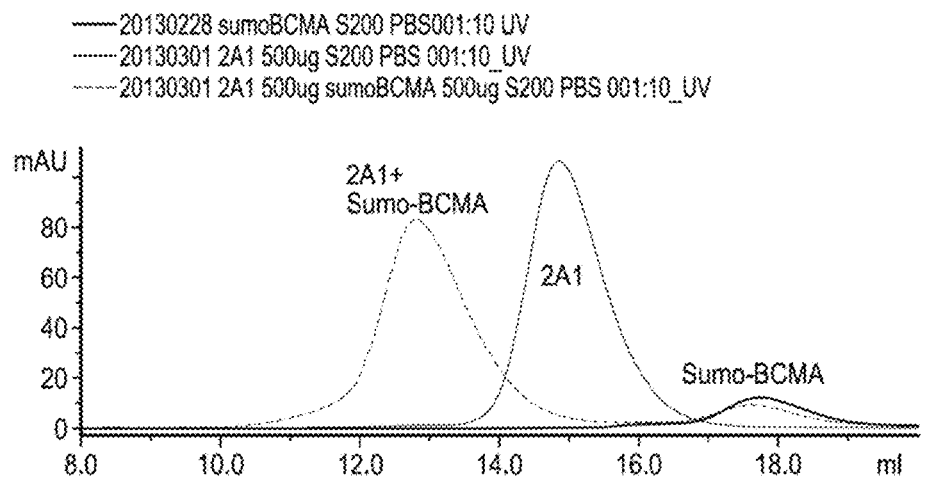
FIG. 49A shows that there were detectable size differences between Sumo and Sumo-BCMA and FIG. 49B shows that the irrelevant antibody control (anti-SA) did not bind Sumo-BCMA.
Figure 49B:
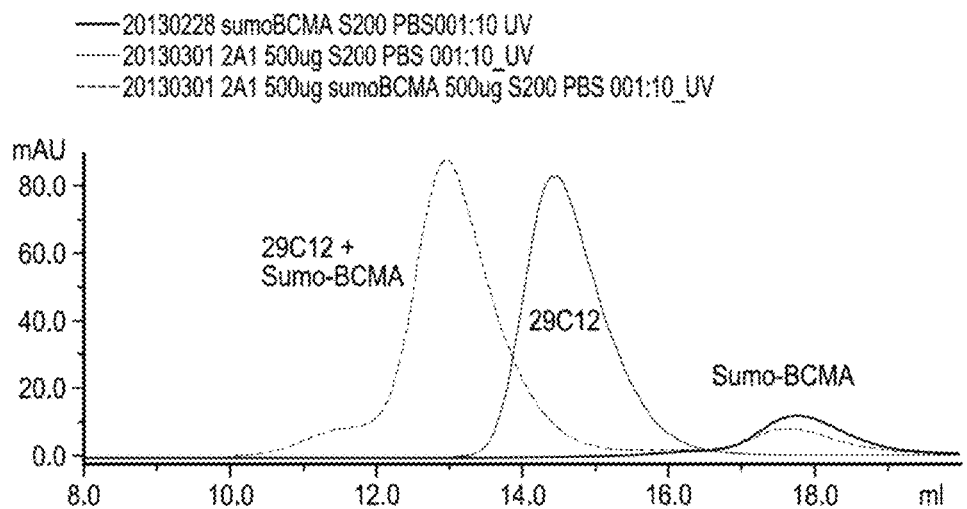
Figure 49C:
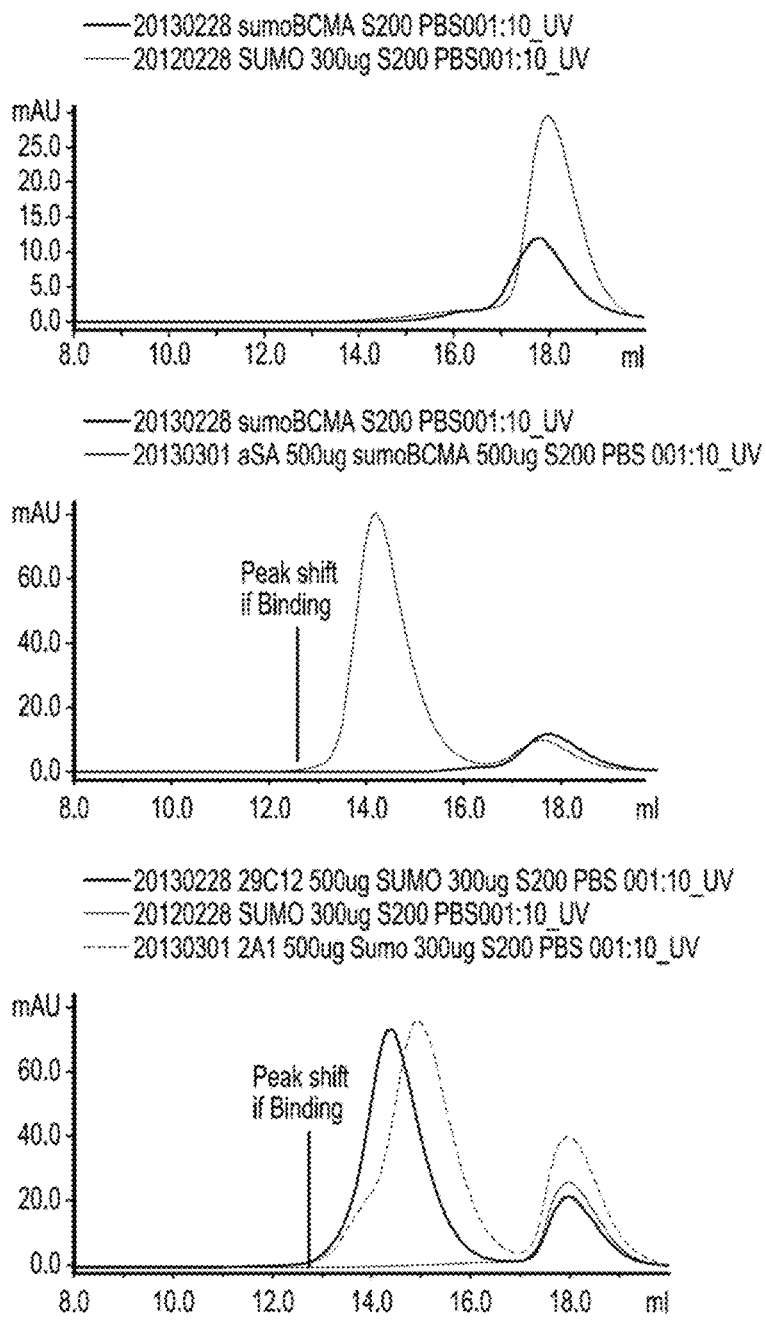
FIG. 49C shows that 2A1 and 29C12 did not bind to Sumo.

In a further experiment to confirm that the 2A1 and 29C12 antibodies were binding the truncated forms of BCMA extracellular domain (the carboxy-terminus fragments), the SEC was scaled-up to provide starting material for analyzing the captured SEC peaks by LC/MS. A Superdex 200™ 10/30 cm SEC column (GE Healthcare Life Sciences) was used according to the manufacturer's recommended condision and run in phosphate buffered saline (PBS). Incubations of antibody with excess levels of sumoBCMA were performed at room temperature for at least 30 minutes. 500 ug of 2A1 or 29C12, as well as 500 ug of either 2A1 or 29C12 plus 500 ug SumoBCMA were run over the SEC column SEC controls included 500 ug 2A1 or 29C12 plus 300 ug Sumo (cleaved from SumoBCMA), and 500 ug of an irrelevant antibody that binds strepavidin (SA) plus 500 ug Sumo-BCMA. FIG. 49A shows that there were detectable size differences between Sumo and Sumo-BCMA (although there may be less than 10-15% Sumo-BCMA in the Sumo preparation). FIG. 49B shows that the irrelevant antibody control (anti-SA) did not bind Sumo-BCMA. FIG. 49C shows that 2A1 and 29C12 did not bind to Sumo.

Liquid chromatography and mass spectrophotometry (LC/MS) was used to identify the forms (i.e., full-length and various truncations) of huBCMA that were bound by 2A1 and 29C12.

Samples:
1. 2A1+Sumo–Total concentration: 0.6 mg/ml
2. 2A1+SumoBCMA–Total concentration: 4.3 mg/ml
3. 29C12+Sumo–Total concentration: 0.6 mg/ml
4. 29C12+SumoBCMA–Total concentration: 2.2 mg/ml
5. Sumo (primarily Sumo with small percentage of Sumo-BCMA)
6. Sumo-BCMA
7. 2A1 antibody
8. 29C12 antibody Protocol:

5 ug of total proteins were reduced in 50 mM Tris/4 M guanidine/9 mM DTT, pH 8.0 at 55° C. for 15 min, and analyzed in Agilent LCTOF system using a Vydac C8 column, 2.1 mm ID×150 mm, 5 µM particle size. The column temperature was 55° C., solvent A was 0.1% TFA in water, solvent B was 0.1% TFA in acetonitrile, and the flow rate was 0.2 ml/min. The gradient in percentage of B was 5-5, 5-10, 10-80, 80-80, 80-5, 5-, in 3, 5, 40, 42, 42.5 and 45 min, respectively. The TOF mass spectrometer was tuned and calibrated in the range of 100 to 3200 m/z. TOF MS conditions included capillary voltage of 4000 V, drying gas flow at 10 L/min, dry gas temperature at 300° C., nebulizer gas flow at 40 L/min, and fragmentor voltage of 300 V. MS data was analyzed in Agilent MassHunter™ Qualitative Analysis program.

Figure 50:
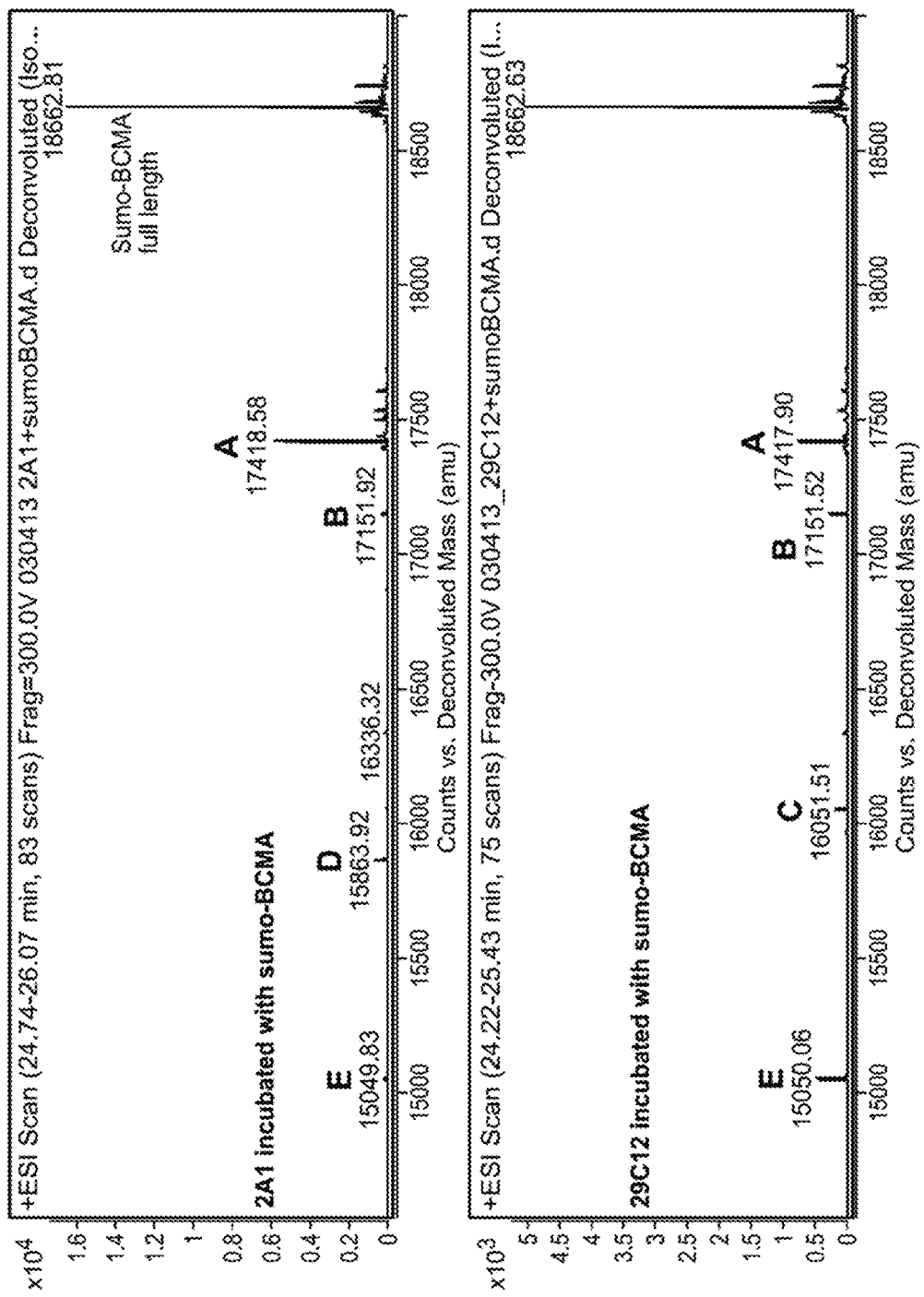
FIG. 50A provides a chromatogram showing the truncated forms of BCMA that were bound by the 2A1 antibody (peaks A, B, D, and E).
FIG. 50B shows the truncated forms of BCMA that were bound by the 29C12 antibody (peaks A, B, C, and E).

2A1 and 29C12 bound full-length and truncated forms of BCMA. As shown in FIG. 50A, truncated forms of BCMA that were bound by the 2A1 antibody included peaks A, B, D, and E, and as shown in FIG. 50B the truncated forms of BCMA that were bound by the 29C12 antibody included peaks A, B, C, and E. With reference to FIGS. 50A and B, peak A corresponds to SEQ ID NO:354, peak D corresponds to SEQ ID NO:355, and peak E corresponds to SEQ ID NO:356 (see FIG. 45). In this more detailed analysis, two additional carboxy-terminus fragments of BCMA that bound the BCMA mAbs were identified (the bold and underlined sections are BCMA):

Peak B:

(SEQ ID NO: 357)
GSSHHHHHHGSGLVPRGSASMSDSEVNQEAKPEVKPEVKPETHINLKVSD

GSSEIFFKIKKTTPLRRLMEAFAKRQGKEMDSLRFLYDGIRIQADQTPED

LDMEDNDHEAHREQIGGAGQCSQNEYFDSLLHACIPCQLRCSSNTPPLTC

QR

Peak C:

(SEQ ID NO: 358)
GSSHHHHHHGSGLVPRGSASMSDSEVNQEAKPEVKPEVKPETHINLKVSD
GSSEIFFKIKKTTPLRRLMEAFAKRQGKEMDSLRFLYDGIRIQADQTPED
LDMEDNDHEAHREQIGGAGQCSQNEYFDSLLHACIPCQLRCS

This data shows that Ab-1 bound progressively smaller fragments of human BCMA (i.e., SEQ ID NOS:350, 354, 357, 355, and 356), all of which retained part of the amino terminus. SEQ ID NO:356 is common to all the BCMA fragments, and therefore shows that Ab-1 binds to the amino terminus of human BCMA. This evidence, together with the differential binding of Ab-1 to different orthologues of BCMA, shows that Ab-1 binds a neutralizing determinant on human BCMA comprising amino acids 1-20 of SEQ ID NO:285, or more specifically a neutralizing determinant comprising amino acids 1-11 of SEQ ID NO:285. It is understood that Ab-1 need not bind every amino acid in the 1 to 20 amino acid domain or the 1 to 11 amino acid domain.

We claim:

1. A method of treating a disease, comprising administering an effective amount of an isolated monoclonal antibody, or BCMA-binding fragment thereof, selected from the group consisting of:
  - an antibody comprising a Vh-CDR1 comprising SEQ ID NO:4, a Vh-CDR2 comprising SEQ ID NO:5, a Vh-CDR3 comprising SEQ ID NO:6, a Vl-CDR1 comprising SEQ ID NO: 106, a Vl-CDR2 comprising SEQ ID NO: 107, and a Vl-CDR3 comprising SEQ ID NO: 108;
  - an antibody comprising a Vh-CDR1 comprising SEQ ID NO: 10, a Vh-CDR2 comprising SEQ ID NO: 11, a Vh-CDR3 comprising SEQ ID NO: 12, a Vl-CDR1 comprising SEQ ID NO: 112, a Vl-CDR2 comprising SEQ ID NO; 113, and a Vl-CDR3 comprising SEQ ID NO: 114;
  - an antibody comprising a Vh-CDR1 comprising SEQ ID NO: 16, a Vh-CDR2 comprising SEQ ID NO:17, a Vh-CDR3 comprising SEQ ID NO:18, a Vl-CDR1 comprising SEQ ID NO:118, a Vl-CDR2 comprising SEQ ID NO: 119, and a Vl-CDR3 comprising SEQ ID NO: 120;
  - an antibody comprising a Vh-CDR1 comprising SEQ ID NO:22, a Vh-CDR2 comprising SEQ ID NO:23, a Vh-CDR3 comprising SEQ ID NO:24, a Vl-CDR1 comprising SEQ ID NO: 124, a Vl-CDR2 comprising SEQ ID NO: 125, and a Vl-CDR3 comprising SEQ ID NO: 126;
  - an antibody comprising a Vh-CDR1 comprising SEQ ID NO:28, a Vh-CDR2 comprising SEQ ID NO:29, a Vh-CDR3 comprising SEQ ID NO:30, a Vl-CDR1 comprising SEQ ID NO: 130, a Vl-CDR2 comprising SEQ ID NO:131, and a Vl-CDR3 comprising SEQ ID NO: 132;
  - an Ab-1Vl domain comprising SEQ ID NO:240 and an Ab-1Vh domain comprising SEQ ID NO:206;
  - an Ab-2Vl domain comprising SEQ ID NO:242 and an Ab-2Vh domain comprising SEQ ID NO:208;
  - an Ab-3Vl domain comprising SEQ ID NO:244 and an Ab-3Vh domain comprising SEQ ID NO:210;
  - an Ab-4Vl domain comprising SEQ ID NO:246 and an Ab-4Vh domain comprising SEQ ID NO:212; and
  - an Ab-5Vl domain comprising SEQ ID NO:248 and an Ab-5Vh domain comprising SEQ ID NO:214;
  - wherein said antibody or fragment thereof specifically binds human BCMA, wherein the disease is selected from the group consisting of: B-cell cancers, multiple myeloma, malignant plasma cell neoplasms, Kahler's disease and Myelomatosis; Plasma cell leukemia; Plasmacytoma; B-cell prolymphocytic leukemia; Hairy cell leukemia; B-cell non-Hodgkin's lymphoma (NHL); Acute myeloid leukemia (AML); Chronic myeloid leukemia (CML); Acute lymphocytic leukemia (ALL); Chronic lymphocytic leukemia (CLL); Follicular lymphoma (including follicular non-Hodgkin's lymphoma types); Burkitt's lymphoma (Endemic Burkitt's lymphoma; Sporadic Burkitt's lymphoma); Marginal zone lymphoma (Mucosa-Associated Lymphoid Tissue; MALT/MALToma; Monocytoid B cell lymphoma; Splenic lymphoma with villous lymphocytes); Mantle cell lymphoma; Large cell lymphoma (Diffuse large cell; Diffuse Mixed Cell; Immunoblastic Lymphoma; Primary Mediastinal B Cell Lymphoma; Angiocentric Lymphoma—pulmonary B cell); Small lymphocytic lymphoma (SLL); Precursor B-lymphoblastic lymphoma; Myeloid leukemia (granulocytic; myelogenous; Acute myeloid leukemia; Chronic myeloid leukemia; Subacute myeloid leukemia; Myeloid sarcoma; Chloroma; Granulocytic sarcoma; Acute promyelocytic leukemia; Acute myelomonocytic leukemia; Waldenstrom's macroglobulinemia, and other B-cell lymphoma.

2. The method of claim 1, wherein the disease is selected from the group consisting of B-cell cancers, multiple myeloma, malignant plasma cell neoplasms, and other B-cell lymphoma.

3. The method of claim 2, wherein the disease is multiple myeloma.

4. The method of claim 1, further comprising one of more additional treatments selected from the group consisting of: chemotherapy, radiation therapy, surgery, proteasome inhibitors, corticosteroids, and stem cell transplants.

5. The method of claim 1, wherein said antibody or fragment is human.

6. The method of claim 1, wherein said antibody or fragment is a chimeric monoclonal antibody.

7. The method of claim 1, wherein said antibody or fragment further comprises a linker.

8. The method of claim 7, wherein said antibody or fragment further comprises a drug or chemotherapeutic agent.

9. The method of claim 8, wherein said antibody or fragment further comprises a linker selected from the group consisting of: 6-maleimidocaproyl, maleimidopropanoyl, valine-citrulline, alanine-phenylalanine, p-aminobenzyloxycarbonyl, Mal-dPEG4-NHS, N-succinimidyl 4-(2-pyridylthio) pentanoate ("SPP"), N-succinimidyl 4-(N-maleimidomethyl) cyclohexane-1 carboxylate ("SMCC" or "MCC"), and N-succinimidyl (4-iodo-acetyl) aminobenzoate ("SIAB").

10. The method of claim 9, wherein said antibody or fragment further comprises a linker wherein said linker is N-succinimidyl 4-(N-maleimidomethyl) cyclohexane-1 carboxylate ("SMCC" or "MCC").

11. The method of claim 9, wherein said antibody or fragment further comprises a drug or chemotherapeutic agent selected from the group consisting of: thiotepa and cyclophosphamide; alkyl sulfonates; aziridines; ethylenimines and methylamelamines; acetogenins; camptothecin; bryostatin; callystatin; CC-1065; cryptophycins; dolastatin; duocarmycin; eleutherobin; pancratistatin; sarcodictyin; spongistatin; nitrogen mustards; nitrosureas; antibiotics; dynemicin; esperamicin; neocarzinostatin chromophore, chromoprotein enediyne antiobiotic chromomophores, aclacinomysins, actinomycin, authramycin, azaserine, bleomycins, cactinomycin, carabicin, caminomycin, carzinophilin; chromomycins, dactinomycin, daunorubicin, detorubicin, 6-diazo-5-oxo-L-norleucine, doxorubicin, epirubicin, esorubicin, idarubicin, marcellomycin, nitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites, methotrexate, 5-fluorouracil (5-FU); folic acid analogues; purine analogs; pyrimidine analogs; androgens; anti-adrenals; folic acid replenisher; aldophosphamide glycoside; aminolevulinic acid; amsacrine; bestrabucil; bisantrene; edatraxate; defofamine; demecolcine; diaziquone; elfomithine; elliptinium acetate; epothilone; etoglucid; gallium nitrate; hydroxyurea; lentinan; lonidamine; maytansinoids; mitoguazone; mitoxantrone; mopidamol; nitracrine; pentostatin; phenamet; pirarubicin; podophyllinic acid; 2-ethylhydrazide; procarbazine; razoxane; rhizoxin; sizofuran; spirogermanium; tenuazonic acid; triaziquone; 2,2′,2″-trichlorotriethylamine; trichothecenes; urethan; vindesine; dacarbazine; mannomustine; mitobronitol; mitolactol; pipobroman; gacytosine; arabinoside ("Ara-C"); cyclophosphamide; thiotepa; taxoids; chlorambucil; gemcitabine; 6-thioguanine; mercaptopurine; methotrexate; platinum analogs; vinblastine; platinum; etoposide; ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid; capecitabine; tamoxifen, raloxifene, aromatase inhibiting 4(5)-imidazoles, 4-hydroxytamoxifen, trioxifene, keoxifene, LY117018, onapristone, toremifene; anti-androgens, Colchicine-site Binders, Combretastatins, Cryptophycins, Discodermolide, Dolastatin and Analogs, Auristatin PHE, Dolastatin 10, ILX-651, Symplostatin 1, TZT-1027, Epothilones, Eleutherobin, FR182877, Halichondrin B, Halimide, Hemiasterlins, Laulimalide, Maytansinoids "DM1," "DM3" or "DM4", Bivatuzumab mertansine, Cantuzumab mertansine, huN901-DM1/BB-10901TAP, MLN591DM1, My9-6-DM1, Trastuzumab-DM1, PC-SPES, Peloruside A, Resveratrol, S-allylmercaptocysteine (SAMC), Spongistatins, Vitilevuamide, Molecular Motor-Kinesins, Designed Colchicine-Site Binders, Spindle Poisons, Bezimidazole Carbamates, CP248/CP461, HMN-214, R440, SDX-103, and T67/T607.

12. The method of claim 11, wherein said drug or chemotherapeutic agent is a Maytansinoid selected from the group consisting of: DM1, DM3 and DM4.

13. The method of claim 12, wherein said drug or chemotherapeutic agent is DM1.

14. The method of claim 13, wherein said antibody or fragment has a drug to antibody ratio of between 1 and 10.

15. The method of claim 14, wherein said antibody or fragment has a drug to antibody ratio of between 2 and 5.

16. The method of claim 1, wherein said method comprises administering an effective amount of a pharmaceutical composition comprising the antibody or fragments thereof of claim 15.

17. The method of claim 16, wherein said pharmaceutical composition further comprising a pharmaceutically acceptable diluent, carrier, solubilizer, emulsifier, and/or a preservative.

* * * * *

SEQUENCE LISTING

<160> NUMBER OF SEQ ID NOS: 359

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1
gattatgctc tgagc                                                    15

<210> SEQ ID NO 2
<211> LENGTH: 57

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gtcagtagaa gcaaagctta tggtgggaca acagattacg ccgcgtctgt gaaaggc        57

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
agcgggtata gcagtggctg gacccgttt gactac                                36

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asp Tyr Ala Leu Ser
1               5

<210> SEQ ID NO 5
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Val Ser Arg Ser Lys Ala Tyr Gly Gly Thr Thr Asp Tyr Ala Ala Ser
1               5                   10                  15

Val Lys Gly

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ser Gly Tyr Ser Ser Gly Trp Thr Pro Phe Asp Tyr
1               5                   10

<210> SEQ ID NO 7
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
agctatgcca tgaac                                                      15
```

<210> SEQ ID NO 8
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gctattagtg ttggtggtga cacatactac gcagactccg tgaagggc                48

<210> SEQ ID NO 9
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gatcaggtta ctatggttcg gggagtttgg tactactacg gtttggacgt c            51

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ser Tyr Ala Met Asn
1               5

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ala Ile Ser Val Gly Gly Asp Thr Tyr Tyr Ala Asp Ser Val Lys Gly
1               5                   10                  15

<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asp Gln Val Thr Met Val Arg Gly Val Trp Tyr Tyr Tyr Gly Leu Asp
1               5                   10                  15

Val

<210> SEQ ID NO 13
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
agctatgcca tgaac                                                        15

<210> SEQ ID NO 14
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gctattagtg tcggtggtga cacatactac gcagactccg tgaagggc                     48

<210> SEQ ID NO 15
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gatcaggtta ctttggttcg gggagtttgg tactactacg gtttggacgt c                 51

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ser Tyr Ala Met Asn
1               5

<210> SEQ ID NO 17
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ala Ile Ser Val Gly Gly Asp Thr Tyr Tyr Ala Asp Ser Val Lys Gly
1               5                   10                  15

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Asp Gln Val Thr Leu Val Arg Gly Val Trp Tyr Tyr Tyr Gly Leu Asp
1               5                   10                  15

Val

<210> SEQ ID NO 19
<211> LENGTH: 15
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 19
ggccactata tacac                                                      15

<210> SEQ ID NO 20
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
tggatctacc ctaatagtgg tggcacaaac tatgcacaga agtttcaggg c              51

<210> SEQ ID NO 21
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gagggcatgg tgactggaga ctattactac taccgtatgg acgtc                    45

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly His Tyr Ile His
1               5

<210> SEQ ID NO 23
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Trp Ile Tyr Pro Asn Ser Gly Gly Thr Asn Tyr Ala Gln Lys Phe Gln
1               5                   10                  15
Gly

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Glu Gly Met Val Thr Gly Asp Tyr Tyr Tyr Tyr Arg Met Asp Val
1               5                   10                  15
```

<210> SEQ ID NO 25
<211> LENGTH: 15
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 25
gattatgctc tgagc                                                      15

<210> SEQ ID NO 26
<211> LENGTH: 57
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 26
gtcagtagaa gcaaagctta tggtgggaca acagattacg ccgcgtctgt gaaaggc        57

<210> SEQ ID NO 27
<211> LENGTH: 36
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 27
agcgggtata gcagtggctg gaccccgttt gactac                               36

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 28

Asp Tyr Ala Leu Ser
1               5

<210> SEQ ID NO 29
<211> LENGTH: 19
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 29

Val Ser Arg Ser Lys Ala Tyr Gly Gly Thr Thr Asp Tyr Ala Ala Ser
1               5                   10                  15

Val Lys Gly

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 30

```
Ser Gly Tyr Ser Ser Gly Trp Thr Pro Phe Asp Tyr
1               5                   10
```

<210> SEQ ID NO 31
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
agctatggct tgcac                                                    15

<210> SEQ ID NO 32
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
cttatctcat atgatggaag taataaatac tatgcagact ccgtgaaggg c             51

<210> SEQ ID NO 33
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
agcagcagct ggacccctct tgactac                                       27

<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

```
Ser Tyr Gly Leu His
1               5
```

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

```
Leu Ile Ser Tyr Asp Gly Ser Asn Lys Tyr Tyr Ala Asp Ser Val Lys
1               5                   10                  15

Gly
```

<210> SEQ ID NO 36
<211> LENGTH: 9
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 36

Ser Ser Ser Trp Thr Pro Leu Asp Tyr
1               5

<210> SEQ ID NO 37
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
agctatggct tgcac                                                       15

<210> SEQ ID NO 38
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
cttatctcat atgatggaag taataaatac tatgcagact ccgtgaaggg c               51

<210> SEQ ID NO 39
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
agcagcagct ggacccctct tgactac                                          27

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ser Tyr Gly Leu His
1               5

<210> SEQ ID NO 41
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Leu Ile Ser Tyr Asp Gly Ser Asn Lys Tyr Tyr Ala Asp Ser Val Lys
1               5                   10                  15
Gly

<210> SEQ ID NO 42
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ser Ser Ser Trp Thr Pro Leu Asp Tyr
1               5

<210> SEQ ID NO 43
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
agctatgcca tgaac                                                        15

<210> SEQ ID NO 44
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
gctattagtg ttggtggtga cacatactac gcagactccg tgaagggc                    48

<210> SEQ ID NO 45
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
gatcaggtta ctatggttcg gggagtttgg tactactacg gtttggacgt c                51

<210> SEQ ID NO 46
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ser Tyr Ala Met Asn
1               5

<210> SEQ ID NO 47
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ala Ile Ser Val Gly Gly Asp Thr Tyr Tyr Ala Asp Ser Val Lys Gly
1               5                   10                  15
```

<210> SEQ ID NO 48
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Asp Gln Val Thr Met Val Arg Gly Val Trp Tyr Tyr Tyr Gly Leu Asp
1               5                   10                  15
Val

<210> SEQ ID NO 49
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
agccatgcca tgagc                                                          15

<210> SEQ ID NO 50
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
gctattagtg gtggtgatgg taacacatac tacgcagact ccgtgaaggg c                  51

<210> SEQ ID NO 51
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
gatcttgttg gagtagtggc tggttactac tactacttcg gaatggacgt c                  51

<210> SEQ ID NO 52
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ser His Ala Met Ser
1               5

<210> SEQ ID NO 53
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

```
Ala Ile Ser Gly Gly Asp Gly Asn Thr Tyr Tyr Ala Asp Ser Val Lys
1               5                   10                  15
Gly

<210> SEQ ID NO 54
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Asp Leu Val Gly Val Val Ala Gly Tyr Tyr Tyr Tyr Phe Gly Met Asp
1               5                   10                  15
Val

<210> SEQ ID NO 55
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
agctatgcca tgaac                                                         15

<210> SEQ ID NO 56
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
gctattagtg tcggtggtga cacatactac gcagactccg tgaagggc                     48

<210> SEQ ID NO 57
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
gatcaggtta ctttggttcg gggagtttgg tactactacg gtttggacgt c                 51

<210> SEQ ID NO 58
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ser Tyr Ala Met Asn
1               5

<210> SEQ ID NO 59
<211> LENGTH: 16
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 59

Ala Ile Ser Val Gly Gly Asp Thr Tyr Tyr Ala Asp Ser Val Lys Gly
1               5                   10                  15

<210> SEQ ID NO 60
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Asp Gln Val Thr Leu Val Arg Gly Val Trp Tyr Tyr Gly Leu Asp
1               5                   10                  15

Val

<210> SEQ ID NO 61
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
agctatgcca tgaac                                                          15

<210> SEQ ID NO 62
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
gctattagtg tcggtggtga cacatactac gcagactccg tgaagggc                      48

<210> SEQ ID NO 63
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
gatcaggtta ctttggttcg gggagtttgg tactactacg gtttggacgt c                  51

<210> SEQ ID NO 64
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ser Tyr Ala Met Asn
1               5
```

```
<210> SEQ ID NO 65
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ala Ile Ser Val Gly Gly Asp Thr Tyr Tyr Ala Asp Ser Val Lys Gly
1               5                   10                  15

<210> SEQ ID NO 66
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Asp Gln Val Thr Leu Val Arg Gly Val Trp Tyr Tyr Gly Leu Asp
1               5                   10                  15

Val

<210> SEQ ID NO 67
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
agttatgcca tgagc                                                    15

<210> SEQ ID NO 68
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
gctattagtg gtggtgctgg taatacatac tacgcagact ccgtgaaggg c             51

<210> SEQ ID NO 69
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
gacggagtgg gaactactgg gggatacttc tactaccacg gtatggacgt c             51

<210> SEQ ID NO 70
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70
```

Ser Tyr Ala Met Ser
1               5

<210> SEQ ID NO 71
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ala Ile Ser Gly Gly Ala Gly Asn Thr Tyr Tyr Ala Asp Ser Val Lys
1               5                   10                  15

Gly

<210> SEQ ID NO 72
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Asp Gly Val Gly Thr Thr Gly Gly Tyr Phe Tyr Tyr His Gly Met Asp
1               5                   10                  15

Val

<210> SEQ ID NO 73
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
agttatgcca tgagc                                                        15

<210> SEQ ID NO 74
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
gctattagtg gtggtgctgg taatacatac tacgcagact ccgtgaaggg c                51

<210> SEQ ID NO 75
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
gacggagtgg gaactactgg gggatacttc tactaccacg gtatggacgt c                51

<210> SEQ ID NO 76
<211> LENGTH: 5
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 76

Ser Tyr Ala Met Ser
1               5

<210> SEQ ID NO 77
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Ala Ile Ser Gly Gly Ala Gly Asn Thr Tyr Tyr Ala Asp Ser Val Lys
1               5                   10                  15

Gly

<210> SEQ ID NO 78
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Asp Gly Val Gly Thr Thr Gly Gly Tyr Phe Tyr Tyr His Gly Met Asp
1               5                   10                  15

Val

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
agcaccaatg ttgcttggaa c                                            21

<210> SEQ ID NO 80
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
gggacattct acaggtccaa ctggtataat gattatgcaa tctctgtgaa aagt        54

<210> SEQ ID NO 81
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
```
ttttatagct ggaactccta ctttgactac 30

<210> SEQ ID NO 82
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Ser Thr Asn Val Ala Trp Asn
1               5

<210> SEQ ID NO 83
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gly Thr Phe Tyr Arg Ser Asn Trp Tyr Asn Asp Tyr Ala Ile Ser Val
1               5                   10                  15

Lys Ser

<210> SEQ ID NO 84
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Phe Tyr Ser Trp Asn Ser Tyr Phe Asp Tyr
1               5                   10

<210> SEQ ID NO 85
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
agctatgcca tgaac 15

<210> SEQ ID NO 86
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
gctattagtg ttggtggtgg cacatactac gcagactccg tgaagggc 48

<210> SEQ ID NO 87
<211> LENGTH: 51
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 87
gatcaggtta ctatggttcg gggagtttgg tactactacg gtttggacgt c            51

<210> SEQ ID NO 88
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ser Tyr Ala Met Asn
1               5

<210> SEQ ID NO 89
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Ala Ile Ser Val Gly Gly Gly Thr Tyr Tyr Ala Asp Ser Val Lys Gly
1               5                   10                  15

<210> SEQ ID NO 90
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Asp Gln Val Thr Met Val Arg Gly Val Trp Tyr Tyr Gly Leu Asp
1               5                   10                  15
Val

<210> SEQ ID NO 91
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
aactatgcca tgaac                                                    15

<210> SEQ ID NO 92
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
gctattagtg tcggtggtga cacatactac gcagactccg tgaagggc                48

<210> SEQ ID NO 93
<211> LENGTH: 51

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
gatcaggtta ctttggttcg gggagtttgg tactactacg gtttggacgt c          51

<210> SEQ ID NO 94
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Asn Tyr Ala Met Asn
1               5

<210> SEQ ID NO 95
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Ala Ile Ser Val Gly Gly Asp Thr Tyr Tyr Ala Asp Ser Val Lys Gly
1               5                   10                  15

<210> SEQ ID NO 96
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Asp Gln Val Thr Leu Val Arg Gly Val Trp Tyr Tyr Tyr Gly Leu Asp
1               5                   10                  15

Val

<210> SEQ ID NO 97
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
agctatgcca tgaac                                                  15

<210> SEQ ID NO 98
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
gctattagtg ttggtggtga cacatactac gcagactccg tgaagggc              48
```

<210> SEQ ID NO 99
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
gatcaggtta ctatggttcg gggagtttgg tactactacg gtttggacgt c          51

<210> SEQ ID NO 100
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ser Tyr Ala Met Asn
1               5

<210> SEQ ID NO 101
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Ala Ile Ser Val Gly Gly Asp Thr Tyr Tyr Ala Asp Ser Val Lys Gly
1               5                   10                  15

<210> SEQ ID NO 102
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Asp Gln Val Thr Met Val Arg Gly Val Trp Tyr Tyr Tyr Gly Leu Asp
1               5                   10                  15

Val

<210> SEQ ID NO 103
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
tctgggagca gctccaacat cggaagtaat actgtaaac                        39

<210> SEQ ID NO 104
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
aattatcatc agcggccctc a                                              21

<210> SEQ ID NO 105
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
gcagcatggg atgacagcct gaatggttgg gtg                                 33

<210> SEQ ID NO 106
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Ser Gly Ser Ser Ser Asn Ile Gly Ser Asn Thr Val Asn
1               5                   10

<210> SEQ ID NO 107
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Asn Tyr His Gln Arg Pro Ser
1               5

<210> SEQ ID NO 108
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Ala Ala Trp Asp Asp Ser Leu Asn Gly Trp Val
1               5                   10

<210> SEQ ID NO 109
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
aggtctagtc agagcctcct gcacagtaat ggaaacaact atttggat                 48

<210> SEQ ID NO 110
<211> LENGTH: 21
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 110
ttgggctctc agcggacctc c                                              21

<210> SEQ ID NO 111
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
atgcaagctc tacagcctcc tcggagg                                        27

<210> SEQ ID NO 112
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Arg Ser Ser Gln Ser Leu Leu His Ser Asn Gly Asn Asn Tyr Leu Asp
1               5                   10                  15

<210> SEQ ID NO 113
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Leu Gly Ser Gln Arg Thr Ser
1               5

<210> SEQ ID NO 114
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Met Gln Ala Leu Gln Pro Pro Arg Arg
1               5

<210> SEQ ID NO 115
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
aggtctagtc agagcctcct gcacagtaat ggaaacaact atttggat                 48

<210> SEQ ID NO 116
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 116
ttgggctctc agcggacctc c                                              21

<210> SEQ ID NO 117
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
atgcaagctc tacagcctcc tcggagg                                        27

<210> SEQ ID NO 118
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Arg Ser Ser Gln Ser Leu Leu His Ser Asn Gly Asn Asn Tyr Leu Asp
1               5                   10                  15

<210> SEQ ID NO 119
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Leu Gly Ser Gln Arg Thr Ser
1               5

<210> SEQ ID NO 120
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Met Gln Ala Leu Gln Pro Pro Arg Arg
1               5

<210> SEQ ID NO 121
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
tccctgagca gcggctacag taattataaa gtggac                              36

<210> SEQ ID NO 122
```

```
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
gtgggcattg gtgggattgt ggggtccaag ggggat                              36

<210> SEQ ID NO 123
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
ggggcagacc atggcagtgg gaacaacttc gtgtatgtc                           39

<210> SEQ ID NO 124
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Ser Leu Ser Ser Gly Tyr Ser Asn Tyr Lys Val Asp
1               5                   10

<210> SEQ ID NO 125
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Val Gly Ile Gly Gly Ile Val Gly Ser Lys Gly Asp
1               5                   10

<210> SEQ ID NO 126
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Gly Ala Asp His Gly Ser Gly Asn Asn Phe Val Tyr Val
1               5                   10

<210> SEQ ID NO 127
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
tctgggagca gctccaacat cggaagtaat actgtaaac                           39
```

<210> SEQ ID NO 128
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
aattatcatc agcggccctc a                                            21

<210> SEQ ID NO 129
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
gcagcatggg atgacagcct gaatggttgg gtg                               33

<210> SEQ ID NO 130
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Ser Gly Ser Ser Ser Asn Ile Gly Ser Asn Thr Val Asn
1               5                   10

<210> SEQ ID NO 131
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Asn Tyr His Gln Arg Pro Ser
1               5

<210> SEQ ID NO 132
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Ala Ala Trp Asp Asp Ser Leu Asn Gly Trp Val
1               5                   10

<210> SEQ ID NO 133
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
cgggcaagtc agggcattag aaatgattta ggc        33

<210> SEQ ID NO 134
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
gctgcatcca gtttgcaaag t        21

<210> SEQ ID NO 135
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
ctacagtatt atagttaccc gctcact        27

<210> SEQ ID NO 136
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Arg Ala Ser Gln Gly Ile Arg Asn Asp Leu Gly
1               5                   10

<210> SEQ ID NO 137
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Ala Ala Ser Ser Leu Gln Ser
1               5

<210> SEQ ID NO 138
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Leu Gln Tyr Tyr Ser Tyr Pro Leu Thr
1               5

<210> SEQ ID NO 139
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
cgggcaagtc agagcattag caactttta aat         33

<210> SEQ ID NO 140
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
gctgcatcca gtttgcaaag t         21

<210> SEQ ID NO 141
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
caacagagtt acagtattcc cact         24

<210> SEQ ID NO 142
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Arg Ala Ser Gln Ser Ile Ser Asn Phe Leu Asn
1               5                   10

<210> SEQ ID NO 143
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Ala Ala Ser Ser Leu Gln Ser
1               5

<210> SEQ ID NO 144
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Gln Gln Ser Tyr Ser Ile Pro Thr
1               5

<210> SEQ ID NO 145
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 145
aggtctagtc agagcctcct gcacagtaat ggaaacaact atttggat                    48

<210> SEQ ID NO 146
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
ttgggctcta atcggacctc c                                                 21

<210> SEQ ID NO 147
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
atgcaagctc tacagcctcc tcggagg                                           27

<210> SEQ ID NO 148
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Arg Ser Ser Gln Ser Leu Leu His Ser Asn Gly Asn Asn Tyr Leu Asp
1               5                   10                  15

<210> SEQ ID NO 149
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Leu Gly Ser Asn Arg Thr Ser
1               5

<210> SEQ ID NO 150
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Met Gln Ala Leu Gln Pro Pro Arg Arg
1               5

<210> SEQ ID NO 151
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
aggtctagtc agagcctcct acatagtaat ggatacaagt atttggat        48

<210> SEQ ID NO 152
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
ttgggttcta atcgggcctc c        21

<210> SEQ ID NO 153
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
atgcaagctc tacaacctcc tcggacg        27

<210> SEQ ID NO 154
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Arg Ser Ser Gln Ser Leu Leu His Ser Asn Gly Tyr Lys Tyr Leu Asp
1               5                   10                  15

<210> SEQ ID NO 155
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Leu Gly Ser Asn Arg Ala Ser
1               5

<210> SEQ ID NO 156
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Met Gln Ala Leu Gln Pro Pro Arg Thr
1               5

<210> SEQ ID NO 157
<211> LENGTH: 48

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
aggtctagtc agagcctcct gcacagtaat ggaaacaact atttggat               48

<210> SEQ ID NO 158
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
ttgggctcta atcggacctc c                                            21

<210> SEQ ID NO 159
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
atgcaagctc tacagcctcc tcggagg                                      27

<210> SEQ ID NO 160
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Arg Ser Ser Gln Ser Leu Leu His Ser Asn Gly Asn Asn Tyr Leu Asp
1               5                   10                  15

<210> SEQ ID NO 161
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Leu Gly Ser Asn Arg Thr Ser
1               5

<210> SEQ ID NO 162
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Met Gln Ala Leu Gln Pro Pro Arg Arg
1               5
```

<210> SEQ ID NO 163
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
aggtctagtc agagcctcct gcacagtaat ggaaacaact atttggat            48

<210> SEQ ID NO 164
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
ttgggctcta atcggacctc c                                         21

<210> SEQ ID NO 165
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
atgcaagctc tacagcctcc tcggagg                                   27

<210> SEQ ID NO 166
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Arg Ser Ser Gln Ser Leu Leu His Ser Asn Gly Asn Asn Tyr Leu Asp
1               5                   10                  15

<210> SEQ ID NO 167
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Leu Gly Ser Asn Arg Thr Ser
1               5

<210> SEQ ID NO 168
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Met Gln Ala Leu Gln Pro Pro Arg Arg
1               5

<210> SEQ ID NO 169
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
agatctagtc agagcctcct gcatagtaat ggatacaact atttggat                48

<210> SEQ ID NO 170
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
ttgacttcta atcgggcctc c                                             21

<210> SEQ ID NO 171
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
atgcaagccc tacaaattcc tcggacg                                       27

<210> SEQ ID NO 172
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Arg Ser Ser Gln Ser Leu Leu His Ser Asn Gly Tyr Asn Tyr Leu Asp
1               5                   10                  15

<210> SEQ ID NO 173
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Leu Thr Ser Asn Arg Ala Ser
1               5

<210> SEQ ID NO 174
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Met Gln Ala Leu Gln Ile Pro Arg Thr
1               5

<210> SEQ ID NO 175
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
aggtctagtc agagcctcct gcacagtaat ggaaacaact atttggat                48

<210> SEQ ID NO 176
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
ttgggctcta atcggacctc c                                             21

<210> SEQ ID NO 177
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
atgcaagctc tacagcctcc tcggagg                                       27

<210> SEQ ID NO 178
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Arg Ser Ser Gln Ser Leu Leu His Ser Asn Gly Asn Asn Tyr Leu Asp
1               5                   10                  15

<210> SEQ ID NO 179
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Leu Gly Ser Asn Arg Thr Ser
1               5

<210> SEQ ID NO 180
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 180

Met Gln Ala Leu Gln Pro Pro Arg Arg
1               5

<210> SEQ ID NO 181
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
accctgagca gcggctacag taattataaa gtggac                              36

<210> SEQ ID NO 182
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
gtgggcactg gtgggattgt gggatccaag ggggat                              36

<210> SEQ ID NO 183
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
ggggcagacc atggcagtga gaccaacttc gtgtatgtc                           39

<210> SEQ ID NO 184
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Thr Leu Ser Ser Gly Tyr Ser Asn Tyr Lys Val Asp
1               5                   10

<210> SEQ ID NO 185
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Val Gly Thr Gly Gly Ile Val Gly Ser Lys Gly Asp
1               5                   10

<210> SEQ ID NO 186
<211> LENGTH: 13
<212> TYPE: PRT
<213> ORGANISM: Artificial Sequence
<220> FEATURE:
<223> OTHER INFORMATION: Description of Artificial Sequence: Synthetic
```

```
    peptide

<400> SEQUENCE: 186

Gly Ala Asp His Gly Ser Glu Thr Asn Phe Val Tyr Val
1               5                   10

<210> SEQ ID NO 187
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
aggtctagtc agagcctcct gcacagtaat ggaaacaact atttggat              48

<210> SEQ ID NO 188
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
ttgggctcta atcggacctc c                                            21

<210> SEQ ID NO 189
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
atgcaagctc tacagcctcc tcggagg                                      27

<210> SEQ ID NO 190
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Arg Ser Ser Gln Ser Leu Leu His Ser Asn Gly Asn Asn Tyr Leu Asp
1               5                   10                  15

<210> SEQ ID NO 191
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Leu Gly Ser Asn Arg Thr Ser
1               5

<210> SEQ ID NO 192
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 192

Met Gln Ala Leu Gln Pro Pro Arg Arg
1               5

<210> SEQ ID NO 193
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
aggtctagtc agagcctcct gcacagtaat ggaaacaact atttggat                48

<210> SEQ ID NO 194
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
ttgggctcta atcggacctc c                                             21

<210> SEQ ID NO 195
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
atgcaagctc tacagcctcc tcggagg                                       27

<210> SEQ ID NO 196
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Arg Ser Ser Gln Ser Leu Leu His Ser Asn Gly Asn Asn Tyr Leu Asp
1               5                   10                  15

<210> SEQ ID NO 197
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Leu Gly Ser Asn Arg Thr Ser
1               5

<210> SEQ ID NO 198
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Met Gln Ala Leu Gln Pro Pro Arg Arg
1               5

<210> SEQ ID NO 199
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
aggtctagtc agagcctcct gcacagtaat ggaaacaact ttttggat               48

<210> SEQ ID NO 200
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
ttgggctcta atcggacctc c                                            21

<210> SEQ ID NO 201
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
atgcaagctc tacggcctcc tcggagg                                      27

<210> SEQ ID NO 202
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Arg Ser Ser Gln Ser Leu Leu His Ser Asn Gly Asn Asn Phe Leu Asp
1               5                   10                  15

<210> SEQ ID NO 203
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Leu Gly Ser Asn Arg Thr Ser
1               5
```

```
<210> SEQ ID NO 204
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Met Gln Ala Leu Arg Pro Pro Arg Arg
1               5

<210> SEQ ID NO 205
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 205
gaggtgcagc tggtggagtc tgggggaggc ttggtaaagc caggggggtc cctgagactc      60
tcctgtgcag cttctggatt cacctttgga gattatgctc tgagctggtt ccgccaggct     120
ccagggaagg ggctggagtg ggtaggtgtc agtagaagca aagcttatgg tgggacaaca     180
gattacgccg cgtctgtgaa aggcagattc accatctcaa gagatgattc aaaagcacc     240 gcctatctgc aaatgaacag cctgaaaacc gaggacacac cgtgtatta ctgtgctagt     300 agcgggtata gcagtggctg acccccgttt gactactggg gccagggaac cctggtcacc     360
gtctcctca                                                             369

<210> SEQ ID NO 206
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Gly Asp Tyr
            20                  25                  30

Ala Leu Ser Trp Phe Arg Gln Ala Pro Gly Lys Gly Leu Glu Trp Val
        35                  40                  45

Gly Val Ser Arg Ser Lys Ala Tyr Gly Gly Thr Thr Asp Tyr Ala Ala
    50                  55                  60

Ser Val Lys Gly Arg Phe Thr Ile Ser Arg Asp Asp Ser Lys Ser Thr
65                  70                  75                  80

Ala Tyr Leu Gln Met Asn Ser Leu Lys Thr Glu Asp Thr Ala Val Tyr
                85                  90                  95

Tyr Cys Ala Ser Ser Gly Tyr Ser Ser Gly Trp Thr Pro Phe Asp Tyr
            100                 105                 110

Trp Gly Gln Gly Thr Leu Val Thr Val Ser Ser
        115                 120

<210> SEQ ID NO 207
<211> LENGTH: 375
<212> TYPE: DNA
<213> ORGANISM: Artificial Sequence
<220> FEATURE:
```

<223> OTHER INFORMATION: Description of Artificial Sequence: Synthetic
polynucleotide

<400> SEQUENCE: 207

```
gaggtgcagc tgttggagtc tggaggaggc ttggtacagc ctgggggtc cctgagactc      60
tcctgtgcag cctctggatt cacctttagc agctatgcca tgaactgggt ccgccaggct    120
ccagggaagg gctggagtg gtctcagct attagtgttg gtggtgacac atactacgca     180
gactccgtga agggccggtt caccatctcc agagacaatt ccaagaacac gctgtatctg    240
caaatgaaca gcctgagagc cgaggacacg gccgtatatt actgtgcgaa agatcaggtt    300
actatggttc ggggagtttg gtactactac ggtttggacg tctggggcca agggaccacg    360
gtcaccgtct cctca                                                      375
```

<210> SEQ ID NO 208
<211> LENGTH: 125
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 208

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Val Gly Gly Asp Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Asp Gln Val Thr Met Val Arg Gly Val Trp Tyr Tyr Tyr Gly Leu
            100                 105                 110

Asp Val Trp Gly Gln Gly Thr Thr Val Thr Val Ser Ser
        115                 120                 125
```

<210> SEQ ID NO 209
<211> LENGTH: 375
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 209

```
gaggtgcagc tgttggagtc tggaggaggc ttggtacagc ctgggggtc cctgagactc      60
tcctgtgcag cctctggatt cacctttagc agctatgcca tgaactgggt ccgccaggct    120
ccagggaagg gctggagtg gtctcagct attagtgtcg gtggtgacac atactacgca     180
gactccgtga agggccggtt caccatctcc agagacaatt ccaagaacac gctatatctg    240
caggtgaaca gcctgagagc cgaggactcg gccgtatatt actgtgcgaa agatcaggtt    300
actttggttc ggggagtttg gtactactac ggtttggacg tctggggcca agggaccacg    360
gtcaccgtct cctca                                                      375
```

<210> SEQ ID NO 210
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 210

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Val Gly Gly Asp Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Val Asn Ser Leu Arg Ala Glu Asp Ser Ala Val Tyr Tyr Cys Ala
                85                  90                  95

Lys Asp Gln Val Thr Leu Val Arg Gly Val Trp Tyr Tyr Gly Leu
            100                 105                 110

Asp Val Trp Gly Gln Gly Thr Thr Val Thr Val Ser Ser
        115                 120                 125

<210> SEQ ID NO 211
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 211
caggtgcagc tggtgcagtc tggggctgag gtgaagaagc ctggggcctc agtgaaggtc       60
tcctgcaagg cttctggata caccttcacc ggccactata tacactgggt gcgacaggcc      120
cctggacaag gcttgagtg atgggatgg atctacccta atagtggtgg cacaaactat        180
gcacagaagt tcagggcag ggtcaccatg accaggaca cgtccatcag cacagcctac         240
atggagctga gtaggctgag atctgacgat tcggccgtgt attactgtgc gagagagggc      300
atggtgactg gagactatta ctactaccgt atggacgtct ggggccaagg gaccacggtc      360
atcgtctcct ca                                                          372

<210> SEQ ID NO 212
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 212

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly His
            20                  25                  30

Tyr Ile His Trp Val Arg Gln Ala Pro Gly Gln Gly Leu Glu Trp Met
        35                  40                  45

Gly Trp Ile Tyr Pro Asn Ser Gly Gly Thr Asn Tyr Ala Gln Lys Phe
            50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Ser Ala Val Tyr Tyr Cys
                85                  90                  95

Ala Arg Glu Gly Met Val Thr Gly Asp Tyr Tyr Tyr Arg Met Asp
            100                 105                 110

Val Trp Gly Gln Gly Thr Thr Val Ile Val Ser Ser
            115                 120

<210> SEQ ID NO 213
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 213
gaggtgcagc tggtggagtc tgggggaggc ttggtaaagc cagggcggtc cctgagactc      60
tcctgtacag cttctggatt caccttttgga gattatgctc tgagctggtt ccgccaggct    120
ccagggaagg ggctggagtg ggtaggtgtc agtagaagca aagcttatgg tgggacaaca    180
gattacgccg cgtctgtgaa aggcagattc accatctcaa gagatgattc aaaaagcttc    240
gcctatctgc aaatgaacag cctgaaaacc gaggacacag ccgtgtatta ctgttgtagt    300
agcgggtata gcagtggctg acccccgttt gactactggg gccagggaac cctggtcacc    360
gtctcctca                                                             369

<210> SEQ ID NO 214
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 214

Glu Val Gln Leu Val Glu Ser Gly Gly Gly Leu Val Lys Pro Gly Arg
1               5                   10                  15

Ser Leu Arg Leu Ser Cys Thr Ala Ser Gly Phe Thr Phe Gly Asp Tyr
            20                  25                  30

Ala Leu Ser Trp Phe Arg Gln Ala Pro Gly Lys Gly Leu Glu Trp Val
        35                  40                  45

Gly Val Ser Arg Ser Lys Ala Tyr Gly Gly Thr Thr Asp Tyr Ala Ala
    50                  55                  60

Ser Val Lys Gly Arg Phe Thr Ile Ser Arg Asp Asp Ser Lys Ser Phe
65                  70                  75                  80

Ala Tyr Leu Gln Met Asn Ser Leu Lys Thr Glu Asp Thr Ala Val Tyr
                85                  90                  95

Tyr Cys Cys Ser Ser Gly Tyr Ser Ser Gly Trp Thr Pro Phe Asp Tyr
            100                 105                 110

Trp Gly Gln Gly Thr Leu Val Thr Val Ser Ser
        115                 120

<210> SEQ ID NO 215
<211> LENGTH: 354

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 215
caggtgcagc tggtggagtc tgggggaggc gtggtccagc ctggggaggtc cctgagactc     60 tcctgtgcag cctctggatt caccttcagt agctatggct tgcactgggt ccgccaggct    120
ccaggcaagg ggctggagtg ggtggcactt atctcatatg atggaagtaa taaatactat    180
gcagactccg tgaagggccg attcaccatc tccagagaca attccaagaa cacactgtat    240
ctgcaaatga acagcctgag agctgaggac acggctgtgt attactgttg gtatagcagc    300
agctggaccc ctcttgacta ctggggccag ggaaccctgg tcaccgtctc ctca          354

<210> SEQ ID NO 216
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 216

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Leu His Trp Val Arg Gln Ala Pro Gly Lys Gly Leu Glu Trp Val
        35                  40                  45

Ala Leu Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Trp Tyr Ser Ser Ser Trp Thr Pro Leu Asp Tyr Trp Gly Gln Gly Thr
            100                 105                 110

Leu Val Thr Val Ser Ser
        115

<210> SEQ ID NO 217
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 217
caggtgcagc tggtggagtc tgggggaggc gtggtccagc ctggggaggtc cctgagactc     60 tcctgtgcag cctctggatt caccttcagt agctatggct tgcactgggt ccgccaggct    120
ccaggcaagg ggctggagtg ggtggcactt atctcatatg atggaagtaa taaatactat    180
gcagactccg tgaagggccg attcaccatc tccagagaca attccaagaa cacactgtat    240
ctgcaaatga acagcctgag agctgaggac acggctgtgt attactgttg gtatagcagc    300
agctggaccc ctcttgacta ctggggccag ggaaccctgg tcaccgtctc ctca          354

<210> SEQ ID NO 218
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 218

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Leu His Trp Val Arg Gln Ala Pro Gly Lys Gly Leu Glu Trp Val
            35                  40                  45

Ala Leu Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Trp Tyr Ser Ser Ser Trp Thr Pro Leu Asp Tyr Trp Gly Gln Gly Thr
            100                 105                 110

Leu Val Thr Val Ser Ser
        115
```

<210> SEQ ID NO 219
<211> LENGTH: 375
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 219

```
gaggtgcagc tgttggagtc tgggggagcc ttggtacagc ctgggggtc cctgagactc      60
tcctgtgcag cctctggatt cacctttagc agctatgcca tgaactgggt ccgccaggct    120
ccagggaagg ggctggagtg ggtctcagct attagtgttg gtggtgacac atactacgca    180
gactccgtga agggccggtt caccatctcc agagacaatt ccaagaacac gctgtatctg    240
caaatgaaca gcctgagagc cgaggacacg gccgtatatt actgtgcgaa agatcaggtt    300
actatggttc gggagttttg gtactactac ggtttggacg tctggggcca agggaccacg    360
gtcaccgtct cctca                                                    375
```

<210> SEQ ID NO 220
<211> LENGTH: 125
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 220

```
Glu Val Gln Leu Leu Glu Ser Gly Gly Ala Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Asn Trp Val Arg Gln Ala Pro Gly Lys Gly Leu Glu Trp Val
            35                  40                  45
```

Ser Ala Ile Ser Val Gly Gly Asp Thr Tyr Tyr Ala Asp Ser Val Lys
            50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                85                  90                  95

Lys Asp Gln Val Thr Met Val Arg Gly Val Trp Tyr Tyr Gly Leu
            100                 105                 110

Asp Val Trp Gly Gln Gly Thr Thr Val Thr Val Ser Ser
            115                 120                 125

<210> SEQ ID NO 221
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 221
gaggtgcagc tgttggagtc tgggggaggc ttggtacagc ctggggggtc cctgagactc    60
tcctgtgcag cctctggatt cacctttagc agccatgcca tgagctgggt ccgccaggct   120
ccagggaagg gctggagtg gtctcggct attagtggtg gtgatggtaa cacatactac    180
gcagactccg tgaagggccg gttcgccatc tccagagaca attccaagaa tgtggtgtat   240
ctgcaaatga acagcctgag agccgaggac acggccgtat atttctgtgc gaaagatctt   300
gttggagtag tggctggtta ctactactac ttcggaatgg acgtctgggg ccaagggacc   360
acggtcaccg tctcctca                                                 378

<210> SEQ ID NO 222
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 222

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser His
            20                  25                  30

Ala Met Ser Trp Val Arg Gln Ala Pro Gly Lys Gly Leu Glu Trp Val
        35                  40                  45

Ser Ala Ile Ser Gly Gly Asp Gly Asn Thr Tyr Tyr Ala Asp Ser Val
    50                  55                  60

Lys Gly Arg Phe Ala Ile Ser Arg Asp Asn Ser Lys Asn Val Val Tyr
 65                  70                  75                  80

Leu Gln Met Asn Ser Leu Arg Ala Glu Asp Thr Ala Val Tyr Phe Cys
                85                  90                  95

Ala Lys Asp Leu Val Gly Val Val Ala Gly Tyr Tyr Tyr Tyr Phe Gly
            100                 105                 110

Met Asp Val Trp Gly Gln Gly Thr Thr Val Thr Val Ser Ser
            115                 120                 125

<210> SEQ ID NO 223
<211> LENGTH: 375
<212> TYPE: DNA

<213> ORGANISM: Artificial Sequence
<220> FEATURE:
<223> OTHER INFORMATION: Description of Artificial Sequence: Synthetic
polynucleotide

<400> SEQUENCE: 223

```
gaggtgcagc tgttggagtc tgggggagcc ttggtacagc ctggggggtc cctgagactc      60
tcctgtgcag cctctggatt cacctttagc agctatgcca tgaactgggt ccgccaggct     120
ccagggaagg ggctggagtg gtctcagct attagtgtcg gtggtgacac atactacgca     180
gactccgtga agggccggtt caccatctcc agagacaatt ccaagaacac gctatatctg     240
cacgtgaaca gcctgagcgc cgaggactcg gccgtatatt actgtgcgaa agatcaggtt     300
actttggttc ggggagtttg gtactactac ggtttggacg tctggggcca agggaccacg     360
gtcaccgtct cctca                                                       375
```

<210> SEQ ID NO 224
<211> LENGTH: 125
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 224

```
Glu Val Gln Leu Leu Glu Ser Gly Gly Ala Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Val Gly Gly Asp Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

His Val Asn Ser Leu Ser Ala Glu Asp Ser Ala Val Tyr Tyr Cys Ala
                85                  90                  95

Lys Asp Gln Val Thr Leu Val Arg Gly Val Trp Tyr Tyr Tyr Gly Leu
            100                 105                 110

Asp Val Trp Gly Gln Gly Thr Thr Val Thr Val Ser Ser
        115                 120                 125
```

<210> SEQ ID NO 225
<211> LENGTH: 375
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 225

```
gaggtgcagc tgttggagtc tgggggagcc ttggtacagc ctggggggtc cctgagactc      60
tcctgtgcag cctctggatt cacctttagc agctatgcca tgaactgggt ccgccaggct     120
ccagggaagg ggctggagtg gtctcagct attagtgtcg gtggtgacac atactacgca     180
gactccgtga agggccggtt caccatctcc agagacaatt ccaagaacac gctatatctg     240
cacgtgaaca gcctgagcgc cgaggactcg gccgtatatt actgtgcgaa agatcaggtt     300
actttggttc ggggagtttg gtactactac ggtttggacg tctggggcca agggaccacg     360
```
gtcaccgtct cctca 375

<210> SEQ ID NO 226
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 226

Glu Val Gln Leu Leu Glu Ser Gly Gly Ala Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Val Gly Gly Asp Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

His Val Asn Ser Leu Ser Ala Glu Asp Ser Ala Val Tyr Tyr Cys Ala
                85                  90                  95

Lys Asp Gln Val Thr Leu Val Arg Gly Val Trp Tyr Tyr Tyr Gly Leu
            100                 105                 110

Asp Val Trp Gly Gln Gly Thr Thr Val Thr Val Ser Ser
        115                 120                 125

<210> SEQ ID NO 227
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 227
gaggtgcagc tgttggaatc tgggggaggc ttggtacagc cggggggtc cctgagactc       60 tcctgtgcag cctctggatt tacctttagc agttatgcca tgagctgggt ccgccaggct     120
ccagggaagg gctgaagtg gtctcagct attagtggtg gtgctggtaa tacatactac      180
gcagactccg tgaagggccg gttcaccatc tccagagaca tttccaagag cacggtgtat     240
ctgcaaatga ccagcctgag agccgaggac acggccatat attactgtgc gaaagacgga     300
gtgggaacta ctgggggata cttctactac cacggtatgg acgtctgggg ccaagggacc     360
acggtcaccg tctcctca                                                    378

<210> SEQ ID NO 228
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 228

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Lys Trp Val
            35                  40                  45

Ser Ala Ile Ser Gly Gly Ala Gly Asn Thr Tyr Tyr Ala Asp Ser Val
 50                  55                  60

Lys Gly Arg Phe Thr Ile Ser Arg Asp Ile Ser Lys Ser Thr Val Tyr
 65                  70                  75                  80

Leu Gln Met Thr Ser Leu Arg Ala Glu Asp Thr Ala Ile Tyr Tyr Cys
                85                  90                  95

Ala Lys Asp Gly Val Gly Thr Thr Gly Gly Tyr Phe Tyr Tyr His Gly
               100                 105                 110

Met Asp Val Trp Gly Gln Gly Thr Thr Val Thr Val Ser Ser
           115                 120                 125

<210> SEQ ID NO 229
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 229
gaggtgcagc tgttggaatc tgggggaggc ttggtacagc cggggggtc cctgagactc      60 tcctgtgcag cctctggatt tacctttagc agttatgcca tgagctgggt ccgccaggct    120
ccagggaagg ggctgaagtg ggtctcagct attagtggtg gtgctggtaa catatactac    180
gcagactccg tgaagggccg gttcaccatc tccagagaca tttccaagag cacggtgtat    240
ctgcaaatga ccagcctgag agccgaggac acggccatat attactgtgc gaaagacgga    300
gtgggaacta ctgggggata cttctactac cacggtatgg acgtctgggg ccaagggacc    360
acggtcaccg tctcctca                                                  378

<210> SEQ ID NO 230
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Lys Trp Val
            35                  40                  45

Ser Ala Ile Ser Gly Gly Ala Gly Asn Thr Tyr Tyr Ala Asp Ser Val
 50                  55                  60

Lys Gly Arg Phe Thr Ile Ser Arg Asp Ile Ser Lys Ser Thr Val Tyr
 65                  70                  75                  80

Leu Gln Met Thr Ser Leu Arg Ala Glu Asp Thr Ala Ile Tyr Tyr Cys
                85                  90                  95

Ala Lys Asp Gly Val Gly Thr Thr Gly Gly Tyr Phe Tyr Tyr His Gly
               100                 105                 110

Met Asp Val Trp Gly Gln Gly Thr Thr Val Thr Val Ser Ser
           115                 120                 125

<210> SEQ ID NO 231
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 231
caggtacagc tgcagcagtc aggtccagga ctggtgaagc cctcgcagac cctctcactc      60
acctgtgcca tctccgggga cagtgtctct agcaccaatg ttgcttggaa ctggatcaga     120
cagtccccat cgagaggcct tgagtggctg gagggacat tctacaggtc caactggtat      180
aatgattatg caatctctgt gaaaagtcga attaccatca acccagacac atccaagaat     240
cagttctccc tgcagctgaa ctctgtgact cccgaggaca cggctgtgta ttactgtgca     300 agatttata gctggaactc ctactttgac tactggggcc aggaatcct ggtcaccgtc       360 tcctca                                                                 366

<210> SEQ ID NO 232
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 232

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Thr
            20                  25                  30

Asn Val Ala Trp Asn Trp Ile Arg Gln Ser Pro Ser Arg Gly Leu Glu
        35                  40                  45

Trp Leu Gly Gly Thr Phe Tyr Arg Ser Asn Trp Tyr Asn Asp Tyr Ala
    50                  55                  60

Ile Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Phe Tyr Ser Trp Asn Ser Tyr Phe Asp Tyr Trp
            100                 105                 110

Gly Gln Gly Ile Leu Val Thr Val Ser Ser
        115                 120

<210> SEQ ID NO 233
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 233
gaggtgcagc tgttggagtc tgggggagcc ttggtacagc ctgggggtc cctgagactc       60 tcctgtgcag cctctggatt cacctttagc agctatgcca tgaactgggt ccgccaggct     120
ccagggaagg gctggagtg gtctcagct attagtgttg gtggtggcac atactacgca       180
gactccgtga agggccggtt caccatctcc agagacaatt ccaagaacac gctatatctg     240
cacgtgaaca gcctgagagc cgaggacacg gccgtatatt attgtgcgaa agatcaggtt     300

```
actatggttc ggggagtttg gtactactac ggtttggacg tctggggcca agggaccacg    360
gtcaccgtct cctca                                                    375
```

<210> SEQ ID NO 234
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 234

```
Glu Val Gln Leu Leu Glu Ser Gly Gly Ala Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Val Gly Gly Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

His Val Asn Ser Leu Arg Ala Glu Asp Thr Ala Val Tyr Tyr Cys Ala
                85                  90                  95

Lys Asp Gln Val Thr Met Val Arg Gly Val Trp Tyr Tyr Gly Leu
            100                 105                 110

Asp Val Trp Gly Gln Gly Thr Thr Val Thr Val Ser Ser
        115                 120                 125
```

<210> SEQ ID NO 235
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 235

```
gaggtgcagc tgttggagtc tgggggagcc ttggtacagc ctggggggtc cctgagactc    60
tcctgtgcag cctctggatt cacctttagc aactatgcca tgaactgggt ccgccaggct    120
ccagggaagg ggctggagtg ggtctcagct attagtgtcg gtggtgacac atactacgca    180
gactccgtga agggccggtt caccatctcc agagacaatt ccaagaacac gctatatctg    240
cacgtgaaca gcctgagcgc cgaggactcg gccgtatatt actgtgcgaa agatcaggtt    300
actttggttc ggggagtttg gtactactac ggtttggacg tctggggcca agggaccacg    360
gtcaccgtct cctca                                                    375
```

<210> SEQ ID NO 236
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 236

```
Glu Val Gln Leu Leu Glu Ser Gly Gly Ala Leu Val Gln Pro Gly Gly
1               5                   10                  15
```

Ser Leu Arg Leu Ser Cys Ala Ala Ser Gly Phe Thr Phe Ser Asn Tyr
            20                  25                  30

Ala Met Asn Trp Val Arg Gln Ala Pro Gly Lys Gly Leu Glu Trp Val
            35                  40                  45

Ser Ala Ile Ser Val Gly Gly Asp Thr Tyr Tyr Ala Asp Ser Val Lys
        50                  55                  60

Gly Arg Phe Thr Ile Ser Arg Asp Asn Ser Lys Asn Thr Leu Tyr Leu
65                  70                  75                  80

His Val Asn Ser Leu Ser Ala Glu Asp Ser Ala Val Tyr Tyr Cys Ala
                85                  90                  95

Lys Asp Gln Val Thr Leu Val Arg Gly Val Trp Tyr Tyr Tyr Gly Leu
            100                 105                 110

Asp Val Trp Gly Gln Gly Thr Thr Val Thr Val Ser Ser
            115                 120             125

<210> SEQ ID NO 237
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 237
gaggtgcagc tgttggagtc tgggggagcc ttggtacagc ctggggggtc cctgagactc    60
tcctgtgcag cctctggatt caccttagc agctatgcca tgaactgggt ccgccaggct   120
ccagggaagg ggctggagtg gtctcagct attagtgttg gtggtgacac atactacgca   180
gactccgtga agggccggtt caccatctcc agagacaatt ccaagaacac gctgtatctg   240
caaatgaaca gcctgagagc cgaggacacg gccgtatatt actgtgcgaa agatcaggtt   300
actatggttc ggggagtttg gtactactac ggtttggacg tctggggcca aggaccacg   360 gtcaccgtct cctca                                                    375

<210> SEQ ID NO 238
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 238

Glu Val Gln Leu Leu Glu Ser Gly Gly Ala Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
            35                  40                  45

Ser Ala Ile Ser Val Gly Gly Asp Thr Tyr Tyr Ala Asp Ser Val Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Asp Gln Val Thr Met Val Arg Gly Val Trp Tyr Tyr Tyr Gly Leu
            100                 105                 110

Asp Val Trp Gly Gln Gly Thr Thr Val Thr Val Ser Ser

<210> SEQ ID NO 239
<211> LENGTH: 333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 239

```
cagtctgtgc tgactcagcc accctcagcg tctgggaccc ccggacagag ggtcaccatc    60
tcttgttctg ggagcagctc aacatcgga agtaatactg taaactggta ccagcagctc   120
ccaggaacgg cccccaaact cctcatcttt aattatcatc agcggccctc agggtccct   180
gaccgattct ctggctccaa gtctggctcc tcagcctccc tggccatcag tgggctccag   240
tctgaggatg aggctgatta ttactgtgca gcatgggatg acagcctgaa tggttgggtg   300
ttcggcggag ggaccaaact gaccgtccta ggc                               333
```

<210> SEQ ID NO 240
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 240

```
Gln Ser Val Leu Thr Gln Pro Pro Ser Ala Ser Gly Thr Pro Gly Gln
  1               5                  10                  15
Arg Val Thr Ile Ser Cys Ser Gly Ser Ser Ser Asn Ile Gly Ser Asn
             20                  25                  30
Thr Val Asn Trp Tyr Gln Gln Leu Pro Gly Thr Ala Pro Lys Leu Leu
         35                  40                  45
Ile Phe Asn Tyr His Gln Arg Pro Ser Gly Val Pro Asp Arg Phe Ser
     50                  55                  60
Gly Ser Lys Ser Gly Ser Ser Ala Ser Leu Ala Ile Ser Gly Leu Gln
 65                  70                  75                  80
Ser Glu Asp Glu Ala Asp Tyr Tyr Cys Ala Ala Trp Asp Asp Ser Leu
                 85                  90                  95
Asn Gly Trp Val Phe Gly Gly Gly Thr Lys Leu Thr Val Leu Gly
            100                 105                 110
```

<210> SEQ ID NO 241
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 241

```
gatattgtga tgactcagtc tccactctcc ctgcccgtca cccctggaga gccggcctcc    60
atctcctgca ggtctagtca gagcctcctg cacagtaatg aaacaactta tttggattgg   120
tacctgcaga agccagggca gtctccacat ctcctgatct ctttgggctc tcagcggacc   180
tccgggggtcc ctgacaggtt cagtggcagt ggatcaggca cagatttac actgaaaatc   240
agcagagtgg aggctgagga tgttggggtt tattactgca tgcaagctct acagcctcct   300
cggaggttcg gccaagggac caagttggaa atcaaacga                          339
```

<210> SEQ ID NO 242
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 242

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Asn Asn Tyr Leu Asp Trp Tyr Leu Gln Lys Pro Gly Gln Ser
        35                  40                  45

Pro His Leu Leu Ile Ser Leu Gly Ser Gln Arg Thr Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Pro Pro Arg Arg Phe Gly Gln Gly Thr Lys Leu Glu Ile Lys
            100                 105                 110

Arg

<210> SEQ ID NO 243
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 243
gatattgtgc tgactcagtc tccactctcc ctgcccgtca cccctggaga gccggcctcc      60
atctcctgca ggtctagtca gagcctcctg cacagtaatg gaaacaacta tttggattgg     120
tacctgcaga agccagggca gtctccacat ctcctgatct ctttgggctc tcagcggacc     180
tccggggtcc ctgacaggtt cagtggcagt ggatcaggca cagattttac actgaaaatc     240
agcagagtgg aggctgagga tgttggggtt tattactgca tgcaagctct acagcctcct     300
cggaggttcg gccaagggac caagttggaa atcaaacga                            339

<210> SEQ ID NO 244
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 244

Asp Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Asn Asn Tyr Leu Asp Trp Tyr Leu Gln Lys Pro Gly Gln Ser
        35                  40                  45

Pro His Leu Leu Ile Ser Leu Gly Ser Gln Arg Thr Ser Gly Val Pro

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Pro Pro Arg Arg Phe Gly Gln Gly Thr Lys Leu Glu Ile Lys
            100                 105                 110

Arg

<210> SEQ ID NO 245
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 245
cagcctgtgc tgactcagcc accttctgca tcagcctccc tgggagcctc ggtcaccctc    60
acctgttccc tgagcagcgg ctacagtaat tataaagtgg actggtacca gcagagacca   120
gggaagggcc cccggtttgt gatgcgagtg ggcattggtg ggattgtggg gtccaagggg   180
gatggcatcc tgatcgcttc tcagtcttgg gctcaggcc tgaatcggta cctgaccatc    240
aagaacatcc aggaagagga tgagagtgac ttccactgtg gggcagacca tggcagtggg   300
aacaacttcg tgtatgtctt cggaactggg accaaggtca ccgtcctagg t            351

<210> SEQ ID NO 246
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 246

Gln Pro Val Leu Thr Gln Pro Pro Ser Ala Ser Ala Ser Leu Gly Ala
1               5                   10                  15

Ser Val Thr Leu Thr Cys Ser Leu Ser Ser Gly Tyr Ser Asn Tyr Lys
                20                  25                  30

Val Asp Trp Tyr Gln Gln Arg Pro Gly Lys Gly Pro Arg Phe Val Met
            35                  40                  45

Arg Val Gly Ile Gly Gly Ile Val Gly Ser Lys Gly Asp Gly Ile Pro
        50                  55                  60

Asp Arg Phe Ser Val Leu Gly Ser Gly Leu Asn Arg Tyr Leu Thr Ile
65                  70                  75                  80

Lys Asn Ile Gln Glu Glu Asp Glu Ser Asp Phe His Cys Gly Ala Asp
                85                  90                  95

His Gly Ser Gly Asn Asn Phe Val Tyr Val Phe Gly Thr Gly Thr Lys
            100                 105                 110

Val Thr Val Leu Gly
        115

<210> SEQ ID NO 247
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 247

```
cagtctgtgc tgactcagcc accctcagcg tctgggaccc ccggacagag ggtcaccatc    60
tcttgttctg ggagcagctc aacatcgga agtaatactg taaactggta ccagcagctc   120
ccaggaacgg cccccaaact cctcatcttt aattatcatc agcggccctc aggggtccct   180
gaccgattct ctggctccaa gtctggctcc tcagcctccc tggccatcag tgggctccag   240
tctgaggatg aggctgatta ttactgtgca gcatgggatg acagcctgaa tggttgggtg   300
ttcggcggag ggaccgaact gaccgtccta ggt                                333
```

<210> SEQ ID NO 248
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 248

```
Gln Ser Val Leu Thr Gln Pro Pro Ser Ala Ser Gly Thr Pro Gly Gln
1               5                   10                  15
Arg Val Thr Ile Ser Cys Ser Gly Ser Ser Ser Asn Ile Gly Ser Asn
            20                  25                  30
Thr Val Asn Trp Tyr Gln Gln Leu Pro Gly Thr Ala Pro Lys Leu Leu
        35                  40                  45
Ile Phe Asn Tyr His Gln Arg Pro Ser Gly Val Pro Asp Arg Phe Ser
    50                  55                  60
Gly Ser Lys Ser Gly Ser Ser Ala Ser Leu Ala Ile Ser Gly Leu Gln
65                  70                  75                  80
Ser Glu Asp Glu Ala Asp Tyr Tyr Cys Ala Ala Trp Asp Asp Ser Leu
                85                  90                  95
Asn Gly Trp Val Phe Gly Gly Gly Thr Glu Leu Thr Val Leu Gly
            100                 105                 110
```

<210> SEQ ID NO 249
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 249

```
gacatccaga tgacccagtc tccatcctcc ctgtctgcat ctgtaggaga cagagtcacc    60
atcacttgcc gggcaagtca gggcattaga aatgatttag ctggtatcag cagaaaacca   120
gggaaagccc ctaagcgcct gatctatgct gcatccagtt tgcaaagtgg ggtcccatca   180
aggttcagcg gcagtggatc tggaacagaa ttcactctca caatcagcag cctgcagcct   240
gaagattttg caacttatta ctgtctacag tattatagtt acccgctcac tttcggcgga   300
gggaccaagg tggagatcaa acga                                          324
```

<210> SEQ ID NO 250
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 250

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Tyr Ser Tyr Pro Leu
                85                  90                  95

Thr Phe Gly Gly Gly Thr Lys Val Glu Ile Lys Arg
            100                 105

<210> SEQ ID NO 251
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 251

```
gacatccaga tgacccagtc tccatcctcc ctgtctgcat ctgtaggaga cagagtcacc    60
atcacttgcc gggcaagtca gagcattagc aacttttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagta ttcccacttt cggcggaggg   300
accaaggtgg agatcaaacg a                                             321
```

<210> SEQ ID NO 252
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 252

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Phe
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ile Pro Thr
                85                  90                  95

Phe Gly Gly Gly Thr Lys Val Glu Ile Lys Arg
            100                 105

```
<210> SEQ ID NO 253
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 253
gatattgtga tgattcagtc tccactctcc ctgcccgtca cccctggaga gccggcctcc      60
atctcctgca ggtctagtca gagcctcctg cacagtaatg gaaacaacta tttggattgg    120
tacctgcaga agccagggca gtctccacat ctcctgatct ctttgggctc taatcggacc    180
tccggggtcc ctgacaggtt cagtggcagt ggatcaggca cagatttac actgaaaatc     240 agcagagtgg aggctgagga tgttggggtt tattactgca tgcaagctct acagcctcct    300
cggaggttcg gccaagggac caagttggaa atcaaacga                           339

<210> SEQ ID NO 254
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 254

Asp Ile Val Met Ile Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Asn Asn Tyr Leu Asp Trp Tyr Leu Gln Lys Pro Gly Gln Ser
        35                  40                  45

Pro His Leu Leu Ile Ser Leu Gly Ser Asn Arg Thr Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Pro Pro Arg Arg Phe Gly Gln Gly Thr Lys Leu Glu Ile Lys
            100                 105                 110

Arg

<210> SEQ ID NO 255
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 255
gatattgtga tgactcagtc tccactctcc ctgcccgtca cccctggaga gccggcctcc      60
atctcctgca ggtctagtca gagcctccta catagtaatg gatacaagta tttggattgg    120
tacctgcaga agccagggca gtctccacag ctcctgatct atttgggttc taatcgggcc    180
tccggggtcc ctgacaggtt cagtggcagt ggatcaggca cagatttac actgaaaatc     240 agcagagtgg aggctgagga tgttggggtt tattactgca tgcaagctct acaacctcct    300
cggacgttcg gccaagggac caaggtggaa atcaaacga                           339
```

<210> SEQ ID NO 256
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 256

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Lys Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Pro Pro Arg Thr Phe Gly Gln Gly Thr Lys Val Glu Ile Lys
            100                 105                 110

Arg
```

<210> SEQ ID NO 257
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 257

```
gttattgtgc tgattcagtc tccactctcc ctgcccgtca cccctggaga gccggcctcc      60
atctcctgca ggtctagtca gagcctcctg cacagtaatg gaaacaacta tttggattgg     120
tacctgcaga agccagggca gtctccacat ctcctgatct ctttgggctc taatcggacc     180 tccgggggtcc ctgacaggtt cagtggcagt ggatcaggca cagattttac actgaaaatc    240
agcagagtgg aggctgagga tgttgggttt tattactgca tgcaagctct acagcctcct    300
cggaggttcg gccaagggac caagttggaa atcaaacga                            339
```

<210> SEQ ID NO 258
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 258

```
Val Ile Val Leu Ile Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Asn Asn Tyr Leu Asp Trp Tyr Leu Gln Lys Pro Gly Gln Ser
        35                  40                  45

Pro His Leu Leu Ile Ser Leu Gly Ser Asn Arg Thr Ser Gly Val Pro
    50                  55                  60
```

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Phe Tyr Tyr Cys Met Gln Ala
                 85                  90                  95

Leu Gln Pro Pro Arg Arg Phe Gly Gln Gly Thr Lys Leu Glu Ile Lys
            100                 105                 110

Arg
```

<210> SEQ ID NO 259
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 259

```
gttattgtgc tgattcagtc tccactctcc ctgcccgtca cccctggaga gccggcctcc       60
atctcctgca ggtctagtca gagcctcctg cacagtaatg aaacaactta tttggattgg     120
tacctgcaga agccagggca gtctccacat ctcctgatct ctttgggctc taatcggacc     180 tccgggggtcc ctgacaggtt cagtggcagt ggatcaggca cagattttac actgaaaatc     240
agcagagtgg aggctgagga tgttgggttt tattactgca tgcaagctct acagcctcct     300
cggaggttcg gccaagggac caagttggaa atcaaacga                             339
```

<210> SEQ ID NO 260
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 260

```
Val Ile Val Leu Ile Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
                 20                  25                  30

Asn Gly Asn Asn Tyr Leu Asp Trp Tyr Leu Gln Lys Pro Gly Gln Ser
             35                  40                  45

Pro His Leu Leu Ile Ser Leu Gly Ser Asn Arg Thr Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Phe Tyr Tyr Cys Met Gln Ala
                 85                  90                  95

Leu Gln Pro Pro Arg Arg Phe Gly Gln Gly Thr Lys Leu Glu Ile Lys
            100                 105                 110

Arg
```

<210> SEQ ID NO 261
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 261
gatattgtga tgactcagtc tccactctcc ctgcccgtca cccctggaga gccggcctcc 60
atctcctgca gatctagtca gagcctcctg catagtaatg gatacaacta tttggattgg 120
tacctgcaga agccagggca gtctccacag ctcctgatct atttgacttc taatcgggcc 180
tccggggtcc ctgacaggtt cagtggcagt ggatcaggca cagatttttc actgaagatc 240
agcagagtgg aggctgagga tgttggggtt tattactgca tgcaagccct acaaattcct 300
cggacgttcg gccaagggac caaggtggaa atcaaacga 339

<210> SEQ ID NO 262
<211> LENGTH: 113
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 262

Asp Ile Val Met Thr Gln Ser Pro Leu Ser Leu Pro Val Thr Pro Gly
1 5 10 15

Glu Pro Ala Ser Ile Ser Cys Arg Ser Ser Gln Ser Leu Leu His Ser
20 25 30

Asn Gly Tyr Asn Tyr Leu Asp Trp Tyr Leu Gln Lys Pro Gly Gln Ser
35 40 45

Pro Gln Leu Leu Ile Tyr Leu Thr Ser Asn Arg Ala Ser Gly Val Pro
50 55 60

Asp Arg Phe Ser Gly Ser Gly Ser Gly Thr Asp Phe Ser Leu Lys Ile
65 70 75 80

Ser Arg Val Glu Ala Glu Asp Val Gly Val Tyr Tyr Cys Met Gln Ala
85 90 95

Leu Gln Ile Pro Arg Thr Phe Gly Gln Gly Thr Lys Val Glu Ile Lys
100 105 110

Arg

<210> SEQ ID NO 263
<211> LENGTH: 339
<212> TYPE: DNA
<213> ORGANISM: Artificial Sequence
<220> FEATURE:
<223> OTHER INFORMATION: Description of Artificial Sequence: Synthetic
polynucleotide
<400> SEQUENCE: 263
gttattgtgc tgattcagtc tccactctcc ctgcccgtca cccctggaga gccggcctcc 60
atctcctgca ggtctagtca gagcctcctg cacagtaatg gaaacaacta tttggattgg 120
tacctgcaga agccagggca gtctccacat ctcctgatct ctttgggctc taatcggacc 180
tccggggtcc ctgacaggtt cagtggcagt ggatcaggca cagattttac actgaaaatc 240
agcagagtgg aggctgagga tgttgggttt tattactgca tgcaagctct acagcctcct 300
cggaggttcg gccaagggac caagttggaa atcaaacga 339

<210> SEQ ID NO 264
<211> LENGTH: 113
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 264

Val Ile Val Leu Ile Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Asn Asn Tyr Leu Asp Trp Tyr Leu Gln Lys Pro Gly Gln Ser
        35                  40                  45

Pro His Leu Leu Ile Ser Leu Gly Ser Asn Arg Thr Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Phe Tyr Tyr Cys Met Gln Ala
                85                  90                  95

Leu Gln Pro Pro Arg Arg Phe Gly Gln Gly Thr Lys Leu Glu Ile Lys
            100                 105                 110

Arg

<210> SEQ ID NO 265
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 265
cagcctgtgc tgactcagcc accttctgca tcagcctccc tgggagcctc ggtcacactc      60
acctgcaccc tgagcagcgg ctacagtaat tataaagtgg actggtacca gcacagacca     120
gggaagggcc cccggtttgt gatgcgagtg ggcactggtg ggattgtggg atccaagggg     180
gatggcatcc ctgatcgctt ctcagtcttg gctcaggcc tgaatcggta cctgaccatc      240
aagaacatcc aagaagagga tgagagtgac ttccactgtg gggcagacca tggcagtgag     300
accaacttcg tgtatgtctt cggaactggg accaaggtca ccgtcctagg t              351

<210> SEQ ID NO 266
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 266

Gln Pro Val Leu Thr Gln Pro Pro Ser Ala Ser Ala Ser Leu Gly Ala
1               5                   10                  15

Ser Val Thr Leu Thr Cys Thr Leu Ser Ser Gly Tyr Ser Asn Tyr Lys
            20                  25                  30

Val Asp Trp Tyr Gln His Arg Pro Gly Lys Gly Pro Arg Phe Val Met
        35                  40                  45

Arg Val Gly Thr Gly Gly Ile Val Gly Ser Lys Gly Asp Gly Ile Pro
    50                  55                  60

Asp Arg Phe Ser Val Leu Gly Ser Gly Leu Asn Arg Tyr Leu Thr Ile
65                  70                  75                  80

Lys Asn Ile Gln Glu Glu Asp Glu Ser Asp Phe His Cys Gly Ala Asp
                85                  90                  95

His Gly Ser Glu Thr Asn Phe Val Tyr Val Phe Gly Thr Gly Thr Lys
            100                 105                 110

<210> SEQ ID NO 267
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 267

```
gttattgtgc tgattcagtc tccactctcc ctgcccgtca cccctggaga gccggcctcc      60
atctcctgca ggtctagtca gagcctcctg cacagtaatg gaaacaacta tttggattgg     120
tacctgcaga agccagggca gtctccacat ctcctgatct ctttgggctc taatcggacc     180
tccggggtcc ctgacaggtt cagtggcagt ggatcaggca cagattttac actgaaaatc     240
agcagagtgg aggctgagga tgttggggttt tattactgca tgcaagctct acagcctcct     300
cggaggttcg gccaagggac caagttggaa atcaaacga                             339
```

<210> SEQ ID NO 268
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 268

```
Val Ile Val Leu Ile Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Asn Asn Tyr Leu Asp Trp Tyr Leu Gln Lys Pro Gly Gln Ser
        35                  40                  45

Pro His Leu Leu Ile Ser Leu Gly Ser Asn Arg Thr Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Phe Tyr Tyr Cys Met Gln Ala
                85                  90                  95

Leu Gln Pro Pro Arg Arg Phe Gly Gln Gly Thr Lys Leu Glu Ile Lys
            100                 105                 110

Arg
```

<210> SEQ ID NO 269
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 269

```
gttattgtgc tgattcagtc tccactctcc ctgcccgtca cccctggaga gccggcctcc      60
atctcctgca ggtctagtca gagcctcctg cacagtaatg gaaacaacta tttggattgg     120
tacctgcaga agccagggca gtctccacat ctcctgatct ctttgggctc taatcggacc     180
tccggggtcc ctgacaggtt cagtggcagt ggatcaggca cagattttac actgaaaatc     240
```

Val Thr Val Leu Gly
    115

```
agcagagtgg aggctgagga tgttgggttt tattactgca tgcaagctct acagcctcct    300
cggaggttcg gccaagggac caagttggaa atcaaacga                           339
```

<210> SEQ ID NO 270
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 270

```
Val Ile Val Leu Ile Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Asn Asn Tyr Leu Asp Trp Tyr Leu Gln Lys Pro Gly Gln Ser
        35                  40                  45

Pro His Leu Leu Ile Ser Leu Gly Ser Asn Arg Thr Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Phe Tyr Tyr Cys Met Gln Ala
                85                  90                  95

Leu Gln Pro Pro Arg Arg Phe Gly Gln Gly Thr Lys Leu Glu Ile Lys
            100                 105                 110

Arg
```

<210> SEQ ID NO 271
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 271

```
gatattgtga tgattcagtc tccactctcc ctgcccgtca cccctggaga gccggcctcc    60
atctcctgca ggtctagtca gagcctcctg cacagtaatg gaaacaactt tttggattgg   120
tacctgcaga agccagggca gtctccacat ctcctgatct ctttgggctc taatcggacc   180
tccggggtcc ctgacaggct cagtggcagt ggatcaggca cagattttac actgaaaatc   240
agcagagtgg aggctgagga tgttgggatt tattactgca tgcaagctct acggcctcct   300
cggaggttcg gccaagggac caagttggaa atcaaacga                          339
```

<210> SEQ ID NO 272
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 272

```
Asp Ile Val Met Ile Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30
```

Asn Gly Asn Asn Phe Leu Asp Trp Tyr Leu Gln Lys Pro Gly Gln Ser
        35                  40                  45

Pro His Leu Leu Ile Ser Leu Gly Ser Asn Arg Thr Ser Gly Val Pro
 50                  55                  60

Asp Arg Leu Ser Gly Ser Gly Ser Gly Thr Asp Phe Thr Leu Lys Ile
 65                  70                  75                  80

Ser Arg Val Glu Ala Glu Asp Val Gly Ile Tyr Tyr Cys Met Gln Ala
                 85                  90                  95

Leu Arg Pro Pro Arg Arg Phe Gly Gln Gly Thr Lys Leu Glu Ile Lys
            100                 105                 110

Arg

<210> SEQ ID NO 273
<211> LENGTH: 1359
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 273
gaggtgcagc tggtggagtc tgggggaggc ttggtaaagc caggggggtc cctgagactc      60
tcctgtgcag cttctggatt cacctttgga gattatgctc tgagctggtt ccgccaggct     120
ccagggaagg gctggagtg gtaggtgtc agtagaagca agcttatgg tgggacaaca        180 gattacgccg cgtctgtgaa aggcagattc accatctcaa gagatgattc aaaagcacc     240 gcctatctgc aaatgaacag cctgaaaacc gaggacacag ccgtgtatta ctgtgctagt     300
agcgggtata gcagtggctg gaccccgttt gactactggg gccagggaac cctggtcacc    360
gtctcctcag ctagcaccaa gggcccatcc gtcttccccc tggcaccctc ctccaagagc    420
acctctgggg gcacagcggc cctgggctgc ctggtcaagg actacttccc cgaaccggtg    480
acggtgtcgt ggaactcagg cgccctgacc agcggcgtgc acaccttccc ggctgtccta    540
cagtcctcag gactctactc cctcagcagc gtggtgaccg tgccctccag cagcttgggc    600
acccagacct acatctgcaa cgtgaatcac aagcccagca acaccaaggt ggacaagaaa    660
gttgagccca aatcttgtga caaaactcac acatgcccac cgtgcccagc acctgaactc    720
ctggggggac cgtcagtctt cctcttcccc ccaaaaccca aggacaccct catgatctcc    780
cggacccctg aggtcacatg cgtggtggtg gacgtgagcc acgaagaccc tgaggtcaag    840
ttcaactggt acgtggacgg cgtggaggtg cataatgcca agacaaagcc gcgggaggag    900
cagtacaaca gcacgtaccg tgtggtcagc gtcctcaccg tcctgcacca ggactggctg    960
aatggcaagg agtacaagtg caaggtctcc aacaaagccc tcccagcccc catcgagaaa   1020
accatctcca aagccaaagg gcagccccga gaaccacagg tgtacaccct gcccccatcc   1080
cgggaggaga tgaccaagaa ccaggtcagc ctgacctgcc tggtcaaagg cttctatccc   1140
agcgacatcg ccgtggagtg ggagagcaat gggcagccgg agaacaacta caagaccacg   1200
cctcccgtgc tggactccga cggctccttc ttcctctata gcaagctcac cgtggacaag   1260
agcaggtggc agcaggggaa cgtcttctca tgctccgtga tgcatgaggc tctgcacaac   1320
cactacacgc agaagagcct ctccctgtct ccgggtaaa                          1359

<210> SEQ ID NO 274
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 274

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Gly Asp Tyr
            20                  25                  30

Ala Leu Ser Trp Phe Arg Gln Ala Pro Gly Lys Gly Leu Glu Trp Val
        35                  40                  45

Gly Val Ser Arg Ser Lys Ala Tyr Gly Gly Thr Thr Asp Tyr Ala Ala
    50                  55                  60

Ser Val Lys Gly Arg Phe Thr Ile Ser Arg Asp Asp Ser Lys Ser Thr
65                  70                  75                  80

Ala Tyr Leu Gln Met Asn Ser Leu Lys Thr Glu Asp Thr Ala Val Tyr
                85                  90                  95

Tyr Cys Ala Ser Ser Gly Tyr Ser Ser Gly Trp Thr Pro Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
```

```
                 385             390             395             400
        Pro Pro Val Leu Asp Ser Asp Gly Ser Phe Phe Leu Tyr Ser Lys Leu
                        405                 410                 415

Thr Val Asp Lys Ser Arg Trp Gln Gln Gly Asn Val Phe Ser Cys Ser
                        420                 425                 430

Val Met His Glu Ala Leu His Asn His Tyr Thr Gln Lys Ser Leu Ser
                        435                 440                 445

Leu Ser Pro Gly Lys
                450
```

<210> SEQ ID NO 275
<211> LENGTH: 1365
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 275

| | | |
|---|---|---|
| gaggtgcagc tgttggagtc tggaggaggc ttggtacagc ctggggggtc cctgagactc | 60 |
| tcctgtgcag cctctggatt cacctttagc agctatgcca tgaactgggt ccgccaggct | 120 |
| ccagggaagg gctggagtg gtctcagct attagtgttg gtggtgacac atactacgca | 180 |
| gactccgtga aggccggtt caccatctcc agagacaatt ccaagaacac gctgtatctg | 240 |
| caaatgaaca gcctgagagc cgaggacacg gccgtatatt actgtgcgaa agatcaggtt | 300 |
| actatggttc ggggagtttg gtactactac ggtttggacg tctggggcca agggaccacg | 360 |
| gtcaccgtct cctcagctag caccaagggc ccatccgtct tccccctggc accctcctcc | 420 |
| aagagcacct ctgggggcac agcggccctg ggctgcctgg tcaaggacta cttccccgaa | 480 |
| ccggtgacgg tgtcgtggaa ctcaggcgcc ctgaccagcg gcgtgcacac cttcccggct | 540 |
| gtcctacagt cctcaggact ctactccctc agcagcgtgg tgaccgtgcc ctccagcagc | 600 |
| ttgggcaccc agacctacat ctgcaacgtg aatcacaagc ccagcaacac caaggtggac | 660 |
| aagaaagttg agcccaaatc ttgtgacaaa actcacacat gcccaccgtg cccagcacct | 720 |
| gaactcctgg ggggaccgtc agtcttcctc ttccccccaa aacccaagga caccctcatg | 780 |
| atctcccgga cccctgaggt cacatgcgtg gtggtggacg tgagccacga agaccctgag | 840 |
| gtcaagttca actggtacgt ggacggcgtg gaggtgcata atgccaagac aaagccgcgg | 900 |
| gaggagcagt acaacagcac gtaccgtgtg gtcagcgtcc tcaccgtcct gcaccaggac | 960 |
| tggctgaatg gcaaggagta caagtgcaag gtctccaaca aagccctccc agcccccatc | 1020 |
| gagaaaacca tctccaaagc caaagggcag ccccgagaac acaggtgta cacccgtgccc | 1080 |
| ccatcccggg aggagatgac caagaaccag gtcagcctga cctgcctggt caaaggcttc | 1140 |
| tatcccagcg acatcgccgt ggagtgggag agcaatgggc agccggagaa caactacaag | 1200 |
| accacgcctc ccgtgctgga ctccgacggc tccttcttcc tctatagcaa gctcaccgtg | 1260 |
| gacaagagca ggtggcagca ggggaacgtc ttctcatgct ccgtgatgca tgaggctctg | 1320 |
| cacaaccact acacgcagaa gagcctctcc ctgtctccgg gtaaa | 1365 |

<210> SEQ ID NO 276
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 276

Glu Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Val Gly Gly Asp Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Lys Asp Gln Val Thr Met Val Arg Gly Val Trp Tyr Tyr Gly Leu
        100                 105                 110

Asp Val Trp Gly Gln Gly Thr Thr Val Thr Val Ser Ser Ala Ser Thr
    115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser 405                 410                 415
Lys Leu Thr Val Asp Lys Ser Arg Trp Gln Gln Gly Asn Val Phe Ser
        420                 425                 430

Cys Ser Val Met His Glu Ala Leu His Asn His Tyr Thr Gln Lys Ser
        435                 440                 445

Leu Ser Leu Ser Pro Gly Lys
        450                 455

<210> SEQ ID NO 277
<211> LENGTH: 1365
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 277

```
gaggtgcagc tgttggagtc tggaggaggc ttggtacagc ctgggggttc cctgagactc      60
tcctgtgcag cctctggatt cacctttagc agctatgcca tgaactgggt ccgccaggct     120
ccagggaagg ggctggagtg ggtctcagct attagtgtcg gtggtgacac atactacgca     180
gactccgtga agggccggtt caccatctcc agagacaatt ccaagaacac gctatatctg     240
caggtgaaca gcctgagagc cgaggactcg gccgtatatt actgtgcgaa agatcaggtt     300
actttggttc ggggagtttg gtactactac ggttttgacg tctggggcca agggaccacg     360
gtcaccgtct cctcagctag caccaagggc ccatccgtct tccccctggc accctcctcc     420
aagagcacct ctgggggcac agcggccctg ggctgcctgg tcaaggacta cttccccgaa     480
ccggtgacgg tgtcgtggaa ctcaggcgcc ctgaccagcg gcgtgcacac cttcccggct     540
gtcctacagt cctcaggact ctactccctc agcagcgtgg tgaccgtgcc ctccagcagc     600
ttgggcaccc agacctacat ctgcaacgtg aatcacaagc ccagcaacac caaggtggac     660
aagaaagttg agcccaaatc ttgtgacaaa actcacacat gcccaccgtg cccagcacct     720
gaactcctgg ggggaccgtc agtcttcctc ttccccccaa aacccaagga caccctcatg     780
atctcccgga cccctgaggt cacatgcgtg gtggtggacg tgagccacga agaccctgag     840
gtcaagttca actggtacgt ggacggcgtg gaggtgcata atgccaagac aaagccgcgg     900
gaggagcagt acaacagcac gtaccgtgtg gtcagcgtcc tcaccgtcct gcaccaggac     960
tggctgaatg gcaaggagta caagtgcaag gtctccaaca aagccctccc agcccccatc    1020
gagaaaacca tctccaaagc caagggcag ccccgagaac acaggtgta cacccctgccc    1080
ccatcccggg aggagatgac caagaaccag gtcagcctga cctgcctggt caaaggcttc    1140
tatcccagcg acatcgccgt ggagtgggag agcaatgggc agccggagaa caactacaag    1200
accacgcctc ccgtgctgga ctccgacggc tccttcttcc tctatagcaa gctcaccgtg    1260
gacaagagca ggtggcagca ggggaacgtc ttctcatgct ccgtgatgca tgaggctctg    1320
cacaaccact acacgcagaa gagcctctcc ctgtctccgg gtaaa               1365
```

<210> SEQ ID NO 278
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 278

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Val Gly Gly Asp Thr Tyr Tyr Ala Asp Ser Val Lys
50                  55                  60

Gly Arg Phe Thr Ile Ser Arg Asp Asn Ser Lys Asn Thr Leu Tyr Leu
65                  70                  75                  80

Gln Val Asn Ser Leu Arg Ala Glu Asp Ser Ala Val Tyr Tyr Cys Ala
            85                  90                  95

Lys Asp Gln Val Thr Leu Val Arg Gly Val Trp Tyr Tyr Tyr Gly Leu
            100                 105                 110

Asp Val Trp Gly Gln Gly Thr Thr Val Thr Val Ser Ser Ala Ser Thr
            115                 120                 125

Lys Gly Pro Ser Val Phe Pro Leu Ala Pro Ser Ser Lys Ser Thr Ser
        130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
            165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Lys Val Glu
210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
            245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
            290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
            325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
            355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
            405                 410                 415

Lys Leu Thr Val Asp Lys Ser Arg Trp Gln Gln Gly Asn Val Phe Ser
```

```
                    420                 425                 430
Cys Ser Val Met His Glu Ala Leu His Asn His Tyr Thr Gln Lys Ser
            435                 440                 445

Leu Ser Leu Ser Pro Gly Lys
        450                 455

<210> SEQ ID NO 279
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 279
cagtctgtgc tgactcagcc accctcagcg tctgggaccc ccggacagag ggtcaccatc    60
tcttgttctg ggagcagctc caacatcgga agtaatactg taaactggta ccagcagctc   120
ccaggaacgg cccccaaact cctcatcttt aattatcatc agcggccctc aggggtccct   180
gaccgattct ctggctccaa gtctggctcc tcagcctccc tggccatcag tgggctccag   240
tctgaggatg aggctgatta ttactgtgca gcatgggatg acagcctgaa tggttgggtg   300
ttcggcggag ggaccaaact gaccgtccta ggccaaccga aagcggcgcc ctcggtcact   360
ctgttcccgc cctcctctga ggagcttcaa gccaacaagg ccacactggt gtgtctcata   420
agtgacttct acccgggagc cgtgacagtg gcctggaagg cagatagcag ccccgtcaag   480
gcgggagtgg agaccaccac acctccaaaa caaagcaaca acaagtacgc ggccagcagc   540
tatctgagcc tgacgcctga gcagtggaag tcccacagaa gctacagctg ccaggtcacg   600
catgaaggga gcaccgtgga agacagtgtc cccctacag aatgttca                648

<210> SEQ ID NO 280
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 280

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Phe Asn Tyr His Gln Arg Pro Ser Gly Val Pro Asp Arg Phe Ser
    50                  55                  60

Gly Ser Lys Ser Gly Ser Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140
```

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
            165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 281
<211> LENGTH: 657
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 281
gatattgtga tgactcagtc tccactctcc ctgcccgtca cccctggaga gccggcctcc      60
atctcctgca ggtctagtca gagcctcctg cacagtaatg aaacaactta tttggattgg     120
tacctgcaga agccagggca gtctccacat ctcctgatct ctttgggctc tcagcggacc     180
tccggggtcc ctgacaggtt cagtggcagt ggatcaggca cagattttac actgaaaatc     240
agcagagtgg aggctgagga tgttgggggtt tattactgca tgcaagctct acagcctcct     300
cggaggttcg gccaagggac caagttggaa atcaaacgaa cggtggctgc accatctgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaagtcta cgcctgcgaa     600
gtcacccatc agggcctgag ctcgcccgtc acaaagagct tcaacagggg agagtgt       657

<210> SEQ ID NO 282
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 282

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Asn Asn Tyr Leu Asp Trp Tyr Leu Gln Lys Pro Gly Gln Ser
        35                  40                  45

Pro His Leu Leu Ile Ser Leu Gly Ser Gln Arg Thr Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Pro Pro Arg Arg Phe Gly Gln Gly Thr Lys Leu Glu Ile Lys
            100                 105                 110

```
Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 283
<211> LENGTH: 657
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 283

```
gatattgtgc tgactcagtc tccactctcc ctgcccgtca cccctggaga gccggcctcc      60
atctcctgca ggtctagtca gagcctcctg cacagtaatg aaacaactta tttggattgg     120
tacctgcaga agccagggca gtctccacat ctcctgatct ctttgggctc tcagcggacc     180
tccggggtcc ctgacaggtt cagtggcagt ggatcaggca cagattttac actgaaaatc     240
agcagagtgg aggctgagga tgttggggtt tattactgca tgcaagctct acagcctcct     300
cggaggttcg gccaagggac caagttggaa atcaaacgaa cggtggctgc accatctgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaagtcta cgcctgcgaa     600
gtcacccatc agggcctgag ctcgcccgtc acaaagagct tcaacagggg agagtgt        657
```

<210> SEQ ID NO 284
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 284

```
Asp Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Asn Asn Tyr Leu Asp Trp Tyr Leu Gln Lys Pro Gly Gln Ser
        35                  40                  45

Pro His Leu Leu Ile Ser Leu Gly Ser Gln Arg Thr Ser Gly Val Pro
    50                  55                  60

Asp Arg Phe Ser Gly Ser Gly Ser Gly Thr Asp Phe Thr Leu Lys Ile
```

```
                65                  70                  75                  80
        Ser Arg Val Glu Ala Glu Asp Val Gly Val Tyr Tyr Cys Met Gln Ala
                            85                  90                  95

Leu Gln Pro Pro Arg Phe Gly Gln Gly Thr Lys Leu Glu Ile Lys
                        100                 105                 110

Arg Thr Val Ala Ala Pro Ser Val Phe Ile Phe Pro Pro Ser Asp Glu
                    115                 120                 125

Gln Leu Lys Ser Gly Thr Ala Ser Val Val Cys Leu Leu Asn Asn Phe
                130                 135                 140

Tyr Pro Arg Glu Ala Lys Val Gln Trp Lys Val Asp Asn Ala Leu Gln
        145                 150                 155                 160

Ser Gly Asn Ser Gln Glu Ser Val Thr Glu Gln Asp Ser Lys Asp Ser
                        165                 170                 175

Thr Tyr Ser Leu Ser Ser Thr Leu Thr Leu Ser Lys Ala Asp Tyr Glu
                    180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
                210                 215

<210> SEQ ID NO 285
<211> LENGTH: 184
<212> TYPE: PRT
<213> ORGANISM: Homo sapiens

<400> SEQUENCE: 285

Met Leu Gln Met Ala Gly Gln Cys Ser Gln Asn Glu Tyr Phe Asp Ser
        1               5                   10                  15

Leu Leu His Ala Cys Ile Pro Cys Gln Leu Arg Cys Ser Ser Asn Thr
                        20                  25                  30

Pro Pro Leu Thr Cys Gln Arg Tyr Cys Asn Ala Ser Val Thr Asn Ser
                    35                  40                  45

Val Lys Gly Thr Asn Ala Ile Leu Trp Thr Cys Leu Gly Leu Ser Leu
                50                  55                  60

Ile Ile Ser Leu Ala Val Phe Val Leu Met Phe Leu Leu Arg Lys Ile
        65                  70                  75                  80

Ser Ser Glu Pro Leu Lys Asp Glu Phe Lys Asn Thr Gly Ser Gly Leu
                        85                  90                  95

Leu Gly Met Ala Asn Ile Asp Leu Glu Lys Ser Arg Thr Gly Asp Glu
                    100                 105                 110

Ile Ile Leu Pro Arg Gly Leu Glu Tyr Thr Val Glu Glu Cys Thr Cys
                115                 120                 125

Glu Asp Cys Ile Lys Ser Lys Pro Lys Val Asp Ser Asp His Cys Phe
        130                 135                 140

Pro Leu Pro Ala Met Glu Glu Gly Ala Thr Ile Leu Val Thr Thr Lys
        145                 150                 155                 160

Thr Asn Asp Tyr Cys Lys Ser Leu Pro Ala Ala Leu Ser Ala Thr Glu
                        165                 170                 175

Ile Glu Lys Ser Ile Ser Ala Arg
                    180

<210> SEQ ID NO 286
<211> LENGTH: 183
<212> TYPE: PRT
<213> ORGANISM: Macaca fascicularis
```

<400> SEQUENCE: 286

Met Leu Gln Met Ala Arg Gln Cys Ser Gln Asn Glu Tyr Phe Asp Ser
1               5                   10                  15

Leu Leu His Asp Cys Lys Pro Cys Gln Leu Arg Cys Ser Ser Thr Pro
            20                  25                  30

Pro Leu Thr Cys Gln Arg Tyr Cys Asn Ala Ser Met Thr Asn Ser Val
        35                  40                  45

Lys Gly Met Asn Ala Ile Leu Trp Thr Cys Leu Gly Leu Ser Leu Ile
    50                  55                  60

Ile Ser Leu Ala Val Phe Val Leu Thr Phe Leu Leu Arg Lys Met Ser
65                  70                  75                  80

Ser Glu Pro Leu Lys Asp Glu Phe Lys Asn Thr Gly Ser Gly Leu Leu
                85                  90                  95

Gly Met Ala Asn Ile Asp Leu Glu Lys Gly Arg Thr Gly Asp Glu Ile
            100                 105                 110

Val Leu Pro Arg Gly Leu Glu Tyr Thr Val Glu Glu Cys Thr Cys Glu
        115                 120                 125

Asp Cys Ile Lys Asn Lys Pro Lys Val Asp Ser Asp His Cys Phe Pro
    130                 135                 140

Leu Pro Ala Met Glu Glu Gly Ala Thr Ile Leu Val Thr Thr Lys Thr
145                 150                 155                 160

Asn Asp Tyr Cys Asn Ser Leu Ser Ala Ala Leu Ser Val Thr Glu Ile
                165                 170                 175

Glu Lys Ser Ile Ser Ala Arg
            180

<210> SEQ ID NO 287
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 287

Glu Val Gln Leu Val Glu Ser Gly Gly Gly Leu Val Lys Pro Gly Arg
1               5                   10                  15

Ser Leu Arg Leu Ser Cys Thr Ala Ser Gly Phe Thr Phe Gly Asp Tyr
            20                  25                  30

Ala Leu Ser Trp Phe Arg Gln Ala Pro Gly Lys Gly Leu Glu Trp Val
        35                  40                  45

Gly Val Ser Arg Ser Lys Ala Tyr Gly Gly Thr Thr Asp Tyr Ala Ala
    50                  55                  60

Ser Val Lys Gly Arg Phe Thr Ile Ser Arg Asp Asp Ser Lys Ser Phe
65                  70                  75                  80

Ala Tyr Leu Gln Met Asn Ser Leu Lys Thr Glu Asp Thr Ala Val Tyr
                85                  90                  95

Tyr Cys Cys Ser Ser Gly Tyr Ser Ser Gly Trp Thr Pro Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

-continued

```
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
            180                 185                 190
Thr Val Pro Ser Ser Ser Leu Gly Thr Gln Thr Tyr Ile Cys Asn Val
        195                 200                 205
Asn His Lys Pro Ser Asn Thr Lys Val Asp Lys Lys Val Glu Pro Lys
    210                 215                 220
Ser Cys Asp Lys Thr His Thr Cys Pro Pro Cys Pro Ala Pro Glu Leu
225                 230                 235                 240
Leu Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
            260                 265                 270
Ser His Glu Asp Pro Glu Val Lys Phe Asn Trp Tyr Val Asp Gly Val
        275                 280                 285
Glu Val His Asn Ala Lys Thr Lys Pro Arg Glu Glu Gln Tyr Asn Ser
    290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
                325                 330                 335
Pro Ile Glu Lys Thr Ile Ser Lys Ala Lys Gly Gln Pro Arg Glu Pro
            340                 345                 350
Gln Val Tyr Thr Leu Pro Pro Ser Arg Glu Glu Met Thr Lys Asn Gln
        355                 360                 365
Val Ser Leu Thr Cys Leu Val Lys Gly Phe Tyr Pro Ser Asp Ile Ala
    370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
            420                 425                 430
Val Met His Glu Ala Leu His Asn His Tyr Thr Gln Lys Ser Leu Ser
        435                 440                 445
Leu Ser Pro Gly Lys
    450

<210> SEQ ID NO 288
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 288

Gln Ser Val Leu Thr Gln Pro Pro Ser Ala Ser Gly Thr Pro Gly Gln
1               5                   10                  15
Arg Val Thr Ile Ser Cys Ser Gly Ser Ser Ser Asn Ile Gly Ser Asn
            20                  25                  30
Thr Val Asn Trp Tyr Gln Gln Leu Pro Gly Thr Ala Pro Lys Leu Leu
        35                  40                  45
Ile Phe Asn Tyr His Gln Arg Pro Ser Gly Val Pro Asp Arg Phe Ser
    50                  55                  60
```

Gly Ser Lys Ser Gly Ser Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
            85                  90                  95

Asn Gly Trp Val Phe Gly Gly Gly Thr Glu Leu Thr Val Leu Gly Gln
        100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
210                 215

<210> SEQ ID NO 289
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 289

Glu Val Gln Leu Val Glu Ser Gly Gly Gly Leu Val Lys Pro Gly Arg
1               5                   10                  15

Ser Leu Arg Leu Ser Cys Thr Ala Ser Gly Phe Thr Phe Gly Asp Tyr
            20                  25                  30

Ala Leu Ser Trp Phe Arg Gln Ala Pro Gly Lys Gly Leu Glu Trp Val
        35                  40                  45

Gly Val Ser Arg Ser Lys Ala Tyr Gly Gly Thr Thr Asp Tyr Ala Ala
    50                  55                  60

Ser Val Lys Gly Arg Phe Thr Ile Ser Arg Asp Asp Ser Lys Ser Phe
65                  70                  75                  80

Ala Tyr Leu Gln Met Asn Ser Leu Lys Thr Glu Asp Thr Ala Val Tyr
            85                  90                  95

Tyr Cys Thr Ser Ser Gly Tyr Ser Ser Gly Trp Thr Pro Phe Asp Tyr
        100                 105                 110

Trp Gly Gln Gly Thr Leu Val Thr Val Ser Ser Ala Ser Thr Lys Gly
    115                 120                 125

Pro Ser Val Phe Pro Leu Ala Pro Ser Ser Lys Ser Thr Ser Gly Gly
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val

```
                195                 200                 205
Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 290
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 290

Glu Val Gln Leu Val Glu Ser Gly Gly Gly Leu Val Lys Pro Gly Gly
1               5                   10                  15

Ser Leu Arg Leu Ser Cys Thr Ala Ser Gly Phe Thr Phe Gly Asp Tyr
            20                  25                  30

Ala Leu Ser Trp Phe Arg Gln Ala Pro Gly Lys Gly Leu Glu Trp Val
        35                  40                  45

Gly Val Ser Arg Ser Lys Ala Tyr Gly Gly Thr Thr Asp Tyr Ala Ala
    50                  55                  60

Ser Val Lys Gly Arg Phe Thr Ile Ser Arg Asp Asp Ser Lys Ser Phe
65                  70                  75                  80

Ala Tyr Leu Gln Met Asn Ser Leu Lys Thr Glu Asp Thr Ala Val Tyr
                85                  90                  95
```

Tyr Cys Thr Ser Ser Gly Tyr Ser Ser Gly Trp Thr Pro Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 291
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 291

```
Glu Val Gln Leu Val Glu Ser Gly Gly Gly Leu Val Lys Pro Gly Arg
1               5                   10                  15

Ser Leu Arg Leu Ser Cys Thr Ala Ser Gly Phe Thr Phe Gly Asp Tyr
            20                  25                  30

Ala Leu Ser Trp Val Arg Gln Ala Pro Gly Lys Gly Leu Glu Trp Val
        35                  40                  45

Gly Val Ser Arg Ser Lys Ala Tyr Gly Gly Thr Thr Asp Tyr Ala Ala
    50                  55                  60

Ser Val Lys Gly Arg Phe Thr Ile Ser Arg Asp Asp Ser Lys Ser Phe
65                  70                  75                  80

Ala Tyr Leu Gln Met Asn Ser Leu Lys Thr Glu Asp Thr Ala Val Tyr
                85                  90                  95

Tyr Cys Thr Ser Ser Gly Tyr Ser Ser Gly Trp Thr Pro Phe Asp Tyr
            100                 105                 110

Trp Gly Gln Gly Thr Leu Val Thr Val Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
            180                 185                 190

Thr Val Pro Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
    275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415
```

```
Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 292
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 292

Glu Val Gln Leu Val Glu Ser Gly Gly Gly Leu Val Lys Pro Gly Arg
1               5                   10                  15

Ser Leu Arg Leu Ser Cys Thr Ala Ser Gly Phe Thr Phe Gly Asp Tyr
            20                  25                  30

Ala Leu Ser Trp Phe Arg Gln Ala Pro Gly Lys Gly Leu Glu Trp Val
        35                  40                  45

Gly Val Ser Arg Ser Lys Ala Tyr Gly Gly Thr Thr Asp Tyr Ala Ala
    50                  55                  60

Ser Val Lys Gly Arg Phe Thr Ile Ser Arg Asp Asn Ser Lys Ser Phe
65                  70                  75                  80

Ala Tyr Leu Gln Met Asn Ser Leu Lys Thr Glu Asp Thr Ala Val Tyr
            85                  90                  95

Tyr Cys Thr Ser Ser Gly Tyr Ser Ser Gly Trp Thr Pro Phe Asp Tyr
        100                 105                 110

Trp Gly Gln Gly Thr Leu Val Thr Val Ser Ser Ala Ser Thr Lys Gly
    115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
        180                 185                 190

Thr Val Pro Ser Ser Ser Leu Gly Thr Gln Thr Tyr Ile Cys Asn Val
    195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
        260                 265                 270

Ser His Glu Asp Pro Glu Val Lys Phe Asn Trp Tyr Val Asp Gly Val
    275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320
```

-continued

```
Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 293
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 293

Glu Val Gln Leu Val Glu Ser Gly Gly Gly Leu Val Lys Pro Gly Arg
1               5                   10                  15

Ser Leu Arg Leu Ser Cys Thr Ala Ser Gly Phe Thr Phe Gly Asp Tyr
            20                  25                  30

Ala Leu Ser Trp Phe Arg Gln Ala Pro Gly Lys Gly Leu Glu Trp Val
        35                  40                  45

Gly Val Ser Arg Ser Lys Ala Tyr Gly Gly Thr Thr Asp Tyr Ala Ala
    50                  55                  60

Ser Val Lys Gly Arg Phe Thr Ile Ser Arg Asp Asp Ser Lys Ser Thr
65                  70                  75                  80

Ala Tyr Leu Gln Met Asn Ser Leu Lys Thr Glu Asp Thr Ala Val Tyr
                85                  90                  95

Tyr Cys Thr Ser Ser Gly Tyr Ser Gly Trp Thr Pro Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
```

```
                210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
            435                 440                 445

Leu Ser Pro Gly Lys
    450

<210> SEQ ID NO 294
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 294

Glu Val Gln Leu Val Glu Ser Gly Gly Gly Leu Val Lys Pro Gly Arg
1               5                   10                  15

Ser Leu Arg Leu Ser Cys Thr Ala Ser Gly Phe Thr Phe Gly Asp Tyr
            20                  25                  30

Ala Leu Ser Trp Phe Arg Gln Ala Pro Gly Lys Gly Leu Glu Trp Val
        35                  40                  45

Gly Val Ser Arg Ser Lys Ala Tyr Gly Gly Thr Thr Asp Tyr Ala Ala
    50                  55                  60

Ser Val Lys Gly Arg Phe Thr Ile Ser Arg Asp Asp Ser Lys Ser Phe
65                  70                  75                  80

Ala Tyr Leu Gln Met Asn Ser Leu Lys Thr Glu Asp Thr Ala Val Tyr
                85                  90                  95

Tyr Cys Ala Ser Ser Gly Tyr Ser Gly Trp Thr Pro Phe Asp Tyr
            100                 105                 110
```

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 295
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 295

Glu Val Gln Leu Val Glu Ser Gly Gly Gly Leu Val Lys Pro Gly Arg
1               5                   10                  15

```
Ser Leu Arg Leu Ser Cys Thr Ala Ser Gly Phe Thr Phe Gly Asp Tyr
         20                  25                  30

Ala Leu Ser Trp Phe Arg Gln Ala Pro Gly Lys Gly Leu Glu Trp Val
         35                  40                  45

Gly Val Ser Arg Ser Lys Ala Tyr Gly Gly Thr Thr Asp Tyr Ala Ala
 50                  55                  60

Ser Val Lys Gly Arg Phe Thr Ile Ser Arg Asp Asp Ser Lys Ser Phe
65                   70                  75                  80

Ala Tyr Leu Gln Met Asn Ser Leu Lys Thr Glu Asp Thr Ala Val Tyr
                 85                  90                  95

Tyr Cys Thr Lys Ser Gly Tyr Ser Ser Gly Trp Thr Pro Phe Asp Tyr
             100                 105                 110

Trp Gly Gln Gly Thr Leu Val Thr Val Ser Ser Ala Ser Thr Lys Gly
         115                 120                 125

Pro Ser Val Phe Pro Leu Ala Pro Ser Ser Lys Ser Thr Ser Gly Gly
     130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                 165                 170                 175

Pro Ala Val Leu Gln Ser Ser Gly Leu Tyr Ser Leu Ser Ser Val Val
             180                 185                 190

Thr Val Pro Ser Ser Ser Leu Gly Thr Gln Thr Tyr Ile Cys Asn Val
         195                 200                 205

Asn His Lys Pro Ser Asn Thr Lys Val Asp Lys Lys Val Glu Pro Lys
     210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                 245                 250                 255

Leu Met Ile Ser Arg Thr Pro Glu Val Thr Cys Val Val Val Asp Val
             260                 265                 270

Ser His Glu Asp Pro Glu Val Lys Phe Asn Trp Tyr Val Asp Gly Val
         275                 280                 285

Glu Val His Asn Ala Lys Thr Lys Pro Arg Glu Glu Gln Tyr Asn Ser
     290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                 325                 330                 335

Pro Ile Glu Lys Thr Ile Ser Lys Ala Lys Gly Gln Pro Arg Glu Pro
             340                 345                 350

Gln Val Tyr Thr Leu Pro Pro Ser Arg Glu Glu Met Thr Lys Asn Gln
         355                 360                 365

Val Ser Leu Thr Cys Leu Val Lys Gly Phe Tyr Pro Ser Asp Ile Ala
     370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                 405                 410                 415

Thr Val Asp Lys Ser Arg Trp Gln Gln Gly Asn Val Phe Ser Cys Ser
             420                 425                 430
```

```
Val Met His Glu Ala Leu His Asn His Tyr Thr Gln Lys Ser Leu Ser
            435                 440                 445

Leu Ser Pro Gly Lys
    450
```

<210> SEQ ID NO 296
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 296

```
Glu Val Gln Leu Val Glu Ser Gly Gly Gly Leu Val Lys Pro Gly Arg
1               5                   10                  15

Ser Leu Arg Leu Ser Cys Thr Ala Ser Gly Phe Thr Phe Gly Asp Tyr
            20                  25                  30

Ala Leu Ser Trp Val Arg Gln Ala Pro Gly Lys Gly Leu Glu Trp Val
        35                  40                  45

Gly Val Ser Arg Ser Lys Ala Tyr Gly Gly Thr Thr Asp Tyr Ala Ala
    50                  55                  60

Ser Val Lys Gly Arg Phe Thr Ile Ser Arg Asp Asp Ser Lys Ser Thr
65                  70                  75                  80

Ala Tyr Leu Gln Met Asn Ser Leu Lys Thr Glu Asp Thr Ala Val Tyr
                85                  90                  95

Tyr Cys Thr Ser Ser Gly Tyr Ser Ser Gly Trp Thr Pro Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335
```

```
Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
            370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys
            450

<210> SEQ ID NO 297
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 297

Glu Val Gln Leu Val Glu Ser Gly Gly Gly Leu Val Lys Pro Gly Arg
1               5                   10                  15

Ser Leu Arg Leu Ser Cys Thr Ala Ser Gly Phe Thr Phe Gly Asp Tyr
            20                  25                  30

Ala Leu Ser Trp Val Arg Gln Ala Pro Gly Lys Gly Leu Glu Trp Val
            35                  40                  45

Gly Val Ser Arg Ser Lys Ala Tyr Gly Gly Thr Thr Asp Tyr Ala Ala
        50                  55                  60

Ser Val Lys Gly Arg Phe Thr Ile Ser Arg Asp Asp Ser Lys Ser Phe
65                  70                  75                  80

Ala Tyr Leu Gln Met Asn Ser Leu Lys Thr Glu Asp Thr Ala Val Tyr
                85                  90                  95

Tyr Cys Ala Ser Ser Gly Tyr Ser Ser Gly Trp Thr Pro Phe Asp Tyr
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
        210                 215                 220

Ser Cys Asp Lys Thr His Thr Cys Pro Pro Cys Pro Ala Pro Glu Leu
```

```
            225                 230                 235                 240
Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
                275                 280                 285

Glu Val His Asn Ala Lys Thr Lys Pro Arg Glu Glu Gln Tyr Asn Ser
            290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Glu Glu Met Thr Lys Asn Gln
                355                 360                 365

Val Ser Leu Thr Cys Leu Val Lys Gly Phe Tyr Pro Ser Asp Ile Ala
            370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
            435                 440                 445

Leu Ser Pro Gly Lys
            450

<210> SEQ ID NO 298
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 298

Glu Val Gln Leu Val Glu Ser Gly Gly Gly Leu Val Lys Pro Gly Arg
1               5                   10                  15

Ser Leu Arg Leu Ser Cys Ala Ala Ser Gly Phe Thr Phe Gly Asp Tyr
                20                  25                  30

Ala Leu Ser Trp Phe Arg Gln Ala Pro Gly Lys Gly Leu Glu Trp Val
            35                  40                  45

Gly Val Ser Arg Ser Lys Ala Tyr Gly Gly Thr Thr Asp Tyr Ala Ala
        50                  55                  60

Ser Val Lys Gly Arg Phe Thr Ile Ser Arg Asp Asp Ser Lys Ser Thr
65                  70                  75                  80

Ala Tyr Leu Gln Met Asn Ser Leu Lys Thr Glu Asp Thr Ala Val Tyr
                85                  90                  95

Tyr Cys Thr Ser Ser Gly Tyr Ser Ser Gly Trp Thr Pro Phe Asp Tyr
                100                 105                 110

Trp Gly Gln Gly Thr Leu Val Thr Val Ser Ser Ala Ser Thr Lys Gly
            115                 120                 125
```

```
Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 299
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 299

Glu Val Gln Leu Val Glu Ser Gly Gly Gly Leu Val Lys Pro Gly Arg
1               5                   10                  15

Ser Leu Arg Leu Ser Cys Thr Ala Ser Gly Phe Thr Phe Gly Asp Tyr
            20                  25                  30
```

```
Ala Leu Ser Trp Val Arg Gln Ala Pro Gly Lys Gly Leu Glu Trp Val
            35                  40                  45

Gly Val Ser Arg Ser Lys Ala Tyr Gly Gly Thr Thr Asp Tyr Ala Ala
 50                  55                  60

Ser Val Lys Gly Arg Phe Thr Ile Ser Arg Asp Asp Ser Lys Ser Phe
 65                  70                  75                  80

Ala Tyr Leu Gln Met Asn Ser Leu Lys Thr Glu Asp Thr Ala Val Tyr
                    85                  90                  95

Tyr Cys Ala Lys Ser Gly Tyr Ser Ser Gly Trp Thr Pro Phe Asp Tyr
                100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
    355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
    435                 440                 445
```

Leu Ser Pro Gly Lys
    450

<210> SEQ ID NO 300
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 300

Glu Val Gln Leu Val Glu Ser Gly Gly Gly Leu Val Lys Pro Gly Arg
1               5                   10                  15

Ser Leu Arg Leu Ser Cys Ala Ala Ser Gly Phe Thr Phe Gly Asp Tyr
            20                  25                  30

Ala Leu Ser Trp Val Arg Gln Ala Pro Gly Lys Gly Leu Glu Trp Val
        35                  40                  45

Gly Val Ser Arg Ser Lys Ala Tyr Gly Gly Thr Thr Asp Tyr Ala Ala
    50                  55                  60

Ser Val Lys Gly Arg Phe Thr Ile Ser Arg Asp Asp Ser Lys Ser Thr
65                  70                  75                  80

Ala Tyr Leu Gln Met Asn Ser Leu Lys Thr Glu Asp Thr Ala Val Tyr
                85                  90                  95

Tyr Cys Thr Ser Ser Gly Tyr Ser Gly Trp Thr Pro Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
                355                 360                 365

Val Ser Leu Thr Cys Leu Val Lys Gly Phe Tyr Pro Ser Asp Ile Ala
            370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
                435                 440                 445

Leu Ser Pro Gly Lys
            450

<210> SEQ ID NO 301
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 301

Glu Val Gln Leu Val Glu Ser Gly Gly Gly Leu Val Lys Pro Gly Arg
1               5                   10                  15

Ser Leu Arg Leu Ser Cys Thr Ala Ser Gly Phe Thr Phe Gly Asp Tyr
            20                  25                  30

Ala Leu Ser Trp Val Arg Gln Ala Pro Gly Lys Gly Leu Glu Trp Val
        35                  40                  45

Gly Val Ser Arg Ser Lys Ala Tyr Gly Gly Thr Thr Asp Tyr Ala Ala
    50                  55                  60

Ser Val Lys Gly Arg Phe Thr Ile Ser Arg Asp Asp Ser Lys Ser Thr
65                  70                  75                  80

Ala Tyr Leu Gln Met Asn Ser Leu Lys Thr Glu Asp Thr Ala Val Tyr
                85                  90                  95

Tyr Cys Ala Ser Ser Gly Tyr Ser Ser Gly Trp Thr Pro Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr

```
                245                 250                 255
Leu Met Ile Ser Arg Thr Pro Glu Val Thr Cys Val Val Asp Val
            260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
            290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
            370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys
            450

<210> SEQ ID NO 302
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 302

Glu Val Gln Leu Val Glu Ser Gly Gly Gly Leu Val Lys Pro Gly Arg
1               5                   10                  15

Ser Leu Arg Leu Ser Cys Ala Ala Ser Gly Phe Thr Phe Gly Asp Tyr
            20                  25                  30

Ala Leu Ser Trp Val Arg Gln Ala Pro Gly Lys Gly Leu Glu Trp Val
            35                  40                  45

Gly Val Ser Arg Ser Lys Ala Tyr Gly Gly Thr Thr Asp Tyr Ala Ala
        50                  55                  60

Ser Val Lys Gly Arg Phe Thr Ile Ser Arg Asp Asp Ser Lys Ser Thr
65                  70                  75                  80

Ala Tyr Leu Gln Met Asn Ser Leu Lys Thr Glu Asp Thr Ala Val Tyr
            85                  90                  95

Tyr Cys Ala Ser Ser Gly Tyr Ser Ser Gly Trp Thr Pro Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
        130                 135                 140
```

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
            435                 440                 445

Leu Ser Pro Gly Lys
        450

<210> SEQ ID NO 303
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 303

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asp Tyr
            20                  25                  30

Ala Leu Ser Trp Val Arg Gln Ala Pro Gly Lys Gly Leu Glu Trp Val
        35                  40                  45

Gly Val Ser Arg Ser Lys Ala Tyr Gly Gly Thr Thr Asp Tyr Ala Ala
    50              55                  60

Ser Val Lys Gly Arg Phe Thr Ile Ser Arg Asp Asp Ser Lys Ser Thr
65              70                  75                  80

Ala Tyr Leu Gln Met Asn Ser Leu Lys Ala Glu Asp Thr Ala Val Tyr
                    85                  90                  95

Tyr Cys Ala Ser Ser Gly Tyr Ser Ser Gly Trp Thr Pro Phe Asp Tyr
            100                 105                 110

Trp Gly Gln Gly Thr Leu Val Thr Val Ser Ser Ala Ser Thr Lys Gly
                115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
                195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
    275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Glu Glu Met Thr Lys Asn Gln
                355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
            435                 440                 445

Leu Ser Pro Gly Lys
        450

-continued

```
<210> SEQ ID NO 304
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 304
```

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asp Tyr
            20                  25                  30

Ala Leu Ser Trp Val Arg Gln Ala Pro Gly Lys Gly Leu Glu Trp Val
        35                  40                  45

Gly Val Ser Arg Ser Lys Ala Tyr Gly Gly Thr Thr Asp Tyr Ala Ala
    50                  55                  60

Ser Val Lys Gly Arg Phe Thr Ile Ser Arg Asp Asp Ser Lys Ser Thr
65                  70                  75                  80

Ala Tyr Leu Gln Met Asn Ser Leu Lys Ala Glu Asp Thr Ala Val Tyr
                85                  90                  95

Tyr Cys Ala Ser Ser Gly Tyr Ser Ser Gly Trp Thr Pro Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

```
Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
        420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 305
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 305

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Phe Asn Tyr His Gln Arg Pro Ser Gly Val Pro Asp Arg Phe Ser
    50                  55                  60

Gly Ser Lys Ser Gly Ser Ser Ala Ser Leu Ala Ile Ser Gly Leu Gln
65                  70                  75                  80

Ser Glu Asp Glu Ala Asp Tyr Tyr Cys Ala Ala Trp Asp Ser Leu
                85                  90                  95

Asn Gly Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 306
<211> LENGTH: 453
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 306

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Leu Ser Trp Val Arg Gln Ala Pro Gly Lys Gly Leu Glu Trp Val
        35                  40                  45

Ser Val Ser Arg Ser Lys Ala Tyr Gly Gly Thr Thr Asp Tyr Ala Ala
50                  55                  60

Ser Val Lys Gly Arg Phe Thr Ile Ser Arg Asp Asn Ser Lys Ser Thr
65                  70                  75                  80

Ala Tyr Leu Gln Met Asn Ser Leu Lys Ala Glu Asp Thr Ala Val Tyr
                85                  90                  95

Tyr Cys Ala Ser Ser Gly Tyr Ser Ser Gly Trp Thr Pro Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

```
Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450
```

<210> SEQ ID NO 307
<211> LENGTH: 453
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 307

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Leu Ser Trp Val Arg Gln Ala Pro Gly Lys Gly Leu Glu Trp Val
        35                  40                  45

Ser Val Ser Arg Ser Lys Ala Tyr Gly Gly Thr Thr Asp Tyr Ala Ala
    50                  55                  60

Ser Val Lys Gly Arg Phe Thr Ile Ser Arg Asp Asn Ser Lys Ser Thr
65                  70                  75                  80

Ala Tyr Leu Gln Met Asn Ser Leu Lys Ala Glu Asp Thr Ala Val Tyr
                85                  90                  95

Tyr Cys Ala Ser Ser Gly Tyr Ser Gly Trp Thr Pro Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Val Glu Pro Lys
    210                 215                 220

Ser Cys Asp Lys Thr His Thr Cys Pro Cys Pro Ala Pro Glu Leu
225                 230                 235                 240

Leu Gly Gly Pro Ser Val Phe Leu Phe Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300
```

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
            370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys
            450

<210> SEQ ID NO 308
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 308

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Leu Ser Trp Val Arg Gln Ala Pro Gly Lys Gly Leu Glu Trp Val
            35                  40                  45

Ser Val Ser Arg Ser Lys Ala Tyr Gly Gly Thr Thr Asp Tyr Ala Ala
            50                  55                  60

Ser Val Lys Gly Arg Phe Thr Ile Ser Arg Asp Asn Ser Lys Ser Thr
65                  70                  75                  80

Ala Tyr Leu Gln Met Asn Ser Leu Lys Ala Glu Asp Thr Ala Val Tyr
            85                  90                  95

Tyr Cys Ala Lys Ser Gly Tyr Ser Ser Gly Trp Thr Pro Phe Asp Tyr
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val

```
                195                 200                 205
Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 309
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 309

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Gly Asp Tyr
            20                  25                  30

Ala Leu Ser Trp Phe Arg Gln Ala Pro Gly Lys Gly Leu Glu Trp Val
        35                  40                  45

Gly Val Ser Arg Ser Lys Ala Tyr Gly Gly Thr Thr Asp Tyr Ala Ala
    50                  55                  60

Ser Val Lys Gly Arg Phe Thr Ile Ser Arg Asp Asp Ser Lys Ser Phe
65                  70                  75                  80

Ala Tyr Leu Gln Met Asn Ser Leu Lys Thr Glu Asp Thr Ala Val Tyr
                85                  90                  95
```

Tyr Cys Ala Ser Ser Gly Tyr Ser Ser Gly Trp Thr Pro Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
        420                 425                 430

Val Met His Glu Ala Leu His Asn His Tyr Thr Gln Lys Ser Leu Ser
    435                 440                 445

Leu Ser Pro Gly Lys
    450

<210> SEQ ID NO 310
<211> LENGTH: 1425
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 310

-continued

```
atggacatga gggtgcccgc tcagctcctg gggctcctgc tgctgtggct gagaggtgcg      60
cgctgtgagg tgcagctggt ggagtctggg ggaggcttgg taaagccagg ggggtccctg     120
agactctcct gtgcagcttc tggattcacc tttggagatt atgctctgag ctggttccgc     180
caggctccag gaaggggct ggagtgggta ggtgtcagta aagcaaagc ttatggtggg      240
acaacagatt acgccgcgtc tgtgaaaggc agattcacca tctcaagaga tgattccaaa     300
agcttcgcct atctgcaaat gaacagcctg aaaaccgagg acacagccgt gtattactgt     360
gctagtagcg ggtatagcag tggctggacc ccgtttgact actggggcca gggaaccctg     420
gtcaccgtct cctcagctag caccaagggc ccatccgtct tccccctggc accctcctcc     480
aagagcacct ctgggggcac agcggccctg ggctgcctgg tcaaggacta cttccccgaa     540
ccggtgacgg tgtcgtggaa ctcaggcgcc ctgaccagcg gcgtgcacac cttcccggct     600
gtcctacagt cctcaggact ctactccctc agcagcgtgg tgaccgtgcc ctccagcagc     660
ttgggcaccc agacctacat ctgcaacgtg aatcacaagc ccagcaacac caaggtggac     720
aagaaagttg agcccaaatc ttgtgacaaa actcacacat gcccaccgtg cccagcacct     780
gaactcctgg ggggaccgtc agtcttcctc ttccccccaa aacccaagga caccctcatg     840
atctcccgga cccctgaggt cacatgcgtg gtggtggacg tgagccacga agaccctgag     900
gtcaagttca actggtacgt ggacggcgtg gaggtgcata atgccaagac aaagccgcgg     960
gaggagcagt acaacagcac gtaccgtgtg gtcagcgtcc tcaccgtcct gcaccaggac    1020
tggctgaatg gcaaggagta caagtgcaag gtctccaaca aagccctccc agcccccatc    1080
gagaaaacca tctccaaagc caaagggcag ccccgagaac cacaggtgta caccctgccc    1140
ccatcccggg aggagatgac caagaaccag gtcagcctga cctgcctggt caaaggcttc    1200
tatcccagcg acatcgccgt ggagtgggag agcaatgggc agccggagaa caactacaag    1260
accacgcctc ccgtgctgga ctccgacggc tccttcttcc tctatagcaa gctcaccgtg    1320
gacaagagca ggtggcagca ggggaacgtc ttctcatgct ccgtgatgca tgaggctctg    1380
cacaaccact acacgcagaa gagcctctcc ctgtctccgg gtaaa                    1425
```

<210> SEQ ID NO 311
<211> LENGTH: 123
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 311

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Gly Asp Tyr
            20                  25                  30

Ala Leu Ser Trp Phe Arg Gln Ala Pro Gly Lys Gly Leu Glu Trp Val
        35                  40                  45

Gly Val Ser Arg Ser Lys Ala Tyr Gly Gly Thr Thr Asp Tyr Ala Ala
    50                  55                  60

Ser Val Lys Gly Arg Phe Thr Ile Ser Arg Asp Asp Ser Lys Ser Phe
65                  70                  75                  80

Ala Tyr Leu Gln Met Asn Ser Leu Lys Thr Glu Asp Thr Ala Val Tyr
                85                  90                  95

Tyr Cys Ala Ser Ser Gly Tyr Ser Ser Gly Trp Thr Pro Phe Asp Tyr
```

```
                    100                 105                 110
Trp Gly Gln Gly Thr Leu Val Thr Val Ser Ser
            115                 120

<210> SEQ ID NO 312
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 312

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Phe Asn Tyr His Gln Arg Pro Ser Gly Val Pro Asp Arg Phe Ser
    50                  55                  60

Gly Ser Lys Ser Gly Ser Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 313
<211> LENGTH: 714
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 313
atggacatga gggtgcccgc tcagctcctg gggctcctgc tgctgtggct gagaggtgcg      60
cgctgtcagt ctgtgctgac tcagccaccc tcagcgtctg gaccccccgg acagagggtc     120
accatctctt gttctgggag cagctccaac atcggaagta atactgtaaa ctggtaccag     180
cagctcccca gaacggcccc caaactcctc atctttaatt atcatcagcg gccctcaggg     240
gtccctgacc gattctctgg ctccaagtct ggctcctcag cctccctggc catcagtggg     300
```

```
ctccagtctg aggatgaggc tgattattac tgtgcagcat gggatgacag cctgaatggt    360
tgggtgttcg gcggagggac caaactgacc gtcctaggcc aaccgaaagc ggcgccctcg    420
gtcactctgt tcccgccctc ctctgaggag cttcaagcca caaggccac actggtgtgt    480 ctcataagtg acttctaccc gggagccgtg acagtggcct ggaaggcaga tagcagcccc    540
gtcaaggcgg gagtggagac caccacaccc tccaaacaaa gcaacaacaa gtacgcggcc    600
agcagctatc tgagcctgac gcctgagcag tggaagtccc acagaagcta cagctgccag    660
gtcacgcatg aagggagcac cgtggagaag acagtggccc ctacagaatg ttca          714
```

<210> SEQ ID NO 314
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 314

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Phe Asn Tyr His Gln Arg Pro Ser Gly Val Pro Asp Arg Phe Ser
    50                  55                  60

Gly Ser Lys Ser Gly Ser Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Trp Val Phe Gly Gly Gly Thr Lys Leu Thr Val Leu
            100                 105                 110
```

<210> SEQ ID NO 315
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 315

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Val Gly Gly Asp Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Val Asn Ser Leu Arg Ala Glu Asp Ser Ala Val Tyr Tyr Cys Ala
                85                  90                  95

Lys Asp Gln Val Thr Leu Val Arg Gly Val Trp Tyr Tyr Tyr Gly Leu
            100                 105                 110

Asp Val Trp Gly Gln Gly Thr Thr Val Thr Val Ser Ser Ala Ser Thr
```

```
            115                 120                 125
Lys Gly Pro Ser Val Phe Pro Leu Ala Pro Ser Ser Lys Ser Thr Ser
        130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 316
<211> LENGTH: 1431
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 316
atggacatga gggtgcccgc tcagctcctg gggctcctgc tgctgtggct gagaggtgcg      60
cgctgtgagg tgcagctgtt ggagtctgga ggaggcttgg tacagcctgg ggggtccctg     120
```

```
agactctcct gtgcagcctc tggattcacc tttagcagct atgccatgaa ctgggtccgc    180
caggctccag ggaaggggct ggagtgggtc tcagctatta gtgtcggtgg tgacacatac    240
tacgcagact ccgtgaaggg ccggttcacc atctccagag acaattccaa gaacacgcta    300
tatctgcagg tgaacagcct gagagccgag gactcggccg tatattactg tgcgaaagat    360
caggttactt tggttcgggg agtttggtac tactacggtt tggacgtctg gggccaaggg    420
accacggtca ccgtctcctc agctagcacc aagggcccat ccgtcttccc cctggcaccc    480
tcctccaaga gcacctctgg gggcacagcg gccctgggct gcctggtcaa ggactacttc    540
cccgaaccgg tgacggtgtc gtggaactca ggcgccctga ccagcggcgt gcacaccttc    600
ccggctgtcc tacagtcctc aggactctac tccctcagca gcgtggtgac cgtgccctcc    660
agcagcttgg gcacccagac ctacatctgc aacgtgaatc acaagcccag caacaccaag    720
gtggacaaga agttgagccc aaatcttgtg acaaaactca cacatgccca ccgtgccca    780
gcacctgaac tcctgggggg accgtcagtc ttcctcttcc ccccaaaacc caaggacacc    840
ctcatgatct cccggacccc tgaggtcaca tgcgtggtgg tggacgtgag ccacgaagac    900
cctgaggtca agttcaactg gtacgtggac ggcgtggagg tgcataatgc caagacaaag    960
ccgcgggagg agcagtacaa cagcacgtac cgtgtggtca gcgtcctcac cgtcctgcac   1020
caggactggc tgaatggcaa ggagtacaag tgcaaggtct ccaacaaagc cctcccagcc   1080
cccatcgaga aaaccatctc caaagccaaa gggcagcccc gagaaccaca ggtgtacacc   1140
ctgcccccat cccgggagga gatgaccaag aaccaggtca gcctgacctg cctggtcaaa   1200
ggcttctatc ccagcgacat cgccgtggag tgggagagca atgggcagcc ggagaacaac   1260
tacaagacca cgcctcccgt gctggactcc gacggctcct tcttcctcta tagcaagctc   1320
accgtggaca agagcaggtg gcagcagggg aacgtcttct catgctccgt gatgcatgag   1380
gctctgcaca accactacac gcagaagagc ctctccctgt ctccgggtaa a            1431
```

<210> SEQ ID NO 317
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 317

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Val Gly Gly Asp Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Val Asn Ser Leu Arg Ala Glu Asp Ser Ala Val Tyr Tyr Cys Ala
                85                  90                  95

Lys Asp Gln Val Thr Leu Val Arg Gly Val Trp Tyr Tyr Tyr Gly Leu
            100                 105                 110

Asp Val Trp Gly Gln Gly Thr Thr Val Thr Val Ser Ser
        115                 120                 125

<210> SEQ ID NO 318
<211> LENGTH: 219
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 318

Asp Ile Val Leu Ile Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Asn Asn Tyr Leu Asp Trp Tyr Leu Gln Lys Pro Gly Gln Ser
        35                  40                  45

Pro His Leu Leu Ile Ser Leu Gly Ser Gln Arg Thr Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Pro Pro Arg Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 319
<211> LENGTH: 723
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 319
atggacatga gggtgcccgc tcagctcctg gggctcctgc tgctgtggct gagaggtgcg      60
cgctgtgata ttgtgctgat tcagtctcca ctctccctgc ccgtcacccc tggagagccg     120
gcctccatct cctgcaggtc tagtcagagc ctcctgcaca gtaatggaaa caactatttg     180
gattggtacc tgcagaagcc agggcagtct ccacatctcc tgatctcttt gggctctcag     240
cggacctccg ggtccctga caggttcagt ggcagtggat caggcacaga ttttacactg     300
aaaatcagca gagtggaggc tgaggatgtt gggggtttatt actgcatgca agctctacag     360
cctcctcgga ggttcggcca aggaccaag ttggaaatca aacgaacggt ggctgcacca     420

```
tctgtcttca tcttcccgcc atctgatgag cagttgaaat ctggaactgc ctctgttgtg    480
tgcctgctga ataacttcta tcccagagag gccaaagtac agtggaaggt ggataacgcc    540
ctccaatcgg gtaactccca ggagagtgtc acagagcagg acagcaagga cagcacctac    600
agcctcagca gcaccctgac gctgagcaaa gcagactacg agaaacacaa agtctacgcc    660
tgcgaagtca cccatcaggg cctgagctcg cccgtcacaa agagcttcaa caggggagag    720
tgt                                                                  723
```

<210> SEQ ID NO 320
<211> LENGTH: 113
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 320

Asp Ile Val Leu Ile Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Asn Asn Tyr Leu Asp Trp Tyr Leu Gln Lys Pro Gly Gln Ser
        35                  40                  45

Pro His Leu Leu Ile Ser Leu Gly Ser Gln Arg Thr Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Pro Pro Arg Arg Phe Gly Gln Gly Thr Lys Leu Glu Ile Lys
            100                 105                 110

Arg

<210> SEQ ID NO 321
<211> LENGTH: 455
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 321

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Val Gly Gly Asp Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Asp Gln Val Thr Met Val Arg Gly Val Trp Tyr Tyr Tyr Gly Leu
            100                 105                 110

Asp Val Trp Gly Gln Gly Thr Thr Val Thr Val Ser Ser Ala Ser Thr

|     |     |     | 115 |     |     |     | 120 |     |     |     | 125 |     |
| --- | --- | --- | --- | --- | --- | --- | --- | --- | --- | --- | --- | --- |

```
Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 322
<211> LENGTH: 1431
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 322
atggacatga gggtgcccgc tcagctcctg gggctcctgc tgctgtggct gagaggtgcg      60
cgctgtgagg tgcagctgtt ggagtctgga ggaggcttgg tacagcctgg ggggtccctg     120
```

```
agactctcct gtgcagcctc tggattcacc tttagcagct atgccatgaa ctgggtccgc    180
caggctccag ggaaggggct ggagtgggtc tcagctatta gtgttggtgg tgacacatac    240
tacgcagact ccgtgaaggg ccggttcacc atctccagag acaattccaa gaacacgctg    300
tatctgcaaa tgaacagcct gagagccgag gacacggccg tatattactg tgcgaaagat    360
caggttacta tggttcgggg agtttggtac tactacggtt tggacgtctg gggccaaggg    420
accacggtca ccgtctcctc agctagcacc aagggcccat ccgtcttccc cctggcaccc    480
tcctccaaga gcacctctgg gggcacagcg gccctgggct gcctggtcaa ggactacttc    540
cccgaaccgg tgacggtgtc gtggaactca ggcgccctga ccagcggcgt gcacaccttc    600
ccggctgtcc tacagtcctc aggactctac tccctcagca gcgtggtgac cgtgccctcc    660
agcagcttgg gcacccagac ctacatctgc aacgtgaatc acaagcccag caacaccaag    720
gtggacaaga aagttgagcc caaatcttgt gacaaaactc acacatgccc accgtgccca    780
gcacctgaac tcctgggggg accgtcagtc ttcctcttcc ccccaaaacc caaggacacc    840
ctcatgatct cccggacccc tgaggtcaca tgcgtggtgg tggacgtgag ccacgaagac    900
cctgaggtca agttcaactg gtacgtggac ggcgtggagg tgcataatgc caagacaaag    960
ccgcgggagg agcagtacaa cagcacgtac cgtgtggtca gcgtcctcac cgtcctgcac   1020
caggactggc tgaatggcaa ggagtacaag tgcaaggtct ccaacaaagc cctcccagcc   1080
cccatcgaga aaaccatctc caaagccaaa gggcagcccc gagaaccaca ggtgtacacc   1140
ctgcccccat cccgggagga gatgaccaag aaccaggtca gcctgacctg cctggtcaaa   1200
ggcttctatc ccagcgacat cgccgtggag tgggagagca atgggcagcc ggagaacaac   1260
tacaagacca cgcctcccgt gctggactcc gacggctcct tcttcctcta tagcaagctc   1320
accgtggaca agagcaggtg gcagcagggg aacgtcttct catgctccgt gatgcatgag   1380
gctctgcaca accactacac gcagaagagc ctctccctgt ctccgggtaa a            1431
```

<210> SEQ ID NO 323
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 323

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Val Gly Gly Asp Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Asp Gln Val Thr Met Val Arg Gly Val Trp Tyr Tyr Tyr Gly Leu
            100                 105                 110

Asp Val Trp Gly Gln Gly Thr Thr Val Thr Val Ser Ser
        115                 120                 125

<210> SEQ ID NO 324
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 324

Asp Ile Val Met Ile Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Asn Asn Tyr Leu Asp Trp Tyr Leu Gln Lys Pro Gly Gln Ser
        35                  40                  45

Pro His Leu Leu Ile Ser Leu Gly Ser Gln Arg Thr Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Pro Pro Arg Arg Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 325
<211> LENGTH: 723
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 325
atggacatga gggtgcccgc tcagctcctg ggctcctgc tgctgtggct gagaggtgcg      60
cgctgtgata ttgtgatgat tcagtctcca ctctccctgc ccgtcacccc tggagagccg     120
gcctccatct cctgcaggtc tagtcagagc ctcctgcaca gtaatggaaa caactatttg     180
gattggtacc tgcagaagcc agggcagtct ccacatctcc tgatctcttt gggctctcag     240
cggacctccg gggtccctga caggttcagt ggcagtggat caggcacaga ttttacactg     300
aaaatcagca gagtggaggc tgaggatgtt ggggtttatt actgcatgca agctctacag     360
cctcctcgga ggttcggcca agggaccaag ttggaaatca aacgaacggt ggctgcacca     420

```
tctgtcttca tcttcccgcc atctgatgag cagttgaaat ctggaactgc ctctgttgtg    480
tgcctgctga ataacttcta tcccagagag gccaaagtac agtggaaggt ggataacgcc    540
ctccaatcgg gtaactccca ggagagtgtc acagagcagg acagcaagga cagcacctac    600
agcctcagca gcaccctgac gctgagcaaa gcagactacg agaaacacaa agtctacgcc    660
tgcgaagtca cccatcaggg cctgagctcg cccgtcacaa agagcttcaa caggggagag    720
tgt                                                                  723
```

<210> SEQ ID NO 326
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 326

Asp Ile Val Met Ile Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Asn Asn Tyr Leu Asp Trp Tyr Leu Gln Lys Pro Gly Gln Ser
        35                  40                  45

Pro His Leu Leu Ile Ser Leu Gly Ser Gln Arg Thr Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Pro Pro Arg Arg Phe Gly Gln Gly Thr Lys Leu Glu Ile Lys
            100                 105                 110

Arg

<210> SEQ ID NO 327
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 327

Val Ile Val Leu Ile Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Asn Asn Tyr Leu Asp Trp Tyr Leu Gln Lys Pro Gly Gln Ser
        35                  40                  45

Pro His Leu Leu Ile Ser Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Phe Tyr Tyr Cys Met Gln Ala
                85                  90                  95

Leu Gln Pro Pro Arg Arg Phe Gly Gln Gly Thr Lys Leu Glu Ile Lys
            100                 105                 110

Arg Thr Val Ala Ala Pro Ser Val Phe Ile Phe Pro Pro Ser Asp Glu

```
                  115                 120                 125
Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
                210                 215

<210> SEQ ID NO 328
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 328

Glu Val Gln Leu Leu Glu Ser Gly Gly Ala Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Val Gly Gly Asp Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

His Val Asn Ser Leu Ser Ala Glu Asp Ser Ala Val Tyr Tyr Cys Ala
                85                  90                  95

Lys Asp Gln Val Thr Leu Val Arg Gly Val Trp Tyr Tyr Tyr Gly Leu
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255
```

```
Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 329
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 329

Val Ile Val Leu Ile Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Asn Asn Tyr Leu Asp Trp Tyr Leu Gln Lys Pro Gly Gln Ser
        35                  40                  45

Pro His Leu Leu Ile Ser Leu Gly Ser Gln Arg Thr Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Phe Tyr Tyr Cys Met Gln Ala
                85                  90                  95

Leu Gln Pro Pro Arg Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160
```

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 330
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 330

Glu Val Gln Leu Leu Glu Ser Gly Gly Ala Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
            35                  40                  45

Ser Ala Ile Ser Val Gly Gly Asp Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

His Val Asn Ser Leu Ser Ala Glu Asp Ser Ala Val Tyr Tyr Cys Ala
                85                  90                  95

Lys Asp Gln Val Thr Leu Val Arg Gly Val Trp Tyr Tyr Gly Leu
            100                 105                 110

Asp Val Trp Gly Gln Gly Thr Thr Val Thr Val Ser Ser Ala Ser Thr
            115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr

```
            290                 295                 300
Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 331
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 331

Val Ile Val Leu Ile Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Asn Asn Tyr Leu Asp Trp Tyr Leu Gln Lys Pro Gly Gln Ser
        35                  40                  45

Pro His Leu Leu Ile Ser Leu Gly Ser Gln Arg Thr Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Phe Tyr Tyr Cys Met Gln Ala
                85                  90                  95

Leu Gln Pro Pro Arg Arg Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190
```

```
Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 332
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 332

Glu Val Gln Leu Leu Glu Ser Gly Gly Ala Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Val Gly Gly Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

His Val Asn Ser Leu Arg Ala Glu Asp Thr Ala Val Tyr Tyr Cys Ala
                85                  90                  95

Lys Asp Gln Val Thr Met Val Arg Gly Val Trp Tyr Tyr Tyr Gly Leu
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335
```

```
Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
            355                 360                 365

Asn Gln Val Ser Leu Thr Cys Leu Val Lys Gly Phe Tyr Pro Ser Asp
        370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
                420                 425                 430

Cys Ser Val Met His Glu Ala Leu His Asn His Tyr Thr Gln Lys Ser
            435                 440                 445

Leu Ser Leu Ser Pro Gly Lys
    450                 455

<210> SEQ ID NO 333
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 333

Val Ile Val Leu Ile Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Asn Asn Tyr Leu Asp Trp Tyr Leu Gln Lys Pro Gly Gln Ser
        35                  40                  45

Pro His Leu Leu Ile Ser Leu Gly Ser Gln Arg Thr Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Phe Tyr Tyr Cys Met Gln Ala
                85                  90                  95

Leu Gln Pro Pro Arg Arg Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

```
<210> SEQ ID NO 334
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 334

Glu Val Gln Leu Leu Glu Ser Gly Gly Ala Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Asn Trp Val Arg Gln Ala Pro Gly Lys Gly Leu Glu Trp Val
        35                  40                  45

Ser Ala Ile Ser Val Gly Gly Asp Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

His Val Asn Ser Leu Ser Ala Glu Asp Ser Ala Val Tyr Tyr Cys Ala
                85                  90                  95

Lys Asp Gln Val Thr Leu Val Arg Gly Val Trp Tyr Tyr Tyr Gly Leu
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365
```

```
Asn Gln Val Ser Leu Thr Cys Leu Val Lys Gly Phe Tyr Pro Ser Asp
    370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Phe Phe Leu Tyr Ser
                405                 410                 415
Lys Leu Thr Val Asp Lys Ser Arg Trp Gln Gln Gly Asn Val Phe Ser
                420                 425                 430
Cys Ser Val Met His Glu Ala Leu His Asn His Tyr Thr Gln Lys Ser
                435                 440                 445
Leu Ser Leu Ser Pro Gly Lys
    450                 455
```

<210> SEQ ID NO 335
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 335

```
Asp Ile Val Met Ile Gln Ser Pro Leu Ser Leu Pro Val Thr Pro Gly
1               5                   10                  15
Glu Pro Ala Ser Ile Ser Cys Arg Ser Ser Gln Ser Leu Leu His Ser
                20                  25                  30
Asn Gly Asn Asn Tyr Leu Asp Trp Tyr Leu Gln Lys Pro Gly Gln Ser
            35                  40                  45
Pro His Leu Leu Ile Ser Leu Gly Ser Gln Arg Thr Ser Gly Val Pro
        50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Met Gln Ala
                85                  90                  95
Leu Gln Pro Pro Arg Arg Phe Gly Gln Gly Thr Lys Leu Glu Ile Lys
                100                 105                 110
Arg Thr Val Ala Ala Pro Ser Val Phe Ile Phe Pro Pro Ser Asp Glu
            115                 120                 125
Gln Leu Lys Ser Gly Thr Ala Ser Val Val Cys Leu Leu Asn Asn Phe
        130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                165                 170                 175
Thr Tyr Ser Leu Ser Ser Thr Leu Thr Leu Ser Lys Ala Asp Tyr Glu
                180                 185                 190
Lys His Lys Val Tyr Ala Cys Glu Val Thr His Gln Gly Leu Ser Ser
            195                 200                 205
Pro Val Thr Lys Ser Phe Asn Arg Gly Glu Cys
        210                 215
```

<210> SEQ ID NO 336
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 336

Glu Val Gln Leu Leu Glu Ser Gly Gly Ala Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Val Gly Gly Asp Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Asp Gln Val Thr Met Val Arg Gly Val Trp Tyr Tyr Gly Leu
            100                 105                 110

Asp Val Trp Gly Gln Gly Thr Thr Val Thr Val Ser Ser Ala Ser Thr
            115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser

```
                    405                 410                 415
Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 337
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 337

Asp Ile Val Met Ile Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Asn Asn Phe Leu Asp Trp Tyr Leu Gln Lys Pro Gly Gln Ser
        35                  40                  45

Pro His Leu Leu Ile Ser Leu Gly Ser Gln Arg Thr Ser Gly Val Pro
    50                  55                  60

Asp Arg Leu Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Ala
                85                  90                  95

Leu Arg Pro Pro Arg Arg Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 338
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 338

Glu Val Gln Leu Leu Glu Ser Gly Gly Ala Leu Val Gln Pro Gly Gly
1               5                   10                  15

Ser Leu Arg Leu Ser Cys Ala Ala Ser Gly Phe Thr Phe Ser Ser Tyr
```

```
                    20                  25                  30
Ala Met Asn Trp Val Arg Gln Ala Pro Gly Lys Gly Leu Glu Trp Val
                35                  40                  45
Ser Ala Ile Ser Val Gly Gly Asp Thr Tyr Tyr Ala Asp Ser Val Lys
            50                  55                  60
Gly Arg Phe Thr Ile Ser Arg Asp Asn Ser Lys Asn Thr Leu Tyr Leu
 65                 70                  75                  80
Gln Met Asn Ser Leu Arg Ala Glu Asp Thr Ala Val Tyr Tyr Cys Ala
                85                  90                  95
Lys Asp Gln Val Thr Met Val Arg Gly Val Trp Tyr Tyr Tyr Gly Leu
                100                 105                 110
Asp Val Trp Gly Gln Gly Thr Thr Val Thr Val Ser Ser Ala Ser Thr
                115                 120                 125
Lys Gly Pro Ser Val Phe Pro Leu Ala Pro Ser Ser Lys Ser Thr Ser
            130                 135                 140
Gly Gly Thr Ala Ala Leu Gly Cys Leu Val Lys Asp Tyr Phe Pro Glu
145                 150                 155                 160
Pro Val Thr Val Ser Trp Asn Ser Gly Ala Leu Thr Ser Gly Val His
                165                 170                 175
Thr Phe Pro Ala Val Leu Gln Ser Ser Gly Leu Tyr Ser Leu Ser Ser
                180                 185                 190
Val Val Thr Val Pro Ser Ser Ser Leu Gly Thr Gln Thr Tyr Ile Cys
                195                 200                 205
Asn Val Asn His Lys Pro Ser Asn Thr Lys Val Asp Lys Lys Val Glu
            210                 215                 220
Pro Lys Ser Cys Asp Lys Thr His Thr Cys Pro Pro Cys Pro Ala Pro
225                 230                 235                 240
Glu Leu Leu Gly Gly Pro Ser Val Phe Leu Phe Pro Pro Lys Pro Lys
                245                 250                 255
Asp Thr Leu Met Ile Ser Arg Thr Pro Glu Val Thr Cys Val Val Val
                260                 265                 270
Asp Val Ser His Glu Asp Pro Glu Val Lys Phe Asn Trp Tyr Val Asp
                275                 280                 285
Gly Val Glu Val His Asn Ala Lys Thr Lys Pro Arg Glu Glu Gln Tyr
            290                 295                 300
Asn Ser Thr Tyr Arg Val Val Ser Val Leu Thr Val Leu His Gln Asp
305                 310                 315                 320
Trp Leu Asn Gly Lys Glu Tyr Lys Cys Lys Val Ser Asn Lys Ala Leu
                325                 330                 335
Pro Ala Pro Ile Glu Lys Thr Ile Ser Lys Ala Lys Gly Gln Pro Arg
                340                 345                 350
Glu Pro Gln Val Tyr Thr Leu Pro Pro Ser Arg Glu Glu Met Thr Lys
                355                 360                 365
Asn Gln Val Ser Leu Thr Cys Leu Val Lys Gly Phe Tyr Pro Ser Asp
            370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Phe Phe Leu Tyr Ser
                405                 410                 415
Lys Leu Thr Val Asp Lys Ser Arg Trp Gln Gln Gly Asn Val Phe Ser
                420                 425                 430
Cys Ser Val Met His Glu Ala Leu His Asn His Tyr Thr Gln Lys Ser
                435                 440                 445
```

```
Leu Ser Leu Ser Pro Gly Lys
    450                 455

<210> SEQ ID NO 339
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 339

Asp Ile Val Leu Ile Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Asn Asn Tyr Leu Asp Trp Tyr Leu Gln Lys Pro Gly Gln Ser
        35                  40                  45

Pro His Leu Leu Ile Ser Leu Gly Ser Gln Arg Thr Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Phe Tyr Tyr Cys Met Gln Ala
                85                  90                  95

Leu Gln Pro Pro Arg Arg Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 340
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 340

Glu Val Gln Leu Leu Glu Ser Gly Gly Ala Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Val Gly Gly Asp Thr Tyr Tyr Ala Asp Ser Val Lys
    50                  55                  60
```

```
Gly Arg Phe Thr Ile Ser Arg Asp Asn Ser Lys Asn Thr Leu Tyr Leu
 65                  70                  75                  80

His Val Asn Ser Leu Ser Ala Glu Asp Ser Ala Val Tyr Tyr Cys Ala
             85                  90                  95

Lys Asp Gln Val Thr Leu Val Arg Gly Val Trp Tyr Tyr Gly Leu
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
450                 455

<210> SEQ ID NO 341
<211> LENGTH: 219
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 341

Val Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Asn Asn Tyr Leu Asp Trp Tyr Leu Gln Lys Pro Gly Gln Ser
        35                  40                  45

Pro His Leu Leu Ile Ser Leu Gly Ser Gln Arg Thr Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Phe Tyr Tyr Cys Met Gln Ala
                85                  90                  95

Leu Gln Pro Pro Arg Arg Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 342
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 342

Glu Val Gln Leu Leu Glu Ser Gly Gly Ala Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Val Gly Gly Asp Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

His Val Asn Ser Leu Ser Ala Glu Asp Ser Ala Val Tyr Tyr Cys Ala
                85                  90                  95
```

Lys Asp Gln Val Thr Leu Val Arg Gly Val Trp Tyr Tyr Tyr Gly Leu
                100                 105                 110

Asp Val Trp Gly Gln Gly Thr Thr Val Thr Val Ser Ser Ala Ser Thr
            115                 120                 125

Lys Gly Pro Ser Val Phe Pro Leu Ala Pro Ser Ser Lys Ser Thr Ser
        130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
        450                 455

<210> SEQ ID NO 343
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 343

```
Val Ile Val Leu Ile Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Asn Asn Tyr Leu Asp Trp Tyr Leu Gln Lys Pro Gly Gln Ser
        35                  40                  45

Pro His Leu Leu Ile Tyr Leu Gly Ser Gln Arg Thr Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Phe Tyr Tyr Cys Met Gln Ala
                85                  90                  95

Leu Gln Pro Pro Arg Arg Phe Gly Gln Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 344
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 344

Glu Val Gln Leu Leu Glu Ser Gly Gly Ala Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Val Gly Gly Asp Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

His Val Asn Ser Leu Ser Ala Glu Asp Ser Ala Val Tyr Tyr Cys Ala
                85                  90                  95

Lys Asp Gln Val Thr Leu Val Arg Gly Val Trp Tyr Tyr Tyr Gly Leu
            100                 105                 110

Asp Val Trp Gly Gln Gly Thr Thr Val Thr Val Ser Ser Ala Ser Thr
            115                 120                 125

Lys Gly Pro Ser Val Phe Pro Leu Ala Pro Ser Ser Lys Ser Thr Ser
```

```
            130                 135                 140
Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
                195                 200                 205

Asn Val Asn His Lys Pro Ser Asn Thr Lys Val Asp Lys Lys Val Glu
            210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
            290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
                355                 360                 365

Asn Gln Val Ser Leu Thr Cys Leu Val Lys Gly Phe Tyr Pro Ser Asp
            370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly Lys
450                 455

<210> SEQ ID NO 345
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 345

Val Ile Val Leu Ile Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30
```

Asn Gly Asn Asn Tyr Leu Asp Trp Tyr Leu Gln Lys Pro Gly Gln Ser
            35                  40                  45

Pro His Leu Leu Ile Ser Leu Gly Ser Gln Arg Thr Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Pro Pro Arg Arg Phe Gly Gln Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 346
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 346

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Val Gly Gly Asp Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

His Val Asn Ser Leu Arg Ala Glu Asp Ser Ala Val Tyr Tyr Cys Ala
                 85                  90                  95

Lys Asp Gln Val Thr Leu Val Arg Gly Val Trp Tyr Tyr Tyr Gly Leu
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
                180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Lys Val Glu
        210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 347
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 347

Val Ile Val Leu Ile Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Asn Asn Tyr Leu Asp Trp Tyr Leu Gln Lys Pro Gly Gln Ser
        35                  40                  45

Pro His Leu Leu Ile Ser Leu Gly Ser Gln Arg Thr Ser Gly Val Pro
    50                  55                  60

Asp Arg Phe Ser Gly Ser Gly Ser Gly Thr Asp Phe Thr Leu Lys Ile

```
               65                  70                  75                  80
        Ser Arg Val Glu Ala Glu Asp Val Gly Val Tyr Tyr Cys Met Gln Ala
                            85                  90                  95

Leu Gln Pro Pro Arg Phe Gly Gln Gly Thr Lys Leu Glu Ile Lys
                        100                 105                 110

Arg Thr Val Ala Ala Pro Ser Val Phe Ile Phe Pro Pro Ser Asp Glu
                        115                 120                 125

Gln Leu Lys Ser Gly Thr Ala Ser Val Val Cys Leu Leu Asn Asn Phe
                130                 135                 140

Tyr Pro Arg Glu Ala Lys Val Gln Trp Lys Val Asp Asn Ala Leu Gln
        145                 150                 155                 160

Ser Gly Asn Ser Gln Glu Ser Val Thr Glu Gln Asp Ser Lys Asp Ser
                            165                 170                 175

Thr Tyr Ser Leu Ser Ser Thr Leu Thr Leu Ser Lys Ala Asp Tyr Glu
                        180                 185                 190

Lys His Lys Val Tyr Ala Cys Glu Val Thr His Gln Gly Leu Ser Ser
                        195                 200                 205

Pro Val Thr Lys Ser Phe Asn Arg Gly Glu Cys
                        210                 215

<210> SEQ ID NO 348
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 348

Glu Val Gln Leu Leu Glu Ser Gly Gly Gly Leu Val Gln Pro Gly Gly
        1               5                   10                  15

Ser Leu Arg Leu Ser Cys Ala Ala Ser Gly Phe Thr Phe Ser Ser Tyr
                        20                  25                  30

Ala Met Asn Trp Val Arg Gln Ala Pro Gly Lys Gly Leu Glu Trp Val
                        35                  40                  45

Ser Ala Ile Ser Val Gly Gly Asp Thr Tyr Tyr Ala Asp Ser Val Lys
                    50                  55                  60

Gly Arg Phe Thr Ile Ser Arg Asp Asn Ser Lys Asn Thr Leu Tyr Leu
        65                  70                  75                  80

Gln Val Asn Ser Leu Arg Ala Glu Asp Ser Ala Val Tyr Tyr Cys Ala
                            85                  90                  95

Lys Asp Gln Val Thr Leu Val Arg Gly Val Trp Tyr Tyr Tyr Gly Leu
                        100                 105                 110

Asp Val Trp Gly Gln Gly Thr Thr Val Thr Val Ser Ser Ala Ser Thr
                        115                 120                 125

Lys Gly Pro Ser Val Phe Pro Leu Ala Pro Ser Ser Lys Ser Thr Ser
                130                 135                 140

Gly Gly Thr Ala Ala Leu Gly Cys Leu Val Lys Asp Tyr Phe Pro Glu
        145                 150                 155                 160

Pro Val Thr Val Ser Trp Asn Ser Gly Ala Leu Thr Ser Gly Val His
                            165                 170                 175

Thr Phe Pro Ala Val Leu Gln Ser Ser Gly Leu Tyr Ser Leu Ser Ser
                        180                 185                 190

Val Val Thr Val Pro Ser Ser Ser Leu Gly Thr Gln Thr Tyr Ile Cys
                        195                 200                 205
```

-continued

Asn Val Asn His Lys Pro Ser Asn Thr Lys Val Asp Lys Lys Val Glu
210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
            245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
            325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
            405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
450                 455

<210> SEQ ID NO 349
<211> LENGTH: 187
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 349

Met Gly Ser Ser His His His His His His Gly Ser Gly Leu Val Pro
1               5                   10                  15

Arg Gly Ser Ala Ser Met Ser Asp Ser Glu Val Asn Gln Glu Ala Lys
            20                  25                  30

Pro Glu Val Lys Pro Glu Val Lys Pro Glu Thr His Ile Asn Leu Lys
        35                  40                  45

Val Ser Asp Gly Ser Ser Glu Ile Phe Phe Lys Ile Lys Lys Thr Thr
    50                  55                  60

Pro Leu Arg Arg Leu Met Glu Ala Phe Ala Lys Arg Gln Gly Lys Glu
65                  70                  75                  80

Met Asp Ser Leu Arg Phe Leu Tyr Asp Gly Ile Arg Ile Gln Ala Asp
                85                  90                  95

Gln Thr Pro Glu Asp Leu Asp Met Glu Asp Asn Asp Ile Ile Glu Ala
            100                 105                 110

-continued

His Arg Glu Gln Ile Gly Gly Ala Gln Arg Cys Phe His Ser Glu Tyr
            115                 120                 125

Phe Asp Ser Leu Leu His Ala Cys Lys Pro Cys Arg Leu Arg Cys Ser
        130                 135                 140

Asn Pro Pro Ala Pro Cys Gln Pro Tyr Cys Asp Pro Ser Met Thr Ser
145                 150                 155                 160

Ser Val Arg Gly Thr Tyr Thr Gly Gly Ser Gly Gly Leu Asn Asp
                165                 170                 175

Ile Phe Glu Ala Gln Lys Ile Glu Trp His Glu
            180                 185

<210> SEQ ID NO 350
<211> LENGTH: 190
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 350

Met Gly Ser Ser His His His His His His Gly Ser Gly Leu Val Pro
1               5                   10                  15

Arg Gly Ser Ala Ser Met Ser Asp Ser Glu Val Asn Gln Glu Ala Lys
            20                  25                  30

Pro Glu Val Lys Pro Glu Val Lys Pro Glu Thr His Ile Asn Leu Lys
        35                  40                  45

Val Ser Asp Gly Ser Ser Glu Ile Phe Phe Lys Ile Lys Lys Thr Thr
50                  55                  60

Pro Leu Arg Arg Leu Met Glu Ala Phe Ala Lys Arg Gln Gly Lys Glu
65                  70                  75                  80

Met Asp Ser Leu Arg Phe Leu Tyr Asp Gly Ile Arg Ile Gln Ala Asp
                85                  90                  95

Gln Thr Pro Glu Asp Leu Asp Met Glu Asp Asn Asp Ile Ile Glu Ala
            100                 105                 110

His Arg Glu Gln Ile Gly Gly Ala Gly Gln Cys Ser Gln Asn Glu Tyr
            115                 120                 125

Phe Asp Ser Leu Leu His Ala Cys Ile Pro Cys Gln Leu Arg Cys Ser
        130                 135                 140

Ser Asn Thr Pro Pro Leu Thr Cys Gln Arg Tyr Cys Asn Ala Ser Val
145                 150                 155                 160

Thr Asn Ser Val Lys Gly Thr Asn Ala Gly Gly Gly Ser Gly Gly Gly
                165                 170                 175

Leu Asn Asp Ile Phe Glu Ala Gln Lys Ile Glu Trp His Glu
            180                 185                 190

<210> SEQ ID NO 351
<211> LENGTH: 48
<212> TYPE: PRT
<213> ORGANISM: Rattus sp.

<400> SEQUENCE: 351

Ala Gln Arg Cys Phe His Ser Glu Tyr Phe Asp Ser Leu Leu His Ala
1               5                   10                  15

Cys Lys Pro Cys Arg Leu Arg Cys Ser Asn Pro Pro Ala Pro Cys Gln
            20                  25                  30

Pro Tyr Cys Asp Pro Ser Met Thr Ser Ser Val Arg Gly Thr Tyr Thr
        35                  40                  45

<210> SEQ ID NO 352
<211> LENGTH: 50
<212> TYPE: PRT
<213> ORGANISM: Homo sapiens

<400> SEQUENCE: 352

Leu Gln Met Ala Gly Gln Cys Ser Gln Asn Glu Tyr Phe Asp Ser Leu
1               5                   10                  15

Leu His Ala Cys Ile Pro Cys Gln Leu Arg Cys Ser Ser Asn Thr Pro
            20                  25                  30

Pro Leu Thr Cys Gln Arg Tyr Cys Asn Ala Ser Val Thr Asn Ser Val
        35                  40                  45

Lys Gly
    50

<210> SEQ ID NO 353
<211> LENGTH: 50
<212> TYPE: PRT
<213> ORGANISM: Macaca fascicularis

<400> SEQUENCE: 353

Leu Gln Met Ala Arg Gln Cys Ser Gln Asn Glu Tyr Phe Asp Ser Leu
1               5                   10                  15

Leu His Asp Cys Lys Pro Cys Gln Leu Arg Cys Ser Ser Thr Pro Pro
            20                  25                  30

Leu Thr Cys Gln Arg Tyr Cys Asn Ala Ser Met Thr Asn Ser Val Lys
        35                  40                  45

Gly Met
    50

<210> SEQ ID NO 354
<211> LENGTH: 155
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 354

Gly Ser Ser His His His His His Gly Ser Gly Leu Val Pro Arg
1               5                   10                  15

Gly Ser Ala Ser Met Ser Asp Ser Glu Val Asn Gln Glu Ala Lys Pro
            20                  25                  30

Glu Val Lys Pro Glu Val Lys Pro Glu Thr His Ile Asn Leu Lys Val
        35                  40                  45

Ser Asp Gly Ser Ser Glu Ile Phe Phe Lys Ile Lys Lys Thr Thr Pro
    50                  55                  60

Leu Arg Arg Leu Met Glu Ala Phe Ala Lys Arg Gln Gly Lys Glu Met
65                  70                  75                  80

Asp Ser Leu Arg Phe Leu Tyr Asp Gly Ile Arg Ile Gln Ala Asp Gln
                85                  90                  95

Thr Pro Glu Asp Leu Asp Met Glu Asp Asn Asp Ile Ile Glu Ala His
            100                 105                 110

Arg Glu Gln Ile Gly Gly Ala Gly Gln Cys Ser Gln Asn Glu Tyr Phe
        115                 120                 125

Asp Ser Leu Leu His Ala Cys Ile Pro Cys Gln Leu Arg Cys Ser Ser
    130                 135                 140

```
Asn Thr Pro Pro Leu Thr Cys Gln Arg Tyr Cys
145                 150                 155
```

<210> SEQ ID NO 355
<211> LENGTH: 141
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 355

```
Gly Ser Ser His His His His His Gly Ser Gly Leu Val Pro Arg
1               5                   10                  15

Gly Ser Ala Ser Met Ser Asp Ser Glu Val Asn Gln Glu Ala Lys Pro
            20                  25                  30

Glu Val Lys Pro Glu Val Lys Pro Glu Thr His Ile Asn Leu Lys Val
            35                  40                  45

Ser Asp Gly Ser Ser Glu Ile Phe Phe Lys Ile Lys Lys Thr Thr Pro
    50                  55                  60

Leu Arg Arg Leu Met Glu Ala Phe Ala Lys Arg Gln Gly Lys Glu Met
65                  70                  75                  80

Asp Ser Leu Arg Phe Leu Tyr Asp Gly Ile Arg Ile Gln Ala Asp Gln
                85                  90                  95

Thr Pro Glu Asp Leu Asp Met Glu Asp Asn Asp Ile Ile Glu Ala His
                100                 105                 110

Arg Glu Gln Ile Gly Gly Ala Gly Gln Cys Ser Gln Asn Glu Tyr Phe
            115                 120                 125

Asp Ser Leu Leu His Ala Cys Ile Pro Cys Gln Leu Arg
    130                 135                 140
```

<210> SEQ ID NO 356
<211> LENGTH: 134
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 356

```
Gly Ser Ser His His His His His Gly Ser Gly Leu Val Pro Arg
1               5                   10                  15

Gly Ser Ala Ser Met Ser Asp Ser Glu Val Asn Gln Glu Ala Lys Pro
            20                  25                  30

Glu Val Lys Pro Glu Val Lys Pro Glu Thr His Ile Asn Leu Lys Val
            35                  40                  45

Ser Asp Gly Ser Ser Glu Ile Phe Phe Lys Ile Lys Lys Thr Thr Pro
    50                  55                  60

Leu Arg Arg Leu Met Glu Ala Phe Ala Lys Arg Gln Gly Lys Glu Met
65                  70                  75                  80

Asp Ser Leu Arg Phe Leu Tyr Asp Gly Ile Arg Ile Gln Ala Asp Gln
                85                  90                  95

Thr Pro Glu Asp Leu Asp Met Glu Asp Asn Asp Ile Ile Glu Ala His
                100                 105                 110

Arg Glu Gln Ile Gly Gly Ala Gly Gln Cys Ser Gln Asn Glu Tyr Phe
            115                 120                 125

Asp Ser Leu Leu His Ala
    130
```

<210> SEQ ID NO 357
<211> LENGTH: 153
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 357

Gly Ser Ser His His His His His Gly Ser Gly Leu Val Pro Arg
1               5                   10                  15

Gly Ser Ala Ser Met Ser Asp Ser Glu Val Asn Gln Glu Ala Lys Pro
            20                  25                  30

Glu Val Lys Pro Glu Val Lys Pro Glu Thr His Ile Asn Leu Lys Val
        35                  40                  45

Ser Asp Gly Ser Ser Glu Ile Phe Phe Lys Ile Lys Lys Thr Thr Pro
    50                  55                  60

Leu Arg Arg Leu Met Glu Ala Phe Ala Lys Arg Gln Gly Lys Glu Met
65                  70                  75                  80

Asp Ser Leu Arg Phe Leu Tyr Asp Gly Ile Arg Ile Gln Ala Asp Gln
                85                  90                  95

Thr Pro Glu Asp Leu Asp Met Glu Asp Asn Asp Ile Ile Glu Ala His
            100                 105                 110

Arg Glu Gln Ile Gly Gly Ala Gly Gln Cys Ser Gln Asn Glu Tyr Phe
        115                 120                 125

Asp Ser Leu Leu His Ala Cys Ile Pro Cys Gln Leu Arg Cys Ser Ser
    130                 135                 140

Asn Thr Pro Pro Leu Thr Cys Gln Arg
145                 150

<210> SEQ ID NO 358
<211> LENGTH: 143
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 358

Gly Ser Ser His His His His His Gly Ser Gly Leu Val Pro Arg
1               5                   10                  15

Gly Ser Ala Ser Met Ser Asp Ser Glu Val Asn Gln Glu Ala Lys Pro
            20                  25                  30

Glu Val Lys Pro Glu Val Lys Pro Glu Thr His Ile Asn Leu Lys Val
        35                  40                  45

Ser Asp Gly Ser Ser Glu Ile Phe Phe Lys Ile Lys Lys Thr Thr Pro
    50                  55                  60

Leu Arg Arg Leu Met Glu Ala Phe Ala Lys Arg Gln Gly Lys Glu Met
65                  70                  75                  80

Asp Ser Leu Arg Phe Leu Tyr Asp Gly Ile Arg Ile Gln Ala Asp Gln
                85                  90                  95

Thr Pro Glu Asp Leu Asp Met Glu Asp Asn Asp Ile Ile Glu Ala His
            100                 105                 110

Arg Glu Gln Ile Gly Gly Ala Gly Gln Cys Ser Gln Asn Glu Tyr Phe
        115                 120                 125

Asp Ser Leu Leu His Ala Cys Ile Pro Cys Gln Leu Arg Cys Ser
    130                 135                 140

```
<210> SEQ ID NO 359
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 359

His His His His His His
1               5
```